US009702007B2

(12) United States Patent  
Tchelet et al.

(10) Patent No.: US 9,702,007 B2  
(45) Date of Patent: Jul. 11, 2017

(54) GENETIC MARKERS PREDICTIVE OF RESPONSE TO GLATIRAMER ACETATE

(71) Applicants: Amir Tchelet, Hod-Hasharon (IL); Michael Hayden, Petach-Tikva (IL); Liat Hayardeny, Tel Aviv (IL); Colin James Douglas Ross, Burnaby (CA); Iris Grossman, Yakir (IL); David Ladkani, Jerusalem (IL)

(72) Inventors: Amir Tchelet, Hod-Hasharon (IL); Michael Hayden, Petach-Tikva (IL); Liat Hayardeny, Tel Aviv (IL); Colin James Douglas Ross, Burnaby (CA); Iris Grossman, Yakir (IL); David Ladkani, Jerusalem (IL)

(73) Assignee: TEVA PHARMACEUTICALS INDUSTRIES, LTD., Petach Tikva (IL)

( * ) Notice: Subject to any disclaimer, the term of this patent is extended or adjusted under 35 U.S.C. 154(b) by 0 days.

(21) Appl. No.: 14/520,280

(22) Filed: Oct. 21, 2014

(65) Prior Publication Data  
US 2015/0110733 A1 Apr. 23, 2015

Related U.S. Application Data

(60) Provisional application No. 62/048,641, filed on Sep. 10, 2014, provisional application No. 62/048,127, filed on Sep. 9, 2014, provisional application No. 61/893,807, filed on Oct. 21, 2013.

(51) Int. Cl.  
*A61K 38/16* (2006.01)  
*C12Q 1/68* (2006.01)

(52) U.S. Cl.  
CPC ............ *C12Q 1/6883* (2013.01); *A61K 38/16* (2013.01); *C12Q 2600/106* (2013.01); *C12Q 2600/156* (2013.01)

(58) Field of Classification Search  
None  
See application file for complete search history.

(56) References Cited

U.S. PATENT DOCUMENTS

| 3,849,550 | A | 11/1974 | Teitelbaum et al. |
|---|---|---|---|
| 5,800,808 | A | 9/1998 | Konfino et al. |
| 5,981,589 | A | 11/1999 | Konfino et al. |
| 6,048,898 | A | 4/2000 | Konfino et al. |
| 6,054,430 | A | 4/2000 | Konfino et al. |
| 6,214,791 | B1 | 4/2001 | Arnon et al. |
| 6,342,476 | B1 | 1/2002 | Konfino et al. |
| 6,362,161 | B1 | 3/2002 | Konfino et al. |
| 6,514,938 | B1 | 2/2003 | Gad et al. |
| 6,620,847 | B2 | 9/2003 | Konfino et al. |
| 6,800,285 | B2 | 10/2004 | Rodriguez et al. |
| 6,800,287 | B2 | 10/2004 | Gad et al. |
| 6,939,539 | B2 | 9/2005 | Konfino et al. |
| 7,022,663 | B2 | 4/2006 | Gilbert et al. |
| 7,033,582 | B2 | 4/2006 | Yong et al. |
| 7,074,580 | B2 | 7/2006 | Gad et al. |
| 7,163,802 | B2 | 1/2007 | Gad et al. |
| 7,199,098 | B2 | 4/2007 | Konfino et al. |
| 7,279,172 | B2 | 10/2007 | Aharoni et al. |
| 7,425,332 | B2 | 9/2008 | Aharoni et al. |
| 7,429,374 | B2 | 9/2008 | Klinger |
| 7,495,072 | B2 | 2/2009 | Dolitzky |
| 7,560,100 | B2 | 7/2009 | Pinchasi et al. |
| 7,566,767 | B2 | 7/2009 | Strominger et al. |
| 7,615,359 | B2 | 11/2009 | Gad et al. |

(Continued)

FOREIGN PATENT DOCUMENTS

| WO | WO 95/31990 | 11/1995 |
|---|---|---|
| WO | WO 98/30227 | 7/1998 |

(Continued)

OTHER PUBLICATIONS

Byun et al., Genome-Wide Pharmacogenomic Analysis of the Response to Interferon Beta Therapy in Multiple Sclerosis, Mar. 2008, Arch. Neurol. 65(3):337-344.*

(Continued)

*Primary Examiner* — John Ulm  
(74) *Attorney, Agent, or Firm* — John P. White; Gary J. Gershik; Cooper & Dunham LLP

(57) ABSTRACT

The present invention provides a method for treating a human subject afflicted with multiple sclerosis or a single clinical attack consistent with multiple sclerosis with a pharmaceutical composition comprising glatiramer acetate and a pharmaceutically acceptable carrier, comprising the steps of:

(i) determining a genotype of the subject at a location corresponding to the location of one or more single nucleotide polymorphisms (SNPs) selected from the group consisting of: Group 1, (ii) identifying the subject as a predicted responder to glatiramer acetate if the genotype of the subject contains one or more A alleles at the location of Group 2, one or more C alleles at the location of Group 3, one or more G alleles at the location of Group 4, or one or more T alleles at the location of kgp18432055, kgp279772, kgp3991733 or kgp7242489; and (iii) administering the pharmaceutical composition comprising glatiramer acetate and a pharmaceutically acceptable carrier to the subject only if the subject is identified as a predicted responder to glatiramer acetate.

20 Claims, 9 Drawing Sheets

(56) References Cited

U.S. PATENT DOCUMENTS

| | | | |
|---|---|---|---|
| 7,625,861 | B2 | 12/2009 | Konfino et al. |
| 7,855,176 | B1 | 12/2010 | Altman et al. |
| 7,923,215 | B2 | 4/2011 | Klinger |
| 7,968,511 | B2 | 6/2011 | Vollmer |
| 8,008,258 | B2 | 8/2011 | Aharoni et al. |
| 8,232,250 | B2 | 7/2012 | Klinger |
| 8,367,605 | B2 | 2/2013 | Konfino et al. |
| 8,389,228 | B2 | 3/2013 | Klinger |
| 8,399,211 | B2 | 3/2013 | Gad et al. |
| 8,399,413 | B2 | 3/2013 | Klinger |
| 8,709,433 | B2 | 4/2014 | Kasper |
| 8,759,302 | B2 | 6/2014 | Dhib-Jalbut |
| 8,815,511 | B2 | 8/2014 | Tchelet et al. |
| 8,920,373 | B2 | 12/2014 | Altman et al. |
| 8,969,302 | B2 | 3/2015 | Klinger |
| 9,018,170 | B2 | 4/2015 | Altman et al. |
| 9,063,153 | B2 | 6/2015 | Kasper |
| 9,155,775 | B1 | 10/2015 | Cohen et al. |
| 9,155,776 | B2 | 10/2015 | Klinger |
| 2002/0077278 | A1 | 6/2002 | Yong et al. |
| 2005/0019322 | A1 | 1/2005 | Rodriguez et al. |
| 2005/0064483 | A1 | 3/2005 | Zang et al. |
| 2005/0170004 | A1 | 8/2005 | Rosenberger |
| 2006/0172942 | A1 | 8/2006 | Dolitzky |
| 2006/0229233 | A1 | 10/2006 | Frankel et al. |
| 2006/0240463 | A1 | 10/2006 | Lancet |
| 2006/0264354 | A1 | 11/2006 | Aharoni et al. |
| 2007/0021324 | A1 | 1/2007 | Dolitzky |
| 2007/0037740 | A1 | 2/2007 | Pinchasi et al. |
| 2007/0054857 | A1 | 3/2007 | Pinchasi et al. |
| 2007/0059798 | A1 | 3/2007 | Gad |
| 2007/0161566 | A1 | 7/2007 | Pinchasi |
| 2007/0244056 | A1 | 10/2007 | Hayardeny et al. |
| 2008/0118553 | A1 | 5/2008 | Frenkel et al. |
| 2008/0131887 | A1* | 6/2008 | Stephan ............... G06F 19/18 435/6.11 |
| 2008/0207526 | A1 | 8/2008 | Strominger et al. |
| 2008/0261894 | A1 | 10/2008 | Kreitman et al. |
| 2009/0048181 | A1 | 2/2009 | Schipper et al. |
| 2009/0149541 | A1 | 6/2009 | Stark et al. |
| 2010/0167983 | A1 | 7/2010 | Kreitman et al. |
| 2010/0285600 | A1 | 11/2010 | Lancet et al. |
| 2010/0298227 | A1 | 11/2010 | Aharoni et al. |
| 2010/0305023 | A1 | 12/2010 | Stark et al. |
| 2011/0060279 | A1 | 3/2011 | Altman et al. |
| 2011/0066112 | A1 | 3/2011 | Altman et al. |
| 2012/0027718 | A1 | 2/2012 | Kreitman et al. |
| 2012/0309671 | A1 | 12/2012 | Klinger |
| 2014/0107208 | A1 | 4/2014 | Comabella et al. |
| 2014/0193827 | A1 | 7/2014 | Schwartz et al. |
| 2014/0271532 | A1 | 9/2014 | Kreitman et al. |
| 2014/0271630 | A1 | 9/2014 | Vollmer |
| 2014/0294899 | A1 | 10/2014 | Kasper et al. |
| 2014/0322158 | A1 | 10/2014 | Dhib-Jalbut |
| 2015/0045306 | A1 | 2/2015 | Tchelet et al. |
| 2015/0110733 | A1 | 4/2015 | Tchelet et al. |
| 2015/0164977 | A1 | 6/2015 | Klinger |
| 2015/0202247 | A1 | 7/2015 | Klinger |
| 2015/0241446 | A1 | 8/2015 | Kasper et al. |

FOREIGN PATENT DOCUMENTS

| | | |
|---|---|---|
| WO | WO 00/18794 | 9/1999 |
| WO | WO 00/05249 | 2/2000 |
| WO | WO 00/05250 | 2/2000 |
| WO | WO 00/20010 | 4/2000 |
| WO | WO 00/27417 | 5/2000 |
| WO | WO 01/60392 | 8/2001 |
| WO | WO 01/93828 | 12/2001 |
| WO | WO 01/97846 | 12/2001 |
| WO | WO 03/048735 | 6/2003 |
| WO | WO 2004/064717 | 8/2004 |
| WO | WO 2004/091573 | 10/2004 |
| WO | WO 2004/103297 | 12/2004 |
| WO | WO 2005/041933 | 5/2005 |
| WO | WO 2005/084377 | 9/2005 |
| WO | WO 2006/029036 | 3/2006 |
| WO | WO 2006/029393 | 3/2006 |
| WO | WO 2006/029411 | 3/2006 |
| WO | WO 2006/083608 | 8/2006 |
| WO | WO 2006/089164 | 8/2006 |
| WO | WO 2006/116602 | 11/2006 |
| WO | WO 2007/030573 | 3/2007 |
| WO | WO 2007/081975 | 7/2007 |
| WO | WO 2009/070298 | 6/2009 |
| WO | WO 2011/008274 | 1/2011 |
| WO | WO 2011/022063 | 2/2011 |
| WO | WO 2012/051106 | 4/2012 |
| WO | WO 2013/055683 | 4/2013 |
| WO | WO 2014/058976 | 4/2014 |
| WO | WO 2014/100639 | 6/2014 |
| WO | WO 2014/100643 | 6/2014 |
| WO | WO 2014/107533 | 7/2014 |
| WO | WO 2014/165280 | 10/2014 |
| WO | WO 2015/061367 | 4/2015 |

OTHER PUBLICATIONS

Jul. 22, 2015 Partial Supplementary European Search Report issued by the European Patent Office in connection with European Patent Application No. 12840243.5.

Grossman et al., "Pharmacogenetics of glatiramer acetate therapy for multiple sclerosis reveals drug-response markers "Pharmacogenetics and Genomics, 2007, 17: 657-666.

International Search Report issued Mar. 30, 2015 in connection with PCT International Application WO 2015/061367 (PCT/US2014/061647), filed Oct. 21, 2014.

Written Opinion of the International Searching Authority issued Mar. 30, 2015 in connection with PCT International Application WO 2015/061367 (PCT/US2014/061647), filed Oct. 21, 2014.

PCT International Preliminary Report on Patentability issued Apr. 15, 2014 for International Application WO 2013/055683 (PCT/US12/59352), filed Oct. 9, 2012.

PCT International Search Report Issued Apr. 18, 2013 for International Application Publication WO 2013/055683 (PCT/US12/59352), filed Oct. 9, 2012.

Written Opinion of the International Searching Authority issued Mar. 22, 2013 for International Application WO 2013/055683 (PCT/US12/59352), filed Oct. 9, 2012.

NCBI Submitted SNP(ss) Details: ss24494172. RefSNP No. rs17771939. [online] Aug. 21, 2004 [Retrieved from the internet on Mar. 7, 2013] <url://www.ncbi.nlm.nih.gov/projects/SNP/snp_ss.cgi?ss=ss24494172>.

NCBI Submitted SNP(ss) Details: ss23143312. RefSNP No. rs9508834 '[online] Mar. 14, 2007, [Retrieved from the internet on Mar. 7, 2013] <url://www.ncbi.nlm.nih.gov/projects/SNP/snp_ss.cgi?ss=ss23143312>

NCBI Submitted SNP(ss) Details: ss24400158. RefSNP No. rs17807327. [online] Aug. 21, 2004 [Retrieved from the internet on Mar. 7, 2013] <url://www.ncbi.nlm.nih.gov/projects/SNP/snp_ss.cgi?ss=ss24400158>.

NCBI Submitted SNP(ss) Details: ss11216977. RefSNP No. rs4344916. [online] Jul. 3, 2003 [Retrieved from the internet on Mar. 7, 2013] <url://www.ncbi.nlm.nih.gov/projects/SNP/snpss.cgi?ss=ss11216977>.

NCBI Submitted SNP(ss) Details: ss44410987. RefSNP No. rs12639443. [online] Jul. 18, 2005 [Retrieved from the Internet on Mar. 7, 2013] <url://www.ncbi.nlm.nih.gov/projects/SNP/snp_ss.cgi?ss=ss44410987>.

NCBI Submitted SNP(ss) Details: ss23440768. RefSNP No. rs17087180. [online] Aug. 20, 2004 [Retrieved from the Internet on Mar. 7, 2013] <url:http://www.ncbi.nlm.nih.gov/projects/SNP/snp_ss.cgi?ss=ss23440768>.

NCBI Reference SNP (refSNP) Cluster Report: rs1007328. [online] Sep. 7, 2000 [Retrieved from the internet on Nov. 29, 2012] <url://www.ncbi.nlm.nih.gov/projects/SNP/snp_ref.cgi?rs=1007328> Note: Document entitled "GRCh.p2 Genome Reference Consortium Human Build 37 patch release 2" uploaded

(56) References Cited

OTHER PUBLICATIONS in support of priority date of rs1007328. <url://www/ncbi.nlm.nih.gov/assembly/GCA_000001405.3/>.
NCBI Reference sequence NT-010274.17—*Homo sapiens* chromosome 15 genomic contig, GRCh37.p5 Primary Assembly [online] Jul. 29, 2011 [Retrieved from the internet on Nov. 29, 2012] <url://www.ncbi.nlm.nih.gov/nuccore/224514936?sat=16&satkey=3691065>.

\* cited by examiner

Equation for Predicted Response Score =

= {[(.0105265)+(SNP1*coefficient)+(SNP2*coefficient)+...+(SNP11*coefficient)]+5.260164102}/79.091729112

The value of SNPs 1-11 to be input in the equation are determined according to this table:

| SNP # | SNP ID | Genotype | Recoded |
|---|---|---|---|
| SNP 1 | rs759458 | G G | 0 |
| | | A G | 1 |
| | | A A | 2 |
| SNP 2 | kgp24415534 | G G | 0 |
| | | A G | 1 |
| | | A A | 2 |
| SNP 3 | rs3135391 | G G | 0 |
| | | A G | 1 |
| | | A A | 2 |
| SNP 4 | kgp8817856 | G G | 0 |
| | | A G | 1 |
| | | A A | 2 |
| SNP 5 | rs1894408 | C C | 0 |
| | | C G | 1 |
| | | G G | 2 |
| SNP 6 | rs16886004 | A G | 0 |
| | | A G | 1 |
| | | G G | 2 |
| SNP 7 | kgp6214351 | A A | 0 |
| | | A G | 1 |
| | | G G | 2 |
| SNP 8 | rs10162089 | A A | 0 |
| | | A G | 1 |
| | | G G | 2 |
| SNP 9 | kgp7747883 | G G | 0 |
| | | A G | 1 |
| | | A A | 2 |
| SNP 10 | kgp6599438 | G G | 0 |
| | | A G | 1 |
| | | A A | 2 |
| SNP 11 | kgp8110667 | G G | 0 |
| | | A G | 1 |
| | | A A | 2 |

The coefficients for each SNP are:

| Code | Covariate Name | Coefficient |
|---|---|---|
| SNP 1 | rs759458 | 0.58926846 |
| SNP 2 | kgp24415534 | -2.3993415 |
| SNP 3 | rs3135391 | -0.1604137 |
| SNP 4 | kgp8817856 | -0.862872 |
| SNP 5 | rs1894408 | 0.31917131 |
| SNP 6 | rs16886004 | 0.80544267 |
| SNP 7 | kgp6214351 | -1.03736 |
| SNP 8 | rs10162089 | 0.48599908 |
| SNP 9 | kgp7747883 | -3.4871921 |
| SNP 10 | kgp6599438 | -3.6183459 |
| SNP 11 | kgp8110667 | 37.3339668 |

Threshold:
Patients with a predicted response score of greater than 0.075 are predicted to be high responders and patients with a predicted response scores of less than 0.075 are predicted to be less likely to respond.

Figure 9

GENETIC MARKERS PREDICTIVE OF RESPONSE TO GLATIRAMER ACETATE

This application claims the benefit of U.S. Provisional Application No. 61/893,807, filed Oct. 21, 2013, U.S. Provisional Application No. 62/048,127, filed Sep. 9, 2014, and U.S. Provisional Application No. 62/048,641, filed Sep. 10, 2014, the contents of which are hereby incorporated by reference.

Throughout this application various publications are referenced. The disclosures of these publications in their entireties are hereby incorporated by reference into this application in order to more fully describe the state of the art to which this invention pertains.

BACKGROUND OF THE INVENTION

Multiple Sclerosis

Multiple sclerosis (MS) is a chronic, debilitating autoimmune disease of the central nervous system (CNS) with either relapsing-remitting (RR) or progressive course leading to neurologic deterioration and disability. At time of initial diagnosis, RRMS is the most common form of the disease (1) which is characterized by unpredictable acute episodes of neurological dysfunction (relapses), followed by variable recovery and periods of clinical stability. The vast majority of RRMS patients eventually develop secondary progressive (SP) disease with or without superimposed relapses. Around 15% of patients develop a sustained deterioration of their neurological function from the beginning; this form is called primary progressive (PP) MS. Patients who have experienced a single clinical event (Clinically Isolated Syndrome or "CIS") and who show lesion dissemination on subsequent magnetic resonance imaging (MRI) scans according to McDonald's criteria, are also considered as having relapsing MS.(2)

With a prevalence that varies considerably around the world, MS is the most common cause of chronic neurological disability in young adults.(3,4) Anderson et al. estimated that there were about 350,000 physician-diagnosed patients with MS in the United States in 1990 (approx. 140 per 100,000 population).(5) It is estimated that about 2.5 million individuals are affected worldwide.(6) In general, there has been a trend toward an increasing prevalence and incidence of MS worldwide, but the reasons for this trend are not fully understood.(5)

Current therapeutic approaches consist of i) symptomatic treatment ii) treatment of acute relapses with corticosteroids and iii) treatment aimed to modify the course of the disease. Currently approved therapies target the inflammatory processes of the disease. Most of them are considered to act as immunomodulators but their mechanisms of action have not been completely elucidated. Immunosuppressants or cytotoxic agents are also used in some patients after failure of conventional therapies. Several medications have been approved and clinically ascertained as efficacious for the treatment of RR-MS; including BETASERON®, AVONEX® and REBIF®, which are derivatives of the cytokine interferon beta (IFNB), whose mechanism of action in MS is generally attributed to its immunomodulatory effects, antagonizing pro-inflammatory reactions and inducing suppressor cells.(7) Other approved drugs for the treatment of MS include Mitoxantrone and Natalizumab.

Glatiramer Acetate

Glatiramer acetate (GA) is the active substance in Copaxone®, a marketed product indicated for reduction of the frequency of relapses in patients with RRMS. Its effectiveness in reducing relapse rate and disability accumulation in RR-MS is comparable to that of other available immunomodulating treatments.(8,9,10) Glatiramer acetate consists of the acetate salts of synthetic polypeptides containing four naturally occurring amino acids: L-glutamic acid, L-alanine, L-tyrosine and L-lysine. The average molecular weight of glatiramer acetate is between 5,000 and 9,000 Daltons. At a daily standard dose of 20 mg, GA is generally well tolerated, however response to the drug is variable. In various clinical trials, GA reduced relapse rates and progression of disability in patients with RR-MS. The therapeutic effect of GA is supported by the results of magnetic resonance imaging (MRI) findings from various clinical centers (11), however there are no validated predictive biomarkers of response to GA treatment.

A possible initial mode of action of GA is associated with binding to MHC molecules and consequent competition with various myelin antigens for their presentation to T cells.(12) A further aspect of its mode of action is the potent induction of T helper 2 (Th2) type cells that presumably can migrate to the brain and lead to in situ bystander suppression.(13) It has been shown that GA treatment in MS results in the induction of GA-specific T cells with predominant Th2 phenotype both in response to GA and cross-reactive myelin antigens.(13,14) Furthermore, the ability of GA-specific infiltrating cells to express anti-inflammatory cytokines such as IL-10 and transforming growth factor-beta (TGF-β) together with brain-derived neurotrophic factor (BDNF) seem to correlate with the therapeutic activity of GA in EAE.(15,16,17)

Clinical experience with GA consists of information obtained from completed and ongoing clinical trials and from post-marketing experience. The clinical program includes three double-blind, placebo-controlled studies in RRMS subjects treated with GA 20 mg/day.(18,19,20) A significant reduction in the number of relapses, compared with placebo, was seen. In the largest controlled study, the relapse rate was reduced by 32% from 1.98 under placebo to 1.34 under GA 20 mg. GA 20 mg has also demonstrated beneficial effects over placebo on MRI parameters relevant to RRMS. A significant effect in median cumulative number of Gd-enhancing lesions over 9 months of treatment (11 lesions in the 20 mg group compared to 17 lesions under placebo) was demonstrated.

The clinical program with GA also includes one double-blind study in chronic-progressive MS subjects,(21) one double-blind placebo-controlled study in primary progressive patients,(22) one double-blind placebo-controlled study in CIS patients(23) and numerous open-label and compassionate use studies, mostly in RRMS. The clinical use of GA has been extensively reviewed and published in the current literature (24,25,26,27).

U.S. Pat. No. 7,855,176 discloses administering glatiramer acetate to patients afflicted with relapsing-remitting multiple sclerosis (RRMS) by subcutaneous injection of 0.5 ml of an aqueous pharmaceutical solution which contains in solution 20 mg glatiramer acetate and 20 mg mannitol (34).

U.S. Patent Application Publication No. US 2011-0046065 A1 discloses administering glatiramer acetate to patients suffering from relapsing-remitting multiple sclerosis by three subcutaneous injections of a therapeutically effective dose of glatiramer acetate over a period of seven days with at least one day between every subcutaneous injection (35).

Pharmacogenomics

Pharmacogenomics is the methodology which associates genetic variability with physiological responses to drug.

Pharmacogenetics is a subset of pharmacogenomics and is defined as "the study of variations in DNA sequence as related to drug response" (ICH E15; fda.gov/downloads/RegulatoryInformation/Guidances/ucm129296.pdf. Pharmacogenetics focuses on genetic polymorphism in genes related to drug metabolism, drug mechanism of action, disease type, and side effects. Pharmacogenetics is the cornerstone of Personalized Medicine which allows the development of more individualized drug therapies to obtain more effective and safe treatment.

Pharmacogenetics has become a core component of many drug development programs, being used to explain variability in drug response among subjects in clinical trials, to address unexpected emerging clinical issues, such as adverse events, to determine eligibility for a clinical trial (pre-screening) to optimize trial yield, to develop drug-linked diagnostic tests to identify patients who are more likely or less likely to benefit from treatment or who may be at risk of adverse events, to provide information in drug labels to guide physician treatment decisions, to better understand the mechanism of action or metabolism of new and existing drugs, and to provide better understanding of disease mechanisms.

Generally, Pharmacogenetics analyses are performed in either of two methodology approaches: Candidate genes research technique, and Genome Wide Association Study (GWAS). Candidate genes research technique is based on the detection of polymorphism in candidate genes pre-selected using the knowledge on the disease, the drug mode of action, toxicology or metabolism of drug. The Genome Wide Association Study (GWAS) enables the detection of more than 1 M (one million) polymorphisms across the genome. This approach is used when related genes are unknown. DNA arrays used for GWAS can be also analyzed per gene as in candidate gene approach.

Pharmacogenetic Studies

Various pharmacogenetic studies were done in MS patients. For example, a Genome-Wide Association study by Byun et al. (36) focused on extreme clinical phenotypes in order to maximize the ability to detect genetic differences between responders and non-responders to interferon-beta. A multi-analytical approach detected significant associations between several SNPs and treatment response. Responders and Non-Responders had significantly different genotype frequencies for SNPs located in many genes, including glypican 5, collagen type XXV a1, hyaluronan proteoglycan link protein, calpastatin, and neuronal PAS domain protein 3. Other studies used pharmacogenetic analyses in order to characterize the genomic profile and gene expression profile of IFN responders and non-responders.

Other pharmacogenetic studies analyzed the genetic background associated with response to Glatiramer Acetate. For examples, Fusco C et al (37) assessed a possible relationship between HLA alleles and response to GA (N=83 RRMS). DRB1*1501 allele frequency was increased in MS patients compared to healthy controls (10.8% vs 2.7%; p=0.001). In DRB1*1501 carriers the response rate was 81.8% compared to 39.4% in non-carriers of DRB1*1501 and to 50% in the whole study population. Grossman et al (38) genotyped HLA-DRB1*1501 and 61 SNPs within a total of 27 other candidate genes, on DNA from two clinical trial cohorts. The study revealed no association between HLA-DRB1*1501 and response to GA. The results of the study are disclosed in the international application published as WO2006/116602 (39).

Pharmacogenetics is the cornerstone of personalized medicine which allows the development of more individualized drug therapies to obtain more effective and safe treatment. Multiple Sclerosis is a complex disease with clinical heterogeneity. In patients afflicted with multiple sclerosis or a single clinical attack consistent with multiple sclerosis, the ability to determine the likelihood of treatment success would be an important tool improving the therapeutic management of the patients. As the therapeutic options for MS and CIS increase, the importance of being able to determine who will respond favorably to therapy and specifically to GA, has become of increasing significance.

SUMMARY OF THE INVENTION

Independent Embodiments

The present invention provides a method for treating a human subject afflicted with multiple sclerosis or a single clinical attack consistent with multiple sclerosis with a pharmaceutical composition comprising glatiramer acetate and a pharmaceutically acceptable carrier, comprising the steps of:

(i) determining a genotype of the subject at a location corresponding to the location of one or more single nucleotide polymorphisms (SNPs) selected from the group consisting of: kgp10090631, kgp1009249, kgp10152733, kgp10224254, kgp10305127, kgp10351364, kgp10372946, kgp10404633, kgp10412303, kgp10523170, kgp1054273, kgp10558725, kgp10564659, kgp10591989, kgp10594414, kgp10619195, kgp10620244, kgp10632945, kgp10633631, kgp10679353, kgp10788130, kgp10826273, kgp10910719, kgp10922969, kgp10948564, kgp10967046, kgp10974833, kgp1098237, kgp11002881, kgp11010680, kgp11077373, kgp11141512, kgp11206453, kgp11210903, kgp1124492, kgp11281589, kgp11285862, kgp11328629, kgp11356379, kgp11407560, kgp11453406, kgp11467007, kgp11514107, kgp11543962, kgp11580695, kgp11627530, kgp11633966, kgp11686146, kgp11702474, kgp11711524, kgp11768533, kgp11804835, kgp11843177, kgp12008955, kgp12083934, kgp12182745, kgp12230354, kgp1224440, kgp12371757, kgp124162, kgp12426624, kgp12557319, kgp1285441, kgp13161760, kgp1355977, kgp1371881, kgp15390522, kgp1683448, kgp1688752, kgp1699628, kgp1753445, kgp1779254, kgp1786079, kgp18379774, kgp18432055, kgp18525257, kgp1912531, kgp19568724, kgp20163979, kgp2023214, kgp2045074, kgp20478926, kgp2092817, kgp21171930, kgp2245775, kgp2262166, kgp22778566, kgp22793211, kgp22811918, kgp22823022, kgp2282938, kgp2299675, kgp23298674, kgp2356388, kgp23672937, kgp23737989, kgp2388352, kgp2391411, kgp24131116, kgp24415534, kgp2446153, kgp2451249, kgp2465184, kgp24729706, kgp24753470, kgp25191871, kgp25216186, kgp25543811, kgp25921291, kgp25952891, kgp26026546, kgp26271158, kgp2638591, kgp26528455, kgp26533576, kgp2688306, kgp26995430, kgp270001, kgp2709692, kgp2715873, kgp27500525, kgp27571222, kgp27640141, kgp2788291, kgp279772, kgp28532436, kgp28586329, kgp28687699, kgp28817122, kgp2923815, kgp29367521, kgp293787, kgp2958113, kgp2959751, kgp297178, kgp29794723, kgp30282494, kgp3048169, kgp304921, kgp3182607, kgp3202939, kgp3205849, kgp3218351, kgp3267884, kgp3276689, kgp337461, kgp3418770, kgp3450875, kgp345301, kgp3477351, kgp3496814, kgp355027, kgp355723, kgp3593828, kgp3598409, kgp3651767, kgp3669685, kgp3730395, kgp3812034, kgp3854180, kgp3933330, kgp3951463, kgp3984567, kgp3991733, kgp4011779, kgp4056892, kgp4096263, kgp4127859, kgp4155998, kgp4162414, kgp4223880, kgp4346717, kgp4370912, kgp4418535, kgp4420791, kgp4479467, kgp4524468, kgp4543470, kgp4559907, kgp4573213, kgp4634875, kgp4705854, kgp4734301, kgp4755147, kgp4812831, kgp4842590, kgp485316, kgp487328, kgp4898179, kgp5002011, kgp5014707, kgp5017029, kgp5053636, kgp5068397, kgp512180, kgp5144181, kgp5159037, kgp5216209, kgp5292386, kgp5334779, kgp5388938, kgp5409955, kgp5440506, kgp5441587, kgp5483926, kgp55646, kgp5564995, kgp5579170, kgp5680955, kgp5869992, kgp5908616, kgp6023196, kgp6032617, kgp6038357, kgp6076976, kgp6091119, kgp6127371, kgp61811, kgp6190988, kgp6214351, kgp6228750, kgp6236949, kgp6469620, kgp6505544, kgp6507761, kgp652534, kgp6539666, kgp6567154, kgp6599438, kgp6603796, kgp6666134, kgp6700691, kgp6737096, kgp6768546, kgp6772915, kgp6835138, kgp6959492, kgp6996560, kgp7059449, kgp7063887, kgp7077322, kgp7092772, kgp7117398, kgp7121374, kgp7178233, kgp7181058, kgp7186699, kgp7189498, kgp7242489, kgp7331172, kgp7416024, kgp7481870, kgp7506434, kgp7521990, kgp759150, kgp767200, kgp7714238, kgp7730397, kgp7747883, kgp7792268, kgp7802182, kgp7804623, kgp7924485, kgp8030775, kgp8036704, kgp8046214, kgp8106690, kgp8107491, kgp8110667, kgp8169636, kgp8174785, kgp8178358, kgp8183049, kgp8192546, kgp8200264, kgp8303520, kgp8335515, kgp8372910, kgp841428, kgp8437961, kgp8440036, kgp85534, kgp8599417, kgp8602316, kgp8615910, kgp8767692, kgp8777935, kgp8793915, kgp8796185, kgp8817856, kgp8869954, kgp8990121, kgp9018750, kgp9071686, kgp9078300, kgp9320791, kgp9354462, kgp9354820, kgp9368119, kgp9410843, kgp9421884, kgp9450430, kgp9530088, kgp9551947, kgp9601362, kgp9627338, kgp9627406, kgp9669946, kgp9699754, kgp971582, kgp97310, kgp974569, kgp9795732, kgp9806386, kgp9854133, kgp9884626, rs10049206, rs10124492, rs10125298, rs10162089, rs10201643, rs10203396, rs10251797, rs10278591, rs10489312, rs10492882, rs10498793, rs10501082, rs10510774, rs10512340, rs1079303, rs10815160, rs10816302, rs10841322, rs10841337, rs10954782, rs11002051, rs11022778, rs11029892, rs11029907, rs11029928, rs11083404, rs11085044, rs11136970, rs11147439, rs11192461, rs11192469, rs11559024, rs1157449, rs11648129, rs11691553, rs12013377, rs12494712, rs12943140, rs13002663, rs13394010, rs13415334, rs13419758, rs1380706, rs1387768, rs1410779, rs1478682, rs1508102, rs1532365, rs1544352, rs1545223, rs1579771, rs1604169, rs1621509, rs1644418, rs16886004, rs16895510, rs16901784, rs16927077, rs16930057, rs17029538, rs17224858, rs17238927, rs17329014, rs17400875, rs17449018, rs17577980, rs17638791, rs1858973, rs1886214, rs1894406, rs1894407, rs1894408, rs196295, rs196341, rs196343, rs197523, rs1979992, rs1979993, rs2043136, rs2058742, rs2071469, rs2071470, rs2071472, rs2074037, rs2136408, rs2139612, rs2175121, rs2241883, rs2309760, rs2325911, rs241435, rs241440, rs241442, rs241443, rs241444, rs241445, rs241446, rs241447, rs241449, rs241451, rs241452, rs241453, rs241454, rs241456, rs2453478, rs2598360, rs2621321, rs2621323, rs2660214, rs2816838, rs2824070, rs2839117, rs2845371, rs2857101, rs2857103, rs2857104, rs2926455, rs2934491, rs3135388, rs3218328, rs343087, rs343092, rs3767955, rs3792135, rs3799383, rs3803277, rs3815822, rs3818675, rs3829539, rs3885907, rs3899755, rs4075692, rs4143493, rs419132, rs423239, rs4254166, rs4356336, rs4360791, rs4449139, rs4584668, rs4669694, rs4709792, rs4738738, rs4769060, rs4780822, rs4782279, rs4822644, rs484482, rs4894701, rs5024722, rs502530, rs543122, rs6032205, rs6032209, rs6110157, rs623011, rs6497396, rs6535882, rs6687976, rs6718758, rs6835202, rs6840089, rs6845927, rs6895094, rs6899068, rs7020402, rs7024953, rs7028906, rs7029123, rs7062312, rs714342, rs7187976, rs7191155, rs720176, rs7217872, rs7228827, rs7348267, rs7496451, rs7524868, rs7563131, rs7579987, rs759458, rs7666442, rs7670525, rs7672014, rs7677801, rs7725112, rs7844274, rs7850, rs7860748, rs7862565, rs7864679, rs7928078, rs7948420, rs8035826, rs8050872, rs8053136, rs8055485, rs823829, rs858341, rs9315047, rs931570, rs9346979, rs9376361, rs9393727, rs9501224, rs9508832, rs950928, rs9579566, rs9597498, rs9670531, rs9671124, rs9671182, rs9817308, rs9834010, rs9876830, rs9913349, rs9931167 and rs9931211 (hereinafter Group 1), (ii) identifying the subject as a predicted responder to glatiramer acetate if the genotype of the subject contains one or more A alleles at the location of kgp10152733, kgp10224254, kgp10305127, kgp10351364, kgp10372946, kgp10404633, kgp10564659, kgp10591989, kgp10594414, kgp10619195, kgp10620244, kgp10633631, kgp10974833, kgp11002881, kgp11285862, kgp11328629, kgp11407560, kgp11514107, kgp11627530, kgp11702474, kgp11711524, kgp11768533, kgp11804835, kgp12083934, kgp12182745, kgp12230354, kgp1224440, kgp124162, kgp12557319, kgp1371881, kgp1699628, kgp1753445, kgp1779254, kgp1786079, kgp18379774, kgp18525257, kgp20163979, kgp2023214, kgp20478926, kgp21171930, kgp2262166, kgp22778566, kgp2465184, kgp24753470, kgp25191871, kgp25216186, kgp25952891, kgp26026546, kgp26533576, kgp27500525, kgp27571222, kgp28532436, kgp28586329, kgp28817122, kgp2958113, kgp29794723, kgp30282494, kgp304921, kgp3205849, kgp3218351, kgp3276689, kgp337461, kgp345301, kgp355027, kgp355723, kgp3593828, kgp3812034, kgp3951463, kgp4162414, kgp4223880, kgp4418535, kgp4543470, kgp4573213, kgp4634875, kgp4755147, kgp4842590, kgp485316, kgp5068397, kgp5334779, kgp5483926, kgp5564995, kgp5869992, kgp5908616, kgp6032617, kgp6038357, kgp6076976, kgp6091119, kgp6127371, kgp61811, kgp6214351, kgp6228750, kgp6236949, kgp6469620, kgp6505544, kgp6507761, kgp6666134, kgp6700691, kgp6772915, kgp6959492, kgp7077322, kgp7117398, kgp7178233, kgp7186699, kgp7506434, kgp759150, kgp7730397, kgp7802182, kgp7804623, kgp7924485, kgp8030775, kgp8036704, kgp8046214, kgp8106690, kgp8110667, kgp8178358, kgp8200264, kgp8372910, kgp841428, kgp8602316, kgp8615910, kgp8793915, kgp8796185, kgp8990121, kgp9018750, kgp9354462, kgp9368119, kgp9410843, kgp9450430, kgp9530088, kgp9627338, kgp9669946, kgp97310, kgp974569, kgp9806386, kgp9884626, rs10049206, rs10124492, rs10125298, rs10162089, rs10203396, rs10251797, rs10278591, rs10489312, rs10492882, rs10498793, rs10501082, rs10510774, rs10512340, rs10815160, rs10816302, rs10841337, rs11029892, rs11029928, rs11192469, rs11559024, rs11648129, rs12013377, rs13394010, rs13415334, rs1478682, rs1544352, rs1545223, rs1604169, rs1621509, rs1644418, rs17029538, rs17400875, rs17449018, rs17577980, rs1858973, rs1894406, rs1894407, rs197523, rs2058742, rs2071469, rs2071472, rs2139612, rs2241883, rs2309760, rs241440, rs241442, rs241444, rs241445, rs241446, rs241449, rs241453, rs241456, rs2453478, rs2660214, rs2824070, rs2845371, rs2857103, rs2926455, rs343087, rs343092, rs3767955, rs3792135, rs3829539, rs3899755, rs4075692, rs4143493, rs423239, rs4254166, rs4356336, rs4584668, rs4780822, rs4782279, rs5024722, rs6032209, rs6110157, rs623011, rs6497396, rs6845927, rs6895094, rs6899068, rs7024953, rs7028906, rs7029123, rs7062312, rs7187976, rs7191155, rs720176, rs7228827, rs7496451, rs7563131, rs759458, rs7666442, rs7670525, rs7677801, rs7725112, rs7850, rs7862565, rs7948420, rs8035826, rs8053136, rs8055485, rs823829, rs9315047, rs9501224, rs9508832, rs950928, rs9597498, rs9670531, rs9671124, rs9817308, rs9834010, rs9876830 or rs9931211 (hereinafter Group 2), one or more C alleles at the location of kgp10910719, kgp11077373, kgp11453406, kgp12426624, kgp2045074, kgp22811918, kgp23298674, kgp2709692, kgp28687699, kgp3496814, kgp3669685, kgp3730395, kgp4056892, kgp4370912, kgp5053636, kgp5216209, kgp5292386, kgp6023196, kgp652534, kgp7059449, kgp7189498, kgp7521990, kgp7792268, kgp8303520, kgp9320791, kgp9795732, rs10201643, rs11022778, rs11136970, rs11147439, rs11691553, rs1579771, rs16901784, rs2136408, rs2325911, rs241443, rs2857104, rs3803277, rs3885907, rs4738738, rs4894701, rs502530, rs6032205, rs6687976, rs6718758, rs6835202, rs714342, rs7524868, rs7844274, rs9393727 or rs9671182 (hereinafter Group 3), one or more G alleles at the location of kgp10090631, kgp1009249, kgp10412303, kgp10523170, kgp1054273, kgp10558725, kgp10632945, kgp10679353, kgp10788130, kgp10826273, kgp10922969, kgp10948564, kgp10967046, kgp1098237, kgp11010680, kgp11141512, kgp11206453, kgp11210903, kgp1124492, kgp11281589, kgp11356379, kgp11467007, kgp11543962, kgp11580695, kgp11633966, kgp11686146, kgp11843177, kgp12008955, kgp12371757, kgp1285441, kgp13161760, kgp1355977, kgp15390522, kgp1683448, kgp1688752, kgp1912531, kgp19568724, kgp2092817, kgp2245775, kgp22793211, kgp22823022, kgp2282938, kgp2299675, kgp2356388, kgp23672937, kgp23737989, kgp2388352, kgp2391411, kgp24131116, kgp24415534, kgp2446153, kgp2451249, kgp24729706, kgp25543811, kgp25921291, kgp26271158, kgp2638591, kgp26528455, kgp2688306, kgp26995430, kgp270001, kgp2715873, kgp27640141, kgp2788291, kgp2923815, kgp29367521, kgp293787, kgp2959751, kgp297178, kgp3048169, kgp3182607, kgp3202939, kgp3267884, kgp3418770, kgp3450875, kgp3477351, kgp3598409, kgp3651767, kgp3854180, kgp3933330, kgp3984567, kgp4011779, kgp4096263, kgp4127859, kgp4155998, kgp4346717, kgp4420791, kgp4479467, kgp4524468, kgp4559907, kgp4705854, kgp4734301, kgp4812831, kgp487328, kgp4898179, kgp5002011, kgp5014707, kgp5017029, kgp512180, kgp5144181, kgp5159037, kgp5388938, kgp5409955, kgp5440506, kgp5441587, kgp55646, kgp5579170, kgp5680955, kgp6190988, kgp6539666, kgp6567154, kgp6599438, kgp6603796, kgp6737096, kgp6768546, kgp6835138, kgp6996560, kgp7063887, kgp7092772, kgp7121374, kgp7181058, kgp7331172, kgp7416024, kgp7481870, kgp767200, kgp7714238, kgp7747883, kgp8107491, kgp8169636, kgp8174785, kgp8183049, kgp8192546, kgp8335515, kgp8437961, kgp8440036, kgp85534, kgp8599417, kgp8767692, kgp8777935, kgp8817856, kgp8869954, kgp9071686, kgp9078300, kgp9354820, kgp9421884, kgp9551947, kgp9601362, kgp9627406, kgp9699754, kgp971582, kgp9854133, rs1079303, rs10841322, rs10954782, rs11002051, rs11029907, rs11083404, rs11085044, rs11192461, rs1157449, rs12494712, rs12943140, rs13002663, rs13419758, rs1380706, rs1387768, rs1410779, rs1508102, rs1532365, rs16886004, rs16895510, rs16927077, rs16930057, rs17224858, rs17238927, rs17329014, rs17638791, rs1886214, rs1894408, rs196295, rs196341, rs196343, rs1979992, rs1979993, rs2043136, rs2071470, rs2074037, rs2175121, rs241435, rs241447, rs241451, rs241452, rs241454, rs2598360, rs2621321, rs2621323, rs2816838, rs2839117, rs2857101, rs2934491, rs3135388, rs3218328, rs3799383, rs3815822, rs3818675, rs419132, rs4360791, rs4449139, rs4669694, rs4709792, rs4769060, rs4822644, rs484482, rs543122, rs6535882, rs6840089, rs7020402, rs7217872, rs7348267, rs7579987, rs7672014, rs7860748, rs7864679, rs7928078, rs8050872, rs858341, rs931570, rs9346979, rs9376361, rs9579566, rs9913349 or rs9931167 (hereinafter Group 4), or one or more T alleles at the location of kgp18432055, kgp279772, kgp3991733 or kgp7242489; and (iii) administering the pharmaceutical composition comprising glatiramer acetate and a pharmaceutically acceptable carrier to the subject only if the subject is identified as a predicted responder to glatiramer acetate.

The present invention also provides a method of identifying a human subject afflicted with multiple sclerosis or a single clinical attack consistent with multiple sclerosis as a predicted responder or as a predicted non-responder to glatiramer acetate, the method comprising determining the genotype of the subject at a location corresponding to the location of one or more single nucleotide polymorphisms (SNPs) selected from the group consisting of Group 1, and identifying the human subject as a predicted responder to glatiramer acetate if the genotype of the subject contains
    one or more A alleles at the location of Group 2,
    one or more C alleles at the location of Group 3,
    one or more G alleles at the location of Group 4, or
    one or more T alleles at the location of kgp18432055, kgp279772, kgp3991733 or kgp7242489,
    or identifying the human subject as a predicted non-responder to glatiramer acetate if the genotype of the subject contains
    no A alleles at the location of Group 2,
    no C alleles at the location of Group 3,
    no G alleles at the location of Group 4, or
    no T alleles at the location of kgp18432055, kgp279772, kgp3991733 or kgp7242489.

The present invention also provides a kit for identifying a human subject afflicted with multiple sclerosis or a single clinical attack consistent with multiple sclerosis as a predicted responder or as a predicted non-responder to glatiramer acetate, the kit comprising at least one probe specific for the location of a SNP selected from the group consisting of Group 1.

The present invention also provides a kit for identifying a human subject afflicted with multiple sclerosis or a single clinical attack consistent with multiple sclerosis as a predicted responder or as a predicted non-responder to glatiramer acetate, the kit comprising at least one pair of PCR primers designed to amplify a DNA segment which includes the location of a SNP selected from the group consisting of Group 1.

The present invention also provides a kit for identifying a human subject afflicted with multiple sclerosis or a single clinical attack consistent with multiple sclerosis as a predicted responder or as a predicted non-responder to glatiramer acetate, the kit comprising a reagent for performing a method selected from the group consisting of restriction fragment length polymorphism (RFLP) analysis, sequencing, single strand conformation polymorphism analysis (SSCP), chemical cleavage of mismatch (CCM), gene chip and denaturing high performance liquid chromatography (DHPLC) for determining the genotype of the subject at a location corresponding to the location of at least one SNP selected from the group consisting of Group 1.

The present invention also provides a kit for identifying a human subject afflicted with multiple sclerosis or a single clinical attack consistent with multiple sclerosis as a predicted responder or as a predicted non-responder to glatiramer acetate, the kit comprising reagents for TaqMan Open Array assay designed for determining the genotype of the subject at a location corresponding to the location of at least one SNP selected from the group consisting of Group 1.

The present invention also provides a kit for identifying a human subject afflicted with multiple sclerosis or a single clinical attack consistent with multiple sclerosis as a predicted responder or as a predicted non-responder to glatiramer acetate, the kit comprising a) at least one probe specific for a location corresponding to the location of at least one SNP;
b) at least one pair of PCR primers designed to amplify a DNA segment which includes a location corresponding to the location of at least one SNP;
c) at least one pair of PCR primers designed to amplify a DNA segment which includes a location corresponding to the location of at least one SNP and at least one probe specific for a location corresponding to the location of at least one SNP;
d) a reagent for performing a method selected from the group consisting of restriction fragment length polymorphism (RFLP) analysis, sequencing, single strand conformation polymorphism analysis (SSCP), chemical cleavage of mismatch (CCM), gene chip and denaturing high performance liquid chromatography (DHPLC) for determining the identity of at least one SNP; or
e) reagents for TaqMan Open Array assay designed for determining the genotype at a location corresponding to the location of at least one SNP, wherein the at least one SNP is selected from the group consisting of Group 1.

The present invention also provides a probe for identifying the genotype of a location corresponding to the location of a SNP selected from the group consisting of kgp10090631, kgp1009249, kgp10148554, kgp10152733, kgp10215554, kgp10224254, kgp10305127, kgp10351364, kgp10372946, kgp10404633, kgp10412303, kgp10523170, kgp1054273, kgp10558725, kgp10564659, kgp10591989, kgp10594414, kgp10619195, kgp10620244, kgp10632945, kgp10633631, kgp10679353, kgp10762962, kgp10788130, kgp10826273, kgp10836214, kgp10910719, kgp10922969, kgp10948564, kgp10967046, kgp10974833, kgp1098237, kgp10989246, kgp11002881, kgp11010680, kgp11077373, kgp11141512, kgp11206453, kgp11210903, kgp1124492, kgp11281589, kgp11285862, kgp11285883, kgp11328629, kgp11356379, kgp11407560, kgp11453406, kgp11467007, kgp11514107, kgp11543962, kgp11580695, kgp11604017, kgp11627530, kgp11633966, kgp11686146, kgp11702474, kgp11711524, kgp11755256, kgp11768533, kgp11804835, kgp11843177, kgp12008955, kgp12083934, kgp1211163, kgp12182745, kgp12230354, kgp1224440, kgp12253568, kgp12371757, kgp124162, kgp12426624, kgp12557319, kgp12562255, kgp1285441, kgp13161760, kgp1355977, kgp1371881, kgp1432800, kgp15390522, kgp1682126, kgp1683448, kgp1688752, kgp1699628, kgp1753445, kgp1758575, kgp1779254, kgp1786079, kgp18379774, kgp18432055, kgp18525257, kgp1912531, kgp19568724, kgp20163979, kgp2023214, kgp2045074, kgp20478926, kgp2092817, kgp21171930, kgp2176915, kgp2245775, kgp2262166, kgp22778566, kgp22793211, kgp22811918, kgp22823022, kgp2282938, kgp22839559, kgp2299675, kgp23298674, kgp2356388, kgp23672937, kgp23737989, kgp2388352, kgp2391411, kgp24131116, kgp24415534, kgp2446153, kgp2451249, kgp24521552, kgp2465184, kgp24729706, kgp24753470, kgp25191871, kgp25216186, kgp25543811, kgp25921291, kgp25952891, kgp26026546, kgp26271158, kgp2638591, kgp26528455, kgp26533576, kgp2688306, kgp26995430, kgp270001, kgp2709692, kgp2715873, kgp27500525, kgp27571222, kgp27640141, kgp2788291, kgp279772, kgp28532436, kgp28586329, kgp28687699, kgp2877482, kgp28817122, kgp2920925, kgp2923815, kgp29367521, kgp293787, kgp2958113, kgp2959751, kgp297178, kgp29794723, kgp2993366, kgp30282494, kgp3048169, kgp304921, kgp3182607, kgp3188, kgp3202939, kgp3205849, kgp3218351, kgp3267884, kgp3276689, kgp3287349, kgp337461, kgp3418770, kgp3420309, kgp3450875, kgp345301, kgp3477351, kgp3488270, kgp3496814, kgp355027, kgp355723, kgp3593828, kgp3598409, kgp3598966, kgp3624014, kgp3651767, kgp3669685, kgp3697615, kgp3730395, kgp3812034, kgp3854180, kgp3933330, kgp394638, kgp3951463, kgp3984567, kgp3991733, kgp4011779, kgp4037661, kgp4056892, kgp4096263, kgp4127859, kgp4137144, kgp4155998, kgp4162414, kgp4223880, kgp433351, kgp4346717, kgp4370912, kgp4418535, kgp4420791, kgp4456934, kgp4479467, kgp4524468, kgp4543470, kgp4559907, kgp4573213, kgp4575797, kgp4591145, kgp4634875, kgp4705854, kgp4734301, kgp4755147, kgp4812831, kgp4842590, kgp485316, kgp487328, kgp4892427, kgp4898179, kgp4970670, kgp4985243, kgp5002011, kgp5014707, kgp5017029, kgp5053636, kgp5068397, kgp512180, kgp5144181, kgp5159037, kgp5216209, kgp5252824, kgp5292386, kgp5326762, kgp5334779, kgp5388938, kgp5409955, kgp541892, kgp5440506, kgp5441587, kgp5483926, kgp55646, kgp5564995, kgp5579170, kgp5680955, kgp5691690, kgp5747456, kgp5869992, kgp5894351, kgp5908616, kgp5924341, kgp5949515, kgp6023196, kgp6032617, kgp6038357, kgp6042557, kgp6076976, kgp6081880, kgp6091119, kgp6127371, kgp61811, kgp6190988, kgp6194428, kgp6213972, kgp6214351, kgp6228750, kgp6236949, kgp625941, kgp6301155, kgp6429231, kgp6469620, kgp6505544, kgp6507761, kgp652534, kgp6539666, kgp6567154, kgp6599438, kgp6603796, kgp6666134, kgp6700691, kgp6737096, kgp6768546, kgp6772915, kgp6828277, kgp6835138, kgp6889327, kgp6959492, kgp6990559, kgp6996560, kgp7006201, kgp7059449, kgp7063887, kgp7077322, kgp7092772, kgp7117398, kgp7121374, kgp7151153, kgp7161038, kgp7178233, kgp7181058, kgp7186699, kgp7189498, kgp7242489, kgp7331172, kgp7416024, kgp7481870, kgp7506434, kgp7521990, kgp759150, kgp7653470, kgp767200, kgp7714238, kgp7730397, kgp7747883, kgp7778345, kgp7792268, kgp7802182, kgp7804623, kgp7924485, kgp7932108, kgp8030775, kgp8036704, kgp8046214, kgp8106690, kgp8107491, kgp8110667, kgp8145845, kgp8169636, kgp8174785, kgp8178358, kgp8183049, kgp8192546, kgp8200264, kgp8303520, kgp8335515, kgp8372910, kgp841428, kgp8437961, kgp8440036, kgp85534, kgp8599417, kgp8602316, kgp8615910, kgp8644305, kgp8767692, kgp8777935, kgp8793915, kgp8796185, kgp8817856, kgp8847137, kgp8869954, kgp8990121, kgp9018750, kgp9071686, kgp9078300, kgp9143704, kgp9320791, kgp9354462, kgp9354820, kgp9368119, kgp9409440, kgp9410843, kgp9421884, kgp9450430, kgp9530088, kgp9551947, kgp956070, kgp9601362, kgp9627338, kgp9627406, kgp9669946, kgp9699754, kgp971582, kgp97310, kgp974569, kgp9795732, kgp9806386, kgp9854133, kgp9884626, kgp9909702, kgp9927782, P1_M_061510_11_106_M, P1_M_061510_18_342_P, P1_M_061510_6_159_P, rs10038844, rs10049206, rs10124492, rs10125298, rs10162089, rs10201643, rs10203396, rs10251797, rs1026894, rs10278591, rs10489312, rs10492882, rs10495115, rs10498793, rs10501082, rs10510774, rs10512340, rs1079303, rs10815160, rs10816302, rs10841322, rs10841337, rs10954782, rs11002051, rs11022778, rs11029892, rs11029907, rs11029928, rs11083404, rs11085044, rs11136970, rs11147439, rs11192461, rs11192469, rs11559024, rs11562998, rs11563025, rs1157449, rs11648129, rs11691553, rs11750747, rs11947777, rs12013377, rs12043743, rs12233980, rs12341716, rs12472695, rs12494712, rs12881439, rs12943140, rs13002663, rs13168893, rs13386874, rs13394010, rs13415334, rs13419758, rs1357718, rs1380706, rs1387768, rs1393037, rs1393040, rs1397481, rs1410779, rs1474226, rs1478682, rs1508102, rs1508515, rs1532365, rs1534647, rs1544352, rs1545223, rs1579771, rs1604169, rs1621509, rs1644418, rs16846161, rs16886004, rs16895510, rs16901784, rs16927077, rs16930057, rs17029538, rs1715441, rs17187123, rs17224858, rs17238927, rs17245674, rs17329014, rs17400875, rs17419416, rs17449018, rs17577980, rs17638791, rs1793174, rs1858973, rs1883448, rs1886214, rs1894406, rs1894407, rs1894408, rs1905248, rs196295, rs196341, rs196343, rs197523, rs1979992, rs1979993, rs2043136, rs2058742, rs2071469, rs2071470, rs2071472, rs2074037, rs209568, rs2136408, rs2139612, rs2175121, rs2241883, rs2309760, rs2325911, rs2354380, rs241435, rs241440, rs241442, rs241443, rs241444, rs241445, rs241446, rs241447, rs241449, rs241451, rs241452, rs241453, rs241454, rs241456, rs2453478, rs2598360, rs2618065, rs2621321, rs2621323, rs263247, rs2660214, rs2662, rs2816838, rs2824070, rs2839117, rs2845371, rs2857101, rs2857103, rs2857104, rs28993969, rs2926455, rs2934491, rs3135388, rs3218328, rs343087, rs343092, rs34647183, rs35615951, rs3767955, rs3768769, rs3792135, rs3799383, rs3803277, rs3815822, rs3818675, rs3829539, rs3847233, rs3858034, rs3858035, rs3858036, rs3858038, rs3885907, rs3894712, rs3899755, rs4075692, rs4143493, rs419132, rs423239, rs4254166, rs4356336, rs4360791, rs4449139, rs4584668, rs4669694, rs4709792, rs4738738, rs4740708, rs4769060, rs4780822, rs4782279, rs4797764, rs4822644, rs484482, rs4894701, rs4978567, rs5024722, rs502530, rs528065, rs543122, rs6032205, rs6032209, rs6110157, rs623011, rs6459418, rs6497396, rs6535882, rs6577395, rs6687976, rs6718758, rs6811337, rs6835202, rs6840089, rs6845927, rs6895094, rs6899068, rs7020402, rs7024953, rs7028906, rs7029123, rs7062312, rs7119480, rs7123506, rs714342, rs7187976, rs7191155, rs720176, rs7217872, rs7228827, rs7231366, rs7348267, rs7496451, rs7524868, rs7563131, rs7579987, rs759458, rs7666442, rs7670525, rs7672014, rs7677801, rs7680970, rs7684006, rs7696391, rs7698655, rs7725112, rs7819949, rs7844274, rs7846783, rs7850, rs7860748, rs7862565, rs7864679, rs7928078, rs7948420, rs7949751, rs7961005, rs8000689, rs8018807, rs8035826, rs8050872, rs8053136, rs8055485, rs823829, rs858341, rs9315047, rs931570, rs9346979, rs9376361, rs9393727, rs9501224, rs9508832, rs950928, rs9579566, rs9597498, rs961090, rs9670531, rs9671124, rs9671182, rs967616, rs9817308, rs9834010, rs9876830, rs9913349, rs9931167, rs9931211, rs9948620 and rs9953274 (hereinafter Group 5).

The present invention also provides glatiramer acetate or a pharmaceutical composition comprising glatiramer acetate for use in treating a human subject afflicted with multiple sclerosis or a single clinical attack consistent with multiple sclerosis which human subject is identified as a predicted responder to glatiramer acetate by:

a) determining a genotype of the subject at a location corresponding to the location of one or more single nucleotide polymorphisms (SNPs) selected from the group consisting of: Group 1, and b) identifying the subject as a predicted responder to glatiramer acetate if the genotype of the subject contains
one or more A alleles at the location of Group 2,
one or more C alleles at the location of Group 3, one or more G alleles at the location of Group 4, or
one or more T alleles at the location of kgp18432055, kgp279772, kgp3991733 or kgp7242489.

The present invention also provides a method of determining the genotype of a human subject comprising identifying whether the genotype of a human subject contains
one or more A alleles at the location of Group 2,
one or more C alleles at the location of Group 3,
one or more G alleles at the location of Group 4, or
one or more T alleles at the location of kgp18432055, kgp279772, kgp3991733 or kgp7242489.

The present invention also provides a method of identifying a human subject afflicted with multiple sclerosis or a single clinical attack consistent with multiple sclerosis who is predicted to have a slower course of disease progression, comprising the steps of:

(i) determining a genotype of the subject at a location corresponding to the location of one or more single nucleotide polymorphisms (SNPs) selected from the group consisting of: kgp10148554, kgp10215554, kgp10762962, kgp10836214, kgp10989246, kgp11285883, kgp11604017, kgp11755256, kgp1211163, kgp12253568, kgp12562255, kgp1432800, kgp1682126, kgp1758575, kgp2176915, kgp22839559, kgp24521552, kgp2877482, kgp2920925, kgp3598966, kgp3624014, kgp3697615, kgp394638, kgp4037661, kgp4137144, kgp433351, kgp4456934, kgp4575797, kgp4591145, kgp4892427, kgp4970670, kgp4985243, kgp5252824, kgp5326762, kgp541892, kgp5691690, kgp5747456, kgp5894351, kgp5924341, kgp5949515, kgp6042557, kgp6081880, kgp6194428, kgp6213972, kgp625941, kgp6301155, kgp6429231, kgp6828277, kgp6889327, kgp6990559, kgp7006201, kgp7151153, kgp7161038, kgp7653470, kgp7778345, kgp7932108, kgp8145845, kgp8644305, kgp8847137, kgp9143704, kgp9409440, kgp956070, kgp9909702, kgp9927782, rs10038844, rs1026894, rs10495115, rs11562998, rs11563025, rs11750747, rs11947777, rs12043743, rs12233980, rs12341716, rs12472695, rs12881439, rs13168893, rs13386874, rs1357718, rs1393037, rs1393040, rs1397481, rs1474226, rs1508515, rs1534647, rs16846161, rs1715441, rs17187123, rs17245674, rs17419416, rs1793174, rs1883448, rs1905248, rs209568, rs2354380, rs2618065, rs263247, rs2662, rs28993969, rs34647183, rs35615951, rs3768769, rs3847233, rs3858034, rs3858035, rs3858036, rs3858038, rs3894712, rs4740708, rs4797764, rs4978567, rs528065, rs6459418, rs6577395, rs6811337, rs7119480, rs7123506, rs7231366, rs7680970, rs7684006, rs7696391, rs7698655, rs7819949, rs7846783, rs7949751, rs7961005, rs8000689, rs8018807, rs961090, rs967616, rs9948620 and rs9953274 (hereinafter Group 6), and (ii) identifying the subject as predicted to have a slower course of disease progression if the genotype of the subject contains one or more A alleles at the location of kgp10762962, kgp11285883, kgp11604017, kgp1211163, kgp12253568, kgp12562255, kgp2176915, kgp24521552, kgp2877482, kgp2993366, kgp3188, kgp3624014, kgp394638, kgp4037661, kgp433351, kgp4456934, kgp4575797, kgp4591145, kgp4892427, kgp4970670, kgp4985243, kgp5252824, kgp5326762, kgp541892, kgp5747456, kgp5894351, kgp6042557, kgp6081880, kgp6194428, kgp6429231, kgp7006201, kgp7151153, kgp7161038, kgp7653470, kgp8145845, kgp8644305, kgp9143704, kgp9409440, kgp9909702, kgp9927782, rs10038844, rs10495115, rs11750747, rs12341716, rs12881439, rs13168893, rs1393040, rs1474226, rs1534647, rs1715441, rs17187123, rs17245674, rs17419416, rs1793174, rs1883448, rs1905248, rs263247, rs34647183, rs35615951, rs3847233, rs3858038, rs4740708, rs528065, rs6459418, rs6577395, rs6811337, rs7680970, rs7684006, rs7698655, rs7961005, rs8018807, rs9948620 or rs9953274 (hereinafter Group 7), one or more C alleles at the location of kgp10836214, kgp1432800, kgp22839559, kgp6301155, kgp6828277, rs2354380, rs2662, rs3858035, rs3894712, rs4797764 or rs7696391 (hereinafter Group 8), one or more G alleles at the location of kgp10148554, kgp10215554, kgp10989246, kgp11755256, kgp1682126, kgp1758575, kgp2920925, kgp3287349, kgp3420309, kgp3488270, kgp3598966, kgp3697615, kgp4137144, kgp5691690, kgp5924341, kgp5949515, kgp6213972, kgp625941, kgp6889327, kgp6990559, kgp7778345, kgp7932108, kgp8847137, kgp956070, rs1026894, rs11562998, rs11563025, rs11947777, rs12233980, rs12472695, rs13386874, rs1357718, rs1393037, rs1397481, rs1508515, rs16846161, rs209568, rs2618065, rs28993969, rs3768769, rs3858034, rs3858036, rs4978567, rs7119480, rs7123506, rs7231366, rs7819949, rs7846783, rs7949751, rs8000689, rs961090 or rs967616 (hereinafter Group 9), or one or more T alleles at the location of rs12043743.

The present invention also provides a kit for identifying a human subject afflicted with multiple sclerosis or a single clinical attack consistent with multiple sclerosis who is predicted to have a slower course of disease progression, the kit comprising a) at least one probe specific for a location corresponding to the location of at least one SNP;

b) at least one pair of PCR primers designed to amplify a DNA segment which includes a location corresponding to the location of at least one SNP;

c) at least one pair of PCR primers designed to amplify a DNA segment which includes a location corresponding to the location of at least one SNP and at least one probe specific for a location corresponding to the location of at least one SNP;

d) a reagent for performing a method selected from the group consisting of restriction fragment length polymorphism (RFLP) analysis, sequencing, single strand conformation polymorphism analysis (SSCP), chemical cleavage of mismatch (CCM), gene chip and denaturing high performance liquid chromatography (DHPLC) for determining the identity of at least one SNP; or e) reagents for TaqMan Open Array assay designed for determining the genotype at a location corresponding to the location of at least one SNP, wherein the at least one SNP is selected from the group consisting of Group 6.

BRIEF DESCRIPTION OF THE DRAWINGS

FIG. 9. shows the algorithm and calculation of values for all genotyped patients of the Gala and FORTE cohorts, based on the 11 SNPs in the predictive model, without including the clinical variables, and using a threshold at ~30% of the population classified as "predicted responders".

DETAILED DESCRIPTION OF THE INVENTION

Embodiments of the Invention

Figure 1:
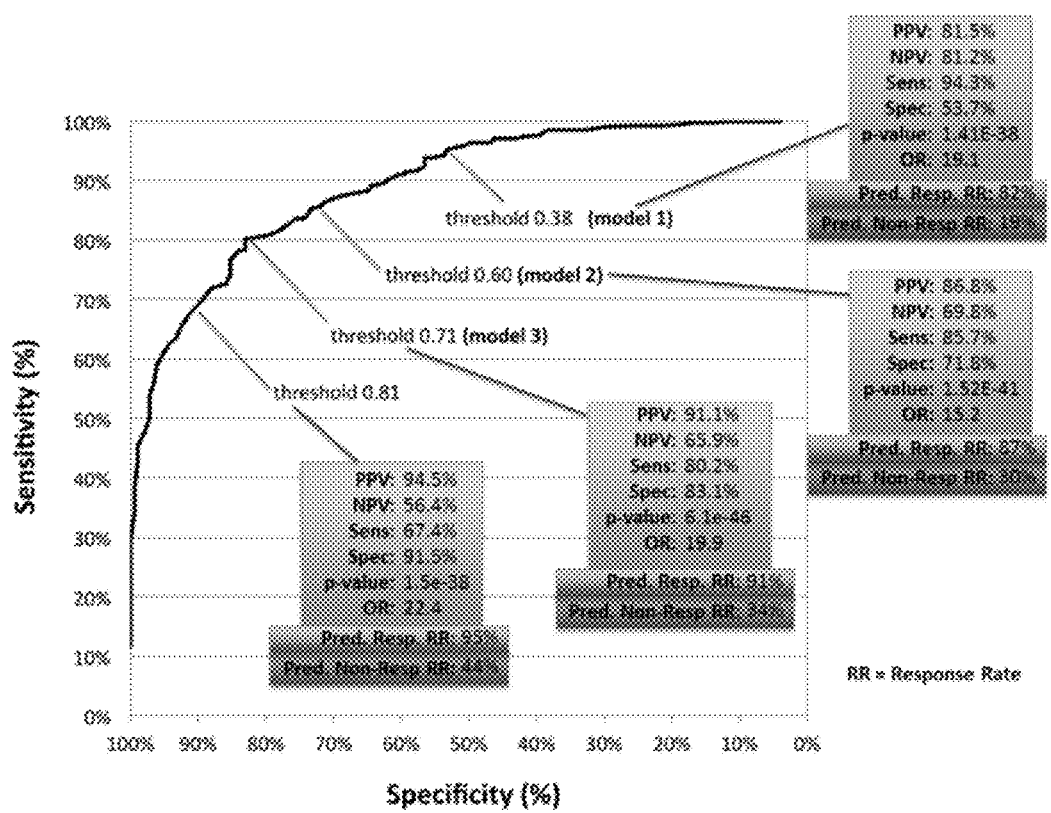
FIG. 1. shows Receiver Operating Characteristics for optimization of test threshold.

The present invention provides a method for treating a human subject afflicted with multiple sclerosis or a single clinical attack consistent with multiple sclerosis with a pharmaceutical composition comprising glatiramer acetate and a pharmaceutically acceptable carrier, comprising the steps of:
 (i) determining a genotype of the subject at a location corresponding to the location of one or more single nucleotide polymorphisms (SNPs) selected from the group consisting of: Group 1,
 (ii) identifying the subject as a predicted responder to glatiramer acetate if the genotype of the subject contains
  one or more A alleles at the location of Group 2,
  one or more C alleles at the location of Group 3,
  one or more G alleles at the location of Group 4, or
  one or more T alleles at the location of kgp18432055, kgp279772, kgp3991733 or kgp7242489; and
 (iii) administering the pharmaceutical composition comprising glatiramer acetate and a pharmaceutically acceptable carrier to the subject only if the subject is identified as a predicted responder to glatiramer acetate.

In some embodiments step (i) further comprises determining a genotype of the subject at a location corresponding to the location of one or more single nucleotide polymorphisms (SNPs) selected from the group consisting of: rs10988087, rs1573706, rs17575455, rs2487896, rs3135391, rs6097801 and rs947603, and wherein step (ii) further comprises identifying the subject as a predicted responder to glatiramer acetate if the genotype of the subject contains one or more A alleles at the location of rs10988087, one or more C alleles at the location of rs17575455, or one or more G alleles at the location of rs1573706, rs2487896, rs3135391, rs6097801 or rs947603.

In some embodiments administering the pharmaceutical composition comprising glatiramer acetate and a pharmaceutically acceptable carrier comprises administering to the human subject three subcutaneous injections of the pharmaceutical composition over a period of seven days with at least one day between every subcutaneous injection.

In some embodiments the pharmaceutical composition is a unit dose of a 1 ml aqueous solution comprising 40 mg of glatiramer acetate.

In some embodiments the pharmaceutical composition is a unit dose of a 1 ml aqueous solution comprising 20 mg of glatiramer acetate.

In some embodiments the pharmaceutical composition is a unit dose of a 0.5 ml aqueous solution comprising 20 mg of glatiramer acetate.

In some embodiments the pharmaceutical composition comprising glatiramer acetate and a pharmaceutically acceptable carrier is administered as a monotherapy.

In some embodiments the pharmaceutical composition comprising glatiramer acetate and a pharmaceutically acceptable carrier is administered in combination with at least one other multiple sclerosis drug.

The present invention also provides a method of identifying a human subject afflicted with multiple sclerosis or a single clinical attack consistent with multiple sclerosis as a predicted responder or as a predicted non-responder to glatiramer acetate, the method comprising determining the genotype of the subject at a location corresponding to the location of one or more single nucleotide polymorphisms (SNPs) selected from the group consisting of Group 1, and identifying the human subject as a predicted responder to glatiramer acetate if the genotype of the subject contains
 one or more A alleles at the location of Group 2,
 one or more C alleles at the location of Group 3,
 one or more G alleles at the location of Group 4, or
 one or more T alleles at the location of kgp18432055, kgp279772, kgp3991733 or kgp7242489,
 or identifying the human subject as a predicted non-responder to glatiramer acetate if the genotype of the subject contains
 no A alleles at the location of Group 2,
 no C alleles at the location of Group 3,
 no G alleles at the location of Group 4, or
 no T alleles at the location of kgp18432055, kgp279772, kgp3991733 or kgp7242489.

In some embodiments the methods further comprise determining a genotype of the subject at a location corresponding to the location of one or more SNPs selected from the group consisting of: rs10988087, rs1573706, rs17575455, rs2487896, rs3135391, rs6097801 and rs947603, and identifying the human subject as a predicted responder to glatiramer acetate if the genotype of the subject contains one or more A alleles at the location of rs10988087, one or more C alleles at the location of rs17575455, or one or more G alleles at the location of rs1573706, rs2487896, rs3135391, rs6097801 or rs947603, or identifying the human subject as a predicted non-responder to glatiramer acetate if the genotype of the subject contains no A alleles at the location of rs10988087, no C alleles at the location of rs17575455, or no G alleles at the location of rs1573706, rs2487896, rs3135391, rs6097801 or rs947603. In some embodiments the genotype is determined from a nucleic acid-containing sample that has been obtained from the subject.

In some embodiments determining the genotype comprises using a method selected from the group consisting of restriction fragment length polymorphism (RFLP) analysis, sequencing, single strand conformation polymorphism analysis (SSCP), chemical cleavage of mismatch (CCM), denaturing high performance liquid chromatography (DHPLC), Polymerase Chain Reaction (PCR) and an array, or a combination thereof.

Figure 8:
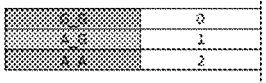
FIG. 8. shows the algorithm and calculation of values for all genotyped patients of the Gala and FORTE cohorts, based on the predictive model (11 SNPs and 2 clinical variables).

In some embodiment, applying the algorithm depicted in FIG. 8 or in FIG. 9 to identify the subject as a predicted responder or as a predicted non-responder to glatiramer acetate.

In some embodiments the genotype is determined using at least one pair of PCR primers and at least one probe.

In some embodiments the array is selected from the group consisting of a gene chip, and a TaqMan Open Array.

In some embodiments the gene chip is selected from the group consisting of a DNA array, a DNA microarray, a DNA chip, and a whole genome genotyping array.

In some embodiments the array is a TaqMan Open Array.

In some embodiments the gene chip is a whole genome genotyping array.

In some embodiments determining the genotype of the subject at the location corresponding to the location of the said one or more SNPs comprises:
(i) obtaining DNA from a sample that has been obtained from the subject;
(ii) optionally amplifying the DNA; and
(iii) subjecting the DNA or the amplified DNA to a method selected from the group consisting of restriction fragment length polymorphism (RFLP) analysis, sequencing, single strand conformation polymorphism analysis (SSCP), chemical cleavage of mismatch (CCM), denaturing high performance liquid chromatography (DHPLC), Polymerase Chain Reaction (PCR) and an array, or a combination thereof, for determining the identity the one or more SNPs.

In some embodiments the array comprises a plurality of probes suitable for determining the identity of the one or more SNPs.

In some embodiments the array is a gene chip.

In some embodiments the gene chip is a whole genome genotyping array.

In some embodiments the human subject is a naïve patient.

In some embodiments the human subject has been previously administered glatiramer acetate.

In some embodiments the human subject has been previously administered a multiple sclerosis drug other than glatiramer acetate.

In some embodiments the genotype is determined at locations corresponding to the locations of 2, 3, 4, 5, 6, 7, 8, 9, 10, 11, 12, 13, 14, 15, 16 or more single nucleotide polymorphisms (SNPs).

In some embodiments the one or more SNPs is selected from the group consisting of kgp24415534, kgp6214351, kgp6599438, kgp7747883, kgp8110667, kgp8817856, rs10162089, rs16886004, rs1894408 and rs759458 (hereinafter Group 10).

In some embodiments the one or more SNPs is selected from the group consisting of kgp24415534, kgp6214351, kgp6599438, kgp7747883, kgp8110667, kgp8817856, rs10162089, rs16886004, rs1894408, rs3135391, and rs759458.

In some embodiments the one or more SNPs is selected from the group consisting of kgp24415534, kgp6214351, kgp6599438, kgp8110667, kgp8817856, rs10162089, rs16886004, rs1894408, rs3135391, and rs759458.

In some embodiments, if rs3135391 is the at least one SNP selected, then selecting at least one SNP other than rs3135391.

In some embodiments the one or more SNPs comprise 2, 3, 4, 5, 6, 7, 8, 9 or 10 of the SNPs selected from the group consisting of Group 10.

In some embodiments the one or more SNPs further comprise rs3135391.

In some embodiments the one or more SNPs comprise 2, 3, 4, 5, 6, 7, 8, 9, 10, or 11 of the SNPs selected from the group consisting of kgp24415534, kgp6214351, kgp6599438, kgp7747883, kgp8110667, kgp8817856, rs10162089, rs16886004, rs1894408, rs3135391 and rs759458.

In some embodiments the one or more single nucleotide polymorphisms (SNPs) further comprise 2, 3, 4, 5, 6, 7, 8, 9 or 10 of the SNPs selected from the group consisting of kgp24415534, kgp6214351, kgp6599438, kgp8110667, kgp8817856, rs10162089, rs16886004, rs1894408, rs3135391 and rs759458.

In some embodiments the genotype of the subject at the location corresponding to the location of one or more of the SNPs is determined indirectly by determining the genotype of the subject at a location corresponding to the location of at least one SNP that is in linkage disequilibrium with the one or more SNPs.

In some embodiments the genotype of the subject at the location corresponding to the location of the one or more SNPs is determined by indirect genotyping.

In some embodiments the indirect genotyping allows identification of the genotype of the subject at the location corresponding to the location of the one or more SNPs with a probability of at least 85.

In some embodiments the indirect genotyping allows identification of the genotype of the subject at the location corresponding to the location of the one or more SNPs with a probability of at least 90%.

In some embodiments the indirect genotyping allows identification of the genotype of the subject at the location corresponding to the location of the one or more SNPs with a probability of at least 99%.

In some embodiments the methods further comprise the step of determining the log number of relapses in the last two years for the human subject.

In some embodiments the methods further comprise the step of determining the baseline Expanded Disability Status Scale (EDSS) score for the human subject.

In some embodiments the methods further comprise determining the genotype of the subject at a location corresponding to the location of one or more single nucleotide polymorphisms (SNPs) selected from the group consisting of: Group 6, and identifying the human subject as a predicted responder to glatiramer acetate if the genotype of the subject contains
one or more A alleles at the location of Group 7,
one or more C alleles at the location of Group 8,
one or more G alleles at the location of Group 9, or
one or more T alleles at the location of rs12043743.

The present invention also provides a kit for identifying a human subject afflicted with multiple sclerosis or a single clinical attack consistent with multiple sclerosis as a predicted responder or as a predicted non-responder to glatiramer acetate, the kit comprising at least one probe specific for the location of a SNP selected from the group consisting of Group 1.

The present invention also provides a kit for identifying a human subject afflicted with multiple sclerosis or a single clinical attack consistent with multiple sclerosis as a predicted responder or as a predicted non-responder to glatiramer acetate, the kit comprising at least one pair of PCR primers designed to amplify a DNA segment which includes the location of a SNP selected from the group consisting of Group 1.

The present invention also provides a kit for identifying a human subject afflicted with multiple sclerosis or a single clinical attack consistent with multiple sclerosis as a predicted responder or as a predicted non-responder to glatiramer acetate, the kit comprising a reagent for performing a method selected from the group consisting of restriction fragment length polymorphism (RFLP) analysis, sequencing, single strand conformation polymorphism analysis (SSCP), chemical cleavage of mismatch (CCM), gene chip and denaturing high performance liquid chromatography (DHPLC) for determining the genotype of the subject at a location corresponding to the location of at least one SNP selected from the group consisting of Group 1.

In some embodiments the gene chip is a whole genome genotyping array.

In some embodiments the kit comprises
(i) at least one pair of PCR primers designed to amplify a DNA segment which includes the location a SNP selected from the group consisting of Group 1, and
(ii) at least one probe specific for the location of a SNP selected from the group consisting of Group 1.

The present invention also provides a kit for identifying a human subject afflicted with multiple sclerosis or a single clinical attack consistent with multiple sclerosis as a predicted responder or as a predicted non-responder to glatiramer acetate, the kit comprising reagents for TaqMan Open Array assay designed for determining the genotype of the subject at a location corresponding to the location of at least one SNP selected from the group consisting of Group 1.

In some embodiments the kit further comprises instructions for use of the kit for identifying a human subject afflicted with multiple sclerosis or a single clinical attack consistent with multiple sclerosis as a predicted responder or as a predicted non-responder to glatiramer acetate.

In some embodiments the one or more single nucleotide polymorphisms (SNPs) are selected from the group consisting of Group 10.

In some embodiments the one or more single nucleotide polymorphisms (SNPs) comprise 2, 3, 4, 5, 6, 7, 8, 9 or 10 of the SNPs selected from the group consisting of Group 10.

In some embodiments the one or more SNPs further comprise rs3135391.

The present invention also provides a kit for identifying a human subject afflicted with multiple sclerosis or a single clinical attack consistent with multiple sclerosis as a predicted responder or as a predicted non-responder to glatiramer acetate, the kit comprising
a) at least one probe specific for a location corresponding to the location of at least one SNP;
b) at least one pair of PCR primers designed to amplify a DNA segment which includes a location corresponding to the location of at least one SNP;
c) at least one pair of PCR primers designed to amplify a DNA segment which includes a location corresponding to the location of at least one SNP and at least one probe specific for a location corresponding to the location of at least one SNP;
d) a reagent for performing a method selected from the group consisting of restriction fragment length polymorphism (RFLP) analysis, sequencing, single strand conformation polymorphism analysis (SSCP), chemical cleavage of mismatch (CCM), gene chip and denaturing high performance liquid chromatography (DHPLC) for determining the identity of at least one SNP; or
e) reagents for TaqMan Open Array assay designed for determining the genotype at a location corresponding to the location of at least one SNP,
wherein the at least one SNP is selected from the group consisting of Group 1.

In some embodiments the at least one single nucleotide polymorphisms (SNPs) are selected from the group consisting of Group 10,
preferably wherein the kit further comprises instructions for use of the kit for identifying a human subject afflicted with multiple sclerosis or a single clinical attack consistent with multiple sclerosis as a predicted responder or as a predicted non-responder to glatiramer acetate.

In some embodiments the at least one single nucleotide polymorphisms (SNPs) comprise 2, 3, 4, 5, 6, 7, 8, 9 or 10 of the SNPs selected from the group consisting of Group 10.

In some embodiments the at least one single nucleotide polymorphisms (SNPs) further comprise rs3135391.

In some embodiments the genotype of the subject at the location corresponding to the location of one or more of the SNPs is determined by indirect genotyping.

In some embodiments the genotype of the subject at the location corresponding to the location of one or more of the SNPs is determined indirectly by determining the genotype of the subject at a location corresponding to the location of at least one SNP that is in linkage disequilibrium with the one or more SNPs.

In some embodiments the kit comprises
a) at least one probe specific for a location corresponding to the location of at least one SNP;
b) at least one pair of PCR primers designed to amplify a DNA segment which includes a location corresponding to the location of at least one SNP;
c) at least one pair of PCR primers designed to amplify a DNA segment which includes a location corresponding to the location of at least one SNP and at least one probe specific for a location corresponding to the location of at least one SNP;
d) a reagent for performing a method selected from the group consisting of restriction fragment length polymorphism (RFLP) analysis, sequencing, single strand conformation polymorphism analysis (SSCP), chemical cleavage of mismatch (CCM), gene chip and denaturing high performance liquid chromatography (DHPLC) for determining the identity of at least one SNP; or
e) reagents for TaqMan Open Array assay designed for determining the genotype at a location corresponding to the location of at least one SNP,
wherein the at least one SNP is in linkage disequilibrium with the one or more SNPs.

In some embodiments determining the genotype of the subject at a location corresponding to the location of at least one SNP that is in linkage disequilibrium with the one or more SNPs identification of the genotype of the subject at the location corresponding to the location of the one or more SNPs with probability of at least 85.

In some embodiments determining the genotype of the subject at a location corresponding to the location of at least one SNP that is in linkage disequilibrium with the one or more SNPs allows identification of the genotype of the subject at the location corresponding to the location of the one or more SNPs with a probability of at least 90%.

In some embodiments determining the genotype of the subject at a location corresponding to the location of at least one SNP that is in linkage disequilibrium with the one or more SNPs allows identification of the genotype of the subject at the location corresponding to the location of the one or more SNPs with a probability of at least 99%.

The present invention also provides a probe for identifying the genotype of a location corresponding to the location of a SNP selected from the group consisting of Group 5.

The present invention also provides a probe for identifying the genotype of a location corresponding to the location of a SNP selected from the group consisting of kgp24415534, kgp6214351, kgp6599438, kgp7747883, kgp8110667, kgp8817856, rs10162089, rs16886004, rs1894408, rs3135391, and rs759458.

In some embodiments the SNP is in linkage disequilibrium with the one or more SNPs.

The present invention also provides glatiramer acetate or a pharmaceutical composition comprising glatiramer acetate for use in treating a human subject afflicted with multiple sclerosis or a single clinical attack consistent with multiple sclerosis which human subject is identified as a predicted responder to glatiramer acetate by:
  a) determining a genotype of the subject at a location corresponding to the location of one or more single nucleotide polymorphisms (SNPs) selected from the group consisting of: Group 1, and
  b) identifying the subject as a predicted responder to glatiramer acetate if the genotype of the subject contains
    one or more A alleles at the location of Group 2,
    one or more C alleles at the location of Group 3,
    one or more G alleles at the location of Group 4, or
    one or more T alleles at the location of kgp18432055, kgp279772, kgp3991733 or kgp7242489.

In some embodiments the genotype of the subject at the location corresponding to the location of one or more of the SNPs is determined indirectly by determining the genotype of the subject at a location corresponding to the location of at least one SNP that is in linkage disequilibrium with the one or more SNPs.

The present invention also provides a method of determining the genotype of a human subject comprising identifying whether the genotype of a human subject contains
  one or more A alleles at the location of Group 2,
  one or more C alleles at the location of Group 3,
  one or more G alleles at the location of Group 4, or
  one or more T alleles at the location of kgp18432055, kgp279772, kgp3991733 or kgp7242489.

In some embodiments identifying whether the genotype of a human subject contains
  one or more A alleles at the location of Group 2,
  one or more C alleles at the location of Group 3,
  one or more G alleles at the location of Group 4, or
  one or more T alleles at the location of kgp18432055, kgp279772, kgp3991733 or kgp7242489 is determined indirectly by determining the genotype of the subject at a location corresponding to the location of at least one SNP that is in linkage disequilibrium with the one or more SNPs.

The present invention also provides a method of determining the genotype of a human subject comprising identifying the genotype of a human subject at the location of kgp6214351, kgp6599438, kgp7747883, kgp8110667, kgp8817856, rs10162089, rs16886004, rs1894408, rs3135391, or rs759458.

The present invention also provides a method of identifying a human subject afflicted with multiple sclerosis or a single clinical attack consistent with multiple sclerosis who is predicted to have a slower course of disease progression, comprising the steps of:
  (i) determining a genotype of the subject at a location corresponding to the location of one or more single nucleotide polymorphisms (SNPs) selected from the group consisting of: Group 6, and
  (ii) identifying the subject as predicted to have a slower course of disease progression if the genotype of the subject contains
    one or more A alleles at the location of Group 7,
    one or more C alleles at the location of Group 8,
    one or more G alleles at the location of Group 9, or
    one or more T alleles at the location of rs12043743.

In some embodiments the genotype of the subject at the location corresponding to the location of one or more of the SNPs is determined indirectly by determining the genotype of the subject at a location corresponding to the location of at least one SNP that is in linkage disequilibrium with the one or more SNPs.

The present invention also provides a kit for identifying a human subject afflicted with multiple sclerosis or a single clinical attack consistent with multiple sclerosis who is predicted to have a slower course of disease progression, the kit comprising
  a) at least one probe specific for a location corresponding to the location of at least one SNP;
  b) at least one pair of PCR primers designed to amplify a DNA segment which includes a location corresponding to the location of at least one SNP;
  c) at least one pair of PCR primers designed to amplify a DNA segment which includes a location corresponding to the location of at least one SNP and at least one probe specific for a location corresponding to the location of at least one SNP;
  d) a reagent for performing a method selected from the group consisting of restriction fragment length polymorphism (RFLP) analysis, sequencing, single strand conformation polymorphism analysis (SSCP), chemical cleavage of mismatch (CCM), gene chip and denaturing high performance liquid chromatography (DHPLC) for determining the identity of at least one SNP; or
  e) reagents for TaqMan Open Array assay designed for determining the genotype at a location corresponding to the location of at least one SNP,
  wherein the at least one SNP is selected from the group consisting of Group 6.

For the foregoing embodiments, each embodiment disclosed herein is contemplated as being applicable to each of the other disclosed embodiments. Thus, all combinations of the various elements described herein are within the scope of the invention.

Definitions

As used herein, genetic marker refers to a DNA sequence that has a known location chromosome. Several non-limiting examples of classes of genet markers include SNP (single nucleotide polymorphism), STR (short tandem repeat), and SFP (single feature polymorphism). VNTR (variable number tandem repeat), microsatellite polymorphism, insertions and deletions. The genetic markers associated with the invention are SNPs. As used herein a SNP or "single nucleotide polymorphism" refers to a specific site in the genome where there is a difference in DNA base between individuals. In some embodiments the SNP is located in a coding region of a gene.

In other embodiments the SNP is located in a noncoding region. of a gene. In still other embodiments the SNP is located in an intergenic region.

Several non-limiting examples of databases from which information on SNPs or genes that are associated with human disease can be retrieved include: NCBI resources, The SNP Consortium LTD, NCBI dbSNP database, International HapMap Project, 1000 Genomes Project, Glovar Variation Browser, SNPStats, PharmGKB, GEN-SniP, and SNPedia.

SNPs are identified herein using the rs identifier numbers in accordance with the NCBI dbSNP database, which is publically available at: ncbi.nlm.nih.gov/projects/SNP/or using the kgp identifier numbers, which were created by Illumina. Genotype at the kgp SNPs can be obtained by using the Illumina genotyping arrays. In addition, SNPs can be identified by the specific location on the chromosome indicated for the specific SNP.

Additional information about identifying SNPs can be obtained from the NCBI database SNP FAQ archive located at ncbi.nlm.nih.gov/books/NBK3848/ or from literature available on the Illumina website located at illumina.com/applications/genotyping/literature.ilmn.

In some embodiments, SNPs in linkage disequilibrium with the SNPs associated with the invention are useful for obtaining similar results. As used herein, linkage disequilibrium refers to the non-random association of SNPs at one loci. Techniques for the measurement of linkage disequilibrium are known in the art. As two SNPs are in linkage disequilibrium if they are inherited together, the information they provide is correlated to a certain extent. SNPs in linkage disequilibrium with the SNPs included in the models can be obtained from databases such as HapMap or other related databases, from experimental setups run in laboratories or from computer-aided in-silico experiments. Determining the genotype of a subject at a position of SNP as specified herein, e.g. as specified by NCBI dbSNP rs identifier, may comprise "direct genotyping", e.g. by determining the identity of the nucleotide of each allele at the locus of SNP, and/or "indirect genotyping", defined herein as evaluating/determining the identity of an allele at one or more loci that are in linkage disequilibrium with the SNP in question, allowing one to infer the identity of the allele at the locus of SNP in question with a substantial degree of confidence. In some cases, indirect genotyping may comprise determining the identity of each allele at one or more loci that are in sufficiently high linkage disequilibrium with the SNP in question so as to allow one to infer the identity of each allele at the locus of SNP in question with a probability of at least 85%, at least 90% or at least 99% certainty.

A genotype at a position of SNP (genotype "at a" SNP) may be represented by a single letter which corresponds to the identity of the nucleotide at the SNP, where A represents adenine, T represents thymine, C represents cytosine, and G represents guanine. The identity of two alleles at a single SNP may be represented by a two letter combination of A, T, C, and G, where the first letter of the two letter combination represents one allele and the second letter represents the second allele, and where A represents adenine, T represents thymine, C represents cytosine, and G represents guanine. Thus, a two allele genotype at a SNP can be represented as, for example, AA, AT, AG, AC, TT, TG, TC, GG, GC, or CC. It is understood that AT, AG, AC, TG, TC, and GC are equivalent to TA, GA, CA, GT, CT, and CG, respectively.

The SNPs of the invention can be used as predictive indicators of the response to GA in subjects afflicted with multiple sclerosis or a single clinical attack consistent with multiple sclerosis. Aspects of the invention relate to determining the presence of SNPs through obtaining a patient DNA sample and evaluating the patient sample for the presence of one or more SNPs, or for a certain set of SNPs. It should be appreciated that a patient DNA sample can be extracted, and a SNP can be detected in the sample, through any means known to one of ordinary skill in art. Some non-limiting examples of known techniques include detection via restriction fragment length polymorphism (RFLP) analysis, arrays including but not limited to planar microarrays or bead arrays, sequencing, single strand conformation polymorphism analysis (SSCP), chemical cleavage of mismatch (CCM), Polymerase chain reaction (PCR) and denaturing high performance liquid chromatography (DHPLC).

In some embodiments, the genotyping array is a whole genome genotyping array. In some embodiments, the Whole-genome genotyping arrays as defined here are arrays that contain hundreds of thousands to millions of genetic sequences (which may also be named "probes"). In some embodiments, Whole-genome genotyping arrays contain 500,000 probes or more. In some embodiments, Whole-genome genotyping arrays contain 1 million probes or more. In some embodiments, Whole-genome genotyping arrays contain 5 million probes or more.

In some embodiments, a SNP is detected through PCR amplification and sequencing of the DNA region comprising the SNP. In some embodiments SNPs are detected using arrays, exemplified by gene chip, including but not limited to DNA arrays or microarrays, DNA chips, and whole genome genotyping arrays, all of which may be for example planar arrays or bead arrays, or a TaqMan open Array. Arrays/Microarrays for detection of genetic polymorphisms, changes or mutations (in general, genetic variations) such as a SNP in a DNA sequence, may comprise a solid surface, typically glass, on which a high number of genetic sequences are deposited (the probes), complementary to the genetic variations to be studied. Using standard robotic printers to apply probes to the array a high density of individual probe features can be obtained, for example probe densities of 600 features per $cm^2$ or more can be typically achieved. The positioning of probes on an array is precisely controlled by the printing device (robot, inkjet printer, photolithographic mask etc) and probes are aligned in a grid. The organization of probes on the array facilitates the subsequent identification of specific probe-target interactions. Additionally it is common, but not necessary, to divide the array features into smaller sectors, also grid-shaped, that are subsequently referred to as sub-arrays. Sub-arrays typically comprise 32 individual probe features although lower (e.g. 16) or higher (e.g. 64 or more) features can comprise each sub-array. In some arrays the probes are connected to beads instead of the solid support. Such arrays are called "bead arrays" or "bead CHIPs".

In some embodiments, detection of genetic variation such as the presence of a SNP involves hybridization to sequences which specifically recognize the normal and the mutant allele in a fragment of DNA derived from a test sample. Typically, the fragment has been amplified, e.g. by using the polymerase chain reaction (PCR), and labeled e.g. with a fluorescent molecule. A laser can be used to detect bound labeled fragments on the chip and thus an individual who is homozygous for the normal allele can be specifically distinguished from heterozygous individuals (in the case of autosomal dominant conditions then these individuals are referred to as carriers) or those who are homozygous for the mutant allele. In some embodiments, the amplification reaction and/or extension reaction is carried out on the microarray or bead itself. For differential hybridization based methods there are a number of methods for analyzing hybridization data for genotyping: Increase in hybridization level: The hybridization levels of probes complementary to the normal and mutant alleles are compared. Decrease in hybridization level: Differences in the sequence between a control sample and a test sample can be identified by a decrease in the hybridization level of the totally complementary oligonucleotides with a reference sequence. A loss approximating 100% is produced in mutant homozygous individuals while there is only an approximately 50% loss in heterozygotes. In Microarrays for examining all the bases of a sequence of "n" nucleotides ("oligonucleotide") of length in both strands, a minimum of "2n" oligonucleotides that overlap with the previous oligonucleotide in all the sequence except in the nucleotide are necessary. Typically the size of the oligonucleotides is about 25 nucleotides. However it should be appreciated that the oligonucleotide can be any length that is appropriate as would be understood by one of ordinary skill in the art. The increased number of oligonucleotides used to reconstruct the sequence reduces errors derived from fluctuation of the hybridization level.

However, the exact change in sequence cannot be identified with this method; in some embodiments this method is combined with sequencing to identify the mutation. Where amplification or extension is carried out on the microarray or bead itself, three methods are presented by way of example: In the Minisequencing strategy, a mutation specific primer is fixed on the slide and after an extension reaction with fluorescent dideoxynucleotides, the image of the Microarray is captured with a scanner. In the Primer extension strategy, two oligonucleotides are designed for detection of the wild type and mutant sequences respectively. The extension reaction is subsequently carried out with one fluorescently labeled nucleotide and the remaining nucleotides unlabelled. In either case the starting material can be either an RNA sample or a DNA product amplified by PCR. In the Tag arrays strategy, an extension reaction is carried out in solution with specific primers, which carry a determined 5[1] sequence or "tag". The use of Microarrays with oligonucleotides complementary to these sequences or "tags" allows the capture of the resultant products of the extension. Examples of this include the high density Microarray "Flex-flex" (Affymetrix). In the Illumina 1M Dou BeadChip array (illumina.com/products/human1m_duo_dna_analysis_beadchip_kits.ilmn), SNP genotypes are generated from fluorescent intensities using the manufacturer's default cluster settings.

In some aspects of the invention measurement of clinical variables comprises part of the prediction model predicting response to GA along with the genetic variables. Some non-limiting examples are age of the patient (in years), gender of patient, clinical manifestations, MRI parameter, country, ancestry, and years of exposure to treatment) "Clinical manifestations" include but are not limited to EDSS score such as baseline EDSS score, log of number of relapses in last 2 Years and relapse rate. "MRI parameters" include but are not limited to the volume and/or number of T1 enhancing lesions and/or T2 enhancing lesions; exemplified by baseline volume of T2 lesion, number of Gd-T1 lesions at baseline. In certain aspect of the invention, the clinical variables taken into account are as measured at the time of the decision about the treatment suitable for the patient, or measured at a time point determined by the physician, researcher or other professional involved in the decision.

The identification of a patient as a responder or as a non-responder to GA based on the presence of at least one SNP from tables 2-32 and 34-44, a set of SNPs from tables 2-32 and 34-44, or the combination of a SNP or a set of SNPs from tables 2-32 and 34-44 with one or more clinical variables described above, may be used for predicting response to GA.

Also within the scope of the invention are kits and instructions for their use. In some embodiments kits associated with the invention are kits for identifying one or more SNPs within a patient sample. In some embodiments a kit may contain primers for amplifying a specific genetic locus. In some embodiments, a kit may contain a probe for hybridizing to a specific SNP. The kit of the invention can include reagents for conducting each of the following assays including but not limited to restriction fragment length polymorphism (RFLP) analysis, arrays including but not limited to planar microarrays or bead arrays, sequencing, single strand conformation polymorphism analysis (SSCP), chemical cleavage of mismatch (CCM), and denaturing high performance liquid chromatography (DHPLC), PCR amplification and sequencing of the DNA region comprising the SNP. A kit of the invention can include a description of use of the contents of the kit for participation in any biological or chemical mechanism disclosed herein. A kit can include instructions for use of the kit components alone or in combination with other methods or compositions for assisting in screening or diagnosing a sample and/or determining whether a subject is a responder or a non-responder to GA. Forms of Multiple Sclerosis:

There are five distinct disease stages and/or types of MS:
1) benign multiple sclerosis;
2) relapsing-remitting multiple sclerosis (RRMS);
3) secondary progressive multiple sclerosis (SPMS);
4) progressive relapsing multiple sclerosis (PRMS); and
5) primary progressive multiple sclerosis (PPMS).

Benign multiple sclerosis is a retrospective diagnosis which is characterized by 1-2 exacerbations with complete recovery, no lasting disability and no disease progression for 10-15 years after the initial onset. Benign multiple sclerosis may, however, progress into other forms of multiple sclerosis.

Patients suffering from RRMS experience sporadic exacerbations or relapses, as well as periods of remission. Lesions and evidence of axonal loss may or may not be visible on MRI for patients with RRMS. SPMS may evolve from RRMS. Patients afflicted with SPMS have relapses, a diminishing degree of recovery during remissions, less frequent remissions and more pronounced neurological deficits than RRMS patients. Enlarged ventricles, which are markers for atrophy of the corpus callosum, midline center and spinal cord, are visible on MRI of patients with SPMS.

PPMS is characterized by a steady progression of increasing neurological deficits without distinct attacks or remissions. Cerebral lesions, diffuse spinal cord damage and evidence of axonal loss are evident on the MRI of patients with PPMS. PPMS has periods of acute exacerbations while proceeding along a course of increasing neurological deficits without remissions. Lesions are evident on MRI of patients suffering from PRMS.(28)

A clinically isolated syndrome (CIS) is a single monosymptomatic attack compatible with MS, such as optic neuritis, brain stem symptoms, and partial myelitis. Patients with CIS that experience a second clinical attack are generally considered to have clinically definite multiple sclerosis (CDMS). Over 80 percent of patients with a CIS and MRI lesions go on to develop MS, while approximately 20 percent have a self-limited process.(29,30) Patients who experience a single clinical attack consistent with MS may have at least one lesion consistent with multiple sclerosis prior to the development of clinically definite multiple sclerosis.

Multiple sclerosis may present with optic neuritis, blurring of vision, diplopia, involuntary rapid eye movement, blindness, loss of balance, tremors, ataxia, vertigo, clumsiness of a limb, lack of co-ordination, weakness of one or more extremity, altered muscle tone, muscle stiffness, spasms, tingling, paraesthesia, burning sensations, muscle pains, facial pain, trigeminal neuralgia, stabbing sharp pains, burning tingling pain, slowing of speech, slurring of words, changes in rhythm of speech, dysphagia, fatigue, bladder problems (including urgency, frequency, incomplete emptying and incontinence), bowel problems (including constipation and loss of bowel control), impotence, diminished sexual arousal, loss of sensation, sensitivity to heat, loss of short term memory, loss of concentration, or loss of judgment or reasoning.

Relapsing Form of Multiple Sclerosis:
  The term relapsing MS includes:
  1) patients with RRMS;
  2) patients with SPMS and superimposed relapses; and
  3) patients with CIS who show lesion dissemination on subsequent MRI scans according to McDonald's criteria.

As used herein, relapsing forms of multiple sclerosis include:
Relapsing-remitting multiple sclerosis (RRMS), characterized by unpredictable acute episodes of neurological dysfunction (relapses), followed by variable recovery and periods of clinical stability;
Secondary Progressive MS (SPMS), wherein patients having RRMS develop sustained deterioration with or without relapses superimposed; and
Primary progressive-relapsing multiple sclerosis (PPRMS) or progressive-relapsing multiple sclerosis (PRMS), an uncommon form wherein patients developing a progressive deterioration from the beginning can also develop relapses later on.

Kurtzke Expanded Disability Status Scale (EDSS):
  The Kurtzke Expanded Disability Status Scale (EDSS) is a method of quantifying disability in multiple sclerosis. The EDSS replaced the previous Disability Status Scales which used to bunch people with MS in the lower brackets. The EDSS quantifies disability in eight Functional Systems (FS) and allows neurologists to assign a Functional System Score (FSS) in each of these. The Functional Systems are: pyramidal, cerebellar, brainstem, sensory, bowel and bladder, visual & cerebral (according to mult-sclerosis.org/expandeddisabilitystatusscale).

Clinical Relapse:
  A clinical relapse, which may also be used herein as "relapse," "confirmed relapse," or "clinically defined relapse," is defined as the appearance of one or more new neurological abnormalities or the reappearance of one or more previously observed neurological abnormalities.
  This change in clinical state must last at least 48 hours and be immediately preceded by a relatively stable or improving neurological state of at least 30 days. This criterion is different from the clinical definition of exacerbation "at least 24 hours duration of symptoms," (31) as detailed in the section "relapse evaluation."

An event is counted as a relapse only when the subject's symptoms are accompanied by observed objective neurological changes, consistent with:
a) an increase of at least 0.5 in the EDSS score or one grade in the score of two or more of the seven FS (32); or,
b) two grades in the score of one of FS as compared to the previous evaluation.

The subject must not be undergoing any acute metabolic changes such as fever or other medical abnormality. A change in bowel/bladder function or in cognitive function must not be entirely responsible for the changes in EDSS or FS scores.

As used herein, a "multiple sclerosis drug" is a drug or an agent intended to treat clinically defined MS, CIS, any form of neurodegenerative or demyelinating diseases, or symptoms of any of the above mentioned diseases. "Multiple sclerosis drugs" may include but are not limited to antibodies, immunosuppressants, anti-inflammatory agents, immunomodulators, cytokines, cytotoxic agents and steroids and may include approved drugs, drugs in clinical trial, or alternative treatments, intended to treat clinically defined MS, CIS or any form of neurodegenerative or demyelinating diseases. "Multiple sclerosis drugs" include but are not limited to Interferon and its derivatives (including BETASERON®, AVONEX® and REBIF®), Mitoxantrone and Natalizumab. Agents approved or in-trial for the treatment of other autoimmune diseases, but used in a MS or CIS patient to treat MS or CIS are also defined as multiple sclerosis drugs.

As used herein, a "naïve patient" is a subject that has not been treated with any multiple sclerosis drugs as defined in the former paragraph.

The administration of glatiramer acetate may be oral, nasal, pulmonary, parenteral, intravenous, intra-articular, transdermal, intradermal, subcutaneous, topical, intramuscular, rectal, intrathecal, intraocular, buccal or by gavage.

As used herein, "GALA" is a phase 3 clinical trial entitled "A Study in Subjects With Relapsing-Remitting Multiple Sclerosis (RRMS) to Assess the Efficacy, Safety and Tolerability of Glatiramer Acetate (GA) Injection 40 mg Administered Three Times a Week Compared to Placebo (GALA)." The GALA trial has the ClinicalTrials.gov Identifier NCT01067521, and additional information about the trial can be found at clinicaltrials.gov/ct2/show/NCT01067521.

As used herein, "FORTE" is a phase 3 clinical trial entitled "Clinical Trial Comparing Treatment of Relapsing-Remitting Multiple Sclerosis (RR-MS) With Two Doses of Glatiramer Acetate (GA)." The FORTE trial has the ClinicalTrials.gov Identifier NCT00337779 and additional information, including study results can be found at clinicaltrials.gov/ct2/show/NCT00337779.

As used herein, "about" with regard to a stated number encompasses a range of +10 percent to −10 percent of the stated value. By way of example, about 100 mg/kg therefore includes the range 90-100 mg/kg and therefore also includes 90, 91, 92, 93, 94, 95, 96, 97, 98, 99, 100, 101, 102, 103, 104, 105, 106, 107, 108, 109 and 110 mg/kg. Accordingly, about 100 mg/kg includes, in an embodiment, 100 mg/kg.

It is understood that where a parameter range is provided, all integers within that range, tenths thereof, and hundredths thereof, are also provided by the invention. For example, "0.2-5 mg/kg" is a disclosure of 0.2 mg/kg, 0.21 mg/kg, 0.22 mg/kg, 0.23 mg/kg etc. up to 0.3 mg/kg, 0.31 mg/kg, 0.32 mg/kg, 0.33 mg/kg etc. up to 0.4 mg/kg, 0.5 mg/kg, 0.6 mg/kg etc. up to 5.0 mg/kg.

All combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

Experimental Details

Description of the Study

Copaxone® (Glatiramer acetate) is a leading drug for the treatment of MS that is marketed by TEVA. Glatiramer acetate significantly improves patient outcomes, but glatiramer acetate treatment is not equally effective in all patients. Individual differences between patients, including inherited genetic factors, can account for significant differences in individual responses to medications. A consequence of this diversity is that no single medication is effective in all patients. Clinical and genetic factors are predictive of patient response to glatiramer acetate.

In the following Examples, predictive genetic factors of glatiramer acetate treatment response are identified and a diagnostic model is demonstrated to help guide MS drug therapy to significantly improve patient outcomes.

EXAMPLES

Example 1 Patient Populations

Response definitions were received from patients from two large glatiramer acetate clinical trial cohorts (GALA, FORTE) and patients were categorized as responder, non-responder, extreme-responder, or extreme non-responder according to the criteria set forth in Table 1.

TABLE 1

Definition of Glatiramer Acetate Responders and Non-Responders and population representation in GALA and FORTE cohorts.

|  |  | Number of samples (% of cohort) | | |
| --- | --- | --- | --- | --- |
|  |  | GALA | FORTE | GALA placebo |
| Responders | Responders: Change in Annual Relapse Rate (ARR) from previous 2 years <−1 | 200 (26%) | 221 (36%) | 97 (25%) |
|  | Extreme Responders:. Change in ARR from previous 2 years <−1 and new T2 Lesions = 0 and Relapse Free | 66 (8.5%) | 95 (16%) | 23 (6%) |
| Non-Responders | Non-Responders: Change in ARR from previous 2 years ≥0 | 123 (16%) | 68 (11%) | 101 (26%) |
|  | Extreme Non-Responders: Change in ARR from previous 2 years ≥0 and new T2 Lesions ≥1 | 79 (10%) | 38 (6%) | 73 (19%) |

Example 2 Patient Genotyping

DNA samples from categorized patients were subject to quality control analysis followed by genotyping with the Illumina OMNI-5M genome wide array. This array tests 4,301,331 variants with a median marker spacing of 360 bp. The array includes 84,004 non-synonymous SNPs including 43,904 variants in the MHC region. Over 800 patients were genotyped.

Genotyping Quality Control

An Illumina-derived algorithm of SNP cluster definitions (i.e., the specific parameters used to determine specific genotypes of each SNP) was used to determine the 4,301,331 genotypes for each of the genotyped samples. For genotyping QC, SNPs were evaluated as either pass, fail, or the SNP cluster calling definitions were revised and the SNP was re-evaluated as pass or fail.

Evaluation of SNPs with poor cluster separation values (i.e., the location of SNP calling clusters were very close together) identified 126 SNPs for which SNP clustering was manually corrected. Evaluation of SNPs that were not in Hardy-Weinburg equilibrium identified 1,000 SNPs for which SNP clustering was manually corrected. Evaluation of SNPs with low GC scores (GC score: an Illumina-developed score of overall SNP performance) identified 10,000 SNPs for which SNP clustering was manually corrected. Evaluation of SNPs with low GC scores also identified 160,000 SNPs for which SNP clustering was revised using Illumina GenomeStudio software to re-define SNP cluster calling definitions. A total of 524 SNPs were scored as "failed" and removed from further analyses due to poor SNP clustering that could not be manually corrected.

In addition, SNPs with low call rates (i.e., a low number of genotype calls were generated from a particular SNP test) were scored as "fail" and removed from further analyses. Applying a "call rate" threshold of >85% to the 4,301,331 SNPs tested (i.e., for each SNP, the % of samples for which a genotype was called) resulted in "fails" for 4,384 SNPs, yielding a total of 4,296,423 SNPs available for subsequent analyses (99.89% of variants tested).

Finally, samples with call rates less than 94% (i.e., samples for which less than 94% of the genotyped SNPs produced genotype calls) were removed. This resulted in the removal of 31 samples with call rates of 49-93%, and resulted in a final cohort of 776 samples for subsequent analyses. Notably, of these 31 excluded samples, 18 (58%) had very low (<1 ng/ul) DNA concentrations and 12 of the other 13 excluded samples had low DNA quality (OD 260/280 ratio <1.8 or >2.0), or low DNA volumes.

For the final 776 samples, the overall median sample genotype call rate was 99.88% (min. 94.26%, max. 99.96%) indicative of high quality genotype data for these samples.

Example 3 Overview of Genetic Analysis

Genotype data was merged with selected clinical data (Responder/Non-Responder status, country, age, gender, ancestry, log of number of relapses in last 2 Years, baseline EDSS score, baseline volume of T2 lesion, number of Gd-T1 lesions at baseline, and years of exposure to treatment). Association and regression analyses were conducted using SVS7 software.

Analyses were conducted using standard association analyses and regression analyses. To maximize the statistical power for high priority variants, the analyses began with focused list of candidate variants (35), then expanded to a larger number of variants in 30 genes, then expanded to variants in 180 candidate genes, and finally expanded to the entire genome-wide analysis.

For each stage of association analyses, results were calculated to identify genetic associations using three genetic models:

1. Allelic Model (chi-square, chi-square −10 LogP, fisher exact, fisher exact −10 LogP, values for fisher and chi-square with Bonferoni correction, Odds Ratios and Confidence Bounds, Regression P-value, Regression −log 10 P, Call Rate (Cases), Call Rate (Controls), Minor Allele Frequency, Allele Freq. (Cases), Allele Freq. (Controls), Major Allele Frequency, Allele Freq. (Cases), Allele Freq. (Controls), Genotype Counts for cases and controls, Missing Genotype Counts, Allele Counts for cases and controls).

2. Additive Model (Cochrane-Armitage Trend Test P-value, Exact for of Cochrane Armitage Trend Test, −log 10 P-values, Correlation/Trend test P-value, Correlation/Trend −log 10 P, Call Rate, Call Rate (Cases), Call Rate (Controls), Minor Allele Frequency, Allele Freq. (Cases), Allele Freq. (Controls).

3. Genotypic Model (chi-square, chi-square −10 LogP, fisher exact, fisher exact −10 LogP, values for fisher and chi-square with Bonferoni correction, Odds Ratios and Confidence Bounds, Regression P-value, Regression −log 10 P, Call Rate (Cases), Call Rate (Controls), Minor Allele Frequency, Allele Freq. (Cases), Allele Freq. (Controls), Major Allele Frequency, Allele Freq. (Cases), Allele Freq. (Controls), Genotype Counts for cases and controls, Missing Genotype Counts, Allele Counts for Cases and controls).

For each stage of regression analyses, results were calculated to identify genetic associations using an additive genetic model.

Example 4 Stages of Analysis

Stage 1. Discovery Cohort (n=318: 198 R vs. 120 NR)—In the first stage of analysis, the discovery cohort (GALA) was analyzed to identify variants associated with good response vs. poor response.

Stage 2. Replication Cohort (n=262: 201 R vs. 61 NR)—In the second stage of each analysis, variants selected in the discovery cohort were analyzed to identify replicating associations in the FORTE replication cohort associated with good response vs. poor response.

Stage 3. Combined Cohorts (n=580: 399 R vs. 111 NR)—In the third stage of the analysis, the combined GALA and FORTE cohorts were analyzed.

Stage 4. Placebo Cohort (n=196: 95 R vs. 101 NR) In the fourth stage of the analysis, the placebo cohort (GALA placebo) was analyzed to identify variants associated with placebo response/non-response. These results will be used to confirm whether significantly associated variants are specific to glatiramer acetate drug response versus disease severity.

An overview of these analyses is presented in Table A. For each stage a step-wise analysis was performed in order to maximize study power.

TABLE A

Overview of the analyses used to identify genetic markers predictive of response to glatiramer acetate.

| | Discovery Cohort | Replication Cohort | Combined Cohorts for Comparative Parameters |
|---|---|---|---|
| Step 1 | Candidate SNPs (35) | Candidate SNPs (35) | Candidate SNPs (35) |
| | −Additive, Allelic, Genotypic, Regression | −Additive, Allelic, Genotypic, Regression | −Additive, Allelic, Genotypic, Regression |
| | Candidate SNPs, Extreme | Candidate SNPs, Extreme | Candidate SNPs, Extreme |
| | −Additive, Allelic, Genotypic, Regression | −Additive, Allelic, Genotypic, Regression | −Additive, Allelic, Genotypic, Regression |
| Step 2 | Candidate Genes (30) | Candidate Genes (30) | Candidate Genes (30) |
| | −Additive, Allelic, Genotypic, Regression | −Additive, Allelic, Genotypic, Regression | −Additive, Allelic, Genotypic, Regression |
| | Candidate Genes, Extreme | Candidate Genes, Extreme | Candidate Genes, Extreme |
| | −Additive, Allelic, Genotypic, Regression | −Additive, Allelic, Genotypic, Regression | −Additive, Allelic, Genotypic, Regression |
| Step 3 | Candidate Genes (180) | Candidate Genes (180) | Candidate Genes (180) |
| | −Additive, Allelic, Genotypic, Regression | −Additive, Allelic, Genotypic, Regression | −Additive, Allelic, Genotypic, Regression |
| | Candidate Genes, Extreme | Candidate Genes, Extreme | Candidate Genes, Extreme |
| | −Additive, Allelic, Genotypic, Regression | −Additive, Allelic, Genotypic, Regression | −Additive, Allelic, Genotypic, Regression |
| Step 4 | Genome-wide | Genome-wide | Genome-wide |
| | −Additive, Allelic, Genotypic, Regression | −Additive, Allelic, Genotypic, Regression | −Additive, Allelic, Genotypic, Regression |
| | +Corrected for ancestry | +Corrected for ancestry | +Corrected for ancestry |
| | +Corrected for clinical covariates | +Corrected for clinical covariates | +Corrected for clinical covariates |
| | +Corrected for top SNP | +Corrected for top SNP | +Corrected for top SNP |
| | Genome-wide, Extreme | Genome-wide, Extreme | Genome-wide, Extreme |
| | −Additive, Allelic, Genotypic, Regression | −Additive, Allelic, Genotypic, Regression | −Additive, Allelic, Genotypic, Regression |
| | +Corrected for clinical covariates | +Corrected for clinical covariates | +Corrected for clinical covariates |
| | +Corrected for top SNP | +Corrected for top SNP | +Corrected for top SNP |

Example 5 Analysis Part 1—Analysis of Candidate Variants

The initial analysis was limited to 35 genetic variants identified in high priority genes. Power (80%) with Bonferroni statistical correction for multiple testing to identify significant genetic associations with an odds ratio >3, for variants with an allele frequency greater than 10%. (Or rare alleles (2.5%) with an odds ratio >7).

Results for Standard Response Definition, Candidate Variants Selected a priori for Additive, Allelic and Genotypic models are presented in tables 2-4, respectively.

TABLE 2

Additive Model, Candidate Variants (Gala, Forte, and Combined cohorts)

| | Source | Name | Ch | Gene | GALA Armitage P-value | GALA Odds Ratio | GALA Allele Freq. (Resp.) | GALA Allele Freq. (Non-Resp.) | FORTE Armitage P-value | FORTE Odds Ratio | FORTE Allele Freq. (Resp.) | FORTE Allele Freq. (Non-Resp.) | COMBINED Armitage P-value | COMBINED Odds Ratio | COMBINED Allele Freq. (Resp.) | COMBINED Allele Freq. (Non-Resp.) | Mutation |
|---|---|---|---|---|---|---|---|---|---|---|---|---|---|---|---|---|---|
| Top Priority | Tchelet GWAS | rs3135391 | 6 | HLA-DRB1 | 0.040 | 0.66 | 17% | 24% | 0.0499 | 0.64 | 23% | 32% | 0.014 | 0.70 | 20% | 27% | *1501, T118T |
| Top Priority | Tchelet GWAS | rs3135388 | 6 | HLA-DRB1 | 0.047 | 0.67 | 17% | 24% | 0.0499 | 0.64 | 23% | 32% | 0.017 | 0.70 | 20% | 27% | *15001 |
| Top Priority | Tchelet GWAS | rs947603 | 10 | CEP55 | 0.054 | 1.48 | 26% | 19% | 0.16 | 1.45 | 23% | 16% | 0.027 | 1.42 | 24% | 18% | |
| | Tsareva 2011 | rs1800629 | 6 | TNF | 0.088 | 0.68 | 12% | 17% | 0.65 | 0.88 | 12% | 14% | 0.09 | 0.75 | 12% | 16% | |
| Top Priority | Tchelet GWAS | rs4344916 | 2 | AC083939.1 | 0.32 | 1.20 | 34% | 30% | 0.48 | 0.87 | 34% | 38% | 0.70 | 1.05 | 34% | 33% | |
| | Tchelet GWAS | rs10950359 | 7 | AC074389.1 | 0.32 | 0.85 | 29% | 33% | 0.40 | 1.23 | 25% | 21% | 0.51 | 0.91 | 27% | 29% | |
| | Tchelet GWAS | rs12256889 | 10 | CYP26C1 | 0.33 | 0.84 | 31% | 35% | 0.064 | 1.56 | 33% | 25% | 0.77 | 1.04 | 32% | 31% | |
| Top Priority | Comi | rs974060 | 7 | TAC1 | 0.34 | 1.18 | 32% | 28% | 0.78 | 0.94 | 27% | 29% | 0.67 | 1.06 | 30% | 28% | |
| Top Priority | Tchelet GWAS | rs17771939 | 8 | AC016885.1 | 0.36 | 1.18 | 29% | 26% | 0.0032 | 0.54 | 28% | 43% | 0.35 | 0.88 | 29% | 31% | |
| Top Priority | Tsareva 2011 | rs6897932 | 5 | IL7RA | 0.39 | 0.84 | 20% | 23% | 0.63 | 0.90 | 24% | 26% | 0.44 | 0.89 | 22% | 24% | Missense T244I |
| Top Priority | Tchelet GWAS | rs11599624 | 10 | P11-655H13 | 0.39 | 1.23 | 15% | 13% | 0.50 | 1.27 | 11% | 9% | 0.43 | 1.17 | 13% | 12% | |
| | Comi | rs1558896 | 7 | TAC1 | 0.40 | 1.15 | 34% | 30% | 0.85 | 0.96 | 29% | 30% | 0.73 | 1.05 | 31% | 30% | |
| Top Priority | Tchelet GWAS | rs11617134 | 13 | P11-629E24 | 0.41 | 0.76 | 5% | 7% | 0.95 | 1.02 | 7% | 7% | 0.64 | 0.89 | 6% | 7% | |
| Top Priority | Tchelet GWAS | rs17575455 | 2 | AC078940.2 | 0.41 | 0.87 | 33% | 36% | 0.0062 | 0.56 | 31% | 44% | 0.019 | 0.73 | 32% | 39% | |
| Top Priority | Grossman 2007 | rs946685 | 1 | IL12RB2 | 0.43 | 1.19 | 17% | 15% | 0.22 | 1.47 | 18% | 13% | 0.17 | 1.28 | 18% | 14% | |
| Top Priority | Tchelet GWAS | rs4343256 | 15 | CRTC3 | 0.47 | 1.27 | 8% | 6% | 0.71 | 0.86 | 7% | 8% | 0.72 | 1.09 | 8% | 7% | |
| | Tchelet GWAS | rs6097801 | 20 | CYP24A1 | 0.47 | 0.84 | 11% | 13% | 0.27 | 0.75 | 14% | 18% | 0.29 | 0.83 | 13% | 15% | |
| | Tchelet GWAS | rs1007328 | 15 | AC012409.1 | 0.50 | 0.89 | 48% | 51% | 0.050 | 0.66 | 47% | 57% | 0.08 | 0.80 | 48% | 53% | |
| Top Priority | Tsareva 2011 | rs231775 | 2 | CTLA4 | 0.51 | 1.12 | 42% | 39% | 0.59 | 1.11 | 40% | 37% | 0.46 | 1.10 | 41% | 38% | Missense T17A |
| Top Priority | Tchelet GWAS | rs9944913 | 18 | NOL4 | 0.52 | 0.84 | 10% | 12% | 0.054 | 0.55 | 9% | 15% | 0.08 | 0.71 | 9% | 13% | |
| Top Priority | Tchelet GWAS | rs1573706 | 20 | PTPRT | 0.55 | 0.88 | 17% | 19% | 0.15 | 0.69 | 17% | 22% | 0.19 | 0.80 | 17% | 20% | |

TABLE 2-continued

Additive Model, Candidate Variants (Gala, Forte, and Combined cohorts)

| | | | | | | GALA | | | | FORTE | | | | COMBINED | | | |
|---|---|---|---|---|---|---|---|---|---|---|---|---|---|---|---|---|---|
| | Source | Name | Ch | Gene | Armitage P-value | Odds Ratio | Allele Freq. (Resp.) | Allele Freq. (Non-Resp.) | Armitage P-value | Odds Ratio | Allele Freq. (Resp.) | Allele Freq. (Non-Resp.) | Armitage P-value | Odds Ratio | Allele Freq. (Resp.) | Allele Freq. (Non-Resp.) | Mutation |
| Top Priority | Grossman 2007 | rs1415148 | 1 | CTSS | 0.56 | 0.90 | 39% | 41% | 0.38 | 1.20 | 41% | 36% | 0.88 | 1.02 | 40% | 39% | |
| | Tchelet GWAS | rs2487896 | 10 | HPSE2 | 0.57 | 0.88 | 14% | 16% | 0.0006 | 0.39 | 12% | 25% | 0.013 | 0.65 | 13% | 19% | |
| | Tchelet GWAS | rs10931091 | 2 | AC074182.1 | 0.58 | 1.17 | 11% | 9% | 0.53 | 0.80 | 7% | 9% | 0.88 | 0.97 | 9% | 9% | |
| Top Priority | Comi | rs269976 | 18 | SLC14A2 | 0.59 | 1.18 | 8% | 7% | 0.22 | 1.75 | 8% | 5% | 0.26 | 1.32 | 8% | 6% | |
| Top Priority | Grossman 2007 | rs2275235 | 1 | CTSS | 0.62 | 0.91 | 34% | 35% | 0.25 | 1.28 | 37% | 31% | 0.66 | 1.06 | 35% | 34% | |
| | Tchelet GWAS | rs4369324 | 10 | P11-655H13 | 0.64 | 1.10 | 25% | 23% | 0.25 | 1.37 | 20% | 15% | 0.49 | 1.11 | 22% | 20% | |
| Top Priority | Tchelet GWAS | rs4148871 | 6 | TAP2 | 0.69 | 0.93 | 21% | 22% | 0.37 | 1.27 | 23% | 19% | 0.79 | 1.04 | 22% | 21% | |
| | Grossman 2007 | rs2001791 | 3 | CD86 | 0.74 | 1.08 | 14% | 13% | 0.036 | 0.58 | 13% | 21% | 0.36 | 0.85 | 14% | 16% | |
| | Tchelet GWAS | rs10988087 | 9 | SET | 0.77 | 0.89 | 4% | 4% | 0.0062 | 0.38 | 4% | 11% | 0.065 | 0.61 | 4% | 7% | |
| | Grossman 2007 | rs1129055 | 3 | CD86 | 0.83 | 1.04 | 26% | 25% | 0.40 | 0.84 | 30% | 34% | 0.97 | 0.99 | 28% | 28% | Missense A228 |
| | Tchelet GWAS | rs10853605 | 18 | MEX3C | 0.91 | 1.02 | 43% | 43% | 0.34 | 1.22 | 44% | 39% | 0.49 | 1.09 | 44% | 41% | |
| Top Priority | Comi | rs4890535 | 18 | SLC14A2 | 0.94 | 1.02 | 9% | 9% | 0.48 | 1.31 | 9% | 7% | 0.66 | 1.10 | 9% | 9% | |
| | Tchelet GWAS | rs2177073 | 18 | DTNA | 0.95 | 1.02 | 11% | 11% | 0.033 | 0.55 | 10% | 17% | 0.21 | 0.79 | 11% | 13% | |
| Top Priority | Tchelet GWAS | rs2521644 | 7 | NPY | 0.97 | 0.99 | 43% | 43% | 0.64 | 1.10 | 47% | 44% | 0.67 | 1.06 | 45% | 44% | |

TABLE 3

Allelic Model, Candidate Variants (Gala, Forte, and Combined cohorts)

| | | | | GALA | | | | | FORTE | | | | | | COMBINED | | | | | |
|---|---|---|---|---|---|---|---|---|---|---|---|---|---|---|---|---|---|---|---|---|
| Name | Ch. | Gene(s) | Fisher's Exact P | Odds Ratio (Minor Allele) | Allele Freq. Resp. | Allele Freq. (Non-Resp.) | Fisher's Exact P | Odds Ratio (Minor Allele) | Allele Freq. Resp. | Allele Freq. (Non-Resp.) | Fisher's Exact P | Odds Ratio (Minor Allele) | Allele Freq. Resp. | Allele Freq. (Non-Resp.) | DD (Cases) | Dd (Cases) | dd (Cases) | DD (Cntls) | Dd (Cntls) | dd (Cntls) |
| rs3135391 | 6 | HLA-DRB1 | 0.041 | 0.66 | 0.17 | 0.24 | 0.057 | 0.64 | 0.23 | 0.32 | 0.015 | 0.70 | 0.20 | 0.27 | 20 | 122 | 257 | 10 | 77 | 94 |
| rs3135388 | 6 | HLA-DRB1 | 0.051 | 0.67 | 0.17 | 0.24 | 0.057 | 0.64 | 0.23 | 0.32 | 0.018 | 0.70 | 0.20 | 0.27 | 20 | 122 | 257 | 10 | 76 | 94 |
| rs947603 | 10 | CEP55 | 0.066 | 1.46 | 0.26 | 0.19 | 0.16 | 1.48 | 0.23 | 0.16 | 0.027 | 1.43 | 0.24 | 0.18 | 22 | 148 | 228 | 8 | 50 | 123 |
| rs1800629 | 6 | TNF | 0.10 | 0.67 | 0.12 | 0.17 | 0.64 | 0.86 | 0.12 | 0.14 | 0.09 | 0.73 | 0.12 | 0.16 | 10 | 77 | 310 | 6 | 46 | 129 |
| rs10950359 | 7 | AC074389.1 | 0.33 | 0.83 | 0.29 | 0.33 | 0.47 | 1.24 | 0.25 | 0.21 | 0.52 | 0.91 | 0.27 | 0.29 | 39 | 138 | 222 | 14 | 77 | 90 |
| rs974060 | 7 | TAC1 | 0.33 | 1.19 | 0.32 | 0.28 | 0.82 | 0.94 | 0.27 | 0.29 | 0.68 | 1.06 | 0.30 | 0.28 | 46 | 145 | 208 | 11 | 81 | 89 |
| rs12256889 | 10 | CYP26C1 | 0.34 | 0.84 | 0.31 | 0.35 | 0.07 | 1.53 | 0.33 | 0.25 | 0.79 | 1.04 | 0.32 | 0.31 | 39 | 178 | 182 | 19 | 75 | 87 |
| rs17771939 | 8 | AC016885.1 | 0.36 | 1.19 | 0.29 | 0.26 | 0.004 | 0.53 | 0.28 | 0.43 | 0.33 | 0.88 | 0.29 | 0.31 | 35 | 159 | 205 | 22 | 70 | 89 |
| rs4344916 | 2 | AC083939.1 | 0.38 | 1.18 | 0.34 | 0.30 | 0.45 | 0.85 | 0.34 | 0.38 | 0.74 | 1.05 | 0.34 | 0.33 | 52 | 167 | 179 | 18 | 83 | 80 |
| rs11599624 | 10 | RP11-655H13.1 | 0.42 | 1.23 | 0.15 | 0.13 | 0.62 | 1.27 | 0.11 | 0.09 | 0.45 | 1.17 | 0.13 | 0.12 | 7 | 92 | 300 | 3 | 36 | 142 |
| rs6897932 | 5 | IL7Ra | 0.43 | 0.84 | 0.20 | 0.23 | 0.63 | 0.89 | 0.24 | 0.26 | 0.45 | 0.89 | 0.22 | 0.24 | 21 | 135 | 242 | 13 | 62 | 106 |
| rs1558896 | 7 | TAC1 | 0.43 | 1.17 | 0.34 | 0.30 | 0.91 | 0.96 | 0.29 | 0.30 | 0.73 | 1.05 | 0.31 | 0.30 | 53 | 142 | 203 | 11 | 87 | 83 |
| rs17575455 | 2 | AC078940.2 | 0.44 | 0.87 | 0.33 | 0.36 | 0.006 | 0.56 | 0.31 | 0.44 | 0.023 | 0.73 | 0.32 | 0.39 | 42 | 170 | 186 | 26 | 89 | 66 |
| rs946685 | 15 | IL12RB2 | 0.44 | 1.20 | 0.17 | 0.15 | 0.27 | 1.41 | 0.18 | 0.13 | 0.20 | 1.27 | 0.18 | 0.14 | 10 | 119 | 268 | 2 | 48 | 131 |
| rs6097801 | 20 | CYP24A1 | 0.46 | 0.83 | 0.11 | 0.13 | 0.24 | 0.72 | 0.14 | 0.18 | 0.26 | 0.82 | 0.13 | 0.15 | 14 | 72 | 313 | 3 | 48 | 130 |
| rs11617134 | 13 | RP11-629E24.2 | 0.48 | 0.74 | 0.05 | 0.07 | 1.00 | 1.03 | 0.07 | 0.07 | 0.69 | 0.88 | 0.06 | 0.07 | 3 | 41 | 355 | 1 | 22 | 158 |
| rs1007328 | 15 | AC012409.1 | 0.51 | 0.90 | 0.48 | 0.51 | 0.063 | 0.67 | 0.47 | 0.57 | 0.10 | 0.80 | 0.48 | 0.53 | 88 | 204 | 107 | 48 | 96 | 37 |
| rs4343256 | 15 | CRTC3 | 0.53 | 1.26 | 0.08 | 0.06 | 0.70 | 0.87 | 0.07 | 0.08 | 0.81 | 1.09 | 0.08 | 0.07 | 1 | 58 | 340 | 0 | 25 | 155 |
| rs231775 | 2 | CTLA4 | 0.56 | 1.11 | 0.42 | 0.39 | 0.60 | 1.13 | 0.40 | 0.37 | 0.48 | 1.10 | 0.41 | 0.38 | 68 | 189 | 142 | 28 | 83 | 70 |
| rs2487896 | 10 | HPSE2 | 0.56 | 0.88 | 0.14 | 0.16 | 0.001 | 0.43 | 0.12 | 0.25 | 0.016 | 0.66 | 0.13 | 0.19 | 6 | 92 | 301 | 6 | 55 | 119 |
| rs1573706 | 20 | PTPRT | 0.59 | 0.88 | 0.17 | 0.19 | 0.18 | 0.70 | 0.17 | 0.22 | 0.21 | 0.81 | 0.17 | 0.20 | 7 | 120 | 272 | 7 | 58 | 116 |
| rs9944913 | 18 | NOL4 | 0.60 | 0.85 | 0.10 | 0.12 | 0.060 | 0.55 | 0.09 | 0.15 | 0.10 | 0.71 | 0.09 | 0.13 | 2 | 71 | 326 | 3 | 40 | 138 |
| rs1415148 | 1 | CTSS | 0.62 | 0.91 | 0.39 | 0.41 | 0.40 | 1.22 | 0.41 | 0.36 | 0.90 | 1.02 | 0.40 | 0.39 | 60 | 195 | 142 | 27 | 88 | 66 |
| rs269976 | 18 | SLC14A2 | 0.65 | 1.19 | 0.08 | 0.07 | 0.32 | 1.73 | 0.08 | 0.05 | 0.29 | 1.33 | 0.08 | 0.06 | 3 | 60 | 336 | 2 | 19 | 160 |
| rs2275235 | 1 | CTSS | 0.67 | 0.92 | 0.34 | 0.35 | 0.28 | 1.30 | 0.37 | 0.31 | 0.69 | 1.06 | 0.35 | 0.34 | 47 | 187 | 164 | 19 | 85 | 77 |
| rs10931091 | 2 | AC074182.1 | 0.68 | 1.16 | 0.11 | 0.09 | 0.56 | 0.78 | 0.07 | 0.09 | 0.91 | 0.97 | 0.09 | 0.09 | 3 | 65 | 331 | 3 | 27 | 150 |
| rs4148871 | 6 | TAP2 | 0.69 | 0.92 | 0.21 | 0.22 | 0.45 | 1.26 | 0.23 | 0.19 | 0.82 | 1.04 | 0.22 | 0.21 | 18 | 137 | 244 | 10 | 56 | 115 |
| rs4369324 | 10 | RP11-655H13.2 | 0.70 | 1.10 | 0.25 | 0.23 | 0.29 | 1.41 | 0.20 | 0.15 | 0.49 | 1.12 | 0.22 | 0.20 | 23 | 132 | 244 | 9 | 56 | 116 |
| rs2001791 | 3 | CD86 | 0.81 | 1.09 | 0.14 | 0.13 | 0.044 | 0.57 | 0.13 | 0.21 | 0.37 | 0.85 | 0.14 | 0.16 | 11 | 87 | 301 | 5 | 47 | 129 |
| rs10988087 | 9 | SET | 0.83 | 0.89 | 0.04 | 0.04 | 0.008 | 0.36 | 0.04 | 0.11 | 0.08 | 0.60 | 0.04 | 0.07 | 1 | 31 | 367 | 1 | 22 | 156 |
| rs10853605 | 18 | MEX3C | 0.93 | 1.02 | 0.43 | 0.43 | 0.35 | 1.23 | 0.44 | 0.39 | 0.52 | 1.09 | 0.44 | 0.41 | 79 | 190 | 130 | 27 | 96 | 58 |
| rs2521644 | 7 | NPY | 1.00 | 0.99 | 0.43 | 0.43 | 0.68 | 1.11 | 0.47 | 0.44 | 0.70 | 1.06 | 0.45 | 0.44 | 83 | 193 | 123 | 33 | 92 | 56 |
| rs2177073 | 18 | DTNA | 1.00 | 1.02 | 0.11 | 0.11 | 0.036 | 0.53 | 0.10 | 0.17 | 0.23 | 0.78 | 0.11 | 0.13 | 4 | 77 | 317 | 5 | 38 | 138 |
| rs4890535 | 18 | SLC14A2 | 1.00 | 1.02 | 0.09 | 0.09 | 0.59 | 1.31 | 0.09 | 0.07 | 0.74 | 1.11 | 0.09 | 0.09 | 5 | 65 | 329 | 4 | 23 | 154 |
| rs1129055 | 3 | CD86 | 1.00 | 1.00 | 0.25 | 0.26 | 1.00 | 1.00 | 0.31 | 0.30 | 1.00 | 1.00 | 0.28 | 0.28 | 45 | 236 | 299 | 33 | 158 | 208 |

TABLE 4

Genotypic Model, Candidate Variants (Gala, Forte, and Combined cohorts)

| | Source | Name | Ch | Gene | GALA Fisher's Exact P | GALA Allele Freq. (Resp.) | GALA Allele Freq. (Non-Resp.) | FORTE Fisher's Exact P | FORTE Allele Freq. (Resp.) | FORTE Allele Freq. (Non-Resp.) | COMBINED Fisher's Exact P | COMBINED Allele Freq. (Resp.) | COMBINED Allele Freq. (Non-Resp.) | DD (Cases) | DD (Controls) | Dd (Cases) | Dd (Controls) | dd (Cases) | dd (Controls) |
|---|---|---|---|---|---|---|---|---|---|---|---|---|---|---|---|---|---|---|---|
| Top Priority | Comi | rs1558896 | 7 | TAC1 | 0.0043 | 34% | 30% | 0.38 | 29% | 30% | 0.0029 | 31% | 30% | 53 | 11 | 142 | 87 | 203 | 83 |
| Top Priority | Comi | rs974060 | 7 | TAC1 | 0.040 | 32% | 28% | 0.60 | 27% | 29% | 0.042 | 30% | 28% | 46 | 11 | 145 | 81 | 208 | 89 |
| | Previous GWAS | rs947603 | 10 | CEP55 | 0.055 | 26% | 19% | 0.43 | 23% | 16% | 0.050 | 24% | 18% | 22 | 8 | 148 | 50 | 228 | 123 |
| | Previous GWAS | rs10853605 | 18 | MEX3C | 0.11 | 43% | 43% | 0.54 | 44% | 39% | 0.31 | 44% | 41% | 79 | 27 | 190 | 96 | 130 | 58 |
| Top Priority | Tchelet GWAS | rs3135391 | 6 | HLA-DRB1 | 0.11 | 17% | 24% | 0.0093 | 23% | 32% | 0.014 | 20% | 27% | 20 | 10 | 122 | 77 | 257 | 94 |
| | Tsareva 2011 | rs1800629 | 6 | TNF | 0.13 | 12% | 17% | 0.33 | 12% | 14% | 0.19 | 12% | 16% | 10 | 6 | 77 | 46 | 310 | 129 |
| Top Priority | Tchelet GWAS | rs3135388 | 6 | HLA-DRB1 | 0.14 | 17% | 24% | 0.0093 | 23% | 32% | 0.018 | 20% | 27% | 20 | 10 | 122 | 76 | 257 | 94 |
| | Previous GWAS | rs10950359 | 7 | AC074389.1 | 0.15 | 29% | 33% | 0.54 | 25% | 21% | 0.18 | 27% | 29% | 39 | 14 | 138 | 77 | 222 | 90 |
| | Grossman 2007 | rs2001791 | 3 | CD86 | 0.19 | 14% | 13% | 0.052 | 13% | 21% | 0.56 | 14% | 16% | 11 | 5 | 87 | 47 | 301 | 129 |
| | Previous GWAS | rs6097801 | 20 | CYP24A1 | 0.20 | 11% | 13% | 0.19 | 14% | 18% | 0.042 | 13% | 15% | 14 | 3 | 72 | 48 | 313 | 130 |
| | Previous GWAS | rs10931091 | 2 | AC074182.1 | 0.26 | 11% | 9% | 0.64 | 7% | 9% | 0.54 | 9% | 9% | 3 | 3 | 65 | 27 | 331 | 150 |
| | Previous GWAS | rs1007328 | 15 | AC012409.1 | 0.29 | 48% | 51% | 0.10 | 47% | 57% | 0.20 | 48% | 53% | 88 | 48 | 204 | 96 | 107 | 37 |
| | Previous GWAS | rs17575455 | 2 | AC078940.2 | 0.30 | 33% | 36% | 0.018 | 31% | 44% | 0.055 | 32% | 39% | 42 | 26 | 170 | 89 | 186 | 66 |
| Top Priority | Comi | rs4890535 | 18 | SLC14A2 | 0.33 | 9% | 9% | 0.91 | 9% | 7% | 0.37 | 9% | 9% | 5 | 4 | 65 | 23 | 329 | 154 |
| | Previous GWAS | rs1573706 | 20 | PTPRT | 0.37 | 17% | 19% | 0.33 | 17% | 22% | 0.24 | 17% | 20% | 7 | 7 | 120 | 58 | 272 | 116 |
| | Previous GWAS | rs12256889 | 10 | CYP26C1 | 0.41 | 31% | 35% | 0.021 | 33% | 25% | 0.75 | 32% | 31% | 39 | 19 | 178 | 75 | 182 | 87 |
| Top Priority | Grossman 2007 | rs1415148 | 2 | CTSS | 0.42 | 39% | 41% | 0.60 | 41% | 36% | 0.99 | 40% | 39% | 60 | 27 | 195 | 88 | 142 | 66 |
| | Previous GWAS | rs4344916 | 2 | AC083939.1 | 0.51 | 34% | 30% | 0.67 | 34% | 38% | 0.49 | 34% | 33% | 52 | 18 | 167 | 83 | 179 | 80 |
| | Grossman 2007 | rs2275235 | 1 | CTSS | 0.54 | 34% | 35% | 0.37 | 37% | 31% | 0.90 | 35% | 34% | 47 | 19 | 187 | 85 | 164 | 77 |
| Top Priority | Comi | rs269976 | 18 | SLC14A2 | 0.55 | 8% | 7% | 0.47 | 8% | 5% | 0.25 | 8% | 6% | 3 | 2 | 60 | 19 | 336 | 160 |
| | Previous GWAS | rs11617134 | 13 | RP11-629E24.2 | 0.57 | 5% | 7% | 0.90 | 7% | 7% | 0.82 | 6% | 7% | 3 | 1 | 41 | 22 | 355 | 158 |
| Top Priority | Grossman 2007 | rs946685 | 1 | IL12RB2 | 0.65 | 17% | 15% | 0.47 | 18% | 13% | 0.40 | 18% | 14% | 10 | 2 | 119 | 48 | 268 | 131 |
| Top Priority | Tchelet GWAS | rs17771939 | 8 | AC016885.1 | 0.67 | 29% | 26% | 0.0095 | 28% | 43% | 0.44 | 29% | 31% | 35 | 22 | 159 | 70 | 205 | 89 |
| | Tsareva 2011 | rs6897932 | 5 | IL7Ra | 0.68 | 20% | 23% | 0.39 | 24% | 26% | 0.62 | 22% | 24% | 21 | 13 | 135 | 62 | 242 | 106 |
| | Tchelet GWAS | rs4148871 | 6 | TAP2 | 0.69 | 21% | 22% | 0.73 | 23% | 19% | 0.66 | 22% | 21% | 18 | 10 | 137 | 56 | 244 | 115 |
| | Previous GWAS | rs2487896 | 10 | HPSE2 | 0.71 | 14% | 16% | 0.0019 | 12% | 25% | 0.049 | 13% | 19% | 6 | 6 | 92 | 55 | 301 | 119 |
| | Previous GWAS | rs11599624 | 10 | RP11-655H13.1 | 0.72 | 15% | 13% | 0.44 | 11% | 9% | 0.69 | 13% | 12% | 7 | 3 | 92 | 36 | 300 | 142 |
| | Previous GWAS | rs2177073 | 18 | DTNA | 0.77 | 11% | 11% | 0.053 | 10% | 17% | 0.23 | 11% | 13% | 4 | 5 | 77 | 38 | 317 | 138 |
| | Grossman 2007 | rs1129055 | 3 | CD86 | 0.78 | 26% | 25% | 0.61 | 30% | 34% | 0.67 | 28% | 28% | 33 | 12 | 158 | 78 | 208 | 91 |
| Top Priority | Tsareva 2011 | rs231775 | 2 | CTLA4 | 0.81 | 42% | 39% | 0.32 | 40% | 37% | 0.77 | 41% | 38% | 68 | 28 | 189 | 83 | 142 | 70 |
| | Previous GWAS | rs10988087 | 9 | SET | 0.83 | 4% | 4% | 0.015 | 4% | 11% | 0.15 | 4% | 7% | 1 | 1 | 31 | 22 | 367 | 156 |
| | Previous GWAS | rs4343256 | 15 | CRTC3 | 0.84 | 8% | 6% | 0.69 | 7% | 8% | 0.93 | 8% | 7% | 1 | 0 | 58 | 25 | 340 | 155 |
| Top Priority | Tchelet GWAS | rs9944913 | 18 | NOL4 | 0.84 | 10% | 12% | 0.073 | 9% | 15% | 0.14 | 9% | 13% | 3 | 3 | 71 | 40 | 326 | 138 |
| | Previous GWAS | rs4369324 | 10 | RP11-655H13.2 | 0.86 | 25% | 23% | 0.29 | 20% | 15% | 0.82 | 22% | 20% | 23 | 9 | 132 | 56 | 244 | 116 |
| Top Priority | Tchelet GWAS | rs2521644 | 7 | NPY | 1.00 | 43% | 43% | 0.83 | 47% | 44% | 0.76 | 45% | 44% | 83 | 33 | 193 | 92 | 123 | 56 |

In some embodiments genetic markers presented in Tables 2, 3 and 4 are identified as predictive of response to glatiramer acetate if the p-value for the GALA cohort is less than about 0.12, less than about 0.08, less than about 0.05, less than about 0.01 or less than about 0.005.

In some embodiments genetic markers presented in Tables 2, 3 and 4 are identified as predictive of response to glatiramer acetate if the p-value for the FORTE cohort is less than about 0.12, less than about 0.08, less than about 0.05, less than about 0.01, less than about 0.005 or less than about 0.001.

In some embodiments genetic markers presented in Tables 2, 3 and 4 are identified as predictive of response to glatiramer acetate if the p-value for the Combined cohort is less than about 0.12, less than about 0.08, less than about 0.05, less than about 0.01, less than about 0.005 or less than about 0.001.

Example 6 Analysis Part 2—Analysis of Candidate Genes (30)

The second analysis was limited to a selected set of genetic variants in 30 priority candidate genes (4,012 variants). Power (80%) to identify significant genetic associations with an odds ratio >4, for variants with an allele frequency greater than 10%. (Or rare alleles (5%) with an odds ratio >6).

Results for Standard Response Definition, Top 30 Candidate Genes Selected a priori for Additive, Allelic and Genotypic models are presented in tables 5-7, respectively.

In some embodiments genetic markers presented in Tables 5, 6 and 7 are identified as predictive of response to glatiramer acetate if the p-value for the GALA cohort is less than about 0.05, less than about 0.01 or less than about 0.005.

In some embodiments genetic markers presented in Tables 5, 6 and 7 are identified as predictive of response to glatiramer acetate if the p-value for the FORTE cohort is less than about 0.10, less than about 0.05, less than about 0.01, less than about 0.005 or less than about 0.001.

TABLE 5

Additive Model, Analysis of Candidate Genes (30) (Gala, Forte, and Combined cohorts)

| Name | Ch. | Gene(s) | GALA ||||  FORTE |||| COMBINED ||
|---|---|---|---|---|---|---|---|---|---|---|---|---|
| | | | Armitage P-value | Odds Ratio | Allele Freq. Resp.) | Allele Freq. (Non-Resp.) | Armitage P-value | Odds Ratio | Allele Freq. Resp.) | Allele Freq. (Non-Resp.) | Armitage P-value | Odds Ratio |
| rs1894407 | 6 | HLA-DOB/TAP2 | 0.002 | 1.77 | 42% | 30% | 0.02 | 1.72 | 40% | 29% | 0.00011 | 1.73 |
| rs1894406 | 6 | HLA-DOB/TAP2 | 0.003 | 1.74 | 40% | 29% | 0.02 | 1.76 | 36% | 25% | 0.00027 | 1.68 |
| kgp11795987 | 6 | ? | 0.003 | 2.04 | 20% | 11% | 0.22 | 1.46 | 16% | 11% | 0.00276 | 1.75 |
| rs1894408 | 6 | HLA-DOB/TAP2 | 0.003 | 1.72 | 42% | 31% | 0.01 | 1.82 | 41% | 28% | 0.00010 | 1.73 |
| kgp9296959 | 10 | ? | 0.004 | 0.20 | 1% | 5% | 0.20 | 2.59 | 4% | 2% | 0.30615 | 0.69 |
| kgp 12268594 | 3 | ? | 0.004 | 0.23 | 1% | 5% | 0.40 | 0.59 | 2% | 3% | 0.00427 | 0.35 |
| kgp26488438 | 6 | TAP 1 | 0.004 | 0.23 | 1% | 5% | 0.57 | 1.85 | 1% | 1% | 0.01316 | 0.37 |
| kgp8900813 | 6 | ? | 0.004 | 1.96 | 20% | 11% | 0.23 | 1.44 | 16% | 11% | 0.00456 | 1.69 |
| kgp6474885 | 6 | TNF | 0.004 | 1.96 | 20% | 11% | 0.26 | 1.41 | 16% | 125 | 0.00506 | 1.68 |
| rs909253 | 6 | TAP2 | 0.004 | 0.61 | 25% | 36% | 0.81 | 0.94 | 27% | 28% | 0.01033 | 0.70 |
| kgp5854183 | 18 | NOL4, NOL4, NOL4, NOL4, NOL4 | 0.005 | 0.14 | 1% | 3% | 0.65 | 1.34 | 3% | 2% | 0.21372 | 0.61 |
| kgp9319993 | 3 | CCR5,CCR5 | 0.005 | 1.60 | 48% | 37% | 0.76 | 1.06 | 45% | 43% | 0.01738 | 1.36 |
| rs2857103 | 6 | TAP2 | 0.006 | 1.70 | 37% | 27% | 0.00 | 2.04 | 36% | 22% | 0.00011 | 1.78 |
| kgp10224254 | 6 | HLA-DOB | 0.006 | 1.63 | 42% | 32% | 0.04 | 1.58 | 39% | 29% | 0.00115 | 1.56 |
| kgp418674 | 6 | LTA, LTA | 0.006 | 0.62 | 25% | 36% | 0.78 | 0.94 | 27% | 28% | 0.01249 | 0.71 |
| rs241451 | 6 | TAP2 | 0.006 | 1.69 | 77% | 27% | 0.01 | 1.86 | 35% | 23% | 0.00026 | 1.72 |
| kgp6137749 | 3 | CCR5, CCR5 | 0.006 | 1.58 | 48% | 37% | 0.85 | 1.04 | 45% | 44% | 0.02225 | 1.34 |
| rs9501224 | 6 | TAP2 | 0.007 | 1.69 | 37% | 27% | 0.00 | 2.04 | 36% | 22% | 0.00013 | 1.77 |
| kgp9296977 | 3 | ? | 0.007 | 1.61 | 37% | 26% | 0.49 | 1.16 | 35% | 31% | 0.00963 | 1.42 |
| rs2071469 | 6 | FILA-DOB | 0.007 | 1.62 | 43% | 32% | 0.04 | 1.58 | 39% | 29% | 0.00140 | 1.55 |
| kgp10991488 | 3 | CCR5, CCR5 | 0.007 | 1.57 | 48% | 37% | 0.75 | 1.07 | 45% | 43% | 0.02091 | 1.35 |
| kgp12106435 | 18 | MBP, MBP | 0.007 | 0.52 | 9% | 16% | 0.08 | 0.57 | 7% | 12% | 0.03055 | 0.52 |
| kgp9394249 | 18 | MBP, MBP | 0.009 | ~Infinity | 3% | 0% | 0.78 | 0.84 | 2% | 2% | 0.08317 | 2.77 |
| kgp4490237 | 6 | ? | 0.009 | 0.28 | 2% | 5% | 0.57 | 1.85 | 1% | 1% | 0.02180 | 0.40 |
| kgp3275166 | 18 | SLC14A2 | 0.010 | ? | 0% | 2% | 0.86 | 1.22 | 1% | 1% | 0.11305 | 0.36 |
| kgp7178883 | 18 | SLC14A2 | 0.010 | 0.27 | 1% | 5% | 0.26 | 3.12 | 3% | 1% | 0.11795 | 0.56 |
| rs241443 | 6 | TAP2 | 0.011 | 1.63 | 37% | 27% | 0.01 | 2.01 | 35% | 22% | 0.00030 | 1.71 |
| kgp5249257 | 3 | CCR5, CCR5 | 0.011 | 1.56 | 37% | 27% | 0.37 | 1.22 | 35% | 30% | 0.00992 | 1.42 |
| kgp721209 | 3 | CCR5, CCR5 | 0.011 | 1.56 | 37% | 27% | 0.37 | 1.22 | 35% | 30% | 0.00992 | 1.42 |
| kgp4209856 | 3 | ? | 0.011 | 1.56 | 37% | 27% | 0.57 | 1.14 | 35% | 32% | 0.01636 | 1.39 |
| kgp10626023 | 18 | NOL4, NOL4, NOL4, NOL4, NOL4 | 0.011 | 1.72 | 24% | 15% | 0.70 | 1.11 | 20% | 18% | 0.03243 | 1.42 |
| kgp5162959 | 3 | CCR5,CCR5 | 0.011 | 1.55 | 37% | 27% | 0.34 | 1.23 | 35% | 30% | 0.00913 | 1.42 |
| kgp2033254 | 6 | PSMB9 | 0.012 | 0.17 | 1% | 3% | 0.68 | 0.60 | 0% | 1% | 0.00750 | 0.22 |
| kgp3509792 | 18 | NOL4, NOL4, NOL4, NOL4, NOL4 | 0.013 | 0.42 | 3% | 8% | 0.10 | 3.26 | 5% | 2% | 0.21865 | 0.71 |

TABLE 5-continued

Additive Model, Analysis of Candidate Genes (30) (Gala, Forte, and Combined cohorts)

| | | | | | | | Combined | | | | | |
|---|---|---|---|---|---|---|---|---|---|---|---|---|
| Name | Allele Freq. Resp.) | Allele Freq. (Non-Resp.) | DD (Cases) | DD (Controls) | Dd (Cases) | Dd (Controls) | dd (Cases) | dd (Controls) | D (Cases) | D (Controls) | d (Cases) | d (Controls) |
| rs1894407 | 41% | 30% | 57 | 16 | 213 | 75 | 128 | 90 | 327 | 107 | 469 | 255 |
| rs1894406 | 38% | 27% | 51 | 13 | 202 | 73 | 146 | 95 | 304 | 99 | 494 | 263 |
| kgp11795987 | 18% | 11% | 16 | 3 | 111 | 33 | 271 | 144 | 143 | 39 | 653 | 321 |
| rs1894408 | 41% | 30% | 58 | 16 | 211 | 74 | 127 | 89 | 327 | 106 | 465 | 252 |
| kgp9296959 | 3% | 4% | 0 | 0 | 20 | 13 | 376 | 168 | 20 | 13 | 772 | 349 |
| kgp 12268594 | 2% | 4% | 0 | 0 | 13 | 16 | 386 | 165 | 13 | 16 | 785 | 346 |
| kgp26488438 | 1% | 4% | 0 | 0 | 11 | 13 | 388 | 168 | 11 | 13 | 787 | 349 |
| kgp8900813 | 18% | 11% | 16 | 3 | 112 | 35 | 270 | 143 | 144 | 41 | 652 | 321 |
| kgp6474885 | 18% | 11% | 16 | 3 | 112 | 35 | 270 | 142 | 144 | 41 | 652 | 319 |
| rs909253 | 26% | 33% | 30 | 19 | 146 | 83 | 220 | 79 | 206 | 121 | 586 | 241 |
| kgp5854183 | 2% | 3% | 0 | 0 | 15 | 11 | 383 | 170 | 15 | 11 | 781 | 351 |
| kgp9319993 | 47% | 39% | 84 | 30 | 203 | 82 | 110 | 69 | 371 | 142 | 423 | 220 |
| rs2857103 | 36% | 25% | 39 | 11 | 211 | 69 | 149 | 100 | 289 | 91 | 509 | 269 |
| kgp10224254 | 40% | 31% | 59 | 18 | 205 | 75 | 135 | 88 | 323 | 111 | 475 | 251 |
| kgp418674 | 26% | 33% | 30 | 19 | 147 | 82 | 222 | 80 | 207 | 120 | 591 | 242 |
| rs241451 | 36% | 26% | 39 | 12 | 207 | 68 | 150 | 100 | 285 | 92 | 507 | 268 |
| kgp6137749 | 47% | 40% | 85 | 30 | 201 | 83 | 111 | 68 | 371 | 143 | 423 | 219 |
| rs9501224 | 36% | 25% | 39 | 11 | 211 | 70 | 149 | 100 | 289 | 92 | 509 | 270 |
| kgp9296977 | 36% | 28% | 53 | 16 | 178 | 68 | 167 | 96 | 284 | 100 | 512 | 260 |
| rs2071469 | 41% | 31% | 59 | 18 | 205 | 76 | 134 | 87 | 323 | 112 | 473 | 250 |
| kgp10991488 | 47% | 39% | 85 | 30 | 194 | 81 | 110 | 68 | 364 | 141 | 414 | 217 |
| kgp12106435 | 8% | 15% | 4 | 7 | 54 | 39 | 334 | 132 | 62 | 53 | 722 | 303 |
| kgp9394249 | 2% | 1% | 1 | 0 | 17 | 3 | 379 | 177 | 19 | 3 | 775 | 357 |
| kgp4490237 | 2% | 4% | 0 | 0 | 12 | 13 | 387 | 168 | 12 | 13 | 786 | 349 |
| kgp3275166 | 1% | 1% | 0 | 0 | 4 | 5 | 394 | 176 | 4 | 5 | 792 | 357 |
| kgp7178883 | 2% | 3% | 1 | 1 | 12 | 10 | 384 | 169 | 14 | 12 | 780 | 348 |
| rs241443 | 36% | 25% | 40 | 11 | 202 | 69 | 152 | 99 | 282 | 91 | 506 | 267 |
| kgp5249257 | 36% | 28% | 54 | 17 | 177 | 67 | 167 | 97 | 285 | 101 | 511 | 261 |
| kgp721209 | 36% | 28% | 54 | 17 | 177 | 67 | 167 | 97 | 285 | 101 | 511 | 261 |
| kgp4209856 | 36% | 28% | 53 | 17 | 178 | 68 | 167 | 95 | 284 | 102 | 512 | 258 |
| kgp10626023 | 22% | 16% | 17 | 9 | 140 | 41 | 242 | 131 | 174 | 59 | 624 | 303 |
| kgp5162959 | 36% | 28% | 54 | 17 | 177 | 67 | 166 | 97 | 285 | 101 | 509 | 261 |
| kgp2033254 | 1% | 2% | 0 | 0 | 4 | 8 | 394 | 173 | 4 | 8 | 792 | 354 |
| kgp3509792 | 4% | 6% | 1 | 1 | 31 | 19 | 367 | 161 | 33 | 21 | 765 | 341 |

TABLE 5b

Additive Model, Analysis of Candidate Genes (30)-replicated p < 0.05 (Gala, Forte, and Combined cohorts)

| | | | GALA | | | | FORTE | | | |
|---|---|---|---|---|---|---|---|---|---|---|
| Name | Ch | Gene | Armitage P-value | Odds Ratio | Allele Freq. (Resp | Allele Freq. (Non-Resp | Armitage P-value | Odds Ratio | Allele Freq. (Resp | Allele Freq. (Non-Resp |
| rs1894407 | 6 | HLA-DOB/TAP2 | 0.002 | 1.77 | 42% | 30% | 0.02 | 1.72 | 40% | 29% |
| rs1894406 | 6 | HLA-DOB/TAP2 | 0.003 | 1.74 | 40% | 29% | 0.02 | 1.76 | 36% | 25% |
| rs1894408 | 6 | HLA-DOB/TAP2 | 0.003 | 1.72 | 42% | 31% | 0.01 | 1.82 | 41% | 28% |
| rs2857103 | 6 | TAP2 | 0.006 | 1.70 | 37% | 27% | 0.00 | 2.04 | 36% | 22% |
| kgp10224254 | 6 | HLA-DOB | 0.006 | 1.63 | 42% | 32% | 0.04 | 1.58 | 39% | 29% |
| rs241451 | 6 | TAP2 | 0.006 | 1.69 | 37% | 27% | 0.01 | 1.86 | 35% | 23% |
| rs9501224 | 6 | TAP2 | 0.007 | 1.69 | 37% | 27% | 0.00 | 2.04 | 36% | 22% |
| rs2071469 | 6 | HLA-DOB | 0.007 | 1.62 | 43% | 32% | 0.04 | 1.58 | 39% | 29% |
| rs241443 | 6 | TAP2 | 0.011 | 1.63 | 37% | 27% | 0.01 | 2.01 | 35% | 22% |
| rs2621323 | 6 | HLA-DOB/TAP2 | 0.019 | 1.56 | 37% | 29% | 0.00 | 2.07 | 36% | 22% |
| rs241456 | 6 | TAP2 | 0.021 | 1.55 | 31% | 23% | 0.01 | 2.00 | 30% | 18% |
| rs2621321 | 6 | HLA-DOB/TAP2 | 0.024 | 1.54 | 32% | 23% | 0.01 | 2.05 | 30% | 18% |
| rs2857104 | 6 | TAP2 | 0.024 | 1.54 | 32% | 23% | 0.01 | 2.03 | 30% | 18% |
| rs2857101 | 6 | TAP2 | 0.025 | 1.53 | 11% | 23% | 0.01 | 2.00 | 30% | 18% |
| rs241446 | 6 | TAP2 | 0.025 | 1.53 | 31% | 23% | 0.01 | 1.96 | 30% | 18% |
| rs241454 | 6 | TAP2 | 0.026 | 1.53 | 31% | 23% | 0.01 | 2.02 | 30% | 18% |
| kgp974569 | 6 | TAP2 | 0.028 | 1.52 | 31% | 23% | 0.01 | 2.02 | 30% | 18% |
| rs241447 | 6 | TAP2 | 0.028 | 1.52 | 31% | 23% | 0.01 | 2.01 | 30% | 18% |
| rs241444 | 6 | TAP2 | 0.028 | 1.52 | 31% | 23% | 0.01 | 2.00 | 30% | 18% |
| rs2071472 | 6 | FILA-DOB | 0.029 | 1.49 | 35% | 27% | 0.02 | 1.79 | 33% | 22% |
| rs2071470 | 6 | HLA-DOB | 0.029 | 1.49 | 35% | 27% | 0.02 | 1.79 | 33% | 22% |
| rs241449 | 6 | TAP2 | 0.033 | 1.50 | 31% | 23% | 0.01 | 1.99 | 30% | 18% |

TABLE 5b-continued

Additive Model, Analysis of Candidate Genes (30)-replicated p < 0.05 (Gala, Forte, and Combined cohorts)

| Name | | | | | | | | | |
|---|---|---|---|---|---|---|---|---|---|
| rs241452 | 6 | TAP2 | 0.033 | 1.50 | 31% | 24% | 0.01 | 2.01 | 30% | 18% |
| rs241453 | 6 | TAP2 | 0.034 | 1.50 | 31% | 23% | 0.01 | 2.02 | 30% | 18% |
| rs241440 | 6 | TAP2 | 0.034 | 1.50 | 31% | 23% | 0.01 | 1.96 | 30% | 18% |
| kgp8036704 | 6 | TAP2 | 0.035 | 1.50 | 31% | 23% | 0.01 | 2.02 | 30% | 18% |
| kgp7747883 | 18 | MBP | 0.036 | 0.70 | 35% | 43% | 0.01 | 0.57 | 33% | 45% |
| rs241445 | 6 | TAP2 | 0.036 | 1.49 | 31% | 24% | 0.01 | 2.00 | 30% | 18% |
| P1_M_06151 | 6 | TAP2 | 0.037 | 1.49 | 31% | 23% | 0.01 | 2.02 | 30% | 18% |
| rs241442 | 6 | TAP2 | 0.039 | 1.48 | 31% | 24% | 0.01 | 2.02 | 30% | 18% |
| kgp2388352 | 6 | TAP2 | 0.042 | 1.47 | 31% | 24% | 0.01 | 2.02 | 30% | 18% |
| kgp25543811 | 18 | MBP | 0.048 | 0.15 | 0% | 2% | 0.01 | 0.10 | 0% | 2% |
| kgp4346717 | 18 | MBP | 0.049 | 0.15 | 0% | 2% | 0.01 | ? | 0% | 2% |
| kgp3182607 | 6 | PSMB9 | 0.049 | 0.15 | 0% | 2% | 0.02 | 0.23 | 1% | 4% |
| rs241435 | 6 | TAP2 | 0.049 | 0.15 | 0% | 2% | 0.02 | 0.23 | 1% | 4% |
| kgp26271158 | 6 | PSMB9 | 0.049 | 0.15 | 0% | 2% | 0.04 | 0.29 | 1% | 4% |

| | COMBINED | | | | | | | | |
|---|---|---|---|---|---|---|---|---|---|
| Name | Armitage P-value | Odds Ratio | Allele Freq. (Resp | Allele Freq. (Non-Resp | DD (Case | DD (Controls) | Dd (Case | Dd (Controls) | dd (Case | dd (Controls) |
| rs1894407 | 0.00011 | 1.73 | 41% | 30% | 57 | 16 | 213 | 75 | 128 | 90 |
| rs1894406 | 0.00027 | 1.68 | 38% | 27% | 51 | 13 | 202 | 73 | 146 | 95 |
| rs1894408 | 0.00010 | 1.73 | 41% | 30% | 58 | 16 | 211 | 74 | 127 | 89 |
| rs2857103 | 0.00011 | 1.78 | 36% | 25% | 39 | 11 | 211 | 69 | 149 | 100 |
| kgp10224254 | 0.00115 | 1.56 | 40% | 31% | 59 | 18 | 205 | 75 | 135 | 88 |
| rs241451 | 0.00026 | 1.72 | 36% | 26% | 39 | 12 | 207 | 68 | 150 | 100 |
| rs9501224 | 0.00013 | 1.77 | 36% | 25% | 39 | 11 | 211 | 70 | 149 | 100 |
| rs2071469 | 0.00140 | 1.55 | 41% | 31% | 59 | 18 | 205 | 76 | 134 | 87 |
| rs241443 | 0.00030 | 1.71 | 36% | 25% | 40 | 11 | 202 | 69 | 152 | 99 |
| rs2621323 | 0.00033 | 1.69 | 37% | 26% | 43 | 12 | 207 | 71 | 149 | 97 |
| rs241456 | 0.00086 | 1.66 | 31% | 21% | 32 | 9 | 180 | 59 | 187 | 113 |
| rs2621321 | 0.00090 | 1.66 | 31% | 22% | 31 | 9 | 183 | 60 | 184 | 112 |
| rs2857104 | 0.00099 | 1.65 | 31% | 22% | 31 | 9 | 183 | 60 | 185 | 112 |
| rs2857101 | 0.00115 | 1.64 | 30% | 21% | 31 | 9 | 181 | 59 | 187 | 112 |
| rs241446 | 0.00126 | 1.63 | 30% | 21% | 32 | 9 | 176 | 59 | 188 | 113 |
| rs241454 | 0.00102 | 1.65 | 31% | 22% | 32 | 9 | 180 | 60 | 185 | 112 |
| kgp974569 | 0.00112 | 1.64 | 31% | 22% | 32 | 9 | 180 | 60 | 186 | 112 |
| rs241447 | 0.00111 | 1.64 | 31% | 22% | 32 | 9 | 180 | 60 | 184 | 111 |
| rs241444 | 0.00122 | 1.63 | 31% | 22% | 32 | 9 | 180 | 60 | 187 | 112 |
| rs2071472 | 0.00221 | 1.56 | 34% | 25% | 40 | 12 | 191 | 67 | 168 | 102 |
| rs2071470 | 0.00221 | 1.56 | 34% | 25% | 40 | 12 | 191 | 67 | 168 | 102 |
| rs241449 | 0.00135 | 1.63 | 30% | 21% | 32 | 9 | 175 | 58 | 188 | 112 |
| rs241452 | 0.00142 | 1.62 | 31% | 22% | 32 | 9 | 179 | 60 | 186 | 111 |
| rs241453 | 0.00131 | 1.63 | 31% | 22% | 32 | 9 | 179 | 60 | 187 | 112 |
| rs241440 | 0.00179 | 1.61 | 30% | 22% | 32 | 9 | 177 | 60 | 189 | 112 |
| kgp8036704 | 0.00155 | 1.63 | 30% | 22% | 29 | 9 | 183 | 60 | 186 | 112 |
| kgp7747883 | 0.00086 | 0.64 | 34% | 44% | 43 | 33 | 181 | 92 | 174 | 56 |
| rs241445 | 0.00156 | 1.62 | 31% | 22% | 32 | 9 | 179 | 60 | 187 | 111 |
| P1_M_06151 | 0.00141 | 1.62 | 30% | 22% | 32 | 9 | 178 | 60 | 187 | 112 |
| rs241442 | 0.00156 | 1.62 | 31% | 22% | 32 | 9 | 179 | 60 | 187 | 111 |
| kgp2388352 | 0.00146 | 1.62 | 31% | 22% | 34 | 10 | 173 | 57 | 185 | 111 |
| kgp25543811 | 0.00229 | 0.12 | 0% | 2% | 0 | 0 | 2 | 7 | 397 | 173 |
| kgp4346717 | 0.00174 | 0.07 | 0% | 2% | 0 | 0 | 1 | 6 | 398 | 175 |
| kgp3182607 | 0.00685 | 0.24 | 1% | 2% | 0 | 0 | 5 | 9 | 394 | 172 |
| rs241435 | 0.00683 | 0.24 | 1% | 2% | 0 | 0 | 5 | 9 | 394 | 172 |
| kgp26271158 | 0.01475 | 0.29 | 1% | 2% | 0 | 0 | 6 | 9 | 393 | 172 |

TABLE 6

Allelic Model, Analysis of Candidate Genes (30) (Gala, Forte, and Combined cohorts)

| | | | | | GALA | | | FORTE | | |
|---|---|---|---|---|---|---|---|---|---|---|
| Name | Ch. | Gene(s) | Mutation | Gene Locations (s) | Fisher's Exact P | Odds Ratio (Minor Allele) | Allele Freq. (Cases) | Allele Freq. (Controls) | Fisher's Exact P | Odds Ratio (Minor Allele) | Allele Freq. (Cases) |
| kgp117959 | 6 | ? | ? | ? | 0.003 | 2.10 | 20% | 11% | 0.248 | 1.49 | 16% |
| kgp511087 | 17 | CCL5 | Silent | INTRON | 0.003 | 0.00 | 0% | 3% | 1.000 | ? | 0% |
| rs1894407 | 6 | ? | ? | ? | 0.003 | 1.68 | 42% | 30% | 0.0247 | 1.67 | 40% |
| kgp89008 | 6 | ? | ? | ? | 0.003 | 2.00 | 20% | 11% | 0.248 | 1.47 | 16% |
| kgp647481 | 6 | TNF | Silent | INTRON | 0.003 | 2.00 | 20% | 11% | 0.307 | 1.44 | 16% |

TABLE 6-continued

Allelic Model, Analysis of Candidate Genes (30) (Gala, Forte, and Combined cohorts)

| Name | | | | | | | | | | |
|---|---|---|---|---|---|---|---|---|---|---|
| rs1894406 | 6 | ? | ? | ? | 0.004 | 1.66 | 40% | 29% | 0.0212 | 1.73 | 36% |
| rs909253 | 6 | LTA, LTA | Silent, Sile | INTRON | 0.004 | 09 | 25% | 36% | 0.816 | 0.95 | 27% |
| rs1894408 | 6 | ? | ? | ? | 0.005 | 1.64 | 42% | 31% | 0.0105 | 1.78 | 41% |
| kgp93199 | 3 | CCR5, CCR5 | Silent, Sile | INTRON | 0.005 | 1.60 | 48% | 37% | 0.835 | 1.06 | 45% |
| kgp92969 | 3 | ? | ? | ? | 0.005 | 1.66 | 37% | 26% | 0.514 | 1.16 | 35% |
| kgp41867 | 6 | LTA, LTA | Missense | EXON | 0.005 | 003 | 25% | 36% | 0.816 | 0.94 | 27% |
| kgp71788 | 18 | SLC14A2 | Silent | INTRON | 0.006 | 0.21 | 1% | 5% | 0.471 | 3.07 | 3% |
| kgp92969 | 10 | ? | ? | ? | 0.006 | 0.21 | 1% | 5% | 0.267 | 2.53 | 4% |
| kgp12106 | 18 | MBP, MBP | Silent, Sile | INTRON | 0.006 | 0.50 | 9% | 16% | 0.089 | 0.54 | 7% |
| kgp613771 | 3 | CCR5, CCR5 | Silent, Sile | UTR | 0.007 | 1.58 | 48% | 37% | 0.917 | 1.04 | 45% |
| kgp10224 | 6 | ? | ? | ? | 0.007 | 1.59 | 42% | 32% | 0.663 | 1.56 | 39% |
| kgp58541 | 18 | NOL4, NOL4, | Silent, Sile | INTRON | 0.008 | 0.15 | 1% | 3% | 1.000 | 1.33 | 3% |
| kgp109914 | 3 | CCR5, CCR5 | Silent, Sile | INTRON | 0.008 | 1.58 | 43% | 37% | 0.755 | 1.07 | 45% |
| kgp93942 | 18 | MBP, MBP | Silent, Sile | INTRON | 0.009 | ? | 3% | 0% | 0.725 | 0.81 | 2% |
| kgp12268 | 3 | ? | ? | ? | 0.009 | 0.24 | 1% | 5% | 0.487 | 0.60 | 2% |
| kgp26488 | 6 | TAP1 | Silent | INTRON | 0.009 | 0.24 | 1% | 5% | 1.000 | 1.83 | 1% |
| kgp516295 | 3 | CCR5, CCR5 | Silent, Sile | INTRON | 0.009 | 1.60 | 37% | 27% | 0.383 | 1.24 | 35% |
| kgp52492 | 3 | CCR5, CCR5 | Silent, Sile | INTRON | 0.009 | 1.61 | 37% | 27% | 0.384 | 1.22 | 35% |
| kgp72120 | 3 | CCR5, CCR5 | Silent, Sile | UTR | 0.009 | 1.61 | 37% | 27% | 0.384 | 1.22 | 35% |
| kgp42098 | 3 | ? | ? | ? | 0.009 | 1.61 | 37% | 27% | 0.584 | 1.14 | 35% |
| rs2071469 | 6 | HLA-DOB | Silent | UTR | 0.009 | 137 | 43% | 32% | 0.053 | 1.56 | 39% |
| rs241451 | 6 | TAP2, TAP2 | Silent, Sile | INTRON | 0.011 | 1.58 | 37% | 27% | 0.0144 | 1.80 | 35% |
| rs2857103 | 6 | TAP2 | Silent | INTRON | 0.011 | 1.59 | 37% | 27% | 0.0057 | 1.94 | 36% |
| kgp10626 | 18 | NOL4, NOL4, | Silent, Sile | INTRON | 0.011 | 1.73 | 24% | 15% | 0.793 | 1.11 | 20% |
| rs9501224 | 6 | TAP2 | Silent | INTRON | 0.012 | 1.57 | 37% | 27% | 0.0057 | 1.94 | 16% |
| kgp44902 | 6 | ? | ? | ? | 0.013 | 0.29 | 2% | 5% | 1.000 | 1.83 | 1% |
| kgp58475 | 4 | IL15, IL15, IL15 | Silent, Sile | INTRON, E | 0.014 | 0.10 | 0% | 3% | 1.000 | 1.53 | 1% |
| kgp350975 | 18 | NOL4, NOL4, | Silent, Sile | INTRON | 0.014 | 0.39 | 3% | 8% | 0.127 | 3.14 | 5% |
| rs3733904 | 5 | ERAP2, ERAP | Silent, Sile | INTRON | 0.016 | 1.61 | 30% | 21% | 0.176 | 1.45 | 24% |
| kgp28530 | 18 | SLC14A2 | Silent | INTRON | 0.016 | ? | 2% | 0% | 1.000 | 1.22 | 2% |

| | FORTE | | COMBINED | | | | | | | |
|---|---|---|---|---|---|---|---|---|---|---|
| Name | Allele Freq. (Controls) | Fisher's Exact P | Odds Ratio (Minor Allele) | Allele Freq. (Resp.) | Allele Freq. (Non-(Resp.)) | DD (Cases) | DD (Controls) | Dd (Cases) | Dd (Controls) | dd (Cases) | dd (Controls) |
| kgp117959 | 11% | 0.0022 | 1.80 | 18% | 11% | 16 | 3 | 111 | 33 | 271 | 144 |
| kgp511087 | 0% | 0.0046 | 0.07 | 0% | 2% | 0 | 0 | 1 | 6 | 398 | 175 |
| rs1894407 | 29% | 0.0002 | 1.66 | 41% | 30% | 57 | 16 | 213 | 75 | 128 | 90 |
| kgp89008 | 11% | 0.0033 | 1.73 | 18% | 11% | 16 | 3 | 112 | 35 | 270 | 143 |
| kgp647481 | 12% | 0.0042 | 1.72 | 18% | 11% | 16 | 3 | 112 | 35 | 270 | 142 |
| rs1894406 | 25% | 0.0004 | 1.63 | 38% | 27% | 51 | 13 | 202 | 73 | 146 | 95 |
| rs909253 | 28% | 0.0112 | 0.70 | 26% | 33% | 30 | 19 | 146 | 83 | 220 | 79 |
| rs1894408 | 28% | 0.0002 | 1.67 | 41% | 30% | 58 | 16 | 211 | 74 | 127 | 89 |
| kgp93199 | 43% | 0.0182 | 1.36 | 47% | 39% | 84 | 30 | 203 | 82 | 110 | 69 |
| kgp92969 | 31% | 0.0086 | 1.44 | 36% | 28% | 53 | 16 | 178 | 68 | 167 | 96 |
| kgp41867d | 28% | 0.0136 | 0.71 | 26% | 33% | 30 | 19 | 147 | 82 | 222 | 80 |
| kgp71788 | 1% | 0.13 | 0.52 | 2% | 3% | 1 | 1 | 12 | 10 | 384 | 169 |
| kgp92969 | 2% | 0.34 | 0.70 | 3% | 4% | 0 | 0 | 20 | 13 | 376 | 168 |
| kgp12106 | 12% | 0.0004 | 0.49 | 8% | 15% | 4 | 7 | 54 | 39 | 334 | 132 |
| kgp613771 | 44% | 0.0255 | 1.34 | 47% | 40% | 85 | 30 | 201 | 83 | 111 | 68 |
| kgp10224 | 29% | 0.0013 | 1.54 | 40% | 31% | 59 | 18 | 205 | 75 | 135 | 88 |
| kgp58541 | 2% | 0.28 | 0.61 | 2% | 3% | 0 | 0 | 15 | 11 | 383 | 170 |
| kgp109914 | 43% | 0.0208 | 1.35 | 47% | 39% | 85 | 30 | 194 | 81 | 110 | 68 |
| kgp93942 | 2% | 0.10 | 2.92 | 2% | 1% | 1 | 0 | 17 | 3 | 379 | 177 |
| kgp12268 | 3% | 0.0075 | 0.36 | 2% | 4% | 0 | 0 | 13 | 16 | 386 | 165 |
| kgp26488 | 1% | 0.0235 | 0.38 | 1% | 4% | 0 | 0 | 11 | 13 | 388 | 168 |
| kgp516295 | 30% | 0.0087 | 1.45 | 36% | 28% | S4 | 17 | 177 | 67 | 166 | 97 |
| kgp52492 | 30% | 0.0087 | 1.44 | 36% | 28% | 54 | 17 | 177 | 67 | 167 | 97 |
| kgp72120 | 30% | 0.0087 | 1.44 | 36% | 28% | 54 | 17 | 177 | 67 | 167 | 97 |
| kgp42098 | 32% | 0.0153 | 1.40 | 36% | 28% | 53 | 17 | 178 | 68 | 167 | 95 |
| rs2071469 | 29% | 0.0017 | 1.52 | 41% | 31% | 59 | 18 | 205 | 76 | 134 | 87 |
| rs241451 | 23% | 0.0004 | 1.64 | 36% | 26% | 39 | 12 | 207 | 68 | 150 | 100 |
| rs2857103 | 22% | 0.0003 | 1.68 | 36% | 25% | 39 | 11 | 211 | 69 | 149 | 100 |
| kgp10626 | 18% | 0.0326 | 1.43 | 22% | 16% | 17 | 9 | 140 | 41 | 242 | 131 |
| rs9501224 | 22% | 0.0003 | 1.67 | 36% | 25% | 39 | 11 | 211 | 70 | 149 | 100 |
| kgp44902 | 1% | 0.0291 | 0.41 | 2% | 4% | 0 | 0 | 12 | 13 | 387 | 168 |
| kgp58475 | 1% | 0.13 | 0.39 | 1% | 2% | 0 | 0 | 6 | 7 | 390 | 174 |
| kgp350975 | 2% | 0.23 | 0.70 | 4% | 6% | 1 | 1 | 31 | 19 | 367 | 161 |
| rs3733904 | 18% | 0.0102 | 1.49 | 27% | 20% | 37 | 4 | 141 | 64 | 221 | 113 |
| kgp28530 | 2% | 0.08 | 3.92 | 2% | 1% | 0 | 0 | 17 | 2 | 382 | 179 |

TABLE 6b

Allelic Model, Analysis of Candidate Genes (30)-replicated p < 0.05 (Gala, Forte, and Combined cohorts)

| Name | Ch | Gene(s) | Mutation | Gene Locations(s) | GALA Fisher's Exact P | GALA Odds Ratio (Minor Allele) | GALA Allele Freq. (Case) | GALA Allele Freq. (Controls) | FORTE Fisher's Exact P | FORTE Odds Ratio (Minor Allele) | FORTE Allele Freq. (Case) |
|---|---|---|---|---|---|---|---|---|---|---|---|
| rs1894407 | 6 | ? | ? | ? | 0.003 | 1.68 | 42% | 30% | 0.0247 | 1.67 | 40% |
| rs1894406 | 6 | ? | ? | ? | 0.004 | 1.66 | 40% | 29% | 0.0212 | 1.73 | 36% |
| rs1894408 | 6 | ? | ? | ? | 0.005 | 1.64 | 42% | 31% | 0.0105 | 1.78 | 41% |
| rs241451 | 6 | TAP2, TAP2 | Silent, Sile | INTRON | 0.011 | 1.58 | 37% | 27% | 0.0144 | 1.80 | 35% |
| rs2857103 | 6 | TAP2 | Silent | INTRON | 0.011 | 1.59 | 37% | 27% | 0.0057 | 1.94 | 36% |
| rs9501224 | 6 | TAP2 | Silent | INTRON | 0.012 | 1.57 | 37% | 27% | 0.0057 | 1.94 | 36% |
| rs241443 | 6 | TAP2, TAP2 | Silent, Sile | INTRON, E | 0.018 | 1.54 | 37% | 2790 | 0.0071 | 1.94 | 35% |
| rs241456 | 6 | TAP2, TAP2 | Silent, Sile | INTRON | 0.023 | 1.53 | 31% | 23% | 0.0104 | 1.93 | 30% |
| rs241446 | 6 | TAP2, TAP2 | Silent, Sile | INTRON, E | 0.028 | 1.52 | 31% | 23% | 0.0140 | 1.90 | 30% |
| rs2857101 | 6 | TAP2, TAP2 | Silent, Sile | INTRON | 0.029 | 1.52 | 31% | 23% | 0.0141 | 1.91 | 30% |
| rs241454 | 6 | TAP2, TAP2 | Silent, Sile | INTRON | 0.029 | 1.51 | 31% | 23% | 0.0103 | 1.95 | 30% |
| rs2621321 | 6 | ? | ? | ? | 0.029 | 1.52 | 32% | 23% | 0.0103 | 1.95 | 30% |
| rs2857104 | 6 | TAP2 | Silent | INTRON | 0.029 | 1.52 | 32% | 23% | 0.0104 | 1.93 | 30% |
| rs2621323 | 6 | ? | ? | ? | 0.030 | 1.48 | 37% | 29% | 0.0041 | 2.01 | 36% |
| rs241449 | 6 | TAP2, TAP2 | Silent, Syn | INTRON, E | 0.034 | 1.50 | 31% | 23% | 0.0104 | 1.92 | 30% |
| rs2071472 | 6 | HLA-DOB | Silent | INTRON | 0.035 | 1.47 | 35% | 27% | 0.0246 | 1.74 | 33% |
| rs2071470 | 6 | HLA-DOB | Silent | UTR | 0.035 | 1.47 | 35% | 27% | 0.0246 | 1.74 | 33% |
| rs241447 | 6 | TAP2, TAP2 | Silent, Mis | INTRON, E | 0.037 | 1.50 | 31% | 23% | 0.0102 | 1.94 | 30% |
| kgp974569 | 6 | TAP2, TAP2 | Silent, Sile | INTRON | 0.037 | 1.50 | 31% | 23% | 0.0103 | 1.95 | 30% |
| rs241444 | 6 | TAP2, TAP2 | Silent, Sile | INTRON, E | 0.037 | 1.50 | 31% | 23% | 0.0104 | 1.93 | 30% |
| rs241452 | 6 | TAP2, TAP2 | Silent, Sile | INTRON | 0.037 | 1.48 | 31% | 24% | 0.0103 | 1.94 | 30% |
| rs241453 | 6 | TAP2, TAP2 | Silent, Sile | INTRON | 0.037 | 1.43 | 31% | 23% | 0.0103 | 1.95 | 30% |
| rs241440 | 6 | TAP2, TAP2 | Silent, Sile | INTRON | 0.037 | 1.48 | 31% | 23% | 0.0140 | 1.90 | 30% |
| kgp7747883 | 18 | MBP, MBP | Silent, Sile | INTRON | 0.043 | 0.70 | 35% | 43% | 0.0129 | 0.59 | 33% |
| kgp2388352 | 6 | TAP2, TAP2 | Synonym | EXON | 0.043 | 1.47 | 31% | 24% | 0.0076 | 1.99 | 30% |
| rs241445 | 6 | TAP2, TAP2 | Silent, Sile | INTRON, E | 0.045 | 1.48 | 31% | 24% | 0.0104 | 1.93 | 30% |
| P1_M_0615 | 6 | TAP2, TAP2 | ? | INTRON | 0.045 | 1.47 | 31% | 23% | 0.0103 | 1.95 | 30% |
| kgp8036704 | 6 | TAP2, TAP2 | Silent, Sile | INTRON | 0.045 | 1.47 | 31% | 23% | 0.0141 | 1.91 | 30% |
| rs241442 | 6 | TAP2, TAP2 | Silent, Sile | INTRON, E | 0.045 | 1.46 | 31% | 24% | 0.0103 | 1.95 | 30% |
| kgp8702370 | 3 | DNAJC13 | Silent | INTRON | 0.049 | 1.68 | 15% | 9% | 0.0079 | 2.88 | 15% |

| Name | FORTE Allele Freq. (Controls) | COMBINED Fisher's Exact | COMBINED Odds Ratio (Minor Allele) | COMBINED Allele Freq. (Case) | COMBINED Allele Freq. (Controls) | DD (Cases) | DD (Controls) | Dd (Cases) | Dd (Controls) | dd (Cases) | dd (Controls) |
|---|---|---|---|---|---|---|---|---|---|---|---|
| rs1894407 | 29% | 0.0002 | 1.66 | 41% | 30% | 57 | 16 | 213 | 75 | 128 | 90 |
| rs1894406 | 25% | 0.0004 | 1.63 | 38% | 27% | 51 | 13 | 202 | 73 | 146 | 95 |
| rs1894408 | 28% | 0.0002 | 1.67 | 41% | 30% | 58 | 16 | 211 | 74 | 127 | 89 |
| rs241451 | 23% | 0.0004 | 1.64 | 36% | 26% | 39 | 12 | 207 | 68 | 150 | 100 |
| rs2857103 | 22% | 0.0003 | 1.68 | 36% | 25% | 39 | 11 | 211 | 69 | 149 | 100 |
| rs9501224 | 22% | 0.0003 | 1.67 | 36% | 25% | 39 | 11 | 211 | 70 | 149 | 100 |
| rs241443 | 22% | 0.0005 | 1.64 | 36% | 25% | 40 | 11 | 202 | 69 | 152 | 99 |
| rs241456 | 18% | 0.0011 | 1.63 | 31% | 21% | 32 | 9 | 180 | 59 | 187 | 113 |
| rs241446 | 18% | 0.0014 | 1.61 | 30% | 21% | 32 | 9 | 176 | 59 | 188 | 113 |
| rs2857101 | 18% | 0.0014 | 1.61 | 30% | 21% | 31 | 9 | 181 | 59 | 187 | 112 |
| rs241454 | 18% | 0.0011 | 1.62 | 31% | 22% | 32 | 9 | 180 | 60 | 185 | 112 |

TABLE 6b-continued

Allelic Model, Analysis of Candidate Genes (30)-replicated p < 0.05 (Gala, Forte, and Combined cohorts)

| | | | | | | | | | | | |
|---|---|---|---|---|---|---|---|---|---|---|---|
| rs2621321 | 18% | 0.0011 | 1.62 | 31% | 22% | 31 | 9 | 183 | 60 | 184 | 112 |
| rs2857104 | 18% | 0.0012 | 1.61 | 31% | 22% | 31 | 9 | 183 | 60 | 185 | 112 |
| rs2621323 | 22% | 0.0006 | 1.62 | 37% | 26% | 43 | 12 | 207 | 71 | 149 | 97 |
| rs241449 | 18% | 0.0016 | 1.61 | 30% | 21% | 32 | 9 | 175 | 58 | 188 | 112 |
| rs2071472 | 22% | 0.0026 | 1.53 | 34% | 25% | 40 | 12 | 191 | 67 | 168 | 102 |
| rs2071470 | 22% | 0.0026 | 1.53 | 34% | 25% | 40 | 12 | 191 | 67 | 168 | 102 |
| rs241447 | 18% | 0.0014 | 1.61 | 31% | 22% | 32 | 9 | 180 | 60 | 184 | 111 |
| kgp974569 | 18% | 0.0014 | 1.61 | 31% | 22% | 32 | 9 | 180 | 60 | 186 | 112 |
| rs241444 | 18% | 0.0014 | 1.60 | 31% | 22% | 32 | 9 | 180 | 60 | 187 | 112 |
| rs241452 | 18% | 0.0018 | 1.59 | 31% | 22% | 32 | 9 | 179 | 60 | 186 | 111 |
| rs241453 | 18% | 0.0014 | 1.60 | 31% | 22% | 32 | 9 | 179 | 60 | 187 | 112 |
| rs241440 | 18% | 0.0022 | 1.58 | 30% | 22% | 32 | 9 | 177 | 60 | 189 | 112 |
| kgp7747883 | 45% | 0.0010 | 0.65 | 34% | 44% | 43 | 33 | 181 | 92 | 174 | 56 |
| kgp2388352 | 18% | 0.0014 | 1.61 | 31% | 22% | 34 | 10 | 173 | 57 | 185 | 111 |
| rs241445 | 18% | 0.0018 | 1.59 | 31% | 22% | 32 | 9 | 179 | 60 | 187 | 111 |
| P1_M_0615 | 18% | 0.0018 | 1.60 | 30% | 22% | 32 | 9 | 178 | 60 | 187 | 112 |
| kgp8036704 | 18% | 0.0022 | 1.58 | 30% | 22% | 29 | 9 | 183 | 60 | 186 | 112 |
| rs241442 | 18% | 0.0018 | 1.59 | 31% | 22% | 32 | 9 | 179 | 60 | 187 | 111 |
| kgp8702370 | 6% | 0.0012 | 1.98 | 15% | 8% | 9 | 0 | 100 | 29 | 290 | 151 |

TABLE 7

Genotypic Model, Analysis of Candidate Genes (30) (Gala, Forte, and Combined cohorts)

| Columns | Ch | Position | GALA | | | FORTE | | | COMBINED |
|---|---|---|---|---|---|---|---|---|---|
| | | | Fisher's Exact P | Allele Freq. (Cases) | Allele Freq. (Controls) | Fisher's Exact P | Allele Freq. (Cases) | Allele Freq. (Controls) | Fisher's Exact P |
| rs1894407 | 6 | 32787036 | 0.001 | 42% | 30% | 0.045 | 40% | 29% | 0.0002 |
| kgp11759837 | 18 | 42876221 | 0.001 | 14% | 14% | 0.95 | 15% | 13% | 0.0322 |
| rs7236910 | 18 | 42879087 | 0.001 | 14% | 14% | 0.95 | 15% | 13% | 0.0322 |
| rs16978335 | 18 | 42876934 | 0.001 | 14% | 14% | 0.95 | 15% | 13% | 0.0408 |
| rs3024491 | 1 | 2.07E+08 | 0.001 | 43% | 47% | 0.92 | 46% | 48% | 0.0123 |
| kgp10839938 | 1 | 2.07E+08 | 0.001 | 44% | 47% | 0.91 | 46% | 48% | 0.0150 |
| rs1894408 | 6 | 32786833 | 0.001 | 42% | 31% | 0.026 | 41% | 28% | 0.0002 |
| rs1878672 | 1 | 2.07E+08 | 0.001 | 44% | 47% | 0.96 | 46% | 48% | 0.0135 |
| rs3024496 | 1 | 2.07E+08 | 0.001 | 44% | 47% | 0.91 | 46% | 48% | 0.0173 |
| rs1800896 | 1 | 2.07E+08 | 0.001 | 44% | 47% | 0.91 | 46% | 48% | 0.0173 |
| rs1800893 | 1 | 2.07E+08 | 0.001 | 44% | 47% | 0.91 | 46% | 48% | 0.0186 |
| rs3024502 | 1 | 2.07E+08 | 0.001 | 43% | 47% | 0.94 | 46% | 48% | 0.0126 |
| rs2222202 | 1 | 2.07E+08 | 0.001 | 43% | 47% | 0.92 | 46% | 48% | 0.0152 |
| kgp5110875 | 17 | 34199695 | 0.003 | 0% | 3% | 1.00 | 0% | 0% | 0.0045 |
| rs1894406 | 6 | 32787056 | 0.003 | 40% | 29% | 0.040 | 36% | 25% | 0.0010 |
| rs2857103 | 6 | 32791299 | 0.004 | 37% | 27% | 0.017 | 36% | 22% | 0.0002 |
| kgp7178883 | 18 | 43176334 | 0.004 | 1% | 5% | 0.47 | 3% | 1% | 0.2122 |
| rs241451 | 6 | 32796480 | 0.004 | 37% | 27% | 0.043 | 35% | 23% | 0.0004 |
| rs9501224 | 6 | 32792910 | 0.005 | 37% | 27% | 0.017 | 36% | 22% | 0.0003 |
| kgp9296959 | 10 | 45944404 | 0.005 | 1% | 5% | 0.26 | 4% | 2% | 0.3354 |
| rs3733904 | 5 | 96216173 | 0.007 | 30% | 21% | 0.31 | 24% | 18% | 0.0039 |
| kgp25437688 | 18 | 43249672 | 0.007 | 1% | 2% | ? | 0% | 0% | 0.0029 |
| kgp25424564 | 18 | 43254660 | 0.007 | 1% | 2% | 0.41 | 0% | 1% | 0.0045 |
| kgp4247664 | 11 | 1.21E+08 | 0.007 | 1% | 2% | 0.14 | 1% | 2% | 00054 |
| kgp22985976 | 11 | 1.21E+08 | 0.007 | 1% | 2% | 0.39 | 1% | 2% | 0.0292 |
| rs9658761 | 10 | 90769886 | 0.007 | 9% | 14% | 0.08 | 14% | 15% | 0.0014 |
| kgp5854183 | 18 | 31783422 | 0.007 | 1% | 3% | 0.77 | 3% | 2% | 0.2779 |
| kgp12268594 | 3 | 1.32E408 | 0.008 | 1% | 5% | 0.48 | 2% | 3% | 0.0067 |
| kgp26488438 | 6 | 32817008 | 0.008 | 1% | 5% | 1.00 | 1% | 1% | 0.0221 |
| kgp9394249 | 18 | 74817362 | 0.008 | 3% | 0% | 0.57 | 2% | 2% | 0.2414 |
| rs11878100 | 18 | 31655157 | 0.009 | 39% | 37% | 0.17 | 40% | 41% | 0.0029 |
| kgp587077 | 18 | 74711130 | 0.009 | 24% | 24% | 0.46 | 22% | 26% | 0.0231 |
| kgp1913209 | 18 | 74697645 | 0.010 | 4% | 8% | 1.00 | 5% | 5% | 0.0681 |
| kgp11795987 | 6 | 31547514 | 0.010 | 20% | 11% | 0.58 | 16% | 11% | 0.0099 |
| kgp10626023 | 18 | 31517144 | 0.011 | 24% | 15% | 0.26 | 20% | 18% | 0.0092 |

TABLE 7-continued

Genotypic Model, Analysis of Candidate Genes (30) (Gala, Forte, and Combined cohorts)

| | COMBINED | | | | | | | |
|---|---|---|---|---|---|---|---|---|
| Columns | Allele Freq. (Cases) | Allele Freq. (Controls) | DD (Cases) | DD (Controls) | Dd (Cases) | Dd (Controls) | dd (Cases) | dd (Controls) |
| rs1894407 | 41% | 30% | 57 | 16 | 213 | 75 | 128 | 90 |
| kgp11759837 | 14% | 14% | 5 | 7 | 105 | 35 | 289 | 139 |
| rs7236910 | 14% | 14% | 5 | 7 | 105 | 35 | 289 | 139 |
| rs16978335 | 14% | 14% | 5 | 7 | 104 | 35 | 290 | 138 |
| rs3024491 | 45% | 47% | 71 | 48 | 214 | 75 | 114 | 58 |
| kgp10839938 | 45% | 47% | 73 | 48 | 214 | 75 | 112 | 58 |
| rs1894408 | 41% | 30% | 58 | 16 | 211 | 74 | 127 | 89 |
| rs1878672 | 45% | 47% | 73 | 48 | 213 | 74 | 113 | 58 |
| rs3024496 | 45% | 47% | 73 | 48 | 213 | 75 | 113 | 58 |
| rs1800896 | 45% | 47% | 73 | 48 | 213 | 75 | 113 | 58 |
| rs1800893 | 45% | 47% | 73 | 48 | 212 | 75 | 113 | 58 |
| rs3024502 | 45% | 47% | 72 | 48 | 213 | 74 | 114 | 58 |
| rs2222202 | 45% | 47% | 72 | 48 | 213 | 75 | 114 | 58 |
| kgp5110875 | 0% | 2% | 0 | 0 | 1 | 6 | 398 | 175 |
| rs1894406 | 38% | 27% | 51 | 13 | 202 | 73 | 146 | 95 |
| rs2857103 | 36% | 25% | 39 | 11 | 211 | 69 | 149 | 100 |
| kgp7178883 | 2% | 3% | 1 | 1 | 12 | 10 | 384 | 169 |
| rs241451 | 36% | 26% | 39 | 12 | 207 | 68 | 150 | 100 |
| rs9501224 | 36% | 25% | 39 | 11 | 211 | 70 | 149 | 100 |
| kgp9296959 | 3% | 4% | 0 | 0 | 20 | 13 | 376 | 168 |
| rs3733904 | 27% | 20% | 37 | 4 | 141 | 64 | 221 | 113 |
| kgp25437688 | 0% | 1% | 1 | 0 | 0 | 5 | 396 | 176 |
| kgp25424564 | 0% | 2% | 1 | 0 | 1 | 6 | 397 | 175 |
| kgp4247664 | 1% | 2% | 1 | 0 | 3 | 8 | 393 | 173 |
| kgp22985976 | 1% | 2% | 1 | 0 | 5 | 8 | 393 | 173 |
| rs9658761 | 11% | 14% | 13 | 1 | 65 | 50 | 321 | 130 |
| kgp5854183 | 2% | 3% | 0 | 0 | 15 | 11 | 383 | 170 |
| kgp12268594 | 2% | 4% | 0 | 0 | 13 | 16 | 386 | 165 |
| kgp26488438 | 1% | 4% | 0 | 0 | 11 | 13 | 388 | 168 |
| kgp9394249 | 2% | 1% | 1 | 0 | 17 | 3 | 379 | 177 |
| rs11878100 | 39% | 39% | 48 | 34 | 215 | 71 | 134 | 75 |
| kgp587077 | 23% | 25% | 27 | 6 | 129 | 78 | 241 | 97 |
| kgp1913209 | 4% | 7% | 2 | 0 | 31 | 24 | 365 | 155 |
| kgp11795987 | 18% | 11% | 16 | 3 | 111 | 33 | 271 | 144 |
| kgp10626023 | 22% | 16% | 17 | 9 | 140 | 41 | 242 | 131 |

TABLE 7b

Genotypic Model, Analysis of Candidate Genes (30)-replicated p < 0.05 (Gala, Forte, and Combined cohorts)

| | | | GALA | | | FORTE | | | COMBINED |
|---|---|---|---|---|---|---|---|---|---|
| Columns | Ch | Position | Fisher's Exact P | Allele Freq. (Case | Allele Freq. (Controls) | Fisher's Exact P | Allele Freq. (Case | Allele Freq. (Controls) | Fisher's Exact P |
| rs1894407 | 6 | 32787036 | 0.001 | 0.42 | 0,30 | 0.045 | 0.40 | 0.29 | 0.0002 |
| rs2857103 | 6 | 32791299 | 0.004 | 0.37 | 0.27 | 0.017 | 0.36 | 0.22 | 0.0002 |
| rs1894408 | 6 | 32786833 | 0.001 | 0.42 | 0.31 | 0.026 | 0.41 | 0.28 | 0.0002 |
| rs9501224 | 6 | 32792910 | 0.005 | 0.37 | 0.27 | 0.017 | 0.36 | 0.22 | 0.0003 |
| rs241451 | 6 | 32796480 | 0.004 | 0.37 | 0.27 | 0.043 | 0.35 | 0.23 | 0.0004 |
| rs241443 | 6 | 32797115 | 0.012 | 0.37 | 0.27 | 0.021 | 0.35 | 0.22 | 0.0008 |
| rs2621323 | 6 | 32788707 | 0.013 | 0.37 | 0.29 | 0.012 | 0.36 | 0.22 | 0.0009 |
| rs1894406 | 6 | 32787056 | 0.003 | 0.40 | 0.29 | 0.040 | 0.36 | 0.25 | 0.0010 |
| rs2621321 | 6 | 32789480 | 0.032 | 0.32 | 0.23 | 0.029 | 0.30 | 0.18 | 0.0023 |
| rs241456 | 6 | 32795965 | 0.029 | 0.31 | 0.23 | 0.035 | 0.30 | 0.18 | 0.0023 |
| rs2857104 | 6 | 32790167 | 0.032 | 0.32 | 0.23 | 0.031 | 0.30 | 0.18 | 0.0025 |
| rs2857101 | 6 | 32794676 | 0.032 | 0.31 | 0.23 | 0.034 | 0.30 | 0.18 | 0.0029 |
| rs241454 | 6 | 32796144 | 0.037 | 0.31 | 0.23 | 0.029 | 0.30 | 0.18 | 0.0029 |
| kgp974569 | 6 | 32796057 | 0.043 | 0.31 | 0.23 | 0.029 | 0.30 | 0.18 | 0.0032 |
| rs241447 | 6 | 32796751 | 0.043 | 0.31 | 0.23 | 0.035 | 0.30 | 0.18 | 0.0032 |
| rs241444 | 6 | 32797109 | 0.043 | 0.31 | 0.23 | 0.035 | 0.30 | 0.18 | 0.0034 |
| kgp8036704 | 6 | 32796521 | 0.042 | 0.31 | 0.23 | 0.038 | 0.30 | 0.18 | 0.0034 |
| kgp2388352 | 6 | 32797297 | 0.037 | 0.31 | 0.24 | 0.025 | 0.30 | 0.18 | 0.0036 |
| rs241446 | 6 | 32796967 | 0.036 | 0.31 | 0.23 | 0.040 | 0.30 | 0.18 | 0.0037 |

TABLE 7b-continued

Genotypic Model, Analysis of Candidate Genes (30)-replicated p < 0.05 (Gala, Forte, and Combined cohorts)

| | | | | | | | | |
|---|---|---|---|---|---|---|---|---|
| rs241449 | 6 | 32796653 | 0.047 | 0.31 | 0.23 | 0.037 | 0.30 | 0.18 | 0.0038 |
| rs241452 | 6 | 32796346 | 0.047 | 0.31 | 0.24 | 0.034 | 0.30 | 0.18 | 0.0040 |

COMBINED

| Columns | Allele Freq. (Case) | Allele Freq. (Controls) | DD (Case) | DD (Controls) | Dd (Case) | Dd (Controls) | dd (Case) | dd (Controls) |
|---|---|---|---|---|---|---|---|---|
| rs1894407 | 0.41 | 0.30 | 57 | 16 | 213 | 75 | 128 | 90 |
| rs2857103 | 0.36 | 0.25 | 39 | 11 | 211 | 69 | 149 | 100 |
| rs1894408 | 0.41 | 0.30 | 58 | 16 | 211 | 74 | 127 | 89 |
| rs9501224 | 0.36 | 0.25 | 39 | 11 | 211 | 70 | 149 | 100 |
| rs241451 | 0.36 | 0.26 | 39 | 12 | 207 | 68 | 150 | 100 |
| rs241443 | 0.36 | 0.25 | 40 | 11 | 202 | 69 | 152 | 99 |
| rs2621323 | 0.37 | 0.26 | 43 | 12 | 207 | 71 | 149 | 97 |
| rs1894406 | 0.38 | 0.27 | 51 | 13 | 202 | 73 | 146 | 95 |
| rs2621321 | 0.31 | 0.22 | 31 | 9 | 183 | 60 | 184 | 112 |
| rs241456 | 0.31 | 0.21 | 32 | 9 | 180 | 59 | 187 | 113 |
| rs2857104 | 0.31 | 0.22 | 31 | 9 | 183 | 60 | 185 | 112 |
| rs2857101 | 0.30 | 0.21 | 31 | 9 | 181 | 59 | 187 | 112 |
| rs241454 | 0.31 | 0.22 | 32 | 9 | 180 | 60 | 185 | 112 |
| kgp974569 | 0.31 | 0.22 | 32 | 9 | 180 | 60 | 186 | 112 |
| rs241447 | 0.31 | 0.22 | 32 | 9 | 180 | 60 | 184 | 111 |
| rs241444 | 0.31 | 0.22 | 32 | 9 | 180 | 60 | 187 | 112 |
| kgp8036704 | 0.30 | 0.22 | 29 | 9 | 183 | 60 | 186 | 112 |
| kgp2388352 | 0.31 | 0.22 | 34 | 10 | 173 | 57 | 185 | 111 |
| rs241446 | 0.30 | 0.21 | 32 | 9 | 176 | 59 | 188 | 113 |
| rs241449 | 0.30 | 0.21 | 32 | 9 | 175 | 58 | 188 | 112 |
| rs241452 | 0.31 | 0.22 | 32 | 9 | 179 | 60 | 186 | 111 |

In some embodiments genetic markers presented in Tables 5, 6 and 7 are identified as predictive of response to glatiramer acetate if the p-value for the Combined cohort is less than about 0.05, less than about 0.01, less than about 0.005, less than about 0.001, less than about 0.0005 or less than about $10^{-4}$.

Example 7 Analysis Part 3—Analysis of Candidate Genes (180)

The third analysis was limited to a selected set of genetic variants in 180 priority candidate genes (25,461 variants).

Results for Standard Response Definition, 180 Candidate Genes Selected a priori for Additive, Allelic and Genotypic models are presented in tables 8-10, respectively.

In some embodiments genetic markers presented in Tables 8, 9 and 10 are identified as predictive of response to glatiramer acetate if the p-value for the GALA cohort is less than about 0.05, less than about 0.01, less than about 0.005, less than about 0.001, less than about 0.0005 or less than about $10^{-4}$.

In some embodiments genetic markers presented in Tables 8, 9 and 10 are identified as predictive of response to glatiramer acetate if the p-value for the FORTE cohort is less than about 0.05, less than about 0.01 or less than about 0.005.

In some embodiments genetic markers presented in Tables 8, 9 and 10 are identified as predictive of response to glatiramer acetate if the p-value for the Combined cohort is less than about 0.05, less than about 0.01, less than about 0.005, less than about 0.001, less than about 0.0005 or less than about $10^{-4}$.

TABLE 8

Additive Model, Analysis of Candidate Genes (180) (Gala, Forte, and Combined cohorts)

| Name | Ch | Position | Gene(s) | Mutation | Gene Locations(s) | GALA Armitage P | GALA Regression Odds Ratio | FORTE Armitage P | FORTE Regression Odds Ratio |
|---|---|---|---|---|---|---|---|---|---|
| rs1894407 | 6 | 32787036 | ? | ? | ? | 0.00175175 | 1.8 | 0.01812361 | 1.7 |
| rs1894406 | 6 | 32787056 | ? | ? | ? | 0.00262814 | 1.7 | 0.01731899 | 1.8 |
| rs1894408 | 6 | 32786833 | ? | ? | ? | 0.00302235 | 1.7 | 0.00929977 | 1.8 |
| kgp6599438 | 20 | 40843626 | PTPRT, PTPRT | Silent, Silent | INTRON | 0.003702 | 0.2 | 0.01551449 | 0.3 |
| kgp293787 | 20 | 40905098 | PTPRT, PTPRT | Silent, Silent | INTRON | 0.00486183 | 0.2 | 0.02186627 | 0.4 |
| rs2857103 | 6 | 32791299 | TAP2 | Silent | INTRON | 0.00572178 | 1.7 | 0.00412662 | 2.0 |
| kgp10224254 | 6 | 3279990417 | ? | ? | ? | 0.0058474 | 1.6 | 0.04442021 | 1.6 |
| rs241451 | 6 | 32796480 | TAP2, TAP2 | Silent, Silent | INTRON | 0.00625568 | 1.7 | 0.01125399 | 1.9 |
| rs9501224 | 6 | 32792910 | TAP2 | Silent | INTRON | 0.00652648 | 1.7 | 0.00412662 | 2.0 |
| rs2071469 | 6 | 32784783 | HLA-DOB | Silent | UTR | 0.00676044 | 1.6 | 0.04442021 | 1.6 |
| rs10162089 | 13 | 31316738 | ALOX5AP, ALOX5AP | Silent, Silent | INTRON | 0.007794 | 1.6 | 0.0315509 | 1.6 |
| rs241443 | 6 | 32797115 | TAP2, TAP2 | Silent, Silent | INTRON, EXON | 0.01054389 | 1.6 | 0.00527858 | 2.0 |
| rs3218328 | 22 | 37524008 | IL2RB | Silent | UTR | 0.01094804 | 0.2 | 0.01393817 | 0.1 |
| kgp5334779 | 6 | 32628420 | HLA-DQB1, HLA-DQB1 | Silent, Silent | INTRON | 0.01680233 | 1.5 | 0.02742446 | 1.7 |
| kgp10632945 | 20 | 4682507 | ? | ? | ? | 0.0187382 | 0.6 | 0.03477091 | 0.6 |
| rs2621323 | 6 | 32788707 | ? | ? | ? | 0.0189772 | 1.6 | 0.00308945 | 2.1 |
| rs1410779 | 9 | 5083173 | JAK2 | Silent | INTRON | 0.01928688 | 0.6 | 0.01286783 | 0.5 |
| kgp4479467 | 6 | 326293311 | HLA-DQB1, HLA-DQB1 | Silent, Silent | INTRON | 0.02026789 | 1.5 | 0.01594443 | 1.8 |
| rs241456 | 6 | 32795965 | TAP2, TAP2 | Silent, Silent | INTRON | 0.02123306 | 1.6 | 0.00854177 | 2.0 |
| rs52621321 | 6 | 32789480 | ? | ? | ? | 0.02375031 | 1.5 | 0.00719304 | 2.0 |
| rs52857104 | 6 | 32790167 | TAP2, TAP2 | Silent, Silent | INTRON | 0.02375031 | 1.5 | 0.00788787 | 2.0 |
| rs2857101 | 6 | 32794676 | TAP2, TAP2 | Silent, Silent | INTRON | 0.0248064 | 1.5 | 0.00932686 | 2.0 |
| rs241446 | 6 | 32796967 | TAP2, TAP2 | Silent, Silent | INTRON, EXON | 0.02486364 | 1.5 | 0.0108596 | 2.0 |
| kgp48913179 | 6 | 32629347 | HLA-DQB1, HLA-DQB1 | Silent, Silent | INTRON | 0.02526492 | 1.5 | 0.01868249 | 1.8 |
| rs241454 | 6 | 32796144 | TAP2, TAP2 | Silent, Silent | INTRON | 0.02565201 | 1.5 | 0.00780448 | 2.0 |
| kgp9699754 | 10 | 79359319 | KCNMA1, KCNMA1, KCNMA1, KCNMA1 | Silent, Silent, Silent, Silent | INTRON | 0.02698903 | ? | 0.04107681 | ? |

TABLE 8-continued

Additive Model, Analysis of Candidate Genes (180) (Gala, Forte, and Combined cohorts)

| Name | Armitage P | Regression Odds Ratio | DD (Cases) | DD (Controls) | | | Dd (Cases) | Dd (Controls) | dd (Cases) | dd (Controls) |
|---|---|---|---|---|---|---|---|---|---|---|
| kgp974569 | | | | | INTRON | | | | 0.00780448 | 2.0 |
| | | | | | | | 0.02848011 | 1.5 | | |
| r5241447 | | 32796057 | | | INTRON, EXON | Silent, Silent | | | 0.00834304 | 2.0 |
| | | | | | | | 0.02848011 | 1.5 | | |
| rs241444 | | 32797109 | | | INTRON, EXON | Silent, Missen Silent, Silent | | | 0.00854177 | 2.0 |
| | | | | | | | 0.02848011 | 1.5 | | |

Combined

| Name | Armitage P | Regression Odds Ratio | DD (Cases) | DD (Controls) | | | Dd (Cases) | Dd (Controls) | dd (Cases) | dd (Controls) |
|---|---|---|---|---|---|---|---|---|---|---|
| rs1894407 | 0.00010632 | 1.7 | 57 | 16 | TAP2, TAP2 | Silent, Silent | 213 | 75 | 128 | 90 |
| rs1894406 | 0.00026627 | 1.7 | 51 | 13 | TAP2, TAP2 | Silent, Silent | 202 | 73 | 146 | 95 |
| rs1894408 | 9.82E-05 | 1.7 | 58 | 16 | TAP2, TAP2 | Silent, Missen | 211 | 74 | 127 | 89 |
| kgp6599438 | 0.00024816 | 0.3 | 0 | 0 | | | 11 | 18 | 386 | 163 |
| kgp293787 | 0.00254833 | 0.4 | 0 | 2 | | | 15 | 15 | 384 | 164 |
| rs2857103 | 0.00011314 | 1.8 | 39 | 11 | TAP2, TAP2 | Silent, Silent | 211 | 69 | 149 | 100 |
| kgp10224254 | 0.001151 | 1.6 | 59 | 18 | | | 205 | 75 | 135 | 88 |
| rs241451 | 0.00025798 | 1.7 | 39 | 12 | | | 207 | 68 | 150 | 100 |
| rs9501224 | 0.00013242 | 1.8 | 39 | 11 | | | 211 | 70 | 149 | 100 |
| rs20071469 | 0.00139647 | 1.6 | 59 | 18 | | | 205 | 76 | 134 | 87 |
| rs10162089 | 0.00139566 | 1.5 | 96 | 24 | | | 190 | 88 | 110 | 67 |
| rs241443 | 0.0003017 | 1.7 | 40 | 11 | | | 202 | 69 | 152 | 99 |
| rs3218328 | 0.00029615 | 0.1 | 0 | 0 | | | 3 | 10 | 395 | 169 |
| rs5334779 | 0.00187388 | 1.6 | 50 | 10 | | | 199 | 83 | 148 | 87 |
| kgp10632945 | 0.00125431 | 0.6 | 10 | 11 | | | 118 | 70 | 270 | 100 |
| rs2621323 | 0.00033291 | 1.7 | 43 | 12 | | | 207 | 71 | 149 | 97 |
| rs1410779 | 0.00173172 | 0.6 | 8 | 10 | | | 112 | 66 | 277 | 105 |
| rs4479467 | 0.00124971 | 1.6 | 54 | 11 | | | 195 | 82 | 147 | 88 |
| rs241456 | 0.00086275 | 1.7 | 32 | 9 | | | 180 | 59 | 187 | 113 |
| rs52621321 | 0.00090026 | 1.7 | 31 | 9 | | | 183 | 60 | 184 | 112 |
| rs52857104 | 0.00098748 | 1.7 | 31 | 9 | | | 181 | 59 | 185 | 112 |
| rs2857101 | 0.0011476 | 1.6 | 31 | 9 | | | 180 | 59 | 187 | 112 |
| rs241446 | 0.00125819 | 1.6 | 32 | 9 | | | 176 | 59 | 188 | 113 |
| kgp48913179 | 0.0019069 | 1.6 | 54 | 11 | | | 195 | 83 | 148 | 87 |
| rs241454 | 0.00101933 | 1.6 | 32 | 9 | | | 180 | 60 | 185 | 112 |
| kgp9699754 | 0.00174374 | ~Infinity | 0 | 0 | | | 21 | 0 | 377 | 179 |
| kgp974569 | 0.00111661 | 1.6 | 32 | 9 | | | 180 | 60 | 186 | 112 |
| r5241447 | 0.00110846 | 1.6 | 32 | 9 | | | 180 | 60 | 184 | 111 |
| rs241444 | 0.00122194 | 1.6 | 32 | 9 | | | 180 | 60 | 187 | 112 |

TABLE 8-continued

Additive Model, Analysis of Candidate Genes (180) (Gala, Forte, and Combined cohorts)

| Name | Ch | Position | Gene(s) | Mutation | Gene Locations(s) | GALA Armitage P | GALA Regression Odds Ratio | FORTE Armitage P | FORTE Regression Odds Ratio |
|---|---|---|---|---|---|---|---|---|---|
| rs2071472 | 6 | 32784620 | HLA-DOB | Silent | INTRON | 0.029144 | 1.5 | 0.018629 | 1.0 |
| rs2071470 | 6 | 32784753 | HLA-DOB | Silent | UTR | 0.029144 | 1.5 | 0.018629 | 1.8 |
| kgp22778566 | 7 | 1950337 | MAD1L1 | Silent, Sile | NTRON | 0.030998 | 1.6 | 0.02869 | 1.9 |
| kgp6032617 | 13 | 31287981 | ALOX5AP | Silent | INTRON | 0.031116 | 0.7 | 0.043799 | 0.6 |
| rs4769360 | 13 | 31337877 | ALOX5AP, | Silent, Sile | INTRON | 0.031432 | 1.4 | 0.031343 | 1.6 |
| rs241449 | 6 | 32796663 | TAP2, TAP | Silent, Syn | NTRON, E | 0.032511 | 1.5 | 0.009222 | 2.0 |
| rs241452 | 6 | 32796346 | TAP2, TAP | Silent, Sile | INTRON | 0.033124 | 1.5 | 0.008432 | 2.0 |
| rs241453 | 6 | 32796226 | TAP2, TAP | Silent | INTRON | 0.033989 | 1.5 | 0.007804 | 2.0 |
| rs241440 | 6 | 32797361 | TAP2, TAP | Silent, Sile | INTRON | 0.033989 | 1.5 | 0.01086 | 2.0 |
| kgp30490 | 20 | 14017077 | MACROD | Silent | INTRON | 0.034256 | 0.5 | 0.015134 | 0.3 |
| kgp8036704 | 6 | 32796521 | TAP2, TAP | Silent, Sile | INTRON | 0.035126 | 1.5 | 0.008613 | 2.0 |
| kgp5440506 | 13 | 31320543 | ALOX5AP, | Silent, Sile | INTRON | 0.036201 | 0.7 | 0.024964 | 0.6 |
| rs7747883 | 18 | 74804250 | MBP, MBP | Silent, Sile | INTRON | 0.035519 | 0.7 | 0.00982 | 0.6 |
| rs241445 | 6 | 32797072 | TAP2, TAP | Silent, Sile | INTRON, E | 0.035654 | 1.5 | 0.008542 | 2.0 |
| rs10815163 | 9 | 5116616 | JAK2 | Silent | INTRON | 0.035753 | 0.7 | 0.036927 | 0.6 |
| P1_M_061510_6_ | 6 | 32795505 | TAP2, TAP | Silent ? | INTRON | 0.036607 | 1.5 | 0.007804 | 2.0 |
| rs9671182 | 13 | 31321138 | ALOX5AP, | Silent, Sile | INTRON | 0.038955 | 0.7 | 0.027648 | 0.6 |
| rs241442 | 6 | 32797168 | TAP2, TAP | Silent, Sile | INTRON, E | 0.039363 | 1.5 | 0.007804 | 2.0 |
| rs433 6336 | 13 | 31319546 | ALOX5AP, | Silent, Sile | INTRON | 0.039764 | 0.7 | 0.027648 | 0.6 |
| kgp238832 | 6 | 32797297 | TAP2, TAP | Synonym | EXON | 0.042477 | 1.5 | 0.007057 | 2.0 |
| rs11147433 | 13 | 31325643 | ALOX5AP, | Silent, Sile | INTRON | 0.043409 | 0.7 | 0.021636 | 0.6 |
| rs2043136 | 3 | 30720304 | TGFBR2, T | Silent, Sile | INTRON | 0.044239 | 1.5 | 0.037491 | 1.7 |
| kgp112815 89 | 7 | 1941033 | MAD1L1 | Silent, Sile | INTRON | 0.045301 | 1.5 | 0.042434 | 1.9 |
| kgp5441587 | 6 | 32827356 | PSMB9 | Silent | UTR | 0.045581 | 0.1 | 0.01974 | 0.2 |
| kgp97310 | 9 | 5122932 | JAK 2 | Silent | INTRON | 0.045767 | 0.7 | 0.019889 | 0.6 |
| rs4360791 | 13 | 31318020 | ALOX5AP, | Silent, | INTRON | 0.046466 | 0.7 | 0.023161 | 0.6 |

TABLE 8-continued

Additive Model, Analysis of Candidate Genes (180) (Gala, Forte, and Combined cohorts)

| Name | Chr | Position | Gene | Mutation Type | Location | Armitage P | Regression Odds Ratio | DD (Cases) | DD (Controls) | Dd (Cases) | Dd (Controls) | dd (Cases) | dd (Controls) |
|---|---|---|---|---|---|---|---|---|---|---|---|---|---|
| kgp25543811 | 18 | 74774894 | MBP, MBP | Silent, Sile | INTRON | 0.048109 | | | | | | | 0.1 |
| kgp23672937 | 7 | 18685891 | HDAC9, H | Silent, Sile | INTRON | 0.049393 | | | | | | | ? |
| kgp4346717 | 18 | 74810199 | MBP, MBP | Silent, Sile | INTRON | 0.049393 | | | | | | | ? |
| rs241435 | 6 | 32798243 | TAP2, TAP | Silent, Sile | INTRON | 0.049393 | | | | | | | 0.2 |
| kgp3182607 | 6 | 32823948 | PS MB9 | Missense | EXON | 0.049393 | | | | | | | 0.2 |
| kgp26271158 | 6 | 32823393 | PS MB9 | Silent, Sile | INTRON | 0.049393 | | | | | | | 0.3 |
| rs4254166 | 13 | 31322949 | ALOX5AP | Silent, Sile | INTRON | 0.049706 | | | | | | | 0.6 |
| kgp2715873 | 13 | 31320249 | ALOX5AP | Silent, Sile | INTRON | 0.049706 | | | | | | | 0.6 |
| rs9670531 | 13 | 31321069 | ALOX5AP | Silent, Sile | INTRON | 0.049706 | | | | | | | 0.6 |

Combined

| Name | Armitage P | Regression Odds Ratio | DD (Cases) | DD (Controls) | Dd (Cases) | Dd (Controls) | dd (Cases) | dd (Controls) |
|---|---|---|---|---|---|---|---|---|
| rs2071472 | 0.002212 | 1.6 | 40 | 12 | 191 | 67 | 168 | 102 |
| rs2071470 | 0.002212 | 1.6 | 40 | 12 | 191 | 67 | 168 | 102 |
| kgp22778566 | 0.007 | 1.6 | 19 | 4 | 156 | 53 | 220 | 117 |
| kgp6032617 | 0.00444 | 0.7 | 23 | 15 | 131 | 79 | 244 | 87 |
| rs4769360 | 0.004432 | 1.4 | 87 | 22 | 183 | 88 | 123 | 71 |
| rs241449 | 0.001348 | 1.6 | 32 | 9 | 175 | 58 | 188 | 112 |
| rs241452 | 0.001424 | 1.6 | 32 | 9 | 179 | 60 | 186 | 111 |
| rs241453 | 0.001311 | 1.6 | 32 | 9 | 179 | 60 | 187 | 112 |

TABLE 8-continued

Additive Model, Analysis of Candidate Genes (180) (Gala, Forte, and Combined cohorts)

| | | | | | | | |
|---|---|---|---|---|---|---|---|
| rs241440 | 0.001795 | 32 | 9 | 177 | 60 | 189 | 112 |
| kgp30490 | 0.008 | 2 | 2 | 19 | 23 | 373 | 154 |
| kgp8036704 | 0.001553 | 29 | 9 | 183 | 60 | 186 | 112 |
| kgp5440506 | 0.007941 | 81 | 45 | 175 | 95 | 138 | 40 |
| kgp7747883 | 0.000864 | 43 | 33 | 181 | 92 | 174 | 56 |
| rs241445 | 0.001555 | 32 | 9 | 179 | 60 | 187 | 111 |
| rs10815163 | 0.009339 | 19 | 14 | 124 | 71 | 248 | 93 |
| P1_M_061510_6_ | 0.001406 | 32 | 9 | 178 | 60 | 187 | 112 |
| rs9671182 | 0.008781 | 82 | 45 | 180 | 96 | 136 | 39 |
| rs241442 | 0.001555 | 32 | 9 | 179 | 60 | 187 | 111 |
| rs433 6336 | 0.008948 | 82 | 46 | 181 | 95 | 136 | 40 |
| kgp238832 | 0.001455 | 34 | 10 | 173 | 57 | 185 | 111 |
| rs11147433 | 0.008096 | 81 | 45 | 180 | 96 | 138 | 40 |
| rs2043136 | 0.004107 | 38 | 7 | 167 | 67 | 191 | 106 |
| kgp11281589 | 0.017556 | 19 | 5 | 155 | 55 | 219 | 117 |
| kgp5441587 | 0.006103 | 0 | 0 | 5 | 9 | 394 | 169 |
| kgp97310 | 0.007785 | 17 | 14 | 125 | 70 | 256 | 97 |
| rs4360791 | 0.008598 | 85 | 48 | 181 | 94 | 133 | 39 |
| kgp25543811 | 0.002288 | 0 | 0 | 2 | 7 | 397 | 173 |
| kgp23672937 | 0.00174 | 0 | 0 | 1 | 6 | 398 | 175 |
| kgp4346717 | 0.006849 | 0 | 0 | 1 | 6 | 398 | 175 |
| rs241435 | 0.006849 | 0 | 0 | 5 | 9 | 394 | 172 |
| kgp3182607 | 0.014748 | 0 | 0 | 5 | 9 | 394 | 172 |
| kgp26271158 | 0.009958 | 0 | 0 | 6 | 9 | 393 | 172 |
| rs4254166 | 0.011301 | 81 | 45 | 182 | 96 | 136 | 40 |
| kgp2715873 | 0.011301 | 82 | 45 | 181 | 96 | 136 | 40 |
| rs9670531 | 0.011301 | 82 | 45 | 181 | 96 | 136 | 40 |

TABLE 9

Allelic Model, Analysis of Candidate Genes (180) (Gala, Forte, and Combined cohorts)

| Name | Chromosome | Position | Gene(s) | Mutation | Gene Locations (s) | GALA Fisher's Exact P | GALA Odds Ratio (Minor Allele) | FORTE Fisher's Exact P | FORTE Odds Ratio (Minor Allele) | COMBINED Fisher's Exact P |
|---|---|---|---|---|---|---|---|---|---|---|
| rs1894408 | 6 | 32786833 | ? | ? | ? | 0.005009 | 1.6 | 0.010522 | 1.8 | 0.000175 |
| rs1894407 | 6 | 32787036 | ? | ? | ? | 0.003054 | 1.7 | 0.02471 | 1.7 | 0.000185 |
| rs2857103 | 6 | 32791299 | TAP2 | Silent | INTRON | 0.011421 | 1.6 | 0.005691 | 1.3 | 0.000254 |
| rs9501224 | 6 | 32792910 | TAP2 | Silent | INTRON | 0.011794 | 1.6 | 0.005691 | 1.9 | 0.000267 |
| rs1894406 | 6 | 32787056 | ? | ? | ? | 0.003758 | 1.7 | 0.02118 | 1.7 | 0.000411 |
| rs241451 | 6 | 32796480 | TAP2, TAP | Silent, Sile | INTRON | 0.011396 | 1.6 | 0.014428 | 1.8 | 0.000429 |
| rs241443 | 6 | 32797115 | TAP2, TAP | Silent, Sile | INTRON, E | 0.018211 | 1.5 | 0.007128 | 1.9 | 0.000515 |
| kgp9699754 | 10 | 79358319 | KCNMA1, | Silent, Sile | INTRON | 0.028334 | ? | 0.045622 | ? | 0.000521 |
| rs2621323 | 6 | 32788707 | ? | ? | ? | 0.030375 | 1.5 | 0.004125 | 2.0 | 0.000593 |
| kgp6599438 | 20 | 40843626 | PTPRT PT | Silent, Sile | INTRON | 0.005974 | 0.2 | 0.025262 | 0.3 | 0.000764 |
| rs3218328 | 22 | 37524008 | IL2RB | Silent | UTR | 0.015946 | 0.2 | 0.041488 | 0.1 | 0.000821 |
| kgp304921 | 20 | 14017077 | MACROD2 | Silent | INTRON | 0.029064 | 0.5 | 0.03 | 0.3 | 0.000838 |
| kgp7747883 | 18 | 74804250 | MBP, MBP | Silent, Sile | INTRON | 0.042737 | 0.7 | 0.012878 | 0.6 | 0.001016 |
| rs241456 | 6 | 32795965 | TAP2, TAP | Silent, Sile | INTRON | 0.023192 | 1.5 | 0.010406 | 1.9 | 0.001099 |
| rs2621321 | 6 | 32789480 | ? | ? | ? | 0.029482 | 1.5 | 0.010334 | 1.9 | 0.001137 |
| rs241454 | 6 | 32796144 | TAP2, TAP | Silent, Sile | INTRON | 0.029427 | 1.5 | 0.010334 | 1.9 | 0.00114 |
| rs2857104 | 6 | 32790167 | TAP2 | Silent | INTRON | 0.029482 | 1.5 | 0.010406 | 1.9 | 0.001153 |
| kgp8702370 | 6 | 1.32E+08 | | Silent | INTRON | 0.04888 | 1.7 | 0.007895 | 2.9 | 0.001162 |
| kgp2388352 | 6 | 32797297 | TAP2, | Synonymo | EXON | 0.043348 | 1.5 | 0.007574 | 2.0 | 0.001352 |
| rs10162089 | 13 | 31316738 | TAP | Silent, Sile | INTRON | 0.003386 | 1.6 | 0.028565 | 1.6 | 0.001361 |
| rs241446 | 6 | 32796967 | TAP2, TAP | Silent, Sile | INTRON, E | 0.028483 | 1.5 | 0.013955 | 1.9 | 0.001374 |
| rs2857101 | 6 | 32794676 | TAP2, TAP | Silent, Sile | INTRON | 0.028792 | 1.5 | 0.014056 | 1.9 | 0.001387 |
| rs241447 | 6 | 32796751 | TAP2, TAP | Silent, Sile | INTRON, E | 0.036579 | 1.5 | 0.010205 | 1.9 | 0.001413 |
| kgp974569 | 6 | 32796057 | TAP2, TAP | Silent, Sile | INTRON | 0.036579 | 1.5 | 0.010334 | 1.9 | 0.001428 |
| rs241444 | 6 | 32797109 | TAP2, TAP | Silent, Sile | INTRON, E | 0.036579 | 1.5 | 0.010406 | 1.9 | 0.001439 |
| rs241453 | 6 | 32796226 | TAP2, TAP | Silent, Sile | INTRON | 0.036822 | 1.5 | 0.010334 | 1.9 | 0.001443 |
| rs241449 | 6 | 32796653 | TAP2, TAP | Silent, Syn | INTRON, E | 0.03449 | 1.5 | 0.010436 | 1.9 | 0.00165 |
| rs241452 | 6 | 32796346 | TAP2, TAP | Silent, Sile | INTRON | 0.036767 | 1.5 | 0.010309 | 1.9 | 0.001782 |
| P1_M_061510_ | 6 | 32795505 | TAP2, TAP | ? | INTRON | 0.044866 | 1.5 | 0.010334 | 1.9 | 0.001787 |
| kgp4479467 | 6 | 32629331 | HLA-DQB1 | Silent, Sile | INTRON | 0.021213 | 1.5 | 0.022971 | 1.7 | 0.001788 |
| rs241445 | 6 | 32797072 | TAP2, TAP | Silent, Sile | INTRON, E | 0.044862 | 1.5 | 0.010406 | 1.5 | 0.001797 |
| rs241442 | 6 | 32797168 | TAP2, TAP | Silent, Sile | INTRON, E | 0.045133 | 1.5 | 0.010334 | 1.9 | 0.001797 |
| kgp10632945 | 20 | 4682507 | ? | ? | ? | 0.020364 | 0.6 | 0.047361 | 0.6 | 0.001896 |
| rs241440 | 6 | 32797361 | TAP2, TAP | Silent, Sile | INTRON | 0.036822 | 1.5 | 0.013955 | 1.9 | 0.002245 |
| kgp8036704 | 6 | 32796521 | TAP2, TAP | Silent, Sile | INTRON | 0.044866 | 1.5 | 0.014056 | 1.3 | 0.002245 |
| rs1410779 | 9 | 5083173 | JAK2 | Silent | INTRON | 0.02267 | 0.6 | 0.019785 | 0.6 | 0.002473 |
| kgp293787 | 20 | 40905098 | PTPRT, PT | Silent, Sile | INTRON | 0.003474 | 0.1 | 0.039188 | 0.4 | 0.002484 |
| rs2071472 | 6 | 32784620 | HLA-DOB | Silent | INTRON | 0.034998 | 1.5 | 0.024565 | 1.7 | 0.002622 |
| rs2071470 | 6 | 32784753 | HLA-DOB | Silent | UTR | 0.034998 | 1.5 | 0.024565 | 1.7 | 0.002622 |
| kgp5334779 | 6 | 32628420 | HLA-DQB1 | Silent, Sile | INTRON | 0.020701 | 1.5 | 0.048854 | 1.6 | 0.002715 |
| kgp4898179 | 6 | 32629347 | HLA-DQB1 | Silent, Sile | INTRON | 0.026883 | 1.5 | 0.029479 | 1.7 | 0.002798 |

TABLE 9-continued

Allelic Model, Analysis of Candidate Genes (180) (Gala, Forte, and Combined cohorts)

| rs4769060 | 13 | 31337877 | ALOX5AP, | Silent, Sile | INTRON | 0.032101 | 1.4 | 0.035596 | 1.6 | 0.003977 |
| rs3803277 | 13 | 31318308 | ALOX5AP, | Silent, Sile | INTRON | 0.048212 | 0.7 | 0.013126 | 0.6 | 0.00521 |
| kgp5440506 | 13 | 31320543 | ALOX5AP, | Silent, Sile | INTRON | 0.038212 | 0.7 | 0.021949 | 0.6 | 0.007278 |
| rs11147439 | 13 | 31325643 | ALOX5AP, | Silent, Sile | INTRON | 0.047187 | 0.7 | 0.022726 | 0.6 | 0.007532 |
| kgp97310 | 9 | 5122932 | JAK2 | Silent | INTRON | 0.041273 | 0 7 | 0.023546 | 0.6 | 0.007654 |
| rs4360791 | 13 | 31318020 | ALOX5AP, | Silent, Sile | INTRON | 0.047959 | 0.7 | 0.022937 | 9.6 | 0.007655 |
| kgp22778566 | 7 | 1950337 | MAD1L1, | Silent, Sile | INTRON | 0.041523 | 1.5 | 0.038052 | 1.8 | 0.008717 |
| rs9671182 | 13 | 31321138 | ALOX5AP, | Silent, Sile | INTRON | 0.058607 | 0.7 | 0.029703 | 0.6 | 0.008926 |
| rs4356336 | 13 | 31319546 | ALOX5AP, | Silent, Sile | INTRON | 0.039248 | 0.7 | 0.029703 | 0.6 | 0.009084 |
| rs10815160 | 9 | 5116616 | JAK2 | Silent | INTRON | 0.040396 | 0.6 | 0.043646 | 0.6 | 0.009679 |

| | COMBINED | | | | | | | |
|---|---|---|---|---|---|---|---|---|
| Name | Odds Ratio (Minor Allele) | Allele Freq. (Case | Allele Freq. (Control | DD (Cases | DD (Controls) | Dd (Case | Dd (Controls) | dd (Cases | dd (Control |
| rs1894408 | 1.7 | 0.41 | 0.30 | 58 | 16 | 211 | 74 | 127 | 89 |
| rs1894407 | 1.7 | 0.41 | 0.30 | 57 | 16 | 213 | 75 | 128 | 90 |
| rs2857103 | 1.7 | 0.36 | 0.25 | 39 | 11 | 211 | 69 | 149 | 100 |
| rs9501224 | 1.7 | 0.36 | 0.25 | 39 | 11 | 211 | 70 | 149 | 100 |
| rs1894406 | 1.6 | 0.38 | 0.27 | 51 | 13 | 202 | 73 | 146 | 95 |
| rs241451 | 1.6 | 0.36 | 0.26 | 39 | 12 | 207 | 68 | 150 | 100 |
| rs241443 | 1.6 | 0.36 | 0.25 | 40 | 11 | 202 | 69 | 152 | 99 |
| kgp9699754 | ? | 0.03 | 0.00 | 0 | 0 | 21 | 0 | 377 | 179 |
| rs2621323 | 1.6 | 0.37 | 0.26 | 43 | 12 | 207 | 71 | 149 | 97 |
| kgp6599438 | 0.3 | 0.01 | 0.05 | 0 | 0 | 11 | 18 | 386 | 163 |
| rs3218328 | 0.1 | 0.00 | 0.03 | 0 | 0 | 3 | 10 | 395 | 169 |
| kgp304921 | 0.4 | 0.03 | 0.08 | 2 | 2 | 19 | 23 | 373 | 154 |
| kgp7747883 | 0.7 | 0.34 | 0.44 | 43 | 33 | 181 | 92 | 174 | 56 |
| rs241456 | 1.6 | 0.31 | 0.21 | 32 | 9 | 180 | 59 | 187 | 113 |
| rs2621321 | 1.6 | 0.31 | 0.22 | 31 | 9 | 183 | 60 | 184 | 112 |
| rs241454 | 1.6 | 0.31 | 0.22 | 32 | 9 | 180 | 60 | 185 | 112 |
| rs2857104 | 1.6 | 0.31 | 0.22 | 31 | 9 | 183 | 60 | 185 | 112 |
| kgp8702370 | 2.0 | 0.15 | 0.08 | 9 | 0 | 100 | 29 | 290 | 151 |
| kgp2388352 | 1.6 | 0.31 | 0.22 | 34 | 10 | 173 | 57 | 185 | 111 |
| rs10162089 | 1.5 | 0.48 | 0.38 | 96 | 24 | 190 | 88 | 110 | 67 |
| rs241446 | 1.6 | 0.30 | 0.21 | 32 | 9 | 176 | 59 | 188 | 113 |
| rs2857101 | 1.6 | 0.30 | 0.21 | 31 | 9 | 181 | 59 | 187 | 112 |
| rs241447 | 1.6 | 0.31 | 0.22 | 32 | 9 | 180 | 60 | 184 | 111 |
| kgp974569 | 1.6 | 0.31 | 0.22 | 32 | 9 | 180 | 60 | 186 | 112 |
| rs241444 | 1.6 | 0.31 | 0.22 | 32 | 9 | 180 | 60 | 187 | 112 |
| rs241453 | 1.6 | 0.31 | 0.22 | 32 | 9 | 179 | 60 | 187 | 112 |
| rs241449 | 1.6 | 0.30 | 0.21 | 32 | 9 | 175 | 58 | 188 | 112 |
| rs241452 | 1.6 | 0.31 | 0.22 | 32 | 9 | 179 | 60 | 186 | 111 |
| P1_M_061510_ | 1.6 | 0.30 | 0.22 | 32 | 9 | 178 | 60 | 187 | 112 |
| kgp4479467 | 1.5 | 0.38 | 0.29 | 54 | 11 | 195 | 82 | 147 | 88 |
| rs241445 | 1.6 | 0.31 | 0.22 | 32 | 9 | 179 | 60 | 187 | 111 |
| rs241442 | 1.6 | 0.31 | 0.22 | 32 | 9 | 179 | 60 | 187 | 111 |
| kgp10632945 | 0.6 | 0.17 | 0.25 | 10 | 11 | 118 | 70 | 270 | 100 |
| rs241440 | 1.6 | 0.30 | 0.22 | 32 | 9 | 177 | 60 | 189 | 112 |
| kgp8036704 | 1.6 | 0.30 | 0.22 | 29 | 9 | 183 | 60 | 186 | 112 |
| rs1410779 | 0.6 | 0.16 | 0.24 | 8 | 10 | 112 | 66 | 277 | 105 |
| kgp293787 | 0.3 | 0.02 | 0.05 | 0 | 2 | 15 | 15 | 384 | 164 |
| rs2071472 | 1.5 | 0.34 | 0.25 | 40 | 12 | 191 | 67 | 168 | 102 |
| rs2071470 | 1.5 | 0.34 | 0.25 | 40 | 12 | 191 | 67 | 168 | 102 |
| kgp5334779 | 1.5 | 0.38 | 0.29 | 50 | 10 | 199 | 83 | 148 | 87 |
| kgp4898179 | 1.5 | 0.38 | 0.29 | 54 | 11 | 195 | 83 | 148 | 87 |
| rs4769060 | 1.5 | 0.45 | 0.36 | 87 | 22 | 189 | 88 | 123 | 71 |
| rs3803277 | 0.7 | 0.43 | 0.52 | 83 | 47 | 180 | 95 | 136 | 39 |
| kgp5440506 | 0.7 | 0.43 | 0.51 | 81 | 45 | 175 | 95 | 138 | 40 |
| rs11147439 | 0.7 | 0.43 | 0.51 | 81 | 45 | 180 | 96 | 138 | 40 |
| kgp97310 | 0.7 | 0.20 | 0.27 | 17 | 14 | 125 | 70 | 256 | 97 |
| rs4360791 | 0.7 | 0.44 | 0.52 | 85 | 48 | 181 | 94 | 133 | 39 |
| kgp22778566 | 1.5 | 0.25 | 0.18 | 19 | 4 | 156 | 53 | 220 | 117 |

TABLE 9-continued

Allelic Model, Analysis of Candidate Genes (180) (Gala, Forte, and Combined cohorts)

| | | | | | | | | |
|---|---|---|---|---|---|---|---|---|
| rs9671182 | 0.7 | 0.43 | 0.52 | 82 | 45 | 180 | 96 | 136 | 39 |
| rs4356336 | 0.7 | 0.43 | 0.52 | 82 | 46 | 181 | 95 | 136 | 40 |
| rs10815160 | 0.7 | 0.21 | 0.28 | 19 | 14 | 124 | 71 | 248 | 93 |

TABLE 10

Genotypic Model, Analysis of Candidate Genes (180) (Gala, Forte, and Combined cohorts)

| | | | GALA | | | | | | FORTE | | |
|---|---|---|---|---|---|---|---|---|---|---|---|
| Columns | Ch | Position | Fisher's Exact P | DD (Cases) | DD (Controls) | Dd (Cases) | Dd (Controls) | dd (Cases) | dd (Controls) | Fisher's Exact | DD (Cases) | DD (Controls) |
| rs1894407 | 6 | 32787036 | 0.0006 | 26 | 13 | 114 | 46 | 58 | 61 | 0.0447 | 31 | 3 |
| rs1894408 | 6 | 32786833 | 0.0011 | 26 | 13 | 113 | 46 | 58 | 59 | 0.0258 | 32 | 3 |
| rs1894406 | 6 | 32787056 | 0.0031 | 25 | 11 | 109 | 47 | 64 | 62 | 0.0398 | 26 | 2 |
| rs2857103 | 6 | 32791299 | 0.0038 | 17 | 9 | 112 | 46 | 69 | 64 | 0.0171 | 22 | 2 |
| rs241451 | 6 | 32796480 | 0.0045 | 17 | 9 | 110 | 46 | 70 | 65 | 0.0429 | 22 | 3 |
| rs9501224 | 6 | 32792910 | 0.0047 | 17 | 9 | 112 | 47 | 69 | 64 | 0.0171 | 22 | 2 |
| kgp6599438 | 20 | 40843626 | 0.0054 | 0 | 0 | 4 | 11 | 193 | 109 | 0.0235 | 0 | 0 |
| rs241443 | 6 | 32797115 | 0.0115 | 18 | 9 | 107 | 47 | 70 | 63 | 0.0208 | 22 | 2 |
| kgp293787 | 20 | 40905098 | 0.0124 | 0 | 1 | 2 | 7 | 196 | 112 | 0.0340 | 0 | 1 |
| rs2621323 | 6 | 32788707 | 0.0134 | 18 | 10 | 111 | 48 | 69 | 61 | 0.0122 | 25 | 2 |
| rs3218328 | 22 | 37524008 | 0.0153 | 0 | 0 | 2 | 7 | 196 | 111 | 0.0409 | 0 | 0 |
| kgp9699754 | 10 | 79358319 | 0.0275 | 0 | 0 | 8 | 0 | 190 | 118 | 0.0430 | 0 | 0 |
| rs241456 | 6 | 32795965 | 0.0287 | 16 | 8 | 92 | 39 | 90 | 73 | 0.0346 | 16 | 1 |
| rs2621321 | 6 | 32789480 | 0.0321 | 16 | 8 | 93 | 40 | 89 | 72 | 0.0291 | 15 | 1 |
| rs2857104 | 6 | 32790167 | 0.0321 | 16 | 8 | 93 | 40 | 89 | 72 | 0.0309 | 15 | 1 |
| rs2857101 | 6 | 32794676 | 0.0321 | 16 | 8 | 92 | 39 | 90 | 72 | 0.0340 | 15 | 1 |
| rs241446 | 6 | 32796967 | 0.0364 | 16 | 8 | 90 | 39 | 90 | 73 | 0.0399 | 16 | 1 |
| kgp2388352 | 6 | 32797297 | 0.0367 | 16 | 9 | 88 | 37 | 89 | 71 | 0.0254 | 16 | 1 |
| rs241454 | 6 | 32796144 | 0.0374 | 16 | 8 | 92 | 40 | 89 | 72 | 0.0291 | 16 | 1 |
| kgp11976832 | 2 | 29990267 | 0.0410 | 2 | 2 | 21 | 4 | 174 | 114 | 0.0394 | 1 | 0 |
| kgp8036704 | 6 | 32796521 | 0.0422 | 15 | 8 | 92 | 40 | 90 | 72 | 0.0377 | 14 | 1 |
| kgp974569 | 6 | 32796057 | 0.0427 | 16 | 8 | 92 | 40 | 90 | 72 | 0.0291 | 16 | 1 |
| rs241447 | 6 | 32796751 | 0.0427 | 16 | 8 | 92 | 40 | 90 | 72 | 0.0347 | 16 | 1 |
| rs241444 | 6 | 32797109 | 0.0427 | 16 | 8 | 92 | 40 | 90 | 72 | 0.0346 | 16 | 1 |
| kgp4470107 | 7 | 18205779 | 0.0446 | 30 | 8 | 63 | 48 | 105 | 64 | 0.0063 | 26 | 5 |
| rs241452 | 6 | 32796346 | 0.0469 | 16 | 8 | 92 | 40 | 90 | 71 | 0.0337 | 16 | 1 |
| rs241449 | 6 | 32796653 | 0.0472 | 16 | 8 | 88 | 38 | 91 | 72 | 0.0365 | 16 | 1 |
| kgp4934352 | 20 | 15669073 | 0.0476 | 2 | 5 | 40 | 33 | 155 | 82 | 0.0099 | 1 | 3 |

| | FORTE | | | | COMBINED | | | | | | |
|---|---|---|---|---|---|---|---|---|---|---|---|
| Columns | Dd (Cases) | Dd (Controls) | dd (Cases) | dd (Controls) | Fisher's Exact | DD (Cases) | DD (Controls) | Dd (Cases) | Dd (Controls) | dd (Cases) | dd (Controls) |
| rs1894407 | 99 | 29 | 70 | 29 | 0.0002 | 57 | 16 | 213 | 75 | 128 | 90 |
| rs1894408 | 98 | 28 | 69 | 30 | 0.0002 | 58 | 16 | 211 | 74 | 127 | 89 |
| rs1894406 | 93 | 26 | 82 | 33 | 0.0010 | 51 | 13 | 202 | 73 | 146 | 95 |
| rs2857103 | 99 | 23 | 80 | 36 | 0.0002 | 39 | 11 | 211 | 69 | 149 | 100 |
| rs241451 | 97 | 22 | 80 | 35 | 0.0004 | 39 | 12 | 207 | 68 | 150 | 100 |
| rs9501224 | 99 | 23 | 80 | 36 | 0.0003 | 39 | 11 | 211 | 70 | 149 | 100 |
| kgp6599438 | 7 | 7 | 193 | 54 | 0.0007 | 0 | 0 | 11 | 18 | 386 | 163 |
| rs241443 | 95 | 22 | 82 | 36 | 0.0008 | 40 | 11 | 202 | 69 | 152 | 99 |
| kgp293787 | 13 | 8 | 188 | 52 | 0.0059 | 0 | 2 | 15 | 15 | 384 | 164 |
| rs2621323 | 96 | 23 | 80 | 36 | 0.0009 | 43 | 12 | 207 | 71 | 149 | 97 |
| rs3218328 | 1 | 3 | 199 | 58 | 0.0008 | 0 | 0 | 3 | 10 | 395 | 169 |
| kgp9699754 | 13 | 0 | 187 | 61 | 0.0005 | 0 | 0 | 21 | 0 | 377 | 179 |
| rs241456 | 88 | 20 | 97 | 40 | 0.0023 | 32 | 9 | 180 | 59 | 187 | 113 |
| rs2621321 | 90 | 20 | 95 | 40 | 0.0023 | 31 | 9 | 183 | 60 | 184 | 112 |
| rs2857104 | 90 | 20 | 96 | 40 | 0.0025 | 31 | 9 | 183 | 60 | 185 | 112 |
| rs2857101 | 89 | 20 | 97 | 40 | 0.0029 | 31 | 9 | 181 | 59 | 187 | 112 |
| rs241446 | 86 | 20 | 98 | 40 | 0.0037 | 32 | 9 | 176 | 59 | 188 | 113 |
| kgp2388352 | 85 | 20 | 96 | 40 | 0.0036 | 34 | 10 | 173 | 57 | 185 | 111 |
| rs241454 | 88 | 20 | 96 | 40 | 0.0029 | 32 | 9 | 180 | 60 | 185 | 112 |
| kgp11976832 | 21 | 1 | 176 | 60 | 0.0019 | 3 | 2 | 42 | 5 | 350 | 174 |
| kgp8036704 | 91 | 20 | 96 | 40 | 0.0034 | 29 | 9 | 183 | 60 | 186 | 112 |
| kgp974569 | 88 | 20 | 96 | 40 | 0.0032 | 32 | 9 | 180 | 60 | 186 | 112 |
| rs241447 | 88 | 20 | 94 | 39 | 0.0032 | 32 | 9 | 180 | 60 | 184 | 111 |
| rs241444 | 88 | 20 | 97 | 40 | 0.0034 | 32 | 9 | 180 | 60 | 187 | 112 |
| kgp4470107 | 75 | 37 | 100 | 19 | 0.0048 | 56 | 13 | 138 | 85 | 205 | 83 |

TABLE 10-continued

Genotypic Model, Analysis of Candidate Genes (180) (Gala, Forte, and Combined cohorts)

| | | | | | | | | | | |
|---|---|---|---|---|---|---|---|---|---|---|
| rs241452 | 87 | 20 | 96 | 40 | 0.0040 | 32 | 9 | 179 | 60 | 186 | 111 |
| rs241449 | 87 | 20 | 97 | 40 | 0.0038 | 32 | 9 | 175 | 58 | 188 | 112 |
| kgp4934352 | 51 | 8 | 148 | 50 | 0.0160 | 3 | 8 | 91 | 41 | 303 | 132 |

Example 8 Analysis Part 4—Genome Wide Analysis

A full genome-wide analysis was then conducted (4 M variants). Power (80%) with Bonferroni statistical correction to identify significant genetic associations with an odds ratio >7, for variants with an allele frequency greater than 10%. (Or rare alleles (5%) with an odds ratio >11). Approximately 4,200 variants were selected for analysis in stage 2 (replication) (P<0.001).

Replication Cohort (n=262: 201 R vs. 61 NR)—In the second stage of analysis, variants selected in the discovery cohort were analyzed to identify replicating associations in the FORTE replication cohort associated with good response vs. poor response. Based upon an analysis of an estimated 4,200 variants, there is statistical power (80%) with Bonferroni correction to identify significant genetic associations with an odds ratio >6.5, for variants with an allele frequency greater than 5%.

Combined Cohorts (n=580: 399 R vs. 111 NR)—In the third stage of the analysis, the combined GALA and FORTE cohorts were analyzed identify variants associated with response/non-response using a full genome-wide analysis (4 M variants).

Results for Standard Response Definition, Genome Wide Analysis for Additive, Allelic and Genotypic models are presented in tables 11-13, respectively.

In some embodiments genetic markers presented in Tables 11, 12 and 13 are identified as predictive of response to glatiramer acetate if the p-value for the GALA cohort is less than about 0.001, less than about 0.0005, less than about $10^{-4}$ or less than about $5*10^{-5}$.

In some embodiments genetic markers presented in Tables 11, 12 and 13 are identified as predictive of response to glatiramer acetate if the p-value for the FORTE cohort is less than about 0.05, less than about 0.01, less than about 0.005, less than about 0.001 or less than about 0.0005.

TABLE 11

Additive Model, Genome Wide Analysis, p-value sorted by GALA cohort (Gala, Forte, and Combined cohorts)

| | | | | | | GALA | | | FORTE | | |
|---|---|---|---|---|---|---|---|---|---|---|---|
| Name | Ch | Position | Gene(s) | Mutation | Gene Locations (s) | Armitage P | Regression Odds Ratio | Allele Freq. (Cases) | Allele Freq (Controls) | Armitage P | Regression Odds Ratio | Allele Freq. (Cases) |
| kgp541056 | 1 | 65738507 | DNAJC6 | Silent | INTRON | 2.75E−05 | 0.44 | 0.18 | 0.33 | 3.24E−02 | 1.79 | 0.26 |
| rs9817308 | 3 | 124182136 | KALRN, KA | Silent, Sile | INTRON | 2.85E−05 | 0.49 | 0.41 | 0.58 | 2.64E−02 | 0.62 | 0.45 |
| rs1749972 | 1 | 65736258 | DNAJC6 | Silent | INTRON | 3.00E−05 | 0.44 | 0.19 | 0.33 | 3.93E−02 | 1.76 | 0.26 |
| kgp24415534 | 2 | 174156875 | ? | ? | ? | 3.40E−05 | 0.05 | 0.00 | 0.06 | 1.10E−02 | 0.14 | 0.00 |
| kgp10594414 | 1 | 216039833 | USH2A | Silent | INTRON | 3.57E−05 | 0.05 | 0.00 | 0.05 | 1.25E−02 | 0.24 | 0.01 |
| rs10841337 | 12 | 19897179 | ? | ? | ? | 4.26E−05 | 0.47 | 0.22 | 0.37 | 4.27E−02 | 0.64 | 0.27 |
| rs543122 | 3 | 124164156 | KALRN,KA | Silent, Sile | INTRON | 4.73E−05 | 0.50 | 0.41 | 0.57 | 1.39E−02 | 0.59 | 0.44 |
| kgp4705854 | 12 | 19907696 | ? | ? | ? | 5.01E−05 | 0.51 | 0.30 | 0.47 | 2.87E−02 | 0.63 | 0.33 |
| kgp8192546 | 12 | 19903173 | ? | ? | ? | 6.52E−05 | 0.47 | 0.21 | 0.36 | 2.64E−02 | 0.62 | 0.26 |
| kgp12008955 | 2 | 73759636 | ALMS1 | Silent | INTRON | 9.26E−05 | ? | 0.00 | 0.04 | 3.65E−04 | 0.12 | 0.01 |
| kgp5564995 | 6 | 26414060 | BTN3A1, B | Silent, Sile | UTR,EXON | 1.56E−04 | 3.35 | 0.15 | 0.06 | 3.98E−02 | 2.30 | 0.14 |
| kgp1699628 | 6 | 18032535 | ? | ? | ? | 1.73E−04 | 0.51 | 0.44 | 0.58 | 2.99E−02 | 0.63 | 0.47 |
| kgp1009249 | 12 | 19838534 | ? | ? | ? | 1.74E−04 | 0.48 | 0.18 | 0.31 | 1.03E−02 | 0.54 | 0.21 |
| rs9579566 | 13 | 30980265 | ? | ? | ? | 2.08E−04 | 0.23 | 0.02 | 0.08 | 9.90E−03 | 0.30 | 0.02 |
| kgp26026546 | 13 | 79972606 | RBM26 | Silent | INTRON | 2.20E−04 | ? | 0.00 | 0.03 | 4.46E−04 | 0.06 | 0.00 |
| rs17577980 | 6 | 32359821 | HCG23 | Silent | INTRON | 2.33E−04 | 2.36 | 0.23 | 0.11 | 5.31E−03 | 2.94 | 0.16 |
| kgp9288015 | 6 | 28194629 | ZNF193, ZN | Silent, Sile | INTRON | 2.71E−04 | 0.48 | 0.14 | 0.26 | 3.92E−02 | 0.61 | 0.22 |
| kgp10619195 | 4 | 99417717 | TSPAN5 | Silent | INTRON | 2.87E−04 | 0.29 | 0.04 | 0.10 | 3.30E−02 | 0.46 | 0.05 |
| kgp6022882 | 6 | 28197186 | ZNF193, ZN | Silent, Sile | INTRON | 3.03E−04 | 0.48 | 014 | 0.24 | 3.95E−02 | 0.61 | 0.22 |
| rs1579771 | 3 | 157278882 | C3or155, C | Silent, Sile | INTRON | 3.35E−04 | 2.02 | 0.38 | 0.25 | 1.64E−02 | 1.81 | 0.36 |
| kgp8474976 | 6 | 32407906 | HLA-DRA | Silent | INTRON | 3.66E−04 | 2.72 | 0.17 | 0.08 | 4.16E−02 | 2.35 | 0.12 |
| kgp6127371 | 4 | 153856357 | ? | ? | ? | 3.69E−04 | 0.18 | 0.01 | 0.06 | 9.38E−03 | 0.28 | 0.02 |
| kgp11210903 | 22 | 30898906 | SEC14L4, S | Silent, Sile | INTRON | 3.70E−04 | 0.10 | 0.01 | 0.05 | 4.98E−02 | 0.19 | 0.00 |
| kgp5869992 | 12 | 49219569 | CACNB3, C | Silent, Sile | INTRON | 3.71E−04 | 0.57 | 0.39 | 0.54 | 2.00E−02 | 0.62 | 0.38 |
| rs6535882 | 4 | 153848128 | ? | ? | ? | 3.83E−04 | 0.18 | 0 01 | 0.06 | 9.06E−03 | 0.27 | 0.02 |
| kgp6700691 | 4 | 153849531 | ? | ? | ? | 3.83E−04 | 0.18 | 0.01 | 0.06 | 9.06E−03 | 0.27 | 0.02 |
| kgp2356388 | 16 | 19771577 | IQCK | Silent | INTRON | 3.88E−04 | 0.43 | 0.12 | 0.22 | 1.94E−03 | 0.45 | 0.14 |
| kgp 3933330 | 7 | 28583709 | CREB5, CR | Silent, Sile | INTRON | 4.00E−04 | 2.42 | 0.20 | 0.09 | 3.21E−02 | 2.15 | 0.16 |
| kgp4559907 | 6 | 133255252 | ? | ? | ? | 4.08E−04 | 0.56 | 0.31 | 0.45 | 3.11E−02 | 0.63 | 0.35 |
| rs10456405 | 6 | 32212867 | ? | ? | ? | 4.24E−04 | 1.94 | 0.33 | 0.19 | 4.00E−02 | 1.80 | 0.22 |
| kgp4127859 | 6 | 32434481 | ? | ? | ? | 4.49E−04 | 2.42 | 0.20 | 0.10 | 1.43E−02 | 2.53 | 0.16 |
| rs11022778 | 11 | 13390860 | ARNTL, AR | Silent, Sile | INTRON | 4.49E−04 | 1.96 | 0.34 | 0.20 | 4.87E−02 | 1.58 | 0.37 |
| rs1508102 | 11 | 116379889 | ? | ? | ? | 4.99E−04 | 0.34 | 0.04 | 0.12 | 4.52E−02 | 0.50 | 0.06 |
| kgp4223880 | 2 | 10584122 | ODC1 | Silent | INTRON | 4.99E−04 | 0.06 | 0.00 | 0.04 | 3.23E−02 | 0.22 | 0.01 |
| kgp9627338 | 17 | 90155 | RPH3AL, R | Silent, Sile | INTRON | 5.01E−04 | 0.47 | 0.10 | 0.21 | 3.13E−03 | 0.43 | 0.11 |

TABLE 11-continued

Additive Model, Genome Wide Analysis, p-value sorted by GALA cohort (Gala, Forte, and Combined cohorts)

| | | | | | | | | | | | | |
|---|---|---|---|---|---|---|---|---|---|---|---|---|
| kgp2446153 | 5 | 152980439 | GRIA1, GR | Silent, Sile | INTRON | 5.31E-04 | 0.06 | 0.00 | 0.04 | 3.17E-02 | 0.22 | 0.01 |
| kgp1786079 | 7 | 144701118 | ? | ? | ? | 5.35E-04 | 0.48 | 0.11 | 0.21 | 9.86E-03 | 0.49 | 0.13 |
| rs7191155 | 16 | 19800213 | IQCK | Missense | EXON | 5.38E-04 | 0.44 | 0.12 | 0.22 | 1.93E-03 | 0.45 | 0.14 |
| rs9931167 | 16 | 19792598 | IQCK | Silent | INTRON | 5.38E-04 | 0.44 | 0.12 | 0.22 | 1.94E-03 | 0.45 | 0.14 |
| rs3829539 | 16 | 19722366 | C16orl88 | Silent | INTRON | 5.38E-04 | 0.44 | 0.12 | 0.22 | 2.10E-03 | 0.45 | 0.15 |
| kgp1584138 | 9 | 124827130 | TTLL11, TT | Silent, Sile | INTRON | 0.000545 | 0.24 | 0.02 | 0.08 | 3.99E-02 | 0.45 | 0.03 |
| kgp24415534 | 2 | 174156875 | ? | ? | ? | 3.40E-05 | 0.05 | 0.00 | 0.05 | 1.10E-05 | 0.14 | 0.00 |
| kgp12008955 | 2 | 73759636 | ALMS1 | Silent | INTRON | 9.26E-05 | ? | 0.00 | 0.04 | 3.65E-04 | 0.12 | 0.01 |
| kgp26026546 | 13 | 79972606 | R6KA26 | Silent | INTRON | 2.20E-04 | ? | 0.00 | 0.03 | 4.46E-04 | 0.06 | 0.00 |
| rs16886004 | 7 | 78021500 | MAGI2 | Silent | INTRON, E | 2.28E-03 | 2.15 | 0.20 | 0.11 | 3.25E-05 | 5.56 | 0.20 |
| kgp25952891 | 13 | 80027089 | ? | ? | ? | 5.58E-04 | ? | 0.03 | 0.03 | 4.30E-04 | 0.06 | 0.00 |
| kgp3450875 | 16 | 57268931 | RSPRY1 | Silent | INTRON | 6.63E-03 | 0.19 | 0.01 | 0.04 | 1.51E-05 | 0.07 | 0.00 |
| rs10251797 | 7 | 78025427 | MAGI2 | Silent | INTRON, E | 3.18E-03 | 2.07 | 0.20 | 0.11 | 4.05E-05 | 5.49 | 0.19 |
| kgp2299675 | 20 | 16933074 | ? | ? | ? | 4.43E-03 | 0.26 | 0.02 | 0.05 | 4.23E-05 | 0.13 | 0.01 |
| kgp10594414 | 1 | 216039833 | USH2A | Silent | INTRON | 3.57E-05 | 0.05 | 0.00 | 0.05 | 1.25E-02 | 0.24 | 0.01 |
| kgp1688752 | 21 | 43016736 | ? | ? | ? | 8.83E-04 | 0.34 | 0.05 | 0.11 | 1.48E-03 | 0.03 | 0.03 |
| kgp12230354 | 5 | 27037978 | CDH9 | Silent | INTRON | 3.70E-03 | 0.21 | 0.01 | 0.05 | 3.31E-05 | 0.14 | 0.02 |
| rs543122 | 3 | 124164156 | KALRN, K | Silent, Sile | INTRON | 4.73E-05 | 0.50 | 0.41 | 0.57 | 1.39E-02 | 0.59 | 0.44 |
| kgp6236949 | 2 | 60301030 | ? | ? | ? | 6.37E-04 | 0.56 | 0.31 | 0.44 | 7.57E-03 | 0.55 | 0.26 |
| kgp9627338 | 17 | 90155 | RPH3AL, B | Silent, Sile | INTRON | 5.01E-04 | 0.47 | 0.10 | 0.21 | 3.13E-03 | 0.43 | 0.11 |
| kgp11141512 | 20 | 35283733 | NDRG3, N | Silent, Sile | INTRON | 3.33E-03 | 0.30 | 0.02 | 0.07 | 3.65E-04 | 0.17 | 0.01 |
| rs9579566 | 13 | 30980265 | ? | ? | ? | 2.08E-04 | 0.23 | 0.02 | 0.08 | 9.90E-03 | 0.30 | 0.02 |
| rs2816838 | 10 | 52714759 | ? | ? | ? | 1.94E-04 | 0.51 | 0.14 | 0.23 | 1.30E-03 | 0.42 | 0.11 |
| kgp40705854 | 12 | 19907696 | ? | ? | ? | 5.01E-05 | 0.51 | 0.30 | 0.47 | 2.37E-02 | 0.63 | 0.33 |
| rs9817308 | 3 | 124182136 | KALRN, KA | Silent, Sile | INTRON | 2.85E-05 | 0.49 | 0.41 | 0.58 | 2.64E-02 | 0.62 | 0.45 |
| kgp8817856 | 6 | 32744440 | ? | ? | ? | 6.02E-04 | 0.53 | 0.36 | 0.49 | 3.73E-04 | 0.46 | 0.42 |
| kgp6214351 | 11 | 75546691 | UV RAG | Silent | INTRON | 3.98E-04 | 0.42 | 0.05 | 0.11 | 2.65E-04 | 0.26 | 0.04 |
| kgp2356388 | 16 | 19771577 | IQCK | Silent | INTRON | 3.88E-04 | 0.43 | 012 | 0.22 | 1.94E-03 | 0.45 | 0.14 |
| kgp7416024 | 9 | 21453902 | ? | ? | ? | 2.14E-03 | 0.13 | 0.01 | 0.04 | 3.81E-04 | 0.12 | 0.01 |
| rs6718758 | 2 | 60328802 | ? | ? | ? | 5.70E-03 | 0.63 | 0.33 | 0.45 | 5.96E-04 | 0.47 | 0.28 |
| rs7579987 | 2 | 60307009 | ? | ? | ? | 6.99E-03 | 0.64 | 0.36 | 0.47 | 3.91E-04 | 0.45 | 0.31 |
| rs7217872 | 17 | 88988 | RPH3AL, R | Silent, Sile | INTRON | 1.03E-03 | 0.49 | 0.11 | 0.20 | 2.42E-03 | 0.42 | 0.11 |
| rs13394010 | 2 | 60302746 | ? | ? | ? | 7.74E-03 | 0.64 | 0.35 | 0.46 | 3.91E-04 | 0.45 | 0.31 |
| rs7191155 | 16 | 19800213 | IQCK | Missense | EXON | 5.38E-04 | 0.44 | 0.12 | 0.22 | 1.93E-03 | 0.45 | 0.14 |
| rs9931167 | 16 | 19792598 | IQCK | Silent | INTRON | 5.38E-04 | 0.44 | 0.12 | 0.22 | 1.94E-03 | 0.45 | 0.14 |
| rs11691553 | 2 | 60303554 | ? | ? | ? | 8.54E-04 | 0.65 | 0.35 | 0.46 | 3.72E-04 | 0.45 | 0.31 |
| rs11648129 | 16 | 19820694 | IQCK | Silent | INTRON | 6.54E-04 | 0.45 | 0.12 | 0.22 | 1.64E-03 | 0.44 | 0.14 |
| kgp25216186 | 1 | 23758427 | ASAP3, AS | Silent, Sile | INTRON | 1.32E-03 | 0.07 | 0.00 | 0.03 | 2.45E-03 | 0.07 | 0.00 |
| kgp29794723 | 10 | 18497332 | ? | ? | ? | 4.77E-03 | 0.31 | 0.02 | 0.07 | 3.54E-04 | 0.18 | 0.02 |
| rs3829539 | 16 | 19722366 | C16orf88 | Silent | INTRON | 5.38E-04 | 0.44 | 0.12 | 0.22 | 2.10E-03 | 0.45 | 0.15 |
| rs6895094 | 5 | 141037277 | ARAP3 | Silent | INTRON | 658E-04 | 0.56 | 0.38 | 0.52 | 1.19E-02 | 0.60 | 0.35 |
| kgp1009249 | 12 | 19838534 | ? | ? | ? | 1.74E-04 | 0.48 | 0.18 | 0.31 | 1.03E-02 | 0.54 | 0.21 |
| rs10203396 | 2 | 60305110 | ? | ? | ? | 8.67E-03 | 0.65 | 0.36 | 0.46 | 4.43E-04 | 0.46 | 0.31 |
| kgp3854180 | 16 | 19721806 | C16orf 88 | Silent | INTRON | 6.54E-04 | 0.45 | 0.12 | 0.22 | 1.94E-03 | 0.45 | 0.14 |
| rs6497396 | 16 | 19735697 | IQCK | Silent | INTRON | 1.30E-03 | 0.48 | 0.13 | 0.23 | 7.65E-04 | 0.43 | 0.16 |
| rs8055485 | 16 | 19750051 | IQCK | Silent | INTRON | 6.54E-04 | 0.45 | 0.12 | 0.22 | 2.10E-03 | 0.45 | 0.15 |
| rs9931211 | 16 | 19813605 | IQCK | Silent | INTRON | 6.54E-04 | 0.45 | 0.12 | 0.22 | 2.10E-03 | 0.45 | 0.15 |

| | FORTE | | | COMBINED | | | | | | |
|---|---|---|---|---|---|---|---|---|---|---|
| Name | Allele Freq (Controls) | Armitage P | Regression Odds Ratio | Allele Freq (Cases) | Allele Freq (Controls) | DD (Cases) | DD (Controls) | Dd (Cases) | Dd (Control) | dd (Cases) | dd (Controls) |
| kgp541056 | 0.16 | 4.67E-02 | 0.75 | 0.22 | 0.27 | 15 | 15 | 146 | 69 | 238 | 97 |
| rs9817308 | 0.57 | 5.18E-06 | 0.55 | 0.43 | 0.57 | 71 | 55 | 199 | 96 | 127 | 29 |
| rs1749972 | 0.17 | 4.33E-02 | 0.74 | 0.22 | 0.28 | 15 | 15 | 146 | 68 | 237 | 95 |
| kgp24415534 | 0.03 | 3.98E-07 | 0.08 | 0.00 | 0.04 | 0 | 0 | 3 | 16 | 396 | 165 |
| kgp10594414 | 0.05 | 2.44E-06 | 0.14 | 0.01 | 0.05 | 0 | 0 | 6 | 18 | 391 | 163 |
| rs10841337 | 0.36 | 1.56E-05 | 0.55 | 0.24 | 0.36 | 22 | 24 | 147 | 84 | 227 | 73 |
| rs543122 | 0.57 | 3.17E-06 | 0.54 | 0.42 | 0.57 | 70 | 54 | 195 | 97 | 131 | 29 |
| kgp4705854 | 0.43 | 4.80E-06 | 0.31 | 0.31 | 0.46 | 41 | 38 | 169 | 89 | 189 | 54 |
| kgp8192546 | 0.36 | 1.29E-05 | 0.55 | 0.24 | 0.36 | 21 | 23 | 146 | 84 | 232 | 74 |
| kgp12008955 | 0.06 | 3.98E-07 | 0.08 | 0.00 | 0.04 | 0 | 0 | 3 | 16 | 396 | 165 |
| kgp5564995 | 0.07 | 2.28E-05 | 2.88 | 0.14 | 0.06 | 1 | 0 | 109 | 21 | 274 | 151 |
| kgp1699628 | 0.58 | 2.72E-05 | 0.57 | 0.45 | 0.58 | 72 | 62 | 218 | 85 | 109 | 32 |
| kgp1009249 | 0.32 | 9.55E-06 | 0.51 | 0.20 | 0.31 | 10 | 16 | 136 | 80 | 253 | 84 |
| rs9579566 | 0.07 | 4.19E-06 | 0.26 | 0.02 | 0.08 | 0 | 1 | 18 | 27 | 381 | 153 |
| kgp26026546 | 0.04 | 4.46E-07 | 0.03 | 0.00 | 0.04 | 0 | 0 | 1 | 13 | 397 | 167 |
| rs17577980 | 0.07 | 1.66E-05 | 2.36 | 0.20 | 0.09 | 13 | 5 | 130 | 23 | 255 | 150 |
| kgp9288015 | 0.30 | 1.76E-04 | 0.57 | 0.18 | 0.28 | 13 | 11 | 117 | 78 | 267 | 92 |
| kgp10619195 | 0.10 | 3.54E-05 | 0.36 | 0.04 | 0.10 | 0 | 2 | 32 | 33 | 366 | 146 |
| kgp6022882 | 0.30 | 1.99E-04 | 0.57 | 0.18 | 0.28 | 13 | 11 | 118 | 78 | 267 | 92 |
| rs1579771 | 0.25 | 1.96E-05 | 1.91 | 0.37 | 0.25 | 39 | 9 | 213 | 71 | 146 | 101 |
| kgp8474976 | 0.06 | 1.64E-04 | 2.39 | 0.15 | 0.07 | 3 | 0 | 111 | 26 | 285 | 155 |
| kgp6127371 | 0.07 | 1.23E-05 | 0.23 | 0.02 | 0.06 | 0 | 0 | 13 | 23 | 384 | 157 |
| kgp11210903 | 0.02 | 1.48E-05 | 0.12 | 0.01 | 0.04 | 0 | 0 | 4 | 14 | 395 | 167 |

TABLE 11-continued

Additive Model, Genome Wide Analysis, p-value sorted by GALA cohort (Gala, Forte, and Combined cohorts)

| | | | | | | | | | | | |
|---|---|---|---|---|---|---|---|---|---|---|---|
| kgp5869992 | 0.50 | 1.13E−05 | 0.58 | 0.38 | 0.53 | 60 | 58 | 184 | 74 | 152 | 48 |
| rs6535882 | 0.07 | 1.24E−05 | 0.23 | 0.02 | 0.06 | 0 | 0 | 13 | 23 | 386 | 158 |
| kgp6700691 | 0.07 | 1.24E−05 | 0.23 | 0.02 | 0.06 | 0 | 0 | 13 | 23 | 386 | 158 |
| kgp2356388 | 0.26 | 5.78E−06 | 0.46 | 0.13 | 0.23 | 4 | 5 | 98 | 75 | 297 | 101 |
| kgp 3933330 | 0.08 | 6.67E−05 | 2.26 | 0.18 | 0.09 | 15 | 1 | 111 | 29 | 271 | 151 |
| kgp4559907 | 0.46 | 6.02E−05 | 0.60 | 0.33 | 0.46 | 46 | 37 | 171 | 91 | 180 | 53 |
| rs10456405 | 0.13 | 2.89E−04 | 1.75 | 0.27 | 0.17 | 35 | 11 | 144 | 38 | 212 | 129 |
| kgp4127859 | 0.07 | 5.43E−05 | 2.32 | 0.18 | 0.09 | 8 | 0 | 127 | 33 | 263 | 148 |
| rs11022778 | 0.27 | 2.37E−05 | 1.86 | 0.35 | 0.23 | 52 | 5 | 176 | 72 | 171 | 104 |
| rs1508102 | 0.11 | 9.87E−05 | 0.42 | 0.05 | 0.12 | 0 | 4 | 41 | 34 | 357 | 143 |
| kgp4223880 | 0.03 | 4.19E−05 | 0.13 | 0.01 | 0.04 | 0 | 0 | 4 | 13 | 394 | 167 |
| kgp9627338 | 0.20 | 3.52E−06 | 0.45 | 0.10 | 0.21 | 6 | 7 | 71 | 61 | 320 | 113 |
| kgp2446153 | 0.03 | 4.35E−05 | 0.13 | 0.01 | 0.04 | 0 | 0 | 4 | 13 | 395 | 168 |
| kgp1786079 | 0.22 | 2.09E−05 | 0.49 | 0.12 | 0.22 | 4 | 11 | 86 | 56 | 308 | 114 |
| rs7191155 | 0.26 | 7.89E−06 | 0.46 | 0.13 | 0.23 | 4 | 5 | 97 | 74 | 295 | 101 |
| rs9931167 | 0.26 | 8.07E−06 | 0.46 | 0.13 | 0.23 | 4 | 5 | 98 | 74 | 297 | 101 |
| rs3829539 | 0.26 | 8.80E−06 | 0.47 | 0.13 | 0.23 | 4 | 5 | 98 | 74 | 297 | 101 |
| kgp1584138 | 0.08 | 1.47E−04 | 0.35 | 0.03 | 0.08 | 1 | 1 | 20 | 26 | 378 | 154 |
| kgp24415534 | 0.03 | 3.98E−07 | 0.08 | 0.00 | 0.04 | 0 | 0 | 3 | 16 | 396 | 165 |
| kgp12008955 | 0.06 | 3.98E−07 | 0.08 | 0.00 | 0.04 | 0 | 0 | 3 | 16 | 396 | 165 |
| kgp26026546 | 0.04 | 4.46E−07 | 0.03 | 0.00 | 0.04 | 0 | 0 | 1 | 13 | 397 | 167 |
| rs16886004 | 0.05 | 9.81E−07 | 2.79 | 0.20 | 0.09 | 6 | 2 | 147 | 28 | 246 | 149 |
| kgp25952891 | 0.04 | 1.41E−06 | 0.04 | 0.00 | 0.03 | 0 | 0 | 1 | 12 | 398 | 168 |
| kgp3450875 | 0.07 | 1.99E−06 | 0.12 | 0.01 | 0.05 | 0 | 0 | 5 | 17 | 394 | 164 |
| rs10251797 | 0.05 | 2.21E−06 | 2.67 | 0.20 | 0.09 | 6 | 2 | 145 | 29 | 248 | 150 |
| kgp2299675 | 0.08 | 2.28E−06 | 0.19 | 0.01 | 0.06 | 0 | 0 | 11 | 23 | 388 | 158 |
| kgp10594414 | 0.05 | 2.44E−06 | 0.14 | 0.01 | 0.05 | 0 | 0 | 6 | 18 | 391 | 163 |
| kgp1688752 | 0.11 | 2.53E−06 | 0.33 | 0.04 | 0.11 | 1 | 2 | 30 | 37 | 368 | 142 |
| kgp12230354 | 0.09 | 2.74E−06 | 0.19 | 0.01 | 0.06 | 0 | 0 | 10 | 22 | 386 | 159 |
| rs543122 | 0.57 | 3.17E−06 | 0.54 | 0.42 | 0.57 | 70 | 54 | 195 | 97 | 131 | 29 |
| kgp6236949 | 0.39 | 3.26E−06 | 0.54 | 0.28 | 0.42 | 30 | 34 | 166 | 85 | 203 | 62 |
| kgp9627338 | 0.20 | 3.52E−06 | 0.45 | 0.10 | 0.21 | 6 | 7 | 71 | 61 | 320 | 113 |
| kgp11141512 | 0.06 | 4.12E−06 | 0.21 | 0.01 | 0.06 | 0 | 1 | 11 | 21 | 388 | 158 |
| rs9579566 | 0.07 | 4.19E−06 | 0.26 | 0.02 | 0.08 | 0 | 1 | 18 | 27 | 381 | 153 |
| rs2816838 | 0.22 | 4.79E−06 | 0.46 | 0.13 | 0.23 | 4 | 8 | 92 | 67 | 303 | 106 |
| kgp40705854 | 0.43 | 4.80E−06 | 0.55 | 0.31 | 0.46 | 41 | 38 | 169 | 89 | 189 | 54 |
| rs9817308 | 0.57 | 5.18E−08 | 0.55 | 0.43 | 0.57 | 71 | 55 | 199 | 96 | 127 | 29 |
| kgp8817856 | 0.60 | 5.33E−06 | 0.53 | 0.39 | 0.53 | 50 | 44 | 208 | 103 | 135 | 34 |
| kgp6214351 | 0.13 | 5.51E−06 | 0.35 | 0.05 | 0.12 | 0 | 2 | 37 | 39 | 361 | 140 |
| kgp2356388 | 0.26 | 5.78E−06 | 0.46 | 0.13 | 0.23 | 4 | 5 | 98 | 75 | 297 | 101 |
| kgp7416024 | 0.06 | 6.06E−06 | 0.13 | 0.01 | 0.04 | 0 | 0 | 5 | 16 | 393 | 165 |
| rs6718758 | 0.44 | 6.08E−06 | 0.55 | 0.31 | 0.44 | 35 | 38 | 175 | 85 | 189 | 58 |
| rs7579987 | 0.48 | 6.43E−06 | 0.55 | 0.33 | 0.47 | 40 | 41 | 184 | 87 | 175 | 52 |
| rs7217872 | 0.21 | 7.50E−06 | 0.47 | 0.11 | 0.21 | 6 | 7 | 74 | 61 | 319 | 113 |
| rs13394010 | 0.48 | 7.81E−06 | 0.56 | 0.33 | 0.47 | 39 | 41 | 185 | 86 | 175 | 53 |
| rs7191155 | 0.26 | 7.89E−06 | 0.46 | 0.13 | 0.23 | 4 | 5 | 97 | 74 | 295 | 101 |
| rs9931167 | 0.26 | 8.07E−06 | 0.46 | 0.13 | 0.23 | 4 | 5 | 98 | 74 | 297 | 101 |
| rs11691553 | 0.48 | 8.19E−06 | 0.56 | 0.33 | 0.47 | 39 | 41 | 183 | 86 | 174 | 53 |
| rs11648129 | 0.26 | 8.23E−06 | 0.47 | 0.13 | 0.23 | 4 | 5 | 97 | 7 | 297 | 102 |
| kgp25216186 | 0.03 | 8.36E−06 | 0.07 | 0.00 | 0.03 | 0 | 0 | 2 | 12 | 397 | 169 |
| kgp29794723 | 0.08 | 8.64E−06 | 0.25 | 0.02 | 0.07 | 0 | 0 | 16 | 26 | 382 | 155 |
| rs3829539 | 0.26 | 8.80E−06 | 0.47 | 0.13 | 0.23 | 4 | 5 | 98 | 74 | 296 | 101 |
| rs6895094 | 0.48 | 9.24E−06 | 0.57 | 0.37 | 0.51 | 56 | 46 | 181 | 92 | 161 | 43 |
| kgp1009249 | 0.32 | 9.55E−06 | 0.51 | 0.20 | 0.31 | 10 | 16 | 136 | 80 | 253 | 84 |
| rs10203396 | 0.48 | 9.72E−06 | 0.56 | 0.33 | 0.47 | 39 | 41 | 186 | 87 | 173 | 53 |
| kgp3854180 | 0.26 | 1.00E−05 | 0.47 | 0.13 | 0.23 | 4 | 5 | 98 | 74 | 297 | 102 |
| rs6497396 | 0.29 | 1.02E−05 | 0.48 | 0.14 | 0.25 | 6 | 6 | 102 | 77 | 290 | 98 |
| rs8055485 | 0.26 | 1.09E−05 | 0.47 | 0.13 | 0.23 | 4 | 5 | 98 | 74 | 296 | 102 |
| rs9931211 | 0.26 | 1.09E−05 | 0.47 | 0.13 | 0.23 | 4 | 5 | 98 | 74 | 296 | 102 |

TABLE 12

Allelic Model, Genome Wide Analysis, p-value sorted by GALA cohort (Gala, Forte, and Combined cohorts)

| Name | Chr | Position | Gene(s) | Mutation | Gene Locations (s) | GALA Fisher's Exact P | GALA Odds Ratio (Minor Allele) | FORTE Fisher's Exact P | FORTE Odds Ratio (Minor Allele) | Fisher's Exact P | Odds Ratio (Minor Allele) | DD (Cases) | DD (Controls) | Dd (Cases) | Dd (Controls) | dd (Cases) | dd (Controls) |
|---|---|---|---|---|---|---|---|---|---|---|---|---|---|---|---|---|---|
| rs9817308 | 3 | 1.24E+08 | KALRN, KA | Silent, Sile | INTRON | 3.87E-05 | 0.50 | 3.01E-02 | 0.63 | 8.10E-06 | 0.56 | 71 | 55 | 199 | 96 | 127 | 29 |
| kgp4705854 | 12 | 19907696 | ? | ? | ? | 4.32E-05 | 0.50 | 3.06E-02 | 0.63 | 4.85E-06 | 0.55 | 41 | 38 | 169 | 89 | 189 | 54 |
| kgp24415534 | 2 | 1.74E+08 | ? | ? | ? | 6.03E-05 | 0.05 | 2.85E-02 | 0.15 | 2.28E-06 | 0.08 | 0 | 0 | 3 | 16 | 396 | 165 |
| kgp10594414 | 1 | 2.16E+08 | USH2A | Silent | INTRON | 6.25E-05 | 0.05 | 2.37E-02 | 0.15 | 1.11E-06 | 0.15 | 0 | 0 | 6 | 18 | 391 | 163 |
| rs543122 | 3 | 1.24E+08 | KALRN, KA | Silent, Sile | INTRON | 7.67E-05 | 0.51 | 1.70E-02 | 0.60 | 4.37E-06 | 0.55 | 70 | 54 | 195 | 97 | 131 | 29 |
| km3819.2546 | 12 | 19903173 | ? | ? | ? | 1.01E-04 | 0.49 | 2.88E-02 | 0.61 | 1.91E-05 | 0.55 | 21 | 23 | 146 | 84 | 232 | 74 |
| rs17577980 | 6 | 33359821 | HCG23 | Silent | INTRON | 1.11E-04 | 2.50 | 6.83E-03 | 2.75 | 6.67E-06 | 2.39 | 13 | 5 | 130 | 23 | 255 | 150 |
| kgp12008955 | 2 | 73759636 | ALMS1 | Silent | INTRON | 1.41E-04 | 0.00 | 2.03E-03 | 0.12 | 2.28E-06 | 0.08 | 0 | 0 | 3 | 16 | 396 | 165 |
| rs10456405 | 6 | 32212867 | ? | ? | ? | 1.42E-04 | 2.11 | 3.72E-02 | 1.85 | 9.81E-05 | 1.86 | 35 | 11 | 144 | 38 | 212 | 129 |
| kgp22779568 | X | 23029377 | ? | ? | ? | 1.52E-04 | 0.42 | 4.82E-02 | 0.58 | 3.73E-05 | 0.50 | 16 | 21 | 68 | 39 | 313 | 121 |
| kgp2784875 | 10 | 68448739 | ? | ? | ? | 1.55E-04 | 2.07 | 4.05E-02 | 1.84 | 1.52E-05 | 1.90 | 94 | 20 | 90 | 40 | 174 | 100 |
| kgp22730987 | X | 1.25E+08 | ? | ? | ? | 1.75E-04 | 2.65 | 4.14E-02 | 2.06 | 1.50E-05 | 2.39 | 30 | 3 | 79 | 24 | 280 | 153 |
| kgp3933330 | 7 | 28583709 | CREB5, CR | Silent, Sile | INTRON | 1.76E-04 | 2.57 | 3.68E-02 | 2.09 | 2.62E-05 | 2.31 | 15 | 1 | 111 | 29 | 271 | 151 |
| kgp20478926 | 8 | 21050249 | ? | ? | ? | 1.80E-04 | 0.23 | 5.60E-04 | 0.25 | 6.56E-07 | 0.26 | 5 | 15 | 14 | 8 | 377 | 156 |
| kgp5869992 | 12 | 49219569 | CACNB3, C | Silent, Sile | INTRON | 2.02E-04 | 0.84 | 2.03E-02 | 0.61 | 6.60E-06 | 0.56 | 60 | 58 | 184 | 74 | 152 | 48 |
| rs9579566 | 13 | 30980265 | ? | ? | ? | 2.52E-04 | 0.23 | 2.24E-02 | 0.32 | 1.45E-05 | 0.26 | 0 | 1 | 18 | 27 | 381 | 153 |
| kgp8372688 | 6 | 32212264 | ? | ? | ? | 2.65E-04 | 1.93 | 3.97E-02 | 1.67 | 9.53E-05 | 1.75 | 51 | 15 | 175 | 55 | 171 | 111 |
| kgp1009249 | 12 | 19838534 | ? | ? | ? | 2.79E-04 | 0.49 | 2.04E-02 | 0.57 | 2.35E-05 | 0.54 | 10 | 16 | 136 | 80 | 253 | 84 |
| kgp1786079 | 7 | 1.45E+08 | ? | ? | ? | 3.11E-04 | 0.44 | 2.02E-02 | 0.53 | 2.57E-05 | 0.49 | 4 | 11 | 86 | 56 | 308 | 114 |
| kgp3919159 | 6 | 32379506 | ? | ? | ? | 3.46E-04 | 2.25 | 2.31E-03 | 2.29 | 1.06E-04 | 2.08 | 13 | 5 | 127 | 27 | 255 | 147 |
| kgp4559907 | 6 | 1.33E+08 | ? | ? | ? | 3.48E-04 | 0.54 | 4.22E-02 | 0.64 | 6.01E-05 | 0.59 | 46 | 37 | 171 | 91 | 180 | 53 |
| kgp26026546 | 13 | 79972606 | RBM26 | Silent | INTRON | 3.66E-04 | 0.00 | 3.19E-03 | 0.06 | 2.24E-06 | 0.03 | 0 | 0 | 1 | 13 | 397 | 167 |
| kgp30662075 | X | 1.14E+08 | HTR2C, HT | Silent, Sile | INTRON,E | 3.92E-04 | 0.00 | 9.14E-03 | 0.21 | 6.62E-05 | 0.15 | 0 | 3 | 5 | 9 | 391 | 169 |
| kgp22793211 | X | 92601576 | ? | ? | ? | 3.96E-04 | 0.55 | 3.25E-03 | 0.54 | 3.81E-06 | 0.55 | 93 | 65 | 126 | 65 | 177 | 50 |
| kgp1699628 | 6 | 18032535 | ? | ? | ? | 3.96E-04 | 0.55 | 3.84E-03 | 0.64 | 4.60E-05 | 0.59 | 72 | 62 | 218 | 85 | 109 | 32 |
| kgp9627338 | 17 | 90155 | RPH3AL, R | Silent, Sile | INTRON | 4.17E-04 | 0.44 | 5.38E-03 | 0.46 | 5.09E-06 | 0.45 | 6 | 7 | 71 | 61 | 320 | 113 |
| rs7228827 | 18 | 76900411 | ATP9B | Silent | INTRON | 5.41E-04 | 2.25 | 2.10E-02 | 2.06 | 2.89E-05 | 2.15 | 20 | 1 | 124 | 37 | 254 | 143 |
| rs6618396 | X | 89549121 | ? | ? | ? | 5.45E-04 | 0.41 | 4.87E-02 | 0.46 | 1.30E-05 | 0.39 | 8 | 13 | 32 | 25 | 357 | 143 |
| kgp4127859 | 6 | 32434481 | ? | ? | ? | 5.88E-04 | 2.31 | 2.31E-02 | 2.30 | 6.64E-05 | 2.18 | 8 | 0 | 127 | 33 | 263 | 148 |
| k8p6236949 | 2 | 60301030 | ? | ? | ? | 6.28E-04 | 0.56 | 1.19E-02 | 0.56 | 4.07E-06 | 0.54 | 30 | 34 | 166 | 85 | 203 | 62 |
| rs5952097 | X | 1.16E+08 | ? | ? | ? | 6.33E-04 | 0.40 | 1.19E-02 | 0.48 | 7.78E-05 | 0.47 | 13 | 11 | 43 | 39 | 343 | 131 |
| rs1508102 | 11 | 1.16E+08 | ? | ? | ? | 6.75E-04 | 0.34 | 4.77E-02 | 0.49 | 1.85E-04 | 0.41 | 0 | 4 | 41 | 34 | 357 | 143 |

TABLE 12-continued

Allelic Model, Genome Wide Analysis, p-value sorted by GALA cohort (Gala, Forte, and Combined cohorts)

| Name | Chr | Position | Gene(s) | Mutation | Gene Locations (s) | GALA Fisher's Exact P | GALA Odds Ratio (Minor Allele) | FORTE Fisher's Exact P | FORTE Odds Ratio (Minor Allele) | Fisher's Exact P | Odds Ratio (Minor Allele) | Combined DD (Cases) | DD (Controls) | Dd (Cases) | Dd (Controls) | dd (Cases) | dd (Controls) |
|---|---|---|---|---|---|---|---|---|---|---|---|---|---|---|---|---|---|
| kgp6127371 | 4 | 1.54E+08 | ? | ? | ? | 7.09E-04 | 0.19 | 1.67E-02 | 0.29 | 6.10E-05 | 0.24 | 0 | 0 | 13 | 23 | 384 | 157 |
| rs6535882 | 4 | 1.54E+08 | ? | ? | ? | 7.25E-04 | 0.19 | 1.63E-02 | 0.29 | 6.13E-05 | 0.24 | 0 | 0 | 13 | 23 | 386 | 158 |
| kgp6790691 | 4 | 1.54E+08 | ? | ? | ? | 7.25E-04 | 0.19 | 1.63E-02 | 0.29 | 6.13E-05 | 0.24 | 0 | 0 | 13 | 23 | 386 | 158 |
| rs4326550 | X | 92580637 | ? | ? | ? | 7.32E-04 | 0.57 | 1.57E-02 | 0.60 | 2.43E-05 | 0.58 | 96 | 64 | 127 | 64 | 176 | 52 |
| kgp4418535 | 6 | 32431558 | ? | ? | ? | 8.39E-04 | 2.28 | 3.24E-02 | 2.25 | 1.24E-04 | 2.14 | 8 | 0 | 125 | 33 | 266 | 148 |
| kgp10372946 | 10 | 1.34E+08 | JAKMI P3 | Silent | INTRON | 8.73E-04 | 12.71 | 2.35E-02 | 7.01 | 1.39E-05 | 10.00 | 0 | 0 | 42 | 2 | 357 | 179 |
| rs1579771 | 3 | 1.57E+08 | C3orf55, C | Silent, Sile | INTRON | 8.82E-04 | 1.85 | 2.77E-02 | 1.69 | 5.03E-05 | 1.77 | 39 | 9 | 213 | 71 | 146 | 101 |
| kgp11804835 | 6 | 32396146 | ? | ? | ? | 8.96E-04 | 2.33 | 1.39E-02 | 2.51 | 5.98E-05 | 2.27 | 8 | 1 | 119 | 28 | 270 | 152 |
| kgp3812034 | 2 | 43427044 | ? | ? | ? | 9.06E-04 | 0.54 | 2.95E-02 | 0.61 | 9.65E-05 | 0.58 | 28 | 26 | 137 | 78 | 226 | 76 |
| kgp20478926 | 8 | 21050249 | ? | ? | ? | 1.80E-04 | 0.23 | 5.60E-04 | 0.25 | 6.56E-07 | 0.26 | 5 | 15 | 14 | 8 | 377 | 156 |
| rs16886004 | 7 | 78021500 | MAG 12 | Silent | INTRON, E | 3.92E-03 | 2.01 | 3.71E-05 | 4.30 | 1.41E-06 | 2.53 | 6 | 2 | 147 | 28 | 246 | 149 |
| kgp26026546 | 13 | 79972606 | RBM26 | Silent | INTRON | 3.66E-04 | 0.01 | 3.19E-03 | 0.06 | 2.24E-06 | 0.03 | 0 | 0 | 1 | 13 | 397 | 167 |
| kgp24415534 | 2 | 1.74E-08 | ? | ? | ? | 6.03E-05 | 0.05 | 2.85E-02 | 0.15 | 2.28E-06 | 0.08 | 0 | 0 | 3 | 16 | 396 | 165 |
| kgp12008955 | 2 | 73759636 | ALMS1 | Silent | INTRON | 1.41E-04 | 0.00 | 2.03E-03 | 0.12 | 2.28E-06 | 0.08 | 0 | 0 | 3 | 16 | 396 | 165 |
| kgp12125601 | 5 | 1.52E-08 | ? | ? | ? | 2.80E-03 | 1.77 | 3.73E-03 | 1.92 | 2.86E-06 | 1.95 | 136 | 35 | 35 | 17 | 219 | 122 |
| rs10251797 | 7 | 78025427 | MAGI2 | Silent | INTRON, E | 4.27E-03 | 1.97 | 5.87E-05 | 4.65 | 3.32E-06 | 2.44 | 6 | 2 | 145 | 29 | 248 | 150 |
| kgp22793211 | X | 92601576 | ? | ? | ? | 3.96E-04 | 0.55 | 3.25E-03 | 0.54 | 3.81E-06 | 0.55 | 93 | 65 | 126 | 65 | 177 | 50 |
| kgp6236949 | 2 | 60301030 | ? | ? | ? | 6.28E-04 | 0.56 | 1.19E-02 | 0.56 | 4.07E-06 | 0.54 | 30 | 34 | 166 | 85 | 203 | 62 |
| rs543122 | 3 | 1.24E-08 | KALRN, KA | Silent, Sile | INTRON | 7.67E-05 | 0.51 | 1.70E-02 | 0.60 | 4.37E-06 | 0.55 | 70 | 54 | 195 | 97 | 131 | 29 |
| kgp24743841 | 1 | 63899572 | ALG6 | Silent | INTRON | 9.49E-04 | 2.85 | 6.85E-03 | 2.70 | 4.63E-06 | 2.88 | 48 | 8 | 20 | 4 | 326 | 165 |
| kgp4705854 | 12 | 19907696 | ? | ? | ? | 4.32E-05 | 0.50 | 3.06E-02 | 0.63 | 4.85E-06 | 0.55 | 41 | 38 | 169 | 89 | 189 | 54 |
| kgp9627338 | 17 | 90155 | RPH3AL, R | Silent, Sile | INTRON | 4.17E-04 | 0.44 | 5.38E-03 | 0.46 | 5.09E-06 | 0.45 | 6 | 7 | 71 | 61 | 320 | 113 |
| kgp16*8752 | 21 | 43016736 | ? | ? | ? | 2.14E-03 | 0.38 | 1.85E-03 | 0.28 | 5.78E-06 | 0.33 | 1 | 2 | 30 | 37 | 368 | 142 |
| kgpS869992 | 12 | 49219569 | CACNB3,C | Silent, Sile | INTRON | 2.02E-04 | 0.54 | 2.03E-02 | 0.61 | 6.60E-06 | 0.56 | 60 | 58 | 184 | 74 | 152 | 48 |

TABLE 12-continued

Allelic Model, Genome Wide Analysis, p-value sorted by GALA cohort (Gala, Forte, and Combined cohorts)

| Name | Chr | Position | Gene(s) | Mutation | Gene Locations (s) | GALA Fisher's Exact P | GALA Odds Ratio (Minor Allele) | FORTE Fisher's Exact P | FORTE Odds Ratio (Minor Allele) | Fisher's Exact P | Odds Ratio (Minor Allele) | Combined DD (Cases) | Combined DD (Controls) | Combined Dd (Cases) | Combined Dd (Controls) | Combined dd (Cases) | Combined dd (Controls) |
|---|---|---|---|---|---|---|---|---|---|---|---|---|---|---|---|---|---|
| rs17577960 | 6 | 32359621 | HC623 | Silent | INTRON | 1.11E-04 | 2.50 | 6.83E-03 | 2.75 | 6.67E-06 | 2.39 | 13 | 5 | 130 | 23 | 255 | 150 |
| kgp25952891 | 13 | 80027089 | ? | ? | ? | 9.94E-04 | 0.00 | 3.13E-03 | 0.06 | 6.71E-06 | 0.04 | 0 | 0 | 1 | 12 | 398 | 168 |
| kgp8110667 | 22 | 32716792 | ? | ? | ? | 4.71E-03 | ? | 6.16E-03 | ? | 7.05E-06 | ? | 1 | 0 | 30 | 0 | 367 | 181 |
| kgp11210241 | 3 | 38537237 | ? | ? | ? | 2.62E-03 | ? | 1.03E-02 | ? | 7.12E-06 | ? | 0 | 0 | 30 | 0 | 368 | 181 |
| rs17687961 | 22 | 32716927 | ? | ? | ? | 4.71E-03 | ? | 6.20E-03 | ? | 7.12E-06 | ? | 1 | 0 | 30 | 0 | 368 | 181 |
| rs12013377 | X | 92620062 | ? | ? | ? | 1.35E-03 | 0.59 | 2.51E-03 | 0.53 | 7.90E-06 | 0.56 | 97 | 66 | 129 | 66 | 173 | 49 |
| rs7579987 | 2 | 60307009 | ? | ? | ? | 7.27E-03 | 0.63 | 7.35E-04 | 0.49 | 7.90E-06 | 0.56 | 40 | 41 | 184 | 87 | 175 | 52 |
| rs6718758 | 2 | 60328802 | ? | ? | ? | 5.30E-03 | 0.62 | 1.23E-03 | 0.49 | 8.06E-06 | 0.55 | 35 | 38 | 175 | 85 | 189 | 58 |
| rs9817308 | 3 | 1.24E-08 | KALRN, KA | Silent, Sile | INTRON | 3.87E-05 | 0.50 | 3.01E-02 | 0.63 | 8.10E-06 | 0.56 | 71 | 55 | 199 | 96 | 127 | 29 |
| kgp22804809 | X | 9258610 | ? | ? | ? | 1.10E-02 | 1.54 | 5.12E-05 | 2.39 | 8.38E-06 | 1.79 | 139 | 38 | 132 | 59 | 127 | 84 |
| rs6895094 | 5 | 1.41E-08 | ARAP3 | Silent | INTRON | 9.49E-04 | 0.57 | 1.07E-02 | 0.58 | 8.54E-06 | 0.56 | 56 | 46 | 181 | 92 | 161 | 43 |
| kgp3450875 | 16 | 57268931 | RSPRY1 | Silent | INTRON | 1.25E-02 | 0.20 | 2.10E-04 | 0.07 | 9.56E-06 | 0.13 | 0 | 0 | 5 | 17 | 394 | 164 |
| rs11691553 | 2 | 60303554 | ? | ? | ? | 9.11E-03 | 0.64 | 7.16E-04 | 0.48 | 1.02E-05 | 0.56 | 39 | 41 | 183 | 86 | 174 | 53 |
| rs13394010 | 2 | 60302746 | ? | ? | ? | 7.30E-03 | 0.64 | 7.35E-04 | 0.49 | 1.04E-05 | 0.56 | 39 | 41 | 185 | 86 | 175 | 53 |
| rs2139612 | X | 9261491 | ? | ? | ? | 1.79E-03 | 0.59 | 3.37E-03 | 0.54 | 1.04E-05 | 0.57 | 96 | 65 | 129 | 67 | 173 | 49 |
| kgp11332629 | 10 | 1.21E-08 | ? | ? | ? | 3.11E-03 | 2.49 | 1.97E-03 | 3.81 | 1.10E-05 | 2.86 | 6 | 0 | 97 | 19 | 295 | 162 |
| kgp10594414 | 1 | 2.16E-08 | USH2A | Silent | ? | 6.25E-05 | 0.05 | 2.37E-02 | 0.24 | 1.11E-05 | 0.15 | 0 | 0 | 6 | 18 | 391 | 163 |
| kgp 11141512 | 20 | 35283733 | NDRG3, N | Silent, Sile | INTRON | 4.28E-03 | 0.29 | 2.03E-03 | 0.12 | 1.19E-05 | 0.20 | 0 | 1 | 11 | 21 | 388 | 158 |
| rs2816838 | 10 | 52714759 | ? | ? | ? | 3.47E-03 | 0.53 | 3.94E-03 | 0.44 | 1.23E-05 | 0.48 | 4 | 8 | 92 | 67 | 303 | 106 |
| kgp2299675 | 20 | 16933074 | ? | ? | ? | 7.25E-03 | 0.27 | 3.48E-04 | 0.14 | 1.24E-05 | 0.21 | 0 | 0 | 11 | 23 | 388 | 158 |
| rs6618396 | X | 89449121 | ? | ? | ? | 5.45E-04 | 0.41 | 4.87E-02 | 0.46 | 1.30E-05 | 0.39 | 8 | 13 | 32 | 25 | 357 | 143 |
| rs7217872 | 17 | 88988 | RPH3AI, R | Silent, Sile | INTRON | 9.84E-04 | 0.46 | 5.73E-03 | 0.45 | 1.39E-05 | 0.46 | 6 | 7 | 74 | 61 | 319 | 113 |
| rs9579866 | 13 | 30980265 | ? | ? | ? | 2.52E-04 | 0.23 | 2.24E-02 | 0.32 | 1.45E-05 | 0.26 | 0 | 1 | 18 | 27 | 381 | 153 |
| rs10203396 | 2 | 60305110 | ? | ? | ? | 9.47E-03 | 0.64 | 1.05E-03 | 0.49 | 1.46E-05 | 0.57 | 39 | 41 | 186 | 87 | 173 | 53 |
| rs13419758 | 2 | 60302920 | ? | ? | ? | 9.47E-03 | 0.64 | 1.07E-03 | 0.49 | 1.48E-05 | 0.57 | 40 | 41 | 185 | 87 | 174 | 53 |
| kgp22730987 | X | 68448739 | ? | ? | ? | 1.75E-04 | 2.65 | 4.14E-02 | 2.06 | 1.50E-05 | 2.39 | 30 | 3 | 79 | 24 | 280 | 153 |
| kgp9320791 | 2 | 60309952 | ? | ? | ? | 9.47E-03 | 0.64 | 1.09E-03 | 0.50 | 1.52E-05 | 0.57 | 39 | 41 | 187 | 87 | 172 | 53 |
| kgp278487S | 10 | 1.25E-08 | ? | ? | ? | 1.55E-04 | 2.07 | 4.05E-02 | 1.64 | 1.52E-05 | 1.90 | 94 | 20 | 90 | 40 | 174 | 100 |
| rs6507761 | 7 | 313681 | ? | ? | ? | 8.80E-03 | 0.64 | 1.70E-03 | 0.51 | 1.53E-05 | 0.57 | 78 | 61 | 185 | 83 | 135 | 37 |
| kgp6214351 | 11 | 75546691 | UVRAG | Silent | INTRON | 4.74E-03 | 0.42 | 1.08E-03 | 0.29 | 1.60E-05 | 0.36 | 0 | 2 | 37 | 39 | 361 | 140 |
| kgp12230354 | 5 | 27037978 | CDH9 | Silent | INTRON | 5.97E-03 | 0.21 | 2.69E-04 | 0.15 | 1.65E-05 | 0.20 | 0 | 0 | 10 | 22 | 386 | 159 |

TABLE 13

Genotypic Model, Genome Wide Analysis, p-value sorted by GALA cohort (Gala, Forte, and Combined cohorts)

| | | | | | | GALA | | | | | | | FORTE |
|---|---|---|---|---|---|---|---|---|---|---|---|---|---|
| Name | Chr | Position | Gene(s) | Mutation | Gene Locations (s) | Fisher's Exact P | DD (Cases) | DD (Controls) | Dd (Cases) | Dd (Controls) | dd (Cases) | dd (Controls) | Fisher's Exact P |
| rs1325607 | 1 | 65751060 | DNAJC6 | Silent | INTRON | 3.2E−05 | 3 | 13 | 64 | 52 | 131 | 55 | 2.4E−02 |
| kgp12418 | 14 | 95359055 | ? | ? | ? | 3.4E−05 | 2 | 7 | 60 | 14 | 136 | 98 | 1.4E−02 |
| kgp96625 | 7 | 76454387 | ? | ? | ? | 3.6E−05 | 32 | 3 | 88 | 44 | 77 | 67 | 7.3E−03 |
| kgp43802 | 14 | 80642167 | ? | ? | ? | 3.9E−05 | 22 | 12 | 64 | 69 | 111 | 39 | 4.2E−02 |
| kgp24415 | 2 | 1.74E+08 | ? | ? | ? | 5.1E−05 | 0 | 12 | 1 | 12 | 197 | 108 | 2.8E−02 |
| kgp10594 | 1 | 2.16E+08 | USH2A | Silent | INTRON | 5.3E−05 | 0 | 0 | 1 | 12 | 196 | 108 | 2.2E−02 |
| kgp54472 | 3 | 1.92E+08 | FGF12 | Silent | INTRON | 6.7E−05 | 2 | 0 | 49 | 9 | 147 | 111 | 3.6E−02 |
| rs2906681 | 7 | 21777119 | DNAH11 | Silent | INTRON | 7.5E−05 | 27 | 35 | 110 | 39 | 61 | 46 | 2.7E−02 |
| rs1757798 | 6 | 32359821 | HCG23 | Silent | INTRON | 9.4E−05 | 11 | 4 | 68 | 17 | 118 | 97 | 1.6E−03 |
| rs9275653 | 6 | 32685865 | ? | ? | ? | 1.0E−04 | 13 | 28 | 99 | 47 | 86 | 44 | 3.3E−02 |
| kgp42459 | 3 | 1.73E+08 | ? | ? | ? | 1.2E−04 | 43 | 6 | 97 | 68 | 58 | 46 | 3.2E−02 |
| kgp12038 | 2 | 73759636 | ALMS1 | Silent | INTRON | 1.3E−04 | 0 | 0 | 0 | 9 | 198 | 111 | 1.8E−03 |
| kgp76468 | 2 | 73234432 | SFXN5 | Silent | INTRON | 1.5E−04 | 2 | 0 | 49 | 10 | 146 | 110 | 2.5E−02 |
| rs6471541 | 8 | 96528845 | LOC10061 | Silent, Sile | INTRON, E | 1.5E−04 | 11 | 3 | 50 | 57 | 137 | 59 | 4.6E−02 |
| rs9817308 | 3 | 1.24E+08 | KALRN, KA | Silent, Sile | INTRON | 1.5E−04 | 30 | 38 | 100 | 61 | 67 | 20 | 4.8E−02 |
| kgp94700 | 2 | 33764717 | RASGRP3, | Silent, Sile | INTRON | 2.1E−04 | 14 | 2 | 88 | 33 | 96 | 85 | 1.4E−02 |
| rs543122 | 3 | 1.24E+08 | KALRN, KA | Silent, Sile | NTRON | 2.3E−04 | 31 | 37 | 99 | 62 | 68 | 20 | 2.2E−02 |
| kgp20932 | 14 | 83364889 | ? | ? | ? | 2.6E−04 | 30 | 21 | 101 | 34 | 67 | 64 | 2.3E−02 |
| kgp36695 | 2 | 34593996 | ? | ? | ? | 2.7E−04 | 8 | 5 | 40 | 49 | 150 | 66 | 2.4E−02 |
| rs1112437 | 2 | 34594367 | ? | ? | ? | 3.3E−04 | 7 | 4 | 39 | 48 | 152 | 68 | 3.1E−02 |
| kgp26026 | 13 | 79972606 | RBM26 | Silent | INTRON | 3.4E−04 | 0 | 0 | 0 | 8 | 198 | 111 | 3.0E−03 |
| kgp93561 | 5 | 15539360 | FBXL7 | Silent | INTRON | 3.5E−04 | 3 | 6 | 66 | 18 | 129 | 96 | 1.2E−02 |
| kgp15936 | 2 | 33760276 | RASGRP3, | Silent, Sile | INTRON | 4.1E−04 | 14 | 2 | 89 | 35 | 95 | 83 | 4.6E−02 |
| rs2005154 | 9 | 36856828 | PAX5 | Silent | INTRON | 4.6E−04 | 0 | 8 | 42 | 30 | 155 | 82 | 3.6E−02 |
| kgp10859 | 2 | 33756408 | RASGRP3, | Silent, Sile | INTRON | 4.6E−04 | 14 | 2 | 87 | 34 | 97 | 84 | 1.2E−02 |
| kgp59033 | 14 | 95352842 | ? | ? | ? | 4.7E−04 | 1 | 5 | 45 | 11 | 152 | 104 | 2.5E−02 |
| kgp44879 | 9 | 36861331 | PAX5 | Silent | INTRON | 5.0E−04 | 0 | 8 | 44 | 31 | 154 | 81 | 1.5E−02 |
| rs6520233 | X | 1.16E+08 | ? | ? | ? | 5.2E−04 | 8 | 6 | 15 | 27 | 175 | 87 | 2.6E−02 |
| rs9579566 | 13 | 30980265 | ? | ? | ? | 5.3E−94 | 0 | 1 | 8 | 18 | 190 | 101 | 2.0E−02 |
| rs1894407 | 6 | 32787036 | ? | ? | ? | 5.6E−04 | 26 | 13 | 114 | 46 | 58 | 61 | 4.5E−02 |
| kgp59671 | 14 | 52506177 | NID2 | Silent | INTRON | 5.7E−04 | 24 | 34 | 105 | 58 | 68 | 26 | 2.2E−02 |
| kgp61273 | 4 | 1.54E+08 | ? | ? | ? | 5.8E−04 | 0 | 0 | 5 | 15 | 192 | 104 | 1.5E−02 |
| kgp10092 | 12 | 19838534 | ? | ? | ? | 5.9E−04 | 4 | 11 | 63 | 51 | 131 | 57 | 2.9E−02 |
| rs6535882 | 4 | 1.54E+08 | ? | ? | ? | 6.0E−04 | 0 | 0 | 5 | 15 | 193 | 105 | 1.5E−02 |
| kgp67006 | 4 | 1.54E+08 | ? | ? | ? | 6.0E−04 | 0 | 0 | 5 | 15 | 193 | 835 | 1.5E−02 |
| kgp39191 | 6 | 32379506 | ? | ? | ? | 6.1E−04 | 11 | 4 | 69 | 20 | 117 | 95 | 1.2E−02 |
| kgp10619 | 4 | 99417717 | TSPAN5 | Silent | INTRON | 6.3E−04 | 0 | 0 | 14 | 25 | 184 | 95 | 3.4E−02 |
| kgp39333 | 7 | 28583709 | CREBS, CR | Silent, Sile | INTRON | 6.3E−04 | 12 | 0 | 54 | 21 | 131 | 99 | 3.0E−02 |
| kgp45244 | 22 | 32724532 | ? | ? | ? | 6.4E−04 | 16 | 4 | 84 | 32 | 91 | 82 | 2.6E−02 |
| kgp10372 | 10 | 1.34E+08 | JAKMIP3 | Silent | INTRON | 7.2E−04 | 0 | 0 | 20 | 1 | 178 | 119 | 2.1E−02 |
| kgp50683 | 16 | 19756348 | IQCK | Silent | INTRON | 8.7E−04 | 6 | 5 | 53 | 55 | 139 | 59 | 2.8E−03 |
| rs924742 | 8 | 68464647 | CPA6 | Silent | INTRON | 9.0E−04 | 23 | 17 | 108 | 40 | 67 | 63 | 4.1E−02 |
| kgp27000 | 16 | 19750275 | IQCK | Silent | INTRON | 9.2E−04 | 3 | 2 | 46 | 50 | 149 | 67 | 5.0E−03 |
| rs1688600 | 7 | 78021500 | MAGI2 | Silent | INTRON, E | 1.2E−03 | 3 | 2 | 73 | 122 | 122 | 94 | 3.0E−05 |
| rs1025179 | 7 | 78025427 | MAGI2 | Silent | INTRON, E | 3.5E−03 | 4 | 2 | 71 | 123 | 123 | 95 | 5.2E−05 |
| rs1757798 | 6 | 32359821 | HCG23 | Silent | INTRON | 9.4E−05 | 11 | 4 | 68 | 17 | 118 | 97 | 1.6E−03 |
| rs1532365 | 12 | 49204421 | ? | ? | ? | 1.3E−03 | 25 | 35 | 91 | 46 | 82 | 38 | 1.6E−03 |
| kgp24415 | 2 | 1.74E+08 | ? | ? | ? | 5.1E−05 | 0 | 0 | 1 | 12 | 197 | 108 | 2.8E−02 |
| kgp12008 | 2 | 73759636 | ALMS1 | Silent | INTRON | 1.3E−04 | 0 | 0 | 0 | 9 | 198 | 111 | 1.8E−03 |
| kgp26026 | 13 | 79972606 | RBM26 | Silent | INTRON | 3.4E−04 | 0 | 0 | 0 | 8 | 198 | 111 | 3.0E−03 |
| rs931570 | 12 | 49195124 | ? | ? | ? | 2.4E−03 | 25 | 34 | 91 | 48 | 82 | 38 | 1.7E−03 |
| rs2453478 | 12 | 49202743 | ? | ? | ? | 1.4E−03 | 25 | 35 | 91 | 47 | 82 | 38 | 4.1E−03 |
| rs2906681 | 7 | 21777119 | DNAH11 | Silent | INTRON | 7.5E−05 | 27 | 35 | 110 | 39 | 61 | 46 | 2.7E−02 |
| kgp60113 | 8 | 57710655 | ? | 7 | 3 | 1.4E−03 | 23 | 33 | 105 | 48 | 70 | 39 | 1.6E−03 |
| kgp259521 | 13 | 80027089 | ? | ? | ? | 9.4E−04 | 0 | 0 | 0 | 7 | 198 | 112 | 3.0E−03 |
| kgp345087 | 16 | 57268931 | RSPRY1 | Silent | INTRON | 1.2E−02 | 0 | 0 | 3 | 9 | 195 | 111 | 1.8E−04 |
| rs9941015 | 16 | 81999495 | ? | ? | ? | 2.0E−03 | 0 | 3 | 23 | 4 | 175 | 113 | 1.6E−03 |
| rs7615587 | 3 | 18816847 | ? | ? | ? | 3.2E−03 | 47 | 18 | 88 | 77 | 63 | 25 | 3.0E−03 |
| rs4143493 | 6 | 51829939 | PKHD1, PK | Silent, Sile | INTRON | 1.2E−02 | 0 | 0 | 31 | 7 | 167 | 113 | 6.9E−04 |
| kgp10594 | 1 | 2.16E+08 | USH2A | Silent | INTRON | 5.3E−05 | 0 | 0 | 1 | 12 | 196 | 108 | 2.2E−02 |
| rs1495901 | 18 | 34235737 | FI-10D3 | Silent | INTRON | 3.1E−02 | 12 | 12 | 82 | 33 | 104 | 75 | 2.0E−03 |
| kgp22996 | 20 | 16933074 | ? | ? | ? | 6.4E−03 | 0 | 0 | 6 | 13 | 192 | 107 | 2.8E−04 |

TABLE 13-continued

Genotypic Model, Genome Wide Analysis, p-value sorted by GALA cohort (Gala, Forte, and Combined cohorts)

| | | | | | | | | | | | | |
|---|---|---|---|---|---|---|---|---|---|---|---|---|
| rs2325911 | 6 | 1.25E+08 | NKAIN2, N | Silent, Sile | INTRON | 2.7E-03 | 4 | 0 | 40 | 43 | 154 | 77 | 2.5E-04 |
| kgp42450 | 3 | 1.73E+08 | ? | ? | ? | 1.2E-04 | 43 | 6 | 97 | 68 | 58 | 46 | 3.2E-02 |
| rs4370047 | 3 | 18808580 | ? | ? | ? | 2.6E-03 | 46 | 18 | 87 | 77 | 64 | 25 | 3.8E-03 |
| rs9816291 | 3 | 18814426 | ? | ? | ? | 2.7E-03 | 47 | 18 | 87 | 77 | 63 | 25 | 3.9E-03 |
| kgp168871 | 21 | 43016736 | ? | ? | ? | 1.4E-03 | 0 | 0 | 18 | 27 | 180 | 93 | 6.6E-03 |
| rs543122 | 3 | 1.24E+08 | KALRN, KA | Silent, Sile | INTRON | 2.3E-04 | 31 | 37 | 99 | 62 | 68 | 20 | 2.2E-02 |
| kgp36695 | 2 | 34593996 | ? | ? | ? | 2.7E-04 | 8 | 5 | 40 | 49 | 150 | 66 | 2.4E-02 |
| kgp12230 | 5 | 27037978 | CDH9 | Silent | INTRON | 5.4E-03 | 0 | 0 | 4 | 11 | 193 | 109 | 2.0E-04 |
| kgp10372 | 10 | 1.34E+08 | MK MIP3 | Silent | INTRON | 7.2E-03 | 0 | 0 | 20 | 1 | 178 | 119 | 2.1E-02 |
| rs1049879 | 6 | 51829707 | PKHD1, PK | Silent, Sile | INTRON | 1.2E-02 | 0 | 0 | 31 | 7 | 167 | 113 | 1.1E-03 |
| kgp50536 | 2 | 2.05E+08 | ? | ? | ? | 1.3E-02 | 0 | 0 | 8 | 14 | 188 | 106 | 5.7E-05 |
| kgp962731 | 17 | 90155 | RPH3AL, R | Silent, Sile | INTRON | 1.4E-03 | 4 | 6 | 33 | 38 | 160 | 76 | 5.7E-03 |
| kgp58695 | 12 | 49219569 | CACNB3, C | Silent, Sile | INTRON | 1.4E-03 | 33 | 39 | 88 | 51 | 77 | 29 | 1.1E-02 |
| kgp62369 | 2 | 60301030 | ? | ? | ? | 2.5E-03 | 18 | 25 | 85 | 56 | 95 | 39 | 2.5E-02 |
| kgp59767 | 22 | 32675303 | ? | ? | ? | 8.1E-03 | 0 | 0 | 11 | 0 | 187 | 120 | 9.0E-03 |
| kgp11210 | 3 | 38537237 | ? | ? | ? | 2.4E-03 | 0 | 0 | 13 | 0 | 185 | 120 | 1.9E-02 |
| rs1768796 | 22 | 32716927 | ? | ? | ? | 4.4E-03 | 0 | 0 | 12 | 0 | 186 | 120 | 1.6E-02 |
| kgp81106 | 22 | 32716792 | ? | ? | ? | 4.4E-03 | 0 | 0 | 12 | 0 | 186 | 120 | 1.1E-02 |
| rs1102277 | 11 | 13390860 | ARNTL, AR | Silent, Sile | INTRON | 1.5E-03 | 24 | 4 | 85 | 41 | 89 | 75 | 1.4E-02 |
| rs2005154 | 9 | 36856828 | PAX5 | Silent | INTRON | 4.6E-04 | 0 | 8 | 42 | 30 | 155 | 82 | 3.6E-02 |
| kgp11141 | 20 | 35283733 | NDRG3, N | Silent, Sile | INTRON | 7.3E-03 | 0 | 1 | 8 | 14 | 190 | 104 | 1.8E-03 |

| | FORTE | | | | | | COMBINED | | | | | |
|---|---|---|---|---|---|---|---|---|---|---|---|---|
| Name | DD (Cases) | DD (Controls) | Dd (Cases) | Dd (Controls) | dd (Cases) | dd (Controls) | Fisher's Exact P | DD (Cases) | DD (Controls) | Dd (Cases) | Dd (Controls) | dd (Cases) | dd (Controls) |
| rs1325607 | 10 | 2 | 85 | 15 | 105 | 44 | 3.8E-02 | 13 | 15 | 149 | 67 | 236 | 99 |
| kgp12418 | 3 | 1 | 43 | 24 | 155 | 36 | 4.1E-02 | 5 | 8 | 103 | 38 | 291 | 134 |
| kgp96625 | 25 | 5 | 85 | 40 | 89 | 16 | 1.6E-03 | 57 | 8 | 173 | 84 | 166 | 83 |
| kgp43802 | 20 | 1 | 76 | 31 | 102 | 29 | 5.0E-05 | 42 | 13 | 140 | 100 | 213 | 68 |
| kgp24415 | 0 | 0 | 2 | 4 | 199 | 57 | 1.9E-06 | 0 | 0 | 3 | 16 | 396 | 165 |
| kgp10594 | 0 | 0 | 5 | 6 | 195 | 55 | 8.9E-06 | 0 | 0 | 6 | 18 | 391 | 163 |
| kgp54472 | 2 | 3 | 43 | 7 | 156 | 51 | 5.1E-05 | 4 | 3 | 92 | 16 | 303 | 162 |
| rs2906681 | 17 | 13 | 104 | 29 | 80 | 19 | 5.0E-06 | 44 | 48 | 214 | 68 | 141 | 65 |
| rs1757798 | 2 | 1 | 62 | 6 | 137 | 53 | 9.1E-07 | 13 | 5 | 130 | 23 | 255 | 150 |
| rs9275653 | 31 | 14 | 97 | 35 | 73 | 12 | 6.2E-64 | 44 | 42 | 196 | 82 | 159 | 56 |
| kgp42459 | 37 | 4 | 105 | 42 | 56 | 15 | 9.7E-06 | 80 | 10 | 202 | 110 | 114 | 61 |
| kgp12038 | 0 | 0 | 3 | 7 | 198 | 54 | 1.9E-06 | 0 | 0 | 3 | 16 | 396 | 165 |
| kgp76468 | 0 | 1 | 38 | 5 | 162 | 55 | 6.7E-05 | 2 | 1 | 87 | 15 | 308 | 165 |
| rs6471541 | 13 | 2 | 68 | 12 | 119 | 47 | 4.9E-02 | 24 | 5 | 118 | 69 | 256 | 106 |
| rs9817308 | 41 | 17 | 99 | 35 | 60 | 9 | 2.2E-05 | 71 | 55 | 199 | 96 | 127 | 29 |
| kgp94700 | 7 | 6 | 79 | 15 | 114 | 40 | 8.2E-04 | 21 | 8 | 167 | 48 | 210 | 125 |
| rs543122 | 39 | 17 | 96 | 35 | 63 | 9 | 1.1E-05 | 70 | 54 | 195 | 97 | 131 | 29 |
| kgp20932 | 37 | 4 | 97 | 40 | 67 | 17 | 3.4E-02 | 67 | 25 | 198 | 74 | 134 | 81 |
| kgp36695 | 9 | 2 | 46 | 25 | 143 | 34 | 1.2E-05 | 17 | 7 | 86 | 74 | 293 | 100 |
| rs1112437 | 8 | 1 | 45 | 24 | 146 | 36 | 2.2E-05 | 15 | 5 | 84 | 72 | 298 | 104 |
| kgp26026 | 0 | 0 | 1 | 5 | 199 | 56 | 1.9E-06 | 0 | 0 | 1 | 13 | 397 | 167 |
| kgp93561 | 1 | 4 | 59 | 13 | 141 | 43 | 2.1E-05 | 4 | 10 | 125 | 31 | 270 | 139 |
| kgp15936 | 7 | 6 | 78 | 16 | 116 | 39 | 3.8E-03 | 21 | 8 | 167 | 51 | 211 | 122 |
| rs2005154 | 0 | 2 | 45 | 9 | 155 | 50 | 2.0E-05 | 0 | 10 | 87 | 39 | 310 | 132 |
| kgp10859 | 5 | 6 | 78 | 15 | 115 | 40 | 2.4E-03 | 19 | 8 | 165 | 49 | 212 | 124 |
| kgp59033 | 0 | 9 | 32 | 18 | 169 | 43 | 1.9E-02 | 1 | 5 | 77 | 29 | 321 | 147 |
| kgp44879 | 0 | 2 | 46 | 8 | 155 | 51 | 2.2E-05 | 0 | 10 | 90 | 39 | 309 | 132 |
| rs6520233 | 7 | 5 | 30 | 16 | 164 | 40 | 1.7E-04 | 15 | 11 | 45 | 43 | 339 | 127 |
| rs9579566 | 0 | 0 | 10 | 9 | 191 | 57 | 2.0E-05 | 0 | 1 | 18 | 27 | 381 | 153 |
| rs1894407 | 31 | 3 | 99 | 29 | 70 | 29 | 2.4E-04 | 57 | 16 | 213 | 75 | 128 | 90 |
| kgp59671 | 36 | 10 | 91 | 39 | 74 | 12 | 4.7E-04 | 60 | 44 | 196 | 97 | 142 | 38 |
| kgp61273 | 0 | 0 | 8 | 8 | 192 | 53 | 4.6E-05 | 0 | 0 | 13 | 23 | 384 | 157 |
| kgp10092 | 6 | 5 | 73 | 29 | 122 | 27 | 4.1E-05 | 10 | 16 | 136 | 80 | 253 | 84 |
| rs6535882 | 0 | 0 | 8 | 8 | 193 | 53 | 4.7E-05 | 0 | 0 | 13 | 23 | 386 | 158 |
| kgp67006 | 0 | 0 | 8 | 8 | 193 | 53 | 4.7E-05 | 0 | 0 | 13 | 23 | 386 | 158 |
| kgp39191 | 2 | 1 | 58 | 7 | 138 | 52 | 3.5E-05 | 13 | 5 | 127 | 27 | 255 | 147 |
| kgp10619 | 0 | 2 | 18 | 8 | 182 | 51 | 1.4E-04 | 0 | 2 | 32 | 33 | 366 | 146 |
| kgp39333 | 3 | 1 | 57 | 8 | 140 | 52 | 2.2E-04 | 15 | 1 | 111 | 29 | 271 | 151 |
| kgp45244 | 11 | 4 | 81 | 13 | 107 | 42 | 8.7E-05 | 27 | 8 | 165 | 45 | 198 | 124 |
| kgp10372 | 0 | 0 | 22 | 1 | 179 | 60 | 1.3E-05 | 0 | 0 | 42 | 2 | 357 | 179 |
| kgp50683 | 4 | 7 | 73 | 27 | 123 | 27 | 7.3E-05 | 10 | 12 | 126 | 82 | 262 | 86 |
| rs924742 | 20 | 8 | 109 | 22 | 72 | 31 | 3.0E-05 | 43 | 25 | 217 | 62 | 139 | 94 |
| kgp27000 | 3 | 4 | 56 | 26 | 142 | 31 | 4.8E-05 | 6 | 6 | 102 | 76 | 291 | 98 |

TABLE 13-continued

Genotypic Model, Genome Wide Analysis, p-value sorted by GALA cohort (Gala, Forte, and Combined cohorts)

| rs1688600 | 3 | 0 | 74 | 6 | 124 | 55 | 2.8E-07 | 6 | 2 | 147 | 28 | 246 | 149 |
|---|---|---|---|---|---|---|---|---|---|---|---|---|---|
| rs1025179 | 2 | 0 | 74 | 6 | 125 | 55 | 3.5E-07 | 6 | 2 | 145 | 29 | 248 | 150 |
| rs1757798 | 1 | 1 | 62 | 6 | 137 | 53 | 9 1E-07 | 13 | 5 | 130 | 23 | 255 | 150 |
| rs1532365 | 18 | 17 | 97 | 22 | 84 | 22 | 1.1E-06 | 43 | 52 | 188 | 68 | 166 | 60 |
| kgp24415 | 0 | 0 | 2 | 4 | 199 | 57 | 1.9E-06 | 0 | 0 | 3 | 16 | 396 | 165 |
| kgp12008 | 0 | 0 | 3 | 7 | 198 | 54 | 1.9E-06 | 0 | 0 | 3 | 16 | 396 | 165 |
| kgp26026 | 0 | 0 | 1 | 5 | 199 | 56 | 1.9E-06 | 0 | 0 | 1 | 13 | 397 | 167 |
| rs931570 | 18 | 17 | 96 | 22 | 85 | 22 | 2.6E-06 | 43 | 51 | 187 | 70 | 167 | 60 |
| rs2453478 | 20 | 17 | 95 | 22 | 83 | 22 | 3.4E-06 | 45 | 52 | 186 | 69 | 165 | 60 |
| rs2906681 | 17 | 13 | 104 | 29 | 80 | 13 | 5.0E-06 | 44 | 48 | 214 | 68 | 141 | 65 |
| kgp60113 | 30 | 22 | 106 | 21 | 64 | 18 | 5.7E-06 | 53 | 55 | 211 | 69 | 134 | 57 |
| kgp259521 | 0 | 0 | 1 | 5 | 200 | 56 | 5.9E-06 | 0 | 0 | 1 | 12 | 398 | 168 |
| kgp345087 | 0 | 0 | 2 | 8 | 199 | 53 | 7.8E-06 | 0 | 0 | 5 | 17 | 394 | 164 |
| rs9941015 | 0 | 3 | 17 | 1 | 483 | 50 | 7.9E-06 | 0 | 6 | 40 | 5 | 358 | 170 |
| rs7615587 | 52 | 9 | 87 | 42 | 60 | 10 | 8.5E-06 | 99 | 27 | 175 | 119 | 123 | 35 |
| rs4143493 | 0 | 0 | 41 | 2 | 160 | 59 | 5.5E-06 | 0 | 0 | 72 | 9 | 327 | 172 |
| kgp10594 | 0 | 0 | 5 | 6 | 195 | 55 | 8.9E-06 | 0 | 0 | 6 | 18 | 391 | 163 |
| rs1495901 | 12 | 12 | 103 | 16 | 86 | 53 | 9.0E-06 | 24 | 24 | 185 | 49 | 190 | 108 |
| kgp22996 | 0 | 0 | 5 | 10 | 196 | 51 | 9.1E-06 | 0 | 0 | 11 | 23 | 388 | 158 |
| rs2325911 | 5 | 3 | 37 | 26 | 158 | 32 | 9.1E-06 | 9 | 3 | 77 | 69 | 312 | 109 |
| kgp42450 | 37 | 4 | 105 | 42 | 56 | 15 | 9.7E-06 | 80 | 10 | 202 | 110 | 114 | 61 |
| rs4370047 | 49 | 9 | 88 | 42 | 62 | 10 | 9.7E-06 | 95 | 27 | 175 | 119 | 126 | 35 |
| rs9816291 | 51 | 9 | 88 | 42 | 60 | 10 | 9.7E-06 | 98 | 27 | 175 | 119 | 123 | 35 |
| kgp168871 | 1 | 2 | 12 | 10 | 185 | 49 | 1.0E-05 | 1 | 2 | 30 | 37 | 368 | 142 |
| rs543122 | 39 | 17 | 96 | 35 | 63 | 9 | 1.1E-05 | 70 | 54 | 195 | 97 | 131 | 29 |
| kgp36695 | 9 | 2 | 46 | 25 | 143 | 34 | 1 2E-05 | 17 | 7 | 86 | 74 | 293 | 100 |
| kgp12230 | 0 | 0 | 6 | 11 | 193 | 50 | 1 2E-05 | 0 | 0 | 10 | 22 | 386 | 159 |
| kgp10372 | 0 | 0 | 22 | 1 | 179 | 60 | 1.3E-05 | 0 | 0 | 42 | 2 | 357 | 179 |
| rs1049879 | 0 | 0 | 40 | 2 | 161 | 59 | 1.3E-05 | 0 | 0 | 71 | 9 | 328 | 172 |
| kgp50536 | 1 | 0 | 9 | 14 | 190 | 47 | 1.4E-05 | 1 | 0 | 17 | 28 | 378 | 153 |
| kgp962731 | 2 | 1 | 38 | 23 | 160 | 37 | 1.5E-09 | 6 | 7 | 71 | 61 | 320 | 113 |
| kgp58695 | 27 | 19 | 96 | 23 | 75 | 19 | 1.5E-05 | 60 | 58 | 184 | 74 | 152 | 48 |
| kgp62369 | 12 | 9 | 81 | 29 | 108 | 23 | 1.7E-05 | 30 | 34 | 166 | 85 | 203 | 62 |
| kgp59767 | 0 | 0 | 18 | 0 | 181 | 61 | 1.7E-05 | 0 | 0 | 29 | 0 | 368 | 181 |
| kgp11210 | 1 | 0 | 17 | 0 | 183 | 61 | 1.8E-05 | 1 | 0 | 30 | 0 | 368 | 181 |
| rs1768796 | 1 | 0 | 18 | 0 | 182 | 61 | 1.8E-05 | 1 | 0 | 30 | 0 | 368 | 181 |
| kgp81106 | 1 | 0 | 18 | 0 | 181 | 61 | 1.8E-05 | 1 | 0 | 30 | 0 | 367 | 181 |
| rs1102277 | 28 | 1 | 91 | 31 | 82 | 29 | 1.9E-05 | 52 | 5 | 176 | 72 | 171 | 104 |
| rs2005154 | 0 | 2 | 45 | 9 | 155 | 50 | 2.0E-05 | 0 | 10 | 87 | 39 | 310 | 132 |
| kgp11141 | 0 | 0 | 3 | 7 | 198 | 54 | 2.0E-05 | 0 | 1 | 11 | 21 | 388 | 158 |

In some embodiments genetic markers presented in Tables 11, 12 and 13 are identified as predictive of response to glatiramer acetate if the p-value for the Combined cohort is less than about 0.05, less than about 0.01, less than about 0.005, less than about 0.001, or less than about 0.0005, less than about $10^{-4}$, less than about $5*10^{-5}$, less than about $10^{-5}$, less than about $5*10^{-6}$, less than about $10^{-6}$ or less than about $5*10^{-7}$.

In the fourth stage of the analysis, the placebo cohort (n=196: 95 R vs. 101 NR) (GALA placebo) was analyzed to identify variants associated with placebo response/non-response. These results will be used to confirm whether significantly associated variants are specific to glatiramer acetate drug response versus disease severity.

Overlap with Placebo Cohort Results:

An analysis to investigate whether any of the highly associated variants (P<0.0001) from the combined cohorts in the additive association analysis showed a similar significant association in the placebo cohort was conducted. This analysis identified two overlapping associations with the placebo associations, which include the $132^{nd}$ top associated variant in the combined cohorts (variant kpg5144181) and the $242^{nd}$ top associated variant in the combined cohort (kpg7063887).

Results for Standard Response Definition, Placebo Cohort Results for Additive, Allelic and Genotypic models are presented in tables 14-16, respectively.

TABLE 14

Additive Model, Genome Wide Placebo Cohort Analysis
GALA PLACEBO cohort

| Name | Chr | Position | Gene(s) | Mutation | Gene Location(s) | Armitage P | Regression Odds Ratio | Allele Freq (Cases) | Allele Freq. (Controls) | DD (Cases) | DD (Controls) | Dd (Cases) | Dd (Controls) | dd (Cases) | dd (Controls) |
|---|---|---|---|---|---|---|---|---|---|---|---|---|---|---|---|
| rs12472695 | 2 | 65804266 | ? | ? | ? | 2.31E-05 | 0.38 | 31% | 51% | 10 | 21 | 39 | 62 | 46 | 18 |
| kgp3188 | 2 | 65804244 | ? | ? | ? | 2.99E-05 | 0.39 | 36% | 56% | 13 | 25 | 41 | 63 | 40 | 13 |
| kgp5747456 | 2 | 23932556 | ? | ? | ? | 3.24E-05 | Infinity | 8% | 0% | 0 | 0 | 15 | 0 | 80 | 101 |
| rs11562998 | 2 | 51814215 | ? | ? | ? | 3.41E-05 | 6.52 | 14% | 2% | 2 | 0 | 23 | 5 | 70 | 96 |
| rs11563025 | 2 | 51864372 | ? | ? | ? | 3.41E-05 | 6.52 | 14% | 14% | 2 | 0 | 23 | 5 | 70 | 96 |

TABLE 14-continued

Additive Model, Genome Wide Placebo Cohort Analysis
GALA PLACEBO cohort

| Name | Chr | Position | Gene(s) | Mutation | Gene Locations (s) | Armitage P | Regression Odds Ratio | Allele Freq (Cases) | Allele Freq. (Controls) | DD (Cases) | DD (Controls) | Dd (Cases) | Dd (Controls) | dd (Cases) | dd (Controls) |
|---|---|---|---|---|---|---|---|---|---|---|---|---|---|---|---|
| rs16846161 | 2 | 2.12E+08 | ERBB4, ERE | Silent, Sile | INTRON | 3.72E-05 | 12.04 | 12% | 1% | 2 | 0 | 18 | 2 | 74 | 97 |
| kgp22839559 |  |  | ? | ? | ? | 3.97E-05 | 2.82 | 34% | 16% | 10 | 2 | 44 | 28 | 40 | 70 |
| kgp12562255 | 1 | 2.01E+08 | ? | ? | ? | 4.21E-05 | 21.79 | 9% | 0% | 0 | 0 | 17 | 1 | 78 | 100 |
| kgp6990559 | 1 | 7014101 | CAMTA1 | Silent | INTRON, E | 4.49E-05 | 0.44 | 35% | 58% | 15 | 35 | 36 | 42 | 43 | 20 |
| rs6577395 | 1 | 6991925 | CANTTA1 | Silent | INTRON, E | 5.34E-05 | 0.45 | 37% | 59% | 16 | 38 | 37 | 43 | 41 | 20 |
| kgp4456934 | 2 | 2.18E+08 | DIRC3 | Silent | INTRON | 5.68E-05 | 3.79 | 21% | 7% | 4 | 0 | 31 | 13 | 60 | 87 |
| rs10495115 | 1 | 2.19E+08 | ? | ? | ? | 6.04E-05 | 2.90 | 30% | 13% | 7 | 2 | 43 | 23 | 45 | 76 |
| kgp4137144 | 1 | 2.19E+08 | 0 | ? | ? | 6.13E-05 | 6.19 | 14% | 3% | 2 | 0 | 22 | 5 | 70 | 95 |
| rs3768769 | 2 | 1.14E+08 | IL36A | Silent | INTRON | 7.21E-05 | 4.30 | 17% | 5% | 2 | 0 | 29 | 10 | 64 | 91 |
| kgp3488270 | 1 | 20335423 | ? | ? | ? | 7.30E-05 | 0.27 | 6% | 21% | 1 | 4 | 10 | 33 | 84 | 63 |
| rs2354380 | 2 | 51826155 | ? | ? | ? | 7.48E-05 | 5.49 | 14% | 3% | 2 | 0 | 23 | 6 | 69 | 95 |
| kgp7151153 | 3 | 79590648 | ROBO1 | Silent | INTRON | 7.86E-05 | 3.98 | 18% | 5% | 4 | 1 | 27 | 8 | 64 | 92 |
| rs28993969 | 2 | 1.14E+08 | ? | ? | ? | 8.51E-05 | 3.67 | 20% | 6% | 4 | 0 | 30 | 13 | 61 | 88 |
| rs12043743 | 1 | 1.97E+08 | KCNT2 | Silent | INTRON | 8.61E-05 | 0.16 | 3% | 13% | 0 | 0 | 5 | 26 | 90 | 75 |
| kgp24521552 | 2 | 1.44E+08 | ARHGAP1 | Silent | INTRON | 8.86E-05 | 4.22 | 17% | 5% | 4 | 0 | 25 | 9 | 66 | 91 |
| kgp11755256 | 2 | 42245135 | ? | ? | ? | 8.99E-05 | 0.38 | 14% | 32% | 1 | 14 | 25 | 37 | 68 | 50 |
| rs528065 | 2 | 23859449 | KLHL29 | Silent | INTRON | 9.24E-05 | 2.45 | 44% | 26% | 19 | 3 | 46 | 46 | 30 | 52 |
| rs13386874 | 2 | 51820543 | ? | ? | ? | 9.25E-05 | 2.64 | 32% | 15% | 12 | 1 | 37 | 28 | 46 | 72 |
| kgp956070 | 2 | 2.06E+08 | PARD3B, P | Silent, Sile | INTRON | 9.39E-05 | 0.37 | 14% | 32% | 2 | 11 | 23 | 41 | 70 | 48 |
| rs35615951 | 2 | 1 34E+08 | NCKAP5, N | Silent, Sile | INTRON | 9.41E-05 | 2.32 | 48% | 28% | 22 | 8 | 46 | 41 | 26 | 52 |
| kgp12253568 | 3 | 79428265 | ROBO1 | Silent | INTRON | 9.55E-05 | 4.29 | 17% | 4% | 4 | 1 | 24 | 6 | 67 | 94 |
| rs1397481 | 2 | 2.06E+08 | PARD3B, P | Silent, Sile | INTRON | 9.56E-05 | 0.37 | 14% | 31% | 2 | 10 | 23 | 43 | 70 | 48 |
| kgp7161038 | 2 | 53521025 | ? | ? | ? | 9.70E-05 | 0.09 | 1% | 10% | 0 | 0 | 2 | 20 | 92 | 81 |
| rs1534647 | 2 | 62038088 | ? | ? | ? | 9.72E-05 | 3.34 | 22% | 8% | 5 | 0 | 32 | 16 | 58 | 85 |
| kgp7799142 | 3 | 13902000 | WNT7A | Silent | INTRON | 1.04E-04 | 0.12 | 2% | 11% | 0 | 0 | 3 | 22 | 91 | 79 |
| kgp6029 | 2 | 1.69E+08 | ? | ? | ? | 1.07E-04 | 0.37 | 13% | 30% | 2 | 11 | 21 | 39 | 72 | 51 |
| kgp8142606 | 2 | 1.74E+08 | ? | ? | ? | 1.10E-04 | 0.22 | 4% | 17% | 0 | 3 | 8 | 27 | 87 | 70 |
| rs6737616 | 2 | 51807660 | ? | ? | ? | 1.18E-04 | 5.98 | 13% | 2% | 1 | 0 | 22 | 5 | 72 | 96 |
| kgp7713264 | 2 | 2.42E+08 | GPR35, GP | Silent, Sile | INTRON | 1.18E-04 | 0.45 | 30% | 51% | 10 | 27 | 37 | 47 | 47 | 26 |
| kgp8055964 | 3 | 1.73E+08 | SPATA16 | Silent | INTRON | 1.19E-04 | Infinity | 7% | 0% | 0 | 0 | 13 | 0 | 82 | 101 |
| rs12712821 | 2 | 42238864 | ? | ? | ? | 1.19E-04 | 0.39 | 15% | 32% | 1 | 14 | 26 | 37 | 68 | 50 |
| rs13424176 | 2 | 42239532 | ? | ? | ? | 1.19E-04 | 0.39 | 15% | 32% | 1 | 14 | 26 | 37 | 68 | 50 |
| kgp9777128 | 2 | 42242872 | ? | ? | ? | 1.19E-04 | 0.39 | 15% | 32% | 1 | 14 | 26 | 37 | 68 | 50 |
| rs10195970 | 2 | 42249643 | ? | ? | ? | 1.19E-04 | 0.39 | 15% | 32% | 1 | 14 | 26 | 37 | 68 | 50 |
| rs10177811 | 2 | 42263580 | ? | ? | ? | 1.19E-04 | 0.39 | 15% | 32% | 1 | 14 | 26 | 37 | 68 | 50 |

TABLE 15

Allelic Model, Genome Wide Placebo Cohort Analysis
GALA PLACEBO cohort

| Name | Chr | Position | Gene(s) | Mutation | Gene Location (s) | Fisher's Exact P | Odds Ratio (Minor Allele) | Allele Freq. (Cases) | Allele Freq. (Controls) | DD (Cases) | DD (Controls) | Dd (Cases) | Dd (Controls) | dd (Cases) | dd (Controls) |
|---|---|---|---|---|---|---|---|---|---|---|---|---|---|---|---|
| kgp-5471255 | 11 | 57870219 | OR9Q1 | Silent | INTRON, E | 1.16E-06 | 0.25 | 9% | 29% | 5 | 25 | 7 | 7 | 81 | 68 |
| kgp-11285883 | 9 | 2953403 | ? | ? | ? | 2.68E-06 | 2.79 | 46% | 23% | 26 | 5 | 35 | 37 | 34 | 59 |

TABLE 15-continued

Allelic Model, Genome Wide Placebo Cohort Analysis
GALA PLACEBO cohort

| Name | Chr | Position | Gene(s) | Mutation | Gene Location(s) | Fisher's Exact P | Odds Ratio (Minor Allele) | Allele Freq. (Cases) | Allele Freq. (Controls) | DD (Cases) | DD (Controls) | Dd (Cases) | Dd (Controls) | dd (Cases) | dd (Controls) |
|---|---|---|---|---|---|---|---|---|---|---|---|---|---|---|---|
| kgp-433351 | 8 | 41496314 | ? | ? | ? | 2.70E−06 | 0.35 | 23% | 46% | 6 | 19 | 32 | 55 | 57 | 27 |
| kgp-10148554 | 4 | 89767803 | FAM-13A | Silent | INTRON | 3.69E−06 | 7.19 | 15% | 2% | 3 | 0 | 23 | 5 | 68 | 96 |
| rs3858038 | 9 | 2988280 | ? | ? | ? | 5.49E−06 | 2.63 | 53% | 30% | 33 | 7 | 34 | 46 | 28 | 48 |
| kgp-2877482 | 6 | 1644677 | GMDS, GM | Silent, Sile | INTRON | 6.08E−06 | 8.20 | 14% | 2% | 0 | 0 | 27 | 4 | 68 | 97 |
| kgp-6042557 | 3 | 1.94E+08 | LOC-10050 | Silent | INTRON | 6.53E−06 | 0.08 | 1% | 12% | 0 | 1 | 2 | 22 | 93 | 77 |
| kgp-22755512 | X | 27326117 | ? | ? | ? | 6.61E−06 | ? | 8% | 0% | 3 | 0 | 10 | 0 | 82 | 101 |
| kgp-10989246 | 4 | 89761443 | FAM-13A | Silent | INTRON | 6.68E−06 | 7.11 | 15% | 3% | 3 | 0 | 23 | 5 | 68 | 95 |
| rs-7698655 | 4 | 89756076 | FAM-13A | Silent | INTRON | 6.76E−06 | 7.10 | 15% | 2% | 3 | 0 | 23 | 5 | 69 | 96 |
| kgp-9409440 | 4 | 89759159 | FAM-13A | Silent | INTRON | 6.76E−06 | 7.10 | 15% | 2% | 3 | 0 | 23 | 5 | 69 | 96 |
| kgp-6889327 | 4 | 89766553 | FAM-13A | Silent | INTRON | 6.76E−06 | 7.10 | 15% | 2% | 3 | 0 | 23 | 5 | 69 | 96 |
| rs-7696391 | 4 | 89789287 | FAM-13A | Silent | INTRON | 6.76E−06 | 7.10 | 15% | 2% | 3 | 0 | 23 | 5 | 69 | 96 |
| rs-11947777 | 4 | 89768744 | FAM-13A | Silent | INTRON | 6.92E−06 | 7.02 | 15% | 3% | 3 | 0 | 23 | 5 | 69 | 95 |
| kgp-6301155 | 4 | 89766647 | FAM-13A | Silent | INTRON | 7.20E−06 | 6.95 | 15% | 3% | 3 | 0 | 23 | 5 | 69 | 94 |
| rs-16846161 | 2 | 2.12E+08 | ERBB4, ERE | Silent, Sile | INTRON | 7.44E−06 | 12.99 | 12% | 1% | 2 | 0 | 18 | 2 | 74 | 97 |
| kgp-7778345 | 9 | 2965090 | ? | ? | ? | 9.91E−06 | 2.59 | 49% | 27% | 27 | 6 | 38 | 42 | 29 | 52 |
| kgp-6990559 | 1 | 7014101 | CAM-TA1 | Silent | INTRON, E | 1.01E−05 | 0.40 | 35% | 58% | 15 | 35 | 36 | 42 | 43 | 20 |
| rs-1393040 | 9 | 2985743 | ? | ? | ? | 1.04E−05 | 2.57 | 48% | 27% | 28 | 6 | 35 | 42 | 31 | 53 |
| rs-6577395 | 1 | 6991925 | CAM-TA1 | Silent | INTRON, E | 1.27E−05 | 0.40 | 37% | 59% | 16 | 38 | 37 | 43 | 41 | 20 |
| rs-7846783 | 9 | 2958182 | ? | ? | ? | 1.28E−05 | 2.58 | 45% | 24% | 25 | 6 | 36 | 37 | 34 | 58 |
| kgp-5747456 | 2 | 23932556 | ? | ? | ? | 1.42E−05 | ? | 8% | 0% | 0 | 0 | 15 | 0 | 80 | 101 |
| kgp-6429231 | 15 | 62931802 | MGC-1588 | Silent | INTRON | 1.42E−05 | ? | 8% | 0% | 0 | 0 | 15 | 0 | 80 | 101 |
| kgp-30689515 | X | 56022365 | ? | ? | ? | 1.42E−05 | ? | 8% | 0% | 4 | 0 | 7 | 0 | 84 | 101 |
| kgp-1682126 | 5 | 2047397 | ? | ? | ? | 1.56E−05 | 0.05 | 1% | 10% | 0 | 1 | 1 | 18 | 94 | 82 |
| kgp-2920925 | 17 | 39694480 | ? | ? | ? | 1.56E−05 | 0.30 | 10% | 27% | 0 | 6 | 19 | 43 | 76 | 52 |
| rs-3894712 | 5 | 73973651 | ? | ? | ? | 1.70E−05 | 0.29 | 9% | 25% | 3 | 5 | 11 | 41 | 81 | 55 |
| rs-7119480 | 11 | 84247636 | DLG2, DLG | Silent, Sile | INTRON, E | 1.71E−05 | 0.34 | 14% | 33% | 1 | 9 | 25 | 48 | 69 | 44 |
| rs-3858035 | 9 | 2968044 | ? | ? | ? | 1.72E−05 | 2.51 | 48% | 27% | 27 | 7 | 37 | 41 | 30 | 53 |
| rs-3847233 | 9 | 2987835 | ? | ? | ? | 1.95E−05 | 2.49 | 52% | 30% | 31 | 7 | 34 | 46 | 28 | 47 |
| kgp-12253568 | 3 | 79428265 | ROBO1 | Silent | INTRON | 2.10E−05 | 4.91 | 17% | 4% | 4 | 1 | 24 | 6 | 67 | 94 |
| kgp-1977942 | 9 | 2938757 | ? | ? | ? | 2.17E−05 | 2.52 | 46% | 26% | 28 | 7 | 32 | 37 | 35 | 56 |
| kgp-22744690 | X | 83601713 | HDX, HDX, | Silent, Sile | INTRON | 2.21E−05 | 7.50 | 13% | 2% | 7 | 0 | 11 | 4 | 77 | 97 |
| rs-8000689 | 13 | 41043438 | TTL, TTL, TT | Silent, Sile | INTRON | 2.22E−05 | 0.42 | 38% | 60% | 14 | 40 | 45 | 41 | 36 | 20 |
| kgp-4892427 | 9 | 2995617 | ? | ? | ? | 2.27E−05 | 2.46 | 52% | 30% | 31 | 7 | 36 | 47 | 28 | 47 |
| rs-11562998 | 2 | 51814215 | ? | ? | ? | 2.36E−05 | 6.53 | 14% | 2% | 2 | 0 | 23 | 5 | 70 | 96 |
| rs-11563025 | 2 | 51864372 | ? | ? | ? | 2.36E−05 | 6.53 | 14% | 2% | 2 | 0 | 23 | 5 | 70 | 96 |
| rs- | 4 | 89772301 | FAM- | Mis- | EXON | 2.37E−05 | 5.88 | 15% | 3% | 3 | 0 | 23 | 6 | 69 | 95 |

TABLE 15-continued

Allelic Model, Genome Wide Placebo Cohort Analysis
GALA PLACEBO cohort

| Name | Chr | Position | Gene(s) | Muta-tion | Gene Location (s) | Fisher's Exact P | Odds Ratio (Minor Allele) | Allele Freq. (Cases) | Allele Freq. (Controls) | DD (Cases) | DD (Controls) | Dd (Cases) | Dd (Controls) | dd (Cases) | dd (Controls) |
|---|---|---|---|---|---|---|---|---|---|---|---|---|---|---|---|
| 7680970 | | | 13A | sense | | | | | | | | | | | |
| kgp-22836129 | X | 1.45E+08 | ? | ? | ? | 2.38E−05 | 5.84 | 15% | 3% | 5 | 0 | 19 | 6 | 70 | 93 |
| kgp-11604017 | 11 | 1.18E+08 | AMICA1, A | Silent, Sile | INTRON | 2.39E−05 | 2.69 | 38% | 18% | 11 | 3 | 48 | 31 | 34 | 67 |
| rs961090 | 15 | 40617414 | ? | ? | ? | 2.40E−05 | 2.97 | 31% | 13% | 9 | 2 | 40 | 22 | 46 | 77 |
| kgp-22760557 | X | 3520721 | ? | ? | ? | 2.40E−05 | 2.97 | 31% | 13% | 16 | 5 | 26 | 16 | 53 | 80 |
| rs-1393037 | 9 | 2968451 | ? | ? | ? | 2.41E−05 | 2.50 | 48% | 27% | 27 | 7 | 37 | 40 | 30 | 52 |
| rs-4978567 | 9 | 1.17E+08 | ? | ? | ? | 2.47E−05 | 0.41 | 32% | 54% | 10 | 27 | 41 | 52 | 44 | 20 |

TABLE 16

Genotypic Model, Genome Wide Placebo Cohort Analysis
GALA PLACEBO cohort

| Name | Chromosome | Position | Gene(s) | Mutation | Gene Locations (s) | Fisher's Exact P | Allele Freq. (Cases) | Allele Freq. (Controls) | DD (Cases) | DD (Controls) | Dd (Cases) | Dd (Controls) | dd (Cases) | dd (Controls) |
|---|---|---|---|---|---|---|---|---|---|---|---|---|---|---|
| kgp541892 | 5 | 73992881 | HEXB | Missense | EXON | 8.76E−07 | 9% | 25% | 3 | 3 | 11 | 44 | 81 | 54 |
| kgp34945 | 14 | 91731724 | ? | ? | ? | 1.53E−06 | 6% | 17% | 3 | 1 | 5 | 32 | 87 | 67 |
| kgp21160 | 14 | 91744233 | CCDC88C | Silent | INTRON | 1.55E−06 | 6% | 17% | 3 | 1 | 5 | 32 | 86 | 67 |
| kgp28774 | 6 | 1644677 | GMDS, GM | Silent, Sile | INTRON | 2.43E−06 | 14% | 2% | 0 | 0 | 27 | 4 | 68 | 97 |
| rs1175074 | 5 | 73973220 | ? | ? | ? | 2.71E−06 | 9% | 25% | 3 | 4 | 11 | 42 | 81 | 55 |
| rs122339 | 5 | 73975094 | ? | ? | ? | 2.71E−06 | 9% | 25% | 3 | 4 | 11 | 42 | 81 | 55 |
| rs1203094 | 1 | 67701765 | IL23R | Silent | INTRON | 3.44E−06 | 36% | 37% | 20 | 5 | 29 | 64 | 46 | 32 |
| rs3894712 | 5 | 73973651 | ? | ? | ? | 3.50E−06 | 9% | 25% | 3 | 5 | 11 | 41 | 81 | 55 |
| rs3858038 | 9 | 2988280 | ? | ? | ? | 4.13E−06 | 53% | 30% | 33 | 7 | 34 | 46 | 28 | 48 |
| kgp625941 | 5 | 73973306 | ? | ? | ? | 5.26E−06 | 9% | 24% | 3 | 4 | 11 | 41 | 81 | 56 |
| rs7159692 | 14 | 91729406 | ? | ? | ? | 6.22E−06 | 7% | 18% | 3 | 1 | 7 | 34 | 85 | 66 |
| k8P433351 | 8 | 41436314 | ? | ? | ? | 7.73E−06 | 23% | 46% | 6 | 19 | 32 | 55 | 57 | 27 |
| kgp604255 | 3 | 1.94E+08 | LOC10050 | Silent | INTRON | 8.38E−06 | 1% | 12% | 0 | 1 | 2 | 22 | 93 | 77 |
| kgp89109 | 8 | 4818950 | CSMD1 | Silent | INTRON | 8.91E−06 | 45% | 33% | 27 | 5 | 32 | 57 | 36 | 39 |
| kgp48182 | 14 | 86277089 | ? | ? | ? | 8.95E−06 | 45% | 36% | 10 | 18 | 66 | 36 | 19 | 47 |
| k8P66017 | 19 | 28886975 | ? | ? | ? | 9 85E−06 | 19% | 31% | 7 | 3 | 21 | 55 | 65 | 42 |
| kgp57474 | 2 | 23932556 | ? | ? | ? | 1.03E−05 | 8% | 0% | 0 | 0 | 15 | 0 | 80 | 101 |
| kgp642923 | 15 | 62931802 | MGC1588 | Silent | INTRON | 1.03E−05 | 8% | 0% | 0 | 0 | 15 | 0 | 80 | 101 |
| kgp82762 | 14 | 91725476 | ? | ? | ? | 1.22E−05 | 7% | 17% | 3 | 1 | 7 | 33 | 85 | 67 |
| kgp68282 | 9 | 8373943 | PTPRD, PT | Silent, Sile | INTRON | 1.23E−05 | 26% | 10% | 3 | 2 | 43 | 17 | 48 | 82 |
| rs3847233 | 9 | 2987835 | ? | ? | ? | 1.32E−05 | 52% | 30% | 31 | 7 | 34 | 46 | 28 | 47 |
| kgp3188 | 2 | 65804244 | ? | ? | ? | 1.34E−05 | 36% | 56% | 13 | 25 | 41 | 63 | 40 | 13 |
| rs1890118 | 6 | 82857479 | ? | ? | ? | 1.48E−05 | 26% | 32% | 13 | 4 | 23 | 56 | 59 | 41 |
| rs2282624 | 11 | 57001911 | APLNR, AP | Silent, Sile | INTRON, E | 1.54E−05 | 30% | 35% | 15 | 5 | 27 | 61 | 53 | 35 |
| kgp48924 | 9 | 2995617 | ? | ? | ? | 1.54E−05 | 52% | 30% | 31 | 7 | 36 | 47 | 28 | 47 |
| kgp11285 | 9 | 2953403 | ? | ? | ? | 1.66E−05 | 46% | 28% | 26 | 5 | 35 | 37 | 34 | 59 |
| rs4740708 | 9 | 2993975 | ? | ? | ? | 1.67E−05 | 51% | 30% | 31 | 7 | 34 | 47 | 29 | 47 |
| rs695915 | 1 | 82664165 | ? | ? | ? | 1.90E−05 | 34% | 28% | 6 | 17 | 51 | 23 | 37 | 61 |
| rs2327006 | 5 | 1.31E+08 | EPB41L2, E | Silent, Sile | INTRON | 1.93E−05 | 22% | 9% | 1 | 2 | 39 | 13 | 55 | 84 |
| kgp933491 | 6 | 1.31E+08 | EPB41L2, E | Silent, Sile | INTRON | 2.05E−05 | 22% | 8% | 2 | 2 | 38 | 13 | 55 | 86 |
| rs193933 | 19 | 8331375 | ? | ? | ? | 2.07E−05 | 27% | 46% | 11 | 17 | 30 | 59 | 54 | 25 |
| kgp12475 | 4 | 1.86E+08 | ACSL1 | Silent | INTRON | 2.11E−05 | 13% | 3% | 0 | 1 | 24 | 4 | 71 | 96 |
| rs1247269 | 2 | 65804266 | ? | ? | ? | 2.11E−05 | 31% | 51% | 10 | 21 | 39 | 62 | 46 | 18 |
| rs1393040 | 9 | 2985743 | ? | ? | ? | 2.31E−05 | 48% | 27% | 28 | 6 | 35 | 42 | 31 | 53 |
| kgp29209 | 17 | 39694480 | ? | ? | ? | 2.33E−05 | 10% | 27% | 0 | 6 | 19 | 43 | 76 | 52 |
| rs209568 | 8 | 17612639 | MTUS1, M | Synonym | EXON | 2.34E−05 | 27% | 11% | 4 | 0 | 44 | 22 | 47 | 79 |
| kgp12562 | 1 | 2.01E+08 | ? | ? | ? | 2.42E−05 | 9% | 0% | 0 | 0 | 17 | 1 | 78 | 100 |
| kgp26263 | 13 | 67483846 | PCDH9, PC | Silent, Sile | INTRON, E | 2.43E−05 | 34% | 49% | 4 | 28 | 56 | 43 | 34 | 30 |

TABLE 16-continued

Genotypic Model, Genome Wide Placebo Cohort Analysis
GALA PLACEBO cohort

| Name | Chromosome | Position | Gene(s) | Mutation | Gene Locations(s) | Fisher's Exact P | Allele Freq. (Cases) | Allele Freq. (Controls) | DD (Cases) | DD (Controls) | Dd (Cases) | Dd (Controls) | dd (Cases) | dd (Controls) |
|---|---|---|---|---|---|---|---|---|---|---|---|---|---|---|
| kgp16821 | 5 | 2047397 | ? | ? | ? | 2.51E-05 | 1% | 10% | 0 | 1 | 1 | 18 | 94 | 82 |
| kgp101485 | 4 | 89767803 | FAM13A | Silent | INTRON | 2.55E-05 | 15% | 2% | 3 | 0 | 23 | 5 | 68 | 96 |
| kgp57600 | 6 | 1.31E+08 | EPB41L2, E | Silent, Sile | INTRON | 2.61E-05 | 20% | 7% | 1 | 2 | 35 | 11 | 58 | 88 |
| kgp783985 | 1 | 95321361 | SLC44A3, S | Silent, Sile | INTRON | 2.67E-05 | 20% | 20% | 0 | 11 | 38 | 19 | 57 | 71 |
| rs1049917 | 6 | 1.31E+08 | EPB41L2, E | Silent, Sile | INTRON | 2.77E-05 | 19% | 7% | 1 | 2 | 35 | 11 | 59 | 88 |
| kgp377813 | 19 | 28893126 | ? | ? | ? | 2.80E-05 | 19% | 32% | 7 | 4 | 23 | 56 | 65 | 41 |
| kgp76534 | 17 | 39694186 | ? | ? | ? | 2.81E-05 | 10% | 27% | 0 | 5 | 19 | 44 | 76 | 52 |
| rs1684616 | 2 | 2.12E+08 | ERBB4, ER | Silent, Sile | INTRON | 2.96E-05 | 12% | 1% | 2 | 0 | 18 | 2 | 74 | 97 |

Example 9 Analysis for Extreme Responders vs. Extreme Non-Responders Part 1—Analysis of Candidate Variants The initial analysis was analyzed to 35 genetic variants in high priority genes. Power (80%) with Bonferroni statistical correction for multiple testing to identify significant genetic associations with an odds ratio >4, for variants with an allele frequency greater than 10%.

Results for Extreme Response Definition, Candidate Variants Selected a priori for Additive, Allelic and Genotypic models are presented in tables 17-19, respectively.

In some embodiments genetic markers presented in Tables 17-19 are identified as predictive of response to glatiramer acetate if the p-value for the GALA cohort is less than about 0.15, less than about 0.13, less than about 0.07 or less than about 0.06.

In some embodiments genetic markers presented in Tables 17-19 are identified as predictive of response to glatiramer acetate if the p-value for the FORTE cohort is less than about 0.10, less than about 0.05, less than about 0.01, less than about 0.005 or less than about 0.001.

In some embodiments genetic markers presented in Tables 17-19 are identified as predictive of response to glatiramer acetate if the p-value for the Combined cohort is less than about 0.10, less than about 0.05, less than about 0.01, less than about 0.005 or less than about 0.001.

TABLE 17

Additive Model, Extreme Response Definition, Candidate Variants (Gala, Forte, and Combined cohorts)

| | | | | GALA | | | | FORTE | | | | COMBINED | | | |
|---|---|---|---|---|---|---|---|---|---|---|---|---|---|---|---|
| Source | Name | Ch | Gene | Armitage P-Value | Odds Ratio | Allele Freq. (Resp.) | Allele Freq. (Non-Resp.) | Armitage P-Value | Odds Ratio | Allele Freq. (Resp.) | Allele Freq. (Non-Resp.) | Armitage P-Value | Odds Ratio | Allele Freq. (Resp.) | Allele Freq. (Non-Resp.) |
| Tchelet GWAS | rs3135391 | 6 | HLA-DRB1 | 0.060 | 0.58 | 18% | 27% | 0.028 | 0.50 | 20% | 33% | 0.0064 | 0.57 | 19% | 29% |
| Tchelet GWAS | rs3135388 | 6 | HLA-DRB1 | 0.069 | 0.59 | 18% | 27% | 0.028 | 0.50 | 20% | 33% | 0.0075 | 0.58 | 19% | 29% |
| Tchelet GWAS | rs2487896 | 10 | HPSE2 | 0.130 | 0.60 | 11% | 17% | 0.0017 | 0.33 | 12% | 29% | 0.0044 | 0.51 | 11% | 20% |
| Tchelet GWAS | rs1085360 | 18 | MEX3C | 0.149 | 0.70 | 36% | 44% | 0.56 | 1.18 | 43% | 39% | 0.54 | 0.90 | 40% | 43% |
| Tchelet GWAS | rs1098808 | 9 | SET | 0.231 | 0.48 | 3% | 6% | 0.0010 | 0.18 | 3% | 14% | 0.0051 | 0.33 | 3% | 8% |
| Comi | rs269976 | 18 | SLC14A2 | 0.288 | 1.62 | 8% | 5% | 0.28 | 2.33 | 6% | 3% | 0.21 | 1.61 | 7% | 5% |
| Tsareva 2011 | rs231775 | 2 | CTLA4 | 0.318 | 1.28 | 43% | 38% | 0.46 | 1.22 | 37% | 31% | 0.39 | 1.16 | 40% | 36% |
| Grossman 2007 | rs946685 | 1 | IL12RB2 | 0.342 | 1.32 | 21% | 17% | 0.84 | 0.92 | 15% | 16% | 0.75 | 1.08 | 18% | 17% |
| Tsareva 2011 | rs1800629 | 6 | TNF | 0.355 | 0.74 | 13% | 17% | 0.86 | 1.07 | 12% | 11% | 0.39 | 0.82 | 13% | 15% |
| Tchelet GWAS | rs1007328 | 15 | AC-012409.1 | 0.364 | 1.24 | 57% | 52% | 0.051 | 0.37 | 45% | 59% | 0.38 | 0.86 | 50% | 54% |
| Tchelet GWAS | rs1225688 | 10 | CYP26C1 | 0.366 | 0.79 | 30% | 34% | 0.23 | 1.46 | 35% | 27% | 0.93 | 1.02 | 33% | 32% |
| Tchelet GWAS | rs1093109 | 2 | AC-074182.1 | 0.387 | 1.38 | 11% | 8% | 0.42 | 0.69 | 7% | 10% | 0.96 | 1.01 | 8% | 8% |
| Tchelet GWAS | rs4148871 | 6 | TAP2 | 0.421 | 0.79 | 17% | 20% | 0.98 | 1.01 | 23% | 23% | 0.83 | 0.95 | 20% | 21% |
| Tchelet GWAS | rs947603 | 10 | CEP55 | 0.436 | 1.26 | 23% | 19% | 0.033 | 2.30 | 24% | 11% | 0.06 | 1.51 | 24% | 17% |

TABLE 17-continued

Additive Model, Extreme Response Definition, Candidate Variants (Gala, Forte, and Combined cohorts)

| | | | | GALA | | | | FORTE | | | | COMBINED | | | |
|---|---|---|---|---|---|---|---|---|---|---|---|---|---|---|---|
| Source | Name | Ch | Gene | Armitage P-Value | Odds Ratio | Allele Freq. (Resp.) | Allele Freq. (Non-Resp.) | Armitage P-Value | Odds Ratio | Allele Freq. (Resp.) | Allele Freq. (Non-Resp.) | Armitage P-Value | Odds Ratio | Allele Freq. (Resp.) | Allele Freq. (Non-Resp.) |
| Grossman 2007 | rs2001791 | 3 | CD86 | 0.439 | 1.29 | 16% | 13% | 0.32 | 0.71 | 15% | 20% | 0.93 | 1.02 | 15% | 15% |
| Tsareva 2011 | rs6897932 | 5 | IL7Ra | 0.493 | 0.82 | 21% | 24% | 0.84 | 1.07 | 24% | 23% | 0.77 | 0.94 | 23% | 24% |
| Comi | rs1558896 | 7 | TAC1 | 0.506 | 1.17 | 33% | 30% | 0.27 | 0.71 | 26% | 33% | 0.70 | 0.93 | 29% | 31% |
| Grossman 2007 | rs1415148 | 1 | CTSS | 0.555 | 0.86 | 36% | 40% | 0.39 | 1.28 | 42% | 36% | 0.79 | 1.05 | 40% | 38% |
| Tchelet GWAS | rs1777193 | 8 | AC-016885.1 | 0.555 | 1.17 | 28% | 25% | 0.000020 | 0.27 | 24% | 53% | 0.067 | 0.71 | 26% | 33% |
| Grossman 2007 | rs2275235 | 1 | CTSS | 0.634 | 0.88 | 32% | 34% | 0.16 | 1.52 | 40% | 30% | 0.41 | 1.16 | 36% | 33% |
| Tchelet GWAS | rs1573706 | 20 | PTPRT | 0.638 | 0.87 | 18% | 20% | 0.00048 | 0.28 | 11% | 29% | 0.0071 | 0.55 | 14% | 23% |
| Tchelet GWAS | rs1159962 | 10 | RP11-655H13.1 | 0.653 | 0.84 | 11% | 12% | 0.98 | 1.01 | 10% | 10% | 0.64 | 0.88 | 10% | 12% |
| Comi | rs974060 | 7 | TAC1 | 0.654 | 1.12 | 30% | 28% | 0.19 | 0.67 | 25% | 33% | 0.57 | 0.90 | 27% | 29% |
| Comi | rs4890535 | 18 | SLC14A2 | 0.656 | 1.19 | 9% | 8% | 0.64 | 1.28 | 9% | 7% | 0.52 | 1.21 | 9% | 7% |
| Tchelet GWAS | rs1757545 | 2 | AC-078940.2 | 0.664 | 0.89 | 30% | 33% | 0.018 | 0.52 | 30% | 47% | 0.11 | 0.75 | 30% | 37% |
| Tchelet GWAS | rs2521644 | 7 | NPY | 0.679 | 1.11 | 45% | 42% | 0.83 | 1.06 | 44% | 43% | 0.64 | 1.09 | 45% | 43% |
| Grossman 2007 | rs1129055 | 3 | CD86 | 0.775 | LO8 | 26% | 24% | 0.19 | 0.68 | 30% | 39% | 0.91 | 0.98 | 28% | 29% |
| Tchelet GWAS | rs4343256 | 15 | CRTC3 | 0.808 | 1.14 | 5% | 5% | 0.044 | 0.37 | 6% | 13% | 0.42 | 0.75 | 5% | 7% |
| Tchelet GWAS | rs6097801 | 20 | CYP24A1 | 0.823 | 0.93 | 14% | 15% | 0.0057 | 0.41 | 9% | 24% | 0.043 | 0.63 | 11% | 17% |
| Tchelet GWAS | rs2177073 | 18 | DTNA | 0.864 | 0.94 | 12% | 13% | 0.10 | 0.51 | 10% | 17% | 0.23 | 0.74 | 11% | 14% |
| Tchelet GWAS | rs1095035 | 7 | AC-074389.1 | 0.866 | 0.96 | 33% | 34% | 0.15 | 1.62 | 29% | 20% | 0.85 | 1.04 | 31% | 30% |
| Tchelet GWAS | rs4369324 | 10 | RP11-655H13.2 | 0.920 | 1.03 | 22% | 22% | 0.35 | 1.42 | 20% | 14% | 0.72 | 1.08 | 21% | 19% |
| Tchelet GWAS | rs1161713 | 13 | RP11-629E24.2 | 0.959 | 0.98 | 7% | 7% | 0.0022 | 0.14 | 2% | 10% | 0.052 | 0.49 | 4% | 8% |
| Tchelet GWAS | rs4344916 | 2 | AC-083939.1 | 0.962 | 1.01 | 31% | 31% | 0.08 | 0.63 | 26% | 39% | 0.24 | 0.81 | 28% | 33% |
| Tchelet GWAS | rs9944913 | 18 | NOL4 | 0.981 | 1.01 | 13% | 13% | 0.36 | 0.66 | 9% | 13% | 0.42 | 0.80 | 11% | 13% |

TABLE 18

Allelic Model, Extreme Response Definition, Candidate Variants (Gala, Forte, and Combined cohorts)

| | | | | | | GALA | | | | | FORTE | | |
|---|---|---|---|---|---|---|---|---|---|---|---|---|---|
| Source | Name | Ch | Position | Gene | Fisher's Exact P | Odds Ratio (Minor Allele) | Allele Freq. (Cases) | Allele Freq. (Controls) | Fisher's Exact P | Odds Ratio (Minor Allele) | Allele Freq. (Cases) |
| Tchelet GWAS | rs3135388 | 6 | 32413051 | HLA-DRB1 | 0.075234 | 0.599034 | 0.181818 | 0.270588 | 0.031164 | 0.500152 | 0.196629 |
| Tchelet GWAS | rs3135391 | 6 | 32410987 | HLA-DRB1 | 0.075291 | 0.591017 | 0.181818 | 0.273256 | 0.031164 | 0.500152 | 0.196629 |
| Tchelet GWAS | rs2487896 | 10 | 1.01E+08 | HPSE2 | 0.135493 | 0.576856 | 0.106061 | 0.170588 | 0.002228 | 0.334395 | 0.117978 |
| Tchelet GWAS | rs1085360 | 18 | 48783342 | MEX3C | 0.195547 | 0.721805 | 0.363636 | 0.44186 | 0.570435 | 1.186638 | 0.426966 |
| Tchelet GWAS | rs1098808 | 9 | 1.31E+08 | SET | 0.281834 | 0.5 | 0.030303 | 0.058824 | 0.001601 | 0.17341 | 0.02809 |
| Tsareva 2011 | rs2311775 | 2 | 2.05E+08 | CTLA4 | 0.347935 | 1.251077 | 0.431818 | 0.377907 | 0.462029 | 1.285714 | 0.370787 |
| Comi | rs269976 | 18 | 42781787 | SLC14A2 | 0.351837 | 1.646465 | 0.083333 | 0.052326 | 0.361631 | 2.239521 | 0.061793 |
| Grossman 2007 | rs946685 | 1 | 67815715 | IL12RB2 | 0.374886 | 1.327586 | 0.212121 | 0.168605 | 0.845141 | 0.929697 | 0.147727 |
| Tchelet GWAS | rs1225688 | 10 | 94827183 | CYP26C1 | 0.38939 | 0.803171 | 0.295455 | 0.343023 | 0.29301 | 1.434664 | 0.348315 |
| Tchelet GWAS | rs1007328 | 15 | 96703373 | AC012409.1 | 0.417114 | 1.227085 | 0.568182 | 0.517442 | 0.0664117 | 0.577402 | 0.449433 |
| Tchelet GWAS | rs1093109 | 2 | 1.85E+08 | AC074182.1 | 0.417558 | 1.451108 | 0.106061 | 0.075581 | 0.428339 | 0.650602 | 0.067416 |
| Tsareva 2011 | rs1800629 | 6 | 31543031 | TNF | 0.419818 | 0.728936 | 0.128788 | 0.168605 | 1 | 1.092949 | 0.123596 |
| Tchelet GWAS | rs4148871 | 6 | 32803316 | TAP2 | 0.46037 | 0.782857 | 0.166667 | 0.203488 | 1 | 1.010036 | 0.230337 |
| Tchelet GWAS | rs947603 | 10 | 95249605 | CEP55 | 0.477454 | 1.238859 | 0.227273 | 0.19186 | 0.023852 | 2.505639 | 0.244313 |
| Grossman 2007 | rs2001791 | 3 | 1.22E+08 | CD86 | 0.507354 | 1.289926 | 0.159091 | 0.127907 | 0.33832 | 0.684211 | 0.146067 |
| Tchelet GWAS | rs1558896 | 7 | 97281912 | TAC1 | 0.533334 | 1.186275 | 0.333333 | 0.296512 | 0.274375 | 0.712121 | 0.258427 |
| Tsareva 2011 | rs6897932 | 5 | 35874575 | IL7Ra | 0.582979 | 0.833333 | 0.212121 | 0.244186 | 0.870305 | 1.075 | 0.241573 |
| Tchelet GWAS | rs1777193 | 8 | 94259105 | AC016885.1 | 0.5999 | 1.168421 | 0.280303 | 0.25 | 2.18E-05 | 0.284084 | 0.241573 |
| Tchelet GWAS | rs1415148 | 1 | 1.51E+08 | CTSS | 0.634082 | 0.87395 | 0.363636 | 0.395349 | 0.3899 | 1.36099 | 0.41954 |
| Grossman 2007 | rs1573706 | 20 | 40921149 | PTPRT | 0.66336 | 0.869841 | 0.181818 | 0.203488 | 0.000892 | 0.298742 | 0.106742 |
| Tchelet GWAS | rs4890535 | 18 | 42760370 | SLC14A2 | 0.676761 | 1.223077 | 0.090909 | 0.075581 | 0.801757 | 1.283951 | 0.089888 |
| Comi | rs974060 | 7 | 97271508 | TAC1 | 0.702366 | 1.123188 | 0.30303 | 0.27907 | 0.206336 | 0.670993 | 0.247191 |
| Tchelet GWAS | rs1757545 | 2 | 76624220 | AC078940.2 | 0.70994 | 0.900621 | 0.30303 | 0.325581 | 0.017315 | 0.483124 | 0.301136 |
| Grossman 2007 | rs2275235 | 1 | 1.51E+08 | CTSS | 0.712828 | 0.893785 | 0.318182 | 0.343023 | 0.187836 | 1.540881 | 0.397727 |
| Tchelet GWAS | rs1159962 | 10 | 1.11E+08 | RP11-655H13.1 | 0.719551 | 0.853107 | 0.106061 | 0.122093 | 1 | 1.0125 | 0.101124 |
| Tchelet GWAS | rs2521644 | 7 | 24427969 | NPY | 0.726947 | 1.096078 | 0.44697 | 0.424419 | 0.887361 | 1.063973 | 0.44382 |
| Grossman 2007 | rs1129055 | 3 | 1.22E+08 | CD86 | 0.79101 | 1.073858 | 0.257576 | 0.244186 | 0.227117 | 0.675259 | 0.297753 |
| Tchelet GWAS | rs6097801 | 20 | 52767434 | CYP24A1 | 0.869321 | 0.928421 | 0.136364 | 0.145349 | 0.002983 | 0.307916 | 0.089388 |
| Tchelet GWAS | rs1095035 | 7 | 1800967 | AC074389.1 | 0.903004 | 0.957627 | 0.333333 | 0.343023 | 0.153622 | 1.650794 | 0.292135 |
| Tchelet GWAS | rs1161713 | 13 | 30590793 | RP11-629E24.2 | 1 | 0.97561 | 0.068182 | 0.069767 | 0.006286 | 0.154286 | 0.016854 |
| Tchelet GWAS | rs2177073 | 18 | 32054724 | DTNA | 1 | 0.940439 | 0.121212 | 0.127907 | 0.122399 | 0.510352 | 0.095506 |
| Tchelet GWAS | rs4343256 | 15 | 91198415 | CRTC3 | 1 | 1.134 | 0.05303 | 0.047059 | 0.065025 | 0.403439 | 0.05618 |
| Tchelet GWAS | rs4344916 | 2 | 35597319 | AC083939.1 | 1 | 1.011611 | 0.310606 | 0.30814 | 0.063797 | 0.563533 | 0.261364 |
| Tchelet GWAS | rs4369324 | 10 | 1.11E+08 | RP11-655H13.2 | 1 | 1.027289 | 0.219697 | 0.215116 | 0.364915 | 1.468531 | 0.196629 |
| Tchelet GWAS | rs9944913 | 18 | 31926438 | NOL4 | 1 | 1.007905 | 0.128788 | 0.127907 | 0.357373 | 0.66941 | 0.089888 |

TABLE 18-continued

Allelic Model, Extreme Response Definition, Candidate Variants (Gala, Forte, and Combined cohorts)

| Source | FORTE Allele Freq. (Controls) | Fisher's Exact P | Odds Ratio (Minor Allele) | Allele Freq. (Cases) | Allele Freq. (Controls) | COMBINED | | | | | |
|---|---|---|---|---|---|---|---|---|---|---|---|
| | | | | | | DD (Cases) | DD (Controls) | Dd (Cases) | Dd (Controls) | dd (Cases) | dd (Controls) |
| Tchelet GWAS | 0.328571 | 0.008221 | 0.582539 | 0.190323 | 0.2875 | 6 | 9 | 47 | 51 | 102 | 60 |
| Tchelet GWAS | 0.328571 | 0.008266 | 0.577575 | 0.190323 | 0.289256 | 6 | 9 | 47 | 52 | 102 | 60 |
| Tchelet GWAS | 0.285714 | 0.003985 | 0.496104 | 0.112903 | 0.204167 | 3 | 6 | 29 | 37 | 123 | 77 |
| Tchelet GWAS | 0.385714 | 0.601035 | 0.899676 | 0.4 | 0.42562 | 28 | 17 | 68 | 69 | 59 | 35 |
| Tchelet GWAS | 0.142857 | 0.006355 | 0.328904 | 0.029032 | 0.083333 | 0 | 1 | 9 | 18 | 146 | 101 |
| Tsareva 2011 | 0.314286 | 0.378507 | 1.171861 | 0.396774 | 0.359504 | 26 | 18 | 71 | 51 | 58 | 52 |
| Comi | 0.028571 | 0.277651 | 1.604167 | 0.070968 | 0.045455 | 0 | 1 | 22 | 9 | 133 | 111 |
| Grossman 2007 | 0.157143 | 0.819741 | 1.073622 | 0.175325 | 0.165289 | 5 | 2 | 44 | 36 | 105 | 83 |
| Tchelet GWAS | 0.271429 | 1 | 1.016072 | 0.325806 | 0.322314 | 15 | 11 | 71 | 56 | 69 | 54 |
| Tchelet GWAS | 0.585714 | 0.392171 | 0.861538 | 0.5 | 0.53719 | 39 | 32 | 77 | 66 | 39 | 23 |
| Tchelet GWAS | 0.1 | 1 | 1.016197 | 0.083871 | 0.082645 | 2 | 3 | 22 | 14 | 131 | 104 |
| Tsareva 2011 | 0.114286 | 0.384855 | 0.797347 | 0.125806 | 0.152893 | 6 | 4 | 27 | 29 | 122 | 88 |
| Tchelet GWAS | 0.228571 | 0.832981 | 0.955227 | 0.203226 | 0.210744 | 4 | 7 | 55 | 37 | 96 | 77 |
| Tchelet GWAS | 0.114286 | 0.056786 | 1.522885 | 0.237013 | 0.169421 | 7 | 6 | 59 | 29 | 88 | 86 |
| Grossman 2007 | 0.2 | 1 | 1.022602 | 0.151613 | 0.14876 | 6 | 2 | 35 | 32 | 114 | 87 |
| Comi | 0.328571 | 0.708106 | 0.928747 | 0.290323 | 0.305785 | 18 | 9 | 54 | 56 | 83 | 56 |
| Tsareva 2011 | 0.228571 | 0.83943 | 0.942433 | 0.229032 | 0.239669 | 8 | 7 | 55 | 44 | 92 | 70 |
| Tchelet GWAS | 0.528571 | 0.072395 | 0.704348 | 0.258065 | 0.330579 | 9 | 16 | 62 | 48 | 84 | 57 |
| Grossman 2007 | 0.357143 | 0.860062 | 1.047893 | 0.395425 | 0.384298 | 25 | 16 | 71 | 61 | 57 | 44 |
| Tchelet GWAS | 0.285714 | 0.009585 | 0.547566 | 0.13871 | 0.227273 | 2 | 7 | 39 | 41 | 114 | 73 |
| Comi | 0.371429 | 0.53794 | 1.235619 | 0.090323 | 0.07438 | 1 | 3 | 26 | 12 | 128 | 106 |
| Comi | 0.328571 | 0.568262 | 0.895176 | 0.270968 | 0.293388 | 14 | 9 | 56 | 53 | 85 | 59 |
| Tchelet GWAS | 0.471429 | 0.120633 | 0.743611 | 0.301948 | 0.367769 | 15 | 17 | 63 | 55 | 76 | 49 |
| Grossman 2007 | 0.3 | 0.471074 | 1.157143 | 0.363636 | 0.330579 | 21 | 11 | 70 | 58 | 63 | 52 |
| Tchelet GWAS | 0.1 | 0.680358 | 0.879753 | 0.103226 | 0.115702 | 2 | 1 | 28 | 26 | 125 | 94 |
| Tchelet GWAS | 0.423571 | 0.666085 | 1.08275 | 0.445161 | 0.42562 | 28 | 22 | 82 | 59 | 45 | 40 |
| Grossman 2007 | 0.385714 | 0.924318 | 0.978163 | 0.280645 | 0.285124 | 12 | 8 | 63 | 53 | 80 | 60 |
| Tchelet GWAS | 0.42857 | 0.034456 | 0.586611 | 0.109677 | 0.173554 | 7 | 3 | 20 | 36 | 128 | 82 |
| Tchelet GWAS | 0.2 | 0.852865 | 1.038535 | 0.309677 | 0.301653 | 21 | 10 | 54 | 53 | 80 | 58 |
| Tchelet GWAS | 0.1 | 0.061019 | 0.472625 | 0.03871 | 0.078512 | 1 | 1 | 10 | 17 | 144 | 103 |
| Tchelet GWAS | 0.171429 | 0.238954 | 0.728817 | 0.106452 | 0.140496 | 2 | 3 | 29 | 28 | 124 | 90 |
| Tchelet GWAS | 0.128571 | 0.477974 | 0.761092 | 0.054839 | 0.070833 | 0 | 0 | 17 | 17 | 138 | 103 |
| Tchelet GWAS | 0.385714 | 0.226351 | 0.797172 | 0.282468 | 0.330579 | 19 | 11 | 49 | 58 | 86 | 52 |
| Tchelet GWAS | 0.142857 | 0.749071 | 1.079398 | 0.206452 | 0.194215 | 6 | 5 | 52 | 37 | 97 | 79 |
| Tchelet GWAS | 0.128571 | 0.503205 | 0.810877 | 0.106452 | 0.128099 | 0 | 2 | 33 | 27 | 122 | 92 |

TABLE 19

Genotypic Model, Extreme Response Definition, Candidate Variants (Gala, Forte, and Combined cohorts

| Source | Name | Ch | Gene | GALA Fisher's Exact P | FORTE Fisher's Exact P | COMBINED Fisher's Exact P | DD (Cases) | DD (Controls) | Dd (Cases) | Dd (Controls) | dd (Cases) | dd (Controls) |
|---|---|---|---|---|---|---|---|---|---|---|---|---|
| Comi | rs4890535 | 18 | SLC14A2 | 0.051225 | 1 | 0.130308 | 1 | 3 | 26 | 12 | 128 | 106 |
| Tchelet GWAS | rs1085360 | 18 | MEX3C | 0.060784 | 0.807531 | 0.09938 | 28 | 17 | 68 | 69 | 59 | 35 |
| Comi | rs1558896 | 7 | TAC1 | 0.108585 | 0.384407 | 0.129289 | 18 | 9 | 54 | 56 | 83 | 56 |
| Comi | rs269976 | 18 | SLC14A2 | 0.131319 | 0.347726 | 0.068507 | 0 | 1 | 22 | 9 | 133 | 111 |
| Grossman 2007 | rs2001791 | 3 | CD86 | 0.163623 | 0.597721 | 0.466835 | 6 | 2 | 35 | 32 | 114 | 87 |
| Tchelet GWAS | rs 947603 | 10 | CEP55 | 0.175968 | 0.018504 | 0.03493 | 7 | 6 | 59 | 29 | 88 | 86 |
| Tchelet GWAS | rs3135391 | 6 | HLA-DRB1 | 0.191442 | 0.061953 | 0.019534 | 6 | 9 | 47 | 52 | 102 | 60 |
| Tchelet GWAS | rs1225688 | 10 | CYP26C1 | 0.211437 | 0.112697 | 1 | 15 | 11 | 71 | 56 | 69 | 54 |
| Tchelet GWAS | rs3135388 | 6 | HLA-DRB1 | 0.229549 | 0.061953 | 0.023584 | 6 | 9 | 47 | 51 | 102 | 60 |
| Tchelet GWAS | rs1098808 | 9 | SET | 0.270151 | 0.003153 | 0.009817 | 0 | 1 | 9 | 18 | 146 | 101 |
| Tchelet GWAS | rs1095035 | 7 | AC074389.1 | 0.290815 | 0.113948 | 0.194248 | 21 | 10 | 54 | 53 | 80 | 58 |
| Tchelet GWAS | rs1159962 | 10 | RP11-655H13.1 | 0.319145 | 0.620619 | 0.848936 | 2 | 1 | 28 | 26 | 125 | 94 |
| Tsareva 2011 | rs231775 | 2 | CTLA4 | 0.323348 | 0.650864 | 0.641801 | 26 | 18 | 71 | 51 | 58 | 52 |
| Tchelet GWAS | rs2487896 | 10 | HPSE2 | 0.339368 | 0.00344 | 0.016573 | 3 | 6 | 29 | 37 | 123 | 77 |
| Tchelet GWAS | rs1007328 | 15 | AC012409.1 | 0.342331 | 0.160261 | 0.490428 | 39 | 32 | 77 | 66 | 39 | 23 |
| Tchelet GWAS | rs1093109 | 2 | AC074182.1 | 0.399287 | 0.574087 | 0.674319 | 2 | 3 | 22 | 14 | 131 | 104 |
| Tchelet GWAS | rs1573706 | 20 | PTPRT | 0.421405 | 0.00156 | 0.022921 | 2 | 7 | 39 | 41 | 114 | 73 |
| Tchelet GWAS | rs4148871 | 6 | TAP2 | 0.500007 | 0.725238 | 0.328473 | 4 | 7 | 55 | 37 | 96 | 77 |
| Comi | rs974060 | 7 | TAC1 | 0.511178 | 0.294494 | 0.443883 | 14 | 9 | 56 | 53 | 85 | 59 |
| Grossman 2007 | rs946685 | 1 | IL12RB2 | 0.545787 | 0.760198 | 0.755453 | 5 | 2 | 44 | 36 | 105 | 83 |
| Tchelet GWAS | rs2521644 | 7 | NPY | 0.549577 | 0.965073 | 0.759357 | 28 | 22 | 82 | 59 | 45 | 40 |
| Tchelet GWAS | rs6097801 | 20 | CYP24A1 | 0.583023 | 0.000194 | 0.001719 | 7 | 3 | 20 | 36 | 128 | 82 |
| Tsareva 2011 | rs1800629 | 6 | TNF | 0.5881 | 0.209578 | 0.420205 | 6 | 4 | 27 | 29 | 122 | 88 |
| Tchelet GWAS | rs4344916 | 2 | AC083939.1 | 0.607658 | 0.028396 | 0.025091 | 19 | 11 | 49 | 58 | 86 | 52 |
| Tchelet GWAS | rs1777193 | 8 | AC016885.1 | 0.737475 | 2.95E−05 | 0.096795 | 9 | 16 | 62 | 48 | 48 | 57 |
| Tsareva 2011 | rs6897932 | 5 | IL7Ra | 0.803461 | 0.772128 | 0.938197 | 8 | 7 | 55 | 44 | 92 | 70 |
| Grossman 2007 | rs1415148 | 1 | CTSS | 0.848296 | 0.504217 | 0.708954 | 25 | 16 | 71 | 61 | 57 | 44 |
| Grossman 2007 | rs2275235 | 1 | CTSS | 0.886713 | 0.22299 | 0.515363 | 21 | 11 | 70 | 58 | 63 | 52 |
| Tchelet GWAS | rs1757545 | 2 | AC078940.2 | 0.911321 | 0.066946 | 0.276505 | 15 | 17 | 63 | 55 | 76 | 49 |
| Tchelet GWAS | rs9944913 | 18 | NOL4 | 0.914654 | 0.312493 | 0.314049 | 0 | 2 | 33 | 27 | 122 | 92 |
| Tchelet GWAS | rs4369324 | 10 | RP11-655H13.2 | 0.953211 | 0.311301 | 0.88185 | 6 | 5 | 52 | 37 | 97 | 79 |
| Tchelet GWAS | rs1161713 | 13 | RP11-629E24.2 | 1 | 0.005284 | 0.060266 | 1 | 1 | 10 | 17 | 144 | 103 |
| Tchelet GWAS | rs4343256 | 15 | CRTC3 | 1 | 0.054967 | 0.463072 | 0 | 0 | 17 | 17 | 138 | 103 |
| Tchelet GWAS | rs2177073 | 18 | DTNA | 1 | 0.177174 | 0.470055 | 2 | 3 | 29 | 28 | 124 | 90 |
| Grossman 2007 | rs1129055 | 3 | CD86 | 1 | 0.36822 | 0.877801 | 12 | 8 | 63 | 53 | 80 | 60 |

Example 10 Analysis for Extreme Responders vs. Extreme Non-Responders Part 2—Analysis of Candidate Genes (30)

The second analysis was analyzed to a selected set of genetic variants in 30 priority candidate genes (4,012 variants). Power (80%) to identify significant genetic associations with an odds ratio >7, for variants with an allele frequency greater than 10%.

Results for Extreme Response Definition, Analysis of Candidate Genes (30) Selected a priori for Additive, Allelic and Genotypic models are presented in tables 20-22, respectively. No variants replicated in both cohorts (P<0.05). Less stringent (P<0.10+P<0.05) values were used.

In some embodiments genetic markers presented in Tables 20-22 are identified as predictive of response to glatiramer acetate if the p-value for the GALA cohort is less than about 0.10, less than about 0.09, less than about 0.08, less than about 0.07 or less than about 0.02.

In some embodiments genetic markers presented in Tables 20-22 are identified as predictive of response to glatiramer acetate if the p-value for the FORTE cohort is less than about 0.05, less than about 0.02, less than about 0.01 or less than about 0.005.

In some embodiments genetic markers presented in Tables 20-22 are identified as predictive of response to glatiramer acetate if the p-value for the Combined cohort is less than about 0.05, less than about 0.01 or less than about 0.005.

TABLE 20

Additive Model, Extreme Response Definition Analysis of Candidate Genes (30) (Gala, Forte, and Combined cohorts)

| | | | GALA | | FORTE | | COMBINED | | | | | | | |
|---|---|---|---|---|---|---|---|---|---|---|---|---|---|---|
| Columns | Gene | Chr | Armitage P | Regression Odds Ratio | Armitage P | Regression Odds Ratio | Armitage P | Regression Odds Ratio | DD (Case | DD (Controls) | Dd (Case | Dd (Controls) | dd (Case | dd (Controls) |
| rs1894408 | HLA-DOB/TAP2 | 6 | 0.089 | 1.50 | 0.003 | 2.85 | 0.0012 | 1.86 | 22 | 10 | 81 | 47 | 50 | 64 |
| rs1894407 | HLA-DOB/TAP2 | 6 | 0.082 | 1.52 | 0.008 | 2.50 | 0.0024 | 1.78 | 21 | 10 | 82 | 48 | 51 | 63 |
| rs1894406 | HLA-DOB/TAP2 | 6 | 0.072 | 1.54 | 0.009 | 2.52 | 0.0037 | 1.74 | 20 | 9 | 78 | 46 | 57 | 66 |
| rs12454490 | SLC14A2 | 18 | 0.082 | 1.88 | 0.033 | 3.66 | 0.0119 | 2.10 | 2 | 1 | 40 | 16 | 113 | 104 |

TABLE 21

Allelic Model, Extreme Response Definition, Analysis of Candidate Genes (30) (Gala, Forte, and Combined cohorts)

| | | | GALA | | | | FORTE | | | |
|---|---|---|---|---|---|---|---|---|---|---|
| Columns | Chr | Position | Fisher's Exact P | Odds Ratio (Minor Allele) | Allele Freq. (Cases) | Allele Freq. (Controls) | Fisher's Exact P | Odds Ratio (Minor Allele) | Allele Freq. (Cases) | Allele Freq. (Controls) |
| rs1894406 | 6 | 32787056 | 0.066 | 1.58 | 39% | 28% | 0.016 | 2.21 | 38% | 21% |
| rs17884784 | 4 | 123541500 | 0.082 | 4.05 | 5% | 1% | 0.024 | 0.09 | 1% | 6% |
| rs1894408 | 6 | 32786833 | 0.087 | 1.53 | 39% | 30% | 0.005 | 2.45 | 42% | 23% |
| rs1894407 | 6 | 32787036 | 0.087 | 1.54 | 39% | 30% | 0.018 | 2.16 | 41% | 24% |

| | COMBINED | | | | | | | | |
|---|---|---|---|---|---|---|---|---|---|
| Columns | Fisher's Exact P | Odds Ratio (Minor Allele) | Allele Freq. (Cases) | Allele Freq. (Controls) | DD (Cases) | DD (Controls) | Dd (Cases) | Dd (Controls) | dd (Cases) | dd (Controls) |
| rs1894406 | 0.005 | 1.71 | 38% | 26% | 20 | 9 | 78 | 46 | 57 | 66 |
| rs17884784 | 1.000 | 0.91 | 2% | 2% | 0 | 0 | 7 | 6 | 147 | 115 |
| rs1894408 | 0.002 | 1.80 | 41% | 28% | 22 | 10 | 81 | 47 | 50 | 64 |
| rs1894407 | 0.003 | 1.72 | 40% | 28% | 21 | 10 | 82 | 48 | 51 | 63 |

TABLE 22

Genotypic Model, Extreme Response Definition, Analysis of
Candidate Genes (30) (Gala, Forte, and Combined cohorts

| Columns | Gene | Chr | Position | GALA Fisher's Exact P | GALA Allele Freq. (Cases) | GALA Allele Freq. (Controls) | FORTE Fisher's Exact P | FORTE Allele Freq. (Cases) | FORTE Allele Freq. (Controls) |
|---|---|---|---|---|---|---|---|---|---|
| kgp11964392 | | 18 | 74768870 | 0.0135 | 45% | 49% | 0.0288 | 53% | 44% |
| kgp776593 | | 11 | 1.21E+08 | 0.0711 | 11% | 6% | 0.0391 | 8% | 1% |
| kgp8702370 | | 3 | 1.32E+08 | 0.0747 | 17% | 11% | 0.0024 | 19% | 3% |
| rs1894407 | HLA-DOB/TAP2 | 6 | 32787036 | 0.0923 | 39% | 30% | 0.0155 | 41% | 24% |

| Columns | COMBINED Fisher's Exact P | Allele Freq. (Cases) | Allele Freq. (Controls) | DD (Cases) | DD (Controls) | Dd (Cases) | Dd (Controls) | dd (Cases) | dd (Controls) |
|---|---|---|---|---|---|---|---|---|---|
| kgp11964392 | 0.0050 | 49% | 48% | 30 | 34 | 91 | 48 | 32 | 39 |
| kgp776593 | 0.0074 | 10% | 5% | 0 | 1 | 30 | 10 | 125 | 110 |
| kgp8702370 | 0.0033 | 18% | 9% | 7 | 0 | 43 | 21 | 105 | 99 |
| rs1894407 | 0.0063 | 28% | 28% | 21 | 10 | 82 | 48 | 51 | 63 |

Example 11 Analysis for Extreme Responders vs. Extreme Non-Responders Part 3—Analysis of Candidate Genes (180)

The third analysis was analyzed to a selected set of genetic variants in 180 priority candidate genes (25,461 variants). Power (80%) to identify significant genetic associations with an odds ratio >7, for variants with an allele frequency greater than 10%.

Results for Extreme Response Definition, Analysis of Candidate Genes (180) Selected a priori for Additive, Allelic and Genotypic models are presented in tables 23-25, respectively.

In some embodiments genetic markers presented in Tables 23-25 are identified as predictive of response to glatiramer acetate if the p-value for the GALA cohort is less than about 0.05, less than about 0.01, less than about 0.005, less than about 0.001, less than about 0.0005 or less than about $10^{-4}$.

In some embodiments genetic markers presented in Tables 23-25 are identified as predictive of response to glatiramer acetate if the p-value for the FORTE cohort is less than about 0.05, less than about 0.01, less than about 0.005 or less than about 0.001.

In some embodiments genetic markers presented in Tables 23-25 are identified as predictive of response to glatiramer acetate if the p-value for the Combined cohort is less than about 0.05, less than about 0.01, less than about 0.005, less than about 0.001, less than about 0.0005 or less than about $10^{-4}$.

TABLE 23

Additive Model, Extreme Response Definition Analysis of Candidate Genes (180) (Gala, Forte, and Combined cohorts)

| Names | Ch | Gene | Function | GALA Armitage P-value | GALA Odds Ratio | GALA Allele Freq. (Resp | GALA Allele Freq. (Non-Resp | FORTE Armitage P-value | FORTE Odds Ratio | FORTE Allele Freq (Resp | FORTE Allele Freq. (Non-Resp |
|---|---|---|---|---|---|---|---|---|---|---|---|
| rs6110157 | 20 | MACROD2 | intron | 0.022 | 0.53 | 22% | 33% | 0.0078 | 0.45 | 18% | 34% |
| kgp4011779 | 10 | HPSE2 | intron | 0.025 | 0.25 | 2% | 8% | 0.023 | ? | 0% | 3% |
| kgp3490814 | 13 | ALOX5AP | intron | 0.029 | 0.60 | 39% | 52% | 0.00086 | 0.37 | 43% | 67% |
| rs10162089 | 13 | ALOX5AP | intron | 0.006 | 1.93 | 56% | 40% | 0.0053 | 2.32 | 46% | 26% |
| rs3885907 | 13 | ALOX5AP | intron | 0.016 | 1.73 | 52% | 38% | 0.0027 | 2.56 | 46% | 24% |
| rs17238927 | 13 | ALOX5AP | intron | 0.042 | 0.15 | 1% | 5% | 0.023 | ? | 0% | 3% |
| rs9671124 | 13 | ALOX5AP | intron | 0.022 | 1.69 | 56% | 42% | 0.0020 | 2.57 | 49% | 27% |
| rs4769060 | 13 | ALOX5AP | intron | 0.030 | 1.69 | 50% | 38% | 0.0037 | 2.43 | 47% | 26% |
| rs4075692 | 13 | ALOX5AP | intron | 0.022 | 1.69 | 56% | 42% | 0.0023 | 2.55 | 49% | 27% |
| rs11147439 | 13 | ALOX5AP | intron | 0.018 | 0.57 | 36% | 50% | 0.0089 | 0.48 | 42% | 61% |
| kgp3276689 | 10 | HPSE2 | intron | 0.044 | 1.90 | 19% | 11% | 0.036 | 2.48 | 21% | 10% |
| kgp304921 | 20 | MACROD2 | intron | 0.042 | 0.34 | 3% | 10% | 0.027 | 0.29 | 3% | 10% |
| rs3803277 | 13 | ALOX5AP | intron | 0.016 | 0.57 | 37% | 51% | 0.012 | 0.49 | 43% | 61% |
| kgp5440506 | 13 | ALOX5AP | intron | 0.017 | 0.57 | 36% | 50% | 0.011 | 0.49 | 43% | 62% |
| rs9671182 | 13 | ALOX5AP | intron | 0.019 | 0.57 | 37% | 51% | 0.014 | 0.50 | 43% | 61% |
| rs4254166 | 13 | ALOX5AP | intron | 0.025 | 0.59 | 37% | 50% | 0.011 | 0.49 | 43% | 61% |
| rs4356336 | 13 | ALOX5AP | intron | 0.020 | 0.58 | 37% | 51% | 0.014 | 0.50 | 43% | 61% |
| rs11002051 | 10 | KCNMA1 | intron | 0.015 | 0.29 | 4% | 11% | 0.028 | 0.38 | 7% | 16% |
| rs10278591 | 7 | MAD1L1 | intron | 0.016 | 1.95 | 30% | 19% | 0.043 | 2.15 | 26% | 14% |
| rs4360791 | 13 | ALOX5AP | intron | 0.018 | 0.57 | 38% | 52% | 0.021 | 0.53 | 44% | 61% |
| kgp2715873 | 13 | ALOX5AP | intron | 0.025 | 0.59 | 37% | 50% | 0.014 | 0.50 | 43% | 61% |
| rs9315047 | 13 | ALOX5AP | intron | 0.025 | 0.59 | 37% | 50% | 0.014 | 0.50 | 43% | 61% |
| rs9670531 | 13 | ALOX5AP | intron | 0.025 | 0.59 | 37% | 50% | 0.014 | 0.50 | 43% | 61% |
| rs4584668 | 13 | ALOX5AP | intron | 0.026 | 0.59 | 37% | 50% | 0.014 | 0.50 | 43% | 61% |

TABLE 23-continued

Additive Model, Extreme Response Definition Analysis of Candidate Genes (180) (Gala, Forte, and Combined cohorts)

| | | | | | | | | | | | |
|---|---|---|---|---|---|---|---|---|---|---|---|
| rs9508832 | 13 | ALOX5AP | intron | 0.022 | 1.73 | 49% | 36% | 0.011 | 2.21 | 41% | 23% |
| kgp7117398 | 7 | MAD1L1 | intron | 0.023 | 1.88 | 30% | 19% | 0.043 | 2.15 | 26% | 14% |
| kgp4370912 | 10 | KCNMA1 | intron | 0.032 | 0.33 | 4% | 10% | 0.028 | 0.38 | 7% | 16% |

| | COMBINED | | | | | | | | |
|---|---|---|---|---|---|---|---|---|---|
| Names | Armitage P-value | Odds Ratio | Allele Freq. (Resp | Allele Freq. (Non-Resp | DD (Cases) | DD (Control) | Dd (Cases) | Dd (Control) | dd (Cases) | dd (Control) |
| rs6110157 | 0.00018 | 0.47 | 81% | 67% | 6 | 13 | 47 | 55 | 100 | 53 |
| kgp4011779 | 0.00025 | 0.13 | 99% | 93% | 0 | 0 | 3 | 16 | 151 | 105 |
| kgp3490814 | 0.00061 | 0.55 | 58% | 43% | 28 | 39 | 73 | 59 | 54 | 23 |
| rs10162089 | 0.00094 | 1.78 | 50% | 64% | 43 | 14 | 69 | 57 | 42 | 48 |
| rs3885907 | 0.00097 | 1.77 | 52% | 66% | 41 | 13 | 68 | 56 | 46 | 52 |
| rs17238927 | 0.0013 | 0.07 | 100% | 96% | 0 | 0 | 1 | 10 | 154 | 110 |
| rs9671124 | 0.0013 | 1.74 | 48% | 62% | 46 | 17 | 70 | 58 | 39 | 46 |
| rs4769060 | 0.0013 | 1.77 | 52% | 66% | 38 | 12 | 73 | 59 | 44 | 50 |
| rs4075692 | 0.0016 | 1.72 | 48% | 62% | 45 | 17 | 71 | 58 | 39 | 46 |
| rs11147439 | 0.0019 | 0.59 | 60% | 47% | 28 | 33 | 67 | 63 | 60 | 25 |
| kgp3276689 | 0.0020 | 2.16 | 80% | 90% | 9 | 0 | 45 | 25 | 100 | 95 |
| kgp304921 | 0.0021 | 0.32 | 97% | 90% | 1 | 2 | 7 | 19 | 144 | 98 |
| rs3803277 | 0.0021 | 0.59 | 59% | 46% | 28 | 35 | 70 | 61 | 57 | 25 |
| kgp5440506 | 0.0025 | 0.60 | 60% | 47% | 29 | 33 | 65 | 62 | 60 | 25 |
| rs9671182 | 0.0028 | 0.60 | 59% | 46% | 29 | 33 | 68 | 63 | 58 | 24 |
| rs4254166 | 0.0029 | 0.60 | 60% | 47% | 28 | 33 | 69 | 63 | 58 | 25 |
| rs4356336 | 0.0029 | 0.60 | 59% | 46% | 29 | 34 | 68 | 62 | 58 | 25 |
| rs11002051 | 0.0031 | 0.39 | 95% | 88% | 0 | 1 | 17 | 28 | 138 | 92 |
| rs10278591 | 0.0032 | 1.88 | 72% | 83% | 13 | 2 | 61 | 38 | 81 | 81 |
| rs4360791 | 0.0034 | 0.61 | 58% | 45% | 30 | 36 | 69 | 60 | 56 | 25 |
| kgp2715873 | 0.0038 | 0.61 | 59% | 47% | 29 | 33 | 68 | 63 | 58 | 25 |
| rs9315047 | 0.0038 | 0.61 | 59% | 47% | 29 | 33 | 68 | 63 | 58 | 25 |
| rs9670531 | 0.0038 | 0.61 | 59% | 47% | 29 | 33 | 68 | 63 | 58 | 25 |
| rs4584668 | 0.0039 | 0.61 | 59% | 47% | 29 | 33 | 68 | 62 | 58 | 25 |
| rs9508832 | 0.0043 | 1.65 | 55% | 68% | 35 | 11 | 68 | 56 | 52 | 54 |
| kgp7117398 | 0.0045 | 1.83 | 72% | 82% | 13 | 2 | 61 | 39 | 81 | 80 |
| kgp4370912 | 0.0074 | 0.42 | 95% | 88% | 0 | 1 | 17 | 26 | 138 | 93 |

TABLE 24

Allelic Model, Extreme Response Definition, Analysis of Candidate Genes (180) (Gala, Forte, and Combined cohorts)

| | | | GALA | | | | FORTE | | | |
|---|---|---|---|---|---|---|---|---|---|---|
| Columns | Chr | Position | Fisher's Exact P | Odds Ratio (Minor Allele) | Allele Freq. (Cases) | Allele Freq. (Controls) | Fisher's Exact P | Odds Ratio (Minor Allele) | Allele Freq. (Cases) | Allele Freq. (Controls) |
| rs6110157 | 20 | 14055947 | 0.0285 | 0.55 | 22% | 33% | 0.006 | 0.41 | 18% | 34% |
| rs9341808 | 6 | 80953257 | 0.0260 | 2.11 | 23% | 13% | 0.003 | 4.34 | 24% | 7% |
| kgp3496814 | 13 | 31336379 | 0.0279 | 0.59 | 39% | 52% | 0.001 | 0.37 | 43% | 67% |
| rs3885907 | 13 | 31314455 | 0.0143 | 1.80 | 52% | 38% | 0.002 | 2.60 | 46% | 24% |
| rs10162089 | 13 | 31316738 | 0.0073 | 1.92 | 56% | 40% | 0.004 | 2.46 | 46% | 26% |
| rs9671124 | 13 | 31324253 | 0.0208 | 1.73 | 56% | 42% | 0.002 | 2.62 | 49% | 27% |
| rs4769060 | 13 | 31337877 | 0.0360 | 1.65 | 50% | 38% | 0.003 | 2.52 | 47% | 26% |
| rs4075692 | 13 | 31323342 | 0.0208 | 1.73 | 56% | 42% | 0.003 | 2.57 | 49% | 27% |
| kgp304921 | 20 | 14017077 | 0.0351 | 0.31 | 3% | 10% | 0.042 | 0.26 | 3% | 10% |
| rs11147439 | 13 | 31325643 | 0.0199 | 0.57 | 36% | 50% | 0.007 | 0.46 | 42% | 61% |
| kgp3276689 | 10 | 100396003 | 0.0453 | 2.01 | 19% | 11% | 0.044 | 2.44 | 21% | 10% |
| kgp5440506 | 13 | 31320543 | 0.0193 | 0.57 | 36% | 50% | 0.010 | 0.46 | 43% | 62% |
| rs3803277 | 13 | 31318308 | 0.0199 | 0.56 | 37% | 51% | 0.011 | 0.48 | 43% | 61% |
| rs9671182 | 13 | 31321138 | 0.0203 | 0.58 | 37% | 51% | 0.011 | 0.48 | 43% | 61% |
| rs4356336 | 13 | 31319546 | 0.0204 | 0.58 | 37% | 51% | 0.011 | 0.48 | 43% | 61% |
| rs4254166 | 13 | 31322949 | 0.0273 | 0.59 | 37% | 50% | 0.011 | 0.47 | 43% | 61% |
| rs4360791 | 13 | 31318020 | 0.0201 | 0.57 | 38% | 52% | 0.017 | 0.50 | 44% | 61% |
| rs10278591 | 7 | 1921362 | 0.0207 | 1.90 | 30% | 19% | 0.045 | 2.15 | 26% | 14% |
| rs4584668 | 13 | 31319553 | 0.0271 | 0.59 | 37% | 50% | 0.011 | 0.48 | 43% | 61% |
| kgp2715873 | 13 | 31320249 | 0.0273 | 0.59 | 37% | 50% | 0.011 | 0.48 | 43% | 61% |
| rs9670531 | 13 | 31321069 | 0.0273 | 0.59 | 37% | 50% | 0.011 | 0.48 | 43% | 61% |
| rs9315047 | 13 | 31321289 | 0.0273 | 0.59 | 37% | 50% | 0.011 | 0.48 | 43% | 61% |
| rs9508832 | 13 | 31314264 | 0.0257 | 1.72 | 49% | 36% | 0.008 | 2.35 | 41% | 23% |
| kgp7117398 | 7 | 1915282 | 0.0301 | 1.83 | 30% | 19% | 0.045 | 2.15 | 26% | 14% |

TABLE 24-continued

Allelic Model, Extreme Response Definition, Analysis of Candidate Genes (180) (Gala, Forte, and Combined cohorts)

| | | | | | | | | | | |
|---|---|---|---|---|---|---|---|---|---|---|
| rs11002051 | 10 | 78921392 | 0.0300 | 0.32 | 4% | 11% | 0.048 | 0.39 | 7% | 16% |
| kgp4370912 | 10 | 78918297 | 0.0452 | 0.35 | 4% | 10% | 0.048 | 0.39 | 7% | 16% |

COMBINED

| Columns | Fisher's Exact P | Odds Ratio (Minor Allele) | Allele Freq. (Cases) | Allele Freq. (Controls) | DD (Cases) | DD (Controls) | Dd (Cases) | Dd (Controls) | dd (Cases) | dd (Controls) |
|---|---|---|---|---|---|---|---|---|---|---|
| rs6110157 | 0.00018 | 0.47 | 19% | 33% | 6 | 13 | 47 | 55 | 100 | 53 |
| rs9341808 | 0.00037 | 2.49 | 24% | 11% | 26 | 9 | 13 | 6 | 99 | 94 |
| kgp3496814 | 0.00058 | 0.55 | 42% | 57% | 28 | 39 | 73 | 59 | 54 | 23 |
| rs3885907 | 0.00070 | 1.83 | 48% | 34% | 41 | 13 | 68 | 56 | 46 | 52 |
| rs10162089 | 0.00070 | 1.82 | 50% | 36% | 43 | 14 | 69 | 57 | 42 | 48 |
| rs9671124 | 0.00106 | 1.78 | 52% | 38% | 46 | 17 | 70 | 58 | 39 | 46 |
| rs4769060 | 0.00130 | 1.77 | 48% | 34% | 38 | 12 | 73 | 59 | 44 | 50 |
| rs4075692 | 0.00143 | 1.76 | 52% | 38% | 45 | 17 | 71 | 58 | 39 | 46 |
| kgp304921 | 0.00145 | 0.29 | 3% | 10% | 1 | 2 | 7 | 19 | 144 | 98 |
| rs11147439 | 0.00148 | 0.58 | 40% | 53% | 28 | 33 | 67 | 63 | 60 | 25 |
| kgp3276689 | 0.00150 | 2.21 | 20% | 10% | 9 | 0 | 45 | 25 | 100 | 95 |
| kgp5440506 | 0.00190 | 0.58 | 40% | 53% | 29 | 33 | 65 | 62 | 60 | 25 |
| rs3803277 | 0.00195 | 0.58 | 41% | 54% | 28 | 35 | 70 | 61 | 57 | 25 |
| rs9671182 | 0.00255 | 0.59 | 41% | 54% | 29 | 33 | 68 | 63 | 58 | 24 |
| rs4356336 | 0.00260 | 0.59 | 41% | 54% | 29 | 34 | 68 | 62 | 58 | 25 |
| rs4254166 | 0.00261 | 0.59 | 40% | 53% | 28 | 33 | 69 | 63 | 58 | 25 |
| rs4360791 | 0.00268 | 0.59 | 42% | 55% | 30 | 36 | 69 | 60 | 56 | 25 |
| rs10278591 | 0.00329 | 1.86 | 28% | 17% | 13 | 2 | 61 | 38 | 81 | 81 |
| rs4584668 | 0.00339 | 0.60 | 41% | 53% | 29 | 33 | 68 | 62 | 58 | 25 |
| kgp2715873 | 0.00345 | 0.60 | 41% | 53% | 29 | 33 | 68 | 63 | 58 | 25 |
| rs9670531 | 0.00345 | 0.60 | 41% | 53% | 29 | 33 | 68 | 63 | 58 | 25 |
| rs9315047 | 0.00345 | 0.60 | 41% | 53% | 29 | 33 | 68 | 63 | 58 | 25 |
| rs9508832 | 0.00372 | 1.69 | 45% | 32% | 35 | 11 | 68 | 56 | 52 | 54 |
| kgp7117398 | 0.00471 | 1.81 | 28% | 18% | 13 | 2 | 61 | 39 | 81 | 80 |
| rs11002051 | 0.00526 | 0.41 | 5% | 12% | 0 | 1 | 17 | 28 | 138 | 92 |
| kgp4370912 | 0.01151 | 0.44 | 5% | 12% | 0 | 1 | 17 | 26 | 138 | 93 |

TABLE 25

Genotypic Model, Extreme Response Definition, Analysis of Candidate Genes (180) (Gala, Forte, and Combined cohorts)

| | | | GALA | | | FORTE | | | COMBINED |
|---|---|---|---|---|---|---|---|---|---|
| Columns | Chromosome | Position | Fisher's Exact P | Allele Freq. (Case) | Allele Freq. (Controls) | Fisher's Exact P | Allele Freq. (Cases) | Allele Freq. (Controls) | Fisher's Exact P |
| kgp17000984 | 6 | 32602425 | 0.434211 | 0.007576 | 0 | ? | 0 | 0 | 1 |
| kgp460147 | 6 | 32602518 | 0.022 | 19% | 12% | 0.022 | 22% | 16% | 0.00020 |
| kgp2535593 | 6 | 32602430 | 0.021 | 19% | 12% | 0.030 | 22% | 16% | 0.00037 |
| kgp6312967 | 6 | 32603488 | 0.021 | 19% | 12% | 0.030 | 22% | 16% | 0.00037 |
| kgp3668352 | 6 | 32603355 | 0.025 | 18% | 12% | 0.030 | 22% | 16% | 0.00039 |
| kgp3752234 | 6 | 32626451 | 0.047 | 19% | 12% | 0.004 | 22% | 13% | 0.00048 |
| rs6110157 | 20 | 14055947 | 0.042 | 22% | 33% | 0.013 | 18% | 34% | 0.00087 |
| rs10162089 | 13 | 31316738 | 0.023 | 56% | 40% | 0.006 | 46% | 26% | 0.0021 |
| rs11147439 | 13 | 31325643 | 0.041 | 36% | 50% | 0.029 | 42% | 61% | 0.0039 |
| kgp5440506 | 13 | 31320543 | 0.033 | 36% | 50% | 0.032 | 43% | 62% | 0.0046 |
| kgp11964392 | 18 | 74768870 | 0.013 | 45% | 49% | 0.029 | 53% | 44% | 0.0050 |
| kgp3293283 | 13 | 31340117 | 0.038 | 8% | 14% | 0.007 | 8% | 21% | 0.0053 |
| rs9671182 | 13 | 31321138 | 0.047 | 37% | 51% | 0.039 | 43% | 61% | 0.0055 |
| rs11002051 | 10 | 78921392 | 0.023 | 4% | 11% | 0.041 | 7% | 16% | 0.0063 |
| kgp5743538 | 13 | 31284424 | 0.013 | 9% | 16% | 0.040 | 13% | 26% | 0.0067 |
| rs4617690 | 13 | 31296938 | 0.013 | 9% | 16% | 0.040 | 13% | 26% | 0.0067 |
| rs3803277 | 13 | 31318308 | 0.050 | 37% | 51% | 0.042 | 43% | 61% | 0.0071 |
| kgp4370912 | 10 | 78918297 | 0.037 | 4% | 10% | 0.041 | 7% | 16% | 0.015 |
| rs17222919 | 13 | 31308329 | 0.026 | 11% | 17% | 0.028 | 14% | 29% | 0.017 |
| rs7088816 | 10 | 1.01E+08 | 0.040 | 16% | 21% | 0.027 | 14% | 29% | 0.027 |
| kgp11997323 | 10 | 1.01E+08 | 0.037 | 16% | 20% | 0.027 | 14% | 29% | 0.031 |
| rs2801405 | 10 | 1.01E+08 | 0.037 | 16% | 20% | 0.027 | 14% | 29% | 0.031 |
| kgp2044262 | 10 | 1.01E+08 | 0.040 | 16% | 21% | 0.044 | 15% | 29% | 0.033 |

TABLE 25-continued

Genotypic Model, Extreme Response Definition, Analysis of Candidate Genes (180) (Gala, Forte, and Combined cohorts)

| | | | COMBINED | | | | | |
|---|---|---|---|---|---|---|---|---|
| Columns | Allele Freq. (Cases | Allele Freq. (Contro | DD (Cases) | DD (Controls) | Dd (Cases) | Dd (Controls | dd (Cases) | dd (Controls |
| kgp17000984 | 0.003226 | 0 | 0 | 0 | 1 | 0 | 154 | 121 |
| kgp460147 | 21% | 13% | 1 | 4 | 63 | 24 | 91 | 93 |
| kgp2535593 | 21% | 13% | 1 | 4 | 62 | 24 | 92 | 92 |
| kgp6312967 | 21% | 13% | 1 | 4 | 62 | 24 | 92 | 92 |
| kgp3668352 | 20% | 13% | 1 | 4 | 61 | 24 | 92 | 93 |
| kgp3752234 | 21% | 13% | 1 | 3 | 62 | 24 | 92 | 93 |
| rs6110157 | 19% | 33% | 6 | 13 | 47 | 55 | 100 | 53 |
| rs10162089 | 50% | 36% | 43 | 14 | 69 | 57 | 42 | 48 |
| rs11147439 | 40% | 53% | 28 | 33 | 67 | 63 | 60 | 25 |
| kgp5440506 | 40% | 53% | 29 | 33 | 65 | 62 | 60 | 25 |
| kgp11964392 | 49% | 48% | 30 | 34 | 91 | 48 | 32 | 39 |
| kgp3293283 | 8% | 16% | 1 | 2 | 23 | 35 | 131 | 84 |
| rs9671182 | 41% | 54% | 29 | 33 | 68 | 63 | 58 | 24 |
| rs11002051 | 5% | 12% | 0 | 1 | 17 | 28 | 138 | 92 |
| kgp5743538 | 12% | 19% | 5 | 3 | 26 | 40 | 124 | 78 |
| rs4617690 | 12% | 19% | 5 | 3 | 26 | 40 | 124 | 78 |
| rs3803277 | 41% | 54% | 28 | 35 | 70 | 61 | 57 | 25 |
| kgp4370912 | 5% | 12% | 0 | 1 | 17 | 26 | 138 | 93 |
| rs17222919 | 13% | 21% | 4 | 4 | 31 | 41 | 120 | 74 |
| rs7088816 | 15% | 23% | 3 | 10 | 40 | 36 | 112 | 75 |
| kgp11997323 | 15% | 23% | 3 | 10 | 40 | 35 | 112 | 76 |
| rs2801405 | 15% | 23% | 3 | 10 | 40 | 35 | 112 | 76 |
| kgp2044262 | 15% | 23% | 3 | 10 | 41 | 36 | 109 | 75 |

Example 12 Analysis for Extreme Responders vs. Extreme Non-Responders Part 4—Genome Wide Analysis A full genome-wide analysis (4 M variants) was then conducted. Power (80%) with Bonferroni statistical correction to identify significant genetic associations with an odds ratio >11, for variants with an allele frequency greater than 10%. Approximately 4200 variants were selected for analysis in stage 2 (replication) (P<0.001).

Results for Extreme Response Definition, Genome Wide Analysis for Additive, Allelic and Genotypic models are presented in tables 23-25, respectively.

In some embodiments genetic markers presented in Tables 26-28 are identified as predictive of response to glatiramer acetate if the p-value for the GALA cohort is less than about 0.05, less than about 0.01, less than about 0.001, less than about 0.0005, less than about $10^{-4}$ or less than about $5*10^{-5}$.

In some embodiments genetic markers presented in Tables 26-28 are identified as predictive of response to glatiramer acetate if the p-value for the FORTE cohort is less than about 0.05, less than about 0.01, less than about 0.001, less than about 0.0005, less than about $10^{-4}$ or less than about $5*10^{-5}$.

In some embodiments genetic markers presented in Tables 26-28 are identified as predictive of response to glatiramer acetate if the p-value for the Combined cohort is less than about $10^{-4}$, less than about $5*10^{-5}$, less than about $10^{-5}$, less than about $5*10^{-6}$, less than about $10^{-6}$ or less than about $5*10^{-7}$.

Stage 4.

Placebo Cohort (n=102: 23 R vs. 79 NR)—The placebo cohort (GALA placebo) was analyzed to identify variants associated with placebo response/non-response.

Results for Standard Response Definition, Placebo Cohort Results for Additive, Allelic and Genotypic models are presented in tables 29-31, respectively.

TABLE 26

Additive Model, Extreme Response Definition, Genome Wide Analysis (Gala, Forte, and Combined cohorts)

| | | | | GALA | | | | FORTE | | | |
|---|---|---|---|---|---|---|---|---|---|---|---|
| Name | Ch | Gene | Location | Armitage P-value | Odds Ratio | Allele Freq. (Resp | Allele Freq. (Non-Resp | Armitage P-value | Odds Ratio | Allele Freq. (Resp | Allele Freq. (Non-Resp |
| kgp6214351 | 11 | UVRAG | INTRON | 2.4E-03 | 0.20 | 3% | 13% | 3.4E-05 | 0.12 | 3% | 17% |
| rs10026108 | 4 | ? | ? | 5.5E-05 | 3.06 | 62% | 41% | 8.3E-03 | 0.42 | 44% | 61% |
| kgp3984567 | 4 | ? | ? | 9.8E-05 | 0.34 | 38% | 59% | 6.9E-03 | 0.42 | 44% | 61% |
| kgp10948564 | 20 | ? | ? | 3.4E-03 | 0.41 | 20% | 33% | 4.4E-03 | 0.41 | 15% | 31% |
| kgp9627338 | 17 | RPH3AL | INTRON | 2.5E-03 | 0.36 | 8% | 22% | 2.3E-04 | 0.23 | 11% | 29% |
| kgp10788130 | 12 | GRIN2B | INTRON | 3.6E-03 | ? | 0% | 7% | 1.5E-04 | 0.08 | 1% | 11% |
| kgp7077322 | 4 | 41334 | INTRON | 1.8E-03 | 0.13 | 2% | 10% | 3.6E-04 | 0.16 | 3% | 16% |
| rs7348267 | 20 | ? | ? | 3.4E-03 | 0.41 | 20% | 33% | 8.9E-03 | 0.44 | 15% | 30% |
| rs6032205 | 20 | ? | ? | 4.4E-03 | 0.41 | 20% | 34% | 1.0E-02 | 0.44 | 15% | 30% |
| kgp11768533 | 11 | ? | ? | 1.1E-03 | 2.52 | 50% | 34% | 1.8E-03 | 2.75 | 47% | 26% |
| rs502530 | 6 | ? | ? | 2.1E-02 | 0.19 | 2% | 7% | 6.2E-05 | ? | 0% | 9% |
| rs1478682 | 11 | ? | ? | 7.5E-04 | 2.57 | 48% | 31% | 2.9E-03 | 2.60 | 45% | 24% |

TABLE 26-continued

Additive Model, Extreme Response Definition, Genome Wide Analysis (Gala, Forte, and Combined cohorts)

| | | | | | | | | | | | |
|---|---|---|---|---|---|---|---|---|---|---|---|
| kgp11467007 | 5 | STC2 | INTRON | 1.5E−03 | 0.17 | 2% | 13% | 1.2E−03 | 0.22 | 5% | 17% |
| rs196295 | 10 | BAG3 | EXON (Synon) | 3.6E−04 | 0.35 | 11% | 30% | 6.1E−03 | 0.41 | 18% | 34% |
| rs196343 | 10 | BAG3 | INTRON | 4.4E−04 | 0.36 | 11% | 30% | 5.3E−03 | 0.40 | 18% | 34% |
| rs7217872 | 17 | RPH3AL, RPH3A1 | INTRON | 3.7E−03 | 0.37 | 8% | 22% | 3.3E−04 | 0.24 | 11% | 29% |
| rs1079303 | 11 | ? | ? | 1.1E−03 | 2.52 | 50% | 34% | 2.3E−03 | 2.66 | 47% | 26% |
| rs10501082 | 11 | ? | ? | 1.1E−03 | 2.52 | 50% | 34% | 2.3E−03 | 2.66 | 47% | 26% |
| rs6718758 | 2 | ? | ? | 6.9E−03 | 0.53 | 31% | 47% | 9.2E−03 | 0.44 | 25% | 41% |
| rs7948420 | 11 | ? | ? | 6.0E−05 | 0.33 | 20% | 42% | 7.0E−03 | 0.46 | 33% | 51% |
| kgp18432055 | 9 | TMEM38B | UTR | 5.2E−04 | 3.51 | 20% | 6% | 8.3E−03 | 4.81 | 16% | 4% |
| rs10954782 | 8 | ? | ? | 3.1E−02 | 1.66 | 52% | 39% | 2.1E−03 | 0.40 | 37% | 59% |
| kgp9078300 | 2 | KLHL29 | INTRON | 1.8E−02 | 2.18 | 21% | 11% | 1.0E−03 | 4.88 | 25% | 7% |
| rs7928078 | 11 | ? | ? | 1.8E−03 | 2.44 | 49% | 34% | 2.3E−03 | 2.66 | 47% | 26% |
| kgp9884626 | 2 | ? | ? | 4.2E−03 | ? | 0% | 6% | 5.4E−03 | ? | 0% | 4% |
| rs9579566 | 13 | ? | ? | 1.4E−03 | ? | 0% | 8% | 7.8E−03 | 0.17 | 2% | 9% |

COMBINED

| Name | Armitage P-value | Odds Ratio | Allele Freq. (Resp) | Allele Freq. (Non-Resp) | DD (Cases) | DD (Controls) | Dd (Cases) | Dd (Controls) | dd (Cases) | dd (Controls) |
|---|---|---|---|---|---|---|---|---|---|---|
| kgp6214351 | 9.1E−07 | 0.17 | 3% | 14% | 0 | 1 | 9 | 32 | 145 | 88 |
| rs10026108 | 3.2E−06 | 0.39 | 42% | 60% | 21 | 36 | 87 | 72 | 47 | 12 |
| kgp3984567 | 4.4E−06 | 0.40 | 41% | 60% | 21 | 36 | 86 | 72 | 48 | 13 |
| kgp10948564 | 6.4E−06 | 0.37 | 17% | 33% | 4 | 8 | 44 | 63 | 107 | 50 |
| kgp9627338 | 8.2E−06 | 0.34 | 10% | 24% | 1 | 7 | 28 | 44 | 125 | 70 |
| kgp10788130 | 9.7E−06 | 0.07 | 1% | 8% | 0 | 1 | 2 | 18 | 153 | 102 |
| kgp7077322 | 1.0E−05 | 0.18 | 3% | 12% | 0 | 0 | 8 | 28 | 146 | 92 |
| rs7348267 | 1.1E−05 | 0.39 | 17% | 32% | 4 | 8 | 44 | 62 | 107 | 51 |
| rs6032205 | 1.4E−05 | 0.39 | 17% | 33% | 4 | 8 | 44 | 62 | 104 | 50 |
| kgp11768533 | 1.5E−05 | 2.37 | 48% | 31% | 32 | 5 | 85 | 66 | 37 | 50 |
| rs502530 | 1.6E−05 | 0.07 | 1% | 7% | 0 | 0 | 2 | 18 | 153 | 103 |
| rs1478682 | 1.7E−05 | 2.34 | 46% | 29% | 31 | 4 | 81 | 63 | 42 | 54 |
| kgp11467007 | 1.8E−05 | 0.24 | 4% | 14% | 0 | 2 | 12 | 30 | 143 | 89 |
| rs196295 | 1.9E−05 | 0.42 | 15% | 31% | 4 | 15 | 39 | 46 | 111 | 60 |
| rs196343 | 2.0E−05 | 0.42 | 15% | 31% | 4 | 15 | 39 | 45 | 112 | 60 |
| rs7217872 | 2.0E−05 | 0.36 | 10% | 24% | 1 | 7 | 29 | 43 | 125 | 71 |
| rs1079303 | 2.2E−05 | 2.33 | 48% | 31% | 32 | 5 | 85 | 66 | 38 | 50 |
| rs10501082 | 2.2E−05 | 2.33 | 48% | 31% | 32 | 5 | 85 | 66 | 38 | 50 |
| rs6718758 | 2.2E−05 | 0.46 | 28% | 45% | 10 | 27 | 66 | 56 | 79 | 38 |
| rs7948420 | 2.2E−05 | 0.46 | 27% | 45% | 12 | 24 | 61 | 61 | 82 | 36 |
| kgp18432055 | 2.3E−05 | 3.61 | 18% | 6% | 5 | 0 | 46 | 14 | 104 | 106 |
| rs10954782 | 2.4E−05 | 2.11 | 58% | 40% | 53 | 18 | 74 | 60 | 28 | 43 |
| kgp9078300 | 2.7E−05 | 2.95 | 23% | 10% | 6 | 1 | 60 | 22 | 88 | 98 |
| rs7928078 | 3.0E−05 | 2.30 | 48% | 31% | 31 | 5 | 85 | 66 | 38 | 50 |
| kgp9884626 | 3.1E−05 | ? | 0% | 5% | 0 | 0 | 0 | 13 | 154 | 108 |
| rs9579566 | 3.2E−05 | 0.11 | 1% | 8% | 0 | 1 | 3 | 18 | 152 | 102 |

TABLE 27

Additive Model, Extreme Response Definition, Genome Wide Analysis (Gala, Forte, and Combined cohorts)

| | | | | | | GALA | | | | FORTE | |
|---|---|---|---|---|---|---|---|---|---|---|---|
| Name | Chromosome | Position | Gene(s) | Mutation | Gene Locations(s) | Fisher's Extact | Odds Ratio (Minor Allele) | Allele Freq. (Case) | Allele Freq. (Controls) | Fisher's Extact | Odds Ratio (Minor Allele) |
| kgp621435 | 11 | 75546691 | UVRAG | Silent | INTRON | 3.08−03 | 0.21 | 3% | 13% | 2.29E−04 | 0.14 |
| rs759458 | 2 | 65245365 | SLC1A4, SL | Missense_ | EXON | 8.18−05 | 2.97 | 36% | 16% | 4.98E−02 | 1.93 |
| rs197523 | 21 | 19337261 | CHODL, CH | Silent, Silen | INTRON | 5.54−05 | 2.94 | 40% | 19% | 3.61E−02 | 1.99 |
| rs7844274 | 8 | 72411302 | ? | ? | ? | 1.13−03 | 0.42 | 21% | 39% | 1.57E−02 | 0.45 |
| kgp107881 | 12 | 13898682 | GRIN2B | Silent | INTRON | 1.51−03 | 0.00 | 0% | 7% | 7.96E−04 | 0.09 |
| rs5918137 | X | 41113080 | ? | ? | ? | 1.69−03 | 2.74 | 24% | 10% | 4.13E−02 | 2.05 |
| kgp191253 | 2 | 1.38E+08 | THSD7B | Silent | INTRON | 1.04−03 | 2.85 | 25% | 10% | 4.44E−03 | 3.45 |
| kgp962733 | 17 | 90155 | RPH3AL, R | Silent, Silen | INTRON | 1.46−03 | 0.32 | 8% | 22% | 1.58E−03 | 0.30 |
| rs196343 | 10 | 1.21E+08 | BAG3 | Silent | INTRON | 8.14−05 | 0.30 | 11% | 30% | 7.18E−03 | 0.42 |

TABLE 27-continued

Additive Model, Extreme Response Definition, Genome Wide Analysis (Gala, Forte, and Combined cohorts)

| | | | | | | | | | | | |
|---|---|---|---|---|---|---|---|---|---|---|---|
| rs196295 | | 10 | 1.21E+08 | BAG3 | Synonymo | EXON | 7.94−05 | 0.30 | 11% | 30% | 1.09E−02 | 0.43 |
| rs343087 kgp18432 | | 12 | 66260924 | HMGA2, H | Silent, Silen | INTRON, EX | 3.77−03 | 2.96 | 18% | 7% | 5.26E−03 | 3.70 |
| rs77251120 | | 9 | 1.09E+08 | TMEM38B | Silent | UTR | 3.76−04 | 3.72 | 20% | 6% | 1.08E−02 | 4.35 |
| rs7028906 | | 5 | 1.74E+08 | ? | ? | ? | 4.85−04 | 3.59 | 21% | 7% | 3.71E−02 | 2.61 |
| rs9579566 | | 9 | 1.08E+08 | ? | ? | ? | 8.10−05 | 4.36 | 21% | 6% | 2.72E−02 | 3.65 |
| kgp239140 | | 13 | 30980265 | ? | ? | ? | 3.90−04 | 0.00 | 0% | 8% | 1.68E−02 | 0.18 |
| kgp320293 | | 2 | 43425645 | ? | ? | ? | 7.83−04 | 0.39 | 18% | 36% | 4.73E−03 | 0.41 |
| kgp988462 | | 12 | 13859947 | GRIN2B | Silent | INTRON | 8.78−03 | 0.10 | 1% | 7% | 6.75E−04 | 0.09 |
| kgp227932 | X | 2 | 2.07E+08 | ? | ? | ? | 5.91−03 | 0.00 | 0% | 6% | 2.23E−02 | 0.00 |
| kgp568095 | | | 92601576 | ? | ? | ? | 1.68−03 | 0.47 | 34% | 52% | 4.17E−03 | 0.44 |
| kgp810749 | | 6 | 1.64E+08 | ? | ? | ? | 6.18−04 | 0.43 | 29% | 48% | 2.57E−02 | 0.51 |
| kgp114670 | | 6 | 1.64E+08 | ? | ? | ? | 1.11−03 | 0.45 | 35% | 54% | 2.91E−02 | 0.52 |
| kgp109485 | | 5 | 1.73E+08 | STC2 | Silent | INTRON | 6.44−04 | 0.16 | 2% | 13% | 4.17E−03 | 0.26 |
| rs7217872 | | 20 | 44082511 | ? | ? | ? | 9.59−03 | 0.49 | 20% | 33% | 4.00E−03 | 0.37 |
| rs343092 rs7948420 | | 17 | 88988 | RPH3AL, R | Silent, Silen | INTRON | 2.31−03 | 0.33 | 8% | 22% | 1.77E−03 | 0.32 |
| rs9913349 rs6718758 | | 12 | 66250940 | HMGA2, H | Silent, Silen | INTRON, EX | 6.14−03 | 2.81 | 17% | 7% | 8.40E−03 | 3.53 |
| rs7948420 | | 11 | 27276450 | ? | ? | ? | 4.80−05 | 0.35 | 20% | 42% | 8.59E−03 | 0.46 |
| rs9913349 | | 17 | 68260070 | ? | ? | ? | 2.63−03 | 2.30 | 32% | 17% | 3.61E−02 | 1.99 |
| rs6718758 | | 2 | 60328802 | ? | ? | ? | 6.51−03 | 0.51 | 31% | 47% | 1.42E−02 | 0.48 |

| | FORTE | | COMBINED | | | | | | | | |
|---|---|---|---|---|---|---|---|---|---|---|---|
| Name | Allele Freq. (Case | Allele Freq. (Controls | Fisher's Extact P | Odds Ratio (Minor Allele | Allele Freq. (Case | Allele Freq. (Controls | DD (Cases) | DD (Control | Dd (Cases) | Dd (Control | dd (Cases) | dd (Control |
| kgp621435 | 97% | 83% | 1.51E−06 | 0.18 | 3% | 14% | 0 | 1 | 9 | 32 | 145 | 88 |
| rs759458 | 64% | 77% | 2.38E−06 | 2.61 | 36% | 18% | 20 | 3 | 71 | 37 | 63 | 81 |
| rs197523 | 63% | 77% | 2.67E−06 | 2.52 | 38% | 20% | 26 | 5 | 67 | 38 | 62 | 78 |
| rs7844274 | 83% | 69% | 2.87E−06 | 0.40 | 19% | 37% | 4 | 18 | 50 | 53 | 100 | 50 |
| kgp107881 | 99% | 89% | 5.83E−06 | 0.07 | 1% | 8% | 0 | 1 | 2 | 18 | 153 | 102 |
| rs5918137 | 68% | 81% | 6.58E−06 | 2.72 | 29% | 13% | 22 | 8 | 44 | 15 | 88 | 98 |
| kgp191253 | 76% | 91% | 6.88E−06 | 2.98 | 25% | 10% | 13 | 3 | 50 | 18 | 91 | 100 |
| kgp962733 | 89% | 71% | 7.24E−06 | 0.34 | 10% | 24% | 1 | 7 | 28 | 44 | 125 | 70 |
| rs196343 | 82% | 66% | 7.88E−06 | 0.39 | 15% | 31% | 4 | 15 | 39 | 45 | 112 | 60 |
| rs196295 | 82% | 66% | 8.19E−06 | 0.39 | 15% | 31% | 4 | 15 | 39 | 46 | 111 | 60 |
| rs343087 | 78% | 93% | 8.46E−06 | 3.40 | 20% | 7% | 12 | 0 | 39 | 17 | 103 | 104 |
| kgp184320 | 84% | 96% | 1.53E−05 | 3.56 | 18% | 6% | 5 | 0 | 46 | 14 | 104 | 106 |
| rs7725112 | 80% | 91% | 1.76E−05 | 3.17 | 20% | 7% | 5 | 1 | 53 | 16 | 97 | 104 |
| rs7028906 | 86% | 96% | 1.76E−05 | 3.63 | 17% | 5% | 4 | 0 | 45 | 13 | 106 | 108 |
| rs9579566 | 98% | 91% | 1.80E−05 | 0.11 | 1% | 8% | 0 | 1 | 3 | 18 | 152 | 102 |
| kgp23914 | 76% | 57% | 1.81E−05 | 0.44 | 21% | 38% | 8 | 20 | 49 | 52 | 96 | 49 |
| kgp320293 | 99% | 88% | 1.87E−05 | 0.11 | 1% | 8% | 0 | 1 | 3 | 18 | 150 | 101 |
| kgp988462 | 100% | 96% | 1.93E−05 | 0.00 | 0% | 5% | 0 | 0 | 0 | 13 | 154 | 108 |
| kgp227932 | 65% | 44% | 1.93E−05 | 0.47 | 35% | 53% | 32 | 41 | 42 | 47 | 78 | 33 |
| kgp568095 | 70% | 54% | 1.94E−05 | 0.46 | 30% | 48% | 13 | 27 | 65 | 61 | 76 | 33 |
| kgp810749 | 66% | 50% | 1.96E−05 | 0.47 | 34% | 53% | 17 | 32 | 72 | 64 | 65 | 25 |
| kgp114670 | 95% | 83% | 1.96E−05 | 0.25 | 4% | 14% | 0 | 2 | 12 | 30 | 143 | 89 |
| kgp109485 | 85% | 69% | 2.02E−05 | 0.42 | 17% | 33% | 4 | 8 | 44 | 63 | 107 | 50 |
| rs7217872 | 89% | 71% | 2.05E−05 | 0.36 | 10% | 24% | 1 | 7 | 29 | 43 | 125 | 71 |

TABLE 27-continued

Additive Model, Extreme Response Definition, Genome Wide Analysis (Gala, Forte, and Combined cohorts)

| rs343092 | 79% | 93% | 2.18E-05 | 3.24 | 20% | 7% | 11 | 0 | 39 | 17 | 105 | 104 |
|---|---|---|---|---|---|---|---|---|---|---|---|---|
| rs7948420 | 67% | 49% | 2.27E-05 | 0.46 | 27% | 45% | 12 | 24 | 61 | 61 | 82 | 36 |
| rs9913349 | 63% | 77% | 2.31E-05 | 2.34 | 35% | 19% | 15 | 5 | 78 | 35 | 62 | 81 |
| rs6718758 | 75% | 59% | 2.36E-05 | 0.46 | 28% | 45% | 10 | 27 | 66 | 56 | 79 | 38 |

TABLE 28

Genotype Model, Extreme Response Definition, Genome Wide Analysis (Gala, Forte, and Combined cohorts)

| | | | | | | Gala | | | FORTE | | |
|---|---|---|---|---|---|---|---|---|---|---|---|
| Name | Chr | Position | Gene(s) | Mutation | Gene Locations (s) | Fisher's Exact | Allele Freq. (Cases) | Allele Freq. (Controls) | Fisher's Exact | Allele Freq. (Cases) | Allele Freq. (Controls) |
| kgp538447 | 3 | 173174758 | NLGN1 | Silent | INTRON | 1.84E-02 | 16% | 13% | 1.84E-05 | 21% | 16% |
| kgp119690 | 3 | 173176753 | NLGN1 | Silent | INTRON | 4.11E-02 | 17% | 15% | 6.40E-06 | 22% | 16% |
| kgp621435 | 11 | 75546691 | UVRAG | Silent | INTRON | 4.62E-03 | 3% | 13% | 1.22E-04 | 3% | 17% |
| kgp983223 | 2 | 144878583 | GTDC1, GT | Silent, | INTRON | 8.34E-04 | 15% | 23% | 4.93E-03 | 12% | 24% |
| kgp109348 | 6 | 41993656 | CCND3, CC | Silent, | INTRON, EX | 1.85E-03 | 46% | 31% | 1.40E-03 | 42% | 42% |
| rs7753265 | 6 | 41993861 | CCND3, CC | Silent, | INTRON, EX | 1.85E-03 | 46% | 31% | 1.40E-03 | 42% | 41% |
| rs2325911 | 6 | 125027223 | NKAIN2, NI | Silent, | INTRON | 1.43E-02 | 11% | 19% | 3.27E-05 | 10% | 29% |
| rs1691691 | 10 | 18458707 | CACNB2, C | Silent, | INTRON | 2.00E-03 | 3% | 12% | 6.65E-03 | 4% | 11% |
| rs1760475 | 10 | 18442940 | CACNB2, C | Silent, | INTRON | 3.45E-03 | 3% | 12% | 6.65E-03 | 4% | 11% |
| rs1691691 | 10 | 18457609 | CACNB2, C | Silent, | INTRON | 3.45E-03 | 3% | 12% | 6.65E-03 | 4% | 11% |
| kgp113435 | 14 | 64495925 | SYNE2, SY N | Silent, | INTRON | 2.38E-02 | 1% | 6% | 3.63E-04 | 1% | 9% |
| kgp107881 | 12 | 13898682 | GRIN2B | Silent | INTRON | 3.75E-03 | 0% | 7% | 6.04E-04 | 1% | 11% |
| rs1002610 | 4 | 40379061 | ? | ? | ? | 2.22E-04 | 62% | 41% | 2.50E-02 | 44% | 61% |
| rs1089589 | 11 | 97400945 | ? | ? | ? | 2.29E-03 | 47% | 50% | 2.68E-03 | 46% | 56% |
| rs1116327 | 11 | 97404580 | ? | ? | ? | 3.10E-03 | 45% | 38% | 4.03E-03 | 43% | 36% |
| rs1478682 | 11 | 27335009 | ? | ? | ? | 1.37E-03 | 48% | 31% | 8.87E-03 | 45% | 24% |
| kgp109485 | 20 | 44082511 | ? | ? | ? | 1.00E-02 | 20% | 33% | 1.40E-02 | 15% | 31% |
| rs7844274 | 8 | 72411302 | ? | ? | ? | 4.78E-03 | 21% | 39% | 9.44E-03 | 17% | 31% |
| rs8014274 | 14 | 97199831 | ? | ? | ? | 6.46E-03 | 22% | 26% | 4.93E-03 | 22% | 20% |
| kgp988462 | 2 | 206731028 | ? | ? | ? | 5.17E-03 | 0% | 6% | 2.16E-02 | 0% | 4% |
| kgp251355 | 15 | 86859449 | AGBL1, LO | Silent, | INTRON, EX | 1.04E-04 | 21% | 28% | 6.32E-03 | 20% | 36% |
| rs4540279 | 6 | 125023343 | NKAIN2, NI | Silent, | INTRON | 3.25E-03 | 11% | 23% | 1.75E-03 | 15% | 30% |
| kgp398456 | 4 | 40379690 | ? | ? | ? | 3.94E-04 | 38% | 59% | 2.29E-02 | 44% | 61% |
| kgp117685 | 11 | 27270451 | ? | ? | ? | 3.49E-03 | 50% | 34% | 5.34E-03 | 47% | 26% |
| rs502530 | 6 | 145584096 | ? | ? | ? | 2.39E-02 | 2% | 7% | 3.63E-04 | 0% | 9% |
| kgp707732 | 4 | 164661252 | Mar-01 | Silent | INTRON | 2.22E-03 | 2% | 10% | 8.81E-04 | 3% | 16% |
| rs7250360 | 19 | 21718822 | ZNF429 | Silent | INTRON | 2.89E-03 | 33% | 43% | 3.87E-02 | 32% | 49% |
| rs4939187 | 11 | 57986892 | ? | ? | ? | 4.09E-03 | 29% | 30% | 1.08E-02 | 38% | 33% |
| rs1007762 | 5 | 83907654 | ? | ? | ? | 2.84E-02 | 15% | 27% | 3.56E-04 | 18% | 37% |
| kgp398342 | 5 | 83907761 | ? | ? | ? | 2.84E-02 | 15% | 27% | 3.56E-04 | 18% | 37% |
| rs7348267 | 20 | 44084386 | ? | ? | ? | 1.00E-02 | 20% | 33% | 2.41E-02 | 15% | 30% |
| rs4482847 | 4 | 141993345 | RNF150 | Silent | INTRON | 4.12E-04 | 30% | 35% | 1.39E-02 | 31% | 24% |
| rs1757798 | 6 | 32359821 | HCG23 | Silent | INTRON | 3.57E-03 | 24% | 10% | 1.85E-03 | 20% | 9% |
| rs1102989 | 11 | 27269546 | ? | ? | ? | 6.91E-04 | 42% | 24% | 4.62E-02 | 39% | 23% |
| kgp112102 | 3 | 38537237 | ? | ? | ? | 2.41E-02 | 5% | 0% | 3.31E-02 | 6% | 0% |
| kgp962733 | 17 | 90155 | RPH3AL, R | Silent, | INTRON | 9.41E-03 | 8% | 22% | 8.11E-04 | 11% | 29% |
| rs1079303 | 11 | 27269598 | ? | ? | ? | 3.49E-03 | 50% | 34% | 6.52E-03 | 47% | 26% |
| rs1050108 | 11 | 27270978 | ? | ? | ? | 3.49E-03 | 50% | 34% | 6.52E-03 | 47% | 26% |
| rs9579566 | 13 | 30980265 | ? | ? | ? | 1.23E-03 | 0% | 8% | 1.50E-02 | 2% | 9% |
| kgp320293 | 12 | 13859947 | GRIN2B | Silent | INTRON | 2.46E-02 | 1% | 7% | 5.06E-04 | 1% | 12% |
| kgp285324 | 15 | 62968836 | TLN2 | Silent | INTRON | 1.11E-03 | 8% | 1% | 1.91E-02 | 7% | 0% |

TABLE 28-continued

Genotype Model, Extreme Response Definition, Genome Wide Analysis (Gala, Forte, and Combined cohorts)

| | COMBINED | | | | | | | | |
|---|---|---|---|---|---|---|---|---|---|
| Name | Fisher's Exact P | Allele Freq. (Cases) | Allele Freq. (Controls) | DD (Cases) | DD (Control) | Dd (Cases) | Dd (Control) | dd (Cases) | dd (Control) |
| kgp538447 | 3.88E−07 | 19% | 14% | 0 | 8 | 58 | 17 | 97 | 96 |
| kgp119690 | 8.99E−07 | 20% | 15% | 0 | 8 | 61 | 20 | 93 | 93 |
| kgp621435 | 1.25E−06 | 3% | 14% | 0 | 1 | 9 | 32 | 145 | 88 |
| kgp983223 | 2.21E−06 | 14% | 24% | 5 | 0 | 32 | 57 | 118 | 64 |
| kgp109348 | 2.80E−06 | 44% | 34% | 20 | 22 | 95 | 38 | 40 | 61 |
| rs7753265 | 2.80E−06 | 44% | 34% | 20 | 22 | 95 | 38 | 40 | 61 |
| rs2325911 | 2.96E−06 | 10% | 21% | 4 | 1 | 24 | 50 | 127 | 70 |
| rs1691691 | 5.46E−06 | 4% | 12% | 2 | 0 | 8 | 29 | 145 | 91 |
| rs1760475 | 5.54E−06 | 4% | 12% | 2 | 0 | 8 | 29 | 145 | 92 |
| rs1691691 | 5.54E−06 | 4% | 12% | 2 | 0 | 8 | 29 | 145 | 92 |
| kgp113435 | 1.08E−05 | 1% | 7% | 1 | 0 | 1 | 16 | 153 | 105 |
| kgp107881 | 1.09E−05 | 1% | 8% | 0 | 1 | 2 | 18 | 153 | 102 |
| rs1002610 | 1.15E−05 | 42% | 60% | 21 | 36 | 87 | 72 | 47 | 12 |
| rs1089589 | 1.17E−05 | 46% | 52% | 42 | 22 | 60 | 80 | 53 | 18 |
| rs1116327 | 1.19E−05 | 44% | 38% | 38 | 8 | 59 | 75 | 58 | 38 |
| rs1478682 | 1.21E−05 | 46% | 29% | 31 | 4 | 81 | 63 | 42 | 54 |
| kgp109485 | 1.35E−05 | 17% | 33% | 4 | 8 | 44 | 63 | 107 | 50 |
| rs7844274 | 1.41E−05 | 19% | 37% | 4 | 18 | 50 | 53 | 100 | 50 |
| rs8014274 | 1.45E−05 | 22% | 24% | 0 | 12 | 67 | 34 | 87 | 75 |
| kgp988462 | 1.58E−05 | 0% | 5% | 0 | 0 | 0 | 13 | 154 | 108 |
| kgp251355 | 1.60E−05 | 21% | 31% | 11 | 4 | 42 | 66 | 102 | 51 |
| rs4540279 | 1.64E−05 | 14% | 25% | 5 | 2 | 32 | 56 | 118 | 63 |
| kgp398456 | 1.67E−05 | 41% | 60% | 21 | 36 | 86 | 72 | 48 | 13 |
| kgp117685 | 1.68E−05 | 48% | 31% | 32 | 5 | 85 | 66 | 37 | 50 |
| rs502530 | 1.77E−05 | 1% | 7% | 0 | 0 | 2 | 18 | 153 | 103 |
| kgp707732 | 1.79E−05 | 3% | 12% | 0 | 0 | 8 | 28 | 146 | 92 |
| rs7250360 | 2.17E−05 | 33% | 45% | 27 | 20 | 47 | 68 | 81 | 33 |
| rs4939187 | 2.18E−05 | 34% | 31% | 6 | 16 | 94 | 42 | 55 | 63 |
| rs1007762 | 2.30E−05 | 17% | 30% | 0 | 12 | 52 | 48 | 103 | 61 |
| kgp398342 | 2.30E−05 | 17% | 30% | 0 | 12 | 52 | 48 | 103 | 61 |
| rs7348267 | 2.36E−05 | 17% | 32% | 4 | 8 | 44 | 62 | 107 | 51 |
| rs4482847 | 2.38E−05 | 31% | 32% | 9 | 23 | 77 | 32 | 69 | 66 |
| rs1757798 | 2.38E−05 | 21% | 10% | 4 | 3 | 58 | 17 | 92 | 100 |
| rs1102989 | 2.39E−05 | 40% | 24% | 22 | 2 | 81 | 54 | 52 | 65 |
| kgp112102 | 2.41E−05 | 6% | 0% | 0 | 0 | 18 | 0 | 137 | 121 |
| kgp962733 | 2.46E−05 | 10% | 24% | 1 | 7 | 28 | 44 | 125 | 70 |
| rs1079303 | 2.51E−05 | 48% | 31% | 32 | 5 | 85 | 66 | 38 | 50 |
| rs1050108 | 2.51E−05 | 48% | 31% | 32 | 5 | 85 | 66 | 38 | 50 |
| rs9579566 | 2.76E−05 | 1% | 8% | 0 | 1 | 3 | 18 | 152 | 102 |
| kgp320293 | 2.84E−05 | 1% | 8% | 0 | 1 | 3 | 18 | 150 | 101 |
| kgp285324 | 2.88E−05 | 7% | 0% | 0 | 0 | 22 | 1 | 133 | 120 |

TABLE 29

Additive Model, Extreme Response Definition, Genome Wide Placebo Cohort Analysis Placebo

| Name | Chr | Position | Gene(s) | Mutation | Gene Locations(s) | Armitage P | Regression Odds Ratio | DD (Cases) | DD (Controls) | Dd (Cases) | Dd (Controls) | dd (Cases) | dd (Controls) |
|---|---|---|---|---|---|---|---|---|---|---|---|---|---|
| rs1978721 | 19 | 30966217 | ZNF536 | Silent | INTRON | 9.89E-09 | 35.3 | 0 | 0 | 11 | 2 | 12 | 77 |
| kgp7344529 | 19 | 30967564 | ZNF536 | Silent | INTRON | 9.89E-09 | 35.3 | 0 | 0 | 11 | 2 | 12 | 77 |
| rs7252241 | 19 | 30967836 | ZNF536 | Silent | INTRON | 9.89E-09 | 35.3 | 0 | 0 | 11 | 2 | 12 | 77 |
| rs1978720 | 19 | 30968371 | ZNF536 | Silent | INTRON | 9.89E-09 | 35.3 | 0 | 0 | 11 | 2 | 12 | 77 |
| rs146166 | 19 | 30965980 | ZNF536 | Silent | INTRON | 1.92E-07 | 13.8 | 0 | 0 | 14 | 8 | 9 | 71 |
| rs8112863 | 19 | 30965063 | ZNF536 | Silent | INTRON | 2.37E-07 | 13.6 | 0 | 0 | 14 | 8 | 9 | 70 |
| kgp2877482 | 6 | 1644677 | GMDS, GMDS | Silent, Silent | ? | 3.47E-07 | 17.2 | 0 | 0 | 11 | 4 | 12 | 75 |
| kgp7851536 | 15 | 27960322 | PCSK6, PCSK6, PCSK6, PCSK6, PCSK6, PCSK6 | Silent, Silent, Silent, Silent, Silent, Silent | ? | 3.76E-07 | ? | 0 | 0 | 7 | 0 | 16 | 79 |
| kgp9348779 | 15 | 101900592 | PCSK6, PCSK6, PCSK6, PCSK6, PCSK6, PCSK6 | Silent, Silent, Silent, Silent, Silent, Silent | INTRON | 3.76E-07 | ? | 0 | 0 | 7 | 0 | 16 | 79 |
| rs2289333 | 15 | 40617209 | ? | ? | ? | 5.68E-07 | 17.9 | 1 | 0 | 9 | 3 | 13 | 76 |
| kgp24711573 | 15 | 40633138 | C15orf52 | Synonymous_A5A | EXON | 5.68E-07 | 17.9 | 1 | 0 | 9 | 3 | 13 | 76 |
| kgp8598661 | 6 | 1627678 | GMDS, GMDS | Silent, Silent | INTRON | 6.01E-07 | 12.5 | 1 | 0 | 11 | 6 | 11 | 73 |
| rs16846841 | 2 | 197063250 | ? | ? | ? | 6.12E-07 | 41.6 | 0 | 0 | 8 | 1 | 15 | 78 |
| rs7565256 | 2 | 79227275 | ? | ? | ? | 6.17E-07 | 9.1 | 4 | 0 | 14 | 22 | 5 | 56 |
| kgp12396787 | 22 | 27267611 | ? | ? | ? | 7.21E-07 | 41.1 | 0 | 0 | 8 | 1 | 15 | 77 |
| kgp6535349 | 15 | 40614200 | ? | ? | ? | 7.54E-07 | 24.4 | 3 | 0 | 9 | 2 | 14 | 76 |
| rs9775757 | 1 | 23068465 | EPHB2, EPHB2 | Silent, Silent | INTRON | 1.13E-06 | 9.2 | 3 | 0 | 15 | 22 | 5 | 57 |
| kgp2151888 | 2 | 79295288 | ? | ? | ? | 1.87E-06 | 8.2 | 3 | 0 | 13 | 19 | 6 | 60 |
| kgp4985243 | 7 | 136556162 | CHRM2, CHRM2, CHRM2, CHRM2, CHRM2, CHRM2, CHRM2, CHRM2 | Silent, Silent, Silent, Silent, Silent, Silent, Silent, Silent | INTRON | 2.25E-06 | 9.3 | 1 | 0 | 13 | 11 | 9 | 68 |
| kgp6870400 | 2 | 79278036 | ? | ? | ? | 2.38E-06 | 7.4 | 4 | 0 | 13 | 22 | 6 | 57 |
| rs1077476 | 15 | 40619743 | ? | ? | ? | 2.53E-06 | 13.1 | 1 | 0 | 9 | 4 | 13 | 74 |
| kgp2136475 | 15 | 40623593 | ? | ? | ? | 2.53E-06 | 13.1 | 1 | 0 | 9 | 4 | 13 | 74 |
| rs4935590 | 10 | 57059483 | ? | ? | ? | 2.59E-06 | 8.2 | 2 | 0 | 12 | 12 | 9 | 67 |
| kgp16907220 | 10 | 57059690 | ? | ? | ? | 2.59E-06 | 8.2 | 2 | 0 | 12 | 12 | 9 | 67 |
| rs1073665 | 10 | 57061057 | ? | ? | ? | 2.59E-06 | 8.2 | 2 | 0 | 12 | 12 | 9 | 67 |
| rs4477500 | 12 | 128645821 | ? | ? | ? | 2.62E-06 | 7.3 | 9 | 2 | 10 | 37 | 3 | 39 |
| rs9016053 | 17 | 69386788 | ? | ? | ? | 2.87E-06 | 10.5 | 1 | 0 | 10 | 7 | 10 | 71 |
| kgp2617488 | 3 | 118491777 | TAMM41 | Silent | INTRON | 2.88E-06 | ? | 0 | 0 | 6 | 0 | 17 | 79 |
| kgp3537954 | 5 | 103927513 | ? | ? | ? | 2.88E-06 | ? | 0 | 0 | 6 | 0 | 17 | 79 |
| kgp9400093 | 5 | 104031832 | ? | ? | ? | 2.88E-06 | ? | 0 | 0 | 6 | 0 | 17 | 79 |
| kgp3681524 | 7 | 145920329 | CNTNAP2 | Silent | INTRON | 2.88E-06 | 7493593408767320.0 | 0 | 0 | 6 | 0 | 17 | 79 |
| rs788303 | 10 | 23646459 | ? | ? | ? | 2.88E-06 | 7493593408767320.0 | 0 | 0 | 6 | 0 | 17 | 79 |
| rs7824246 | 12 | 11333716 | ? | ? | ? | 2.88E-06 | 4545094153837080.00 | 0 | 0 | 6 | 0 | 17 | 79 |
| kgp27533766 | 12 | 65501698 | WIF1 | Silent | INTRON | 2.88E-06 | 7493593408767270.0 | 0 | 0 | 6 | 0 | 17 | 79 |
| kgp4089310 | 18 | 7309451 | ? | ? | ? | 2.88E-06 | 7493593408767270.0 | 0 | 0 | 6 | 0 | 17 | 79 |
| rs17225585 | 17 | 69370430 | ? | ? | ? | 3.05E-06 | 10.2 | 1 | 0 | 11 | 7 | 11 | 69 |
| rs13104183 | 4 | 113323634 | ALPK1, ALPK1, ALPK1 | Silent, Silent, Silent | INTRON, EXON | 3.43E-06 | 6.7 | 4 | 0 | 10 | 16 | 8 | 63 |
| kgp11962282 | 10 | 88223587 | WAPAL | Silent | INTRON | 3.61E-06 | 10.5 | 1 | 0 | 10 | 6 | 12 | 73 |
| rs3934982 | 2 | 242926558 | ? | ? | ? | 3.66E-06 | 11.5 | 0 | 0 | 9 | 5 | 14 | 74 |
| rs896539 | 3 | 135473872 | ? | ? | ? | 3.77E-06 | 10.6 | 0 | 0 | 12 | 8 | 10 | 71 |
| rs6743255 | 2 | 205363596 | ? | ? | ? | 4.33E-06 | 7.7 | 2 | 0 | 13 | 15 | 8 | 64 |

TABLE 29-continued

Additive Model, Extreme Response Definition, Genome Wide Placebo Cohort Analysis Placebo

| Name | Chr | Position | Gene(s) | Mutation | Gene Locations (s) | Armitage P | Regression Odds Ratio | DD (Cases) | DD (Controls) | Dd (Cases) | Dd (Controls) | dd (Cases) | dd (Controls) |
|---|---|---|---|---|---|---|---|---|---|---|---|---|---|
| kgp5046752 | 2 | 179650234 | TTN, TTN, TTN, TTN, TTN | Silent, Silent, Silent, Silent, Silent | INTRON | 4.67E-06 | 34.1 | 0 | 0 | 7 | 1 | 16 | 78 |
| kgp3420885 | 13 | 112188913 | ? | ? | ? | 4.67E-06 | 34.1 | 0 | 0 | 7 | 1 | 16 | 78 |
| kgp3423367 | 19 | 54113722 | ? | ? | ? | 4.67E-06 | 34.1 | 0 | 0 | 7 | 1 | 16 | 78 |
| kgp9522435 | 19 | 30951753 | ZNF536 | Silent | INTRON | 4.71E-06 | 20.5 | 0 | 0 | 8 | 2 | 15 | 77 |
| kgp5544649 | 19 | 30958606 | ZNF536 | Silent | INTRON | 4.71E-06 | 20.5 | 0 | 0 | 8 | 2 | 15 | 77 |
| kgp3185857 | 22 | 27269249 | ? | ? | ? | 4.71E-06 | 20.5 | 0 | 0 | 8 | 2 | 15 | 77 |
| kgp5863276 | 22 | 27274898 | ? | ? | ? | 4.71E-06 | 20.5 | 0 | 0 | 8 | 2 | 15 | 77 |
| rs17825388 | 17 | 69380584 | ? | ? | ? | 4.74E-06 | 9.2 | 1 | 0 | 11 | 8 | 11 | 71 |
| rs1942396 | 18 | 69347308 | ? | ? | ? | 4.74E-06 | 9.2 | 1 | 0 | 11 | 8 | 11 | 71 |
| kgp2575625 | 2 | 218219226 | DIRC3 | Silent | INTRON | 5.23E-06 | 8.6 | 1 | 0 | 12 | 10 | 10 | 69 |
| kgp11688655 | 2 | 218219697 | DIRC3 | Silent | INTRON | 5.23E-06 | 8.6 | 1 | 0 | 12 | 10 | 10 | 69 |
| kgp3778675 | 2 | 218226516 | DIRC3 | Silent | INTRON | 5.23E-06 | 8.6 | 1 | 0 | 12 | 10 | 10 | 69 |
| rs10488907 | 4 | 113312105 | ALPK1, ALPK1, ALPK1 | Silent, Silent, Silent | INTRON, EXON | 5.36E-06 | 7.5 | 2 | 0 | 12 | 13 | 9 | 66 |
| kgp2832863 | 3 | 8820301 | ? | ? | ? | 5.38E-06 | 33.7 | 0 | 0 | 7 | 1 | 16 | 77 |
| kgp6643157 | 3 | 13145604 | ? | ? | ? | 5.46E-06 | 20.3 | 0 | 0 | 8 | 2 | 15 | 76 |
| kgp4292871 | 22 | 27274445 | ? | ? | ? | 5.46E-06 | 20.3 | 0 | 0 | 8 | 2 | 15 | 76 |
| rs6643055 | X | 111782861 | ? | ? | ? | 5.65E-06 | 18.3 | 1 | 0 | 7 | 2 | 15 | 77 |
| rs12005792 | 9 | 87236739 | ? | ? | ? | 6.46E-06 | 6.8 | 3 | 1 | 15 | 22 | 5 | 56 |
| rs888829 | 15 | 40607689 | ? | ? | ? | 6.98E-06 | 10.6 | 1 | 0 | 9 | 5 | 13 | 74 |
| kgp1305638 | 6 | 122195448 | ? | ? | ? | 7.74E-06 | 29.6 | 1 | 0 | 6 | 1 | 16 | 78 |
| rs6673115 | 1 | 230669649 | EPHB2, EPHB2 | Silent, Silent | INTRON | 8.25E-06 | 6.7 | 5 | 1 | 14 | 30 | 4 | 48 |
| kgp7380442 | 22 | 28746343 | TTC28 | Silent | INTRON | 8.80E-06 | ? | 1 | 0 | 5 | 0 | 17 | 79 |
| kgp4898364 | 22 | 29092726 | CHEK2, CHEK2, CHEK2 | Silent, Silent, Silent | INTRON | 8.80E-06 | ? | 1 | 0 | 5 | 0 | 17 | 79 |
| kgp9420863 | 1 | 105167334 | ? | ? | ? | 9.42E-06 | 9.0 | 0 | 0 | 13 | 10 | 10 | 69 |
| kgp100271 | 1 | 105186472 | ? | ? | ? | 9.42E-06 | 9.0 | 0 | 0 | 13 | 10 | 10 | 69 |
| kgp4009576 | 1 | 105189899 | ? | ? | ? | 9.42E-06 | 9.0 | 0 | 0 | 13 | 10 | 10 | 69 |
| kgp11130156 | 12 | 20871256 | SLCO1C1, SLCO1C1, SLCO1C1 | Silent, Silent, Silent | INTRON | 9.52E-06 | 6.4 | 2 | 1 | 13 | 13 | 8 | 65 |
| rs10746192 | 12 | 81942162 | PPFIA2, PPFIA2, PPFIA2, PPFIA2, PPFIA2, PPFIA2 | Silent, Silent, Silent, Silent, Silent, Silent | INTRON | 9.87E-06 | 8.0 | 8 | 5 | 15 | 45 | 0 | 29 |
| kgp8919080 | 7 | 84958459 | ? | ? | ? | 9.94E-06 | 8.9 | 1 | 0 | 10 | 7 | 12 | 72 |

TABLE 30

Allelic Model, Extreme Response Definition, Genome Wide Placebo Cohort Analysis
Placebo

| Name | Chr | Position | Gene(s) | Mutation | Gene Locations (s) | Fisher's Exact P | Odds Ratio (Minor Allele) |
|---|---|---|---|---|---|---|---|
| kgp106385 | 3 | 196573166 | ? | ? | ? | 1.00E−06 | 0.1 |
| rs1978721 | 19 | 30966217 | ZNF536 | Silent | INTRON | 1.49E−06 | 24.5 |
| kgp734452 | 19 | 30967564 | ZNF536 | Silent | INTRON | 1.49E−06 | 24.5 |
| rs7252241 | 19 | 30967836 | ZNF536 | Silent | INTRON | 1.49E−06 | 24.5 |
| rs1978720 | 19 | 30968371 | ZNF536 | Silent | INTRON | 1.49E−06 | 24.5 |
| kgp183404 | 3 | 196579489 | ? | ? | ? | 2.26E−06 | 0.1 |
| kgp860737 | 17 | 20459947 | ? | ? | ? | 4.36E−06 | 0.0 |
| rs2289333 | 15 | 40617209 | ? | ? | ? | 5.79E−06 | 16.2 |
| kgp247157 | 15 | 40633138 | C15orf52 | Synonymo | EXON | 5.79E−06 | 16.2 |
| rs7565256 | 2 | 79227275 | ? | ? | ? | 7.04E−06 | 5.6 |
| kgp859866 | 6 | 1627678 | GMDS, GM | Silent, Silen | INTRON | 8.30E−06 | 10.0 |
| rs1310418 | 4 | 113323634 | ALPK1, ALP | Silent, Silen | INTRON, EX | 9.26E−06 | 6.1 |
| rs4477500 | 12 | 128645821 | ? | ? | ? | 9.70E−06 | 4.9 |
| kgp359896 | 4 | 7649861 | SORCS2 | Silent | INTRON | 9.97E−06 | 0.0 |
| kgp111645 | 17 | 20459328 | ? | ? | ? | 1.07E−05 | 0.1 |
| kgp146166 | 19 | 30965980 | ZNF536 | Silent | INTRON | 1.22E−05 | 8.2 |
| rs8112863 | 19 | 30965063 | ZNF536 | Silent | INTRON | 1.38E−05 | 8.1 |
| rs2555629 | 4 | 175430288 | HPGD, HPG | Silent, Silen | INTRON, EX | 1.40E−05 | 4.6 |
| kgp215188 | 2 | 79295288 | ? | ? | ? | 1.44E−05 | 5.6 |
| kgp553777 | 20 | 35531097 | SAMHD1 | Silent | INTRON | 1.68E−05 | 5.5 |
| kgp400475 | 20 | 35539858 | SAMHD1 | Silent | INTRON | 1.68E−05 | 5.5 |
| kgp977575 | 1 | 23068465 | EPHB2, EPH | Silent, Silen | INTRON | 1.68E−05 | 5.2 |
| kgp687040 | 2 | 79278036 | ? | ? | ? | 1.68E−05 | 5.2 |
| rs763318 | 4 | 12963574 | ? | ? | ? | 1.70E−05 | 5.4 |
| rs4935590 | 10 | 57059483 | ? | ? | ? | 1.73E−05 | 6.5 |
| rs1690722 | 10 | 57059690 | ? | ? | ? | 1.73E−05 | 6.5 |
| rs1073665 | 10 | 57061057 | ? | ? | ? | 1.73E−05 | 6.5 |
| kgp596929 | 4 | 12976777 | ? | ? | ? | 1.73E−05 | 4.5 |
| kgp287748 | 6 | 1644677 | GMDS, GM | Silent, Silen | INTRON | 1.81E−05 | 12.1 |
| rs4916561 | 3 | 196576109 | ? | ? | ? | 1.84E−05 | 0.1 |
| kgp228237 | X | 31244702 | DMD, DMD | Silent, Silen | INTRON | 1.91E−05 | 0.1 |
| rs1077476 | 15 | 40619743 | ? | ? | ? | 2.00E−05 | 11.9 |
| kgp213647 | 15 | 40623593 | ? | ? | ? | 2.00E−05 | 11.9 |
| kgp785153 | 15 | 27960322 | ? | ? | ? | 2.04E−05 | ? |
| kgp934877 | 15 | 101900592 | PCSK6, PCS | Silent, Silen | INTRON | 2.04E−05 | ? |

| Name | Allele Freq. (Cases) | Allele Freq. (Controls) | DD (Cases) | DD (Controls) | Dd (Cases) | Dd (Controls) | dd (Cases) | dd (Controls) |
|---|---|---|---|---|---|---|---|---|
| kgp106385 | 7% | 44% | 0 | 17 | 3 | 35 | 20 | 27 |
| rs1978721 | 24% | 1% | 0 | 0 | 11 | 2 | 12 | 77 |
| kgp734455 | 24% | 1% | 0 | 0 | 11 | 2 | 12 | 77 |
| rs7252241 | 24% | 1% | 0 | 0 | 11 | 2 | 12 | 77 |
| rs1978720 | 24% | 1% | 0 | 0 | 11 | 2 | 12 | 77 |
| kgp183404 | 7% | 42% | 0 | 14 | 3 | 38 | 20 | 27 |
| kgp860737 | 2% | 35% | 0 | 10 | 1 | 35 | 20 | 34 |
| rs2289333 | 24% | 2% | 1 | 0 | 9 | 3 | 13 | 76 |
| kgp247157 | 24% | 2% | 1 | 0 | 9 | 3 | 13 | 76 |
| rs7565256 | 48% | 14% | 4 | 0 | 14 | 22 | 5 | 56 |
| kgp859866 | 28% | 4% | 1 | 0 | 11 | 6 | 11 | 73 |
| rs1310418 | 41% | 10% | 4 | 0 | 10 | 16 | 8 | 63 |
| rs4477500 | 64% | 26% | 9 | 2 | 10 | 37 | 3 | 39 |
| kgp359896 | 2% | 31% | 0 | 7 | 1 | 35 | 22 | 37 |
| kgp111645 | 4% | 35% | 0 | 9 | 2 | 36 | 21 | 32 |
| kgp146166 | 30% | 5% | 0 | 0 | 14 | 8 | 9 | 71 |
| rs8112863 | 30% | 5% | 0 | 0 | 14 | 8 | 9 | 70 |
| rs2555629 | 61% | 25% | 11 | 4 | 6 | 32 | 6 | 43 |
| kgp215188 | 43% | 12% | 3 | 0 | 13 | 19 | 6 | 60 |
| kgp553777 | 41% | 11% | 4 | 1 | 11 | 16 | 8 | 62 |
| kgp400475 | 41% | 11% | 4 | 1 | 11 | 16 | 8 | 62 |
| kgp97757S | 46% | 14% | 3 | 0 | 15 | 22 | 5 | 57 |
| kgp687040 | 46% | 14% | 4 | 0 | 13 | 22 | 6 | 57 |
| rs763318 | 83% | 47% | 15 | 20 | 8 | 33 | 0 | 25 |
| rs4935590 | 35% | 8% | 2 | 0 | 12 | 12 | 9 | 67 |
| rs1690722 | 35% | 8% | 2 | 0 | 12 | 12 | 9 | 67 |
| rs1073665 | 35% | 8% | 2 | 0 | 12 | 12 | 9 | 67 |
| kgp596929 | 70% | 34% | 11 | 10 | 10 | 33 | 2 | 36 |
| kgp287748 | 24% | 3% | 0 | 0 | 11 | 4 | 12 | 75 |
| rs4916561 | 7% | 38% | 0 | 12 | 3 | 36 | 20 | 30 |
| kgp228237 | 2% | 30% | 0 | 17 | 1 | 14 | 22 | 48 |
| rs1077476 | 24% | 3% | 1 | 0 | 9 | 4 | 13 | 74 |

TABLE 30-continued

Allelic Model, Extreme Response Definition, Genome Wide Placebo Cohort Analysis
Placebo

| | | | | | | | | |
|---|---|---|---|---|---|---|---|---|
| kgp213647 | 24% | 3% | 1 | 0 | 9 | 4 | 13 | 74 |
| kgp785153 | 15% | 0% | 0 | 0 | 7 | 0 | 16 | 79 |
| kgp934877 | 15% | 0% | 0 | 0 | 7 | 0 | 16 | 79 |

TABLE 31

Genotype Model, Extreme Response Definition, Genome Wide Placebo Cohort Analysis
Placebo

| Name | Chr | Position | Gene(s) | Mutation | Gene Locations (s) | Fisher's Exact P |
|---|---|---|---|---|---|---|
| rs1978721 | 19 | 30966217 | ZNF536 | Silent | INTRON | 4.57E−07 |
| kgp7344529 | 19 | 30967564 | ZNF536 | Silent | INTRON | 4.57E−07 |
| rs7252241 | 19 | 30967836 | ZNF536 | Silent | INTRON | 4.57E−07 |
| rs1978720 | 19 | 30968371 | ZNF536 | Silent | INTRON | 4.57E−07 |
| kgp146166 | 19 | 30965980 | ZNF536 | Silent | INTRON | 1.91E−06 |
| rs8112863 | 19 | 30965063 | ZNF536 | Silent | INTRON | 2.19E−06 |
| rs7565256 | 2 | 79227275 | ? | ? | ? | 2.25E−06 |
| kgp6295377 | 19 | 30953846 | ZNF536 | Silent | INTRON | 3.08E−06 |
| rs4477500 | 12 | 128645821 | ? | ? | ? | 3.54E−06 |
| rs11705401 | 22 | 37678096 | ? | ? | ? | 3.97E−06 |
| kgp2536097 | 6 | 25181978 | ? | ? | ? | 5.58E−06 |
| rs2109066 | 19 | 28835327 | ? | ? | ? | 5.93E−06 |
| kgp2877482 | 6 | 1644677 | GMDS, GM | Silent, Silen | INTRON | 6.14E−06 |
| kgp9775757 | 1 | 23068465 | EPHB2, EPH | Silent, Silen | INTRON | 6.34E−06 |
| kgp6601755 | 19 | 28886975 | ? | ? | ? | 6.76E−06 |
| kgp8598661 | 6 | 1627678 | GMDS, GM | Silent, Silen | INTRON | 8.89E−06 |
| rs2159327 | 19 | 28835571 | ? | ? | ? | 9.75E−06 |
| kgp2151888 | 2 | 79295288 | ? | ? | ? | 9.91E−06 |
| rs2289333 | 15 | 40617209 | ? | ? | ? | 1.01E−05 |
| kgp2471573 | 15 | 40633138 | C15orf52 | Synonymo | EXON | 101E−05 |
| kgp6870400 | 2 | 79278036 | ? | ? | ? | 1.27E−05 |
| kgp6850713 | 19 | 28885593 | ? | ? | ? | 1.28E−05 |
| kgp7851536 | 15 | 27960322 | ? | ? | ? | 1.33E−05 |
| kgp9348779 | 15 | 101900592 | PCSK6, PCS | Silent, Silen | INTRON | 1.33E−05 |
| rs995834 | 19 | 28866596 | ? | ? | ? | 1.39E−05 |
| rs1773631 | 10 | 25665449 | GPR158 | Silent | INTRON | 1.43E−05 |
| kgp8034516 | 8 | 97282138 | PTDSS1 | Silent | INTRON | 1.46E−05 |
| rs13280716 | 8 | 97282560 | PTDSS1 | Silent | INTRON | 1.46E−05 |
| kgp303315 | 8 | 97283313 | PTDSS1 | Silent | INTRON | 1.46E−05 |
| kgp5433489 | 8 | 97302091 | PTDSS1 | Silent | INTRON | 1.46E−05 |
| rs17707686 | 8 | 97312442 | PTDSS1 | Silent | INTRON | 1.46E−05 |
| rs727047 | 22 | 37677719 | ? | ? | ? | 1.48E−05 |
| kgp7521451 | 8 | 97297894 | PTDSS1 | Silent | INTRON | 1.49E−05 |
| rs2056136 | 12 | 20867893 | SLCO1C1, S | Silent, Silen | INTRON | 1.50E−05 |
| rs10746192 | 12 | 81942162 | PPFIA2, PP | Silent, Silen | INTRON | 1.54E−05 |
| rs2555629 | 4 | 175430288 | HPGD, HPG | Silent, Silen | INTRON, EX | 1.57E−05 |
| kgp12537012 | 8 | 97285429 | PTDSS1 | Silent | INTRON | 1.60E−05 |
| rs9969509 | 8 | 97293953 | PTDSS1 | Silent | INTRON | 1.60E−05 |
| kgp6535349 | 15 | 40614200 | ? | ? | ? | 1.60E−05 |
| rs16846841 | 2 | 197063250 | ? | ? | ? | 1.73E−05 |
| kgp12396787 | 22 | 27267611 | ? | ? | ? | 1.87E−05 |
| kgp4985243 | 7 | 136556162 | CHRM2, CH | Silent, Silen | INTRON | 1.91E−05 |
| rs4935590 | 10 | 57059483 | ? | ? | ? | 1.98E−05 |
| rs16907220 | 10 | 57059690 | ? | ? | ? | 1.98E−05 |
| rs1073665 | 10 | 57061057 | ? | ? | ? | 1.98E−05 |
| rs2292275 | 1 | 163292217 | NUF2, NUF | Silent, Silen | INTRON, EX | 2.11E−05 |
| rs7962380 | 12 | 128643018 | ? | ? | ? | 2.27E−05 |
| kgp10638512 | 3 | 196573166 | ? | ? | ? | 2.34E−05 |

| Name | Allele Freq. (Cases) | Allele Freq. (Controls) | DD (Cases) | DD (Controls) | Dd (Cases) | Dd (Controls) | dd (Cases) | dd (Controls) |
|---|---|---|---|---|---|---|---|---|
| rs1978721 | 24% | 1% | 0 | 0 | 11 | 2 | 12 | 77 |
| kgp7344529 | 24% | 1% | 0 | 0 | 11 | 2 | 12 | 77 |
| rs7252241 | 24% | 1% | 0 | 0 | 11 | 2 | 12 | 77 |
| rs1978720 | 24% | 1% | 0 | 0 | 11 | 2 | 12 | 77 |
| kgp146166 | 30% | 5% | 0 | 0 | 14 | 8 | 9 | 71 |
| rs8112863 | 30% | 5% | 0 | 0 | 14 | 8 | 9 | 70 |
| rs7565256 | 48% | 14% | 4 | 0 | 14 | 22 | 5 | 56 |
| kgp6295377 | 20% | 2% | 0 | 1 | 9 | 1 | 14 | 77 |

TABLE 31-continued

Genotype Model, Extreme Response Definition, Genome Wide Placebo Cohort Analysis
Placebo

| | | | | | | | | |
|---|---|---|---|---|---|---|---|---|
| rs4477500 | 64% | 26% | 9 | 2 | 10 | 37 | 3 | 39 |
| rs11705401 | 13% | 37% | 2 | 4 | 2 | 50 | 19 | 25 |
| kgp2536097 | 74% | 41% | 14 | 8 | 6 | 48 | 3 | 23 |
| rs2109066 | 9% | 31% | 2 | 5 | 0 | 39 | 21 | 35 |
| kgp2877482 | 24% | 3% | 0 | 0 | 11 | 4 | 12 | 75 |
| kgp9775757 | 46% | 14% | 3 | 0 | 15 | 22 | 5 | 57 |
| kgp6601755 | 11% | 33% | 2 | 3 | 1 | 45 | 19 | 30 |
| kgp8598661 | 28% | 4% | 1 | 0 | 11 | 6 | 11 | 73 |
| rs2159327 | 9% | 31% | 2 | 5 | 0 | 39 | 20 | 35 |
| kgp2151888 | 43% | 12% | 3 | 0 | 13 | 19 | 6 | 60 |
| rs2289333 | 24% | 2% | 1 | 0 | 9 | 3 | 13 | 76 |
| kgp2471573 | 24% | 2% | 1 | 0 | 9 | 3 | 13 | 76 |
| kgp6870400 | 46% | 14% | 4 | 0 | 13 | 22 | 6 | 57 |
| kgp6850713 | 7% | 32% | 1 | 3 | 1 | 44 | 20 | 32 |
| kgp7851536 | 15% | 0% | 0 | 0 | 7 | 0 | 16 | 79 |
| kgp9348779 | 15% | 0% | 0 | 0 | 7 | 0 | 16 | 79 |
| rs995834 | 11% | 32% | 2 | 4 | 1 | 43 | 20 | 32 |
| rs1773631 | 27% | 7% | 0 | 2 | 12 | 7 | 10 | 70 |
| kgp8034516 | 20% | 3% | 0 | 1 | 9 | 2 | 14 | 76 |
| rs13280716 | 20% | 3% | 0 | 1 | 9 | 2 | 14 | 76 |
| kgp303315 | 20% | 3% | 0 | 1 | 9 | 2 | 14 | 76 |
| kgp5433489 | 20% | 3% | 0 | 1 | 9 | 2 | 14 | 76 |
| rs17707686 | 20% | 3% | 0 | 1 | 9 | 2 | 14 | 76 |
| rs727047 | 13% | 35% | 2 | 4 | 2 | 48 | 19 | 27 |
| kgp7521451 | 20% | 4% | 0 | 2 | 9 | 2 | 13 | 74 |
| rs2056136 | 35% | 9% | 1 | 1 | 14 | 12 | 8 | 66 |
| rs10746192 | 67% | 35% | 8 | 5 | 15 | 45 | 0 | 29 |
| rs2555629 | 61% | 25% | 11 | 4 | 6 | 32 | 6 | 43 |
| kgp12537012 | 20% | 3% | 0 | 1 | 9 | 2 | 14 | 75 |
| rs9969509 | 20% | 3% | 0 | 1 | 9 | 2 | 14 | 75 |
| kgp6535349 | 20% | 1% | 0 | 0 | 9 | 2 | 14 | 76 |
| rs16846841 | 17% | 1% | 0 | 0 | 8 | 1 | 15 | 78 |
| kgp12396787 | 17% | 1% | 0 | 0 | 8 | 1 | 15 | 77 |
| kgp4985243 | 33% | 7% | 1 | 0 | 13 | 11 | 9 | 68 |
| rs4935590 | 35% | 8% | 2 | 0 | 12 | 12 | 9 | 67 |
| rs16907220 | 35% | 8% | 2 | 0 | 12 | 12 | 9 | 67 |
| rs1073665 | 35% | 8% | 2 | 0 | 12 | 12 | 9 | 67 |
| rs2292275 | 57% | 27% | 4 | 6 | 18 | 30 | 1 | 42 |
| rs7962380 | 67% | 34% | 11 | 5 | 9 | 44 | 3 | 30 |
| kgp10638512 | 7% | 44% | 0 | 17 | 3 | 35 | 20 | 27 |

Example 13 Association Analyses Corrected for Ancestry

A Principal Components Analysis (PCA) was performed in order to investigate potential population stratification among cases and controls. Sample-specific Eigen values were calculated to produce an output of 1st and 2nd Principal Components which can be used to infer patient ancestry.

An association analysis was performed using an Additive Genetic Model with Principal Components Analysis correction for population stratification; results are presented in Table 32.

TABLE 32

Regression, Additive Model, Corrected for ancestry by PCA

| | | | | | Gala | | | FORTE | | |
|---|---|---|---|---|---|---|---|---|---|---|
| Name | Chr | Position | Gene(s) | Mutation | Gene Locations (s) | Regression P | Allele Freq. (Cases) | Allele Freq. (Controls) | Regression P | Allele Freq. (Cases) | Allele Freq. (Controls) |
| kgp24415 | 2 | 1.74E+08 | ? | ? | ? | 1.91E-05 | 0% | 5% | 1.28E-02 | 0% | 3% |
| kgp26026 | 13 | 79972606 | RBM26 | Silent | INTRON | 1.47E-04 | 0% | 3% | 2.92E-04 | 0% | 4% |
| kgp12008 | 2 | 73759636 | ALMS1 | Silent | INTRON | 1.49E-04 | 0% | 4% | 2.26E-04 | 1% | 6% |
| rs1688600 | 7 | 78021500 | MAGI2 | Silent | INTRON, E | 1.93E-03 | 20% | 11% | 3.01E-05 | 20% | 5% |
| kgp25952 | 13 | 80027089 | ? | | ? | 4.30E-04 | 0% | 3% | 2.86E-04 | 0% | 4% |
| kgp11141 | 20 | 35283733 | NDRG3, N | Silent, Sile | INTRON | 2.69E-03 | 2% | 7% | 3.18E-05 | 1% | 6% |
| kgp34508 | 16 | 57268931 | RSPRY1 | Silent | INTRON | 5.32E-03 | 1% | 4% | 1.47E-05 | 0% | 7% |
| kgp22996 | 20 | 16933074 | ? | ? | ? | 5.73E-03 | 2% | 5% | 3.71E-05 | 1% | 8% |
| kgp12230 | 5 | 27037978 | CDH9 | Silent | INTRON | 2.71E-03 | 1% | 5% | 7.14E-06 | 2% | 9% |
| kgp96273 | 17 | 90155 | RPH3AL, R | Silent, Sile | INTRON | 6.18E-04 | 10% | 21% | 3.96E-03 | 11% | 20% |

TABLE 32-continued

Regression, Additive Model, Corrected for ancestry by PCA

| | | | | | | Gala | | | FORTE | | |
|---|---|---|---|---|---|---|---|---|---|---|---|
| Name | Chr | Position | Gene(s) | Mutation | Gene Locations (s) | Regression P | Allele Freq. (Cases) | Allele Freq. (Controls) | Regression P | Allele Freq. (Cases) | Allele Freq. (Controls) |
| rs1025179 | 7 | 78025427 | MAGI2 | Silent | INTRON, E | 1.71E−03 | 20% | 11% | 3.76E−05 | 19% | 5% |
| rs2816838 | 10 | 52714759 | ? | ? | ? | 1.20E−03 | 14% | 25% | 1.38E−03 | 11% | 22% |
| kgp62369 | 2 | 60301030 | ? | ? | ? | 3.77E−04 | 31% | 44% | 4.52E−03 | 26% | 39% |
| kgp23563 | 16 | 19771577 | IQCK | Silent | INTRON | 1.76E−04 | 13% | 22% | 1.39E−03 | 14% | 26% |
| kgp77303 | 16 | 19740243 | IQCK | Silent | INTRON | 2.39E−04 | 13% | 22% | 1.06E−03 | 14% | 26% |
| kgp47058 | 12 | 19907696 | ? | ? | ? | 2.12E−05 | 30% | 47% | 3.99E−02 | 33% | 43% |
| rs7191155 | 16 | 19800213 | IQCK | Missense | EXON | 2.52E−04 | 12% | 22% | 1.18E−03 | 14% | 26% |
| kgp80307 | 8 | 6328607 | MCPH1 | Silent | INTRON | 1.62E−04 | 2% | 5% | 1.78E−05 | 1% | 7% |
| rs9931167 | 16 | 19792598 | IQCK | Silent | INTRON | 2.53E−04 | 12% | 22% | 1.39E−03 | 14% | 20% |
| rs7217872 | 17 | 88988 | RPH3AL, R | Silent, Sile | INTRON | 1.35E−03 | 11% | 20% | 3.00E−03 | 11% | 21% |
| rs1164812 | 16 | 19820694 | IQCK | Silent | INTRON | 3.15E−04 | 12% | 22% | 1.08E−03 | 14% | 26% |
| rs3829539 | 16 | 19722366 | C16orf88 | Silent | INTRON | 2.51E−04 | 12% | 22% | 1.40E−03 | 15% | 26% |
| rs2660214 | 10 | 52732452 | ? | ? | ? | 1.68E−03 | 14% | 23% | 1.84E−03 | 11% | 22% |
| rs6718758 | 2 | 60328802 | ? | ? | ? | 3.14E−03 | 33% | 45% | 4.38E−04 | 28% | 44% |
| kgp10594 | 1 | 2.16E+08 | USH2A | Silent | INTRON | 2.20E−05 | 0% | 5% | 2.84E−02 | 1% | 5% |
| rs1858973 | 16 | 19743649 | IQCK | Silent | INTRON | 3.15E−04 | 12% | 22% | 1.38E−03 | 15% | 26% |
| kgp88178 | 6 | 32744440 | ? | ? | ? | 6.70E−04 | 36% | 49% | 4.72E−04 | 42% | 60% |
| kgp38541 | 16 | 19721806 | C16orf88 | Silent | INTRON | 3.14E−04 | 12% | 22% | 1.29E−03 | 14% | 26% |
| kgp29794 | 10 | 18397332 | ? | ? | ? | 3.45E−03 | 2% | 7% | 2.96E−04 | 2% | 8% |
| rs543122 | 3 | 1.24E+08 | KALRN, KA | Silent, Sile | INTRON | 2.87E−05 | 41% | 57% | 1.56E−02 | 44% | 57% |
| kgp25216 | 1 | 23758427 | ASAP3, AS | Silent, Sile | INTRON | 1.03E−03 | 0% | 3% | 3.25E−03 | 0% | 3% |
| rs8055485 | 16 | 19750051 | IQCK | Silent | INTRON | 3.15E−04 | 12% | 22% | 1.51E−03 | 15% | 26% |
| rs9931211 | 16 | 19813605 | IQCK | Silent | INTRON | 3.15E−04 | 12% | 22% | 1.51E−03 | 15% | 26% |
| rs9817308 | 3 | 1.24E+08 | KALRN, KA | Silent, Sile | INTRON | 2.46E−05 | 41% | 58% | 3.14E−02 | 45% | 57% |
| kgp62143 | 11 | 75546691 | UVRAG | Silent | INTRON | 4.73E−03 | 5% | 11% | 1.34E−04 | 4% | 13% |
| rs9579566 | 13 | 30980265 | ? | ? | ? | 1.22E−04 | 2% | 8% | 1.55E−02 | 2% | 7% |
| kgp50683 | 16 | 19756348 | IQCK | Silent | INTRON | 1.52E−04 | 16% | 27% | 2.10E−03 | 20% | 34% |
| rs6497396 | 16 | 19735697 | IQCK | Silent | INTRON | 2.47E−04 | 13% | 23% | 1.48E−03 | 16% | 29% |
| rs7228827 | 18 | 76900411 | ATP98 | Silent | INTRON | 2.53E−04 | 21% | 11% | 8.65E−03 | 20% | 11% |
| rs950928 | 16 | 19824638 | IQCK | Silent | INTRON | 5.52E−04 | 13% | 22% | 1.64E−03 | 15% | 26% |
| rs7579987 | 2 | 60307009 | ? | ? | ? | 3.85E−03 | 36% | 47% | 4.94E−04 | 31% | 48% |
| kgp10305 | 11 | 99881768 | CNTN5, CN | Silent, Sile | INTRON | 3.08E−03 | 10% | 18% | 1.45E−03 | 7% | 16% |
| kgp10910 | 16 | 19803199 | IQCK | Silent | INTRON | 4.44E−04 | 12% | 21% | 1.39E−03 | 14% | 26% |
| kgp16887 | 21 | 43016736 | ? | ? | ? | 1.94E−03 | 5% | 11% | 3.96E−03 | 3% | 11% |
| kgp11002 | 11 | 1.18E+08 | CD3G | Silent | INTRON | 4.13E−03 | 1% | 3% | 2.94E−04 | 0% | 4% |
| rs6895094 | 5 | 1.41E+08 | ARAP3 | Silent | INTRON | 6.18E−04 | 38% | 52% | 1.33E−02 | 35% | 48% |
| rs2074037 | 16 | 19725130 | C16orf88 | Silent | INTRON | 5.92E−04 | 13% | 22% | 1.25E−03 | 14% | 26% |
| kgp27000 | 16 | 19750275 | IQCK | Silent | INTRON | 2.51E−04 | 13% | 23% | 2.90E−03 | 15% | 28% |

| | COMBINED | | | | | | | | |
|---|---|---|---|---|---|---|---|---|---|
| Name | Regression P | Allele Freq. (Cases) | Allele Freq. (Controls) | DD (Cases) | DD (Control) | Dd (Cases) | Dd (Control) | dd (Cases) | dd (Control) |
| kgp24415 | 2.24E−07 | 0% | 4% | 0 | 0 | 3 | 16 | 396 | 165 |
| kgp26026 | 2.54E−07 | 0% | 4% | 0 | 0 | 1 | 13 | 397 | 167 |
| kgp12008 | 6.38E−07 | 0% | 4% | 0 | 0 | 3 | 16 | 396 | 165 |
| rs1688600 | 8.60E−07 | 20% | 9% | 6 | 2 | 147 | 28 | 246 | 149 |
| kgp25952 | 8.77E−07 | 0% | 3% | 0 | 0 | 1 | 12 | 398 | 168 |
| kgp11141 | 9.79E−07 | 1% | 6% | 0 | 1 | 11 | 21 | 388 | 158 |
| kgp34508 | 1.26E−06 | 1% | 5% | 0 | 0 | 5 | 17 | 394 | 164 |
| kgp22996 | 1.48E−06 | 1% | 6% | 0 | 0 | 11 | 23 | 388 | 158 |
| kgp12230 | 1.71E−06 | 1% | 6% | 0 | 0 | 10 | 22 | 386 | 159 |
| kgp96273 | 1.87E−06 | 10% | 21% | 6 | 7 | 71 | 61 | 320 | 113 |
| rs1025179 | 1.98E−06 | 20% | 9% | 6 | 2 | 145 | 29 | 248 | 150 |
| rs2816838 | 2.41E−06 | 13% | 23% | 4 | 8 | 92 | 67 | 303 | 106 |
| kgp62369 | 2.86E−06 | 28% | 42% | 30 | 34 | 166 | 85 | 203 | 62 |
| kgp23563 | 2.92E−06 | 13% | 23% | 4 | 5 | 98 | 75 | 297 | 101 |
| kgp77303 | 3.08E−06 | 13% | 23% | 4 | 5 | 99 | 74 | 295 | 101 |
| kgp47058 | 3.44E−06 | 31% | 46% | 41 | 38 | 169 | 89 | 189 | 54 |
| rs7191155 | 4.02E−06 | 13% | 23% | 4 | 5 | 97 | 74 | 295 | 101 |
| kgp80307 | 4.03E−06 | 1% | 6% | 0 | 1 | 9 | 18 | 388 | 162 |
| rs9931167 | 4.16E−06 | 13% | 23% | 4 | 5 | 98 | 74 | 297 | 101 |
| rs7217872 | 4.20E−06 | 11% | 21% | 6 | 7 | 74 | 61 | 319 | 113 |
| rs1164812 | 4.25E−06 | 13% | 23% | 4 | 5 | 97 | 74 | 297 | 102 |
| rs3829539 | 4.53E−06 | 13% | 23% | 4 | 5 | 98 | 74 | 296 | 101 |

TABLE 32-continued

Regression, Additive Model, Corrected for ancestry by PCA

| Name | Chr Position | Gene(s) | Mutation | Gene Locations (s) | Gala | | | FORTE | | |
|---|---|---|---|---|---|---|---|---|---|---|
| | | | | | Regression P | Allele Freq. (Cases) | Allele Freq. (Controls) | Regression P | Allele Freq. (Cases) | Allele Freq. (Controls) |
| rs2660214 | 4.68E−06 | 13% | 23% | 4 | 8 | 94 | 66 | 301 | 107 | |
| rs6718758 | 4.69E−06 | 31% | 44% | 35 | 38 | 175 | 85 | 189 | 58 | |
| kgp10594 | 4.94E−06 | 1% | 5% | 0 | 0 | 6 | 18 | 391 | 163 | |
| rs1858973 | 5.09E−06 | 13% | 23% | 4 | 5 | 99 | 74 | 295 | 102 | |
| kgp88178 | 5.13E−06 | 39% | 53% | 50 | 44 | 208 | 103 | 135 | 34 | |
| kgp38541 | 5.23E−06 | 13% | 23% | 4 | 5 | 98 | 74 | 297 | 102 | |
| kgp29794 | 5.49E−06 | 2% | 7% | 0 | 0 | 16 | 26 | 382 | 155 | |
| rs543122 | 5.65E−06 | 42% | 57% | 70 | 54 | 195 | 97 | 131 | 29 | |
| kgp25216 | 5.69E−06 | 0% | 3% | 0 | 0 | 2 | 12 | 397 | 169 | |
| rs8055485 | 5.77E−06 | 13% | 23% | 4 | 5 | 98 | 74 | 296 | 102 | |
| rs9931211 | 5.77E−06 | 13% | 23% | 4 | 5 | 98 | 74 | 296 | 102 | |
| rs9817308 | 5.89E−06 | 43% | 57% | 71 | 55 | 199 | 96 | 127 | 29 | |
| kgp62143 | 6.31E−06 | 5% | 12% | 0 | 2 | 37 | 39 | 361 | 140 | |
| rs9579566 | 6.66E−06 | 2% | 8% | 0 | 1 | 18 | 27 | 381 | 153 | |
| kgp50683 | 6.70E−06 | 18% | 29% | 10 | 12 | 126 | 82 | 262 | 86 | |
| rs6497396 | 6.74E−06 | 14% | 25% | 6 | 6 | 102 | 77 | 290 | 98 | |
| rs7228827 | 6.90E−06 | 21% | 11% | 20 | 1 | 124 | 37 | 254 | 143 | |
| rs950928 | 6.96E−06 | 14% | 24% | 4 | 5 | 102 | 75 | 293 | 100 | |
| rs7579987 | 7.14E−06 | 33% | 47% | 40 | 41 | 184 | 87 | 175 | 52 | |
| kgp10305 | 7.23E−06 | 8% | 17% | 3 | 6 | 61 | 50 | 334 | 123 | |
| kgp10910 | 7.43E−06 | 13% | 23% | 4 | 5 | 98 | 73 | 297 | 102 | |
| kgp16887 | 7.70E−06 | 4% | 11% | 1 | 2 | 30 | 37 | 368 | 142 | |
| kgp11002 | 8.07E−06 | 0% | 4% | 0 | 0 | 3 | 13 | 394 | 167 | |
| rs6895094 | 8.17E−06 | 37% | 51% | 56 | 46 | 181 | 92 | 161 | 43 | |
| rs2074037 | 8.40E−06 | 14% | 23% | 4 | 5 | 101 | 73 | 294 | 101 | |
| kgp27000 | 8.56E−06 | 14% | 24% | 6 | 6 | 102 | 76 | 291 | 98 | |

Example 14 Regression Analysis

Regression analysis was conducted using an additive genetic model to identify additional clinical and genetic variants that are highly associated with response after correction for the most significantly associated variables.

For clinical factors, regression analyses revealed two highly associated clinical covariates: "Log number of relapses in the last two years" significantly associated with response to glatiramer acetate (combined cohorts p-value $3.6 \times 10^{-32}$, odds ratio 14.5 (95% CI 8.6-24.4)) and "Baseline Expanded Disability Status Scale (EDSS) Score" (combined cohorts p-value $5.9 \times 10^{-10}$, odds ratio 0.62 (95% CI 8.6-24.4)) with higher baseline EDSS scores (increased MS disability) associated with increased likelihood of non-response to glatiramer acetate. Importantly, these clinical factors were significantly associated with glatiramer acetate response in both the GALA and FORTE patient cohorts.

TABLE 33

Clinical co-variates associated with response to glatiramer acetate.

| Variable | GALA cohort (N = 318) | | | FORTE cohort (N = 262) | | | COMBINED cohorts (N = 580) | | |
|---|---|---|---|---|---|---|---|---|---|
| | Odds Ratio | (95% CI) | P-Value | Odds Ratio | (95% CI) | P-Value | Odds Ratio | (95% CI) | P-Value |
| Log of No. of Relapses in Last 2 Years | 16.78 | 8.4-33.4 | 2.3E−21 | 53.19 | 14.8-191.7 | 1.4E−11 | 14.50 | 8.6-24.4 | 3.6E−32 |
| Baseline EDSS Score | 0.62 | 0.5-0.8 | 3.0E−06 | 0.71 | 0.5-0.9 | 0.010 | 0.62 | 0.5-0.7 | 5.9E−10 |
| Age | 0.97 | 0.9-1.0 | 0.034 | 0.98 | 0.9-1.0 | 0.22 | 0.97 | 1.0-1.0 | 0.012 |
| PCA Component 3 (EV = 2.41024) | Inf. | | 0.06 | Inf. | | 0.07 | Infinity | | 0.017 |
| No. of Gd-T1 Lesions at Baseline | 0.97 | 0.9-1.0 | 0.10 | 0.96 | 0.9-1.0 | 0.11 | 0.97 | 0.9-1.0 | 0.034 |

Results of regression analyses for the Additive Models are presented in Tables 34-37.

In some embodiments, all of the genetic markers presented in Tables 34-37 are identified as predictive of response to glatiramer acetate.

TABLE 34

Regression Analysis, Additive Model (Gala cohort)

| Predictor | Chr | Position | Gene | COMBINED P-Value | Odds Ratio |
|---|---|---|---|---|---|
| rs16886004 | 7 | 78021500 | MAGI2 | 3.10E−07 | 2.79 |
| kgp26026546 | 13 | 79972606 | | 7.45E−07 | 0.03 |
| rs10251797 | 7 | 78025427 | MAGI2 | 7.93E−07 | 2.67 |
| kgp8110667 | 22 | 32716792 | | 9.48E−07 | Infinity |
| kgp11210241 | 3 | 38537237 | | 9.74E−07 | Infinity |
| rs17687961 | 22 | 32716927 | | 9.74E−07 | Infinity |
| kgp12008955 | 2 | 73759636 | | 1.08E−06 | 0.08 |
| kgp24415534 | 2 | 1.74E+08 | | 1.08E−06 | 0.08 |
| kgp5976729 | 22 | 32675303 | | 2.12E−06 | Infinity |
| kgp25952891 | 13 | 80027089 | | 2.38E−06 | 0.04 |
| rs543122 | 3 | 1.24E+08 | | 2.81E−06 | 0.54 |
| kgp6236949 | 2 | 60301030 | | 3.70E−06 | 0.54 |
| rs9817308 | 3 | 1.24E+08 | | 4.60E−06 | 0.55 |
| kgp10372946 | 10 | 1.34E+08 | | 4.62E−06 | 0.53 |
| kgp8817856 | 6 | 32744440 | | 4.90E−06 | 0.53 |
| kgp11328629 | 10 | 1.21E+08 | | 5.02E−06 | 2.95 |
| kgp4705854 | 12 | 19907696 | | 5.19E−06 | 0.55 |
| rs4143493 | 6 | 51829939 | | 5.24E−06 | 4.21 |
| kgp3450875 | 16 | 57268931 | | 5.60E−06 | 0.12 |
| kgp1688752 | 21 | 43016736 | | 5.79E−06 | 0.33 |
| kgp9627338 | 17 | 90155 | | 6.00E−06 | 0.45 |
| rs17577980 | 6 | 32359821 | | 6.15E−06 | 2.36 |
| kgp3418770 | 10 | 59425598 | | 6.31E−06 | 10.31 |
| kgp2299675 | 20 | 16933074 | | 6.55E−06 | 0.19 |
| rs6718758 | 2 | 60328802 | | 6.61E−06 | 0.55 |
| rs7579987 | 2 | 60307009 | | 6.71E−06 | 0.55 |
| kgp10594414 | 1 | 2.16E+08 | | 6.80E−06 | 0.14 |
| rs10498793 | 6 | 51829707 | | 7.20E−06 | 4.14 |
| rs2816838 | 10 | 52714759 | | 7.32E−06 | 0.46 |
| kgp12230354 | 5 | 27037978 | | 7.64E−06 | 0.19 |
| rs13394010 | 2 | 60302746 | | 8.16E−06 | 0.56 |
| rs11029892 | 11 | 27269546 | | 8.23E−06 | 1.94 |
| kgp2356388 | 16 | 19771577 | | 8.28E−06 | 0.46 |
| rs11691553 | 2 | 60303554 | | 8.55E−06 | 0.56 |
| kgp5564995 | 6 | 26414060 | | 9.08E−06 | 2.88 |
| rs6895094 | 5 | 1.41E+08 | | 9.18E−06 | 0.57 |
| kgp10352965 | 7 | 30647900 | | 9.40E−06 | 7.44 |
| kgp26116630 | 6 | 48158833 | | 9.42E−06 | 16.38 |
| kgp7059449 | 2 | 41255455 | | 9.98E−06 | 4.93 |
| rs10203396 | 2 | 60305110 | | 1.01E−05 | 0.56 |
| kgp11843177 | 11 | 27316568 | | 1.01E−05 | 1.95 |
| rs9579566 | 13 | 30980265 | | 1.04E−05 | 0.26 |
| kgp11141512 | 20 | 35283733 | | 1.06E−05 | 0.21 |

TABLE 35

Regression Analysis, Additive Model Corrected for Log Relapse and EDSS (Gala, Forte, Combined cohorts)

| Name | Chromosome | Position | Gene(s) | Mutation | Gene Locations (s) | GALA P-value* | Odds Ratio | FORTE P-value* | Odds Ratio | COMBINED P-value* | Odds Ratio |
|---|---|---|---|---|---|---|---|---|---|---|---|
| kgp8817856 | 6 | 32744440 | ? | ? | ? | 8.04E−29 | 0.48 | 1.18E−16 | 0.32 | 9.16E−43 | 0.39 |
| rs454748 | 6 | 32213210 | ? | ? | ? | 1.60E−30 | 2.32 | 4.89E−14 | 1.78 | 6.67E−42 | 2.16 |
| kgp5447044 | 6 | 26501768 | BTN1A1 | Silent | INTRON | 2.47E−29 | 0.31 | 2.37E−14 | 0.41 | 1.55E−41 | 0.35 |
| rs16901784 | 6 | 26555433 | ? | ? | ? | 1.19E−29 | 0.29 | 2.19E−14 | 0.40 | 1.64E−41 | 0.34 |
| rs2143466 | 6 | 32309323 | C6orf10 | Silent | INTRON | 6.41E−30 | 2.18 | 6.55E−14 | 1.75 | 1.88E−41 | 2.10 |
| kgp9938485 | 6 | 27021173 | ? | ? | ? | 4.37E−29 | 0.42 | 5.52E−14 | 0.50 | 2.22E−41 | 0.42 |
| rs3799383 | 6 | 26510748 | ? | ? | ? | 3.25E−29 | 0.31 | 2.37E−14 | 0.41 | 2.65E−41 | 0.34 |
| rs4897704 | 8 | 1.35E+08 | ? | ? | ? | 6.20E−32 | 2.67 | 7.64E−14 | 1.72 | 2.78E−41 | 2.05 |
| kgp3478190 | 8 | 69080975 | PREX2 | Silent | INTRON | 2.18E−29 | 2.07 | 4.90E−14 | 1.95 | 2.80E−41 | 2.09 |
| rs2820263 | 6 | 1.05E+08 | ? | ? | ? | 8.15E−29 | 1.80 | 1.40E−15 | 2.53 | 2.82E−41 | 2.09 |
| kgp12230354 | 5 | 27037978 | CDH9 | Silent | INTRON | 1.39E−28 | 0.13 | 5.86E−15 | 0.13 | 2.82E−41 | 0.12 |

TABLE 35-continued

Regression Analysis, Additive Model Corrected for Log Relapse and EDSS (Gala, Forte, Combined cohorts)

| Name | Chromo-some | Position | Gene(s) | Mutation | Gene Locations(s) | GALA P-value* | GALA Odds Ratio | FORTE P-value* | FORTE Odds Ratio | COMBINED P-value* | COMBINED Odds Ratio |
|---|---|---|---|---|---|---|---|---|---|---|---|
| rs9393727 | 6 | 26500011 | ? | ? | ? | 2.92E−29 | 0.31 | 2.87E−14 | 0.41 | 3.25E−41 | 0.34 |
| kgp31017880 | X | 97136288 | ? | ? | ? | 3.71E−30 | 19.90 | 5.62E−14 | Infinity | 3.34E−41 | 24.31 |
| kgp3438641 | 5 | 98186154 | ? | ? | ? | 1.24E−29 | 4.24 | 6.31E−15 | 7.61 | 3.46E−41 | 4.51 |
| kgp12113592 | 5 | 98160214 | ? | ? | ? | 2.07E−29 | 4.18 | 6.70E−15 | 7.53 | 3.54E−41 | 4.45 |
| rs9650120 | 8 | 1.35E+08 | ? | ? | ? | 6.72E−31 | 2.55 | 3.20E−14 | 1.90 | 4.40E−41 | 2.08 |
| kgp3931548 | 5 | 98146468 | ? | ? | ? | 1.51E−29 | 4.17 | 6.31E−15 | 7.61 | 4.59E−41 | 4.45 |
| rs727637 | 5 | 98213991 | CHD1 | Silent | INTRON | 1.51E−29 | 4.17 | 6.31E−15 | 7.61 | 4.59E−41 | 4.45 |
| kgp1892256 | 5 | 98257441 | CHD1 | Silent | INTRON | 1.51E−29 | 4.17 | 6.31E−15 | 7.61 | 4.59E−41 | 4.45 |
| rs9501224 | 6 | 32792910 | TAP2 | Silent | INTRON | 5.89E−29 | 2.07 | 7.52E−16 | 3.15 | 4.80E−41 | 2.24 |
| kgp11199573 | 2 | 2.02E+08 | ? | ? | ? | 4.05E−29 | 2.00 | 5.40E−15 | 2.23 | 4.97E−41 | 2.04 |
| kgp7903189 | 5 | 98229104 | CHD1 | Silent | INTRON | 1.15E−29 | 3.43 | 5.21E−15 | 7.77 | 5.73E−41 | 3.90 |
| rs2820259 | 6 | 1.05E+08 | ? | ? | ? | 7.65E−29 | 1.80 | 8.55E−15 | 2.20 | 5.90E−41 | 1.99 |
| rs2857103 | 6 | 32791299 | TAP2 | Silent | INTRON | 5.55E−29 | 2.13 | 7.52E−16 | 3.15 | 6.22E−41 | 2.27 |
| kgp9421884 | 19 | 11049860 | ? | ? | ? | 8.34E−28 | 0.39 | 1.80E−15 | 0.24 | 6.64E−41 | 0.29 |
| rs6920256 | 6 | 26537801 | ? | ? | ? | 8.77E−29 | 0.35 | 2.37E−14 | 0.41 | 6.74E−41 | 0.36 |
| kgp1688752 | 21 | 43016736 | ? | ? | ? | 7.35E−30 | 0.22 | 2.38E−14 | 0.30 | 7.23E−41 | 0.28 |
| kgp6754792 | 6 | 26456074 | ? | ? | ? | 1.63E−29 | 0.25 | 1.45E−13 | 0.49 | 7.65E−41 | 0.34 |
| kgp95865 | 9 | 14204068 | NFIB, NFIB | Silent, Silen | INTRON | 6.17E−29 | 3.29 | 2.80E−14 | 4.31 | 7.69E−41 | 3.78 |
| rs241451 | 6 | 32796480 | TAP2, TAP2 | Silent, Silen | INTRON | 6.05E−29 | 2.11 | 2.29E−15 | 2.80 | 8.11E−41 | 2.15 |

TABLE 36

Regression Analysis, Additive Model Corrected for top SNP rs1686004 (Gala, Forte, and Combined cohorts)

| Name | Chr | Position | Gene(s) | Mutation | Gene Locations(s) | GALA P-value | GALA Odds Ratio | FORTE P-value | FORTE Odds Ratio | COMBINED P-value | COMBINED Odds Ratio |
|---|---|---|---|---|---|---|---|---|---|---|---|
| kgp6996560 | 13 | 110124242 | ? | ? | ? | 6.61E−05 | 0.17 | 2.43E−08 | 0.02 | 2.03E−11 | 0.09 |
| rs4143493 | 6 | 51829939 | PKHD1, PKHD1 | Silent, Silent | INTRON | 8.56E−05 | 3.34 | 3.58E−08 | 8.13 | 2.15E−11 | 4.60 |
| kgp28541695 | 15 | 24985550 | ? | ? | ? | 4.99E−07 | ~Infinity | 2.77E−06 | 5.87 | 2.93E−11 | 17.52 |
| rs10498793 | 6 | 51829707 | PKHD1, PKHD1 | Silent, Silent | INTRON | 8.56E−05 | 3.34 | 5.18E−08 | 7.78 | 3.18E−11 | 4.50 |
| kgp4705854 | 12 | 19907696 | ? | ? | ? | 6.52E−07 | 0.47 | 3.84E−06 | 0.64 | 3.31E−11 | 0.53 |
| kgp6236949 | 2 | 60301030 | ? | ? | ? | 2.13E−05 | 0.55 | 7.45E−07 | 0.53 | 3.61E−11 | 0.53 |
| kgp12230354 | 5 | 27037978 | CDH9 | Silent | INTRON | 8.6E−05 | 0.18 | 1.21E−08 | 0.10 | 3.62E−11 | 0.16 |
| kgp29794723 | 10 | 18397332 | ? | ? | ? | 6.52E−05 | 0.26 | 5.1E−08 | 0.13 | 3.63E−11 | 0.20 |
| kgp971582 | 6 | 51921703 | PKHD1, PKHD1 | Synonymous_N529N, Synonymous_N529N | EXON | 4.38E−05 | 3.35 | 1.51E−07 | 5.24 | 4.17E−11 | 3.96 |
| kgp4812831 | 6 | 51910905 | PKHD1, PKHD1 | Missense_N830S, Missense_N830S | EXON | 4.38E−05 | 3.35 | 1.63E−07 | 5.34 | 4.7E−11 | 3.99 |
| kgp4162414 | 6 | 51868165 | PKHD1, PKHD1 | Silent, Silent | INTRON | 5.42E−05 | 3.29 | 1.63E−07 | 5.34 | 5.5E−11 | 3.96 |
| kgp2688306 | 7 | 28560259 | CREB5, CREB5, CREB5 | Silent, Silent, Silent | INTRON | 1.25E−05 | 3.03 | 4.92E−07 | 3.62 | 5.55E−11 | 3.15 |
| rs7579987 | 2 | 60307009 | ? | ? | ? | 0.000169 | 0.62 | 5.22E−08 | 0.44 | 5.73E−11 | 0.54 |
| kgp9627338 | 17 | 90155 | RPH3AL, RPH3AL, RPH3AL, RPH3AL | Silent, Silent, Silent, Silent | INTRON | 9.23E−06 | 0.44 | 1.19E−06 | 0.45 | 5.92E−11 | 0.44 |
| kgp11328629 | 10 | 120711084 | ? | ? | ? | 5.3E−05 | 2.68 | 9.89E−08 | 4.12 | 6.08E−11 | 3.07 |
| rs2816838 | 10 | 52714759 | ? | ? | ? | 5.23E−05 | 0.50 | 2.7E−07 | 0.40 | 6.29E−11 | 0.45 |
| kgp24415534 | 2 | 174156875 | ? | ? | ? | 1.71E−06 | 0.05 | 5.58E−06 | 0.21 | 6.85E−11 | 0.09 |
| rs10203396 | 2 | 60305110 | ? | ? | ? | 0.000191 | 0.63 | 5.5E−08 | 0.44 | 7.36E−11 | 0.54 |
| rs13394010 | 2 | 60302746 | ? | ? | ? | 0.000193 | 0.63 | 5.22E−08 | 0.44 | 7.44E−11 | 0.54 |
| rs6718758 | 2 | 60328802 | ? | ? | ? | 0.000165 | 0.63 | 8.83E−08 | 0.45 | 7.74E−11 | 0.54 |
| rs11691553 | 2 | 60303554 | ? | ? | ? | 0.000235 | 0.63 | 4.41E−08 | 0.44 | 7.92E−11 | 0.54 |
| kgp1009249 | 12 | 19838534 | ? | ? | ? | 1.96E−06 | 0.43 | 2.46E−06 | 0.56 | 8.26E−11 | 0.49 |
| rs13419758 | 2 | 60302920 | ? | ? | ? | 0.000177 | 0.63 | 7.51E−08 | 0.45 | 8.34E−11 | 0.55 |
| kgp9320791 | 2 | 60309952 | ? | ? | ? | 0.000191 | 0.63 | 6.84E−08 | 0.45 | 9.04E−11 | 0.55 |
| rs11029892 | 11 | 27269546 | ? | ? | ? | 6.68E−05 | 1.82 | 1.98E−07 | 2.22 | 9.28E−11 | 1.98 |
| kgp2350730 | 1 | 88444077 | ? | ? | ? | 2.24E−06 | 4.82 | 3.98E−06 | 2.43 | 9.28E−11 | 3.62 |
| kgp8192546 | 12 | 19903173 | ? | ? | ? | 5.84E−07 | 0.43 | 4.85E−06 | 0.64 | 9.46E−11 | 0.52 |
| rs17165909 | 7 | 93551606 | GNG11 | Silent | INTRON | 0.000131 | 5.91 | 4.06E−08 | ~Infinity | 9.49E−11 | 10.50 |
| rs10841337 | 12 | 19897179 | ? | ? | ? | 3.73E−07 | 0.43 | 5.67E−06 | 0.68 | 9.49E−11 | 0.53 |

TABLE 36-continued

Regression Analysis, Additive Model Corrected for top SNP rs1686004 (Gala, Forte, and Combined cohorts)

| | | | | | | GALA | | FORTE | | COMBINED | |
|---|---|---|---|---|---|---|---|---|---|---|---|
| Name | Chr | Position | Gene(s) | Mutation | Gene Locations(s) | P-value | Odds Ratio | P-value | Odds Ratio | P-value | Odds Ratio |
| rs7217872 | 17 | 88988 | RPH3AL, RPH3AL, RPH3AL, RPH3AL | Silent, Silent, Silent, Silent | INTRON | 2.06E−05 | 0.46 | 4.59E−07 | 0.44 | 1.01E−10 | 0.45 |
| rs17638791 | 6 | 51940816 | PKHD1, PKHD1 | Silent, Silent | INTRON | 7.65E−05 | 3.02 | 1.63E−07 | 5.34 | 1.07E−10 | 3.67 |
| rs10841322 | 12 | 19866642 | ? | ? | ? | 2.66E−07 | 0.42 | 1.04E−05 | 0.71 | 1.1E−10 | 0.52 |
| kgp3933330 | 7 | 28583709 | CREB5, CREB5, CREB5 | Silent, Silent, Silent | INTRON | 4.2E−06 | 2.52 | 1.52E−06 | 2.41 | 1.16E−10 | 2.40 |
| kgp10305127 | 11 | 99881768 | CNTN5, CNTN5, CNTN5, CNTN5 | Silent, Silent, Silent, Silent | INTRON, EXON | 0.000109 | 0.49 | 2.85E−07 | 0.34 | 1.25E−10 | 0.41 |
| kgp6507761 | 7 | 319681 | ? | ? | ? | 0.000227 | 0.65 | 1.06E−07 | 0.49 | 1.25E−10 | 0.57 |
| kgp7506434 | 1 | 13823114 | LRRC38 | Silent | INTRON | 4.04E−05 | 0.10 | 7.69E−07 | 0.08 | 1.26E−10 | 0.08 |
| rs11022778 | 11 | 13390860 | ARNTL, ARNTL, ARNTL | Silent, Silent, Silent | INTRON | 1.4E−05 | 1.98 | 2.46E−06 | 1.70 | 1.26E−10 | 1.91 |
| kgp5908616 | 2 | 60329823 | ? | ? | ? | 0.0002 | 0.64 | 1.12E−07 | 0.46 | 1.27E−10 | 0.56 |
| kgp12122821 | 6 | 51938210 | PKHD1, PKHD1 | Silent, Silent | INTRON | 7.65E−05 | 3.02 | 1.93E−07 | 5.16 | 1.29E−10 | 3.61 |
| kgp10594414 | 1 | 216039833 | USH2A | Silent | INTRON | 1.05E−06 | 0.05 | 3.23E−06 | 0.26 | 1.31E−10 | 0.14 |

TABLE 37

Regression Analysis, Additive Model Corrected for rs1686004 + Log Relapse + EDSS (Gala, Forte, and Combined cohorts)

| | | | | | Gene | GALA | | FORTE | | COMBINED | |
|---|---|---|---|---|---|---|---|---|---|---|---|
| Name | Chr | Position | Gene(s) | Mutation | Locations (s) | P-value | Odds Ratio | P-value | Odds Ratio | P-value | Odds Ratio |
| kgp8817856 | 6 | 32744440 | HLA | ? | ? | 2.41E−28 | 0.49 | 1.01E−19 | 0.32 | 7.56E−45 | 0.40 |
| kgp3438641 | 5 | 98186154 | ? | ? | ? | 1.57E−29 | 4.50 | 9.08E−20 | 13.26 | 8.62E−45 | 5.49 |
| kgp12113592 | 5 | 98160214 | ? | ? | ? | 2.60E−29 | 4.43 | 1.18E−19 | 13.10 | 1.06E−44 | 5.40 |
| kgp3931548 | 5 | 98146468 | ? | ? | ? | 1.96E−29 | 4.42 | 9.08E−20 | 13.26 | 1.26E−44 | 5.39 |
| rs727637 | 5 | 98213991 | CHD1 | Silent | INTRON | 1.96E−29 | 4.42 | 9.08E−20 | 13.26 | 1.26E−44 | 5.39 |
| kgp1892256 | 5 | 98257441 | CHD1 | Silent | INTRON | 1.96E−29 | 4.42 | 9.08E−20 | 13.26 | 1.26E−44 | 5.39 |
| kgp31017880 | X | 97136288 | ? | ? | ? | 3.74E−30 | 22.62 | 1.58E−17 | Inf. | 1.59E−44 | 31.18 |
| kgp12230354 | 5 | 27037978 | CHD9 | Silent | INTRON | 1.36E−28 | 0.11 | 5.47E−19 | 0.09 | 1.60E−44 | 0.10 |
| kgp3478190 | 8 | 69080975 | PREX2 | Silent | INTRON | 2.47E−29 | 2.14 | 2.07E−18 | 2.34 | 1.67E−44 | 2.22 |
| kgp7903189 | 5 | 98229104 | CHD1 | Silent | INTRON | 1.71E−29 | 3.60 | 8.77E−20 | 13.26 | 2.01E−44 | 4.68 |
| rs11956636 | 5 | 98159347 | ? | ? | ? | 2.82E−29 | 4.27 | 9.46E−20 | 13.27 | 2.81E−44 | 5.21 |
| kgp11841858 | 5 | 98284488 | ? | ? | ? | 1.46E−29 | 3.84 | 1.83E−18 | 7.04 | 4.78E−44 | 4.38 |
| kgp409852 | 5 | 98142161 | ? | ? | ? | 1.96E−29 | 4.42 | 6.53E−19 | 7.99 | 5.38E−44 | 4.73 |
| rs1434781 | 8 | 69066793 | PREX2 | Silent | INTRON | 4.93E−29 | 2.05 | 3.59E−18 | 2.21 | 6.24E−44 | 2.12 |
| rs2143466 | 6 | 32309323 | C6orf10 | Silent | INTRON | 1.87E−29 | 2.13 | 1.04E−17 | 1.95 | 6.35E−44 | 2.12 |
| rs454748 | 6 | 32213210 | ? | ? | ? | 6.95E−30 | 2.24 | 1.19E−17 | 1.87 | 6.51E−44 | 2.10 |
| rs2217788 | 8 | 69064811 | PREX2 | Silent | INTRON | 4.02E−29 | 2.08 | 4.53E−18 | 2.22 | 7.01E−44 | 2.14 |
| rs2820263 | 6 | 1.05E+08 | ? | ? | ? | 2.80E−28 | 1.71 | 1.22E−19 | 2.75 | 7.49E−44 | 2.11 |
| rs17166414 | 5 | 98202363 | CHD1 | Silent | INTRON | 4.48E−29 | 4.14 | 9.87E−19 | 9.98 | 8.17E−44 | 4.82 |
| rs4713208 | 6 | 29283579 | ? | ? | ? | 6.45E−33 | 0.26 | 1.83E−16 | 1.11 | 8.43E−44 | 0.47 |
| rs720831 | 6 | 29284518 | ? | ? | ? | 6.45E−33 | 0.26 | 1.83E−16 | 1.11 | 8.43E−44 | 0.47 |
| kgp9832356 | 5 | 98262916 | ? | ? | ? | 4.48E−29 | 4.14 | 5.42E−19 | 10.27 | 9.52E−44 | 4.86 |
| kgp5447044 | 6 | 26501768 | BTN1A1 | Silent | INTRON | 7.65E−29 | 0.33 | 7.91E−18 | 0.43 | 9.64E−44 | 0.36 |
| rs2820259 | 6 | 1.05E+08 | ? | ? | ? | 2.31E−28 | 1.71 | 3.55E−19 | 2.54 | 9.66E−44 | 2.02 |
| rs16901784 | 6 | 26555433 | ? | ? | ? | 4.13E−29 | 0.31 | 6.44E−18 | 0.42 | 1.12E−43 | 0.35 |
| kgp4356222 | 5 | 98105883 | RGMB, FLJ | Silent, Sile | INTRON, EXON | 2.19E−29 | 4.75 | 2.36E−18 | 7.77 | 1.20E−43 | 5.03 |
| rs4897704 | 8 | 1.35E+08 | ? | ? | ? | 3.72E−31 | 2.54 | 1.23E−17 | 1.89 | 1.23E−43 | 2.04 |
| kgp4269732 | 5 | 98275939 | ? | ? | ? | 4.48E−29 | 4.14 | 6.76E−19 | 10.25 | 1.29E−43 | 4.86 |
| kgp9938485 | 6 | 27021173 | ? | ? | ? | 9.70E−29 | 0.43 | 3.85E−17 | 0.57 | 1.45E−43 | 0.44 |
| kgp6703510 | 5 | 98296594 | ? | ? | ? | 7.60E−29 | 3.91 | 5.36E−19 | 10.26 | 1.46E−43 | 4.73 |
| kgp3203641 | 5 | 98245912 | CHD1 | Silent | INTRON | 4.48E−29 | 4.14 | 7.05E−19 | 10.23 | 1.54E−43 | 4.86 |
| kgp11324749 | 8 | 69066259 | PREX2 | Silent | INTRON | 6.00E−29 | 2.04 | 4.09E−18 | 2.23 | 1.64E−43 | 2.12 |
| rs7737398 | 5 | 97974536 | ? | ? | ? | 9.10E−30 | 5.46 | 8.14E−18 | 4.88 | 1.64E−43 | 4.77 |

Example 15 Selection of Genetic Markers Predictive of Response to Glatiramer Acetate Based on the analyses above, genetic markers were selected as Predictive of Response to Glatiramer Acetate based on the following p-value thresholds: Priority candidate variants: P<0.05 (combined cohorts); Priority Genes: Replicated P<0.05 in both cohorts; GWAS: P<10-4 (combined cohorts); and Placebo P<10-4 (placebo cohort).

The selected genetic markers are presented in Tables 38-41. Alleles associated with response are highlighted.

TABLE 38

Standard Response SNPs

| | STANDARD PHENOTYPE | | | | | | | Gala Cohort | | | | Forte Cohort | | | |
|---|---|---|---|---|---|---|---|---|---|---|---|---|---|---|---|
| Prioritized Variants | Name | Chromosome | Position | Gene(s) | Major Allele (d) | Minor Allele (D) | P-value (Armitage Test) | Odds Ratio (Minor Allele) | Minor Allele Freq. (Responders) | Allele Freq. (Non-Responders) | P-value (Armitage Test) | Odds Ratio (Minor Allele) | Minor Allele Freq. (Responders) | Allele Freq. (Non-Responders) |
| 0 - Priority in Predictive Model | kgp24415534 | 2 | 174156875 | | G | A | 3.40E-05 | 0.05 | 0.003 | 0.050 | 1.10E-02 | 0.14 | 0.005 | 0.033 |
| 0 - Priority in Predictive Model | kgp12008955 | 2 | 73759636 | ALMS1 | G | A | 9.26E-05 | Zero | 0.000 | 0.038 | 3.65E-04 | 0.12 | 0.007 | 0.057 |
| | kgp26026546 | 13 | 79972606 | RBM26 | A | C | 2.20E-04 | Zero | 0.000 | 0.034 | 4.46E-04 | 0.06 | 0.003 | 0.041 |
| | rs16886004 | 7 | 78021500 | MAGI2 | A | G | 2.28E-03 | 2.15 | 0.199 | 0.110 | 3.25E-05 | 5.56 | 0.199 | 0.049 |
| | kgp25952891 | 13 | 80027089 | | A | G | 5.58E-04 | Zero | 0.000 | 0.029 | 4.30E-04 | 0.06 | 0.002 | 0.041 |
| | kgp3450875 | 16 | 57268931 | RSPRY1 | G | A | 6.63E-03 | 0.19 | 0.008 | 0.038 | 1.51E-05 | 0.07 | 0.005 | 0.066 |
| | rs10251797 | 7 | 78025427 | MAGI2 | C | A | 3.18E-03 | 2.07 | 0.199 | 0.113 | 4.05E-05 | 5.49 | 0.194 | 0.049 |
| | kgp2299675 | 20 | 16933074 | | G | G | 4.43E-03 | 0.26 | 0.015 | 0.054 | 4.23E-05 | 0.13 | 0.012 | 0.082 |
| | kgp1094414 | 1 | 216039833 | USH2A | A | G | 3.57E-05 | 0.05 | 0.003 | 0.050 | 1.25E-02 | 0.24 | 0.013 | 0.049 |
| | kgp1688752 | 21 | 43016736 | | G | A | 8.83E-04 | 0.34 | 0.045 | 0.113 | 1.45E-03 | 0.33 | 0.035 | 0.115 |
| | kgp12230554 | 5 | 27037978 | CDH9 | A | C | 3.70E-03 | 0.21 | 0.010 | 0.046 | 3.31E-05 | 0.14 | 0.015 | 0.090 |
| | rs543122 | 3 | 124164156 | KALRN | G | A | 4.73E-05 | 0.50 | 0.407 | 0.571 | 1.39E-05 | 0.59 | 0.439 | 0.566 |
| | kgp6236949 | 2 | 60301030 | | A | G | 6.37E-04 | 0.56 | 0.306 | 0.442 | 7.57E-03 | 0.55 | 0.261 | 0.385 |
| | kgp9627338 | 17 | 90155 | RPH3AL | A | G | 5.01E-04 | 0.47 | 0.104 | 0.208 | 3.13E-03 | 0.43 | 0.105 | 0.205 |
| | kgp11141512 | 20 | 35283733 | NDRG3 | G | A | 3.33E-03 | 0.30 | 0.020 | 0.067 | 3.65E-04 | 0.12 | 0.007 | 0.057 |
| | rs9579566 | 13 | 30980265 | | G | A | 2.08E-04 | 0.23 | 0.020 | 0.083 | 9.90E-03 | 0.30 | 0.025 | 0.074 |
| | rs2816838 | 10 | 52714759 | | G | A | 1.94E-03 | 0.51 | 0.139 | 0.233 | 1.80E-03 | 0.42 | 0.112 | 0.221 |
| | kgp4705854 | 12 | 19907696 | | G | A | 5.01E-05 | 0.51 | 0.303 | 0.467 | 2.87E-02 | 0.63 | 0.326 | 0.434 |
| | rs9817308 | 3 | 124182136 | KALRN | A | C | 2.85E-05 | 0.49 | 0.406 | 0.576 | 2.64E-02 | 0.62 | 0.453 | 0.566 |
| | kgp8817856 | 6 | 32744440 | | G | A | 6.02E-04 | 0.53 | 0.364 | 0.492 | 373E-04 | 0.46 | 0.419 | 0.598 |
| 0 - Priority in Predictive Model | kgp6214351 | 11 | 75546691 | UVRAG | A | G | 3.98E-03 | 0.42 | 0.051 | 0.113 | 2.65E-04 | 0.26 | 0.043 | 0.131 |
| 0 - Priority in Predictive Model | kgp2356388 | 16 | 19771577 | IQCK | G | A | 3.88E-04 | 0.43 | 0.121 | 0.221 | 1.94E-03 | 0.45 | 0.144 | 0.262 |
| | kgp7416024 | 9 | 21453902 | | G | A | 2.14E-03 | 0.13 | 0.005 | 0.038 | 3.81E-04 | 0.12 | 0.008 | 0.057 |
| | rs6718758 | 2 | 60328802 | | C | A | 5.70E-03 | 0.63 | 0.333 | 0.446 | 5.96E-04 | 0.47 | 0.281 | 0.443 |
| | rs7579987 | 2 | 60307009 | | G | C | 6.99E-03 | 0.64 | 0.356 | 0.466 | 3.91E-04 | 0.45 | 0.306 | 0.475 |
| | rs13394010 | 17 | 88988 | RPH3AL | G | A | 1.03E-03 | 0.49 | 0.106 | 0.204 | 2.42E-03 | 0.42 | 0.109 | 0.213 |
| | rs7217872 | 2 | 60302746 | | A | G | 7.74E-03 | 0.64 | 0.354 | 0.462 | 3.91E-04 | 0.45 | 0.306 | 0.475 |
| | rs7191155 | 16 | 19800213 | IQCK | G | A | 5.38E-04 | 0.44 | 0.121 | 0.218 | 1.93E-03 | 0.45 | 0.144 | 0.262 |
| | rs9931167 | 16 | 19792598 | IQCK | G | A | 5.38E-04 | 0.44 | 0.121 | 0.218 | 1.94E-03 | 0.45 | 0.144 | 0.262 |
| | rs11691553 | 2 | 60303554 | | C | A | 8.54E-04 | 0.65 | 0.355 | 0.462 | 3.72E-04 | 0.45 | 0.305 | 0.475 |
| | rs11648129 | 16 | 19820694 | IQCK | A | G | 6.54E-04 | 0.45 | 0.121 | 0.217 | 1.64E-03 | 0.44 | 0.143 | 0.262 |
| | kgp25216186 | 1 | 23758427 | ASAP3 | A | G | 1.32E-03 | 0.07 | 0.003 | 0.033 | 2.45E-03 | 0.07 | 0.002 | 0.033 |
| | kgp29794723 | 10 | 18397332 | | A | C | 4.77E-03 | 0.31 | 0.023 | 0.067 | 3.54E-04 | 0.18 | 0.018 | 0.082 |
| | kgp3829539 | 16 | 19722366 | C16orf88 | A | G | 5.38E-04 | 0.44 | 0.121 | 0.218 | 2.10E-03 | 0.45 | 0.145 | 0.262 |
| | rs6895094 | 5 | 141037277 | ARAP3 | A | C | 6.58E-03 | 0.56 | 0.384 | 0.521 | 1.19E-02 | 0.60 | 0.353 | 0.484 |
| | kgp1009249 | 12 | 19838534 | | G | A | 1.74E-04 | 0.48 | 0.179 | 0.307 | 1.03E-02 | 0.54 | 0.211 | 0.320 |
| | rs10203396 | 2 | 60305110 | | A | G | 8.67E-03 | 0.65 | 0.356 | 0.463 | 4.43E-04 | 0.46 | 0.308 | 0.475 |

TABLE 38-continued

Standard Response SNPs

| Prioritized Variants | STANDARD PHENOTYPE | | | | | | Gala Cohort | | | | Forte Cohort | | | |
|---|---|---|---|---|---|---|---|---|---|---|---|---|---|---|
| Name | Chromosome | Position | Gene(s) | Major Allele (d) | Minor Allele (D) | P-value (Armitage Test) | Odds Ratio (Minor Allele) | Minor Allele Freq. (Responders) | Allele Freq. (Non-Responders) | P-value (Armitage Test) | Odds Ratio (Minor Allele) | Minor Allele Freq. (Responders) | Allele Freq. (Non-Responders) |
| kgp3854180 | 16 | 19721806 | C16orf88 | G | A | 6.54E-04 | 0.45 | 0.121 | 0.217 | 1.94E-03 | 0.45 | 0.144 | 0.262 |
| rs6497396 | 16 | 19735697 | IQCK | A | G | 1.30E-03 | 0.48 | 0.131 | 0.225 | 7.65E-04 | 0.43 | 0.155 | 0.287 |
| rs13419758 | 2 | 60302920 | | G | A | 8.67E-03 | 0.65 | 0.356 | 0.463 | 5.22E-04 | 0.47 | 0.308 | 0.475 |
| rs8055485 | 16 | 19750051 | IQCK | A | G | 6.54E-04 | 0.45 | 0.121 | 0.217 | 2.10E-03 | 0.45 | 0.145 | 0.262 |
| rs9931211 | 16 | 19813605 | IQCK | A | G | 6.54E-04 | 0.45 | 0.121 | 0.217 | 2.10E-03 | 0.45 | 0.145 | 0.262 |
| kgp5869992 | 12 | 49219569 | CACNB3 | A | G | 3.71E-03 | 0.57 | 0.389 | 0.542 | 2.00E-02 | 0.62 | 0.379 | 0.500 |
| kgp9320791 | 2 | 60309952 | | C | G | 8.67E-03 | 0.65 | 0.356 | 0.463 | 5.27E-04 | 0.46 | 0.310 | 0.475 |
| kgp7730397 | 16 | 19740243 | IQCK | A | G | 1.09E-03 | 0.47 | 0.126 | 0.218 | 1.64E-03 | 0.44 | 0.143 | 0.262 |
| kgp11002881 | 11 | 118219897 | CD3G | A | G | 4.98E-03 | 0.14 | 0.005 | 0.034 | 4.46E-04 | 0.06 | 0.003 | 0.041 |
| kgp3205849 | 10 | 121531725 | INPP5F | A | G | 8.42E-05 | 0.48 | 0.172 | 0.312 | 5.88E-03 | 0.63 | 0.183 | 0.262 |
| kgp6127371 | 4 | 153856357 | | A | G | 3.69E-04 | 0.18 | 0.013 | 0.063 | 9.38E-03 | 0.28 | 0.020 | 0.066 |
| kgp10305127 | 11 | 99881768 | CNTN5 | A | G | 4.21E-03 | 0.51 | 0.101 | 0.182 | 2.60E-03 | 0.39 | 0.068 | 0.156 |
| rs6535882 | 4 | 153848128 | | G | A | 3.83E-04 | 0.18 | 0.013 | 0.063 | 9.06E-03 | 0.27 | 0.020 | 0.066 |
| kgp6700691 | 4 | 153849531 | | A | G | 3.83E-04 | 0.18 | 0.013 | 0.063 | 9.06E-53 | 0.27 | 0.020 | 0.066 |
| rs11029892 | 11 | 27269546 | | G | A | 1.72E-03 | 1.83 | 0.343 | 0.229 | 3.44E-03 | 2.08 | 0.358 | 0.221 |
| kgp270001 | 16 | 19750275 | IQCK | G | A | 1.08E-03 | 0.48 | 0.131 | 0.227 | 1.44 5-03 | 0.45 | 0.154 | 0.279 |
| kgp81922546 | 12 | 19903173 | | G | A | 6.52E-05 | 0.47 | 0.215 | 0.355 | 2.64E-02 | 0.62 | 0.256 | 0.361 |
| kgp5068397 | 16 | 19756348 | IQCK | A | G | 7.59E-04 | 0.50 | 0.164 | 0.273 | 1.56E-03 | 0.47 | 0.203 | 0.336 |
| kgp10910719 | 16 | 19803199 | IQCK | C | G | 9.01E-04 | 0.46 | 0.121 | 0.214 | 1.94E-03 | 0.45 | 0.144 | 0.262 |
| kgp2959751 | 6 | 58719342 | | G | A | 9.81E-04 | 0.22 | 0.015 | 0.063 | 7.48E-03 | 0.24 | 0.015 | 0.057 |
| kgp950928 | 16 | 19824638 | IQCK | A | G | 6.59E-04 | 0.45 | 0.126 | 0.223 | 3.11E-03 | 0.46 | 0.149 | 0.262 |
| rs1858973 | 16 | 19743649 | IQCK | A | G | 6.54E-04 | 0.45 | 0.121 | 0.217 | 2.67E-03 | 0.46 | 0.148 | 0.262 |
| rs2660214 | 10 | 52732452 | | A | G | 3.98E-03 | 0.54 | 0.141 | 0.229 | 2.37E-03 | 0.43 | 0.114 | 0.221 |
| kgp2709692 | 18 | 3000808 | LPIN2 | C | A | 2.36E-03 | 0.27 | 0.020 | 0.067 | 5.25E-03 | 0.19 | 0.010 | 0.049 |
| kgp11210903 | 22 | 30898906 | SEC14L4 | G | A | 3.70E-04 | 0.10 | 0.005 | 0.046 | 4.98E-02 | 0.19 | 0.005 | 0.025 |
| kgp8030775 | 8 | 6328607 | MCPH1 | A | C | 2.54E-02 | 0.36 | 0.018 | 0.050 | 1.69E-05 | 0.07 | 0.005 | 0.066 |
| rs10841337 | 12 | 19897179 | | A | G | 4.26E-05 | 0.47 | 0.217 | 0.367 | 4.27E-02 | 0.64 | 0.265 | 0.361 |
| kgp8178358 | 14 | 70923024 | ADAM21 | A | A | 3.36E-03 | 0.08 | 0.003 | 0.029 | 3.81E-04 | 0.12 | 0.008 | 0.057 |
| kgp11843177 | 11 | 27316568 | | A | C | 1.95E-03 | 1.85 | 0.321 | 0.210 | 4.13E-03 | 2.07 | 0.338 | 0.205 |
| kgp23737989 | 7 | 97217288 | | G | A | 3.27E-03 | 0.08 | 0.003 | 0.029 | 1.57E-03 | Zero | 0.000 | 0.025 |
| rs7187976 | 16 | 19708196 | C16orf62 | A | G | 1.08E-03 | 0.48 | 0.131 | 0.227 | 1.83E-03 | 0.45 | 0.157 | 0.279 |
| rs1757980 | 6 | 32359821 | HCG23 | A | C | 2.33E-04 | 2.36 | 0.228 | 0.106 | 5.31E-03 | 2.94 | 0.164 | 0.067 |
| kgp5908616 | 2 | 60329823 | | G | A | 8.71E-03 | 0.65 | 0.346 | 0.454 | 1.05E-02 | 0.48 | 0.295 | 0.451 |
| kgp26995430 | 3 | 53359406 | DCP1A | G | A | 3.40E-05 | 0.05 | 0.003 | 0.050 | 2.14E-01 | 0.39 | 0.010 | 0.025 |
| kgp6996560 | 13 | 110124242 | | G | A | 7.81E-03 | 0.23 | 0.010 | 0.042 | 4.30E-04 | 0.06 | 0.002 | 0.041 |
| rs4782279 | 16 | 19759007 | IQCK | A | C | 1.26E-03 | 0.49 | 0.136 | 0.233 | 1.99E-03 | 0.46 | 0.158 | 0.279 |
| rs8053136 | 16 | 19767129 | IQCK | A | C | 1.22E-03 | 0.53 | 0.179 | 0.288 | 1.68E-03 | 0.47 | 0.210 | 0.344 |
| kgp11328629 | 10 | 120711084 | | G | A | 2.03E-03 | 2.62 | 0.134 | 0.058 | 3.11E-03 | 3.81 | 0.140 | 0.041 |
| kgp8200264 | 10 | 12858372 | CAMK1D | A | G | 8.64E-04 | 0.26 | 0.020 | 0.076 | 3.36E-03 | 0.31 | 0.033 | 0.098 |
| kgp6835138 | 20 | 40712994 | PTPRT | G | A | 6 20E-05 | 0.08 | 0.005 | 0.054 | 1.26E-01 | 0.36 | 0.012 | 0.033 |
| kgp841428 | 5 | 141036337 | ARAP3 | A | G | 9.84E-04 | 0.57 | 0.384 | 0.517 | 1.52E-02 | 0.61 | 0.358 | 0.484 |

TABLE 38-continued

Standard Response SNPs

| | STANDARD PHENOTYPE | | | | | | Gala Cohort | | | | Forte Cohort | | | |
|---|---|---|---|---|---|---|---|---|---|---|---|---|---|---|
| Prioritized Variants Name | Chromosome | Position | Gene(s) | Major Allele (d) | Minor Allele (D) | P-value (Armitage Test) | Odds Ratio (Minor Allele) | Minor Allele Freq. (Responders) | Allele Freq. (Non-Responders) | P-value (Armitage Test) | Odds Ratio (Minor Allele) | Minor Allele Freq. (Responders) | Allele Freq. (Non-Responders) |
| rs3815822 | 16 | 29872361 | CDIPT | A | G | 3.18E-03 | 1.62 | 0.490 | 0.367 | 4.87E-03 | 1.85 | 0.527 | 0.385 |
| rs1579771 | 3 | 157278882 | C3orf55 | A | C | 3.35E-04 | 2.02 | 0.376 | 0.246 | 1.64E-02 | 1.81 | 0.356 | 0.246 |
| kgp4734301 | 11 | 27315427 | | A | G | 2.36E-03 | 1.83 | 0.321 | 0.213 | 4.13E-03 | 2.07 | 0.338 | 0.205 |
| rs11029928 | 11 | 27319188 | | G | A | 2.36E-03 | 1.83 | 0.321 | 0.213 | 4.13E-03 | 2.07 | 0.338 | 0.205 |
| rs10841322 | 12 | 19866642 | | G | A | 3.20E-05 | 0.46 | 0.217 | 0.367 | 9.47E-02 | 0.69 | 0.251 | 0.328 |
| kgp1786079 | 7 | 144701118 | | A | G | 5.35E-04 | 0.48 | 0.130 | 0.213 | 9.86E-02 | 0.49 | 0.130 | 0.221 |
| kgp5053636 | 2 | 205356730 | | C | A | 1.01E-02 | 0.32 | 0.106 | 0.058 | 1.02E-04 | 0.22 | 0.028 | 0.115 |
| kgp9601362 | 9 | 18959317 | FAM154A | G | A | 4.29E-03 | 0.40 | 0.038 | 0.097 | 2.94E-03 | 0.26 | 0.025 | 0.083 |
| kgp8183049 | 13 | 40634155 | | G | A | 5.58E-04 | Zero | 0.000 | 0.029 | 6.90E-02 | 2.30 | 0.000 | 0.008 |
| kgp5564995 | 6 | 26414060 | BTN3A1 | C | A | 1.56E-04 | 3.35 | 0.153 | 0.057 | 3.98E-02 | 2.30 | 0.137 | 0.070 |
| kgp27500525 | 9 | 30278677 | | A | G | 3.79E-03 | Zero | 0.000 | 0.021 | 1.57E-03 | Zero | 0.000 | 0.025 |
| rs11022778 | 11 | 13390860 | ARNTL | A | C | 4.49E-04 | 1.96 | 0.336 | 0.204 | 4.87E-02 | 1.58 | 0.366 | 0.270 |
| kgp10826273 | 2 | 176263817 | | G | A | 5.89E-04 | Zero | 0.000 | 0.029 | 6.96E-02 | Zero | 0.000 | 0.008 |
| rs12494712 | 3 | 116796116 | | A | G | 1.36E-02 | 1.74 | 0.220 | 0.142 | 1.24E-02 | 2.54 | 0.274 | 0.131 |
| kgp1779254 | 12 | 73686930 | | A | G | 3.12E-04 | 0.08 | 0.003 | 0.029 | 2.45E-03 | 0.07 | 0.002 | 0.033 |
| kgp6190988 | 5 | 10699522 | DAP | G | A | 3.27E-03 | 0.08 | 0.003 | 0.029 | 2.22E-03 | 0.07 | 0.002 | 0.033 |
| kgp6507761 | 7 | 319681 | | A | G | 8.94E-03 | 0.65 | 0.457 | 0.567 | 2.00E-03 | 0.54 | 0.400 | 0.566 |
| rs2074037 | 16 | 19725130 | C16orf88 | G | A | 1.49E-03 | 0.47 | 0.126 | 0.216 | 2.46E-03 | 0.46 | 0.147 | 0.262 |
| rs4143493 | 6 | 51829939 | PKHD1 | G | A | 8.85E-04 | 3.00 | 0.078 | 0.029 | 157E-03 | 7.56 | 0.102 | 0.016 |
| kgp1699628 | 6 | 18032535 | FAM154A | A | G | 1.73E-04 | 0.51 | 0.437 | 0.585 | 2.99E-02 | 0.63 | 0.470 | 0.582 |
| rs7024953 | 9 | 18960334 | | A | G | 4.68E-03 | 0.40 | 0.038 | 0.096 | 3.41E-03 | 0.27 | 0.025 | 0.082 |
| kgp10974833 | 13 | 77339132 | | A | G | 3.27E-03 | 0.08 | 0.003 | 0.029 | 2.59E-03 | 0.07 | 0.003 | 0.033 |
| kgp10412303 | 2 | 205303530 | | G | A | 1.21E-02 | 0.37 | 0.025 | 0.067 | 1.73E-04 | 0.21 | 0.027 | 0.107 |
| kgp9669946 | 17 | 65735872 | NOL11 | A | G | 1.28E-03 | 0.51 | 0.154 | 0.256 | 3.31E-03 | 0.50 | 0.179 | 0.303 |
| rs17224858 | 3 | 124205297 | KALRN | G | A | 3.71E-05 | 0.45 | 0.172 | 0.313 | 1.22E-01 | 0.69 | 0.204 | 0.270 |
| rs6840089 | 4 | 153713220 | ARFIP1 | A | G | 8.57E-04 | 0.20 | 0.013 | 0.058 | 9.06E-03 | 0.27 | 0.020 | 0.066 |
| rs7666442 | 4 | 153753101 | ARFIP1 | A | G | 8.57E-04 | 0.20 | 0.013 | 0.058 | 9.06E-03 | 0.27 | 0.020 | 0.066 |
| rs7672014 | 4 | 153818501 | ARFIP1 | G | A | 8.57E-04 | 0.20 | 0.013 | 0.058 | 9.06E-03 | 0.27 | 0.020 | 0.066 |
| rs7677801 | 4 | 153795067 | ARFIP1 | A | G | 8.68E-04 | 0.20 | 0.013 | 0.059 | 9.38E-03 | 0.28 | 0.020 | 0.066 |
| rs4469694 | 2 | 11263948 | FLJ33534 | G | A | 1.85E-03 | 0.48 | 0.094 | 0.182 | 1.43E-02 | 0.46 | 0.083 | 0.156 |
| kgp10523170 | 16 | 5221617 | | A | G | 2.00E-02 | 0.12 | 0.003 | 0.021 | 9.95E-05 | 0.05 | 0.002 | 0.057 |
| kgp5216209 | 3 | 170740453 | SLC2A2 | C | A | 1.75E-03 | 0.21 | 0.013 | 0.055 | 4.56E-03 | 0.24 | 0.017 | 0.066 |
| rs720176 | 16 | 19721515 | C16orf88 | A | G | 1.77E-03 | 0.48 | 0.128 | 0.217 | 2.67E-03 | 0.46 | 0.148 | 0.262 |
| kgp7481870 | 16 | 19729016 | C16orf88, IQCK | G | C | 5.94E-04 | 0.45 | 0.133 | 0.231 | 8.16E-03 | 0.50 | 0.160 | 0.262 |
| rs1532365 | 12 | 49204421 | | G | A | 1.90E-03 | 0.61 | 0.356 | 0.487 | 1.26E-03 | 0.59 | 0.334 | 0.459 |
| rs12943140 | 17 | 65738773 | NOL11 | A | G | 1.42E-03 | 0.51 | 0.155 | 0.256 | 3.47E-03 | 0.50 | 0.179 | 0.303 |
| kgp11702474 | 4 | 153712868 | ARFIP1 | G | A | 8.97E-04 | 0.20 | 0.013 | 0.058 | 9.38E-03 | 0.28 | 0.020 | 0.066 |
| rs10498793 | 6 | 51829707 | PKHD1 | G | A | 8.85E-03 | 3.00 | 0.078 | 0.029 | 1.94E-03 | 7.33 | 0.100 | 0.016 |
| kgp6539666 | 3 | 157292022 | C3orf55 | A | G | 9.41E-04 | 1.94 | 0.354 | 0.238 | 1.61E-02 | 1.83 | 0.354 | 0.246 |
| kgp10679353 | 16 | 19800133 | IQCK | G | A | 1.51E-03 | 0.49 | 0.129 | 0.221 | 2.30E-03 | 0.46 | 0.159 | 0.279 |

TABLE 38-continued

Standard Response SNPs

| STANDARD PHENOTYPE | | | | | | | | Gala Cohort | | | | Forte Cohort | | | |
|---|---|---|---|---|---|---|---|---|---|---|---|---|---|---|---|
| Prioritized Variants Name | Chromosome | Position | Gene(s) | Major Allele (d) | Minor Allele (D) | P-value (Armitage Test) | Odds Ratio (Minor Allele) | Minor Allele Freq. (Responders) | Allele Freq. (Non-Responders) | | P-value (Armitage Test) | Odds Ratio (Minor Allele) | Minor Allele Freq. (Responders) | Allele Freq. (Non-Responders) | |
|---|---|---|---|---|---|---|---|---|---|---|---|---|---|---|---|
| kgp9410843 | 10 | 121484477 | | A | G | 2.25E-04 | 0.50 | 0.173 | 0.304 | | 6.76E-02 | 0.64 | 0.186 | 0.262 | |
| kgp6772915 | 9 | 18978739 | FAM154A | A | C | 8.72E-03 | 0.42 | 0.041 | 0.093 | | 1.83E-02 | 0.24 | 0.023 | 0.082 | |
| kgp20478926 | 8 | 21050249 | | A | G | 1.67E-03 | 0.38 | 0.023 | 0.092 | | 2.91E-03 | 0.44 | 0.038 | 0.133 | |
| kgp10619195 | 4 | 99417717 | TSPAN5 | A | G | 2.87E-04 | 0.29 | 0.035 | 0.104 | | 3.30E-02 | 0.46 | 0.045 | 0.098 | |
| rs1544352 | 16 | 19713882 | | A | G | 2.28E-03 | 0.50 | 0.132 | 0.221 | | 2.15E-03 | 0.45 | 0.153 | 0.270 | |
| kgp15390522 | 1 | 205017962 | CNTN2 | G | A | 2.14E-03 | 0.13 | 0.005 | 0.035 | | 1.37E-02 | 0.10 | 0.002 | 0.025 | |
| kgp24729706 | 22 | 49286357 | LOC100128946 | A | G | 1.13E-03 | 0.24 | 0.018 | 0.067 | | 4.15E-02 | 0.29 | 0.012 | 0.041 | |
| rs931570 | 12 | 49195124 | | G | A | 2.42E-03 | 0.61 | 0.356 | 0.483 | | 1.11E-02 | 0.59 | 0.332 | 0.459 | |
| kgp10591989 | 17 | 65697118 | | G | A | 1.60E-03 | 0.48 | 0.111 | 0.200 | | 9.17E-03 | 0.50 | 0.110 | 0.205 | |
| kgp12557319 | 6 | 8794609 | | A | G | 2.04E-02 | 0.12 | 0.003 | 0.021 | | 8.27E-05 | 0.08 | 0.005 | 0.057 | |
| kgp345301 | 16 | 19730554 | IQCK | A | C | 2.05E-03 | 0.48 | 0.122 | 0.209 | | 2.28E-03 | 0.45 | 0.146 | 0.262 | |
| kgp8615910 | 5 | 30927198 | | A | T | 1.47E-04 | 0.42 | 0.111 | 0.221 | | 5.56E-02 | 0.59 | 0.135 | 0.205 | |
| kgp2245775 | 13 | 91402506 | | G | A | 2.67E-02 | 0.66 | 0.258 | 0.338 | | 8.86E-04 | 0.43 | 0.185 | 0.320 | |
| kgp29367521 | 4 | 134471944 | | G | A | 4.84E-02 | 0.14 | 0.005 | 0.034 | | 2.02E-03 | 0.11 | 0.005 | 0.042 | |
| kgp7506434 | 1 | 13823114 | LRRC38 | A | G | 5.24E-03 | 0.14 | 0.005 | 0.033 | | 2.36E-03 | 0.09 | 0.002 | 0.041 | |
| rs4780822 | 16 | 19727998 | C16orf88, IQCK | A | G | 2.32E-03 | 0.50 | 0.129 | 0.217 | | 1.71E-03 | 0.45 | 0.156 | 0.279 | |
| kgp512180 | 16 | 10829457 | | G | A | 2.02E-03 | 0.57 | 0.235 | 0.349 | | 9.63E-03 | 0.55 | 0.229 | 0.344 | |
| rs1604169 | 5 | 84215343 | | A | C | 1.45E-02 | 0.66 | 0.386 | 0.483 | | 2.13E-03 | 0.50 | 0.323 | 0.467 | |
| kgp25921291 | 13 | 78418857 | | G | A | 2.49E-03 | 0.18 | 0.008 | 0.046 | | 7.68E-03 | 0.17 | 0.007 | 0.041 | |
| rs16901784 | 6 | 26555433 | | C | A | 1.57E-03 | 0.45 | 0.073 | 0.154 | | 2.10E-03 | 0.43 | 0.105 | 0.213 | |
| kgp6228750 | 1 | 110261382 | | A | G | 1.92E-02 | 0.44 | 0.040 | 0.083 | | 3.30E-04 | 0.26 | 0.030 | 0.115 | |
| kgp9354820 | 15 | 93793636 | | G | A | 2.86E-04 | 0.06 | 0.003 | 0.046 | | 1.17E-01 | 0.29 | 0.007 | 0.025 | |
| kgp8106690 | 12 | 128734969 | | A | G | 2.00E-02 | 0.61 | 0.141 | 0.213 | | 2.38E-02 | 0.40 | 0.128 | 0.270 | |
| kgp5144181 | 2 | 30364733 | | G | A | 3.79E-02 | 0.49 | 0.040 | 0.079 | | 8.32E-05 | 0.16 | 0.017 | 0.090 | |
| kgp9627406 | 9 | 132997137 | NCS1 | G | A | 9.94E-04 | 0.39 | 0.070 | 0.163 | | 2.89E-01 | 0.58 | 0.030 | 0.050 | |
| kgp2262166 | 9 | 18960393 | FAM154A | A | C | 4.45E-03 | 0.40 | 0.038 | 0.096 | | 5.93E-03 | 0.30 | 0.027 | 0.082 | |
| kgp4223880 | 2 | 10584122 | ODC1 | A | G | 4.99E-04 | 0.06 | 0.003 | 0.038 | | 3.23E-02 | 0.22 | 0.008 | 0.033 | |
| kgp611811 | 1 | 160346794 | | A | C | 5.90E-03 | 0.20 | 0.008 | 0.042 | | 2.45E-03 | 0.07 | 0.002 | 0.033 | |
| kgp9421884 | 19 | 11049860 | | G | A | 9.65E-02 | 0.56 | 0.048 | 0.079 | | 3.73E-06 | 0.24 | 0.047 | 0.180 | |
| rs8050872 | 16 | 19803846 | IQCK | G | A | 199E-03 | 0.51 | 0.136 | 0.229 | | 2.88E-03 | 0.47 | 0.162 | 0.279 | |
| rs7864679 | 9 | 18945868 | FAM154A | A | A | 1.69E-03 | 0.48 | 0.046 | 0.096 | | 7.87E-04 | 0.21 | 0.020 | 0.082 | |
| kgp2446153 | 5 | 152980439 | GRIA1 | G | A | 5.31E-04 | 0.06 | 0.003 | 0.038 | | 3.17E-02 | 0.22 | 0.007 | 0.033 | |
| kgp7804623 | 1 | 41125455 | RIMS3 | G | A | 2.90E-04 | 1.99 | 0.346 | 0.208 | | 5.58E-02 | 1.57 | 0.336 | 0.246 | |
| rs3792135 | 2 | 100062163 | REV1 | A | G | 5.97E-04 | 0.48 | 0.120 | 0.227 | | 3.49E-02 | 0.55 | 0.131 | 0.205 | |
| rs8035826 | 15 | 94832144 | | C | A | 4.54E-02 | 1.59 | 0.465 | 0.345 | | 1.05E-02 | 1.76 | 0.513 | 0.385 | |
| kgp85534 | 2 | 145744582 | | G | A | 2.11E-04 | 0.13 | 0.008 | 0.055 | | 1.26E-01 | 0.36 | 0.012 | 0.033 | |
| rs11192461 | 10 | 107266483 | | G | A | 7.86E-03 | 0.49 | 0.081 | 0.146 | | 7.33E-04 | 0.38 | 0.087 | 0.197 | |
| kgp297178 | 9 | 18942635 | FAM154A | G | A | 2.48E-02 | 0.48 | 0.043 | 0.088 | | 3.36E-04 | 0.18 | 0.017 | 0.082 | |
| kgp2045074 | 6 | 51187450 | | C | A | 4.02E-02 | 0.10 | 0.005 | 0.046 | | 2.05E-01 | 0.30 | 0.005 | 0.016 | |
| rs10049206 | 3 | 157233698 | | G | A | 5.70E-04 | 1.97 | 0.369 | 0.246 | | 2.77E-02 | 1.71 | 0.356 | 0.254 | |

TABLE 38-continued

Standard Response SNPs

| Prioritized Variants | STANDARD PHENOTYPE | | | | | Gala Cohort | | | | Forte Cohort | | | |
|---|---|---|---|---|---|---|---|---|---|---|---|---|---|
| Name | Chromosome | Position | Gene(s) | Major Allele (d) | Minor Allele (D) | P-value (Armitage Test) | Odds Ratio (Minor Allele) | Minor Allele Freq. (Responders) | Allele Freq. (Non-Responders) | P-value (Armitage Test) | Odds Ratio (Minor Allele) | Minor Allele Freq. (Responders) | Allele Freq. (Non-Responders) |
| rs9834010 | 3 | 157236222 | | C | A | 5.70E-04 | 1.97 | 0.369 | 0.246 | 2.77E-02 | 1.71 | 0.356 | 0.254 |
| kgp971582 | 6 | 51921703 | PKHD1 | A | G | 4.96E-03 | 2.99 | 0.091 | 0.033 | 4.76E-03 | 4.89 | 0.104 | 0.025 |
| kgp22793211 | X | 92601576 | | G | A | 2.20E-03 | 0.65 | 0.391 | 0.538 | 8.20E-03 | 0.61 | 0.396 | 0.550 |
| kgp4573213 | 3 | 124199924 | KALRN | A | G | 5.14E-05 | 0.45 | 0.174 | 0.313 | 1.43E-01 | 0.71 | 0.208 | 0.270 |
| kgp19568724 | 14 | 21486590 | NDRG2 | G | A | 1.32E-03 | 0.07 | 0.003 | 0.033 | 5.09E-03 | 0.19 | 0.010 | 0.049 |
| kgp9071686 | 9 | 21419168 | | G | A | 1.19E-03 | 0.16 | 0.005 | 0.029 | 3.65E-04 | 0.12 | 0.007 | 0.057 |
| kgp652534 | 4 | 13612751 | BOD1L | C | G | 2.84E-01 | 0.45 | 0.008 | 0.017 | 4.68E-07 | 0.05 | 0.005 | 0.082 |
| kgp1224440 | 1 | 247399991 | | A | C | 3.76E-03 | 0.52 | 0.096 | 0.179 | 1.21E-03 | 0.41 | 0.122 | 0.238 |
| kgp2465184 | 9 | 18942204 | FAM154A | A | C | 2.48E-02 | 0.48 | 0.043 | 0.088 | 3.54E-04 | 0.18 | 0.018 | 0.052 |
| kgp11543962 | 10 | 109579303 | | G | A | 1.42E-02 | 0.21 | 0.008 | 0.034 | 3.81E-06 | 0.12 | 0.008 | 0.057 |
| kgp4543470 | 2 | 213559411 | | A | C | 3.80E-06 | 0.36 | 0.106 | 0.246 | 4.45E-01 | 0.80 | 0.161 | 0.189 |
| kgp55779170 | 17 | 65681762 | PITPNC1 | G | A | 2.00E-03 | 0.44 | 0.076 | 0.151 | 3.74E-03 | 0.45 | 0.093 | 0.192 |
| kgp4812831 | 6 | 51910905 | PKHD1 | A | G | 4.96E-03 | 2.99 | 0.091 | 0.033 | 4.61E-03 | 4.95 | 0.102 | 0.025 |
| rs2598360 | 9 | 114155899 | KIAA0368 | G | A | 4.06E-03 | 0.61 | 0.386 | 0.500 | 7.26E-03 | 0.58 | 0.361 | 0.500 |
| kgp10633631 | 8 | 17504188 | MTUS1 | A | G | 9.73E-03 | Zero | 0.000 | 0.017 | 5.52E-04 | Zero | 0.000 | 0.041 |
| kgp3651767 | 16 | 84992155 | | G | A | 6.93E-02 | 0.29 | 0.008 | 0.025 | 1.43E-05 | 0.09 | 0.007 | 0.074 |
| rs823829 | 9 | 114105079 | | A | C | 1.84E-03 | 0.58 | 0.407 | 0.529 | 1.58E-02 | 0.61 | 0.391 | 0.516 |
| kgp279772 | 8 | 2105576 | | T | A | 6.51E-03 | 0.61 | 0.237 | 0.338 | 8.63E-04 | 0.47 | 0.256 | 0.410 |
| kgp20163979 | 8 | 79366479 | | A | C | 2.33E-04 | Zero | 0.000 | 0.033 | 3.69E-01 | 0.30 | 0.002 | 0.008 |
| kgp21171930 | 4 | 80362934 | | A | G | 3.79E-03 | Zero | 0.000 | 0.021 | 2.45E-03 | 0.07 | 0.002 | 0.033 |
| kgp2092817 | 5 | 39632583 | | G | A | 8.09E-03 | 0.10 | 0.003 | 0.025 | 1.57E-03 | Zero | 0.000 | 0.025 |
| kgp3598409 | 15 | 51652449 | GLDN | G | A | 5.89E-04 | Zero | 0.000 | 0.029 | 7.37E-02 | 0.15 | 0.002 | 0.016 |
| kgp6469620 | 1 | 41235946 | NFYC | G | A | 1.54E-03 | 1.75 | 0.401 | 0.275 | 2.30E-02 | 1.66 | 0.418 | 0.303 |
| rs3818675 | 10 | 12858045 | CAMK1D | G | A | 1.81E-03 | 0.28 | 0.020 | 0.071 | 5.56E-03 | 0.32 | 0.030 | 0.090 |
| kgp9530088 | 11 | 30501054 | MPPED2 | A | G | 4.45E-02 | 0.70 | 0.276 | 0.350 | 2.34E-04 | 0.44 | 0.221 | 0.392 |
| rs2453478 | 12 | 49202743 | | A | G | 1.81E-03 | 0.61 | 0.356 | 0.488 | 1.98E-02 | 0.62 | 0.341 | 0.459 |
| kgp10558725 | 18 | 3070717 | MYOM1 | G | A | 7.81E-03 | 0.23 | 0.010 | 0.042 | 1.79E-02 | 0.14 | 0.008 | 0.049 |
| kgp28586329 | 8 | 6304848 | MCPH1 | A | G | 8.09E-03 | 0.10 | 0.003 | 0.025 | 1.61E-03 | Zero | 0.000 | 0.025 |
| kgp30282494 | 5 | 72863824 | UTP15 | A | C | 3.27E-03 | 0.08 | 0.003 | 0.029 | 1.02E-02 | Zero | 0.000 | 0.016 |
| rs7524868 | 1 | 41106774 | RIMS3 | A | C | 1.68E-04 | 2.05 | 0.351 | 0.208 | 9.59E-02 | 1.48 | 0.333 | 0.254 |
| kgp9806386 | 5 | 138068054 | | A | C | 5.89E-04 | Zero | 0.000 | 0.029 | 7.57E-02 | 0.15 | 0.003 | 0.016 |
| kgp4127859 | 6 | 32434481 | ERG | G | A | 4.49E-04 | 2.42 | 0.205 | 0.100 | 1.43E-02 | 2.53 | 0.155 | 0.074 |
| kgp1753445 | 21 | 39811162 | | A | C | 7.36E-03 | 2.09 | 0.162 | 0.092 | 2.76E-03 | 3.12 | 0.177 | 0.067 |
| kgp9354462 | 2 | 149894403 | | A | C | 2.89E-03 | 0.61 | 0.305 | 0.425 | 1.18E-02 | 0.58 | 0.290 | 0.410 |
| kgp26533576 | 6 | 99139642 | | A | C | 2.40E-02 | 0.13 | 0.008 | 0.054 | 3.78E-01 | 0.45 | 0.008 | 0.016 |
| kgp2023214 | 16 | 76293345 | | G | A | 5.03E-03 | 0.52 | 0.083 | 0.163 | 4.31E-01 | 0.45 | 0.078 | 0.172 |
| kgp6768546 | 4 | 153864174 | FHDII | G | A | 1.95E-03 | 0.23 | 0.015 | 0.059 | 9.06E-03 | 0.27 | 0.020 | 0.066 |
| kgp1098237 | 9 | 114173681 | KIAA0368 | G | A | 3.51E-03 | 0.61 | 0.379 | 0.496 | 9.79E-03 | 0.59 | 0.358 | 0.492 |
| kgp4559907 | 6 | 133255252 | | G | A | 4.08E-04 | 0.56 | 0.311 | 0.454 | 3.11E-02 | 0.63 | 0.352 | 0.459 |
| rs1644418 | 10 | 128558409 | CAMKID | A | G | 1.77E-03 | 0.26 | 0.018 | 0.067 | 5.33E-03 | 0.32 | 0.030 | 0.090 |

TABLE 38-continued

Standard Response SNPs

| STANDARD PHENOTYPE | | | | | | | Gala Cohort | | | | Forte Cohort | | | |
|---|---|---|---|---|---|---|---|---|---|---|---|---|---|---|
| Prioritized Variants Name | Chromosome | Position | Gene(s) | Major Allele (d) | Minor Allele (D) | P-value (Armitage Test) | Odds Ratio (Minor Allele) | Minor Allele Freq. (Responders) | Allele Freq. (Non-Responders) | P-value (Armitage Test) | Odds Ratio (Minor Allele) | Minor Allele Freq. (Responders) | Allele Freq. (Non-Responders) |
| kgp11804835 | 6 | 32396146 | | C | A | 8.85E-04 | 2.34 | 0.190 | 0.092 | 9.90E-03 | 2.77 | 0.150 | 0.066 |
| rs7029123 | 9 | 114136169 | KIAA0368 | A | G | 6.13E-03 | 0.63 | 0.391 | 0.500 | 6.39E-03 | 0.57 | 0.358 | 0.500 |
| kgp2688306 | 7 | 28560259 | CREB5 | A | G | 1.51E-03 | 2.84 | 0.126 | 0.050 | 1.23E-02 | 3.21 | 0.118 | 0.041 |
| kgp2638591 | 8 | 108994382 | RSPO2 | G | A | 1.11E-03 | 0.32 | 0.035 | 0.096 | 1.32E-02 | 0.39 | 0.047 | 0.107 |
| rs2845371 | 22 | 17178213 | | G | A | 5.95E-03 | 1.59 | 0.467 | 0.353 | 9.08E-03 | 1.78 | 0.508 | 0.377 |
| kgp5409955 | 9 | 18980841 | FAM154A | G | A | 2.34E-03 | 0.35 | 0.033 | 0.092 | 2.86E-02 | 0.35 | 0.025 | 0.066 |
| rs7228827 | 18 | 76900411 | ATP9B | G | A | 6.44E-04 | 2.27 | 0.215 | 0.108 | 2.61E-02 | 1.98 | 0.198 | 0.107 |
| kgp1912531 | 2 | 137850215 | THSD7B | A | G | 4.12E-03 | 2.00 | 0.192 | 0.104 | 9.55E-03 | 2.22 | 0.215 | 0.107 |
| kgp4162414 | 6 | 51868165 | PKHD1 | G | A | 6.71E-03 | 2.89 | 0.088 | 0.033 | 4.61E-03 | 4.95 | 0.102 | 0.025 |
| rs2926455 | 10 | 107260501 | | A | G | 8.73E-03 | 0.50 | 0.083 | 0.148 | 1.03E-03 | 0.39 | 0.090 | 0.197 |
| kgp3669685 | 7 | 78028723 | MAG2 | A | C | 5.48E-03 | 1.80 | 0.254 | 0.160 | 3.26E-03 | 2.40 | 0.254 | 0.131 |
| kgp7059449 | 2 | 41255455 | | A | C | 3.03E-02 | 2.89 | 0.056 | 0.021 | 1.57E-03 | 12.79 | 0.092 | 0.008 |
| rs3899755 | X | 68447361 | | C | A | 7.42E-05 | 2.48 | 0.227 | 0.088 | 1.92E-01 | 1.42 | 0.204 | 0.148 |
| rs2309760 | 4 | 185391332 | ODZ3 | A | G | 1.87E-03 | 0.61 | 0.369 | 0.500 | 5.20E-02 | 0.67 | 0.320 | 0.418 |
| kgp2788291 | 18 | 45153979 | | G | A | 9.15E-03 | 0.57 | 0.119 | 0.197 | 1.21E-03 | 0.41 | 0.122 | 0.238 |
| kgp3933330 | 7 | 28583709 | CREB5 | A | G | 4.00E-04 | 2.42 | 0.198 | 0.088 | 3.21E-02 | 2.15 | 0.158 | 0.082 |
| rs7062312 | X | 68447052 | | G | A | 7.68E-05 | 2.49 | 0.226 | 0.088 | 1.92E-01 | 1.42 | 0.204 | 0.148 |
| kgp337461 | 6 | 125019969 | NKAIN2 | A | G | 2.96E-02 | 0.61 | 0.126 | 0.189 | 1.84E-04 | 0.39 | 0.119 | 0.262 |
| rs6899068 | 5 | 126591501 | | G | A | 6.36E-03 | 1.60 | 0.414 | 0.304 | 1.48E-02 | 2.19 | 0.396 | 0.246 |
| kgp8046214 | 4 | 153726582 | ARFIP1 | A | G | 8.57E-04 | 0.20 | 0.013 | 0.058 | 2.48E-02 | 0.31 | 0.020 | 0.058 |
| rs6835202 | 4 | 153855186 | | C | A | 1.75E-03 | 0.21 | 0.013 | 0.055 | 9.06E-03 | 0.27 | 0.020 | 0.066 |
| kgp10620244 | 8 | 133472755 | KCNQ3 | G | A | 1.29E-03 | 2.11 | 0.220 | 0.117 | 2.23E-02 | 1.96 | 0.219 | 0.123 |
| kgp11407560 | 2 | 65096583 | | A | G | 2.01E-04 | 0.25 | 0.025 | 0.092 | 2.75E-02 | 0.59 | 0.025 | 0.041 |
| rs3799383 | 6 | 26510748 | | G | A | 1.90E-03 | 0.45 | 0.071 | 0.150 | 3.43E-01 | 0.59 | 0.025 | 0.041 |
| rs6845927 | 4 | 153799603 | ARFIP1 | A | C | 2.20E-03 | 0.24 | 0.015 | 0.058 | 2.58E-03 | 0.44 | 0.107 | 0.213 |
| rs10489312 | 1 | 175526526 | TNR | G | A | 1.28E-03 | 0.50 | 0.121 | 0.221 | 9.38E-03 | 0.28 | 0.020 | 0.066 |
| kgp11633966 | 11 | 377701793 | | G | A | 3.96E-03 | 0.56 | 0.172 | 0.267 | 1.88E-02 | 0.53 | 0.135 | 0.221 |
| rs7496451 | 15 | 25718875 | | G | A | 8.50E-03 | 1.82 | 0.220 | 0.138 | 2.75E-02 | 0.57 | 0.129 | 0.213 |
| kgp3048169 | 4 | 78109591 | | G | A | 5.55E-04 | 0.46 | 0.106 | 0.208 | 6.16E-03 | 2.18 | 0.259 | 0.139 |
| kgp8990121 | 9 | 27215039 | TEK | C | A | 1.08E-03 | 2.57 | 0.157 | 0.071 | 7.04E-02 | 0.60 | 0.109 | 0.172 |
| kgp26528455 | 6 | 72737785 | RIMS1 | G | A | 2.26E-03 | 0.26 | 0.018 | 0.063 | 3.93E-02 | 1.96 | 0.177 | 0.098 |
| kgp4755147 | 2 | 149894654 | | A | C | 2.91E-03 | 0.61 | 0.308 | 0.429 | 1.23E-02 | 0.32 | 0.017 | 0.066 |
| kgp10372946 | 10 | 133980657 | JAKMIP3 | G | A | 1.26E-03 | 13.37 | 0.051 | 0.004 | 1.57E-02 | 0.59 | 0.294 | 0.410 |
| rs1380706 | 2 | 57864042 | | A | G | 2.87E-03 | 1.68 | 0.393 | 0.271 | 2.45E-02 | 7.37 | 0.055 | 0.008 |
| kgp12182745 | 8 | 125465203 | TRMT12 | A | T | 1.17E-03 | 0.41 | 0.054 | 0.133 | 2.34E-02 | 1.67 | 0.424 | 0.311 |
| kgp3951463 | 3 | 157280172 | C3orf55 | C | A | 1.42E-03 | 1.87 | 0.348 | 0.233 | 8.88E-03 | 0.53 | 0.041 | 0.083 |
| kgp8602316 | 7 | 335911 | | G | A | 8.14E-03 | 1.59 | 0.393 | 0.288 | 2.46E-02 | 3.75 | 0.348 | 0.246 |
| rs16927077 | 11 | 10620629 | MRVI1-AS1 | G | A | 5.86E-03 | 0.53 | 0.106 | 0.183 | 6.93E-03 | 1.77 | 0.440 | 0.295 |
| kgp6959492 | 4 | 153687676 | | A | G | 1.89E-03 | 0.21 | 0.013 | 0.054 | 4.35E-02 | 0.48 | 0.055 | 0.107 |
| kgp8793915 | 11 | 109012665 | | A | G | 1.42E-03 | Zero | 0.000 | 0.025 | 9.06E-02 | 0.27 | 0.020 | 0.066 |
| kgp13161760 | 21 | 18192806 | | G | A | 3.27E-03 | 0.08 | 0.003 | 0.029 | 1.45E-02 | Zero | 0.000 | 0.025 |

TABLE 38-continued

Standard Response SNPs

| Prioritized Variants | STANDARD PHENOTYPE | | | | | | Gala Cohort | | | | Forte Cohort | | | |
|---|---|---|---|---|---|---|---|---|---|---|---|---|---|---|
| Name | Chromosome | Position | Gene(s) | Major Allele (d) | Minor Allele (D) | P-value (Armitage Test) | Odds Ratio (Minor Allele) | Minor Allele Freq. (Responders) | Allele Freq. (Non-Responders) | P-value (Armitage Test) | Odds Ratio (Minor Allele) | Minor Allele Freq. (Responders) | Allele Freq. (Non-Responders) |
| kgp6567154 | 4 | 3442146 | | G | C | 9.31E-03 | 0.64 | 0.274 | 0.375 | 1.61E-03 | 0.51 | 0.274 | 0.426 |
| kgp2282938 | 22 | 32719612 | | G | A | 1.70E-02 | 0.28 | 0.013 | 0.042 | 2.96E-04 | 0.18 | 0.018 | 0.083 |
| kgp355723 | 8 | 75270402 | GDAP1 | A | G | 2.94E-01 | 0.39 | 0.005 | 0.013 | 1.13E-06 | Zero | 0.000 | 0.057 |
| rs10201643 | 2 | 149905641 | LYPD6B | C | A | 3.22E-03 | 0.62 | 0.308 | 0.429 | 1.51E-02 | 0.59 | 0.294 | 0.410 |
| kgp27640141 | 12 | 118805689 | TAOK3 | G | A | 2.02E-02 | 0.14 | 0.003 | 0.025 | 2.54E-04 | Zero | 0.000 | 0.033 |
| rs7670525 | 4 | 153814538 | ARFIP1 | A | G | 1.97E-03 | 0.21 | 0.013 | 0.054 | 9.06E-03 | 0.27 | 0.020 | 0.066 |
| kgp28817122 | 8 | 122487115 | | A | A | 9.13E-03 | 0.28 | 0.015 | 0.050 | 1.34E-03 | 0.21 | 0.018 | 0.074 |
| kgp5014707 | 9 | 1702186 | | G | A | 2.54E-02 | Zero | 0.000 | 0.013 | 2.54E-04 | Zero | 0.000 | 0.033 |
| kgp7092772 | 14 | 22379841 | | A | G | 9.73E-03 | Zero | 0.000 | 0.017 | 1.57E-03 | Zero | 0.000 | 0.025 |
| kgp3477351 | 19 | 295864 | | G | A | 2.54E-02 | Zero | 0.000 | 0.013 | 2.54E-04 | Zero | 0.000 | 0.033 |
| kgp23298674 | 21 | 20962564 | | C | A | 1.49E-03 | Zero | 0.000 | 0.025 | 6.90E-02 | Zero | 0.000 | 0.008 |
| kgp12083934 | 16 | 10828979 | | A | G | 3.15E-03 | 0.58 | 0.233 | 0.343 | 1.13E-02 | 0.56 | 0.230 | 0.344 |
| kgp485316 | 7 | 15372018 | AGMO | G | A | 8.50E-05 | 1.93 | 0.490 | 0.325 | 1.49E-01 | 1.36 | 0.443 | 0.369 |
| kgp25191871 | 1 | 115687027 | | A | C | 6.93E-03 | 0.38 | 0.030 | 0.081 | 5.66E-02 | 0.27 | 0.023 | 0.074 |
| kgp24131116 | 2 | 213906695 | IKZF2 | G | A | 9.91E-03 | Zero | 0.000 | 0.017 | 1.57E-03 | Zero | 0.000 | 0.025 |
| kgp9854133 | 3 | 31334098 | | G | A | 6.08E-04 | Zero | 0.000 | 0.029 | ? | Zero | 0.000 | 0.000 |
| kgp22811918 | X | 21960214 | SMS | C | A | 4.90E-03 | 0.52 | 0.063 | 0.142 | 1.38E-02 | 0.45 | 0.047 | 0.115 |
| kgp7792268 | 13 | 23070499 | | C | A | 6.43E-04 | 0.18 | 0.010 | 0.058 | 7.70E-02 | 0.35 | 0.015 | 0.041 |
| kgp11356379 | 11 | 9814612 | LOC283104, SBF2 | G | A | 1.37E-02 | 0.66 | 0.353 | 0.457 | 1.59E-03 | 0.48 | 0.336 | 0.483 |
| kgp25712222 | 12 | 56245724 | | A | G | 9.10E-03 | 0.11 | 0.003 | 0.029 | 1.65E-03 | Zero | 0.000 | 0.025 |
| rs1886214 | 13 | 42948531 | | G | A | 4.17E-03 | 1.79 | 0.272 | 0.171 | 1.06E-02 | 1.99 | 0.285 | 0.172 |
| kgp1054273 | 12 | 67131774 | | G | A | 2.33E-04 | Zero | 0.000 | 0.033 | 2.03E-01 | 0.30 | 0.005 | 0.016 |
| kgp9551947 | 18 | 42502140 | SETBP1 | G | A | 3.79E-02 | Zero | 0.000 | 0.021 | 2.25E-03 | 0.11 | 0.005 | 0.041 |
| kgp5483926 | 3 | 144352913 | | A | C | 6.84E-02 | Zero | 0.000 | 0.008 | 1.51E-05 | 0.07 | 0.005 | 0.065 |
| kgp4155998 | 1 | 184734012 | | G | A | 2.76E-02 | 0.19 | 0.005 | 0.025 | 2.54E-04 | Zero | 0.000 | 0.033 |
| kgp2958113 | 5 | 163341388 | | A | C | 2.76E-02 | 0.19 | 0.005 | 0.025 | 2.54E-04 | Zero | 0.000 | 0.033 |
| kgp8335515 | 11 | 4926211 | | G | A | 8.09E-03 | 0.10 | 0.003 | 0.025 | 2.45E-03 | 0.07 | 0.002 | 0.033 |
| kgp5388938 | 8 | 79087167 | | C | A | 9.26E-05 | Zero | 0.000 | 0.038 | 6.79E-01 | 0.60 | 0.005 | 0.008 |
| kgp28687699 | 8 | 79225285 | | A | G | 9.26E-05 | Zero | 0.000 | 0.038 | 6.79E-01 | 0.60 | 0.005 | 0.008 |
| kgp116275307 | 14 | 78954642 | NRXN3 | A | G | 2.83E-03 | 0.41 | 0.048 | 0.113 | 3.48E-03 | 0.40 | 0.070 | 0.156 |
| kgp24753470 | 1 | 26013940 | MANIC1 | A | C | 1.19E-02 | 0.16 | 0.005 | 0.029 | 1.61E-02 | Zero | 0.000 | 0.025 |
| kgp1285441 | 3 | 56931141 | ARHGEF3 | G | A | 8.54E-04 | 0.49 | 0.124 | 0.225 | 3.75E-02 | 0.57 | 0.137 | 0.213 |
| rs17638791 | 6 | 51940816 | PKHD1 | A | G | 7.32E-03 | 2.73 | 0.093 | 0.038 | 4.61E-03 | 4.95 | 0.102 | 0.025 |
| rs2325911 | 6 | 125027223 | NKAIN2 | C | A | 3.65E-02 | 0.61 | 0.121 | 0.179 | 1.48E-04 | 0.39 | 0.118 | 0.262 |
| kgp10967046 | 15 | 66274387 | MEGF11 | G | A | 5.49E-02 | 0.50 | 0.041 | 0.075 | 1.04E-04 | 0.24 | 0.030 | 0.123 |
| rs12013377 | X | 92620062 | | A | G | 5.41E-03 | 0.67 | 0.409 | 0.542 | 6.48E-03 | 0.60 | 0.400 | 0.557 |
| kgp7186699 | 4 | 184878777 | STOX2 | G | A | 1.79E-02 | 2.38 | 0.088 | 0.038 | 1.13E-03 | 13.37 | 0.100 | 0.008 |
| kgp9368119 | 7 | 11707419 | THSD7A | A | G | 1.06E-02 | 0.65 | 0.427 | 0.529 | 1.75E-02 | 0.60 | 0.343 | 0.459 |
| kgp124162 | 11 | 72356846 | PDE2A | A | G | 1.89E-02 | 0.21 | 0.013 | 0.054 | 1.55E-02 | 0.28 | 0.018 | 0.057 |
| kgp8440036 | 4 | 78058785 | | G | A | 6.77E-04 | 0.25 | 0.018 | 0.075 | 9.68E-02 | 0.43 | 0.020 | 0.049 |
| rs4738738 | 8 | 59844254 | TOX | A | C | 1.63E-02 | 1.49 | 0.424 | 0.324 | 6.74E-04 | 2.22 | 0.425 | 0.254 |

TABLE 38-continued

Standard Response SNPs

| | STANDARD PHENOTYPE | | | | | Gala Cohort | | | | Forte Cohort | | | |
|---|---|---|---|---|---|---|---|---|---|---|---|---|---|
| Prioritized Variants | Name | Chromosome | Position | Gene(s) | Major Allele (d) | Minor Allele (D) | P-value (Armitage Test) | Odds Ratio (Minor Allele) | Minor Allele Freq. (Responders) | Allele Freq. (Non-Responders) | P-value (Armitage Test) | Odds Ratio (Minor Allele) | Minor Allele Freq. (Responders) | Allele Freq. (Non-Responders) |
| | kgp7802182 | 18 | 56759170 | | A | G | 2.53E-02 | 0.67 | 0.222 | 0.304 | 7.43E-04 | 0.44 | 0.194 | 0.336 |
| | kgp2923815 | 19 | 43931355 | | G | A | 3.62E-03 | 0.44 | 0.066 | 0.133 | 1.21E-02 | 0.42 | 0.063 | 0.131 |
| | rs3767955 | 1 | 41104475 | RIMS3 | G | A | 2.57E-04 | 2.00 | 0.351 | 0.213 | 1.04E-01 | 1.47 | 0.331 | 0.254 |
| | kgp3418770 | 10 | 59425598 | | A | G | 5.89E-03 | 6.24 | 0.048 | 0.008 | 6.50E-03 | Infinity | 0.056 | 0.000 |
| | rs17449018 | 9 | 7060825 | KDM4C | G | A | 3.68E-04 | 2.03 | 0.326 | 0.195 | 7.93E-02 | 1.53 | 0.311 | 0.230 |
| | kgp4524468 | 22 | 32724532 | | A | G | 1.99E-04 | 2.16 | 0.304 | 0.169 | 7.14E-02 | 1.62 | 0.259 | 0.178 |
| | kgp4418535 | 6 | 32431558 | | C | A | 5.99E-04 | 2.37 | 0.202 | 0.100 | 1.80E-02 | 2.46 | 0.152 | 0.074 |
| | kgp2283022 | X | 9742468 | | G | A | 7.11E-02 | 0.71 | 0.151 | 0.214 | 8.53E-05 | 0.41 | 0.115 | 0.280 |
| | kgp7063887 | 1 | 189928568 | | G | A | 8.17E-03 | 0.48 | 0.058 | 0.121 | 1.47E-02 | 0.36 | 0.030 | 0.082 |
| | rs1621509 | 7 | 2969680 | CARD11 | G | A | 2.25E-03 | 2.06 | 0.226 | 0.133 | 3.02E-02 | 1.82 | 0.253 | 0.158 |
| | kgp4842590 | 1 | 110249364 | | A | C | 2.30E-02 | 0.37 | 0.020 | 0.055 | 5.15E-04 | 0.17 | 0.010 | 0.066 |
| | rs11192469 | 10 | 107282331 | | A | G | 1.11E-02 | 0.51 | 0.081 | 0.143 | 1.30E-03 | 0.39 | 0.085 | 0.189 |
| | kgp8303520 | 7 | 154911234 | | C | A | 5.76E-03 | 0.63 | 0.449 | 0.563 | 3.00E-02 | 0.64 | 0.376 | 0.492 |
| | rs13415334 | 2 | 60324127 | | A | G | 1.42E-02 | 0.67 | 0.374 | 0.475 | 2.98E-02 | 0.52 | 0.341 | 0.484 |
| | rs9876830 | 3 | 157311299 | C3orf55 | G | A | 1.35E-03 | 1.89 | 0.351 | 0.238 | 2.85E-02 | 1.72 | 0.346 | 0.246 |
| | kgp11285862 | 21 | 18177980 | | A | G | 1.36E-03 | 0.07 | 0.003 | 0.033 | 4.46E-02 | 0.19 | 0.002 | 0.025 |
| | rs2824070 | 21 | 18205972 | | G | A | 3.48E-03 | 0.20 | 0.010 | 0.046 | 1.11E-02 | 0.24 | 0.010 | 0.049 |
| | rs7181058 | 14 | 98385698 | | G | A | 2.11E-03 | 0.24 | 0.015 | 0.058 | 4.15E-02 | 0.29 | 0.012 | 0.041 |
| | kgp5002011 | 1 | 110265738 | | G | A | 3.87E-03 | 0.46 | 0.035 | 0.071 | 2.96E-04 | 0.25 | 0.025 | 0.107 |
| | rs2139612 | X | 92614918 | | A | C | 6.26E-03 | 0.68 | 0.412 | 0.542 | 7.28E-03 | 0.61 | 0.395 | 0.549 |
| | rs7860748 | 9 | 114202502 | KIAA0368 | G | A | 5.70E-03 | 0.63 | 0.381 | 0.492 | 9.79E-03 | 0.59 | 0.358 | 0.492 |
| | rs17029538 | 2 | 65096800 | | A | C | 2.02E-04 | 0.26 | 0.028 | 0.097 | 4.36E-01 | 0.65 | 0.027 | 0.041 |
| | kgp1371607 | 16 | 76291607 | | A | G | 6.85E-03 | 0.53 | 0.083 | 0.160 | 6.32E-03 | 0.46 | 0.075 | 0.164 |
| | rs10492882 | 16 | 76293394 | | A | G | 1.03E-02 | 0.55 | 0.083 | 0.155 | 3.04E-03 | 0.44 | 0.075 | 0.172 |
| | rs9393727 | 6 | 26500011 | | C | G | 2.78E-03 | 0.46 | 0.074 | 0.150 | 2.76E-03 | 0.44 | 0.108 | 0.213 |
| | rs1894408 | 6 | 32786833 | | C | G | 3.02E-03 | 1.72 | 0.419 | 0.305 | 9.30E-03 | 1.82 | 0.407 | 0.279 |
| 0 - Priority genes, Predictive Model | | | | | | | | | | | | | | |
| | rs2839117 | 21 | 47550754 | COL6A2 | G | A | 1.24E-02 | 0.59 | 0.334 | 0.213 | 1.25E-03 | 0.45 | 0.137 | 0.262 |
| | kgp8437961 | 2 | 99960003 | EIF5B | G | A | 2.79E-03 | 0.50 | 0.099 | 0.183 | 1.07E-02 | 0.48 | 0.110 | 0.197 |
| | rs1508102 | 11 | 116379889 | | G | A | 4.99E-04 | 0.34 | 0.043 | 0.117 | 4.52E-02 | 0.50 | 0.060 | 0.115 |
| | rs4449139 | 2 | 124875366 | CNTNAP5 | G | A | 5.12E-03 | 0.63 | 0.389 | 0.504 | 3.76E-02 | 0.55 | 0.408 | 0.557 |
| | rs11559024 | 19 | 45821183 | CKM | A | G | 2.50E-03 | Zero | 0.000 | 0.029 | 1.18E-02 | 0.15 | 0.005 | 0.033 |
| 2 - Priority genes | rs1894407 | 6 | 32787036 | | C | A | 1.75E-03 | 1.77 | 0.419 | 0.300 | 1.81E-02 | 1.72 | 0.403 | 0.287 |
| 2 - Priority genes | rs2857103 | 6 | 32791299 | TAP2 | C | A | 5.72E-03 | 1.70 | 0.369 | 0.269 | 4.13E-03 | 2.04 | 0.356 | 0.221 |
| 2 - Priority genes | rs9501224 | 6 | 32792910 | TAP2 | G | A | 6.53E-03 | 1.69 | 0.369 | 0.271 | 4.13E-03 | 2.04 | 0.356 | 0.221 |
| 0 - Priority in Predictive Model | kgp8110667 | 22 | 32716792 | | G | A | 5.97E-03 | Infinity | 0.030 | 0.000 | 1.46E-02 | Infinity | 0.050 | 0.000 |

TABLE 38-continued

Standard Response SNPs

| STANDARD PHENOTYPE | | | | | | | Gala Cohort | | | | Forte Cohort | | | |
|---|---|---|---|---|---|---|---|---|---|---|---|---|---|---|
| Prioritized Variants | Name | Chromosome | Position | Gene(s) | Major Allele (d) | Minor Allele (D) | P-value (Armitage Test) | Odds Ratio (Minor Allele) | Minor Allele Freq. (Responders) | Allele Freq. (Non-Responders) | P-value (Armitage Test) | Odds Ratio (Minor Allele) | Minor Allele Freq. (Responders) | Allele Freq. (Non-Responders) |
| 0 - Priority genes, Predictive Model | kgp6599438 | 20 | 40843626 | PTPRT | G | A | 3.70E-03 | 0.21 | 0.010 | 0.046 | 1.55E-02 | 0.28 | 0.018 | 0.057 |
| 2 - Priority genes | rs241451 | 6 | 32796480 | TAP2 | A | G | 6.26E-03 | 1.69 | 0.365 | 0.267 | 1.13E-02 | 1.86 | 0.354 | 0.233 |
| 2 - Priority genes | rs1894406 | 6 | 32787056 | TAP2 | G | A | 2.63E-03 | 1.74 | 0.402 | 0.288 | 1.73E-02 | 1.76 | 0.361 | 0.246 |
| 2 - Priority genes | rs3218328 | 22 | 37524008 | IL2RB | G | A | 1.09E-02 | 0.16 | 0.005 | 0.030 | 1.39E-02 | 0.10 | 0.003 | 0.025 |
| 2 - Priority genes | rs241443 | 6 | 32797115 | TAP2 | A | C | 1.05E-02 | 1.63 | 0.367 | 0.273 | 5.28E-03 | 2.01 | 0.349 | 0.217 |
| 2 - Priority genes | rs2621323 | 6 | 32788707 | TAP2 | A | G | 1.90E-02 | 1.56 | 0.371 | 0.286 | 3.09E-03 | 2.07 | 0.363 | 0.221 |
| 2 - Priority genes | kgp304921 | 20 | 14017077 | MACROD2 | A | G | 3.43E-02 | 0.50 | 0.038 | 0.081 | 1.51E-02 | 0.32 | 0.020 | 0.066 |
| 2 - Priority genes | rs241456 | 6 | 32795965 | TAP2 | G | A | 2.12E-02 | 1.55 | 0.313 | 0.229 | 8.54E-03 | 20.0 | 0.299 | 0.180 |
| 0 - Priority genes, Predictive Model | kgp7747883 | 18 | 74804250 | MBP | G | A | 3.55E-02 | 0.70 | 0.346 | 0.429 | 9.82E-03 | 0.57 | 0.325 | 0.451 |
| 2 - Priority genes | rs2621321 | 6 | 32789480 | | A | G | 2.38E-02 | 1.54 | 0.316 | 0.233 | 7.19E-03 | 2.05 | 0.300 | 0.180 |
| 2 - Priority genes | rs2857104 | 6 | 32790167 | TAP2 | G | C | 2.38E-02 | 1.54 | 0.316 | 0.233 | 7.89E-03 | 2.03 | 0.299 | 0.180 |
| 2 - Priority genes | rs241454 | 6 | 32796144 | TAP2 | A | G | 2.57E-02 | 1.53 | 0.315 | 0.233 | 7.80E-03 | 2.02 | 0.300 | 0.180 |
| 2 - Priority genes | rs241447 | 6 | 32796751 | TAP2 | G | A | 2.85E-02 | 1.52 | 0.313 | 0.233 | 8.34E-03 | 2.01 | 0.303 | 0.183 |
| 2 - Priority genes | kgp974569 | 6 | 32796057 | TAP2 | G | A | 2.85E-02 | 1.52 | 0.313 | 0.233 | 7.80E-03 | 2.02 | 0.300 | 0.180 |
| 2 - Priority genes | rs2857101 | 6 | 32794676 | TAP2 | A | G | 2.48E-02 | 1.53 | 0.313 | 0.231 | 9.33E-03 | 2.00 | 0.296 | 0.180 |
| 2 - Priority genes | kgp10224254 | 6 | 32785904 | TAP2 | C | A | 5.85E-03 | 1.63 | 0.424 | 0.317 | 4.44E-02 | 1.58 | 0.386 | 0.287 |
| 2 - Priority genes | rs241444 | 6 | 32797109 | TAP2 | G | A | 2.85E-02 | 1.52 | 0.313 | 0.233 | 8.54E-03 | 2.00 | 0.299 | 0.180 |
| 2 - Priority genes | kgp4479467 | 6 | 32629331 | HLA-DQB1 | A | G | 2.03E-02 | 1.50 | 0.391 | 0.300 | 1.59E-02 | 1.80 | 0.374 | 0.262 |
| 2 - Priority genes | kgp10632945 | 20 | 4682507 | | G | A | 1.87E-02 | 0.62 | 0.177 | 0.254 | 3.48E-02 | 0.59 | 0.170 | 0.254 |
| 2 - Priority genes | rs241446 | 6 | 32796967 | TAP2 | G | A | 2.49E-02 | 1.53 | 0.311 | 0.229 | 1.09E-02 | 1.96 | 0.295 | 0.180 |
| 2 - Priority genes | rs241453 | 6 | 32796226 | TAP2 | A | G | 3.40E-02 | 1.50 | 0.311 | 0.233 | 7.80E-03 | 2.02 | 0.300 | 0.180 |
| 2 - Priority genes | rs241449 | 6 | 32796653 | TAP2 | C | A | 3.25E-02 | 1.50 | 0.308 | 0.229 | 9.22E-03 | 1.99 | 0.298 | 0.180 |
| 0 - Priority genes, Predictive Model | rs10162089 | 13 | 31316738 | ALOXSAP | G | A | 7.79E-03 | 1.56 | 0.508 | 0.398 | 3.16E-02 | 1.58 | 0.457 | 0.344 |
| 2 - Priority genes | rs2071469 | 6 | 32784783 | HLA-DOB | G | A | 6.76E-03 | 1.62 | 0.426 | 0.321 | 4.44E-02 | 1.58 | 0.386 | 0.287 |
| 2 - Priority genes | p1_m_061510_6_159_p | 6 | 32795505 | TAP2 | I | D | 3.66E-02 | 1.49 | 0.310 | 0.233 | 7.80E-03 | 2.02 | 0.300 | 0.180 |
| 2 - Priority genes | rs241452 | 6 | 32796346 | TAP2 | A | G | 3.31E-02 | 1.50 | 0.313 | 0.235 | 8.43E-03 | 2.01 | 0.299 | 0.180 |
| 2 - Priority genes | kgp2388352 | 6 | 32797297 | TAP2 | G | A | 4.25E-02 | 1.47 | 0.311 | 0.235 | 7.06E-03 | 2.02 | 0.304 | 0.180 |
| 2 - Priority genes | kgp8036704 | 6 | 32796521 | TAP2 | G | A | 3.51E-02 | 1.50 | 0.310 | 0.233 | 8.61E-03 | 2.02 | 0.296 | 0.180 |
| 2 - Priority genes | rs241442 | 6 | 32797168 | TAP2 | G | A | 3.94E-02 | 1.48 | 0.311 | 0.235 | 7.80E-03 | 2.02 | 0.300 | 0.180 |
| 2 - Priority genes | rs241445 | 6 | 32797072 | TAP2 | G | A | 3.57E-02 | 1.49 | 0.312 | 0.235 | 8.54E-03 | 2.00 | 0.299 | 0.180 |
| 2 - Priority genes | rs1410779 | 9 | 5083173 | JAK2 | G | A | 1.93E-02 | 0.61 | 0.145 | 0.217 | 1.29E-02 | 0.54 | 0.178 | 0.279 |
| 2 - Priority genes | kgp23672937 | 7 | 18685891 | HDAC9 | G | A | 4.94E-02 | 0.15 | 0.003 | 0.017 | 9.97E-03 | Zero | 0.000 | 0.016 |
| 2 - Priority genes | kgp4346717 | 18 | 74810199 | MBP | G | A | 4.94E-02 | 0.15 | 0.003 | 0.017 | 9.97E-03 | Zero | 0.000 | 0.016 |
| 2 - Priority genes | kgp9699754 | 10 | 79358319 | KCNMA1 | A | G | 2.70E-02 | Infinity | 0.020 | 0.000 | 4.11E-02 | Infinity | 0.033 | 0.000 |
| 2 - Priority genes | rs241440 | 6 | 32797361 | TAP2 | G | A | 3.40E-02 | 1.50 | 0.311 | 0.233 | 1.09E-02 | 1.96 | 0.295 | 0.180 |
| 2 - Priority genes | fgp5334779 | 6 | 32628420 | HLA-DQB1 | G | A | 1.68E-02 | 1.53 | 0.391 | 0.298 | 2.74E-02 | 1.73 | 0.362 | 0.262 |
| 2 - Priority genes | kgp4898179 | 6 | 32629347 | HLA-DQB1 | A | G | 2.53E-02 | 1.48 | 0.391 | 0.304 | 1.87E-02 | 1.77 | 0.372 | 0.262 |
| 0 - Priority in Predictive Model | rs759458 | 2 | 65245365 | SLC1A4 | G | A | 1.08E-03 | 1.90 | 0.303 | 0.183 | 4.74E-01 | 1.18 | 0.288 | 0.254 |

TABLE 38-continued

Standard Response SNPs

| | STANDARD PHENOTYPE | | | | | | Gala Cohort | | | | Forte Cohort | | |
|---|---|---|---|---|---|---|---|---|---|---|---|---|---|
| Prioritized Variants | Name | Chromosome | Position | Gene(s) | Major Allele (d) | Minor Allele (D) | P-value (Armitage Test) | Odds Ratio (Minor Allele) | Minor Allele Freq. (Responders) | Allele Freq. (Non-Responders) | P-value (Armitage Test) | Odds Ratio (Minor Allele) | Minor Allele Freq. (Responders) | Allele Freq. (Non-Responders) |
| 2 - Priority genes | rs2071472 | 6 | 32784620 | HLA-DOB | G | A | 2.91E-02 | 1.49 | 0.348 | 0.267 | 1.86E-02 | 1.79 | 0.331 | 0.221 |
| 2 - Priority genes | rs2071470 | 6 | 32784753 | HLA-DOB | A | G | 2.91E-02 | 1.49 | 0.348 | 0.267 | 1.86E-02 | 1.79 | 0.331 | 0.221 |
| 2 - Priority genes | kgp25543811 | 18 | 74774894 | MBP, MBP | G | A | 4.81E-02 | 0.15 | 0.003 | 0.017 | 1.37E-02 | 0.10 | 0.002 | 0.025 |
| 2 - Priority genes | kgp293787 | 20 | 40905098 | PTPRT | G | A | 4.86E-03 | 0.15 | 0.005 | 0.038 | 2.19E-02 | 0.39 | 0.032 | 0.082 |
| 2 - Priority genes | rs2043136 | 3 | 30720304 | TGFBR2 | A | G | 4.42E-02 | 1.47 | 0.306 | 0.233 | 3.75E-02 | 1.67 | 0.308 | 0.208 |
| 2 - Priority genes | rs4769060 | 13 | 31337877 | ALOXSAP | A | G | 3.14E-02 | 1.42 | 0.472 | 0.383 | 3.13E-02 | 1.60 | 0.438 | 0.328 |
| 2 - Priority genes | kgp6032617 | 13 | 31287981 | ALOXSAP | A | G | 3.11E-02 | 0.68 | 0.212 | 0.292 | 4.38E-02 | 1.62 | 0.233 | 0.320 |
| 2 - Priority genes | kgp5441587 | 6 | 32827356 | PSMB9 | G | A | 4.56E-02 | 0.14 | 0.003 | 0.017 | 1.97E-02 | 0.23 | 0.010 | 0.041 |
| 2 - Priority genes | rs241435 | 6 | 32798243 | TAP2, TAP2 | G | A | 4.94E-02 | 0.15 | 0.003 | 0.017 | 1.97E-02 | 0.23 | 0.010 | 0.041 |
| 2 - Priority genes | kgp3182607 | 6 | 32823948 | PSMB9 | G | A | 4.94E-02 | 0.15 | 0.003 | 0.017 | 1.97E-02 | 0.23 | 0.010 | 0.041 |
| 2 - Priority genes | kgp22778566 | 7 | 1950337 | MAD1L1 | G | A | 3.10E-02 | 1.56 | 0.276 | 0.199 | 2.87E-02 | 1.95 | 0.216 | 0.131 |
| 2 - Priority genes | kgp97310 | 9 | 5122932 | JAK2 | A | G | 4.58E-02 | 0.68 | 0.174 | 0.242 | 1.99E-02 | 0.58 | 0.225 | 0.328 |
| 2 - Priority genes | kgp5440506 | 13 | 31320543 | ALOXSAP | C | A | 3.82E-02 | 0.71 | 0.393 | 0.479 | 2.50E-02 | 0.63 | 0.462 | 0.583 |
| 2 - Priority genes | rs11147439 | 13 | 31325643 | ALOXSAP | C | A | 4.34E-02 | 0.72 | 0.396 | 0.479 | 2.16E-02 | 0.62 | 0.460 | 0.582 |
| 2 - Priority genes | rs4360791 | 13 | 31318020 | ALOXSAP | G | A | 4.65E-02 | 0.72 | 0.409 | 0.492 | 2.32E-02 | 0.63 | 0.470 | 0.590 |
| 2 - Priority genes | rs9671182 | 13 | 31321138 | ALOXSAP | C | G | 3.90E-02 | 0.7 | 0.398 | 0.483 | 2.76E-02 | 0.64 | 0.465 | 0.582 |
| 2 - Priority genes | rs4356336 | 13 | 31319546 | ALOXSAP | A | G | 3.98E-02 | 0.71 | 0.399 | 0.483 | 2.76E-02 | 0.64 | 0.465 | 0.582 |
| 2 - Priority genes | rs10815160 | 9 | 5116616 | JAK2 | A | C | 3.58E-02 | 0.66 | 0.180 | 0.252 | 3.69E-02 | 0.62 | 0.234 | 0.328 |
| 2 - Priority genes | rs4254166 | 13 | 31322949 | ALOXSAP | A | G | 4.97E-02 | 0.72 | 0.399 | 0.479 | 2.40E-02 | 0.63 | 0.463 | 0.580 |
| 2 - Priority genes | kgp2715873 | 13 | 31320249 | ALOXSAP | A | G | 4.97E-02 | 0.72 | 0.399 | 0.479 | 2.76E-02 | 0.64 | 0.465 | 0.582 |
| 2 - Priority genes | rs9670531 | 13 | 31321069 | ALOXSAP | A | G | 4.97E-02 | 0.72 | 0.399 | 0.479 | 2.76E-02 | 0.64 | 0.465 | 0.582 |
| 1 - Priority variants | rs2487896 | 10 | 100802380 | HPSE2 | G | A | 5.73E-01 | 0.88 | 0.139 | 0.155 | 5.50E-04 | 0.39 | 0.122 | 0.246 |
| 0 - Priority variants | rs3135391 | 6 | 32410987 | HLA-DRA | G | A | 3.99E-02 | 0.66 | 0.174 | 0.242 | 4.99E-02 | 0.64 | 0.231 | 0.320 |
| Predictive Model | | | | | | | | | | | | | | |
| 2 - Priority genes | kgp26271158 | 6 | 32823393 | PSMB9 | G | A | 4.94E-02 | 0.15 | 0.003 | 0.017 | 4.15E-02 | 0.29 | 0.012 | 0.041 |
| 1 - Priority variants | rs3135388 | 6 | 32413051 | | G | A | 4.72E-02 | 0.67 | 0.174 | 0.239 | 4.99E-02 | 0.64 | 0.231 | 0.320 |
| 2 - Priority genes | kgp11281589 | 7 | 1941003 | MAD1L1 | A | G | 4.53E-02 | 1.49 | 0.282 | 0.211 | 4.24E-02 | 1.85 | 0.210 | 0.131 |
| 1 - Priority variants | rs17575455 | 2 | 76624220 | | C | A | 4.13E-01 | 0.87 | 0.331 | 0.363 | 6.21E-03 | 0.56 | 0.308 | 0.443 |
| 1 - Priority variants | rs947603 | 10 | 95249605 | | A | G | 5.39E-02 | 1.48 | 0.258 | 0.192 | 1.59E-01 | 1.45 | 0.225 | 0.164 |

(Note:
Odds Ratio > 1 = Minor Allele is associated with Response,
Odds Ratio < 1 = Minor Allele Associated with Non-Response)

TABLE 38

Standard Response SNPs

| | STANDARD PHENOTYPE | | | | | | | | | Combined | | | | | |
|---|---|---|---|---|---|---|---|---|---|---|---|---|---|---|---|
| Prioritized Variants | Name | Chromosome | Position | Gene(s) | Major Allele (d) | Minor Allele (D) | P-value (Armitage Test) | Odds Ratio (Minor Allele) | Minor Allele Freq. (Responders) | Allele Freq. (Non-responders) | DD (Responders) | DD (Non-responders) | Dd (Responders) | Dd (Non-responders) | dd (Responders) | dd (Non-responders) |
| 0 - Priority in Predictive Model | kgp24415534 | 2 | 174156875 | | G | A | 3.98E-07 | 0.08 | 0.004 | 0.044 | 0 | 0 | 3 | 16 | 396 | 165 |
| | kgp12008955 | 2 | 73759636 | ALMS1 | G | A | 3.98E-07 | 0.08 | 0.004 | 0.044 | 0 | 0 | 3 | 16 | 396 | 165 |
| | kgp26026546 | 13 | 79972606 | RBM26 | A | C | 4.46E-07 | 0.03 | 0.001 | 0.036 | 0 | 0 | 1 | 13 | 397 | 167 |
| 0 - Priority in Predictive Model | rs16886004 | 7 | 78021500 | MAGI2 | A | G | 9.81E-07 | 2.79 | 0.199 | 0.089 | 6 | 2 | 147 | 28 | 246 | 149 |
| | kgp25952891 | 13 | 80027089 | | A | G | 1.41E-06 | 0.04 | 0.001 | 0.033 | 0 | 0 | 1 | 12 | 398 | 168 |
| | kgp3450875 | 16 | 57268931 | RSPRY1 | G | A | 1.99E-06 | 0.12 | 0.006 | 0.047 | 0 | 0 | 5 | 17 | 394 | 164 |
| | rs10251797 | 7 | 78025427 | MAGI2 | C | A | 2.21E-06 | 2.67 | 0.197 | 0.091 | 6 | 2 | 145 | 29 | 248 | 150 |
| | kgp2299675 | 20 | 16933074 | | G | A | 2.28E-06 | 0.19 | 0.014 | 0.064 | 0 | 0 | 11 | 23 | 388 | 158 |
| | kgp10594414 | 1 | 216039833 | USH2A | A | G | 2.44E-06 | 0.14 | 0.008 | 0.050 | 0 | 0 | 6 | 18 | 391 | 163 |
| | kgp1688752 | 21 | 43016736 | | G | A | 2.53E-06 | 0.33 | 0.040 | 0.113 | 1 | 2 | 30 | 37 | 368 | 142 |
| | kgp12230354 | 5 | 27037978 | CDH9 | A | C | 2.74E-06 | 0.19 | 0.013 | 0.061 | 0 | 0 | 10 | 22 | 386 | 159 |
| | rs543122 | 3 | 124164156 | KALRN | G | A | 3.17E-06 | 0.54 | 0.423 | 0.569 | 70 | 54 | 195 | 97 | 131 | 29 |
| | kgp6236949 | 2 | 60301030 | | A | G | 3.26E-06 | 0.54 | 0.283 | 0.423 | 30 | 34 | 166 | 85 | 203 | 62 |
| | kgp9627338 | 17 | 90155 | RPH3AL | A | G | 3.52E-06 | 0.45 | 0.105 | 0.207 | 6 | 7 | 7 | 61 | 320 | 113 |
| | kgp11441512 | 20 | 35283733 | NDRG3 | G | A | 4.12E-06 | 0.21 | 0.014 | 0.064 | 0 | 1 | 11 | 21 | 388 | 158 |
| | rs9579566 | 13 | 30980265 | | G | A | 4.19E-06 | 0.26 | 0.023 | 0.080 | 0 | 1 | 18 | 27 | 381 | 153 |
| | rs2816838 | 10 | 52714759 | | G | A | 4.79E-06 | 0.46 | 0.125 | 0.229 | 4 | 8 | 92 | 67 | 303 | 106 |
| | kgp4705854 | 12 | 19907696 | | G | A | 4.80E-06 | 0.55 | 0.315 | 0.456 | 41 | 38 | 169 | 89 | 189 | 54 |
| 0 - Priority in Predictive Model | rs9817308 | 3 | 124182136 | KALRN | A | C | 5.18E-06 | 0.55 | 0.429 | 0.572 | 71 | 55 | 199 | 96 | 127 | 29 |
| | kgp8817856 | 6 | 32744440 | | G | A | 5.33E-06 | 0.53 | 0.392 | 0.528 | 50 | 44 | 208 | 103 | 135 | 34 |
| 0 - Priority in Predictive Model | kgp6214351 | 11 | 75546691 | UVRAG | A | G | 5.51E-06 | 0.35 | 0.046 | 0.119 | 0 | 2 | 37 | 39 | 361 | 140 |
| | kgp2356388 | 16 | 19771577 | IQCK | G | A | 5.78E-06 | 0.46 | 0.133 | 0.235 | 4 | 5 | 98 | 75 | 297 | 101 |
| | kgp74416024 | 9 | 21453902 | | G | A | 6.06E-06 | 0.13 | 0.006 | 0.044 | 0 | 0 | 5 | 16 | 393 | 165 |
| | rs6718758 | 2 | 6328802 | | G | A | 6.08E-06 | 0.55 | 0.307 | 0.445 | 35 | 38 | 175 | 85 | 189 | 58 |
| | rs7579987 | 2 | 60307009 | | C | C | 6.43E-06 | 0.55 | 0.331 | 0.469 | 40 | 41 | 584 | 87 | 175 | 52 |
| | kgp7217872 | 17 | 88988 | RPH3AL | G | A | 7.50E-06 | 0.47 | 0.108 | 0.207 | 6 | 7 | 74 | 61 | 319 | 113 |
| | rs13394010 | 2 | 60302746 | | A | G | 7.81E-06 | 0.56 | 0.330 | 0.467 | 39 | 41 | 185 | 86 | 295 | 53 |
| | rs7191155 | 16 | 19800213 | IQCK | G | A | 7.89E-06 | 0.46 | 0.133 | 0.233 | 4 | 5 | 97 | 74 | 295 | 101 |
| | rs9931167 | 16 | 19792598 | IQCK | G | A | 8.07E-06 | 0.46 | 0.133 | 0.233 | 5 | 5 | 98 | 74 | 297 | 101 |
| | rs11691553 | 2 | 60303554 | | C | A | 8.19E-06 | 0.56 | 0.330 | 0.467 | 39 | 41 | 183 | 86 | 174 | 53 |
| | rs11648129 | 16 | 19820694 | IQCK | A | G | 8.23E-06 | 0.47 | 0.132 | 0.232 | 4 | 5 | 97 | 74 | 297 | 102 |
| | kgp25216186 | 1 | 23752427 | ASAP3 | A | G | 8.36E-06 | 0.07 | 0.003 | 0.033 | 0 | 0 | 2 | 12 | 397 | 169 |
| | kgp29794723 | 10 | 18397332 | | A | G | 8.64E-06 | 0.25 | 0.020 | 0.072 | 4 | 0 | 16 | 26 | 382 | 155 |
| | kgp3829539 | 16 | 19722366 | C16orf88 | A | G | 8.80E-06 | 0.47 | 0.133 | 0.233 | 4 | 5 | 98 | 74 | 296 | 101 |

TABLE 38-continued

Standard Response SNPs

| | STANDARD PHENOTYPE | | | | | | | | | Combined | | | | | |
|---|---|---|---|---|---|---|---|---|---|---|---|---|---|---|---|
| Prioritized Variants Name | Chromosome | Position | Gene(s) | Major Allele (d) | Minor Allele (D) | P-value (Armitage Test) | Odds Ratio (Minor Allele) | Minor Allele Freq. (Responders) | Allele Freq. (Non-responders) | DD (Responders) | DD (Non-responders) | Dd (Responders) | Dd (Non-responders) | dd (Responders) | dd (Non-responders) |
| rs6895094 | 5 | 141037277 | ARAP3 | A | C | 9.24E-06 | 0.57 | 0.368 | 0.508 | 56 | 46 | 181 | 92 | 161 | 43 |
| kgp1009249 | 12 | 19838334 | | G | A | 9.55E-06 | 0.51 | 0.195 | 0.311 | 10 | 16 | 136 | 80 | 253 | 84 |
| rs10203396 | 2 | 60305110 | | A | G | 9.72E-06 | 0.56 | 0.332 | 0.467 | 39 | 41 | 186 | 87 | 173 | 53 |
| kgp3854180 | 16 | 19721806 | C16orf88 | G | A | 1.00E-05 | 0.47 | 0.133 | 0.232 | 4 | 5 | 98 | 74 | 297 | 102 |
| rs6497396 | 16 | 19735697 | IQCK | A | G | 1.02E-05 | 0.48 | 0.143 | 0.246 | 6 | 6 | 102 | 77 | 290 | 98 |
| rs13419758 | 2 | 60302920 | | G | A | 1.09E-05 | 0.56 | 0.332 | 0.467 | 40 | 41 | 185 | 87 | 174 | 53 |
| rs8055485 | 16 | 19750051 | IQCK | A | G | 1.09E-05 | 0.47 | 0.133 | 0.232 | 4 | 5 | 98 | 74 | 296 | 102 |
| rs9931211 | 16 | 19813605 | IQCK | A | G | 1.09E-05 | 0.47 | 0.133 | 0.232 | 4 | 5 | 98 | 74 | 296 | 102 |
| kgp5869992 | 12 | 49219569 | CACNB3 | C | G | 1.13E-05 | 0.58 | 0.384 | 0.528 | 60 | 58 | 184 | 74 | 152 | 48 |
| kgp9320791 | 2 | 60309952 | | C | G | 1.15E-05 | 0.56 | 0.333 | 0.467 | 39 | 41 | 187 | 87 | 172 | 53 |
| kgp7730397 | 16 | 19740243 | IQCK | A | G | 1.15E-05 | 0.47 | 0.134 | 0.233 | 4 | 5 | 99 | 74 | 295 | 101 |
| kgp11002881 | 11 | 118219897 | CD3G | A | G | 1.17E-05 | 0.10 | 0.004 | 0.036 | 0 | 0 | 3 | 13 | 394 | 167 |
| kgp3205849 | 10 | 121531725 | INPP5F | A | G | 1.18E-05 | 0.53 | 0.178 | 0.295 | 13 | 18 | 115 | 69 | 269 | 91 |
| kgp6127371 | 4 | 153856357 | | A | G | 1.23E-05 | 0.23 | 0.016 | 0.064 | 0 | 0 | 13 | 23 | 384 | 157 |
| kgp10305127 | 11 | 99881768 | CNTN5 | A | G | 1.23E-05 | 0.44 | 0.084 | 0.173 | 3 | 6 | 61 | 50 | 334 | 123 |
| rs6535882 | 4 | 153848128 | | G | A | 1.24E-05 | 0.23 | 0.016 | 0.064 | 0 | 0 | 13 | 23 | 386 | 158 |
| kgp6700691 | 4 | 153849531 | | A | G | 1.24E-05 | 0.23 | 0.016 | 0.064 | 0 | 0 | 13 | 23 | 386 | 158 |
| rs11029892 | 11 | 27269546 | | G | A | 1.25E-05 | 1.94 | 0.351 | 0.227 | 44 | 5 | 192 | 72 | 163 | 104 |
| kgp270001 | 16 | 19750275 | IQCK | G | A | 1.27E-05 | 0.48 | 0.143 | 0.244 | 6 | 6 | 102 | 76 | 291 | 98 |
| kgp8192546 | 12 | 19903173 | | G | A | 1.29E-05 | 0.55 | 0.236 | 0.359 | 21 | 23 | 146 | 84 | 232 | 74 |
| kgp5068397 | 16 | 19756348 | IQCK | A | G | 1.32E-05 | 0.51 | 0.183 | 0.294 | 10 | 12 | 126 | 82 | 262 | 86 |
| kgp10910719 | 16 | 19803199 | IQCK | C | A | 1.39E-05 | 0.47 | 0.133 | 0.231 | 4 | 5 | 98 | 73 | 297 | 302 |
| kgp2959751 | 6 | 58719342 | | G | A | 1.39E-05 | 0.22 | 0.015 | 0.061 | 0 | 0 | 12 | 22 | 387 | 159 |
| rs950928 | 16 | 19824638 | IQCK | A | G | 1.43E-05 | 0.48 | 0.138 | 0.236 | 4 | 5 | 102 | 75 | 293 | 300 |
| rs1858973 | 16 | 19743649 | IQCK | A | G | 1.44E-05 | 0.48 | 0.134 | 0.232 | 4 | 5 | 99 | 74 | 295 | 102 |
| rs2660214 | 10 | 52732452 | | A | G | 1.45E-05 | 0.48 | 0.128 | 0.227 | 0 | 8 | 94 | 66 | 301 | 107 |
| kgp2709692 | 18 | 3000808 | LPIN2 | C | G | 1.45E-05 | 0.22 | 0.015 | 0.061 | 0 | 0 | 12 | 22 | 386 | 159 |
| kgp112210903 | 22 | 30898906 | SEC14L4 | G | A | 1.48E-05 | 0.12 | 0.005 | 0.039 | 0 | 1 | 4 | 14 | 395 | 167 |
| kgp8030775 | 8 | 6328607 | MCPH1 | A | C | 1.48E-05 | 0.20 | 0.011 | 0.055 | 0 | 1 | 9 | 18 | 388 | 162 |
| rs10841337 | 12 | 19897179 | | A | G | 1.56E-05 | 0.55 | 0.241 | 0.365 | 22 | 24 | 147 | 84 | 227 | 73 |
| kgp8178358 | 14 | 7092024 | ADAM21 | A | G | 1.57E-05 | 0.12 | 0.005 | 0.039 | 0 | 0 | 4 | 14 | 393 | 167 |
| kgp11843177 | 11 | 27316568 | | A | G | 1.59E-05 | 1.95 | 0.330 | 0.208 | 39 | 4 | 185 | 67 | 175 | 109 |
| kgp23737989 | 7 | 97217288 | | A | G | 1.60E-05 | 0.04 | 0.001 | 0.028 | 0 | 4 | 1 | 10 | 398 | 171 |
| rs7187976 | 16 | 19708196 | C16orf62 | G | A | 1.65E-05 | 0.49 | 0.144 | 0.244 | 6 | 6 | 103 | 76 | 290 | 98 |
| rs1757980 | 6 | 32359821 | HCG23 | G | A | 1.66E-05 | 2.36 | 0.196 | 0.093 | 13 | 5 | 130 | 23 | 255 | 150 |
| kgp5908616 | 2 | 60329823 | | A | C | 1.67E-05 | 0.57 | 0.320 | 0.453 | 37 | 42 | 181 | 80 | 180 | 59 |
| kgp26995430 | 3 | 53359406 | DCP1A | G | A | 1.69E-05 | 0.14 | 0.006 | 0.041 | 0 | 0 | 5 | 15 | 394 | 166 |
| kgp6996560 | 13 | 110124242 | | G | A | 1.69E-05 | 0.14 | 0.006 | 0.041 | 0 | 0 | 5 | 15 | 394 | 166 |
| rs4782279 | 16 | 19759007 | IQCK | A | C | 1.71E-05 | 0.50 | 0.147 | 0.249 | 7 | 7 | 103 | 76 | 288 | 98 |
| rs8053136 | 16 | 19767129 | IQCK | A | C | 1.76E-05 | 0.52 | 0.195 | 0.307 | 12 | 14 | 131 | 83 | 255 | 84 |
| kgp11328629 | 10 | 120711084 | | G | A | 1.79E-05 | 2.95 | 0.137 | 0.052 | 6 | 0 | 97 | 19 | 295 | 162 |
| kgp8200264 | 10 | 12858372 | CAMK1D | A | G | 1.87E-05 | 0.30 | 0.026 | 0.083 | 0 | 2 | 21 | 26 | 376 | 152 |

TABLE 38-continued

Standard Response SNPs

| Prioritized Variants | STANDARD PHENOTYPE | | | | | | | | | | Combined | | | | | |
|---|---|---|---|---|---|---|---|---|---|---|---|---|---|---|---|---|
| Name | Chromosome | Position | Gene(s) | Major Allele (d) | Minor Allele (D) | P-value (Armitage Test) | Odds Ratio (Minor Allele) | Minor Allele Freq. (Responders) | Allele Freq. (Non-responders) | DD (Responders) | DD (Non-responders) | Dd (Responders) | Dd (Non-responders) | dd (Responders) | dd (Non-responders) |
| kgp6835138 | 20 | 40712994 | PTPRT | G | A | 1.88E-05 | 0.17 | 0.009 | 0.047 | 0 | 0 | 7 | 17 | 392 | 164 |
| kgp841428 | 5 | 141036337 | ARAP3 | A | G | 1.93E-05 | 0.58 | 0.371 | 0.506 | 56 | 46 | 183 | 91 | 159 | 44 |
| rs3815822 | 16 | 29872361 | CDIPT | A | C | 1.96E-05 | 1.74 | 0.509 | 0.373 | 102 | 26 | 202 | 83 | 95 | 72 |
| rs1579771 | 3 | 157278882 | C3orf55 | A | G | 1.96E-05 | 1.91 | 0.366 | 0.246 | 39 | 9 | 213 | 71 | 146 | 101 |
| kgp4734301 | 11 | 27315427 | | G | A | 1.96E-05 | 1.93 | 0.330 | 0.210 | 39 | 4 | 185 | 68 | 175 | 109 |
| rs11029928 | 11 | 27191188 | | G | A | 1.96E-05 | 1.93 | 0.330 | 0.210 | 39 | 4 | 185 | 68 | 175 | 109 |
| rs10841322 | 12 | 19866642 | | A | G | 2.00E-05 | 0.55 | 0.234 | 0.354 | 20 | 21 | 147 | 86 | 232 | 74 |
| kgp1786079 | 7 | 144701118 | | C | A | 2.09E-05 | 0.49 | 0.118 | 0.215 | 4 | 11 | 86 | 56 | 308 | 114 |
| kgp5053636 | 2 | 205356730 | FAM154A | G | A | 2.13E-05 | 0.29 | 0.024 | 0.077 | 1 | 0 | 17 | 28 | 378 | 153 |
| kgp9601362 | 9 | 18959317 | | G | A | 2.21E-05 | 0.33 | 0.031 | 0.092 | 0 | 3 | 25 | 27 | 372 | 149 |
| kgp8183049 | 13 | 40634155 | | G | A | 2.23E-05 | Zero | 0.000 | 0.022 | 0 | 0 | 0 | 8 | 399 | 172 |
| kgp5564995 | 6 | 26414060 | BTN3A1 | C | A | 2.28E-05 | 2.88 | 0.145 | 0.061 | 1 | 0 | 109 | 21 | 274 | 151 |
| kgp27500525 | 9 | 30278677 | | G | A | 2.35E-05 | Zero | 0.000 | 0.022 | 0 | 0 | 0 | 8 | 399 | 173 |
| rs11022778 | 11 | 13390860 | ARNTL | A | C | 2.37E-05 | 1.86 | 0.351 | 0.227 | 52 | 5 | 176 | 72 | 171 | 104 |
| kgp10826273 | 11 | 176263817 | | G | A | 2.41E-05 | Zero | 0.000 | 0.022 | 0 | 0 | 0 | 8 | 398 | 173 |
| rs12494712 | 3 | 116796616 | | A | G | 2.44E-05 | 2.05 | 0.247 | 0.138 | 23 | 2 | 151 | 46 | 225 | 133 |
| kgp1779254 | 12 | 73686930 | | G | A | 2.47E-05 | 0.08 | 0.003 | 0.031 | 0 | 0 | 2 | 12 | 397 | 169 |
| kgp6190988 | 5 | 10699522 | DAP | G | A | 2.47E-05 | 0.08 | 0.003 | 0.031 | 0 | 0 | 2 | 11 | 397 | 169 |
| kgp6507761 | 7 | 319681 | | A | G | 2.55E-05 | 0.59 | 0.428 | 0.566 | 78 | 61 | 185 | 83 | 135 | 37 |
| rs2074037 | 16 | 19725130 | C16orf88 | G | A | 2.55E-05 | 0.49 | 0.137 | 0.232 | 4 | 5 | 101 | 73 | 294 | 101 |
| rs4143493 | 6 | 51829939 | PKHD1 | G | A | 2.57E-05 | 4.21 | 0.090 | 0.025 | 0 | 0 | 72 | 9 | 327 | 172 |
| kgp1699628 | 6 | 18032535 | | A | G | 2.72E-05 | 0.57 | 0.454 | 0.584 | 72 | 62 | 218 | 85 | 109 | 32 |
| rs7024953 | 9 | 18960334 | FAM154A | A | G | 2.74E-05 | 0.34 | 0.031 | 0.091 | 0 | 3 | 25 | 27 | 372 | 151 |
| kgp10974833 | 13 | 77339132 | | A | G | 2.78E-05 | 0.08 | 0.003 | 0.030 | 0 | 0 | 2 | 11 | 395 | 170 |
| kgp10412303 | 2 | 205303530 | | G | A | 2.83E-05 | 0.30 | 0.026 | 0.080 | 0 | 1 | 2 | 27 | 378 | 153 |
| kgp9669946 | 17 | 65735872 | NOL11 | A | G | 2.86E-05 | 0.53 | 0.167 | 0.272 | 12 | 10 | 109 | 78 | 278 | 92 |
| rs17224858 | 3 | 124205297 | KALRN | G | A | 2.89E-05 | 0.54 | 0.188 | 0.298 | 10 | 19 | 130 | 70 | 259 | 92 |
| rs6840089 | 4 | 153713220 | ARFIP1 | A | G | 3.06E-05 | 0.24 | 0.016 | 0.061 | 0 | 0 | 13 | 22 | 386 | 159 |
| rs7666442 | 4 | 153753101 | ARFIP1 | A | G | 3.06E-05 | 0.24 | 0.016 | 0.061 | 0 | 0 | 13 | 22 | 386 | 159 |
| rs7672014 | 4 | 153818501 | ARFIP1 | G | A | 3.06E-05 | 0.24 | 0.016 | 0.061 | 0 | 0 | 13 | 22 | 383 | 158 |
| rs7677801 | 4 | 153795067 | ARFIP1 | A | G | 3.15E-05 | 0.24 | 0.016 | 0.061 | 0 | 0 | 13 | 22 | 383 | 158 |
| rs4469694 | 2 | 11263948 | FLJ33534 | G | A | 3.15E-05 | 0.46 | 0.008 | 0.173 | 2 | 6 | 66 | 50 | 328 | 170 |
| kgp10523170 | 16 | 5221617 | | G | A | 3.16E-05 | 0.08 | 0.003 | 0.033 | 0 | 1 | 2 | 10 | 397 | 170 |
| kgp5216209 | 3 | 170740453 | SLC2A2 | C | G | 3.18E-05 | 0.23 | 0.015 | 0.058 | 0 | 0 | 12 | 21 | 387 | 159 |
| rs720176 | 16 | 19721515 | C16orf88 | A | G | 3.20E-05 | 0.49 | 0.138 | 0.232 | 4 | 5 | 101 | 74 | 290 | 102 |
| kgp74811870 | 16 | 19729016 | C16orf88, IQCK | G | C | 3.20E-05 | 0.49 | 0.146 | 0.242 | 4 | 5 | 17 | 77 | 282 | 98 |
| rs1532365 | 12 | 49204421 | | G | A | 3.23E-05 | 0.59 | 0.345 | 0.478 | 43 | 52 | 188 | 68 | 166 | 60 |
| rs12943140 | 17 | 65738773 | NOL11 | G | A | 3.24E-05 | 0.53 | 0.167 | 0.272 | 12 | 10 | 108 | 78 | 275 | 92 |
| kgp11702474 | 4 | 153712868 | ARFIP1 | A | G | 3.31E-05 | 0.24 | 0.016 | 0.061 | 0 | 0 | 13 | 22 | 384 | 159 |
| rs10498793 | 6 | 51829707 | PKHD1 | G | A | 3.34E-05 | 4.14 | 0.089 | 0.025 | 0 | 0 | 71 | 9 | 328 | 172 |

TABLE 38-continued

Standard Response SNPs

| Prioritized Variants | | | | | | | | | | | Combined | | | | |
|---|---|---|---|---|---|---|---|---|---|---|---|---|---|---|---|
| | STANDARD PHENOTYPE | | | | | | | | | | | | | | |
| Name | Chromosome | Position | Gene(s) | Major Allele (d) | Minor Allele (D) | P-value (Armitage Test) | Odds Ratio (Minor Allele) | Minor Allele Freq. (Responders) | Allele Freq. (Non-responders) | DD (Responders) | DD (Non-responders) | Dd (Responders) | Dd (Non-responders) | dd (Responders) | dd (Non-responders) |
| kgp6539666 | 3 | 157292022 | C3orf55 | A | G | 3.39E-05 | 1.90 | 0.354 | 0.240 | 34 | 7 | 213 | 73 | 150 | 101 |
| kgp10679353 | 16 | 19800133 | IQCK | G | A | 3.39E-05 | 0.50 | 0.144 | 0.240 | 5 | 7 | 105 | 73 | 289 | 101 |
| kgp9410843 | 10 | 121484477 | | A | G | 3.48E-05 | 0.55 | 0.180 | 0.290 | 13 | 18 | 116 | 69 | 266 | 94 |
| kgp6772915 | 9 | 18978739 | FAM154A | A | C | 3.50E-05 | 0.33 | 0.032 | 0.089 | 0 | 2 | 25 | 28 | 371 | 149 |
| kgp20478926 | 8 | 21050249 | | A | G | 3.53E-05 | 0.44 | 0.030 | 0.106 | 5 | 15 | 14 | 8 | 377 | 156 |
| kgp10619195 | 4 | 99417717 | TSPAN5 | A | G | 3.54E-05 | 0.36 | 0.040 | 0.102 | 0 | 2 | 32 | 33 | 366 | 146 |
| rs1544352 | 16 | 19713882 | | A | G | 3.54E-05 | 0.50 | 0.142 | 0.238 | 6 | 5 | 101 | 76 | 290 | 100 |
| kgp15390522 | 1 | 205017962 | CNTN2 | G | A | 3.59E-05 | 0.11 | 0.004 | 0.033 | 0 | 0 | 3 | 12 | 396 | 169 |
| kgp24729706 | 22 | 49286357 | LOC100128946 | G | A | 3.60E-05 | 0.24 | 0.015 | 0.058 | 0 | 0 | 12 | 21 | 386 | 160 |
| rs931570 | 12 | 49195124 | | G | A | 3.61E-05 | 0.59 | 0.344 | 0.475 | 43 | 51 | 187 | 70 | 167 | 60 |
| kgp10591989 | 17 | 65697118 | | A | G | 3.63E-05 | 0.49 | 0.111 | 0.202 | 7 | 5 | 74 | 63 | 317 | 113 |
| kgp12557319 | 6 | 8794609 | | A | G | 3.69E-05 | 0.11 | 0.004 | 0.033 | 0 | 0 | 3 | 12 | 395 | 169 |
| kgp345301 | 16 | 19730554 | IQCK | A | C | 3.69E-05 | 0.49 | 0.134 | 0.228 | 4 | 5 | 98 | 71 | 293 | 102 |
| kgp8615910 | 5 | 30927198 | | A | T | 3.72E-05 | 0.49 | 0.123 | 0.215 | 4 | 7 | 90 | 64 | 304 | 110 |
| kgp2245775 | 13 | 91402506 | | G | A | 3.76E-05 | 0.55 | 0.221 | 0.331 | 13 | 18 | 150 | 84 | 235 | 79 |
| kgp29367521 | 4 | 134471944 | | G | A | 3.81E-05 | 0.13 | 0.005 | 0.036 | 0 | 0 | 4 | 13 | 395 | 166 |
| kgp7506434 | 1 | 13823114 | LRRC38 | A | G | 3.83E-05 | 0.11 | 0.004 | 0.036 | 0 | 1 | 3 | 11 | 395 | 169 |
| rs4780822 | 16 | 19727998 | C16orf88, IQCK | A | G | 3.85E-05 | 0.50 | 0.143 | 0.238 | 5 | 6 | 103 | 74 | 288 | 101 |
| kgp512180 | 16 | 10829457 | | G | A | 3.89E-05 | 0.56 | 0.232 | 0.347 | 19 | 22 | 147 | 81 | 233 | 77 |
| rs1604169 | 5 | 84215343 | | A | C | 3.91E-05 | 0.57 | 0.355 | 0.478 | 41 | 40 | 201 | 93 | 157 | 48 |
| kgp25921291 | 13 | 78418857 | | G | A | 3.92E-05 | 0.17 | 0.008 | 0.044 | 0 | 1 | 6 | 14 | 393 | 165 |
| rs16901784 | 6 | 26555433 | | C | A | 4.02E-05 | 0.47 | 0.089 | 0.174 | 2 | 8 | 67 | 47 | 329 | 126 |
| kgp6228750 | 1 | 110261382 | | A | G | 4.06E-05 | 0.35 | 0.035 | 0.094 | 1 | 1 | 26 | 32 | 372 | 148 |
| kgp9354820 | 15 | 93793636 | | A | G | 4.07E-05 | 0.14 | 0.005 | 0.039 | 0 | 1 | 4 | 12 | 395 | 168 |
| kgp8106690 | 12 | 128734969 | | A | G | 4.09E-05 | 0.51 | 0.135 | 0.232 | 8 | 9 | 90 | 66 | 296 | 106 |
| kgp5144181 | 2 | 30364733 | | A | G | 4.10E-05 | 0.32 | 0.029 | 0.083 | 1 | 0 | 21 | 30 | 377 | 151 |
| kgp9627406 | 9 | 132997137 | NCS1 | G | A | 4.10E-05 | 0.38 | 0.048 | 0.120 | 0 | 4 | 35 | 27 | 328 | 124 |
| kgp2262166 | 9 | 18960393 | FAM154A | A | C | 4.15E-05 | 0.35 | 0.033 | 0.091 | 0 | 3 | 26 | 27 | 373 | 151 |
| kgp4223880 | 2 | 10584122 | ODC1 | A | G | 4.19E-05 | 0.13 | 0.005 | 0.036 | 0 | 0 | 4 | 13 | 394 | 167 |
| kgp61811 | 1 | 160346794 | | A | C | 4.19E-05 | 0.14 | 0.005 | 0.039 | 0 | 1 | 4 | 12 | 394 | 168 |
| kgp9421884 | 19 | 11049860 | | G | A | 4.23E-05 | 0.39 | 0.048 | 0.113 | 0 | 3 | 38 | 35 | 361 | 143 |
| rs8050872 | 16 | 19803846 | IQCK | G | A | 4.27E-05 | 0.51 | 0.149 | 0.246 | 7 | 7 | 105 | 75 | 287 | 99 |
| rs7864679 | 9 | 18945868 | FAM154A | G | A | 4.34E-05 | 0.35 | 0.033 | 0.091 | 0 | 3 | 26 | 27 | 372 | 151 |
| kgp24446153 | 5 | 152980439 | GRIA1 | G | A | 4.35E-05 | 0.13 | 0.005 | 0.036 | 0 | 0 | 4 | 13 | 395 | 168 |
| kgp7804623 | 1 | 41125455 | RIMS3 | G | A | 4.36E-05 | 1.82 | 0.341 | 0.221 | 47 | 8 | 178 | 64 | 174 | 109 |
| rs3792135 | 2 | 100062163 | REV1 | A | G | 4.38E-05 | 0.51 | 0.125 | 0.219 | 4 | 10 | 91 | 59 | 300 | 111 |
| rs8035826 | 15 | 94832144 | | C | A | 4.40E-05 | 1.71 | 0.489 | 0.358 | 97 | 22 | 195 | 85 | 106 | 73 |
| kgp85534 | 2 | 14574582 | | G | A | 4.57E-05 | 0.20 | 0.010 | 0.047 | 0 | 0 | 8 | 17 | 391 | 163 |
| rs11192461 | 10 | 107266483 | | G | A | 4.60E-05 | 0.45 | 0.084 | 0.163 | 1 | 4 | 65 | 51 | 333 | 126 |

TABLE 38-continued

Standard Response SNPs

| Prioritized Variants | STANDARD PHENOTYPE | | | | | | | | | Combined | | | | | |
|---|---|---|---|---|---|---|---|---|---|---|---|---|---|---|---|
| Name | Chromosome | Position | Gene(s) | Major Allele (d) | Minor Allele (D) | P-value (Armitage Test) | Odds Ratio (Minor Allele) | Minor Allele Freq. (Responders) | Allele Freq. (Non-responders) | DD (Responders) | DD (Non-responders) | Dd (Responders) | Dd (Non-responders) | dd (Responders) | dd (Non-responders) |
| kgp297178 | 9 | 18942635 | FAM154A | G | A | 4.66E-05 | 0.34 | 0.030 | 0.086 | 0 | 2 | 24 | 27 | 375 | 152 |
| kgp2045074 | 6 | 51187450 | | C | A | 4.74E-05 | 0.33 | 0.005 | 0.036 | 0 | 0 | 4 | 13 | 392 | 168 |
| rs10049206 | 3 | 157233698 | | G | A | 4.80E-05 | 1.85 | 0.362 | 0.249 | 38 | 9 | 213 | 72 | 148 | 100 |
| rs9834010 | 3 | 157236222 | | C | A | 4.80E-05 | 1.85 | 0.362 | 0.249 | 34 | 9 | 213 | 72 | 148 | 100 |
| kgp971582 | 6 | 51921703 | PKHD1 | A | G | 4.82E-05 | 3.60 | 0.098 | 0.030 | 2 | 0 | 74 | 11 | 323 | 170 |
| kgp22793211 | X | 92601576 | | G | A | 4.82E-05 | 0.64 | 0.394 | 0.542 | 93 | 65 | 126 | 65 | 177 | 50 |
| kgp4573213 | 3 | 124199924 | KALRN | A | G | 4.83E-05 | 0.55 | 0.191 | 0.298 | 10 | 19 | 132 | 70 | 256 | 92 |
| kgp19568724 | 14 | 21486590 | NDRG2 | G | A | 4.84E-05 | 0.15 | 0.006 | 0.039 | 0 | 0 | 5 | 14 | 394 | 167 |
| kgp9071686 | 9 | 21419168 | | G | A | 4.84E-05 | 0.15 | 0.006 | 0.039 | 0 | 0 | 5 | 14 | 394 | 167 |
| kgp652534 | 4 | 13612751 | BOD1L | C | G | 4.84E-05 | 0.15 | 0.006 | 0.039 | 0 | 0 | 5 | 14 | 394 | 167 |
| kgp1224440 | 1 | 247399991 | | A | C | 4.84E-05 | 0.50 | 0.109 | 0.199 | 2 | 11 | 83 | 50 | 314 | 120 |
| kgp2465184 | 9 | 18942204 | FAM154A | A | C | 4.87E-05 | 0.34 | 0.030 | 0.086 | 0 | 2 | 24 | 27 | 374 | 152 |
| kgp11543962 | 10 | 109579303 | | G | A | 4.88E-05 | 0.17 | 0.008 | 0.042 | 0 | 0 | 6 | 15 | 392 | 165 |
| kgp4543470 | 2 | 213559411 | | A | C | 4.90E-05 | 0.51 | 0.134 | 0.227 | 5 | 7 | 96 | 68 | 296 | 106 |
| kgp5579170 | 17 | 65681762 | PITPNC1 | G | A | 4.94E-05 | 0.46 | 0.084 | 0.165 | 5 | 2 | 57 | 55 | 336 | 122 |
| kgp4812831 | 6 | 51910905 | PKHD1 | A | G | 4.94E-05 | 3.62 | 0.096 | 0.030 | 1 | 0 | 75 | 11 | 323 | 170 |
| rs2598360 | 9 | 114155899 | KIAA0368 | G | A | 5.01E-05 | 0.59 | 0.373 | 0.500 | 51 | 48 | 196 | 85 | 152 | 48 |
| kgp10633631 | 8 | 17504188 | MTUS1 | A | G | 5.02E-05 | Zero | 0.000 | 0.025 | 0 | 1 | 0 | 7 | 399 | 173 |
| kgp3651767 | 16 | 84992155 | | G | A | 5.08E-05 | 0.17 | 0.008 | 0.041 | 0 | 0 | 6 | 15 | 393 | 166 |
| rs823829 | 9 | 114105079 | | T | C | 5.10E-05 | 0.59 | 0.398 | 0.525 | 57 | 52 | 204 | 86 | 138 | 43 |
| kgp279772 | 8 | 2105576 | | A | C | 5.15E-05 | 0.57 | 0.247 | 0.362 | 25 | 20 | 146 | 91 | 226 | 70 |
| kgp20163979 | 8 | 79366479 | | A | C | 5.17E-05 | 0.05 | 0.001 | 0.025 | 0 | 0 | 1 | 9 | 398 | 172 |
| kgp21171930 | 4 | 80362934 | | A | G | 5.17E-05 | 0.05 | 0.001 | 0.025 | 0 | 0 | 1 | 9 | 398 | 172 |
| kgp2092817 | 5 | 39632583 | GLDN | A | A | 5.17E-05 | 0.05 | 0.001 | 0.025 | 0 | 0 | 1 | 9 | 398 | 172 |
| kgp3598409 | 15 | 51652449 | NFYC | G | A | 5.17E-05 | 0.05 | 0.001 | 0.025 | 0 | 0 | 1 | 9 | 398 | 172 |
| kgp6469620 | 1 | 41235946 | CAMK1D | G | A | 5.21E-05 | 1.74 | 0.410 | 0.285 | 64 | 18 | 198 | 67 | 136 | 96 |
| rs3818675 | 10 | 12858045 | MPPED2 | G | A | 5.23E-05 | 0.32 | 0.025 | 0.077 | 0 | 2 | 20 | 24 | 378 | 155 |
| kgp9530088 | 11 | 30501054 | | A | G | 5.23E-05 | 0.57 | 0.248 | 0.364 | 25 | 21 | 146 | 89 | 224 | 70 |
| rs2453478 | 12 | 49202743 | MYOM1 | A | A | 5.25E-05 | 0.60 | 0.348 | 0.478 | 45 | 52 | 186 | 69 | 165 | 60 |
| kgp10558725 | 18 | 3070717 | MCPH1 | G | A | 5.25E-05 | 0.15 | 0.009 | 0.044 | 0 | 0 | 7 | 16 | 391 | 165 |
| kgp28886329 | 8 | 6304848 | UTP15 | A | G | 5.30E-05 | 0.05 | 0.001 | 0.025 | 0 | 0 | 1 | 9 | 397 | 172 |
| kgp30282494 | 5 | 72863824 | RIMS3 | G | G | 5.30E-05 | 0.05 | 0.001 | 0.025 | 0 | 0 | 1 | 9 | 397 | 172 |
| rs7524868 | 1 | 41106774 | | A | C | 5.35E-05 | 1.81 | 0.342 | 0.224 | 47 | 8 | 179 | 65 | 173 | 108 |
| kgp9806386 | 5 | 138068054 | | A | C | 5.42E-05 | 0.05 | 0.001 | 0.025 | 0 | 0 | 1 | 9 | 396 | 172 |
| kgp4127859 | 6 | 32434481 | | A | G | 5.43E-05 | 2.32 | 0.180 | 0.091 | 8 | 0 | 127 | 33 | 263 | 148 |
| kgp1753445 | 21 | 39811162 | ERG | A | A | 5.45E-05 | 2.40 | 0.169 | 0.083 | 6 | 0 | 123 | 30 | 270 | 150 |
| kgp9354462 | 2 | 149894403 | | G | C | 5.45E-05 | 0.59 | 0.297 | 0.420 | 37 | 32 | 162 | 88 | 198 | 61 |
| kgp26533576 | 6 | 99139642 | | A | C | 5.57E-05 | 0.17 | 0.008 | 0.041 | 0 | 0 | 6 | 15 | 390 | 166 |
| kgp2023214 | 16 | 76293345 | | A | G | 5.66E-05 | 0.49 | 0.080 | 0.166 | 8 | 8 | 48 | 44 | 342 | 129 |

TABLE 38-continued

Standard Response SNPs

| | STANDARD PHENOTYPE | | | | | | | | | | Combined | | | | |
|---|---|---|---|---|---|---|---|---|---|---|---|---|---|---|---|
| Prioritized Variants Name | Chromo-some | Position | Gene(s) | Major Allele (d) | Minor Allele (D) | P-value (Armitage Test) | Odds Ratio (Minor Allele) | Minor Allele Freq. (Responders) | Allele Freq. (Non-responders) | DD (Re-spond-ers) | DD (Non-respond-ers) | Dd (Re-spond-ers) | Dd (Non-respond-ers) | dd (Re-spond-ers) | dd (Non-respond-ers) |
| kgp6768546 | 4 | 153864174 | FHD11 | G | A | 5.85E-05 | 0.26 | 0.018 | 0.061 | 0 | 0 | 14 | 22 | 385 | 158 |
| kgp1098237 | 9 | 114173681 | KIAA0368 | G | A | 5.98E-05 | 0.60 | 0.368 | 0.494 | 52 | 46 | 190 | 86 | 157 | 48 |
| kgp4559907 | 6 | 133255252 | | G | A | 6.02E-05 | 0.60 | 0.331 | 0.456 | 46 | 37 | 171 | 91 | 180 | 53 |
| rs1644418 | 10 | 12858409 | CAMKID | A | G | 6.11E-05 | 0.31 | 0.024 | 0.075 | 0 | 2 | 19 | 23 | 380 | 156 |
| kgp11804835 | 6 | 32396146 | | C | A | 6.12E-05 | 2.35 | 0.170 | 0.083 | 8 | 1 | 119 | 28 | 270 | 152 |
| rs7029123 | 9 | 114136169 | KIAA0368 | A | G | 6.19E-05 | 0.60 | 0.375 | 0.500 | 52 | 48 | 195 | 85 | 152 | 48 |
| kgp2688306 | 9 | 28560259 | CREB5 | A | G | 6.20E-05 | 2.90 | 0.122 | 0.047 | 3 | 1 | 91 | 15 | 304 | 164 |
| kgp2638591 | 7 | 108994382 | RSPO2 | G | A | 6.21E-05 | 0.36 | 0.041 | 0.099 | 0 | 0 | 33 | 36 | 366 | 145 |
| rs2845371 | 22 | 17178213 | | G | A | 6.21E-05 | 1.70 | 0.487 | 0.361 | 93 | 21 | 198 | 88 | 103 | 71 |
| kgp5409955 | 9 | 18980841 | FAM154A | G | A | 6.27E-05 | 0.34 | 0.029 | 0.083 | 0 | 2 | 23 | 26 | 374 | 153 |
| rs7228827 | 18 | 76900411 | ATP9B | A | G | 6.28E-05 | 2.12 | 0.206 | 0.108 | 20 | 1 | 124 | 37 | 254 | 143 |
| kgp1912531 | 2 | 137850215 | THSD7B | A | G | 6.34E-05 | 2.12 | 0.204 | 0.105 | 18 | 4 | 126 | 30 | 254 | 147 |
| kgp4162414 | 6 | 51868165 | PKHD1 | G | A | 6.35E-05 | 3.56 | 0.095 | 0.030 | 1 | 0 | 74 | 11 | 324 | 170 |
| rs2926455 | 10 | 107260501 | | A | G | 6.37E-05 | 0.46 | 0.086 | 0.165 | 1 | 4 | 67 | 51 | 331 | 124 |
| kgp3669685 | 7 | 78028723 | MAGI2 | A | C | 6.38E-05 | 1.98 | 0.254 | 0.150 | 21 | 4 | 159 | 46 | 216 | 130 |
| kgp7059449 | 2 | 41254555 | | A | C | 6.39E-05 | 4.93 | 0.074 | 0.017 | 1 | 0 | 57 | 6 | 340 | 175 |
| rs3899755 | X | 68447361 | | C | A | 6.44E-05 | 2.00 | 0.216 | 0.108 | 34 | 4 | 104 | 31 | 261 | 146 |
| rs2309760 | 4 | 183591332 | ODZ3 | A | G | 6.56E-05 | 0.61 | 0.344 | 0.472 | 53 | 44 | 168 | 83 | 177 | 54 |
| kgp2788291 | 18 | 45153979 | | G | A | 6.64E-05 | 0.51 | 0.120 | 0.211 | 5 | 9 | 86 | 58 | 308 | 113 |
| kgp3933330 | 7 | 28583709 | CREB5 | A | G | 6.67E-05 | 2.26 | 0.178 | 0.086 | 15 | 1 | 111 | 29 | 271 | 151 |
| rs7062312 | X | 68447052 | | G | A | 6.68E-05 | 2.01 | 0.215 | 0.108 | 33 | 4 | 105 | 31 | 260 | 146 |
| rs6899068 | 6 | 125019969 | NKAIN2 | A | G | 6.76E-05 | 0.51 | 0.123 | 0.214 | 9 | 5 | 80 | 67 | 310 | 108 |
| kgp337461 | 5 | 126591501 | | G | A | 6.78E-05 | 1.75 | 0.405 | 0.285 | 62 | 13 | 199 | 77 | 138 | 91 |
| kgp8046214 | 4 | 153726582 | ARFIP1 | A | G | 6.80E-05 | 0.25 | 0.016 | 0.058 | 0 | 0 | 13 | 21 | 386 | 159 |
| rs6835202 | 4 | 153855186 | | C | A | 6.80E-05 | 0.25 | 0.016 | 0.058 | 0 | 0 | 13 | 21 | 386 | 159 |
| kgp10620244 | 8 | 133472755 | KCNQ3 | G | A | 6.83E-05 | 2.05 | 0.219 | 0.119 | 20 | 4 | 135 | 35 | 244 | 142 |
| kgp11407560 | 2 | 65096583 | | A | G | 6.84E-05 | 0.31 | 0.025 | 0.075 | 1 | 0 | 18 | 27 | 380 | 153 |
| rs3799383 | 6 | 26510748 | | G | A | 6.85E-05 | 0.48 | 0.089 | 0.171 | 2 | 8 | 67 | 46 | 329 | 127 |
| rs6845927 | 4 | 153799603 | ARFIP1 | A | C | 6.87E-05 | 0.26 | 0.018 | 0.061 | 0 | 0 | 14 | 22 | 383 | 159 |
| rs10489312 | 1 | 175526526 | TNR | A | G | 6.87E-05 | 0.52 | 0.128 | 0.221 | 6 | 10 | 90 | 60 | 302 | 111 |
| kgp11633966 | 11 | 37701793 | | G | A | 6.88E-05 | 0.54 | 0.150 | 0.249 | 11 | 10 | 98 | 70 | 290 | 101 |
| rs7496451 | 15 | 25718875 | | A | G | 6.89E-05 | 2.01 | 0.239 | 0.138 | 23 | 0 | 145 | 50 | 231 | 131 |
| kgp3048169 | 4 | 78109591 | | G | A | 6.94E-05 | 0.51 | 0.108 | 0.196 | 5 | 9 | 76 | 53 | 318 | 119 |
| kgp8990121 | 9 | 27215039 | TEK | C | A | 6.94E-05 | 2.35 | 0.167 | 0.080 | 10 | 0 | 113 | 29 | 276 | 152 |
| kgp26528455 | 6 | 72737785 | RIMS1 | G | A | 6.99E-05 | 0.28 | 0.018 | 0.064 | 0 | 1 | 12 | 21 | 386 | 159 |
| kgp4755147 | 2 | 149894654 | | A | C | 7.15E-05 | 0.59 | 0.301 | 0.422 | 38 | 32 | 161 | 88 | 195 | 60 |
| kgp10372946 | 10 | 133980657 | JAXMIP3 | G | A | 7.17E-05 | 10.53 | 0.053 | 0.006 | 0 | 0 | 42 | 2 | 357 | 179 |
| rs1380706 | 2 | 57864042 | | A | G | 7.29E-05 | 1.72 | 0.409 | 0.285 | 64 | 17 | 190 | 68 | 135 | 94 |

TABLE 38-continued

Standard Response SNPs

| Prioritized Variants | STANDARD PHENOTYPE | | | | Major Allele (d) | Minor Allele (D) | P-value (Armitage Test) | Odds Ratio (Minor Allele) | Minor Allele Freq. (Responders) | Allele Freq. (Non-responders) | Combined | | | | |
|---|---|---|---|---|---|---|---|---|---|---|---|---|---|---|---|
| Name | Chromosome | Position | Gene(s) | | | | | | | | DD (Responders) | DD (Non-responders) | Dd (Responders) | Dd (Non-responders) | dd (Responders) | dd (Non-responders) |
| kgp12182745 | 8 | 125465203 | TRMT12 | A | T | 7.30E-05 | 0.43 | 0.047 | 0.117 | 3 | 6 | 31 | 30 | 357 | 144 |
| kgp3951463 | 3 | 157280172 | C3orf55 | C | A | 7.32E-05 | 1.83 | 0.348 | 0.238 | 36 | 8 | 205 | 70 | 157 | 103 |
| kgp8602316 | 7 | 335911 | | G | A | 7.36E-05 | 1.70 | 0.417 | 0.291 | 74 | 18 | 184 | 68 | 140 | 93 |
| rs16927077 | 11 | 10620629 | MRV11-AS1 | G | A | 7.38E-05 | 0.47 | 0.080 | 0.157 | 2 | 5 | 60 | 47 | 337 | 129 |
| kgp6959492 | 4 | 153687676 | | A | G | 7.39E-05 | 0.26 | 0.016 | 0.058 | 0 | 0 | 13 | 21 | 386 | 160 |
| kgp8793915 | 11 | 109012665 | | A | G | 7.40E-05 | Zero | 0.000 | 0.019 | 0 | 0 | 0 | 7 | 399 | 173 |
| kgp13161760 | 21 | 18192806 | | G | A | 7.40E-05 | 0.05 | 0.001 | 0.028 | 0 | 1 | 1 | 7 | 398 | 172 |
| kgp6567154 | 4 | 3442146 | | G | C | 7.47E-05 | 0.59 | 0.274 | 0.392 | 28 | 32 | 161 | 78 | 207 | 71 |
| kgp2282938 | 22 | 32719612 | GDAP1 | G | A | 7.47E-05 | 0.25 | 0.015 | 0.056 | 0 | 0 | 12 | 20 | 386 | 159 |
| kgp355723 | 8 | 75270402 | LYPD6B | A | G | 7.54E-05 | 0.09 | 0.003 | 0.028 | 0 | 0 | 2 | 10 | 396 | 169 |
| rs102016643 | 2 | 149905641 | TAOK3 | C | A | 7.56E-05 | 0.60 | 0.301 | 0.422 | 40 | 32 | 160 | 88 | 199 | 60 |
| kgp27640141 | 12 | 118805689 | ARFIP1 | G | A | 7.57E-05 | 0.05 | 0.001 | 0.028 | 0 | 1 | 1 | 8 | 397 | 172 |
| rs7670525 | 4 | 153814538 | | G | A | 7.66E-05 | 0.26 | 0.016 | 0.058 | 0 | 0 | 13 | 21 | 385 | 160 |
| kgp28817122 | 8 | 122487115 | | A | G | 7.66E-05 | 0.26 | 0.016 | 0.058 | 0 | 0 | 13 | 21 | 385 | 160 |
| kgp5014707 | 9 | 1702186 | | G | A | 7.75E-05 | Zero | 0.000 | 0.019 | 0 | 0 | 0 | 7 | 399 | 174 |
| kgp7092772 | 14 | 22379841 | | G | A | 7.75E-05 | Zero | 0.000 | 0.019 | 0 | 0 | 0 | 7 | 399 | 174 |
| kgp3477351 | 19 | 295864 | | C | A | 7.75E-05 | Zero | 0.000 | 0.019 | 0 | 0 | 0 | 7 | 399 | 174 |
| kgp23298674 | 21 | 20962564 | | C | A | 7.75E-05 | Zero | 0.000 | 0.019 | 0 | 0 | 0 | 7 | 399 | 174 |
| kgp12083934 | 16 | 10828979 | | A | G | 7.75E-05 | 0.58 | 0.232 | 0.344 | 20 | 22 | 143 | 79 | 232 | 78 |
| kgp485316 | 7 | 15372018 | AGMO | G | A | 7.80E-05 | 1.67 | 0.466 | 0.340 | 94 | 17 | 183 | 89 | 121 | 75 |
| kgp25191871 | 1 | 115687027 | | A | C | 7.84E-05 | 0.33 | 0.026 | 0.078 | 0 | 2 | 21 | 24 | 376 | 153 |
| kgp24131116 | 2 | 213906695 | IKZF2 | G | A | 7.91E-05 | Zero | 0.000 | 0.019 | 0 | 0 | 0 | 7 | 398 | 174 |
| kgp9854133 | 3 | 31334098 | SMS | G | A | 7.91E-05 | Zero | 0.000 | 0.019 | 0 | 0 | 0 | 7 | 398 | 174 |
| kgp22811918 | X | 21960214 | | C | A | 8.00E-05 | 0.48 | 0.055 | 0.133 | 5 | 12 | 34 | 24 | 360 | 145 |
| kgp77922688 | 13 | 23070499 | LOC283104, SBF2 | C | A | 8.06E-05 | 0.24 | 0.013 | 0.052 | 0 | 1 | 10 | 17 | 388 | 163 |
| kgp11356379 | 11 | 9814612 | | G | A | 8.09E-05 | 0.59 | 0.344 | 0.466 | 41 | 37 | 186 | 89 | 162 | 49 |
| kgp27571222 | 12 | 56245724 | | A | G | 8.10E-05 | 0.05 | 0.001 | 0.028 | 0 | 1 | 1 | 8 | 394 | 172 |
| rs1886214 | 13 | 42948531 | SETBP1 | A | G | 8.21E-05 | 1.89 | 0.278 | 0.171 | 31 | 3 | 159 | 56 | 207 | 122 |
| kgp1054273 | 12 | 67131774 | | A | G | 8.21E-05 | 0.09 | 0.003 | 0.028 | 0 | 0 | 2 | 10 | 397 | 171 |
| kgp9551947 | 18 | 42502140 | | G | A | 8.21E-05 | 0.09 | 0.003 | 0.028 | 0 | 0 | 2 | 10 | 397 | 171 |
| kgp5483926 | 3 | 144352913 | | A | C | 8.21E-05 | 0.09 | 0.003 | 0.028 | 0 | 0 | 2 | 10 | 397 | 171 |
| kgp4155998 | 1 | 184734012 | | A | G | 8.21E-05 | 0.09 | 0.003 | 0.028 | 0 | 0 | 2 | 10 | 397 | 171 |
| kgp2958113 | 5 | 163341388 | | A | C | 8.21E-05 | 0.09 | 0.003 | 0.028 | 0 | 0 | 2 | 10 | 397 | 171 |
| kgp8335515 | 11 | 4926211 | | G | A | 8.21E-05 | 0.09 | 0.003 | 0.028 | 0 | 0 | 2 | 10 | 397 | 171 |
| kgp5388938 | 8 | 79087167 | | G | A | 8.21E-05 | 0.09 | 0.003 | 0.028 | 0 | 0 | 2 | 10 | 397 | 171 |
| kgp28687699 | 8 | 79255285 | NRXN3 | C | A | 8.21E-05 | 0.09 | 0.003 | 0.028 | 0 | 0 | 2 | 10 | 397 | 171 |
| kgp11627530 | 14 | 78954642 | MANIC1 | A | G | 8.35E-05 | 0.43 | 0.059 | 0.128 | 0 | 5 | 47 | 36 | 352 | 139 |
| kgp24753470 | 1 | 26013940 | ARHGEF3 | G | A | 8.41E-05 | 0.09 | 0.003 | 0.028 | 0 | 0 | 2 | 10 | 396 | 171 |
| kgp1285441 | 3 | 56931141 | PKHD1 | G | A | 8.44E-05 | 0.52 | 0.130 | 0.221 | 8 | 6 | 88 | 68 | 303 | 107 |
| rs17638791 | 6 | 51940816 | NKAIN2 | A | G | 8.49E-05 | 3.35 | 0.098 | 0.033 | 1 | 0 | 76 | 12 | 322 | 169 |
| rs2325911 | 6 | 125027223 | MEGF11 | C | A | 8.57E-05 | 0.51 | 0.119 | 0.207 | 9 | 3 | 77 | 69 | 312 | 109 |
| kgp10967046 | 15 | 66274387 | | A | G | 8.61E-05 | 0.36 | 0.035 | 0.091 | 1 | 1 | 26 | 31 | 371 | 149 |
| rs12013377 | X | 92620062 | STOX2 | A | G | 8.64E-05 | 0.65 | 0.405 | 0.547 | 97 | 66 | 129 | 66 | 173 | 49 |
| kgp7186699 | 4 | 184878777 | | G | A | 8.64E-05 | 3.55 | 0.094 | 0.028 | 4 | 1 | 67 | 8 | 328 | 172 |

TABLE 38-continued

Standard Response SNPs

| | | STANDARD PHENOTYPE | | | | | | | | | | Combined | | | | | |
|---|---|---|---|---|---|---|---|---|---|---|---|---|---|---|---|---|---|
| Prioritized Variants | Name | Chromosome | Position | Gene(s) | Major Allele (d) | Minor Allele (D) | P-value (Armitage Test) | Odds Ratio (Minor Allele) | Minor Allele Freq. (Responders) | Allele Freq. (Non-responders) | DD (Responders) | DD (Non-responders) | Dd (Responders) | Dd (Non-responders) | dd (Responders) | dd (Non-responders) |
| | kgp9368119 | 7 | 11707419 | THSD7A | A | G | 8.76E-05 | 0.60 | 0.385 | 0.506 | 52 | 47 | 203 | 89 | 144 | 45 |
| | kgp124162 | 11 | 72356846 | PDE2A | A | G | 8.78E-05 | 0.25 | 0.015 | 0.055 | 0 | 0 | 12 | 20 | 386 | 161 |
| | kgp8440036 | 4 | 78058785 | | G | A | 8.79E-05 | 0.30 | 0.019 | 0.066 | 1 | 2 | 13 | 20 | 385 | 159 |
| | rs4738738 | 8 | 59844254 | TOX | A | C | 8.80E-05 | 1.69 | 0.424 | 0.300 | 80 | 13 | 177 | 82 | 140 | 85 |
| | kgp7802182 | 18 | 56759170 | | A | G | 8.86E-05 | 0.57 | 0.208 | 0.315 | 19 | 16 | 128 | 82 | 252 | 83 |
| | kgp2923815 | 19 | 43931355 | | G | A | 8.87E-05 | 0.43 | 0.064 | 0.133 | 1 | 2 | 49 | 44 | 348 | 135 |
| | rs3767955 | 1 | 41104475 | | A | G | 8.91E-05 | 1.78 | 0.341 | 0.227 | 46 | 8 | 180 | 66 | 173 | 107 |
| | kgp3418770 | 10 | 59425598 | RIMS3 | A | G | 8.92E-05 | 10.31 | 0.052 | 0.006 | 0 | 0 | 41 | 2 | 354 | 178 |
| | rs17449018 | 9 | 7060825 | | G | A | 8.97E-05 | 1.82 | 0.318 | 0.207 | 41 | 4 | 172 | 66 | 186 | 109 |
| | kgp4524468 | 22 | 32724532 | KDM4C | A | G | 8.98E-05 | 1.89 | 0.281 | 0.172 | 27 | 8 | 165 | 45 | 198 | 124 |
| | kgp4418535 | 6 | 32431558 | | C | A | 9.00E-05 | 2.26 | 0.177 | 0.091 | 5 | 0 | 125 | 33 | 266 | 148 |
| | kgp22823022 | X | 9742468 | | G | A | 9.00E-05 | 0.56 | 0.133 | 0.236 | 17 | 16 | 70 | 51 | 305 | 109 |
| | kgp7063887 | 1 | 189928568 | | G | A | 9.14E-05 | 0.41 | 0.044 | 0.108 | 0 | 6 | 35 | 27 | 363 | 148 |
| | rs1621509 | 7 | 2969680 | | A | C | 9.29E-05 | 2.00 | 0.239 | 0.142 | 15 | 4 | 160 | 43 | 222 | 133 |
| | kgp4842590 | 1 | 110249364 | CARD11 | A | G | 9.32E-05 | 0.27 | 0.015 | 0.058 | 1 | 1 | 10 | 19 | 387 | 160 |
| | rs11192469 | 10 | 107282331 | | C | A | 9.38E-05 | 0.47 | 0.083 | 0.158 | 1 | 4 | 64 | 49 | 333 | 127 |
| | kgp8303520 | 7 | 154911234 | | A | G | 9.41E-05 | 0.61 | 0.412 | 0.539 | 68 | 56 | 188 | 82 | 137 | 42 |
| | rs13415334 | 2 | 60324127 | | A | G | 9.46E-05 | 0.60 | 0.357 | 0.478 | 47 | 42 | 191 | 88 | 161 | 50 |
| | rs9876830 | 3 | 157311299 | C3orf55 | G | A | 9.48E-05 | 1.82 | 0.348 | 0.240 | 35 | 8 | 208 | 71 | 156 | 102 |
| | kgp11285862 | 21 | 18177980 | | A | G | 9.56E-05 | 0.09 | 0.003 | 0.030 | 0 | 1 | 2 | 9 | 396 | 171 |
| | rs2824070 | 21 | 18205972 | | G | A | 9.57E-05 | 0.22 | 0.010 | 0.047 | 0 | 0 | 8 | 15 | 389 | 164 |
| | rs7181058 | 14 | 98385698 | | A | C | 9.62E-05 | 0.24 | 0.014 | 0.052 | 0 | 0 | 11 | 19 | 388 | 162 |
| | kgp5002011 | 1 | 110265738 | | A | G | 9.66E-05 | 0.35 | 0.030 | 0.083 | 1 | 1 | 22 | 28 | 376 | 152 |
| | rs2139612 | X | 92614918 | KIAA0368 | A | C | 9.68E-05 | 0.65 | 0.403 | 0.544 | 96 | 65 | 129 | 67 | 173 | 49 |
| | rs7860748 | 9 | 114202502 | | G | A | 9.73E-05 | 0.61 | 0.370 | 0.492 | 52 | 46 | 191 | 86 | 156 | 49 |
| | rs17029538 | 2 | 65096800 | | A | C | 9.73E-05 | 0.33 | 0.025 | 0.078 | 1 | 0 | 20 | 28 | 378 | 152 |
| | kgp1371881 | 16 | 76291607 | | A | G | 9.74E-05 | 0.50 | 0.079 | 0.161 | 8 | 8 | 47 | 42 | 344 | 130 |
| | rs10492882 | 16 | 76293394 | | A | G | 9.74E-05 | 0.50 | 0.079 | 0.161 | 8 | 8 | 47 | 42 | 344 | 130 |
| | rs9393727 | 6 | 26500011 | | C | G | 9.75E-05 | 0.49 | 0.091 | 0.171 | 2 | 8 | 68 | 46 | 327 | 127 |
| | rs1894408 | 6 | 32788833 | | C | G | 9.82E-05 | 1.73 | 0.413 | 0.296 | 58 | 16 | 211 | 74 | 127 | 89 |
| 0 - Priority genes, Predictive Model | rs2839117 | 21 | 47550754 | COL6A2 | G | A | 9.85E-05 | 0.54 | 0.135 | 0.229 | 9 | 11 | 90 | 61 | 300 | 109 |
| | kgp8437961 | 2 | 99960003 | EIF5B | G | A | 9.85E-05 | 0.50 | 0.105 | 0.188 | 4 | 6 | 75 | 56 | 318 | 119 |
| | rs1508102 | 11 | 116379889 | | G | A | 9.87E-05 | 0.42 | 0.052 | 0.116 | 0 | 4 | 41 | 34 | 357 | 143 |
| | rs4449139 | 2 | 124875366 | CNTNAP5 | G | A | 9.93E-05 | 0.61 | 0.398 | 0.522 | 61 | 53 | 195 | 83 | 142 | 45 |
| | rs11559024 | 19 | 45821183 | CKJM | A | G | 1.00E-04 | 0.09 | 0.003 | 0.030 | 0 | 1 | 2 | 9 | 394 | 171 |
| 2 - Priority genes | rs1894407 | 6 | 32787036 | | C | A | 1.06E-04 | 1.73 | 0.411 | 0.296 | 57 | 16 | 213 | 75 | 128 | 90 |
| 2 - Priority genes | rs2857103 | 6 | 32791299 | TAP2 | C | A | 1.13E-04 | 1.78 | 0.362 | 0.253 | 39 | 11 | 211 | 69 | 149 | 100 |
| 2 - Priority genes | rs9501224 | 6 | 32792910 | TAP2 | G | A | 1.32E-04 | 1.77 | 0.362 | 0.254 | 39 | 11 | 211 | 70 | 149 | 100 |
| 0 - Priority in Predictive Model | kgp8110667 | 22 | 32716792 | | G | A | 1.44E-04 | Infinity | 0.040 | 0.000 | 1 | 0 | 30 | 0 | 367 | 381 |
| 0 - Priority genes, Predictive Model | kgp6599438 | 20 | 40843626 | PTPRT | G | A | 2.48E-04 | 0.26 | 0.014 | 0.050 | 0 | 0 | 11 | 18 | 386 | 163 |
| 2 - Priority genes | rs241451 | 6 | 32796480 | TAP2 | A | G | 2.58E-04 | 1.72 | 0.360 | 0.256 | 39 | 12 | 207 | 68 | 150 | 100 |

TABLE 38-continued

Standard Response SNPs

| Prioritized Variants | STANDARD PHENOTYPE | | | | | | | | | | | Combined | | | | | |
|---|---|---|---|---|---|---|---|---|---|---|---|---|---|---|---|---|---|
| | Name | Chromosome | Position | Gene(s) | Major Allele (d) | Minor Allele (D) | P-value (Armitage Test) | Odds Ratio (Minor Allele) | Minor Allele Freq. (Responders) | Allele Freq. (Non-responders) | DD (Responders) | DD (Non-responders) | Dd (Responders) | Dd (Non-responders) | dd (Responders) | dd (Non-responders) |
| 2 - Priority genes | rs1894406 | 6 | 32787056 | IL2RB | G | A | 2.66E-04 | 1.68 | 0.381 | 0.273 | 51 | 13 | 202 | 73 | 146 | 95 |
| 2 - Priority genes | rs3218328 | 22 | 37524008 | | G | A | 2.96E-04 | 0.13 | 0.004 | 0.028 | 0 | 0 | 3 | 10 | 395 | 169 |
| 2 - Priority genes | rs241443 | 6 | 32797115 | TAP2 | A | C | 3.02E-04 | 1.71 | 0.358 | 0.254 | 40 | 11 | 202 | 69 | 152 | 99 |
| 2 - Priority genes | rs2621323 | 6 | 32788707 | | A | G | 3.33E-04 | 1.69 | 0.367 | 0.264 | 43 | 12 | 207 | 71 | 149 | 97 |
| 2 - Priority genes | kgp304921 | 20 | 14017077 | MACROD2 | G | G | 8.00E-04 | 0.41 | 0.029 | 0.075 | 2 | 2 | 19 | 23 | 373 | 154 |
| 2 - Priority genes | rs241456 | 6 | 32795965 | TAP2 | G | A | 8.63E-04 | 1.66 | 0.306 | 0.213 | 32 | 9 | 180 | 59 | 187 | 113 |
| 0 - Priority genes, Predictive Model | kgp7747883 | 18 | 74804250 | MBP | G | A | 8.64E-04 | 0.64 | 0.335 | 0.436 | 43 | 33 | 182 | 92 | 174 | 56 |
| 2 - Priority genes | rs2621321 | 6 | 32789480 | | A | G | 9.00E-04 | 1.66 | 0.308 | 0.215 | 31 | 9 | 183 | 60 | 184 | 112 |
| 2 - Priority genes | rs2857104 | 6 | 32790167 | TAP2 | G | C | 9.87E-04 | 1.65 | 0.307 | 0.215 | 31 | 9 | 183 | 60 | 185 | 112 |
| 2 - Priority genes | rs241454 | 6 | 32796144 | TAP2 | A | G | 1.02E-03 | 1.65 | 0.307 | 0.215 | 32 | 9 | 180 | 60 | 185 | 112 |
| 2 - Priority genes | rs241447 | 6 | 32796751 | TAP2 | A | G | 1.11E-03 | 1.64 | 0.308 | 0.217 | 32 | 9 | 180 | 60 | 184 | 111 |
| 2 - Priority genes | kgp974569 | 6 | 32796057 | TAP2 | A | G | 1.15E-03 | 1.64 | 0.307 | 0.215 | 32 | 9 | 180 | 60 | 186 | 112 |
| 2 - Priority genes | rs2857101 | 6 | 32794676 | TAP2 | A | G | 1.15E-03 | 1.64 | 0.305 | 0.214 | 31 | 9 | 181 | 59 | 187 | 112 |
| 2 - Priority genes | kgp10224254 | 6 | 32785904 | | C | A | 1.15E-03 | 1.56 | 0.405 | 0.307 | 59 | 18 | 205 | 75 | 135 | 88 |
| 2 - Priority genes | rs241444 | 6 | 32797109 | TAP2 | G | A | 1.22E-03 | 1.63 | 0.306 | 0.215 | 32 | 9 | 180 | 60 | 187 | 112 |
| 2 - Priority genes | kgp4479467 | 6 | 32629331 | HLA-DQB1 | A | G | 1.25E-03 | 1.58 | 0.383 | 0.287 | 54 | 11 | 195 | 82 | 147 | 88 |
| 2 - Priority genes | kgp10632945 | 20 | 4682507 | | G | A | 1.25E-03 | 0.61 | 0.173 | 0.254 | 10 | 11 | 118 | 70 | 270 | 100 |
| 2 - Priority genes | rs241446 | 6 | 32796967 | TAP2 | A | G | 1.26E-03 | 1.63 | 0.303 | 0.213 | 32 | 9 | 176 | 59 | 188 | 113 |
| 2 - Priority genes | rs241453 | 6 | 32796226 | TAP2 | G | A | 1.31E-03 | 1.63 | 0.305 | 0.215 | 32 | 9 | 179 | 60 | 187 | 112 |
| 2 - Priority genes | rs241449 | 6 | 32796653 | TAP2 | C | A | 1.35E-03 | 1.63 | 0.303 | 0.212 | 32 | 9 | 175 | 58 | 188 | 112 |
| 0 - Priority genes, Predictive Model | rs10162089 | 13 | 31316738 | ALOX5AP | G | A | 1.40E-03 | 1.51 | 0.482 | 0.380 | 96 | 24 | 190 | 88 | 110 | 67 |
| 2 - Priority genes | rs2071469 | 6 | 32784783 | HLA-DOB | G | A | 1.40E-03 | 1.55 | 0.406 | 0.309 | 59 | 18 | 205 | 76 | 134 | 87 |
| 2 - Priority genes | p1_m_061510_6_159_p | 6 | 32795505 | TAP2 | I | D | 1.41E-03 | 1.62 | 0.305 | 0.215 | 32 | 9 | 178 | 60 | 187 | 112 |
| 2 - Priority genes | rs241452 | 6 | 32796346 | TAP2 | A | G | 1.42E-03 | 1.62 | 0.306 | 0.217 | 32 | 9 | 179 | 60 | 186 | 111 |
| 2 - Priority genes | kgp2388352 | 6 | 32797297 | TAP2 | A | A | 1.46E-03 | 1.63 | 0.307 | 0.216 | 34 | 10 | 173 | 57 | 185 | 111 |
| 2 - Priority genes | kgp8036704 | 6 | 32796521 | TAP2 | G | A | 1.55E-03 | 1.63 | 0.303 | 0.215 | 29 | 9 | 183 | 60 | 186 | 112 |
| 2 - Priority genes | rs241442 | 6 | 32797168 | TAP2 | G | A | 1.56E-03 | 1.62 | 0.305 | 0.217 | 32 | 9 | 179 | 60 | 187 | 111 |
| 2 - Priority genes | rs241445 | 6 | 32797072 | TAP2 | G | A | 1.56E-03 | 1.62 | 0.305 | 0.217 | 32 | 9 | 179 | 60 | 187 | 111 |
| 2 - Priority genes | rs1410779 | 9 | 5083173 | JAK2 | G | A | 1.73E-03 | 0.61 | 0.161 | 0.238 | 8 | 10 | 112 | 66 | 277 | 105 |
| 2 - Priority genes | kgp2672937 | 7 | 18685891 | HDAC9 | G | A | 1.74E-03 | 0.07 | 0.001 | 0.017 | 0 | 0 | 1 | 6 | 398 | 175 |
| 2 - Priority genes | kgp4346717 | 18 | 74810199 | MBP | G | A | 1.74E-03 | 0.07 | 0.001 | 0.017 | 0 | 0 | 1 | 6 | 398 | 175 |
| 2 - Priority genes | kgp9699754 | 10 | 79358319 | KCNMA1 | A | G | 1.74E-03 | Infinity | 0.026 | 0.000 | 0 | 0 | 21 | 0 | 377 | 179 |
| 2 - Priority genes | rs241440 | 6 | 32797361 | TAP2 | G | A | 1.79E-03 | 1.61 | 0.303 | 0.215 | 32 | 9 | 177 | 60 | 189 | 112 |
| 2 - Priority genes | fgp5334779 | 6 | 32628420 | HLA-DQB1 | G | A | 1.87E-03 | 1.56 | 0.377 | 0.286 | 50 | 10 | 199 | 83 | 148 | 87 |
| 2 - Priority genes | kgp4898179 | 6 | 32629347 | HLA-DQB1 | G | A | 1.91E-03 | 1.55 | 0.382 | 0.290 | 54 | 11 | 195 | 83 | 148 | 87 |
| 0 - Priority in Predictive Model | rs759458 | 2 | 65245365 | SLC1A4 | G | A | 2.01E-03 | 1.59 | 0.295 | 0.207 | 38 | 15 | 159 | 61 | 201 | 113 |
| 2 - Priority genes | rs2071472 | 6 | 32784620 | HLA-DOB | A | G | 2.21E-03 | 1.56 | 0.340 | 0.251 | 40 | 12 | 191 | 67 | 168 | 102 |
| 2 - Priority genes | rs2071470 | 6 | 32784753 | HLA-DOB | G | A | 2.21E-03 | 1.56 | 0.340 | 0.251 | 40 | 12 | 191 | 67 | 168 | 102 |
| 2 - Priority genes | kgp25543811 | 18 | 74774894 | MBP, MBP | G | A | 2.29E-03 | 0.12 | 0.003 | 0.019 | 0 | 0 | 2 | 7 | 397 | 173 |
| 2 - Priority genes | kgp293787 | 20 | 40905098 | PTPRT | G | A | 2.55E-03 | 0.37 | 0.019 | 0.052 | 0 | 2 | 15 | 15 | 384 | 164 |

TABLE 38-continued

Standard Response SNPs

| | STANDARD PHENOTYPE | | | | | | | | | | | Combined | | | | | |
|---|---|---|---|---|---|---|---|---|---|---|---|---|---|---|---|---|---|
| Prioritized Variants | Name | Chromosome | Position | Gene(s) | Major Allele (d) | Minor Allele (D) | P-value (Armitage Test) | Odds Ratio (Minor Allele) | Minor Allele Freq. (Responders) | Allele Freq. (Non-responders) | DD (Responders) | DD (Non-responders) | Dd (Responders) | Dd (Non-responders) | dd (Responders) | dd (Non-responders) |
| 2 - Priority genes | rs2043136 | 3 | 30720304 | TGFBR2 | A | G | 4.11E-03 | 1.53 | 0.307 | 0.225 | 38 | 7 | 167 | 67 | 191 | 106 |
| 2 - Priority genes | rs4769060 | 13 | 31337877 | ALOXSAP | A | G | 4.43E-03 | 1.45 | 0.455 | 0.365 | 87 | 22 | 189 | 88 | 123 | 71 |
| 2 - Priority genes | kgp6032617 | 13 | 31287981 | ALOXSAP | A | G | 4.44E-03 | 0.67 | 0.222 | 0.301 | 23 | 15 | 131 | 79 | 244 | 87 |
| 2 - Priority genes | kgp5441587 | 6 | 32827356 | PSMB9 | G | A | 6.10E-03 | 0.24 | 0.006 | 0.025 | 0 | 0 | 5 | 9 | 394 | 169 |
| 2 - Priority genes | rs241435 | 6 | 32798243 | TAP2, TAP2 | G | A | 6.85E-03 | 0.24 | 0.006 | 0.025 | 0 | 0 | 5 | 9 | 394 | 172 |
| 2 - Priority genes | kgp3182607 | 6 | 32823948 | PSMB9 | G | A | 6.85E-03 | 0.24 | 0.006 | 0.025 | 0 | 0 | 5 | 9 | 394 | 172 |
| 2 - Priority genes | kgp22778566 | 7 | 1950337 | MAD1L1 | A | G | 7.00E-03 | 1.57 | 0.246 | 0.175 | 19 | 4 | 156 | 53 | 220 | 117 |
| 2 - Priority genes | kgp97310 | 9 | 5122932 | JAK2 | A | G | 7.79E-03 | 0.68 | 0.200 | 0.271 | 17 | 14 | 125 | 70 | 256 | 97 |
| 2 - Priority genes | kgp5440506 | 13 | 31320543 | ALOXSAP | C | A | 7.94E-03 | 0.72 | 0.428 | 0.514 | 81 | 45 | 175 | 95 | 138 | 40 |
| 2 - Priority genes | rs11147439 | 13 | 31325643 | ALOXSAP | C | A | 8.10E-03 | 0.72 | 0.429 | 0.514 | 81 | 45 | 180 | 96 | 138 | 40 |
| 2 - Priority genes | rs4360791 | 13 | 31318020 | ALOXSAP | G | A | 8.60E-03 | 0.72 | 0.440 | 0.525 | 85 | 48 | 181 | 94 | 133 | 39 |
| 2 - Priority genes | rs9671182 | 13 | 31321138 | ALOXSAP | C | G | 8.78E-03 | 0.72 | 0.432 | 0.517 | 82 | 45 | 180 | 96 | 136 | 39 |
| 2 - Priority genes | rs4356336 | 13 | 31319546 | ALOXSAP | A | G | 8.95E-03 | 0.72 | 0.432 | 0.517 | 82 | 46 | 181 | 95 | 136 | 40 |
| 2 - Priority genes | rs108l5160 | 9 | 5116616 | JAK2 | A | C | 9.34E-03 | 0.68 | 0.207 | 0.278 | 19 | 14 | 124 | 71 | 248 | 93 |
| 2 - Priority genes | rs4254166 | 13 | 31322949 | ALOXSAP | A | G | 9.96E-03 | 0.72 | 0.431 | 0.514 | 81 | 45 | 182 | 96 | 136 | 40 |
| 2 - Priority genes | kgp2715873 | 13 | 31320249 | ALOXSAP | A | G | 1.13E-02 | 0.73 | 0.432 | 0.514 | 82 | 45 | 181 | 96 | 136 | 40 |
| 2 - Priority genes | rs9670531 | 13 | 31321069 | ALOXSAP | G | A | 1.13E-02 | 0.73 | 0.432 | 0.514 | 82 | 45 | 181 | 96 | 136 | 40 |
| 1 - Priority variants | rs2487896 | 10 | 100802380 | HPSE2 | G | A | 1.29E-02 | 0.65 | 0.130 | 0.186 | 6 | 6 | 92 | 55 | 301 | 119 |
| 0 - Priority variants | rs3135391 | 6 | 32410987 | HLA-DRA | G | A | 1.44E-02 | 0.70 | 0.203 | 0.268 | 20 | 10 | 122 | 77 | 257 | 94 |
| Predictive Model | | | | | | | | | | | | | | | | |
| 2 - Priority genes | kgp26271158 | 6 | 32823393 | PSMB9 | G | A | 1.47E-02 | 0.29 | 0.008 | 0.025 | 0 | 0 | 6 | 9 | 393 | 172 |
| 1 - Priority variants | rs3135388 | 6 | 32413051 | | G | A | 1.66E-02 | 0.70 | 0.203 | 0.267 | 20 | 10 | 122 | 76 | 257 | 94 |
| 2 - Priority genes | kgp11281589 | 7 | 1941003 | MAD1L1 | A | G | 1.76E-02 | 1.48 | 0.246 | 0.184 | 19 | 5 | 155 | 55 | 219 | 117 |
| 1 - Priority variants | rs15755455 | 2 | 76624220 | | C | A | 1.94E-02 | 0.73 | 0.319 | 0.390 | 42 | 26 | 170 | 89 | 186 | 66 |
| 1 - Priority variants | rs947603 | 10 | 95249605 | | A | G | 2.65E-02 | 1.42 | 0.241 | 0.182 | 22 | 8 | 148 | 50 | 228 | 123 |

(Note:
Odds Ratio >1 = Minor Allele is associated with Response,
Odds Ratio <1 = Minor Allele Associated with Non-Response)

TABLE 39

Extreme Response SNPs

| | | | | | | | | Gala cohort | | | | Forte cohort | | | |
|---|---|---|---|---|---|---|---|---|---|---|---|---|---|---|---|
| Prioritized Variants | Name | Chromosome | Position | Gene(s) | Major Allele (d) | Minor Allele (D) | P-value (Armitage Test) | Odds Ratio (Minor Allele) | Minor Allele Freq. (Responders) | Allele Freq. (Non-Responders) | P-value (Armitage Test) | Odds Ratio (Minor Allele) | Minor Allele Freq. (Responders) | Allele Freq. (Non-Responders) |
| 0 - Priority - Model | kgp6214351 | 11 | 75546691 | UVRAG | A | G | 2.44E-03 | 0.20 | 0.030 | 0.128 | 3.36E-05 | 0.12 | 0.028 | 0.171 |
| 0 - Priority - Model | rs759458 | 2 | 65245365 | SLC1A4 | G | A | 4.44E-05 | 3.31 | 0.356 | 0.157 | 4.89E-02 | 1.86 | 0.364 | 0.229 |
| | rs7844274 | 8 | 72411302 | | C | A | 1.15E-03 | 0.42 | 0.212 | 0.390 | 1.38E-02 | 0.45 | 0.170 | 0.314 |
| | kgp3984567 | 4 | 40379690 | | G | A | 9.80E-05 | 0.34 | 0.379 | 0.587 | 6.90E-03 | 0.42 | 0.438 | 0.614 |
| | kgp11580695 | 10 | 3896635 | | G | G | 5.50E-05 | 0.18 | 0.053 | 0.212 | 1.02E-01 | 0.50 | 0.073 | 0.143 |
| | kgp10948564 | 20 | 44082511 | | G | C | 3.35E-03 | 0.41 | 0.197 | 0.331 | 4.38E-03 | 0.41 | 0.146 | 0.314 |
| | rs197523 | 21 | 19337261 | CHODL | G | A | 6.01E-05 | 2.89 | 0.402 | 0.186 | 4.34E-02 | 1.86 | 0.371 | 0.229 |
| | kgp12371757 | 21 | 19458272 | | G | A | 4.17E-05 | 0.21 | 0.068 | 0.244 | 6.77E-02 | 0.49 | 0.112 | 0.200 |
| | kgp9627338 | 17 | 90155 | RPH3AL | C | G | 2.55E-03 | 0.36 | 0.083 | 0.221 | 2.27E-04 | 0.23 | 0.108 | 0.286 |
| | rs7850 | 2 | 65249922 | SLC1A4 | C | A | 5.39E-07 | 8.99 | 0.212 | 0.035 | 2.42E-01 | 1.74 | 0.140 | 0.086 |
| | kgp7189498 | 2 | 65250677 | SLC1A4 | G | C | 8.57E-07 | 8.77 | 0.215 | 0.037 | 2.08E-01 | 1.82 | 0.145 | 0.086 |
| | kgp10788130 | 12 | 13898682 | GRIN2B | G | A | 3.62E-03 | Zero | 0.000 | 0.070 | 1.48E-04 | 0.08 | 0.011 | 0.114 |
| | kgp7242489 | 2 | 65250541 | SLC1A4 | A | T | 6.51E-07 | 8.88 | 0.212 | 0.035 | 2.42E-01 | 1.74 | 0.140 | 0.086 |
| | kgp7077322 | 4 | 164661252 | | A | C | 1.82E-03 | 0.13 | 0.015 | 0.100 | 3.59E-04 | 0.16 | 0.034 | 0.157 |
| | rs7348267 | 20 | 44084386 | | G | A | 3.35E-03 | 0.41 | 0.197 | 0.331 | 8.93E-03 | 0.44 | 0.146 | 0.300 |
| | kgp7121374 | 2 | 65246727 | SLC1A4 | A | G | 6.51E-07 | 8.88 | 0.212 | 0.035 | 3.18E-01 | 1.57 | 0.148 | 0.100 |
| | kgp4127859 | 2 | 32434481 | | A | A | 1.28E-04 | 3.79 | 0.235 | 0.076 | 2.67E-02 | 2.89 | 0.193 | 0.086 |
| | kgp8107491 | 6 | 164295151 | | G | A | 7.53E-04 | 0.43 | 0.348 | 0.541 | 2.00E-02 | 0.50 | 0.341 | 0.500 |
| | rs16895510 | 6 | 164319963 | | G | A | 1.81E-04 | 0.33 | 0.162 | 0.355 | 9.67E-02 | 0.55 | 0.182 | 0.271 |
| | rs6032205 | 20 | 44082799 | | C | A | 4.36E-03 | 0.41 | 0.203 | 0.335 | 9.99E-03 | 0.44 | 0.148 | 0.300 |
| | kgp11768533 | 11 | 27270451 | | G | A | 1.14E-03 | 2.52 | 0.500 | 0.337 | 1.79E-03 | 2.75 | 0.472 | 0.257 |
| | rs502530 | 6 | 145584096 | | C | A | 2.10E-02 | 0.19 | 0.015 | 0.070 | 6.23E-05 | Zero | 0.000 | 0.086 |
| | rs1478682 | 11 | 27335009 | | G | A | 7.52E-04 | 2.57 | 0.485 | 0.314 | 2.93E-02 | 2.60 | 0.449 | 0.243 |
| | kgp1124492 | 1 | 105554880 | | G | A | 9.05E-04 | 0.26 | 0.068 | 0.194 | 6.10E-02 | 0.41 | 0.057 | 0.129 |
| | kgp11843177 | 11 | 27316568 | | A | G | 4.45E-04 | 2.69 | 0.394 | 0.218 | 1.55E-02 | 2.28 | 0.371 | 0.214 |
| | kgp11467007 | 5 | 172750436 | STC2 | G | A | 1.49E-03 | 0.17 | 0.023 | 0.128 | 1.24E-03 | 0.22 | 0.051 | 0.171 |
| | rs196295 | 10 | 121436362 | BAG3 | G | A | 3.59E-04 | 0.35 | 0.114 | 0.302 | 6.11E-03 | 0.41 | 0.182 | 0.343 |
| | rs11029892 | 11 | 27269546 | | A | G | 5.83E-04 | 2.63 | 0.417 | 0.244 | 1.11E-02 | 2.36 | 0.393 | 0.229 |
| | rs9913349 | 17 | 68260070 | | A | G | 2.13E-03 | 2.39 | 0.318 | 0.169 | 2.74E-02 | 2.10 | 0.371 | 0.229 |
| | kgp5680955 | 6 | 164297121 | | A | G | 6.88E-04 | 0.43 | 0.288 | 0.483 | 2.10E-02 | 0.51 | 0.301 | 0.457 |
| | kgp6236949 | 2 | 60301030 | | A | G | 1.30E-03 | 0.45 | 0.280 | 0.465 | 6.45E-02 | 0.56 | 0.242 | 0.357 |
| | rs196343 | 10 | 121417957 | BAG3 | G | A | 4.43E-04 | 0.36 | 0.114 | 0.300 | 5.34E-03 | 0.40 | 0.180 | 0.343 |
| | rs7217872 | 17 | 88988 | RPH3AL | G | A | 3.72E-03 | 0.37 | 0.083 | 0.215 | 3.34E-04 | 0.24 | 0.112 | 0.286 |
| | kgp4634875 | 7 | 11704583 | THSD7A | C | A | 3.67E-03 | 2.01 | 0.545 | 0.378 | 1.15E-02 | 0.46 | 0.416 | 0.588 |
| | kgp4418535 | 6 | 32431558 | | C | A | 2.45E-04 | 3.58 | 0.227 | 0.076 | 2.93E-02 | 2.84 | 0.191 | 0.086 |
| | rs1079303 | 11 | 27269598 | | A | G | 1.14E-03 | 2.52 | 0.500 | 0.337 | 2.32E-03 | 2.66 | 0.466 | 0.257 |
| | rs10501082 | 11 | 27270978 | | G | A | 1.14E-03 | 2.52 | 0.500 | 0.337 | 2.32E-03 | 2.66 | 0.466 | 0.257 |
| | rs6718758 | 2 | 60328802 | | C | A | 6.94E-03 | 0.53 | 0.311 | 0.471 | 9.16E-03 | 0.44 | 0.253 | 0.414 |

TABLE 39-continued

Extreme Response SNPs

| EXTREME PHENOTYPE | | | | | | | Gala cohort | | | | Forte cohort | | | |
|---|---|---|---|---|---|---|---|---|---|---|---|---|---|---|
| Prioritized Variants Name | Chromosome | Position | Gene(s) | Major Allele (d) | Minor Allele (D) | P-value (Armitage Test) | Odds Ratio (Minor Allele) | Minor Allele Freq. (Responders) | Allele Freq. (Non-Responders) | P-value (Armitage Test) | Odds Ratio (Minor Allele) | Minor Allele Freq. (Responders) | Allele Freq. (Non-Responders) |
| rs7725112 | 5 | 173996604 | | G | A | 2.09E-04 | 3.94 | 0.212 | 0.070 | 3.76E-02 | 2.58 | 0.197 | 0.086 |
| kgp4734301 | 11 | 27315427 | | A | G | 5.37E-04 | 2.64 | 0.394 | 0.221 | 1.55E-02 | 2.28 | 0.371 | 0.214 |
| rs1029928 | 11 | 27319188 | | G | A | 5.37E-04 | 2.64 | 0.394 | 0.223 | 1.55E-02 | 2.28 | 0.371 | 0.214 |
| rs7948420 | 11 | 27276450 | | A | G | 6.04E-05 | 0.33 | 0.205 | 0.424 | 6.96E-03 | 0.46 | 0.326 | 0.514 |
| kgp18432055 | 9 | 108536427 | TMEM38B | A | T | 5.20E-04 | 3.51 | 0.205 | 0.065 | 8.25E-03 | 4.81 | 0.163 | 0.043 |
| rs10954782 | 8 | 31076640 | | A | G | 3.11E-02 | 1.66 | 0.515 | 0.390 | 2.07E-03 | 0.40 | 0.371 | 0.586 |
| kgp8599417 | 6 | 164319353 | | G | A | 2.53E-04 | 0.34 | 0.159 | 0.345 | 9.67E-02 | 0.55 | 0.182 | 0.271 |
| rs7028906 | 9 | 108450368 | | G | A | 1.23E-04 | 4.13 | 0.212 | 0.058 | 1.93E-02 | 4.17 | 0.140 | 0.043 |
| kgp9078300 | 2 | 23615634 | KLHL29 | A | G | 1.83E-02 | 2.18 | 0.208 | 0.110 | 9.97E-04 | 4.88 | 0.253 | 0.071 |
| rs7563131 | 2 | 65248271 | SLC1A4 | G | A | 8.76E-07 | 9.70 | 0.200 | 0.029 | 4.39E-01 | 1.42 | 0.136 | 0.100 |
| rs7928078 | 11 | 27271285 | | A | G | 1.84E-03 | 2.44 | 0.492 | 0.337 | 2.32E-03 | 2.66 | 0.466 | 0.257 |
| rs1157449 | 8 | 73277404 | | G | A | 4.28E-03 | 0.37 | 0.106 | 0.227 | 2.48E-02 | 0.40 | 0.073 | 0.171 |
| kgp9884626 | 2 | 206731028 | | A | G | 4.15E-03 | Zero | 0.000 | 0.058 | 5.43E-03 | Zero | 0.000 | 0.043 |
| rs11083404 | 18 | 28087536 | | A | G | 1.85E-01 | 1.45 | 0.273 | 0.209 | 2.86E-05 | 5.40 | 0.388 | 0.114 |
| rs9579566 | 13 | 30980265 | | G | A | 1.39E-03 | Zero | 0.000 | 0.081 | 7.80E-03 | 0.17 | 0.017 | 0.086 |
| kgp5292386 | 5 | 159424526 | | C | A | 3.96E-03 | 0.21 | 0.030 | 0.116 | 2.60E-02 | 0.21 | 0.017 | 0.071 |
| rs7496451 | 15 | 25718875 | | G | A | 2.61E-02 | 2.10 | 0.212 | 0.122 | 1.28E-03 | 4.21 | 0.270 | 0.100 |
| kgp5017029 | 17 | 44868049 | WNT3 | G | A | 9.30E-03 | 0.22 | 0.023 | 0.100 | 2.37E-03 | 0.11 | 0.011 | 0.086 |
| kgp1355977 | 6 | 145573380 | | G | A | 3.29E-02 | 0.21 | 0.015 | 0.064 | 6.23E-05 | Zero | 0.000 | 0.086 |
| rs11029907 | 11 | 27295271 | | C | G | 1.84E-03 | 2.44 | 0.492 | 0.337 | 2.49E-03 | 2.64 | 0.466 | 0.257 |
| kgp6038357 | 11 | 272276484 | | G | A | 1.14E-03 | 2.52 | 0.500 | 0.337 | 3.19E-03 | 2.56 | 0.461 | 0.257 |
| kgp110773773 | 1722750120 | | STC2 | C | A | 3.30E-03 | 0.22 | 0.030 | 0.129 | 1.24E-03 | 0.22 | 0.051 | 0.171 |
| kgp3202939 | 12 | 13859947 | GRIN2B | G | A | 1.36E-02 | 0.12 | 0.008 | 0.070 | 1.12E-04 | 0.07 | 0.011 | 0.118 |
| kgp116686146 | 2 | 142745416 | LRP1B | G | A | 8.92E-05 | 0.12 | 0.015 | 0.122 | 3.01E-02 | 0.29 | 0.034 | 0.100 |
| rs11085044 | 19 | 3890641 | ATCAY | G | A | 1.87E-04 | 0.40 | 0.227 | 0.453 | 3.17E-01 | 0.74 | 0.236 | 0.300 |
| kgp3730395 | 9 | 91520540 | | C | A | 1.01E-02 | 0.52 | 0.288 | 0.430 | 4.63E-04 | 0.36 | 0.287 | 0.529 |
| rs2175121 | 9 | 108497519 | TMEM38B | A | G | 8.41E-04 | 3.26 | 0.205 | 0.070 | 7.57E-03 | 4.88 | 0.165 | 0.043 |
| kgp487328 | 22 | 26134026 | | G | A | 6.03E-05 | 0.19 | 0.061 | 0.215 | 5.89E-01 | 0.77 | 0.079 | 0.100 |
| kgp1912531 | 2 | 137850215 | THSD7B | A | G | 1.22E-03 | 2.73 | 0.250 | 0.105 | 1.23E-02 | 2.81 | 0.244 | 0.086 |
| kgp9450430 | 20 | 44085460 | | A | G | 6.01E-03 | 0.44 | 0.197 | 0.326 | 1.74E-02 | 0.47 | 0.146 | 0.286 |
| kgp2391411 | 2 | 43425645 | | G | A | 7.19E-04 | 0.39 | 0.182 | 0.360 | 5.85E-03 | 0.47 | 0.236 | 0.429 |
| rs10816302 | 9 | 108486533 | TMEM38B | G | A | 8.41E-04 | 3.26 | 0.205 | 0.070 | 8.25E-03 | 4.81 | 0.163 | 0.043 |
| rs7020402 | 9 | 108530638 | TMEM38B | A | G | 8.41E-04 | 3.26 | 0.205 | 0.070 | 8.25E-03 | 4.81 | 0.163 | 0.043 |
| rs1979993 | 9 | 108534505 | TMEM38B | A | G | 8.41E-04 | 3.26 | 0.205 | 0.070 | 8.25E-03 | 4.81 | 0.163 | 0.043 |
| rs1979992 | 9 | 108535330 | TMEM38B | A | G | 8.41E-04 | 3.26 | 0.205 | 0.070 | 8.25E-03 | 4.81 | 0.163 | 0.043 |
| rs6032209 | 20 | 44087073 | | A | G | 6.33E-03 | 0.45 | 0.208 | 0.341 | 2.28E-02 | 0.49 | 0.152 | 0.286 |
| kgp7521990 | 1 | 105666878 | | C | A | 4.53E-03 | 0.34 | 0.069 | 0.186 | 8.31E-03 | 0.30 | 0.067 | 0.171 |
| kgp2451249 | 1 | 223872873 | CAPN8 | A | G | 3.06E-03 | 3.43 | 0.152 | 0.052 | 1.55E-02 | 3.66 | 0.174 | 0.057 |
| kgp8796185 | 1 | 223716508 | | G | A | 4.13E-03 | 3.32 | 0.344 | 0.047 | 2.22E-02 | 3.18 | 0.180 | 0.071 |
| rs2241883 | 2 | 88424066 | FABP1 | A | G | 1.18E-03 | 0.43 | 0.273 | 0.453 | 4.71E-02 | 0.54 | 0.275 | 0.400 |

TABLE 39-continued

Extreme Response SNPs

| | EXTREME PHENOTYPE | | | | | | Gala cohort | | | | | Forte cohort | | | |
|---|---|---|---|---|---|---|---|---|---|---|---|---|---|---|---|
| Prioritized Variants | Name | Chromosome | Position | Gene(s) | Major Allele (d) | Minor Allele (D) | P-value (Armitage Test) | Odds Ratio (Minor Allele) | Minor Allele Freq. (Responders) | Allele Freq. (Non-Responders) | P-value (Armitage Test) | Odds Ratio (Minor Allele) | Minor Allele Freq. (Responders) | Allele Freq. (Non-Responders) |
| | rs343087 | 12 | 66260924 | HMGA2 | G | A | 5.81E-03 | 2.59 | 0.182 | 0.070 | 1.04E-02 | 3.25 | 0.222 | 0.071 |
| | rs4894701 | 3 | 174931730 | NAALADL2 | A | C | 2.64E-03 | 2.14 | 0.547 | 0.378 | 1.97E-02 | 0.50 | 0.438 | 0.600 |
| | kgp18525257 | 9 | 108499628 | TMEM38B | G | A | 1.10E-03 | 3.27 | 0.197 | 0.070 | 8.25E-03 | 4.81 | 0.163 | 0.043 |
| | kgp18379774 | 9 | 108504407 | TMEM38B | G | A | 1.10E-03 | 3.27 | 0.197 | 0.070 | 8.25E-03 | 4.81 | 0.163 | 0.043 |
| | rs10512340 | 9 | 108511163 | TMEM38B | G | A | 1.10E-03 | 3.27 | 0.197 | 0.070 | 8.25E-03 | 4.81 | 0.163 | 0.043 |
| | rs10125298 | 9 | 108555594 | | C | A | 1.10E-03 | 3.27 | 0.197 | 0.070 | 8.25E-03 | 4.81 | 0.163 | 0.043 |
| | kgp759150 | 4 | 40385906 | | G | A | 3.21E-03 | 2.09 | 0.583 | 0.419 | 7.28E-04 | 3.23 | 0.528 | 0.314 |
| | rs10124492 | 9 | 108527455 | TMEM38B | T | A | 1.25E-03 | 3.14 | 0.200 | 0.070 | 7.57E-03 | 4.88 | 0.163 | 0.043 |
| | kgp3812034 | 2 | 43427044 | | A | G | 9.26E-04 | 0.40 | 0.189 | 0.365 | 6.74E-03 | 0.47 | 0.238 | 0.429 |
| | rs5024722 | 7 | 141858688 | | C | G | 2.52E-02 | 0.52 | 0.189 | 0.297 | 1.52E-03 | 0.34 | 0.136 | 0.314 |
| | rs11691553 | 2 | 60303554 | | C | A | 5.69E-03 | 0.52 | 0.323 | 0.488 | 2.06E-02 | 0.48 | 0.284 | 0.429 |
| | kgp11453406 | 10 | 121435955 | BAG3 | C | A | 4.93E-04 | 0.40 | 0.174 | 0.372 | 3.47E-02 | 0.49 | 0.233 | 0.357 |
| | rs196341 | 10 | 121416611 | BAG3 | G | A | 7.33E-04 | 0.41 | 0.177 | 0.371 | 2.73E-02 | 0.48 | 0.227 | 0.357 |
| | rs10203396 | 2 | 60305110 | | A | G | 5.80E-03 | 0.52 | 0.326 | 0.488 | 2.22E-02 | 0.48 | 0.287 | 0.429 |
| | rs7579987 | 2 | 60307009 | | G | C | 5.80E-03 | 0.52 | 0.326 | 0.488 | 2.22E-02 | 0.48 | 0.287 | 0.429 |
| | rs7862565 | 9 | 108592419 | | G | A | 1.06E-03 | 3.47 | 0.182 | 0.058 | 2.11E-02 | 3.52 | 0.163 | 0.057 |
| | kgp11514107 | 2 | 65247253 | SLC1A4 | G | A | 8.67E-06 | 6.07 | 0.212 | 0.047 | 2.42E-01 | 1.74 | 0.140 | 0.086 |
| | rs4822644 | 22 | 26134163 | | G | A | 8.28E-05 | 0.21 | 0.068 | 0.227 | 5.56E-01 | 0.76 | 0.090 | 0.114 |
| | rs2136408 | 9 | 108497654 | TMEM38B | A | C | 9.59E-04 | 3.22 | 0.205 | 0.071 | 9.89E-03 | 4.66 | 0.163 | 0.044 |
| | rs1545223 | 2 | 88423510 | FABP1 | A | G | 1.59E-03 | 0.44 | 0.277 | 0.453 | 4.71E-02 | 0.54 | 0.275 | 0.400 |
| | rs17329014 | 2 | 60299921 | | G | A | 7.67E-03 | 0.50 | 0.235 | 0.378 | 1.94E-02 | 0.48 | 0.185 | 0.329 |
| | rs2058742 | 17 | 70040547 | | C | A | 5.12E-03 | 2.13 | 0.333 | 0.192 | 1.26E-02 | 2.38 | 0.360 | 0.200 |
| | kgp4420791 | 12 | 89819166 | POC1B | G | A | 5.14E-02 | 0.24 | 0.015 | 0.058 | 2.69E-05 | 0.04 | 0.006 | 0.114 |
| | kgp7714238 | 6 | 145587514 | | G | A | 2.10E-02 | 0.19 | 0.015 | 0.070 | 5.03E-04 | 0.05 | 0.006 | 0.086 |
| | rs13394010 | 2 | 60302746 | | A | G | 6.13E-03 | 0.52 | 0.326 | 0.488 | 2.22E-02 | 0.48 | 0.287 | 0.429 |
| | kgp7924485 | 2 | 60292120 | | A | C | 2.04E-02 | 0.50 | 0.152 | 0.262 | 4.46E-03 | 0.36 | 0.097 | 0.243 |
| | kgp8174785 | 1 | 110053148 | | G | C | 6.72E-03 | 0.51 | 0.258 | 0.413 | 1.26E-02 | 0.39 | 0.236 | 0.371 |
| | kgp10090631 | 7 | 11754881 | THSD7A | A | G | 3.50E-02 | 1.67 | 0.447 | 0.327 | 3.08E-03 | 2.59 | 0.539 | 0.338 |
| | kgp1683448 | 9 | 108449079 | | A | G | 2.68E-04 | 4.49 | 0.177 | 0.047 | 3.87E-02 | 3.60 | 0.129 | 0.044 |
| | kgp8777935 | 6 | 139004920 | | A | G | 8.38E-03 | 1.93 | 0.424 | 0.279 | 1.05E-02 | 2.08 | 0.478 | 0.286 |
| | rs16930057 | 8 | 63906122 | | G | A | 1.04E-04 | 0.27 | 0.091 | 0.273 | 1.87E-01 | 0.61 | 0.148 | 0.214 |
| | kgp7181058 | 14 | 93885698 | | G | A | 2.56E-02 | Zero | 0.000 | 0.064 | 1.09E-01 | Zero | 0.000 | 0.014 |
| | kgp117111524 | 9 | 108546438 | | G | A | 1.66E-03 | 3.14 | 0.192 | 0.070 | 8.25E-03 | 4.81 | 0.163 | 0.043 |
| | kgp6505544 | 7 | 71953948 | | G | A | 1.89E-03 | 3.08 | 0.205 | 0.087 | 1.42E-02 | 3.26 | 0.202 | 0.071 |
| | rs623011 | 17 | 68259446 | | G | A | 5.73E-03 | 2.32 | 0.258 | 0.134 | 4.39E-02 | 2.07 | 0.320 | 0.200 |
| | kgp355027 | 11 | 115964147 | | A | G | 9.27E-03 | 0.41 | 0.106 | 0.215 | 2.70E-03 | 0.31 | 0.098 | 0.243 |
| | kgp767200 | 5 | 3221345 | | A | C | 2.83E-05 | 4.41 | 0.262 | 0.094 | 1.10E-01 | 2.06 | 0.184 | 0.103 |
| | kgp5908616 | 10 | 60329823 | INPP5F | A | G | 1.62E-02 | 0.58 | 0.326 | 0.471 | 8.04E-03 | 0.43 | 0.261 | 0.429 |
| | kgp3205849 | 12 | 121531725 | | C | C | 1.63E-04 | 0.33 | 0.129 | 0.331 | 1.15E-01 | 0.59 | 0.195 | 0.286 |
| | kgp9320791 | 2 | 60309952 | | C | G | 5.80E-03 | 0.52 | 0.326 | 0.488 | 2.56E-02 | 0.49 | 0.290 | 0.429 |

TABLE 39-continued

Extreme Response SNPs

| EXTREME PHENOTYPE | | | | | | | Gala cohort | | | | Forte cohort | | | |
|---|---|---|---|---|---|---|---|---|---|---|---|---|---|---|
| Prioritized Variants | Name | Chromosome | Position | Gene(s) | Major Allele (d) | Minor Allele (D) | P-value (Armitage Test) | Odds Ratio (Minor Allele) | Minor Allele Freq. (Responders) | Allele Freq. (Non-Responders) | P-value (Armitage Test) | Odds Ratio (Minor Allele) | Minor Allele Freq. (Responders) | Allele Freq. (Non-Responders) |
| | kgp3267884 | 9 | 14639380 | ZDHHC21 | G | A | 1.21E-03 | 0.41 | 0.212 | 0.384 | 1.03E-01 | 0.59 | 0.202 | 0.300 |
| | rs13002663 | 2 | 145220163 | ZEB2, ZEB2 | G | A | 1.08E-02 | 0.55 | 0.318 | 0.471 | 3.61E-03 | 0.40 | 0.298 | 0.486 |
| | kgp8767692 | 15 | 66333821 | MEGF11 | G | A | 2.29E-02 | 0.24 | 0.023 | 0.081 | 6.05E-04 | 0.09 | 0.011 | 0.100 |
| | kgp28532436 | 15 | 62968836 | TLN2 | G | A | 9.69E-04 | 15.18 | 0.076 | 0.006 | 2.23E-02 | Infinity | 0.067 | 0.000 |
| | rs9346979 | 6 | 164309479 | | G | A | 1.23E-03 | 0.45 | 0.295 | 0.483 | 4.65E-02 | 0.56 | 0.309 | 0.443 |
| | rs714342 | 11 | 110807983 | | A | C | 3.45E-03 | 2.13 | 0.447 | 0.291 | 4.86E-02 | 1.95 | 0.478 | 0.357 |
| | kgp8869954 | 2 | 135163015 | MGAT5 | G | A | 3.62E-03 | 0.22 | 0.030 | 0.128 | 3.67E-03 | 0.25 | 0.051 | 0.157 |
| | kgp2709692 | 18 | 3000808 | LPIN2 | C | C | 3.29E-02 | 0.21 | 0.015 | 0.064 | 2.95E-04 | Zero | 0.000 | 0.071 |
| | rs10510774 | 3 | 54919351 | CACNA2D3 | A | G | 7.25E-04 | 0.23 | 0.053 | 0.176 | 1.08E-01 | 0.46 | 0.068 | 0.129 |
| | kgp8169636 | 18 | 29206763 | B4GALT6 | G | A | 1.12E-02 | 0.32 | 0.045 | 0.134 | 1.26E-02 | 0.24 | 0.022 | 0.100 |
| | kgp3593828 | 5 | 173993252 | | C | A | 6.50E-04 | 2.56 | 0.341 | 0.169 | 1.87E-02 | 2.49 | 0.281 | 0.143 |
| | kgp110010680 | 15 | 25717889 | | A | G | 5.83E-02 | 1.87 | 0.205 | 0.128 | 1.08E-03 | 4.31 | 0.273 | 0.100 |
| | rs1387768 | 5 | 173993166 | | A | G | 7.86E-04 | 2.53 | 0.341 | 0.171 | 1.65E-02 | 2.54 | 0.284 | 0.143 |
| | kgp11627530 | 14 | 78954642 | NRXN3 | A | G | 1.79E-02 | 0.32 | 0.038 | 0.116 | 3.37E-04 | 0.20 | 0.039 | 0.186 |
| | kgp10404633 | 9 | 138136993 | | G | A | 1.73E-03 | 8.40 | 0.083 | 0.012 | 2.76E-02 | 7.45 | 0.090 | 0.014 |
| | kgp8372910 | 9 | 138138723 | | G | A | 1.73E-03 | 8.40 | 0.083 | 0.012 | 2.76E-02 | 7.45 | 0.090 | 0.014 |
| | kgp11206453 | 3 | 54928104 | CACNA2D3 | G | A | 8.39E-04 | 0.24 | 0.053 | 0.174 | 1.02E-01 | 0.45 | 0.067 | 0.129 |
| | rs11136970 | 8 | 604262 | | A | C | 3.39E-02 | 1.72 | 0.331 | 0.221 | 6.18E-03 | 2.40 | 0.432 | 0.243 |
| | kgp9795732 | 15 | 88117171 | | C | A | 1.33E-03 | 0.30 | 0.069 | 0.208 | 2.88E-02 | 0.45 | 0.091 | 0.200 |
| | rs2934491 | 16 | 84905542 | CRISPLD2 | G | A | 7.45E-03 | 0.52 | 0.295 | 0.448 | 9.75E-03 | 0.45 | 0.275 | 0.443 |
| | kgp9368119 | 7 | 11707419 | THSD7A | A | G | 2.23E-02 | 0.58 | 0.379 | 0.512 | 1.08E-02 | 0.44 | 0.298 | 0.457 |
| | rs4709792 | 6 | 164316375 | | G | A | 1.21E-03 | 0.45 | 0.288 | 0.477 | 4.65E-02 | 0.56 | 0.309 | 0.443 |
| | rs17400875 | 2 | 60295736 | | A | C | 7.67E-03 | 0.50 | 0.235 | 0.378 | 2.48E-02 | 0.50 | 0.191 | 0.329 |
| | kgp10152733 | 9 | 108462735 | TMEM38B | G | A | 1.50E-03 | 3.01 | 0.205 | 0.076 | 8.25E-03 | 4.81 | 0.163 | 0.043 |
| | kgp12426624 | 3 | 54926209 | CACNA2D3 | C | A | 1.90E-03 | 0.27 | 0.061 | 0.174 | 4.78E-02 | 0.39 | 0.067 | 0.143 |
| | kgp55646 | 10 | 121282886 | RGS10 | G | A | 1.09E-02 | 0.53 | 0.265 | 0.407 | 7.63E-03 | 0.43 | 0.233 | 0.400 |
| | kgp10922969 | 6 | 80260277 | | G | A | 7.52E-02 | 0.50 | 0.076 | 0.141 | 1.28E-04 | 0.13 | 0.028 | 0.157 |
| | kgp7331172 | 18 | 66533114 | CCDC102B | A | G | 1.95E-05 | 4.29 | 0.273 | 0.093 | 1.70E-01 | 1.79 | 0.185 | 0.114 |
| | kgp6666134 | 10 | 129386358 | | T | A | 7.27E-03 | 2.10 | 0.295 | 0.163 | 1.00E-02 | 2.58 | 0.320 | 0.157 |
| | kgp6603796 | 16 | 84910897 | CRISPLD2 | G | A | 7.24E-03 | 0.50 | 0.269 | 0.419 | 8.24E-03 | 0.45 | 0.253 | 0.429 |
| | kgp9018750 | 6 | 164312470 | | A | G | 1.23E-03 | 0.45 | 0.295 | 0.483 | 5.29E-02 | 0.57 | 0.313 | 0.443 |
| | rs858341 | 6 | 132160455 | ENPP1 | A | G | 1.05E-02 | 2.26 | 0.462 | 0.279 | 8.21E-02 | 1.67 | 0.466 | 0.343 |
| | kgp4096263 | 15 | 70333438 | | A | G | 4.37E-04 | 3.81 | 0.195 | 0.059 | 4.01E-02 | 3.10 | 0.149 | 0.057 |
| | kgp5159037 | 2 | 65255764 | | A | G | 2.59E-05 | 4.31 | 0.250 | 0.070 | 2.62E-01 | 1.61 | 0.176 | 0.118 |
| | rs423239 | 9 | 92856946 | | A | G | 3.11E-03 | 2.61 | 0.220 | 0.093 | 1.50E-02 | 3.08 | 0.213 | 0.086 |
| | rs343092 | 12 | 66250940 | HMGA2 | C | A | 9.60E-03 | 2.44 | 0.174 | 0.070 | 1.23E-02 | 3.22 | 0.275 | 0.071 |
| | kgp7178233 | 5 | 117621827 | | C | A | 2.69E-03 | 2.57 | 0.242 | 0.110 | 7.02E-02 | 1.98 | 0.275 | 0.171 |
| | kgp3218351 | 11 | 110802128 | | C | A | 3.59E-03 | 2.16 | 0.432 | 0.279 | 4.32E-02 | 1.95 | 0.455 | 0.329 |
| | kgp10564659 | | 223733531 | | G | A | 7.40E-03 | 3.09 | 0.136 | 0.047 | 2.66E-02 | 3.08 | 0.176 | 0.071 |
| | P1_M_061510_11_106_M | 11 | 27308202 | | D | I | 5.93E-05 | 0.32 | 0.205 | 0.419 | 1.14E-02 | 0.48 | 0.354 | 0.529 |
| | kgp6023196 | 17 | 68271273 | | A | C | 3.52E-03 | 2.28 | 0.311 | 0.169 | 7.11E-02 | 1.81 | 0.360 | 0.243 |
| | kgp4056892 | 20 | 44087774 | | C | G | 1.95E-02 | 0.50 | 0.205 | 0.314 | 1.60E-02 | 0.46 | 0.135 | 0.271 |
| | rs484482 | 15 | 55418825 | | A | G | 1.53E-04 | 5.80 | 0.152 | 0.035 | 7.88E-02 | 2.88 | 0.119 | 0.043 |
| | kgp673709 | 15 | 66299395 | MEGF11 | G | A | 3.55E-02 | 0.31 | 0.030 | 0.087 | 6.05E-04 | 0.09 | 0.011 | 0.100 |
| | kgp6076976 | 1 | 105663380 | | A | T | 2.57E-03 | 0.27 | 0.053 | 0.161 | 3.03E-02 | 0.35 | 0.062 | 0.143 |

TABLE 39-continued

Extreme Response SNPs

| EXTREME PHENOTYPE | | | | | | Gala cohort | | | | | Forte cohort | | | |
|---|---|---|---|---|---|---|---|---|---|---|---|---|---|---|
| Prioritized Variants | Name | Chromosome | Position | Gene(s) | Major Allele (d) | Minor Allele (D) | P-value (Armitage Test) | Odds Ratio (Minor Allele) | Minor Allele Freq. (Responders) | Allele Freq. (Non-Responders) | P-value (Armitage Test) | Odds Ratio (Minor Allele) | Minor Allele Freq. (Responders) | Allele Freq. (Non-Responders) |
| | rs9597498 | 13 | 57657550 | | G | A | 2.81E-03 | 1.98 | 0.470 | 0.291 | 1.44E-02 | 2.06 | 0.449 | 0.271 |
| | rs419132 | 6 | 32210799 | | A | G | 4.24E-05 | 2.62 | 0.523 | 0.271 | 1.05E-01 | 1.66 | 0.381 | 0.271 |
| | kgp29794723 | 10 | 18397332 | | A | G | 1.33E-02 | 0.18 | 0.015 | 0.076 | 2.55E-03 | 0.11 | 0.011 | 0.086 |
| | kgp6091119 | 17 | 44879640 | WNT3 | A | A | 1.28E-02 | 0.27 | 0.030 | 0.110 | 7.80E-03 | 0.17 | 0.017 | 0.086 |
| | kgp10351364 | 8 | 103604706 | | G | A | 5.14E-03 | 2.02 | 0.559 | 0.393 | 3.01E-03 | 2.65 | 0.523 | 0.324 |
| | rs9376361 | 6 | 139006406 | | A | G | 2.74E-03 | 2.07 | 0.455 | 0.285 | 4.52E-02 | 1.76 | 0.477 | 0.329 |
| | kgp3991733 | 1 | 105671167 | | T | A | 1.36E-02 | 0.40 | 0.076 | 0.176 | 3.12E-03 | 0.26 | 0.067 | 0.186 |
| | rs6687976 | 1 | 105674536 | | C | A | 1.36E-02 | 0.40 | 0.076 | 0.176 | 3.12E-03 | 0.26 | 0.067 | 0.186 |
| 2 - Priority Genes (extreme) | rs6110157 | 20 | 14055947 | MACROD2 | A | G | 2.18E-02 | 0.53 | 0.215 | 0.331 | 7.82E-03 | 0.45 | 0.176 | 0.343 |
| 2 - Priority Genes (extreme) | kgp4011779 | 10 | 100454360 | HPSE2 | G | A | 2.48E-02 | 0.25 | 0.023 | 0.081 | 2.30E-02 | Zero | 0.000 | 0.029 |
| 0 - Priority - Model | rs16886004 | 7 | 78021500 | MAGI2 | A | G | 3.05E-02 | 2.04 | 0.189 | 0.100 | 9.21E-03 | 3.64 | 0.202 | 0.071 |
| 2 - Priority Genes | kgp34496814 | 13 | 31336379 | ALOX5AP | C | A | 2.87E-02 | 0.60 | 0.394 | 0.523 | 8.60E-04 | 0.37 | 0.433 | 0.671 |
| 0 - Priority - Model, Priority Gene | rs0162089 | 13 | 31316738 | ALOX5AP | G | A | 5.86E-03 | 1.93 | 0.561 | 0.399 | 5.29E-03 | 2.32 | 0.460 | 0.257 |
| 2 - Priority Genes | rs3885907 | 13 | 31314455 | ALOX5AP | A | C | 1.59E-02 | 1.73 | 0.523 | 0.378 | 2.74E-03 | 2.56 | 0.455 | 0.243 |
| 0 - Priority - Model | rs1894408 | 6 | 32786833 | | C | G | 8.94E-02 | 1.50 | 0.392 | 0.297 | 2.63E-03 | 2.85 | 0.420 | 0.229 |
| 0 - Priority - Model | kgp8817856 | 6 | 32744440 | | G | G | 3.61E-02 | 0.58 | 0.369 | 0.483 | 9.23E-03 | 0.45 | 0.369 | 0.543 |
| 2 - Priority Genes | rs17238927 | 13 | 31332391 | ALOX5AP | G | A | 4.20E-02 | 0.15 | 0.008 | 0.047 | 2.30E-02 | Zero | 0.000 | 0.029 |
| 2 - Priority Genes | rs967124 | 13 | 31324253 | ALOX5AP | G | A | 2.25E-02 | 1.69 | 0.561 | 0.424 | 1.97E-03 | 2.57 | 0.494 | 0.271 |
| 2 - Priority Genes | rs4769060 | 13 | 31337877 | ALOX5AP | A | G | 3.03E-02 | 1.69 | 0.500 | 0.378 | 3.71E-03 | 2.43 | 0.466 | 0.257 |
| 0 - Priority - Model | kgp24415534 | 2 | 174156875 | | G | A | 4.38E-02 | 0.15 | 0.008 | 0.047 | 2.30E-02 | Zero | 0.000 | 0.029 |
| 2 - Priority Genes | rs4075692 | 13 | 31323342 | ALOX5AP | G | A | 2.25E-02 | 1.69 | 0.561 | 0.424 | 2.31E-03 | 2.55 | 0.489 | 0.271 |
| 2 - Priority Genes (extreme) | rs11147439 | 13 | 31325643 | ALOX5AP | C | A | 1.83E-02 | 0.57 | 0.364 | 0.500 | 8.86E-03 | 0.48 | 0.421 | 0.614 |
| 2 - Priority Genes (extreme) | kgp3276689 | 10 | 100396003 | HPSE2 | C | A | 4.39E-02 | 1.90 | 0.192 | 0.106 | 3.64E-02 | 2.48 | 0.213 | 0.100 |
| 2 - Priority Genes (extreme) | kgp304921 | 20 | 14017077 | MACROD2 | G | A | 4.20E-02 | 0.34 | 0.031 | 0.095 | 2.65E-02 | 0.29 | 0.025 | 0.100 |
| 2 - Priority Genes | rs3803277 | 13 | 31318308 | ALOX5AP | C | A | 1.63E-02 | 0.57 | 0.371 | 0.512 | 1.25E-02 | 0.49 | 0.433 | 0.614 |
| 2 - Priority Genes (extreme) | kgp5440506 | 13 | 31320543 | ALOX5AP | G | A | 1.74E-02 | 0.57 | 0.362 | 0.500 | 1.14E-02 | 0.49 | 0.427 | 0.618 |
| 2 - Priority Genes | rs9671182 | 13 | 31321138 | ALOX5AP | C | G | 1.93E-02 | 0.57 | 0.371 | 0.506 | 1.38E-02 | 0.50 | 0.433 | 0.614 |
| 0 - Priority - Model | kgp8110667 | 22 | 32716792 | | G | A | 9.44E-03 | Infinity | 0.038 | 0.000 | 1.15E-01 | Infinity | 0.034 | 0.000 |
| 2 - Priority Genes (extreme) | rs4254166 | 13 | 31322949 | ALOX5AP | A | G | 2.51E-02 | 0.59 | 0.371 | 0.500 | 1.05E-02 | 0.49 | 0.427 | 0.614 |

TABLE 39-continued

Extreme Response SNPs

| EXTREME PHENOTYPE | | | | | | | Gala cohort | | | | Forte cohort | | | |
|---|---|---|---|---|---|---|---|---|---|---|---|---|---|---|
| Prioritized Variants | Name | Chromosome | Position | Gene(s) | Major Allele (d) | Minor Allele (D) | P-value (Armitage Test) | Odds Ratio (Minor Allele) | Minor Allele Freq. (Responders) | Allele Freq. (Non-Responders) | P-value (Armitage Test) | Odds Ratio (Minor Allele) | Minor Allele Freq. (Responders) | Allele Freq. (Non-Responders) |
| 2 - Priority Genes (extreme) | rs4456336 | 13 | 31319546 | ALOX5AP | A | G | 2.03E-02 | 0.58 | 0.371 | 0.506 | 1.38E-02 | 0.50 | 0.433 | 0.614 |
| 2 - Priority Genes (extreme) | rs11002051 | 10 | 78921392 | KCNMA1 | G | A | 1.50E-02 | 0.29 | 0.038 | 0.110 | 2.78E-02 | 0.38 | 0.067 | 0.157 |
| 2 - Priority Genes (extreme) | rs10278591 | 7 | 1921362 | MAD1L1 | G | A | 1.63E-02 | 1.95 | 0.303 | 0.186 | 4.33E-02 | 2.15 | 0.264 | 0.143 |
| 2 - Priority Genes (extreme) | rs4360791 | 13 | 31318020 | ALOX5AP | G | A | 1.79E-02 | 0.57 | 0.379 | 0.517 | 2.10E-02 | 0.53 | 0.444 | 0.614 |
| 2 - Priority Genes (extreme) | kgp2715873 | 13 | 31320249 | ALOX5AP | G | A | 2.51E-02 | 0.59 | 0.371 | 0.500 | 1.38E-02 | 0.50 | 0.433 | 0.614 |
| 2 - Priority Genes (extreme) | rs9670531 | 13 | 31321069 | ALOX5AP | A | G | 2.51E-02 | 0.59 | 0.371 | 0.500 | 1.38E-02 | 0.50 | 0.433 | 0.614 |
| 2 - Priority Genes (extreme) | rs9315047 | 13 | 31321289 | ALOX5AP | A | T | 2.51E-02 | 0.59 | 0.371 | 0.500 | 1.38E-02 | 0.50 | 0.433 | 0.614 |
| 2 - Priority Genes (extreme) | rs4584668 | 13 | 31319553 | ALOX5AP | A | T | 2.60E-02 | 0.59 | 0.371 | 0.500 | 1.38E-02 | 0.50 | 0.433 | 0.614 |
| 2 - Priority Genes (extreme) | rs9508832 | 13 | 31314264 | ALOX5AP | G | A | 2.16E-02 | 1.73 | 0.492 | 0.360 | 1.08E-02 | 2.21 | 0.410 | 0.229 |
| 1 - Priority Variant (extreme) | rs2487896 | 10 | 100802380 | HPSE2 | G | A | 1.30E-01 | 0.60 | 0.106 | 0.171 | 3.66E-03 | 0.33 | 0.118 | 0.286 |
| 2 - Priority Genes (extreme) | kgp7117398 | 7 | 1915282 | MAD1L1 | C | A | 2.26E-02 | 1.88 | 0.303 | 0.192 | 4.33E-02 | 2.15 | 0.264 | 0.143 |
| 1 - Priority Variant (extreme) | rs10988087 | 9 | 131443671 | | A | G | 2.31E-01 | 0.48 | 0.030 | 0.059 | 1.01E-03 | 0.18 | 0.028 | 0.143 |
| 0 - Priority - Model | kgp6599438 | 20 | 40843626 | PTPRT | G | A | 6.74E-03 | Infinity | 0.000 | 0.052 | 1.57E-01 | 0.36 | 0.022 | 0.057 |
| 0 - Priority - Model, Priority Variant | rs3135391 | 6 | 32410987 | HLA-DRA | G | A | 6.04E-02 | 0.58 | 0.182 | 0.273 | 2.79E-02 | 0.50 | 0.197 | 0.329 |
| 1 - Priority Variant (extreme) | rs1573706 | 20 | 40921149 | PTPRT | G | A | 6.38E-01 | 0.87 | 0.182 | 0.203 | 4.80E-04 | 0.28 | 0.107 | 0.286 |
| 2 - Priority Genes (extreme) | kgp4370912 | 10 | 78918297 | KCNMA1 | C | A | 3.18E-02 | 0.33 | 0.038 | 0.100 | 2.78E-02 | 0.38 | 0.067 | 0.157 |
| 1 - Priority Variant (extreme) | rs3135388 | 6 | 32413051 | | G | A | 6.92E-02 | 0.59 | 0.182 | 0.271 | 2.79E-02 | 0.50 | 0.197 | 0.329 |
| 0 - Priority - Model | kgp7747883 | 18 | 74804250 | MBP | G | A | 2.44E-01 | 0.76 | 0.364 | 0.430 | 3.55E-02 | 0.53 | 0.290 | 0.429 |
| 1 - Priority Variant (extreme) | rs6097801 | 20 | 52767434 | | G | A | 8.23E-01 | 0.93 | 0.136 | 0.145 | 5.74E-03 | 0.41 | 0.090 | 0.243 |

(Note:
Odds Ratio >1 = Minor Allele is associated with Response,
Odds Ratio <1 = Minor Allele Associated with Non-Response)

TABLE 39

Extreme Response SNPs

| | EXTREME PHENOTYPE | | | | | | | | | | | Combined | | | | | |
|---|---|---|---|---|---|---|---|---|---|---|---|---|---|---|---|---|---|
| Prioritized Variants | Name | Chromosome | Position | Gene(s) | Major Allele (d) | Minor Allele (D) | P-value (Armitage Test) | Odds Ratio (Minor Allele) | Minor Allele Freq. (Responders) | Allele Freq. (Non-Responders) | DD (Responders) | DD (Non-responders) | Dd (Responders) | Dd (Non-responders) | dd (Responders) | dd (Non-responders) |
| 0 - Priority - Model | kgp6214351 | 11 | 75546691 | UVRAG | A | G | 9.09E-07 | 0.17 | 0.029 | 0.140 | 0 | 1 | 9 | 32 | 145 | 88 |
| 0 - Priority - Model | rs759458 | 2 | 65245365 | SLC1A4 | G | A | 2.92E-06 | 2.64 | 0.360 | 0.178 | 20 | 3 | 71 | 37 | 63 | 81 |
| | rs7844274 | 8 | 72411302 | | C | A | 3.82E-06 | 0.40 | 0.188 | 0.368 | 4 | 18 | 50 | 53 | 100 | 50 |
| | kgp3984567 | 4 | 40379690 | | G | A | 4.36E-06 | 0.40 | 0.413 | 0.595 | 21 | 36 | 86 | 72 | 48 | 13 |
| | kgp11580695 | 10 | 3896635 | | G | C | 5.42E-06 | 0.28 | 0.065 | 0.192 | 0 | 4 | 20 | 38 | 135 | 78 |
| | kgp10948564 | 20 | 44082511 | | G | A | 6.43E-06 | 0.37 | 0.168 | 0.326 | 4 | 8 | 44 | 63 | 107 | 50 |
| | rs197523 | 21 | 19337261 | CHODL | G | A | 7.05E-06 | 2.39 | 0.384 | 0.198 | 26 | 5 | 67 | 38 | 62 | 78 |
| | kgp12371757 | 9 | 19458272 | | A | G | 7.23E-06 | 0.33 | 0.094 | 0.231 | 0 | 6 | 29 | 44 | 126 | 71 |
| | kgp9627338 | 17 | 90155 | RPH3AL | C | A | 8.19E-06 | 0.34 | 0.097 | 0.240 | 1 | 7 | 28 | 44 | 125 | 70 |
| | rs7850 | 2 | 65249922 | SLC1A4 | C | A | 8.39E-06 | 4.22 | 0.171 | 0.050 | 3 | 0 | 47 | 12 | 105 | 109 |
| | kgp7189498 | 2 | 65250677 | SLC1A4 | G | C | 8.87E-06 | 4.23 | 0.175 | 0.051 | 3 | 0 | 47 | 12 | 101 | 105 |
| | kgp10788130 | 12 | 13898682 | GRIN2B | G | A | 9.66E-06 | 0.07 | 0.006 | 0.083 | 0 | 1 | 2 | 18 | 153 | 102 |
| | kgp7242489 | 2 | 65250341 | SLC1A4 | A | T | 9.71E-06 | 4.19 | 0.171 | 0.050 | 3 | 0 | 47 | 12 | 105 | 108 |
| | rs7077322 | 4 | 164661252 | | A | C | 1.04E-05 | 0.18 | 0.026 | 0.117 | 0 | 0 | 5 | 28 | 146 | 92 |
| | rs7348267 | 20 | 44084386 | | G | A | 1.10E-05 | 0.39 | 0.168 | 0.322 | 4 | 8 | 44 | 62 | 107 | 51 |
| | kgp7121374 | 2 | 65246727 | SLC1A4 | A | G | 1.20E-05 | 3.99 | 0.175 | 0.054 | 3 | 0 | 48 | 13 | 103 | 107 |
| | kgp4127859 | 6 | 32434481 | | G | A | 1.21E-05 | 3.38 | 0.211 | 0.079 | 5 | 0 | 55 | 19 | 94 | 102 |
| | kgp8107491 | 6 | 164295151 | | G | A | 1.21E-05 | 0.45 | 0.344 | 0.529 | 17 | 32 | 72 | 64 | 65 | 25 |
| | rs16895510 | 6 | 164319963 | | G | A | 1.30E-05 | 0.40 | 0.173 | 0.331 | 3 | 11 | 47 | 58 | 303 | 52 |
| | rs6032205 | 20 | 44082799 | | C | A | 1.43E-05 | 0.39 | 0.171 | 0.325 | 4 | 8 | 44 | 62 | 104 | 50 |
| | kgp11768533 | 11 | 27270451 | | A | G | 1.54E-05 | 2.37 | 0.484 | 0.314 | 32 | 5 | 85 | 66 | 37 | 50 |
| | rs502530 | 6 | 145584096 | | C | A | 1.56E-05 | 0.07 | 0.006 | 0.074 | 0 | 0 | 2 | 18 | 153 | 103 |
| | rs1478682 | 11 | 27335009 | | G | A | 1.67E-05 | 2.34 | 0.464 | 0.293 | 31 | 4 | 81 | 63 | 42 | 54 |
| | kgp1124492 | 20 | 105554880 | | G | A | 1.74E-05 | 0.28 | 0.062 | 0.175 | 0 | 2 | 19 | 38 | 135 | 80 |
| | kgp11843177 | 11 | 27316568 | | A | G | 1.82E-05 | 2.43 | 0.381 | 0.217 | 20 | 2 | 78 | 48 | 57 | 70 |
| | kgp11467007 | 5 | 172750436 | STC2 | G | A | 1.83E-05 | 0.24 | 0.039 | 0.140 | 0 | 2 | 12 | 30 | 143 | 89 |
| | rs196295 | 10 | 121436362 | BAG3 | G | A | 1.86E-05 | 0.42 | 0.153 | 0.314 | 4 | 15 | 39 | 46 | 111 | 60 |
| | rs11029892 | 11 | 27269546 | | A | G | 1.89E-05 | 2.41 | 0.403 | 0.240 | 22 | 2 | 81 | 54 | 52 | 65 |
| | rs9913349 | 17 | 68260070 | | A | G | 1.59E-05 | 2.45 | 0.348 | 0.186 | 15 | 5 | 78 | 35 | 62 | 81 |
| | kgp5680955 | 6 | 164297121 | | A | G | 1.90E-05 | 0.46 | 0.295 | 0.475 | 13 | 27 | 65 | 61 | 76 | 33 |
| | kgp6236949 | 6 | 60301030 | | A | G | 1.93E-05 | 0.45 | 0.258 | 0.434 | 8 | 25 | 64 | 55 | 83 | 41 |
| | rs196343 | 10 | 121417957 | BAG3 | G | A | 2.00E-05 | 0.42 | 0.152 | 0.313 | 4 | 15 | 39 | 45 | 112 | 60 |
| | rs7217872 | 17 | 88988 | RPH3AL | G | A | 2.04E-05 | 0.36 | 0.100 | 0.236 | 1 | 7 | 29 | 43 | 125 | 71 |
| | kgp4634875 | 7 | 11704583 | THSD7A | C | A | 2.15E-05 | 2.18 | 0.568 | 0.388 | 48 | 16 | 80 | 61 | 27 | 43 |
| | kgp4418535 | 6 | 32431558 | | C | A | 2.15E-05 | 3.26 | 0.206 | 0.079 | 5 | 0 | 54 | 19 | 96 | 102 |
| | rs1079303 | 11 | 27269598 | | A | G | 2.19E-05 | 2.33 | 0.481 | 0.314 | 32 | 5 | 85 | 66 | 38 | 50 |
| | rs10501082 | 11 | 27270978 | | C | A | 2.19E-05 | 2.33 | 0.481 | 0.314 | 32 | 5 | 85 | 66 | 38 | 50 |
| | rs6718758 | 2 | 60328802 | | C | A | 2.22E-05 | 0.46 | 0.277 | 0.455 | 10 | 27 | 66 | 56 | 79 | 38 |
| | rs7725112 | 5 | 173996604 | | G | A | 2.22E-05 | 3.27 | 0.203 | 0.074 | 5 | 1 | 53 | 16 | 97 | 104 |
| | kgp4734301 | 11 | 27315427 | | A | G | 2.24E-05 | 2.40 | 0.381 | 0.219 | 20 | 2 | 78 | 49 | 57 | 70 |
| | rs1029928 | 11 | 27319188 | | A | G | 2.24E-05 | 2.40 | 0.381 | 0.219 | 20 | 2 | 78 | 49 | 57 | 70 |
| | rs7948420 | 11 | 27276450 | | G | A | 2.24E-05 | 0.46 | 0.274 | 0.450 | 12 | 24 | 61 | 61 | 82 | 36 |
| | kgp18432055 | 9 | 108536427 | TMEM38B | A | T | 2.33E-05 | 3.61 | 0.181 | 0.058 | 5 | 0 | 46 | 14 | 104 | 106 |
| | rs10954782 | 8 | 31076640 | | A | G | 2.36E-05 | 2.11 | 0.581 | 0.397 | 53 | 18 | 74 | 60 | 28 | 43 |

TABLE 39-continued

Extreme Response SNPs

| Prioritized Variants | EXTREME PHENOTYPE | | | | | | | | | Combined | | | | | |
|---|---|---|---|---|---|---|---|---|---|---|---|---|---|---|---|
| Name | Chromosome | Position | Gene(s) | Major Allele (d) | Minor Allele (D) | P-value (Armitage Test) | Odds Ratio (Minor Allele) | Minor Allele Freq. (Responders) | Allele Freq. (Non-Responders) | DD (Responders) | DD (Non-responders) | Dd (Responders) | Dd (Non-responders) | dd (Responders) | dd (Non-responders) |
| kgp8599417 | 6 | 164319353 | | G | A | 2.37E-05 | 0.40 | 0.172 | 0.324 | 3 | 10 | 47 | 57 | 104 | 52 |
| rs7028906 | 9 | 108450368 | | G | A | 2.57E-05 | 3.74 | 0.171 | 0.054 | 4 | 0 | 45 | 13 | 106 | 108 |
| kgp9078300 | 2 | 23615634 | KLHL29 | A | G | 2.65E-05 | 2.95 | 0.234 | 0.099 | 6 | 1 | 60 | 22 | 88 | 98 |
| rs7563131 | 2 | 65248271 | SLC1A4 | G | A | 2.85E-05 | 3.90 | 0.163 | 0.050 | 3 | 0 | 44 | 12 | 106 | 108 |
| rs7928078 | 11 | 27271285 | | G | G | 3.04E-05 | 2.30 | 0.477 | 0.314 | 31 | 5 | 85 | 66 | 38 | 50 |
| rs1157449 | 8 | 73277404 | | G | A | 3.05E-05 | 0.34 | 0.087 | 0.211 | 1 | 4 | 25 | 43 | 129 | 74 |
| kgp9884626 | 2 | 206731028 | | A | G | 3.08E-05 | Zero | 0.000 | 0.054 | 0 | 0 | 0 | 13 | 154 | 108 |
| rs11083404 | 18 | 28087536 | | A | A | 3.14E-05 | 2.41 | 0.339 | 0.182 | 16 | 3 | 73 | 38 | 66 | 80 |
| rs9579566 | 13 | 30980265 | | G | A | 3.19E-05 | 0.11 | 0.010 | 0.083 | 0 | 1 | 3 | 18 | 152 | 102 |
| kgp5292386 | 5 | 159442526 | | C | A | 3.22E-05 | 0.18 | 0.023 | 0.103 | 0 | 0 | 7 | 25 | 148 | 96 |
| rs7496451 | 15 | 25718875 | | G | A | 3.25E-05 | 2.89 | 0.245 | 0.116 | 4 | 0 | 68 | 28 | 83 | 93 |
| kgp5017029 | 17 | 4868049 | WNT3 | G | A | 3.26E-05 | 0.15 | 0.016 | 0.096 | 0 | 1 | 5 | 21 | 149 | 98 |
| kgp1355977 | 6 | 145573380 | | G | A | 3.26E-05 | 0.08 | 0.006 | 0.070 | 0 | 0 | 2 | 17 | 153 | 104 |
| rs11029907 | 11 | 27295271 | | C | G | 3.27E-05 | 2.29 | 0.477 | 0.314 | 31 | 5 | 84 | 66 | 38 | 50 |
| kgp6038357 | 11 | 27276484 | | G | A | 3.31E-05 | 2.27 | 0.477 | 0.314 | 32 | 5 | 84 | 66 | 39 | 50 |
| kgp11077373 | 5 | 172750120 | STC2 | C | A | 3.32E-05 | 0.26 | 0.042 | 0.142 | 3 | 2 | 13 | 30 | 142 | 88 |
| kgp3202939 | 12 | 13859947 | GRIN2B | G | A | 3.33E-05 | 0.11 | 0.010 | 0.083 | 0 | 1 | 3 | 18 | 150 | 101 |
| kgp11686146 | 2 | 142745416 | LRP1B | G | A | 3.41E-05 | 0.21 | 0.026 | 0.116 | 0 | 2 | 8 | 24 | 147 | 95 |
| rs11085044 | 19 | 3890641 | ATCAY | G | A | 3.52E-05 | 0.48 | 0.232 | 0.409 | 14 | 22 | 44 | 55 | 97 | 44 |
| kgp3730395 | 9 | 91520540 | | C | A | 3.53E-05 | 0.47 | 0.287 | 0.459 | 14 | 23 | 61 | 65 | 80 | 33 |
| rs2175121 | 9 | 108497519 | TMEM38B | A | A | 3.58E-05 | 3.42 | 0.182 | 0.062 | 5 | 0 | 46 | 15 | 103 | 106 |
| rs487328 | 22 | 26134026 | | G | A | 3.73E-05 | 0.31 | 0.071 | 0.182 | 0 | 2 | 22 | 40 | 133 | 79 |
| kgp1912531 | 2 | 137850215 | THSD7B | A | G | 3.79E-05 | 2.64 | 0.247 | 0.099 | 13 | 3 | 50 | 18 | 91 | 100 |
| kgp9450430 | 20 | 44085460 | | A | A | 3.80E-05 | 0.41 | 0.168 | 0.314 | 4 | 9 | 44 | 58 | 107 | 54 |
| kgp2391411 | 3 | 43425645 | | G | A | 3.87E-05 | 0.46 | 0.212 | 0.380 | 8 | 20 | 49 | 52 | 96 | 49 |
| rs10816302 | 9 | 108486533 | TMEM38B | G | A | 4.07E-05 | 3.39 | 0.181 | 0.062 | 5 | 0 | 46 | 15 | 104 | 106 |
| rs7020402 | 9 | 108530638 | TMEM38B | A | G | 4.07E-05 | 3.39 | 0.181 | 0.062 | 5 | 0 | 46 | 15 | 104 | 106 |
| rs1979993 | 9 | 108534505 | TMEM38B | A | A | 4.07E-05 | 3.39 | 0.181 | 0.062 | 5 | 0 | 46 | 15 | 104 | 106 |
| rs1979992 | 9 | 108535330 | TMEM38B | A | A | 4.07E-05 | 3.39 | 0.181 | 0.062 | 5 | 0 | 46 | 15 | 104 | 106 |
| rs6032209 | 20 | 44087073 | | A | G | 4.09E-05 | 0.42 | 0.175 | 0.325 | 4 | 11 | 46 | 56 | 104 | 53 |
| kgp7521990 | 1 | 105666878 | | C | A | 4.38E-05 | 0.32 | 0.068 | 0.182 | 1 | 3 | 19 | 38 | 134 | 80 |
| kgp2451249 | 1 | 223872873 | | A | G | 4.39E-05 | 3.66 | 0.165 | 0.054 | 3 | 0 | 45 | 13 | 107 | 108 |
| kgp8796185 | 1 | 223716508 | CAPN8 | G | A | 4.39E-05 | 3.66 | 0.165 | 0.054 | 3 | 0 | 45 | 13 | 107 | 108 |
| rs2241883 | 2 | 88424066 | FABP1 | A | G | 4.46E-05 | 0.46 | 0.274 | 0.438 | 9 | 22 | 67 | 62 | 79 | 37 |
| rs343087 | 12 | 66260924 | HMGA2 | G | A | 4.49E-05 | 2.97 | 0.205 | 0.070 | 12 | 0 | 39 | 17 | 103 | 104 |
| rs4894701 | 3 | 174931730 | NAALADL2 | A | C | 4.62E-05 | 2.12 | 0.556 | 0.384 | 44 | 16 | 81 | 61 | 27 | 44 |
| kgp18525257 | 9 | 108499628 | TMEM38B | G | A | 4.63E-05 | 3.41 | 0.177 | 0.062 | 4 | 0 | 47 | 15 | 104 | 106 |
| kgp18379774 | 9 | 108504407 | TMEM38B | G | A | 4.63E-05 | 3.41 | 0.177 | 0.062 | 4 | 0 | 47 | 15 | 104 | 106 |
| rs105123340 | 9 | 108511163 | TMEM38B | G | A | 4.63E-05 | 3.41 | 0.177 | 0.062 | 4 | 0 | 47 | 15 | 104 | 106 |
| rs10125298 | 9 | 108555594 | | C | A | 4.63E-05 | 3.41 | 0.177 | 0.062 | 4 | 0 | 47 | 15 | 104 | 106 |
| kgp759150 | 4 | 40385906 | | G | A | 4.79E-05 | 2.19 | 0.552 | 0.388 | 42 | 13 | 86 | 68 | 26 | 40 |
| rs10124492 | 9 | 108527455 | TMEM38B | T | A | 4.79E-05 | 3.36 | 0.180 | 0.062 | 5 | 0 | 45 | 15 | 103 | 106 |
| kgp3812034 | 2 | 43427044 | | A | G | 4.88E-05 | 0.47 | 0.217 | 0.383 | 8 | 20 | 50 | 52 | 94 | 48 |
| rs5024722 | 7 | 141858688 | | A | G | 4.90E-05 | 0.41 | 0.159 | 0.302 | 3 | 9 | 43 | 55 | 108 | 57 |

TABLE 39-continued

Extreme Response SNPs

| Prioritized Variants Name | EXTREME PHENOTYPE | | | | | | | | | | Combined | | | | | |
|---|---|---|---|---|---|---|---|---|---|---|---|---|---|---|---|---|
| | Chromosome | Position | Gene(s) | Major Allele (d) | Minor Allele (D) | P-value (Armitage Test) | Odds Ratio (Minor Allele) | Minor Allele Freq. (Responders) | Allele Freq. (Non-Responders) | DD (Responders) | DD (Non-responders) | Dd (Responders) | Dd (Non-responders) | dd (Responders) | dd (Non-responders) |
| rs11691553 | 2 | 60303554 | | C | A | 4.92E-05 | 0.47 | 0.301 | 0.471 | 11 | 28 | 70 | 57 | 72 | 35 |
| kgp11453406 | 10 | 121435955 | BAG3 | C | A | 4.96E-05 | 0.46 | 0.208 | 0.368 | 5 | 19 | 54 | 51 | 95 | 51 |
| rs196341 | 10 | 121416611 | BAG3 | G | A | 5.02E-05 | 0.46 | 0.206 | 0.367 | 5 | 19 | 53 | 50 | 95 | 51 |
| rs10203396 | 2 | 60305110 | | A | G | 5.26E-05 | 0.48 | 0.303 | 0.471 | 11 | 28 | 72 | 58 | 72 | 35 |
| rs7579987 | 2 | 60307009 | | G | C | 5.26E-05 | 0.48 | 0.303 | 0.471 | 11 | 25 | 72 | 58 | 72 | 35 |
| rs7862565 | 9 | 108392419 | | G | A | 5.29E-05 | 3.46 | 0.171 | 0.058 | 4 | 0 | 45 | 14 | 106 | 107 |
| kgp11514107 | 2 | 65247253 | SLC1A4 | G | A | 5.29E-05 | 3.46 | 0.171 | 0.058 | 3 | 1 | 47 | 12 | 105 | 108 |
| rs4822644 | 22 | 26134163 | | G | A | 5.29E-05 | 0.34 | 0.081 | 0.194 | 0 | 3 | 25 | 41 | 130 | 77 |
| rs2136408 | 9 | 108497654 | TMEM38B | A | C | 5.39E-05 | 3.33 | 0.181 | 0.063 | 5 | 0 | 46 | 15 | 104 | 104 |
| rs1545223 | 2 | 88423510 | FABP1 | A | G | 5.51E-05 | 0.46 | 0.276 | 0.438 | 9 | 22 | 67 | 62 | 78 | 37 |
| rs17329014 | 2 | 60299921 | | G | A | 5.65E-05 | 0.46 | 0.206 | 0.364 | 5 | 18 | 54 | 52 | 96 | 51 |
| rs2058742 | 17 | 70040547 | | C | A | 5.65E-05 | 2.30 | 0.348 | 0.194 | 17 | 4 | 74 | 39 | 64 | 78 |
| kgp4420791 | 12 | 89819166 | POC1B | G | A | 5.74E-05 | 0.11 | 0.010 | 0.074 | 0 | 0 | 3 | 18 | 152 | 103 |
| kgp7714238 | 6 | 145587514 | | G | A | 5.74E-05 | 0.11 | 0.010 | 0.074 | 0 | 0 | 3 | 15 | 152 | 103 |
| rs13394010 | 2 | 60302746 | | A | G | 5.76E-05 | 0.48 | 0.303 | 0.471 | 11 | 28 | 72 | 57 | 72 | 35 |
| kgp7924485 | 2 | 60292120 | | A | G | 5.80E-05 | 0.40 | 0.120 | 0.256 | 2 | 9 | 33 | 44 | 119 | 68 |
| kgp8174785 | 1 | 110053148 | | G | C | 5.85E-05 | 0.45 | 0.245 | 0.401 | 5 | 19 | 66 | 59 | 84 | 43 |
| kgp10090631 | 7 | 11754881 | THSD7A | A | G | 5.85E-05 | 2.11 | 0.500 | 0.331 | 38 | 10 | 79 | 58 | 38 | 50 |
| rs1683448 | 9 | 108449079 | | A | G | 5.95E-05 | 3.90 | 0.149 | 0.046 | 2 | 0 | 42 | 11 | 110 | 109 |
| kgp8777935 | 6 | 139004920 | | A | G | 5.98E-05 | 2.05 | 0.455 | 0.281 | 33 | 12 | 75 | 44 | 47 | 65 |
| rs16930057 | 8 | 63906122 | | G | A | 5.99E-05 | 0.40 | 0.123 | 0.256 | 1 | 8 | 36 | 46 | 117 | 67 |
| kgp7181058 | 14 | 98385698 | | G | A | 6.10E-05 | Zero | 0.000 | 0.050 | 0 | 0 | 0 | 12 | 155 | 109 |
| kgp117111524 | 9 | 108346438 | | A | G | 6.20E-05 | 3.34 | 0.175 | 0.062 | 4 | 0 | 46 | 15 | 104 | 106 |
| kgp6505544 | 7 | 71953948 | | G | A | 6.23E-05 | 3.00 | 0.203 | 0.083 | 5 | 0 | 53 | 20 | 97 | 101 |
| rs623011 | 17 | 68259446 | | G | A | 6.26E-05 | 2.47 | 0.294 | 0.153 | 9 | 3 | 73 | 31 | 73 | 87 |
| kgp355027 | 11 | 115964147 | | A | G | 6.28E-05 | 0.37 | 0.101 | 0.223 | 1 | 4 | 29 | 46 | 123 | 71 |
| kgp767200 | 5 | 3221345 | | A | G | 6.46E-05 | 2.95 | 0.217 | 0.097 | 2 | 1 | 62 | 21 | 88 | 97 |
| kgp5908616 | 2 | 60329823 | | A | C | 6.48E-05 | 0.49 | 0.289 | 0.459 | 11 | 29 | 67 | 53 | 76 | 39 |
| kgp3205849 | 10 | 121531725 | INPP5F | A | G | 6.51E-05 | 0.44 | 0.167 | 0.318 | 4 | 14 | 43 | 47 | 106 | 57 |
| rs9320791 | 6 | 60309952 | | C | G | 6.54E-05 | 0.48 | 0.305 | 0.471 | 11 | 28 | 72 | 58 | 71 | 35 |
| kgp3267884 | 9 | 14639380 | ZDHHC21 | G | A | 6.61E-05 | 0.46 | 0.206 | 0.360 | 3 | 18 | 58 | 51 | 94 | 52 |
| rs13002663 | 2 | 145220163 | ZEB2, ZEB2 | G | A | 6.62E-05 | 0.49 | 0.306 | 0.475 | 12 | 30 | 71 | 55 | 72 | 36 |
| kgp8767692 | 15 | 66333821 | MEGF11 | G | A | 6.68E-05 | 0.16 | 0.016 | 0.087 | 0 | 0 | 5 | 21 | 150 | 100 |
| kgp28532436 | 15 | 62968836 | TLN2 | G | A | 6.70E-05 | 19.85 | 0.071 | 0.004 | 4 | 0 | 22 | 1 | 133 | 120 |
| rs9346979 | 6 | 164309479 | | G | A | 6.81E-05 | 0.49 | 0.303 | 0.471 | 15 | 26 | 64 | 62 | 76 | 33 |
| rs714342 | 11 | 110807983 | | A | C | 6.91E-05 | 2.21 | 0.465 | 0.310 | 25 | 9 | 94 | 57 | 36 | 55 |
| kgp8869954 | 2 | 135163015 | MGAT5 | G | A | 7.03E-05 | 0.27 | 0.042 | 0.136 | 0 | 2 | 13 | 29 | 142 | 90 |
| kgp2709692 | 18 | 3000808 | LPIN2 | C | A | 7.22E-05 | 0.09 | 0.006 | 0.066 | 0 | 0 | 2 | 16 | 152 | 105 |
| rs10510774 | 3 | 54919351 | CACNA2D3 | A | G | 7.26E-05 | 0.30 | 0.062 | 0.163 | 0 | 1 | 19 | 37 | 135 | 82 |
| kgp8169636 | 18 | 29206763 | B4GALT6 | G | A | 7.44E-05 | 0.25 | 0.032 | 0.124 | 0 | 3 | 10 | 24 | 145 | 94 |
| rs3593828 | 5 | 173993252 | | C | A | 7.46E-05 | 2.36 | 0.306 | 0.161 | 12 | 4 | 71 | 31 | 72 | 86 |
| kgp11010680 | 15 | 25717889 | | A | G | 7.47E-05 | 2.73 | 0.244 | 0.120 | 4 | 0 | 67 | 29 | 83 | 92 |
| rs1387768 | 5 | 173993166 | | A | G | 7.54E-05 | 2.37 | 0.308 | 0.163 | 12 | 4 | 71 | 31 | 71 | 85 |
| kgp11627530 | 14 | 78954642 | NRXN3 | A | G | 7.55E-05 | 0.28 | 0.039 | 0.136 | 0 | 4 | 12 | 25 | 143 | 92 |

TABLE 39-continued

Extreme Response SNPs

| Prioritized Variants | Name | Chromosome | Position | Gene(s) | Major Allele (d) | Minor Allele (D) | P-value (Armitage Test) | Odds Ratio (Minor Allele) | Minor Allele Freq. (Responders) | Allele Freq. (Non-Responders) | DD (Responders) | DD (Non-responders) | Dd (Responders) | Dd (Non-responders) | dd (Responders) | dd (Non-responders) |
|---|---|---|---|---|---|---|---|---|---|---|---|---|---|---|---|---|
| EXTREME PHENOTYPE | | | | | | | | | | | Combined | | | | | |
| | kgp10404633 | 9 | 138136993 | | G | A | 7.60E-05 | 8.30 | 0.087 | 0.012 | 0 | 0 | 27 | 3 | 126 | 118 |
| | kgp8372910 | 9 | 138138723 | | G | A | 7.60E-05 | 8.30 | 0.087 | 0.012 | 0 | 0 | 27 | 3 | 128 | 118 |
| | kgp11206453 | 3 | 54928104 | CACNA2D3 | G | A | 7.63E-05 | 0.31 | 0.061 | 0.161 | 0 | 1 | 19 | 37 | 136 | 83 |
| | rs11136970 | 8 | 604262 | | A | C | 7.68E-05 | 2.13 | 0.390 | 0.227 | 23 | 8 | 74 | 39 | 57 | 74 |
| | kgp9795732 | 15 | 88117171 | | C | A | 7.71E-05 | 0.37 | 0.082 | 0.206 | 2 | 7 | 21 | 35 | 130 | 77 |
| | rs2934491 | 16 | 84905542 | CRISPLD2 | G | A | 7.81E-05 | 0.48 | 0.284 | 0.446 | 12 | 23 | 64 | 62 | 79 | 36 |
| | kgp9368119 | 7 | 11707419 | THSD7A | A | G | 7.87E-05 | 0.48 | 0.332 | 0.496 | 15 | 28 | 73 | 64 | 67 | 29 |
| | rs4709792 | 6 | 164316375 | | G | A | 7.93E-05 | 0.49 | 0.300 | 0.467 | 15 | 26 | 63 | 61 | 77 | 34 |
| | rs17400875 | 2 | 60295736 | | A | C | 7.94E-05 | 0.47 | 0.210 | 0.364 | 5 | 18 | 55 | 52 | 95 | 51 |
| | kgp10152733 | 9 | 108462735 | TMEM38B | G | A | 7.97E-05 | 3.17 | 0.181 | 0.066 | 5 | 0 | 46 | 16 | 104 | 105 |
| | kgp12426624 | 3 | 54926209 | CACNA2D3 | C | A | 7.99E-05 | 0.31 | 0.065 | 0.165 | 0 | 1 | 20 | 38 | 135 | 82 |
| | kgp55646 | 10 | 121282886 | RGS10 | G | A | 8.00E-05 | 0.47 | 0.247 | 0.405 | 11 | 17 | 54 | 64 | 89 | 40 |
| | kgp10922969 | 6 | 80260277 | | G | A | 8.07E-05 | 0.29 | 0.049 | 0.146 | 0 | 2 | 15 | 31 | 139 | 87 |
| | kgp7331172 | 18 | 66533114 | CCDC102B | A | G | 8.21E-05 | 2.78 | 0.223 | 0.099 | 6 | 0 | 57 | 24 | 92 | 97 |
| | kgp6666134 | 10 | 129386358 | | T | A | 8.36E-05 | 2.32 | 0.309 | 0.161 | 15 | 3 | 64 | 33 | 73 | 85 |
| | kgp6603796 | 16 | 84910897 | CRISPLD2 | G | A | 8.42E-05 | 0.48 | 0.260 | 0.421 | 10 | 21 | 58 | 60 | 82 | 40 |
| | kgp9018750 | 6 | 164312470 | | A | G | 8.44E-05 | 0.49 | 0.305 | 0.471 | 15 | 26 | 64 | 62 | 75 | 33 |
| | rs858341 | 6 | 132160455 | ENPP1 | A | G | 8.44E-05 | 2.06 | 0.464 | 0.298 | 33 | 10 | 76 | 52 | 44 | 59 |
| | kgp4096263 | 15 | 70333438 | | A | G | 8.58E-05 | 0.58 | 0.169 | 0.058 | 4 | 0 | 43 | 14 | 104 | 106 |
| | kgp5159037 | 2 | 65255764 | | A | G | 8.60E-05 | 2.85 | 0.208 | 0.083 | 7 | 1 | 50 | 38 | 97 | 101 |
| | rs423239 | 10 | 92856946 | HMGA2 | G | A | 8.62E-05 | 2.77 | 0.216 | 0.091 | 7 | 0 | 53 | 20 | 95 | 100 |
| | rs343092 | 12 | 66250940 | HMGA2 | C | A | 8.67E-05 | 2.87 | 0.197 | 0.070 | 11 | 0 | 39 | 17 | 105 | 104 |
| | kgp7178233 | 5 | 117621827 | | C | A | 8.81E-05 | 2.53 | 0.261 | 0.128 | 10 | 0 | 61 | 31 | 84 | 90 |
| | kgp3218351 | 11 | 110802128 | | G | A | 9.03E-05 | 2.19 | 0.445 | 0.293 | 24 | 7 | 90 | 57 | 41 | 57 |
| | kgp10564659 | 1 | 223733531 | | G | G | 9.08E-05 | 3.48 | 0.159 | 0.054 | 3 | 0 | 43 | 13 | 108 | 108 |
| | P1_M_061510_11_106_M | 11 | 27308202 | | D | 1 | 9.08E-05 | 0.48 | 0.290 | 0.450 | 13 | 22 | 64 | 65 | 78 | 34 |
| | kgp6023196 | 17 | 68271273 | | A | C | 9.22E-05 | 2.25 | 0.339 | 0.190 | 15 | 5 | 75 | 36 | 65 | 80 |
| | kgp4056892 | 20 | 44087774 | | C | G | 9.23E-05 | 0.43 | 0.165 | 0.302 | 3 | 9 | 45 | 55 | 107 | 57 |
| | rs484482 | 15 | 55418825 | | A | G | 9.31E-05 | 4.13 | 0.133 | 0.037 | 2 | 0 | 37 | 9 | 115 | 112 |
| | kgp6299395 | 15 | 66299395 | MEGF11 | G | A | 9.33E-05 | 0.18 | 0.019 | 0.091 | 0 | 0 | 6 | 22 | 149 | 99 |
| | kgp6076976 | 1 | 105663380 | | A | T | 9.53E-05 | 0.30 | 0.058 | 0.155 | 0 | 12 | 18 | 35 | 137 | 83 |
| | rs9597498 | 13 | 57657550 | | G | A | 9.71E-05 | 1.97 | 0.458 | 0.285 | 37 | 11 | 68 | 45 | 50 | 64 |
| | rs419132 | 13 | 32210799 | | A | G | 9.75E-05 | 2.02 | 0.442 | 0.271 | 32 | 11 | 72 | 42 | 50 | 65 |
| | kgp29794723 | 10 | 18397332 | | A | G | 9.75E-05 | 0.14 | 0.013 | 0.079 | 0 | 2 | 4 | 19 | 150 | 102 |
| | kgp6091119 | 17 | 44879640 | WNT3 | A | G | 9.98E-05 | 0.21 | 0.023 | 0.103 | 0 | 0 | 7 | 21 | 148 | 98 |
| | kgp10351364 | 8 | 103604706 | | G | A | 1.00E-04 | 2.09 | 0.538 | 0.373 | 40 | 13 | 77 | 62 | 29 | 43 |
| | rs9376361 | 6 | 139006406 | | A | G | 1.00E-04 | 1.99 | 0.468 | 0.298 | 34 | 14 | 76 | 44 | 44 | 63 |
| | kgp3991733 | 1 | 105671167 | | T | A | 1.01E-04 | 0.34 | 0.071 | 0.179 | 1 | 3 | 20 | 37 | 134 | 80 |
| | rs6687976 | 1 | 105674536 | | C | A | 1.01E-04 | 0.34 | 0.071 | 0.179 | 1 | 3 | 20 | 37 | 134 | 80 |
| 2 - Priority Genes (extreme) | rs6110157 | 20 | 14055947 | MACROD2 | A | G | 1.82E-04 | 0.47 | 0.193 | 0.335 | 6 | 13 | 47 | 55 | 100 | 53 |
| 2 - Priority Genes (extreme) | kgp4011779 | 10 | 100454360 | HPSE2 | G | A | 2.53E-04 | 0.13 | 0.010 | 0.066 | 0 | 0 | 3 | 16 | 151 | 105 |

TABLE 39-continued

Extreme Response SNPs

| EXTREME PHENOTYPE | | | | | | | | | | | Combined | | | | |
|---|---|---|---|---|---|---|---|---|---|---|---|---|---|---|---|
| Prioritized Variants | Name | Chromosome | Position | Gene(s) | Major Allele (d) | Minor Allele (D) | P-value (Armitage Test) | Odds Ratio (Minor Allele) | Minor Allele Freq. (Responders) | Allele Freq. (Non-Responders) | DD (Responders) | DD (Non-responders) | Dd (Responders) | Dd (Non-responders) | dd (Responders) | dd (Non-responders) |
| 0 - Priority - Model | rs16886004 | 7 | 78021500 | MAGI2 | A | G | 6.08E-04 | 2.48 | 0.197 | 0.092 | 4 | 2 | 53 | 18 | 98 | 100 |
| 2 - Priority Genes | kgp3496814 | 13 | 31336379 | ALOX5AP | C | A | 6.09E-04 | 0.55 | 0.416 | 0.566 | 28 | 39 | 73 | 59 | 54 | 23 |
| 0 - Priority - Model, Priority Gene | rs0162089 | 13 | 31316738 | ALOX5AP | G | A | 9.40E-04 | 1.78 | 0.503 | 0.357 | 43 | 14 | 69 | 57 | 42 | 48 |
| 2 - Priority Genes (extreme) | rs3885907 | 13 | 31314455 | ALOX5AP | A | C | 9.70E-04 | 1.77 | 0.484 | 0.339 | 41 | 13 | 68 | 56 | 46 | 52 |
| 0 - Priority - Model | rs1894408 | 6 | 32786833 | | C | G | 1.15E-03 | 1.86 | 0.408 | 0.277 | 22 | 10 | 81 | 47 | 50 | 64 |
| 2 - Priority Genes | kgp8817856 | 6 | 32744440 | | G | A | 1.17E-03 | 0.54 | 0.369 | 0.500 | 17 | 26 | 79 | 69 | 57 | 26 |
| 2 - Priority Genes (extreme) | rs17238927 | 13 | 31332391 | ALOX5AP | G | A | 1.25E-03 | 0.07 | 0.003 | 0.042 | 0 | 0 | 1 | 10 | 154 | 110 |
| 2 - Priority Genes (extreme) | rs967124 | 13 | 31324253 | ALOX5AP | G | A | 1.26E-03 | 1.74 | 0.523 | 0.380 | 46 | 17 | 70 | 58 | 39 | 46 |
| 2 - Priority Genes (extreme) | rs4769060 | 13 | 31337877 | ALOX5AP | A | G | 1.27E-03 | 1.77 | 0.481 | 0.343 | 38 | 12 | 73 | 59 | 44 | 50 |
| 0 - Priority - Model | kgp24415534 | 2 | 174156875 | | G | A | 1.32E-03 | 0.07 | 0.003 | 0.041 | 0 | 0 | 1 | 10 | 154 | 111 |
| 2 - Priority Genes | rs4075692 | 13 | 31323342 | ALOX5AP | G | A | 1.55E-03 | 1.72 | 0.519 | 0.380 | 45 | 17 | 71 | 58 | 39 | 46 |
| 2 - Priority Genes (extreme) | rs11147439 | 13 | 31325643 | ALOX5AP | C | A | 1.86E-03 | 0.59 | 0.397 | 0.533 | 28 | 33 | 67 | 63 | 60 | 25 |
| 2 - Priority Genes (extreme) | kgp3276689 | 10 | 100396003 | HPSE2 | C | A | 1.97E-03 | 2.16 | 0.205 | 0.104 | 9 | 0 | 45 | 25 | 100 | 95 |
| 2 - Priority Genes (extreme) | kgp304921 | 20 | 14017077 | MACROD2 | A | G | 2.05E-03 | 0.32 | 0.030 | 0.097 | 1 | 2 | 7 | 19 | 144 | 98 |
| 2 - Priority Genes (extreme) | rs3803277 | 13 | 31318308 | ALOX5AP | C | A | 2.06E-03 | 0.59 | 0.406 | 0.541 | 28 | 35 | 70 | 61 | 57 | 25 |
| 2 - Priority Genes (extreme) | kgp5440506 | 13 | 31320543 | ALOX5AP | G | A | 2.49E-03 | 0.60 | 0.399 | 0.533 | 29 | 33 | 65 | 62 | 60 | 25 |
| 2 - Priority Genes (extreme) | rs9671182 | 13 | 31321138 | ALOX5AP | C | G | 2.75E-03 | 0.60 | 0.406 | 0.538 | 29 | 33 | 68 | 63 | 58 | 24 |
| 0 - Priority - Model | kgp8110667 | 22 | 32716792 | | G | A | 2.78E-03 | Infinity | 0.035 | 0.000 | 0 | 0 | 11 | 0 | 144 | 121 |
| 2 - Priority Genes | rs4254166 | 13 | 31322949 | ALOX5AP | A | G | 2.87E-03 | 0.60 | 0.403 | 0.533 | 28 | 33 | 69 | 63 | 58 | 25 |
| 2 - Priority Genes (extreme) | rs4356336 | 13 | 31319546 | ALOX5AP | A | G | 2.90E-03 | 0.60 | 0.406 | 0.537 | 29 | 34 | 68 | 62 | 58 | 25 |
| 2 - Priority Genes (extreme) | rs11002051 | 10 | 78921392 | KCNMA1 | G | A | 3.11E-03 | 0.39 | 0.055 | 0.124 | 0 | 1 | 17 | 28 | 138 | 92 |
| 2 - Priority Genes (extreme) | rs102785 91 | 7 | 1921362 | MAD1L1 | G | A | 3.15E-03 | 1.88 | 0.281 | 0.174 | 13 | 2 | 61 | 38 | 81 | 81 |
| 2 - Priority Genes (extreme) | rs4360791 | 13 | 31318020 | ALOX5AP | G | A | 3.39E-03 | 0.61 | 0.416 | 0.545 | 30 | 36 | 69 | 60 | 56 | 25 |
| 2 - Priority Genes (extreme) | kgp2715873 | 13 | 31320249 | ALOX5AP | G | A | 3.78E-03 | 0.61 | 0.406 | 0.533 | 29 | 33 | 68 | 63 | 58 | 25 |

TABLE 39-continued

Extreme Response SNPs

| | | EXTREME PHENOTYPE | | | | | | | | | | Combined | | | | | |
|---|---|---|---|---|---|---|---|---|---|---|---|---|---|---|---|---|---|
| Prioritized Variants | Name | Chromosome | Position | Gene(s) | Major Allele (d) | Minor Allele (D) | P-value (Armitage Test) | Odds Ratio (Minor Allele) | Minor Allele Freq. (Responders) | Allele Freq. (Non-Responders) | DD (Responders) | DD (Non-responders) | Dd (Responders) | Dd (Non-responders) | dd (Responders) | dd (Non-responders) |
| 2 - Priority Genes (extreme) | rs9670531 | 13 | 31321069 | ALOX5AP | A | G | 3.78E-03 | 0.61 | 0.406 | 0.533 | 29 | 33 | 68 | 63 | 58 | 25 |
| 2 - Priority Genes (extreme) | rs9315047 | 13 | 31321289 | ALOX5AP | A | T | 3.78E-03 | 0.61 | 0.406 | 0.533 | 29 | 33 | 68 | 63 | 58 | 25 |
| 2 - Priority Genes (extreme) | rs4584668 | 13 | 31319553 | ALOX5AP | A | T | 3.85E-03 | 0.61 | 0.406 | 0.533 | 29 | 33 | 68 | 62 | 58 | 25 |
| 2 - Priority Genes (extreme) | rs9508832 | 13 | 31314264 | ALOX5AP | G | A | 4.31E-03 | 1.65 | 0.445 | 0.322 | 35 | 11 | 68 | 56 | 52 | 54 |
| 1 - Priority Variant (extreme) | rs2487896 | 10 | 100802380 | HPSE2 | G | A | 4.38E-03 | 0.51 | 0.113 | 0.204 | 3 | 6 | 29 | 37 | 123 | 77 |
| 2 - Priority Genes (extreme) | kgp7117398 | 7 | 1915282 | MAD1L1 | C | A | 4.55E-43 | 1.83 | 0.281 | 0.178 | 13 | 2 | 61 | 39 | 81 | 80 |
| 1 - Priority Variant (extreme) | rs10988087 | 9 | 131443671 | | A | G | 5.08E-03 | 0.33 | 0.029 | 0.083 | 0 | 1 | 9 | 18 | 146 | 101 |
| 0 - Priority - Model | kgp6599438 | 20 | 40843626 | PTPRT | G | A | 5.13E-03 | 0.22 | 0.013 | 0.054 | 0 | 0 | 4 | 13 | 151 | 108 |
| 0 - Priority - Model, Priority Variant | rs3135391 | 6 | 32410987 | HLA-DRA | G | A | 6.38E-03 | 0.57 | 0.190 | 0.289 | 6 | 9 | 47 | 52 | 102 | 60 |
| 1 - Priority Variant (extreme) | rs1573706 | 20 | 40921149 | PTPRT | G | A | 7.11E-03 | 0.55 | 0.139 | 0.227 | 2 | 7 | 39 | 41 | 114 | 73 |
| 2 - Priority Genes (extreme) | kgp4370912 | 10 | 78918297 | KCNMA1 | C | A | 7.39E-03 | 0.42 | 0.055 | 0.117 | 0 | 1 | 17 | 26 | 138 | 93 |
| 1 - Priority Variant (extreme) | rs3135388 | 6 | 32413051 | | G | A | 7.54E-03 | 0.58 | 0.190 | 0.288 | 6 | 9 | 47 | 51 | 102 | 60 |
| 0 - Priority - Model | kgp7747883 | 18 | 74804250 | MBP | G | A | 9.26E-03 | 0.63 | 0.321 | 0.430 | 16 | 22 | 67 | 60 | 71 | 39 |
| 1 - Priority Variant (extreme) | rs6097801 | 20 | 52767434 | | G | A | 4.35E-02 | 0.63 | 0.110 | 0.174 | 7 | 3 | 20 | 36 | 128 | 82 |

(Note:
Odds Ratio >1 = Minor Allele is associated with Response,
Odds Ratio <1 = Minor Allele Associated with Non-Response)

TABLE 40

Placebo SNPs
PLACEBO COHORT

| Name | Chromosome | Position | Gene(s) | Major Allele (d) | Minor Allele (D) | P-value (Armitage Test) | Odds Ratio (Minor Allele) | Minor Allele Freq. (Responders) | Minor Allele Freq. (Non-Responders) | DD (Responders) | DD (Non-Responders) | Dd (Responders) | Dd (Non-Responders) | dd (Responders) | dd (Non-Responders) |
|---|---|---|---|---|---|---|---|---|---|---|---|---|---|---|---|
| kgp433351 | 8 | 41496314 | | A | G | 2.69E-06 | 0.339857466 | 0.231578947 | 0.46039604 | 6 | 19 | 32 | 55 | 57 | 27 |
| kgp2877482 | 6 | 1644677 | GMDS | G | A | 2.73E-06 | 9.628676471 | 0.142105263 | 0.01980198 | 0 | 0 | 27 | 4 | 68 | 97 |
| kgp2920925 | 17 | 39694480 | | G | A | 9.45E-06 | 0.270722068 | 0.1 | 0.272277228 | 0 | 6 | 19 | 43 | 76 | 52 |
| rs209568 | 8 | 17612639 | MTUS1 | A | G | 1.13E-05 | 3.636556912 | 0.273684211 | 0.108910891 | 4 | 0 | 44 | 22 | 47 | 79 |
| kgp7653470 | 17 | 39694186 | | A | G | 1.14E-05 | 0.269888943 | 0.1 | 0.267326733 | 0 | 5 | 19 | 44 | 76 | 52 |
| rs7119480 | 11 | 84247636 | DLG2 | G | A | 1.31E-05 | 0.313880826 | 0.142105263 | 0.326732673 | 0 | 9 | 25 | 48 | 69 | 44 |
| kgp10148554 | 4 | 89767803 | FAM13A | A | G | 1.54E-05 | 6.801291939 | 0.154255319 | 0.024752475 | 3 | 0 | 23 | 5 | 68 | 96 |
| kgp11285883 | 9 | 2953403 | | C | A | 1.57E-05 | 2.463968851 | 0.457894737 | 0.232673267 | 26 | 5 | 35 | 37 | 34 | 59 |
| kgp6042557 | 3 | 194440716 | LOC100507391 | A | G | 1.64E-05 | 0.074707387 | 0.010526316 | 0.12 | 0 | 1 | 2 | 22 | 93 | 77 |
| kgp10989246 | 4 | 89761443 | FAM13A | A | G | 1.74E-05 | 6.733466513 | 0.154255319 | 0.025 | 3 | 0 | 23 | 5 | 68 | 95 |
| kgp11604017 | 11 | 118074117 | AMICA1 | G | A | 1.74E-05 | 2.890031976 | 0.376344086 | 0.183168327 | 11 | 3 | 48 | 31 | 34 | 67 |
| rs3858038 | 9 | 2988280 | | C | A | 1.75E-05 | 2.390793359 | 0.526315789 | 0.297029703 | 33 | 7 | 34 | 46 | 28 | 48 |
| rs7698655 | 4 | 89756076 | FAM13A | G | A | 1.79E-05 | 6.706712195 | 0.152631579 | 0.024752475 | 3 | 0 | 23 | 5 | 69 | 96 |
| kgp9409440 | 4 | 89759159 | FAM13A | G | A | 1.79E-05 | 6.706712195 | 0.152631579 | 0.024752475 | 3 | 0 | 23 | 5 | 69 | 96 |
| kgp6889327 | 4 | 89766553 | FAM13A | A | G | 1.79E-05 | 6.706712195 | 0.152631579 | 0.024752475 | 3 | 0 | 23 | 5 | 69 | 96 |
| rs7696391 | 4 | 89789287 | FAM13A | A | C | 1.79E-05 | 6.706712195 | 0.152631579 | 0.024752475 | 3 | 0 | 23 | 5 | 69 | 96 |
| rs11947777 | 4 | 89768744 | FAM13A | A | G | 2.02E-05 | 6.639861024 | 0.152631579 | 0.025 | 3 | 0 | 23 | 5 | 69 | 95 |
| kgp6301155 | 4 | 89766647 | FAM13A | G | C | 2.29E-05 | 6.573008284 | 0.152631579 | 0.025252525 | 3 | 0 | 23 | 5 | 69 | 94 |
| kgp12472695 | 2 | 65804266 | | G | A | 2.31E-05 | 0.381410892 | 0.310526316 | 0.514851485 | 10 | 21 | 39 | 62 | 46 | 18 |
| rs4978567 | 9 | 116880005 | | G | A | 2.50E-05 | 0.400621674 | 0.321052632 | 0.535353535 | 10 | 27 | 41 | 52 | 44 | 20 |
| rs17419416 | 6 | 15862865 | | A | G | 2.51E-05 | 0.2975848 | 0.105263158 | 0.272277228 | 0 | 7 | 20 | 41 | 75 | 53 |
| kgp77783456 | 9 | 2965090 | | A | G | 2.56E-05 | 2.42370702 | 0.489361702 | 0.27 | 27 | 6 | 38 | 42 | 29 | 52 |
| rs2618065 | 11 | 75991931 | | G | A | 2.73E-05 | 0.343008454 | 0.194736842 | 0.376237624 | 2 | 10 | 33 | 56 | 60 | 35 |
| kgp3188 | 2 | 65804244 | | A | G | 2.99E-05 | 0.38880492 | 0.356382979 | 0.559405941 | 13 | 25 | 41 | 63 | 40 | 13 |
| rs9948620 | 18 | 13358206 | C18orf1 | G | A | 3.14E-05 | 2.776643091 | 0.404255319 | 0.217821782 | 12 | 3 | 52 | 38 | 30 | 60 |
| kgp5747456 | 2 | 23932556 | | G | A | 3.24E-05 | 2.04E+16 | 0.078947368 | 0 | 0 | 0 | 15 | 0 | 80 | 101 |
| kgp6429231 | 15 | 62931802 | MGC15885 | G | A | 3.24E-05 | 2.04E+16 | 0.078947368 | 0 | 0 | 0 | 15 | 0 | 80 | 101 |
| kgp10215554 | 16 | 8753573 | | A | G | 3.30E-05 | 4.029736689 | 0.205263158 | 0.064356436 | 3 | 0 | 33 | 13 | 59 | 88 |
| rs7123506 | 11 | 84218362 | DLG2 | G | A | 3.35E-05 | 0.312509142 | 0.121052632 | 0.287128713 | 0 | 7 | 23 | 44 | 72 | 50 |
| rs1715441 | 11 | 118072181 | AMICA1 | G | A | 3.37E-05 | 2.763225218 | 0.368421053 | 0.183168317 | 11 | 3 | 48 | 31 | 36 | 67 |
| rs17931174 | 11 | 118074337 | AMICA1 | G | A | 3.37E-05 | 2.763225218 | 0.368421053 | 0.183168317 | 11 | 3 | 48 | 31 | 36 | 67 |
| rs11562998 | 2 | 51814215 | | A | G | 3.41E-05 | 6.516129255 | 0.142105263 | 0.024752475 | 2 | 0 | 23 | 5 | 70 | 96 |
| rs11563025 | 2 | 51864372 | | A | G | 3.41E-05 | 6.516129255 | 0.142105263 | 0.024752475 | 2 | 0 | 23 | 5 | 70 | 96 |
| kgp9909702 | 8 | 112741367 | | A | C | 3.46E-05 | 0.411700671 | 0.378947368 | 0.589108911 | 14 | 33 | 44 | 53 | 37 | 15 |
| kgp541892 | 5 | 73992881 | HEXB | A | G | 3.56E-05 | 0.287914141 | 0.089473684 | 0.247524752 | 3 | 3 | 11 | 44 | 81 | 54 |
| rs961090 | 15 | 40617414 | | A | G | 3.56E-05 | 2.930247466 | 0.305263158 | 0.128712871 | 9 | 2 | 40 | 22 | 46 | 77 |

TABLE 40-continued

Placebo SNPs
PLACEBO COHORT

| Name | Chromosome | Position | Gene(s) | Major Allele (d) | Minor Allele (D) | P-value (Armitage Test) | Odds Ratio (Minor Allele) | Minor Allele Freq. (Responders) | Minor Allele Freq. (Non-Responders) | DD (Responders) | DD (Non-Responders) | Dd (Responders) | Dd (Non-Responders) | dd (Responders) | dd (Non-Responders) |
|---|---|---|---|---|---|---|---|---|---|---|---|---|---|---|---|
| kgp3697615 | 12 | 92450247 | LOC25602I | C | G | 3.67E-05 | 2.591824755 | 0.445054945 | 0.245 | 16 | 6 | 49 | 37 | 26 | 57 |
| rs16846161 | 2 | 212297838 | ERBB4 | A | G | 3.72E-05 | 12.04169614 | 0.117021277 | 0.01010101 | 2 | 0 | 18 | 2 | 74 | 97 |
| kgp6828277 | 9 | 8373943 | PTPRD | C | C | 3.76E-05 | 3.336857878 | 0.260638298 | 0.103960396 | 3 | 2 | 43 | 17 | 48 | 82 |
| rs2662 | 17 | 39670098 | KRT15 | C | A | 3.79E-05 | 0.296809986 | 0.105263158 | 0.262376238 | 0 | 5 | 20 | 43 | 75 | 53 |
| rs7949751 | 11 | 118072373 | AMICA1 | A | G | 3.80E-05 | 2.71195424 | 0.378947368 | 0.193069307 | 11 | 4 | 50 | 31 | 34 | 66 |
| rs1393040 | 9 | 2985743 | | G | A | 3.82E-05 | 2.338232703 | 0.484042553 | 0.267326733 | 28 | 6 | 35 | 42 | 31 | 53 |
| kgp22839559 | | | | A | C | 3.97E-05 | 2.824453621 | 0.340425532 | 0.16 | 10 | 2 | 44 | 28 | 40 | 70 |
| rs3894712 | 5 | 73973651 | | C | A | 3.98E-05 | 0.299943516 | 0.089473684 | 0.252475248 | 3 | 5 | 11 | 41 | 81 | 55 |
| kgp9143704 | 17 | 14355591 | | G | A | 4.08E-05 | 2.349680919 | 0.589473684 | 0.376237624 | 33 | 35 | 46 | 46 | 16 | 40 |
| kgp5949515 | 5 | 62708211 | | G | A | 4.12E-05 | 0.425742574 | 0.236842105 | 0.425742574 | 3 | 36 | 39 | 54 | 53 | 31 |
| rs10038844 | 5 | 62709953 | | A | G | 4.12E-05 | 0.376608267 | 0.236842105 | 0.425742574 | 3 | 16 | 39 | 54 | 53 | 33 |
| kgp12562255 | 1 | 201348672 | | G | A | 4.21E-05 | 21.79487179 | 0.089473684 | 0.004950495 | 0 | 0 | 17 | 1 | 78 | 100 |
| kgp4575797 | 11 | 118083664 | AMICA1 | G | A | 4.25E-05 | 2.730419244 | 0.368421053 | 0.185 | 11 | 3 | 48 | 31 | 36 | 66 |
| rs34647183 | 4 | 171919792 | | G | A | 4.28E-05 | 2.800107938 | 0.336842105 | 0.158415842 | 10 | 2 | 44 | 28 | 41 | 71 |
| kgp5326762 | 4 | 171939426 | | G | A | 4.28E-05 | 2.800107938 | 0.336842105 | 0.158415842 | 10 | 2 | 44 | 28 | 41 | 71 |
| rs6811337 | 4 | 171939724 | | G | A | 4.23E-05 | 2.800107938 | 0.336842105 | 0.158415842 | 10 | 2 | 44 | 28 | 41 | 71 |
| rs7680970 | 4 | 89772301 | FAM13A | C | A | 4.40E-05 | 5.589687003 | 0.152631579 | 0.02970297 | 3 | 0 | 23 | 6 | 69 | 95 |
| kgp7006201 | 20 | 55123573 | | G | A | 4.42E-05 | 9.27027027 | 0.110526316 | 0.014851485 | 0 | 0 | 21 | 3 | 74 | 98 |
| rs4797764 | 18 | 13342265 | C18orf1 | A | C | 4.48E-05 | 2.492752353 | 0.521276596 | 0.321732178 | 22 | 10 | 54 | 45 | 18 | 46 |
| kgp6990559 | 1 | 70144031 | CAMTA1 | G | A | 4.49E-05 | 0.44328707 | 0.35106383 | 0.577319588 | 15 | 35 | 36 | 42 | 43 | 20 |
| kgp4970670 | 8 | 17626306 | MTUS1 | G | A | 4.50E-05 | 3.327473192 | 0.252631579 | 0.099009901 | 4 | 1 | 40 | 18 | 51 | 82 |
| rs1474226 | 6 | 122363499 | | A | G | 4.68E-05 | 0.404824911 | 0.3 | 0.5 | 9 | 22 | 39 | 57 | 47 | 22 |
| kgp5894351 | 16 | 76018855 | | C | A | 4.73E-05 | 2.627713518 | 0.457894737 | 0.27 | 14 | 7 | 59 | 40 | 22 | 53 |
| kgp4892427 | 9 | 2995617 | | G | A | 4.74E-05 | 2.303512108 | 0.515789474 | 0.303980198 | 31 | 7 | 36 | 47 | 28 | 47 |
| rs11750747 | 5 | 73973220 | | A | G | 4.86E-05 | 0.299314836 | 0.089473684 | 0.247524752 | 3 | 4 | 11 | 42 | 81 | 55 |
| rs12233980 | 5 | 73975094 | | G | A | 4.86E-05 | 0.299314836 | 0.089473684 | 0.247524752 | 3 | 4 | 11 | 42 | 81 | 55 |
| kgp3624014 | 16 | 6442184 | RBFOX1 | G | A | 4.92E-05 | 2.364225084 | 0.573624211 | 0.366336634 | 30 | 14 | 49 | 46 | 16 | 41 |
| kgp3598966 | 4 | 7649861 | SORCS2 | G | A | 4.94E-05 | 0.324801511 | 0.110526316 | 0.277227723 | 1 | 8 | 19 | 40 | 75 | 53 |
| kgp10762962 | 15 | 34983455 | | G | A | 5.10E-05 | 4.525507056 | 0.173684211 | 0.044554455 | 3 | 0 | 27 | 9 | 65 | 92 |
| rs3847233 | 9 | 2987835 | | G | A | 5.11E-05 | 2.294890779 | 0.516129032 | 0.3 | 31 | 7 | 34 | 46 | 28 | 47 |
| rs7819949 | 8 | 41387921 | GINS4 | G | A | 5.23E-05 | 0.376526131 | 0.242105263 | 0.425742574 | 6 | 12 | 34 | 62 | 55 | 27 |
| kgp4985243 | 7 | 136556162 | CHRM2 | G | A | 5.24E-05 | 3.777144291 | 0.210526316 | 0.074257426 | 2 | 0 | 36 | 15 | 57 | 86 |
| rs6577395 | 1 | 6991925 | CAMTA1 | A | G | 5.34E-05 | 0.451723966 | 0.367021277 | 0.589108911 | 16 | 38 | 37 | 43 | 41 | 20 |
| kgp4037661 | 16 | 76019450 | | C | A | 5.36E-05 | 2.607793598 | 0.457446809 | 0.27 | 14 | 7 | 58 | 40 | 22 | 53 |
| rs17187123 | 11 | 171969779 | LOC100506122 | G | A | 5.39E-05 | 2.760718495 | 0.335106383 | 0.158415842 | 10 | 2 | 43 | 28 | 41 | 71 |
| rs9953274 | 18 | 13317297 | C18orf1 | G | A | 5.43E-05 | 2.632532227 | 0.415789474 | 0.232673267 | 14 | 3 | 51 | 41 | 30 | 57 |
| rs7846783 | 9 | 2958182 | | A | G | 5.46E-05 | 2.308218163 | 0.452631579 | 0.242574257 | 25 | 6 | 36 | 37 | 34 | 58 |
| rs3858035 | 9 | 2968044 | | A | C | 5.50E-05 | 2.297809929 | 0.484042553 | 0.272277222 | 27 | 7 | 37 | 41 | 30 | 53 |

TABLE 40-continued

Placebo SNPs
PLACEBO COHORT

| Name | Chromosome | Position | Gene(s) | Major Allele (d) | Minor Allele (D) | P-value (Armitage Test) | Odds Ratio (Minor Allele) | Minor Allele Freq. (Responders) | Minor Allele Freq. (Non-Responders) | DD (Responders) | DD (Non-Responders) | Dd (Responders) | Dd (Non-Responders) | dd (Responders) | dd (Non-Responders) |
|---|---|---|---|---|---|---|---|---|---|---|---|---|---|---|---|
| kgp1682126 | 5 | 2047397 | | G | A | 5.53E-05 | 0.048188869 | 0.005263158 | 0.099009901 | 0 | 1 | 1 | 18 | 94 | 82 |
| rs17245674 | 4 | 171884710 | | G | A | 5.64E-05 | 2.786056066 | 0.331578947 | 0.158415842 | 9 | 2 | 45 | 28 | 41 | 71 |
| rs967616 | 4 | 171888222 | | A | G | 5.64E-05 | 2.786056066 | 0.331578947 | 0.158415842 | 9 | 2 | 45 | 28 | 41 | 71 |
| kgp4456934 | 2 | 218174378 | DIRC3 | G | A | 5.68E-05 | 3.792998699 | 0.205263158 | 0.065 | 4 | 0 | 31 | 13 | 60 | 87 |
| rs12881439 | 14 | 37105853 | | A | G | 5.87E-05 | 0.337727502 | 0.142105263 | 0.306930693 | 0 | 8 | 27 | 46 | 68 | 47 |
| kgp9927782 | 14 | 37108518 | | A | G | 5.87E-05 | 0.337727502 | 0.142105263 | 0.306930693 | 0 | 8 | 27 | 46 | 68 | 47 |
| rs8000689 | 13 | 41043438 | TTL | G | A | 6.00E-05 | 0.446273903 | 0.384210526 | 0.599004901 | 14 | 40 | 45 | 41 | 36 | 20 |
| kgp8145845 | 6 | 15873989 | | A | C | 6.04E-05 | 0.348762475 | 0.189473684 | 0.356435644 | 0 | 9 | 36 | 54 | 59 | 38 |
| rs10495115 | 1 | 219089109 | | C | A | 6.04E-05 | 2.896745105 | 0.3 | 0.133663366 | 7 | 2 | 43 | 23 | 45 | 76 |
| rs3858034 | 9 | 2964750 | | A | G | 6.07E-05 | 2.302490296 | 0.478947368 | 0.27 | 27 | 6 | 37 | 42 | 31 | 52 |
| kgp4137144 | 1 | 219091068 | | A | G | 6.13E-05 | 6.188590011 | 0.138297872 | 0.025 | 2 | 0 | 22 | 5 | 70 | 95 |
| kgp7932108 | 9 | 110434545 | | A | G | 6.22E-05 | 3.182096036 | 0.25 | 0.094059406 | 6 | 1 | 35 | 17 | 53 | 83 |
| kgp8847137 | 11 | 118078958 | AMICA1 | A | G | 6.37E-05 | 2.66389832 | 0.365591398 | 0.185 | 11 | 3 | 46 | 31 | 36 | 66 |
| kgp1393037 | 9 | 2968451 | | A | G | 6.42E-05 | 2.286704865 | 0.484042553 | 0.272727273 | 27 | 7 | 37 | 40 | 30 | 52 |
| rs1508515 | 4 | 171932189 | | C | G | 6.80E-05 | 2.721514946 | 0.333333333 | 0.158415842 | 10 | 2 | 42 | 28 | 41 | 71 |
| rs7684006 | 4 | 18140181 | | G | A | 6.80E-05 | 2.292936797 | 0.552631579 | 0.346534653 | 30 | 12 | 45 | 46 | 20 | 43 |
| kgp4591145 | 8 | 112807116 | | A | G | 7.17E-05 | 0.414208739 | 0.394736842 | 0.589108911 | 13 | 32 | 49 | 55 | 33 | 14 |
| rs3768769 | 2 | 113764983 | IL36A | A | G | 7.21E-05 | 4.303214495 | 0.173684211 | 0.04950495 | 2 | 0 | 29 | 10 | 64 | 91 |
| kgp3488270 | 1 | 20335423 | | G | C | 7.30E-05 | 0.266656346 | 0.063157895 | 0.205 | 1 | 4 | 10 | 33 | 84 | 63 |
| rs2354380 | 2 | 51826155 | | A | C | 7.48E-05 | 5.489851381 | 0.143617021 | 0.02970297 | 2 | 0 | 23 | 6 | 69 | 95 |
| rs13168893 | 5 | 62732760 | | A | C | 7.49E-05 | 0.390251325 | 0.268421053 | 0.45049505 | 4 | 17 | 43 | 57 | 48 | 27 |
| kgp6213972 | 3 | 194426284 | | G | A | 7.52E-05 | 0.216811903 | 0.042105263 | 0.168316832 | 0 | 3 | 8 | 28 | 87 | 70 |
| rs1357718 | 5 | 105355890 | | A | G | 7.71E-05 | 4.070798901 | 0.186370213 | 0.060606061 | 1 | 0 | 33 | 12 | 60 | 87 |
| kgp5924341 | 6 | 23943424 | | G | A | 7.77E-05 | 0.161887188 | 0.026315789 | 0.135 | 0 | 1 | 5 | 25 | 90 | 74 |
| rs6459418 | 6 | 15860342 | | A | C | 7.78E-05 | 0.353819225 | 0.191489362 | 0.356435644 | 0 | 9 | 36 | 54 | 58 | 38 |
| rs1905248 | 12 | 52007003 | SCN8A | G | A | 7.84E-05 | 2.853251243 | 0.310526316 | 0.148514851 | 6 | 2 | 47 | 26 | 42 | 73 |
| kgp71511153 | 3 | 79590648 | ROBO1 | G | A | 7.86E-05 | 3.980515837 | 0.184210526 | 0.04950495 | 4 | 1 | 27 | 8 | 64 | 92 |
| rs3858036 | 9 | 2968107 | | A | G | 7.92E-05 | 2.248089873 | 0.478947368 | 0.272277228 | 27 | 7 | 37 | 41 | 31 | 53 |
| kgp10836214 | 9 | 2969061 | | A | G | 7.92E-05 | 2.248089873 | 0.478947368 | 0.272277228 | 27 | 7 | 37 | 41 | 31 | 53 |
| rs625941 | 5 | 73973306 | | G | A | 7.95E-05 | 0.3102772 | 0.089473684 | 0.242574257 | 3 | 4 | 11 | 41 | 81 | 56 |
| kgp2176915 | 5 | 36732366 | | C | A | 8.12E-05 | 0.253163456 | 0.084210526 | 0.004950495 | 0 | 0 | 16 | 1 | 79 | 100 |
| rs4740708 | 9 | 2993975 | | A | G | 8.20E-05 | 2.230445246 | 0.510638298 | 0.301980198 | 31 | 7 | 34 | 47 | 29 | 47 |
| kgp1432800 | 9 | 111389847 | | A | C | 8.22E-05 | 4.705307757 | 0.157894737 | 0.03960396 | 2 | 0 | 26 | 8 | 67 | 93 |
| rs7231366 | 18 | 13332691 | C18orf1 | A | G | 8.23E-05 | 2.523395135 | 0.421052632 | 0.237373737 | 14 | 5 | 52 | 37 | 29 | 57 |
| rs28993969 | 2 | 113762224 | | A | G | 8.51E-05 | 3.673422044 | 0.2 | 0.064356436 | 4 | 0 | 30 | 13 | 61 | 88 |
| kgp3420309 | 2 | 15213767 | | A | G | 8.60E-05 | 5.414105514 | 0.142105263 | 0.02970297 | 2 | 0 | 23 | 6 | 70 | 95 |
| kgp3287349 | 4 | 15224995 | | A | G | 8.60E-05 | 5.414105514 | 0.142105263 | 0.02970297 | 2 | 0 | 23 | 6 | 70 | 95 |

TABLE 40-continued

Placebo SNPs
PLACEBO COHORT

| Name | Chromosome | Position | Gene(s) | Major Allele (d) | Minor Allele (D) | P-value (Armitage Test) | Odds Ratio (Minor Allele) | Minor Allele Freq. (Responders) | Minor Allele Freq. (Non-Responders) | DD (Responders) | DD (Non-Responders) | Dd (Responders) | Dd (Non-Responders) | dd (Responders) | dd (Non-Responders) |
|---|---|---|---|---|---|---|---|---|---|---|---|---|---|---|---|
| rs12043743 | 1 | 196502836 | KCNT2 | T | A | 8.61E-05 | 0.160256411 | 0.026315789 | 0.128712871 | 0 | 0 | 5 | 26 | 90 | 75 |
| kgp394638 | 10 | 112163082 | | G | A | 8.68E-05 | 3.443845133 | 0.215789474 | 0.070707071 | 6 | 0 | 29 | 14 | 60 | 85 |
| kgp24521552 | 2 | 144072847 | ARHGAP15 | C | A | 8.86E-05 | 4.219905015 | 0.173684211 | 0.045 | 4 | 0 | 25 | 9 | 66 | 91 |
| rs263247 | 8 | 131792219 | | A | G | 8.87E-05 | 0.379472909 | 0.175531915 | 0.351485149 | 3 | 11 | 27 | 49 | 64 | 41 |
| kgp2993366 | 6 | 6726140 | | C | A | 8.88E-05 | 2.392490753 | 0.538043478 | 0.340206186 | 25 | 10 | 49 | 46 | 18 | 41 |
| kgp11755256 | 2 | 42445135 | | G | A | 8.99E-05 | 0.379232018 | 0.143617021 | 0.321782178 | 1 | 14 | 25 | 37 | 68 | 50 |
| rs8018807 | 14 | 27905391 | | A | G | 9.00E-05 | 0.445075158 | 0.319148936 | 0.524752475 | 10 | 30 | 40 | 46 | 44 | 25 |
| rs7961005 | 12 | 75849475 | | A | A | 9.06E-05 | 0.325552876 | 0.105263158 | 0.26 | 0 | 7 | 20 | 38 | 75 | 55 |
| kgp1211163 | 11 | 98961805 | CNTN5 | C | A | 9.12E-05 | 5.531933083 | 0.136842105 | 0.02970297 | 1 | 0 | 24 | 6 | 70 | 95 |
| rs528065 | 2 | 238594491 | KLHL29 | G | A | 9.24E-05 | 2.448976995 | 0.442105263 | 0.257425743 | 19 | 3 | 46 | 46 | 30 | 52 |
| rs13386874 | 2 | 51820543 | | A | G | 9.25E-05 | 2.638975938 | 0.321052632 | 0.148514851 | 12 | 1 | 37 | 28 | 46 | 72 |
| kgp1758575 | 12 | 14433784 | | A | G | 9.25E-05 | 2.322238139 | 0.457894737 | 0.262376238 | 18 | 10 | 51 | 33 | 26 | 5 |
| kg6081880 | 4 | 171852630 | | G | A | 9.39E-05 | 2.692096282 | 0.326315789 | 0.158415842 | 9 | 2 | 44 | 28 | 42 | 71 |
| kgp956070 | 2 | 205936350 | PARD3B | G | A | 9.39E-05 | 0.371996312 | 0.142105263 | 0.315 | 2 | 11 | 23 | 41 | 70 | 48 |
| rs35615951 | 2 | 133778855 | NCKAP5 | G | A | 9.41E-05 | 2.317383014 | 0.478723404 | 0.282178218 | 22 | 8 | 46 | 41 | 26 | 52 |
| kgp8644305 | 18 | 74021780 | | G | A | 9.50E-05 | 8.396863212 | 0.110526316 | 0.014851485 | 1 | 0 | 19 | 3 | 75 | 98 |
| P1_M_061510_18_342_P | 18 | 51319566 | | T | D | 9.51E-05 | 0.229965157 | 0.054347826 | 0.173267327 | 0 | 0 | 10 | 35 | 82 | 66 |
| kgp12253568 | 3 | 794282659 | ROBO1 | G | A | 9.55E-05 | 4.28904266 | 0.163421053 | 0.03960396 | 4 | 1 | 24 | 6 | 67 | 94 |
| rs1397481 | 2 | 205894489 | PARD3B | G | A | 9.56E-05 | 0.368096506 | 0.142105263 | 0.311881188 | 2 | 10 | 23 | 43 | 70 | 48 |
| rs1026894 | 12 | 52019159 | SCN8A | A | G | 9.57E-05 | 2.756153394 | 0.326315789 | 0.163366337 | 7 | 2 | 48 | 29 | 40 | 70 |
| kgp7161038 | 2 | 53521025 | | A | G | 9.70E-05 | 0.088043478 | 0.010638298 | 0.099009901 | 0 | 0 | 2 | 20 | 92 | 81 |
| rs1534647 | 2 | 62038088 | | G | G | 9.72E-05 | 3.3378955 | 0.221052632 | 0.079207921 | 5 | 0 | 32 | 16 | 58 | 85 |
| kgp5252824 | 4 | 123558223 | | A | G | 9.87E-05 | 0.051605754 | 0.005263158 | 0.094059406 | 0 | 1 | 1 | 17 | 94 | 83 |
| kgp5691690 | 5 | 135207935 | SLC25A48 | G | A | 9.87E-05 | 0.051605754 | 0.005263158 | 0.094059406 | 0 | 1 | 1 | 17 | 94 | 83 |
| rs12341716 | 9 | 22947192 | | A | G | 9.91E-05 | 0.339667103 | 0.126315789 | 0.282178218 | 1 | 6 | 22 | 45 | 72 | 50 |
| kgp6194428 | 6 | 15873854 | | A | G | 0.000100412 | 0.361610208 | 0.189473684 | 0.351485149 | 0 | 9 | 36 | 53 | 59 | 39 |
| rs1883448 | 6 | 15877727 | | A | G | 0.000100412 | 0.361610208 | 0.189473684 | 0.351485149 | 0 | 9 | 36 | 53 | 59 | 39 |

(Note:
Odds Ratio >1 = Minor Allele is associated with Response,
Odds Ratio <1 = Minor Allele Associated with Non-Response)

TABLE 41

Predictive Model SNPs

| | | STANDARD PHENOTYPE | | | | | Gala cohort |
|---|---|---|---|---|---|---|---|
| Prioritized Variants | Name | Chromosome | Position | Gene(s) | Major Allele (d) | Minor Allele (D) | P-value (Armitage Test) |
| 0 - Priority genes, Predictive Model | rs1894408 | 6 | 32786833 | | C | G | 3.02E-03 |
| 0 - Priority genes, Predictive Model | kgp6599438 | 20 | 40843626 | PTPRT | G | A | 3.70E-03 |
| 0 - Priority genes, Predictive Model | kgp7747883 | 18 | 74804250 | MBP | G | A | 3.55E-02 |
| 0 - Priority genes, Predictive Model | rs10162089 | 13 | 31316738 | ALOX5AP | G | A | 7.79E-03 |
| 0 - Priority in Predictive Model | kgp24415534 | 2 | 174156875 | | G | A | 3.40E-05 |
| 0 - Priority in Predictive Model | rs16886004 | 7 | 78021500 | MAGI2 | A | G | 2.28E-03 |
| 0 - Priority in Predictive Model | kgp8817856 | 6 | 32744440 | | G | A | 6.02E-04 |
| 0 - Priority in Predictive Model | kgp6214351 | 11 | 75546691 | UVRAG | A | G | 3.98E-03 |
| 0 - Priority in Predictive Model | kgp8110667 | 22 | 32716792 | | G | A | 5.97E-03 |
| 0 - Priority in Predictive Model | rs759458 | 2 | 65245365 | SLC1A4 | G | A | 1.08E-03 |
| 0 - Priority variants, Predictive Model | rs3135391 | 6 | 32410987 | HLA-DRA | G | A | 3.99E-02 |

| | Gala cohort | | | Forte cohort | | | |
|---|---|---|---|---|---|---|---|
| Prioritized Variants | Odds Ratio (Minor Allele) | Minor Allele Freq. (Responders) | Allele Freq. (Non-Responders) | P-value (Armitage Test) | Odds Ratio (Minor Allele) | Minor Allele Freq. (Responders) | Allele Freq. (Non-Responders) |
| 0 - Priority genes, Predictive Model | 1.72 | 0.419 | 0.305 | 9.30E-03 | 1.82 | 0.407 | 0.279 |
| 0 - Priority genes, Predictive Model | 0.21 | 0.010 | 0.046 | 1.55E-02 | 0.28 | 0.018 | 0.057 |
| 0 - Priority genes, Predictive Model | 0.70 | 0.346 | 0.429 | 9.82E-03 | 0.57 | 0.325 | 0.451 |
| 0 - Priority genes, Predictive Model | 1.56 | 0.508 | 0.398 | 3.16E-02 | 1.58 | 0.457 | 0.344 |
| 0 - Priority in Predictive Model | 0.05 | 0.003 | 0.050 | 1.10E-02 | 0.14 | 0.005 | 0.033 |
| 0 - Priority in Predictive Model | 2.15 | 0.199 | 0.110 | 3.25E-05 | 5.56 | 0.199 | 0.049 |
| 0 - Priority in Predictive Model | 0.53 | 0.364 | 0.492 | 3.73E-04 | 0.46 | 0.419 | 0.598 |
| 0 - Priority in Predictive Model | 0.42 | 0.051 | 0.113 | 2.65E-04 | 0.26 | 0.043 | 0.131 |
| 0 - Priority in Predictive Model | Infinity | 0.030 | 0.000 | 1.46E-02 | Infinity | 0.050 | 0.000 |
| 0 - Priority in Predictive Model | 1.90 | 0.303 | 0.183 | 4.74E-01 | 1.18 | 0.288 | 0.254 |
| 0 - Priority variants, Predictive Model | 0.66 | 0.174 | 0.242 | 4.99E-02 | 0.64 | 0.231 | 0.320 |

(Note:
Odds Ratio >1 = Minor Allele is associated with Response,
Odds Ratio <1 = Minor Allele Associated with Non-Response)

TABLE 41

Predictive Model SNPs

| | | STANDARD PHENOTYPE | | | | | Combined | |
|---|---|---|---|---|---|---|---|---|
| Prioritized Variants | Name | Chromosome | Position | Gene(s) | Major Allele (d) | Minor Allele (D) | P-value (Armitage Test) | Odds Ratio (Minor Allele) |
| 0 - Priority genes, Predictive Model | rs1894408 | 6 | 32786833 | | C | G | 9.82E-05 | 1.73 |

TABLE 41-continued

| Prioritized Variants | | | | | | | | |
|---|---|---|---|---|---|---|---|---|
| Predictive Model SNPs | | | | | | | | |
| 0 - Priority genes, Predictive Model | kgp6599438 | 20 | 40843626 | PTPRT | G | A | 2.48E-04 | 0.26 |
| 0 - Priority genes, Predictive Model | kgp7747883 | 18 | 74804250 | MBP | G | A | 8.64E-04 | 0.64 |
| 0 - Priority genes, Predictive Model | rs10162089 | 13 | 31316738 | ALOX5AP | G | A | 1.40E-03 | 1.51 |
| 0 - Priority in Predictive Model | kgp24415534 | 2 | 174156875 |  | G | A | 3.98E-07 | 0.08 |
| 0 - Priority in Predictive Model | rs16886004 | 7 | 78021500 | MAGI2 | A | G | 9.81E-07 | 2.79 |
| 0 - Priority in Predictive Model | kgp8817856 | 6 | 32744440 |  | G | A | 5.33E-06 | 0.53 |
| 0 - Priority in Predictive Model | kgp6214351 | 1 | 75546691 | UVRAG | A | G | 5.51E-06 | 0.35 |
| 0 - Priority in Predictive Model | kgp8110667 | 22 | 32716792 |  | G | A | 1.44E-04 | Infinity |
| 0 - Priority in Predictive Model | rs759458 | 2 | 65245365 | SLC1A4 | G | A | 2.01E-03 | 1.59 |
| 0 - Priority variants, Predictive Model | rs3135391 | 6 | 32410987 | HLA-DRA | G | A | 1.44E-02 | 0.70 |

| Prioritized Variants | Minor Allele Freq. (Responders) | Allele Freq. (Non-Responders) | Combined | | | | | |
|---|---|---|---|---|---|---|---|---|
| | | | DD (Responders) | DD (Non-responders) | DD (Responders) | DD (Non-responders) | DD (Responders) | DD (Non-responders) |
| 0 - Priority genes, Predictive Model | 0.413 | 0.296 | 58 | 16 | 211 | 74 | 127 | 89 |
| 0 - Priority genes, Predictive Model | 0.014 | 0.050 | 0 | 0 | 11 | 18 | 386 | 163 |
| 0 - Priority genes, Predictive Model | 0.335 | 0.436 | 43 | 33 | 181 | 92 | 174 | 56 |
| 0 - Priority genes, Predictive Model | 0.482 | 0.380 | 96 | 24 | 190 | 88 | 110 | 67 |
| 0 - Priority in Predictive Model | 0.004 | 0.044 | 0 | 0 | 3 | 16 | 396 | 165 |
| 0 - Priority in Predictive Model | 1.199 | 0.089 | 6 | 2 | 147 | 28 | 246 | 149 |
| 0 - Priority in Predictive Model | 0.392 | 0.528 | 50 | 44 | 208 | 103 | 135 | 34 |
| 0 - Priority in Predictive Model | 0.046 | 0.119 | 0 | 2 | 37 | 39 | 361 | 140 |
| 0 - Priority in Predictive Model | 0.040 | 0.000 | 1 | 0 | 30 | 0 | 367 | 181 |
| 0 - Priority in Predictive Model | 0.295 | 0.207 | 38 | 7 | 159 | 61 | 201 | 113 |
| 0 - Priority variants, Predictive Model | 0.203 | 0.268 | 20 | 10 | 122 | 77 | 257 | 94 |

(Note:
Odds Ratio >1 = Minor Allele is associated with Response,
Odds Ratio <1 = Minor Allele Associated with Non-Response)

Example 16 Selection of Genetic Markers for Predictive Models

A total of 11 genetic variants were selected for inclusion in a preliminary multi-marker risk prediction model. Importantly, many of the identified genes have been previously implicated in MS and/or glatiramer acetate response (i.e., MAGI2, HLA-DOB/TAP2 region, MBP, ALOX5AP, and the HLA-DRB1-15:01 polymorphism).

Variants were identified and selected using a multi-step approach, beginning with the selection of replicated variants from a priority list of 35 candidate variants. This led to one variant selected for inclusion into the model: rs3135391, a marker of HLA-DRB1*1501, P<0.05 in Gala, P<0.05 in Forte, P=0.014 combined, odds ratio 1.6).

This was followed by selection of three replicated variants from a list of 4,012 variants in 30 priority genes (kgp8817856 in HLA-DQB2/DOB, p<0.001 in Gala, p<0.001 in Forte, p-value 5.33E-06, odds ratio 0.53; rs1894408 in HLA-DOB/TAP2, p<0.01 in Gala, p<0.01 in Forte, p-value 0.000098, odds ratio 1.7; and kgp7747883 in MBP, p<0.05 in Gala, p<0.01 in Forte, p-value 0.00086, odds ratio 0.64).

This was followed by a selection of two variants from a list of 25,000 candidate variants in 180 second priority genes (kgp6599438 in PTPRT, p<0.01 in Gala, p<0.05 in Forte, p-value 0.00025, odds ratio 0.26; and rs10162089 in ALOX5AP, p<0.01 in Gala, p<0.05 in Forte, p-value 0.0014, odds ratio 1.5).

Finally, three variants were selected from the entire genome-wide panel (rs16886004 in MAGI2, p<0.005 in Gala, p<0.00005 in Forte, p-value 0.00000098 combined, odds ratio 2.8; kgp24415534 in the ZAK/CDCA7 gene region, p<0.00005 in Gala, p<0.05 in Forte, p-value 0.000000398, odds ratio 0.08; and kgp8110667 in the RFPL3/SLC5A4 region, p<0.01 in Gala, p<0.05 in Forte, p-value 0.00014, odds ratio: infinity).

In addition, two variants were selected from the entire genome-wide panel using an extreme phenotype definition (kgp6214351 in the UVRAG gene, combined p-value 0.0000055, odds ratio 0.35; and rs759458 in SLC1A4, combined p-value 0.002; odds ratio 1.6). The statistics of the selected 11 SNPs are shown for the additive, allelic, and genotypic genetic models. The statistics of the selected 11 SNPs are shown for the additive, allelic, and genotypic genetic models (Tables 42, 43 and 44a and 44b, respectively).

TABLE 42

Additive Model Characteristics of Individual SNPs in Model

Addtitive Model

| | | | | | | | GALA Cohort | | | | Forte Cohort | |
|---|---|---|---|---|---|---|---|---|---|---|---|---|
| Gene(s) | Name | Chr | Position | Mutation | Locations | Source | Armitage P-value | Odds Ratio (Regression) | Allele Freq. (Resp.) | Allele Freq. (Non-Resp.) | Armitage P-value | Odds Ratio (Regression) |
| ZAK/CDCA7 | kgp24415534 | 2 | 174156875 | non-coding | — | GWAS, Additive | 3.40E−05 | 0.05 | 0% | 5% | 0.010967 | 0.14 |
| UVRAG | kgp6214351 | 11 | 75546691 | non-coding | IN-TRON | GWAS, Additive, Extreme | 0.003983 | 0.42 | 5% | 11% | 0.000265 | 0.26 |
| PTPRT | kgp6599438 | 20 | 40843626 | non-coding | IN-TRON | Candidate Genes (180) | 0.003702 | 0.21 | 1% | 5% | 0.015514 | 0.28 |
| MBP | kgp7747883 | 18 | 74804250 | non-coding | IN-TRON | Candidate Genes (30) | 0.035519 | 0.70 | 35% | 43% | 0.00982 | 0.57 |
| RFPL3/SLC5A4 region | kgp8110667 | 22 | 32716792 | non-coding | — | GWAS, Additive | 0.005975 | Inf. | 3% | 0% | 0.014628 | Inf. |
| HLA-DQB2/DOB | kgp8817856 | 6 | 32744440 | non-coding | — | Candidate genes (30) + GWAS | 0.000602 | 0.53 | 36% | 49% | 0.000373 | 0.46 |
| ALOX5AP | rs10162089 | 13 | 31316738 | non-coding | IN-TRON | Candidate Genes (180) | 0.007794 | 1.56 | 51% | 40% | 0.031551 | 1.58 |
| MAGI2 | rs16886004 | 7 | 78021500 | non-coding | IN-TRON | GWAS, Additive | 0.002281 | 2.15 | 20% | 11% | 3.25E−05 | 5.56 |
| HLA-DOB/TAP2 | rs1894408 | 6 | 32786833 | non-coding | — | Candidate Genes (30) | 0.003022 | 1.72 | 42% | 31% | 0.0093 | 1.82 |
| HLA-DRA/DRB1*1501 | rs3135391 | 6 | 32410987 | Synon T118T | EXON | Candidate variants | 0.03985 | 0.66 | 17% | 24% | 0.049871 | 0.64 |
| SLC1A4 | rs759458 | 2 | 65245365 | Non-synon V101I | EXON | GWAS, Additive, Extreme | 0.001079 | 1.90 | 30% | 18% | 0.47426 | 1.18 |

| | Forte Cohort | | Combined cohort | | | | | | | | |
|---|---|---|---|---|---|---|---|---|---|---|---|
| Gene(s) | Allele Freq. (Resp.) | Allele Freq. (Non-Resp.) | Armitage P-value | Odds Ratio (Regression) | Allele Freq. (Resp.) | Allele Freq. (Non-Resp.) | DD (Resp.) | DD (Non-Resp.) | Dd (Resp.) | Dd (Non-Resp.) | dd (Resp.) | dd (Non-Resp.) |
| ZAK/CDCA7 | 0% | 3% | 3.98E−07 | 0.08 | 0% | 4% | 0 | 0 | 3 | 16 | 396 | 165 |
| UVRAG | 4% | 13% | 5.51E−06 | 0.35 | 5% | 12% | 0 | 2 | 37 | 39 | 361 | 140 |
| PTPRT | 2% | 6% | 0.000248 | 0.26 | 1% | 5% | 0 | 0 | 11 | 18 | 386 | 163 |
| MBP | 33% | 45% | 0.000864 | 0.64 | 34% | 44% | 43 | 33 | 181 | 92 | 174 | 56 |
| RFPL3/SLC5A4 region | 5% | 0% | 0.000144 | Inf. | 4% | 0% | 1 | 0 | 30 | 0 | 367 | 181 |
| HLA-DQB2/DOB | 42% | 60% | 5.33E−06 | 0.53 | 39% | 53% | 50 | 44 | 208 | 103 | 135 | 34 |
| ALOX5AP | 46% | 34% | 0.001396 | 1.51 | 48% | 38% | 96 | 24 | 190 | 88 | 110 | 67 |
| MAGI2 | 20% | 5% | 9.81E−07 | 2.79 | 20% | 9% | 6 | 2 | 147 | 28 | 246 | 149 |
| HLA-DOB/TAP2 | 41% | 28% | 9.82E−05 | 1.73 | 41% | 30% | 58 | 16 | 211 | 74 | 127 | 89 |
| HLA-DRA/DRB1*1501 | 23% | 32% | 0.014366 | 0.70 | 20% | 27% | 20 | 10 | 122 | 77 | 257 | 94 |
| SLC1A4 | 29% | 25% | 0.002005 | 1.59 | 30% | 21% | 38 | 7 | 159 | 61 | 201 | 113 |

TABLE 42-continued

Additive Model Characteristics of Individual SNPs in Model

Additive Model, Extreme Phenotype

| Gene(s) | Name | Chr | Position | Mutation | Locations | Source | GALA Cohort ||||  Forte Cohort ||
|---|---|---|---|---|---|---|---|---|---|---|---|---|
| | | | | | | | Armitage P-value | Odds Ratio (Regression) | Allele Freq. (Resp.) | Allele Freq. (Non-Resp.) | Armitage P-value | Odds Ratio (Regression) |
| ZAK/CDCA7 | kgp24415534 | 2 | 174156875 | non-coding | — | GWAS, Additive | 4.38E-02 | 0.15 | 1% | 5% | 0.022992 | 0.00 |
| UVRAG | kgp6214351 | 11 | 75546691 | non-coding | INTRON | GWAS, Additive, Extreme | 0.002442 | 0.20 | 3% | 13% | 3.36E-05 | 0.12 |
| PTPRT | kgp6599438 | 20 | 40843626 | non-coding | INTRON | Candidate Genes (180) | 0.006737 | 0.00 | 0% | 5% | 0.157158 | 0.36 |
| MBP | kgp7747883 | 18 | 74804250 | non-coding | INTRON | Candidate Genes (30) | 0.243651 | 0.76 | 36% | 43% | 0.035452 | 0.53 |
| RFPL3/SLC5A4 region | kgp8110667 | 22 | 32716792 | non-coding | — | GWAS, Additive | 0.009445 | Inf. | 4% | 0% | 0.115337 | Inf. |
| HLA-DQB2/DOB | kgp8817856 | 6 | 32744440 | non-coding | — | Candidate genes (30) + GWAS | 0.036059 | 0.58 | 37% | 48% | 0.009234 | 0.45 |
| ALOX5AP | rs10162089 | 13 | 31316738 | non-coding | INTRON | Candidate Genes (180) | 0.005861 | 1.93 | 58% | 40% | 0.005285 | 2.32 |
| MAGI2 | rs16886004 | 7 | 78021500 | non-coding | INTRON | GWAS, Additive | 0.030517 | 2.04 | 19% | 10% | 9.21E-03 | 3.64 |
| HLA-DOB/TAP2 | rs1894408 | 6 | 32786833 | non-coding | — | Candidate Genes (30) | 0.08935 | 1.50 | 39% | 30% | 0.002633 | 2.85 |
| HLA-DRA/DRB1*1501 | rs3135391 | 6 | 32410987 | Synon T118T | EXON | Candidate variants | 0.060413 | 0.58 | 18% | 27% | 0.027901 | 0.50 |
| SLC1A4 | rs759458 | 2 | 65245365 | Non-synon V101I | EXON | GWAS, Additive, Extreme | 4.44E-05 | 3.31 | 36% | 16% | 0.048948 | 1.86 |

| Gene(s) | Forte Cohort || Combined cohort ||| DD (Resp.) | DD (Non-Resp.) | Dd (Resp.) | Dd (Non-Resp.) | dd (Resp.) | dd (Non-Resp.) |
|---|---|---|---|---|---|---|---|---|---|---|---|
| | Allele Freq. (Resp.) | Allele Freq. (Non-Resp.) | Armitage P-value | Odds Ratio (Regression) | Allele Freq. (Resp.) | Allele Freq. (Non-Resp.) | | | | | | |
| ZAK/CDCA7 | 0% | 3% | 1.32E-03 | 0.07 | 0% | 4% | 0 | 0 | 1 | 10 | 154 | 111 |
| UVRAG | 3% | 17% | 9.09E-07 | 0.17 | 3% | 14% | 0 | 1 | 9 | 32 | 145 | 88 |
| PTPRT | 2% | 6% | 0.005127 | 0.22 | 1% | 5% | 0 | 0 | 4 | 13 | 151 | 108 |
| MBP | 29% | 43% | 0.00926 | 0.63 | 32% | 43% | 16 | 22 | 67 | 60 | 71 | 39 |
| RFPL3/SLC5A4 region | 3% | 0% | 0.002785 | Inf. | 4% | 0% | 0 | 0 | 11 | 0 | 144 | 121 |
| HLA-DQB2/DOB | 37% | 54% | 1.17E-03 | 0.54 | 37% | 50% | 17 | 29 | 79 | 69 | 57 | 26 |
| ALOX5AP | 46% | 26% | 0.00094 | 1.78 | 50% | 36% | 43 | 14 | 69 | 57 | 42 | 48 |
| MAGI2 | 20% | 7% | 6.08E-04 | 2.48 | 20% | 9% | 4 | 2 | 53 | 18 | 98 | 100 |
| HLA-DOB/TAP2 | 42% | 23% | 1.15E-03 | 1.86 | 41% | 28% | 22 | 10 | 81 | 47 | 50 | 64 |
| HLA-DRA/DRB1*1501 | 20% | 33% | 0.006382 | 0.57 | 19% | 29% | 6 | 9 | 47 | 52 | 102 | 60 |
| SLC1A4 | 36% | 23% | 2.92E-04 | 2.64 | 36% | 18% | 20 | 3 | 71 | 37 | 63 | 81 |

TABLE 43

Allelic Model Characteristics of Individual SNPs in Model

| | | | | | | | Allelic Model | | | | | | | | | | | |
|---|---|---|---|---|---|---|---|---|---|---|---|---|---|---|---|---|---|---|
| | | | | | | | GALA Cohort | | | | Forte Cohort | Forte cohort | | | Combined cohort | | | |
| Gene(s) | Name | Chr | Position | Mutation | Locations | Source | Fisher Exact P-Value | Odds Ratio (Minor Allele) | (95% | CI) | Fisher Exact P-Value | Odds Ratio (Minor Allele) | (95% | CI) | Fisher Exact P-Value | Odds Ratio (Minor Allele) | (95% | CI) |
| ZAK/CDCA7 | kgp24415534 | 2 | 174156875 | non-coding | — | GWAS, Additive | 6.03E−05 | 0.05 | 0.01 | 0.37 | 0.028468 | 0.15 | 0.03 | 0.82 | 2.28E−06 | 0.08 | 0.02 | 0.28 |
| UVRAG | kgp6214351 | 11 | 75546691 | non-coding | INTRON | GWAS, Additive, Extreme | 0.004741 | 0.42 | 0.23 | 0.77 | 0.001081 | 0.29 | 0.14 | 0.60 | 1.06E−05 | 0.36 | 0.23 | 0.57 |
| PTPRT | kgp6599438 | 20 | 40843626 | non-coding | INTRON | Candidate Genes (180) | 0.005974 | 0.21 | 0.07 | 0.68 | 0.025262 | 0.29 | 0.10 | 0.85 | 0.000764 | 0.27 | 0.13 | 0.57 |
| MBP | kgp7747883 | 18 | 74804250 | non-coding | INTRON | Candidate Genes (30) | 0.042737 | 0.70 | 0.51 | 0.98 | 0.012878 | 0.59 | 0.39 | 0.89 | 0.001016 | 0.65 | 0.51 | 0.84 |
| RFPL3/SLC5A4 region | kgp8110667 | 22 | 32716792 | non-coding | — | GWAS, Additive | 0.004709 | Inf. | — | — | 0.006157 | Inf. | — | — | 7.05E−06 | Inf. | — | — |
| HLA-DQB2/DOB | kgp8817856 | 6 | 32744440 | non-coding | — | Candidate genes (30) + GWAS | 0.00202 | 0.59 | 0.43 | 0.82 | 0.000595 | 0.48 | 0.32 | 0.73 | 1.75E−05 | 0.58 | 0.45 | 0.74 |
| ALOX5AP | rs10162089 | 13 | 31316738 | non-coding | INTRON | Candidate Genes (180) | 0.008386 | 1.56 | 1.12 | 2.16 | 0.028565 | 1.60 | 1.05 | 2.45 | 0.001361 | 1.52 | 1.18 | 1.96 |
| MAGI2 | rs16886004 | 7 | 78021500 | non-coding | INTRON | GWAS, Additive | 0.003923 | 2.01 | 1.25 | 3.24 | 3.71E−05 | 4.80 | 2.04 | 11.31 | 1.41E−06 | 2.53 | 1.69 | 3.79 |
| HLA-DOB/TAP2 | rs1894408 | 6 | 32786833 | non-coding | — | Candidate Genes (30) | 0.005009 | 1.64 | 1.17 | 2.31 | 0.010522 | 1.78 | 1.14 | 2.77 | 1.75E−04 | 1.67 | 1.28 | 2.18 |
| HLA-DRA/DRB1*1501 | rs3135391 | 6 | 32410987 | Synon T118T | EXON | Candidate variants | 0.041273 | 0.66 | 0.45 | 0.98 | 0.056736 | 0.64 | 0.41 | 1.00 | 0.01498 | 0.70 | 0.52 | 0.93 |
| SLC1A4 | rs759458 | 2 | 65245365 | Non-synon V101I | EXON | GWAS, Additive, Extreme | 0.000762 | 1.91 | 1.31 | 2.86 | 0.492021 | 1.18 | 0.75 | 1.88 | 0.001627 | 1.60 | 1.19 | 2.16 |

| Gene(s) | D (Resp.) | D (Non-Resp.) | d (Resp.) | d (Non-Resp.) |
|---|---|---|---|---|
| ZAK/CDCA7 | 3 | 16 | 795 | 346 |
| UVRAG | 37 | 43 | 759 | 319 |
| PTPRT | 11 | 18 | 783 | 344 |
| MBP | 267 | 158 | 529 | 204 |
| RFPL3/SLC5A4 region | 32 | 0 | 764 | 362 |
| HLA-DQB2/DOB | 308 | 191 | 478 | 171 |
| ALOX5AP | 382 | 136 | 410 | 222 |
| MAGI2 | 159 | 32 | 639 | 326 |
| HLA-DOB/TAP2 | 327 | 106 | 465 | 252 |
| HLA-DRA/DRB1*1501 | 162 | 97 | 636 | 265 |
| SLC1A4 | 235 | 75 | 561 | 287 |

TABLE 43-continued

Allelic Model Characteristics of Individual SNPs in Model

Allelic Model, Extreme Phenotype

| Gene(s) | Name | Chr | Position | Mutation | Locations | Source | GALA Cohort Fisher Exact P-Value | Odds Ratio (Minor Allele) | (95% | CI) | Forte Cohort Fisher Exact P-Value |
|---|---|---|---|---|---|---|---|---|---|---|---|
| ZAK/CDCA7 | kgp24415534 | 2 | 174156875 | non-coding | — | GWAS, Additive | 0.08289 | 0.16 | 0.02 | 1.27 | 0.078849 |
| UVRAG | kgp6214351 | 11 | 75546691 | non-coding | INTRON | GWAS, Additive, Extreme | 0.003078 | 0.21 | 0.07 | 0.63 | 0.000229 |
| PTPRT | kgp6599438 | 20 | 40843626 | non-coding | INTRON | Candidate Genes (180) | 0.00588 | 0.00 | — | — | 0.226931 |
| MBP | kgp7747883 | 18 | 74804250 | non-coding | INTRON | Candidate Genes (30) | 0.288087 | 0.76 | 0.48 | 1.21 | 0.050093 |
| RFPL3/SLC5A4 region | kgp8110667 | 22 | 32716792 | non-coding | — | GWAS, Additive | 0.014777 | Inf. | — | — | 0.188468 |
| HLA-DQB2/DOB | kgp8817856 | 6 | 32744440 | non-coding | — | Candidate genes (30) + GWAS | 0.060533 | 0.63 | 0.39 | 1.00 | 0.015048 |
| ALOX5AP | rs10162089 | 13 | 31316738 | non-coding | INTRON | Candidate Genes (180) | 0.007258 | 1.92 | 1.21 | 3.05 | 0.003862 |
| MAGI2 | rs16886004 | 7 | 78021500 | non-coding | INTRON | GWAS, Additive | 0.029731 | 2.10 | 1.08 | 4.08 | 1.30E−02 |
| HLA-DOB/TAP2 | rs1894408 | 6 | 32786833 | non-coding | — | Candidate Genes (30) | 0.086712 | 1.53 | 0.95 | 2.48 | 0.005246 |
| HLA-DRA/DRB1*1501 | rs3135391 | 6 | 32410987 | Synon T118T | EXON | Candidate variants | 0.075291 | 0.59 | 0.34 | 1.03 | 0.031164 |
| SLC1A4 | rs759458 | 2 | 65245365 | Non-synon V101I | EXON | GWAS, Additive, Extreme | 8.18E−05 | 2.97 | 1.72 | 5.12 | 0.049785 |

| | Forte cohort | | | Combined cohort | | | | | | | |
|---|---|---|---|---|---|---|---|---|---|---|---|
| | Odds Ratio (Minor Allele) | (95% | CI) | Fisher Exact P-Value | Odds Ratio (Minor Allele) | (95% | CI) | D (Resp.) | D (Non-Resp.) | d (Resp.) | d (Non-Resp.) |
| ZAK/CDCA7 | 0.00 | — | — | 1.58E−03 | 0.08 | 0.01 | 0.59 | 1 | 10 | 309 | 232 |
| UVRAG | 0.14 | 0.05 | 0.42 | 1.51E−06 | 0.18 | 0.09 | 0.39 | 9 | 34 | 299 | 208 |
| PTPRT | 0.38 | 0.09 | 1.56 | 0.010717 | 0.23 | 0.07 | 0.72 | 4 | 13 | 306 | 229 |
| MBP | 0.54 | 0.31 | 0.97 | 0.009895 | 0.63 | 0.44 | 0.89 | 99 | 104 | 209 | 138 |
| RFPL3/SLC5A4 region | Inf. | — | — | 0.003203 | Inf. | — | — | 11 | 0 | 299 | 242 |
| HLA-DQB2/DOB | 0.49 | 0.28 | 0.86 | 2.35E−03 | 0.59 | 0.42 | 0.82 | 113 | 121 | 193 | 121 |
| ALOX5AP | 2.46 | 1.34 | 4.54 | 0.000699 | 1.82 | 1.29 | 2.58 | 155 | 85 | 153 | 153 |
| MAGI2 | 3.30 | 1.24 | 8.78 | 7.06E−04 | 2.43 | 1.44 | 4.08 | 61 | 22 | 249 | 218 |
| HLA-DOB/TAP2 | 2.45 | 1.30 | 4.61 | 1.58E−03 | 1.80 | 1.26 | 2.59 | 125 | 67 | 181 | 175 |
| HLA-DRA/DRB1*1501 | 0.50 | 0.27 | 0.93 | 0.008266 | 0.58 | 0.39 | 0.86 | 59 | 70 | 251 | 172 |
| SLC1A4 | 1.93 | 1.02 | 3.65 | 2.38E−06 | 2.61 | 1.74 | 3.90 | 111 | 43 | 197 | 199 |

TABLE 44a

Genotypic Model Characteristics of Individual SNPs in Model

Allelic Model

| | | | | | | | GALA Cohort | | | | Forte |
|---|---|---|---|---|---|---|---|---|---|---|---|
| Gene(s) | Name | Chr | Position | Mutation | Locations | Source | Fisher Exact P-Value | Odds Ratio (Minor Allele) | (95% | CI) | Cohort Fisher Exact P-Value |
| ZAK/ CDCA7 | kgp24415534 | 2 | 174156875 | non-coding | — | GWAS, Additive | 6.03E−05 | 0.05 | 0.01 | 0.37 | 0.028468 |
| UVRAG | kgp6214351 | 11 | 75546691 | non-coding | INTRON | GWAS, Additive, Extreme | 0.004741 | 0.42 | 0.23 | 0.77 | 0.001081 |
| PTPRT | kgp6599438 | 20 | 40843626 | non-coding | INTRON | Candidate Genes (180) | 0.005974 | 0.21 | 0.07 | 0.68 | 0.025262 |
| MBP | kgp7747883 | 18 | 74804250 | non-coding | INTRON | Candidate Genes (30) | 0.042737 | 0.70 | 0.51 | 0.98 | 0.012878 |
| RFPL3/ SLC5A4 region | kgp8110667 | 22 | 32716792 | non-coding | — | GWAS, Additive | 0.004709 | Inf. | — | — | 0.006157 |
| HLA-DQB2/ DOB | kgp8817856 | 6 | 32744440 | non-coding | — | Candidate genes (30) + GWAS | 0.00202 | 0.59 | 0.43 | 0.82 | 0.000595 |
| ALOX5AP | rs10162089 | 13 | 31316738 | non-coding | INTRON | Candidate Genes (180) | 0.008386 | 1.56 | 1.12 | 2.16 | 0.028565 |
| MAGI2 | rs16886004 | 7 | 78021500 | non-coding | INTRON | GWAS, Additive | 0.003923 | 2.01 | 1.25 | 3.24 | 3.71E−05 |
| HLA-DOB/ TAP2 | rs1894408 | 6 | 32786833 | non-coding | — | Candidate Genes (30) | 0.005009 | 1.64 | 1.17 | 2.31 | 0.010522 |
| HLA-DRA/ DRB1*1501 | rs3135391 | 6 | 32410987 | Synon T118T | EXON | Candidate variants | 0.041273 | 0.66 | 0.45 | 0.98 | 0.056736 |
| SLC1A4 | rs759458 | 2 | 65245365 | Nonsynon V101I | EXON | GWAS, Additive, Extreme | 0.000762 | 1.94 | 1.31 | 2.86 | 0.492021 |

| | Forte Cohort | | | Combined cohort | | | | | | | |
|---|---|---|---|---|---|---|---|---|---|---|---|
| Gene(s) | Odds Ratio (Minor Allele) | (95% | CI) | Fisher Exact P-Value | Odds Ratio (Minor Allele) | (95% | CI) | D (Resp.) | D (Non-Resp.) | d (Resp.) | d (Non-Resp.) |
| ZAK/ CDCA7 | 0.15 | 0.03 | 0.82 | 2.28E−06 | 0.08 | 0.02 | 0.28 | 3 | 16 | 795 | 346 |
| UVRAG | 0.29 | 0.14 | 0.60 | 1.60E−05 | 0.36 | 0.23 | 0.57 | 37 | 43 | 759 | 319 |
| PTPRT | 0.29 | 0.10 | 0.85 | 0.000764 | 0.27 | 0.13 | 0.57 | 11 | 18 | 783 | 344 |
| MBP | 0.59 | 0.39 | 0.89 | 0.001016 | 0.65 | 0.51 | 0.84 | 267 | 158 | 529 | 204 |
| RFPL3/ SLC5A4 region | Inf. | — | — | 7.05E−06 | Inf. | — | — | 32 | 0 | 764 | 362 |
| HLA-DQB2/ DOB | 0.48 | 0.32 | 0.73 | 1.75E−05 | 0.58 | 0.45 | 0.74 | 308 | 191 | 478 | 171 |
| ALOX5AP | 1.60 | 1.05 | 2.45 | 0.001361 | 1.52 | 1.18 | 1.96 | 382 | 136 | 410 | 222 |
| MAGI2 | 4.80 | 2.04 | 11.31 | 1.41E−06 | 2.53 | 1.69 | 3.79 | 159 | 32 | 639 | 326 |
| HLA-DOB/ TAP2 | 1.78 | 1.14 | 2.77 | 1.75E−04 | 1.67 | 1.28 | 2.18 | 327 | 106 | 465 | 252 |
| HLA-DRA/ DRB1*1501 | 0.64 | 0.41 | 1.00 | 0.01498 | 0.70 | 0.52 | 0.93 | 162 | 97 | 636 | 265 |
| SLC1A4 | 1.18 | 0.75 | 1.88 | 0.001627 | 1.60 | 1.19 | 2.16 | 235 | 75 | 561 | 287 |

Allelic Model, Extreme Phenotype

| | | | | | | | GALA Cohort | | | | Forte |
|---|---|---|---|---|---|---|---|---|---|---|---|
| Gene(s) | Name | Chr | Position | Mutation | Locations | Source | Fisher Exact P-Value | Odds Ratio (Minor Allele) | (95% | CI) | Cohort Fisher Exact P-Value |
| ZAK/ CDCA7 | kgp24415534 | 2 | 174156875 | non-coding | — | GWAS, Additive | 0.08289 | 0.16 | 0.02 | 1.27 | 0.078849 |

TABLE 44a-continued

Genotypic Model Characteristics of Individual SNPs in Model

| Gene | SNP-kgp | Chr | Position | Coding | Region | Source | P-value | OR | 95% low | 95% high | Fisher P |
|---|---|---|---|---|---|---|---|---|---|---|---|
| UVRAG | kgp6214351 | 11 | 75546691 | non-coding | INTRON | GWAS, Additive, Extreme | 0.003078 | 0.21 | 0.07 | 0.63 | 0.000229 |
| PTPRT | kgp6599438 | 20 | 40843626 | non-coding | INTRON | Candidate Genes (180) | 0.00588 | 0.00 | — | — | 0.226931 |
| MBP | kgp7747883 | 18 | 74804250 | non-coding | INTRON | Candidate Genes (30) | 0.288087 | 0.76 | 0.48 | 1.21 | 0.050093 |
| RFPL3/ SLC5A4 region | kgp8110667 | 22 | 32716792 | non-coding | — | GWAS, Additive | 0.014777 | Inf. | — | — | 0.188468 |
| HLA-DQB2/ DOB | kgp8817856 | 6 | 32744440 | non-coding | — | Candidate genes (30) + GWAS | 0.060533 | 0.63 | 0.39 | 1.00 | 0.015048 |
| ALOX5AP | rs10162089 | 13 | 31316738 | non-coding | INTRON | Candidate Genes (180) | 0.007258 | 1.92 | 1.21 | 3.05 | 0.003862 |
| MAGI2 | rs16886004 | 7 | 78021500 | non-coding | INTRON | GWAS, Additive | 0.029731 | 2.10 | 1.08 | 4.08 | 1.30E−02 |
| HLA-DOB/ TAP2 | rs1894408 | 6 | 32786833 | non-coding | — | Candidate Genes (30) | 0.086712 | 1.53 | 0.95 | 2.48 | 0.005246 |
| HLA-DRA/ DRB1*1501 | rs3135391 | 6 | 32410987 | Synon T118T | EXON | Candidate variants | 0.075291 | 0.59 | 0.34 | 1.03 | 0.031164 |
| SLC1A4 | rs759458 | 2 | 65245365 | Nonsynon V101I | EXON | GWAS, Additive, Extreme | 8.18E−05 | 2.97 | 1.72 | 5.12 | 0.049785 |

| | Forte Cohort | | | Combined cohort | | | | | | |
|---|---|---|---|---|---|---|---|---|---|---|
| Gene(s) | Odds Ratio (Minor Allele) | (95% | CI) | Fisher Exact P-Value | Odds Ratio (Minor Allele) | (95% | CI) | D (Resp.) | D (Non-Resp.) | d (Resp.) | d (Non-Resp.) |
| ZAK/ CDCA7 | 0.00 | — | — | 1.58E−03 | 0.08 | 0.01 | 0.59 | 1 | 10 | 309 | 232 |
| UVRAG | 0.14 | 0.05 | 0.42 | 1.51E−06 | 0.18 | 0.09 | 0.39 | 9 | 34 | 299 | 208 |
| PTPRT | 0.38 | 0.09 | 1.56 | 0.010717 | 0.23 | 0.07 | 0.72 | 4 | 13 | 306 | 229 |
| MBP | 0.54 | 0.31 | 0.97 | 0.009895 | 0.63 | 0.44 | 0.89 | 99 | 104 | 209 | 138 |
| RFPL3/ SLC5A4 region | Inf. | — | — | 0.003203 | Inf. | — | — | 11 | 0 | 299 | 242 |
| HLA-DQB2/ DOB | 0.49 | 0.28 | 0.86 | 2.35E−03 | 0.59 | 0.42 | 0.82 | 113 | 121 | 193 | 121 |
| ALOX5AP | 2.46 | 1.34 | 4.54 | 0.000699 | 1.82 | 1.29 | 2.58 | 155 | 85 | 153 | 153 |
| MAGI2 | 3.30 | 1.24 | 8.78 | 7.06E−04 | 2.43 | 1.44 | 4.08 | 61 | 22 | 249 | 218 |
| HLA-DOB/ TAP2 | 2.45 | 1.30 | 4.61 | 1.58E−03 | 1.80 | 1.26 | 2.59 | 125 | 67 | 181 | 175 |
| HLA-DRA/ DRB1*1501 | 0.50 | 0.27 | 0.93 | 0.008266 | 0.58 | 0.39 | 0.86 | 59 | 70 | 251 | 172 |
| SLC1A4 | 1.93 | 1.02 | 3.65 | 2.38E−06 | 2.61 | 1.74 | 3.90 | 111 | 43 | 197 | 199 |

TABLE 44b

Genotypic Model Characteristics of Individual SNPs in Model

| SNP-rs | SNP-kgp |
|---|---|
| rs759458 | |
| rs139890339 | kgp24415534 |
| rs3135391 | |
| rs28724893 | kgp8817856 |
| rs1894408 | |
| rs16886004 | |
| rs80191572 | kgp6214351 |
| rs10162089 | |
| rs1789054 | kgp7747883 |
| rs117602254 | kgp6599438 |
| rs73166319 | kgp8110667 |

Example 17 Preliminary Predictive Model: Clinical and Genetic Factors Combined

A predictive model was generated based on the 11 SNPs shown in tables 42, 43, 44a and 44b and the two Clinical co-variants shown in table 33.

Receiver Operating Characteristic (ROC) analysis was performed using the actual value (case or control) and predicted value for each sample from the multi-marker regression model (FIG. 1). For these preliminary analyses, two risk groups were defined using the predicted values from the multi-marker regression model. The predictive threshold value was set at 0.71 (termed "model 3") based on a variety of factors after consultation with the Teva team and Teva MS clinical experts.

Figure 2:
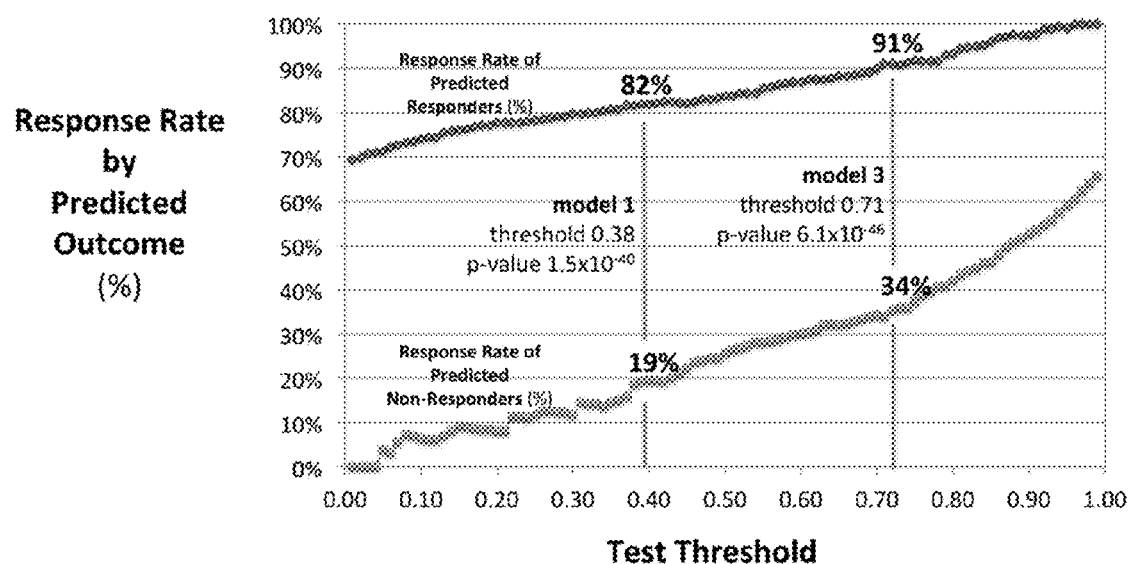
FIG. 2. shows Response Rate of Predicted Responders (green line) and Response Rate of Predicted Non-Responders (red line) by predictive test threshold.
Figure 3:
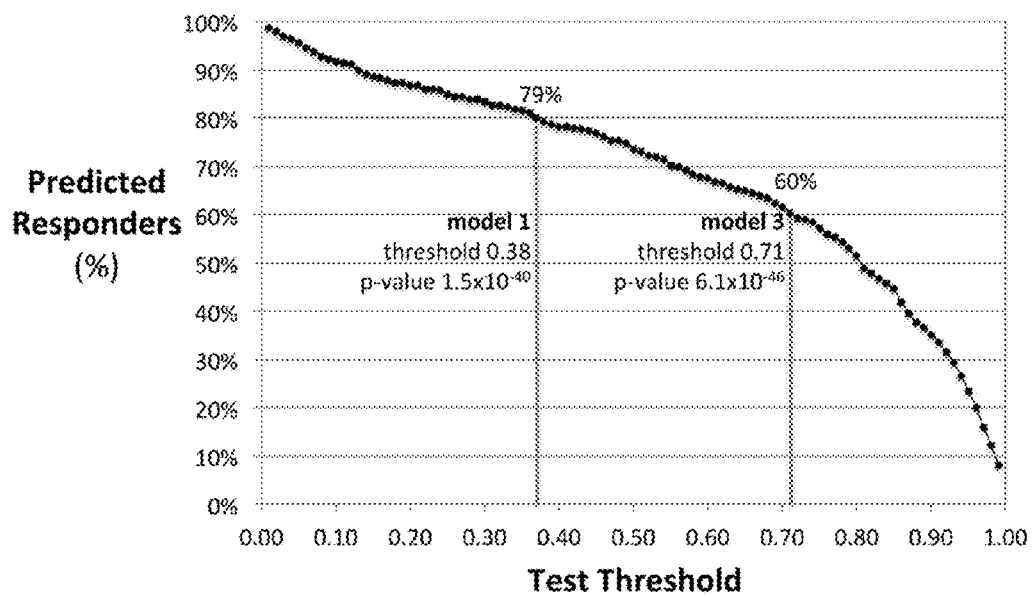
FIG. 3. shows overall percent of Predicted Responders by predictive test threshold.
Figure 4:
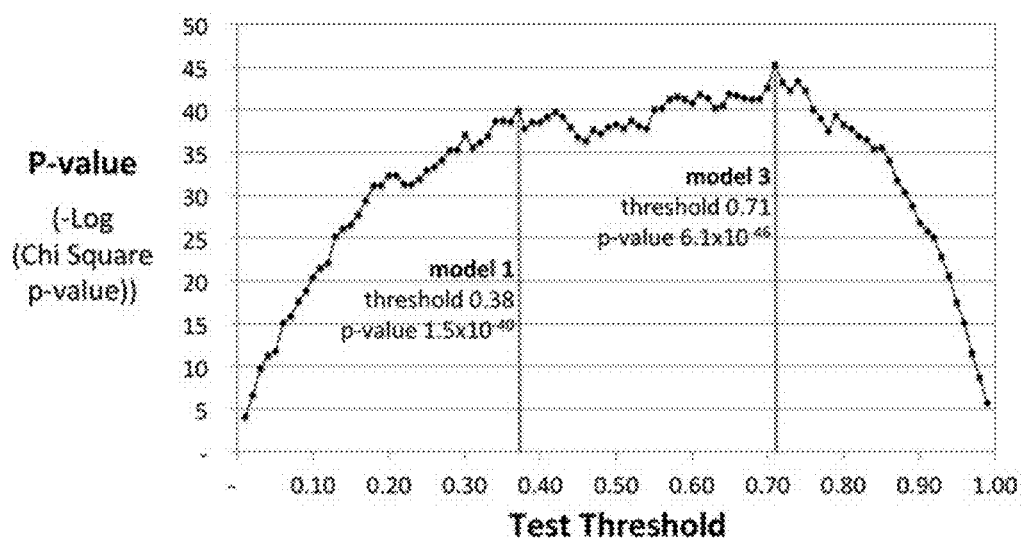
FIG. 4. shows chi square P-values (−Log P-value) of different test thresholds in the ability of the test to differentiate between cases and controls. A threshold of 0.71 demonstrated the most significant p-value.

Ultimately, a threshold that best differentiated between responders and non-responders (minimum positive predictive value of 90% or higher) (FIG. 2), while maximizing the number of predicted responders (predicted responders >60% (FIG. 3) was selected. This threshold also coincided with the lowest p-value of all the thresholds examined (Chi square p-value $6.1 \times 10^{-46}$, odds ratio 19.9) (FIG. 4). The positive predictive value of all predicted value (% of all predicted responders to be true responders) was 91.1%, sensitivity (% of all true responders detected) was 80.2%; specificity (% of all true non-responders classified as non-responders) was 83.1%; and the negative predictive value (% of all true non-responders classified as non-responders) was 65.9%.

Example 18 Patient Responses Predicted by the Preliminary Predictive Model

Figure 5:
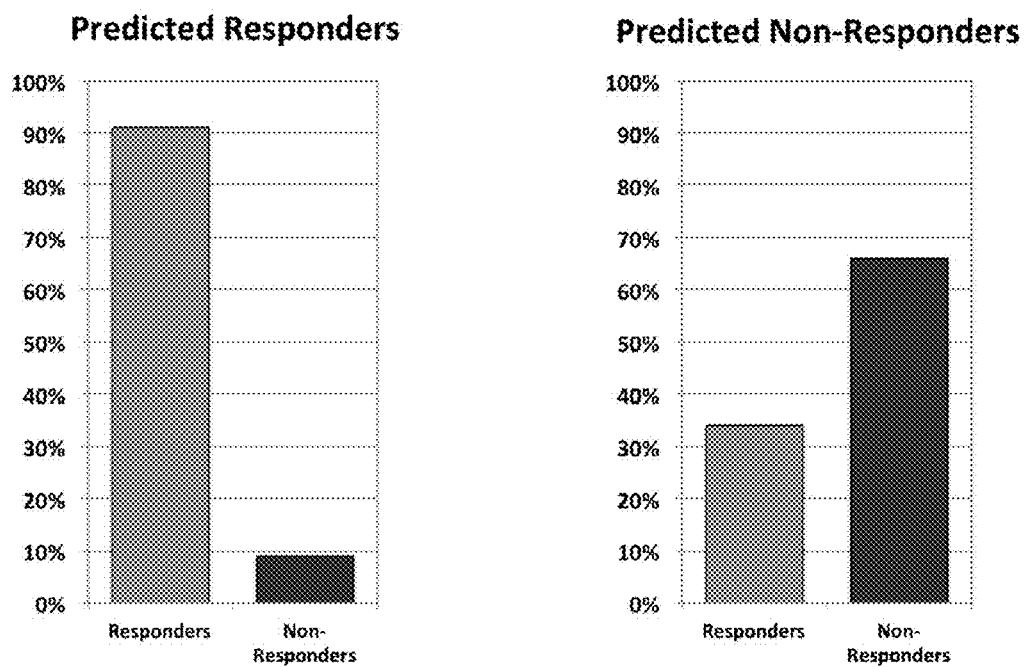
FIG. 5. shows overall Response to glatiramer acetate as Predicted by Model (model 3, threshold 0.71) for Predicted Responders (left panel) and Predicted Non-Responders (right panel).

For the genotyped patients of the Gala and Forte cohorts, based on the predictive model, 60% of patients were classified as "predicted responders" with a response rate of 91.1% (as defined by the a priori definition of responders and non-responders). While 40% of patients were classified as "predicted non-responders" with an overall response rate of 34% (FIG. 5).

Compared to the "predicted non-responders", the "predicted responders" exhibited a 2.7-fold improved response rate (91% vs. 34%) ($P<10^{-40}$); and the "predicted responders" had a 34% improvement in response rate compared to the overall cohort (68% vs. 91%).

The annualized relapse rate (ARR) of the "predicted responders" (0.21±0.03 standard error of the mean) was reduced (improved) by 60% compared to the overall patient cohort (0.53±0.04), and reduced (improved) by 80% compared to the "predicted non-responders" (1.04±0.08) (p-value $2.2 \times 10^{-25}$).

The number of confirmed relapses (nrelapse) of the "predicted responders" (0.19±0.03 standard error of the mean) was reduced (improved) by 58% compared to the overall patient cohort (0.46±0.03), and reduced (improved) by 78% compared to the "predicted non-responders" (0.88±0.06) (p-value $7.70 \times 10^{-32}$).

The number of T1 enhancing lesions at month 12 was significantly reduced (improved) by 47% in the "predicted responders" compared to the "predicted non-responders" (0.91±0.18 versus 1.70±0.38; p-value 0.043). Similarly, EDSS progression was significantly delayed (improved) by 72% in the "predicted responders" versus the "predicted non-responders" (0.03±0.01 vs. 0.10±0.02; p-value 0.00095), and showed a strong trend with a 49% reduced progression compared to the overall cohort (value 0.057, p-value 0.08).

Predictive Modeling

A predictive model based on the identified markers was developed and tested in the full cohorts, including intermediate responders. Additional independent cohorts are used to evaluate and confirm the predictive model.

DNA was collected from consenting RRMS patients in one year GALA study (40 mg Copaxone TIW, or placebo) and one year FORTE study (20 mg Copaxone or 40 mg Copaxone daily) ("PGx population") (Table 45) The PGx (i.e. the population studied for genetic analyses) and ITT (intent to treat) populations did not differ on baseline characteristics.

Figure 6:
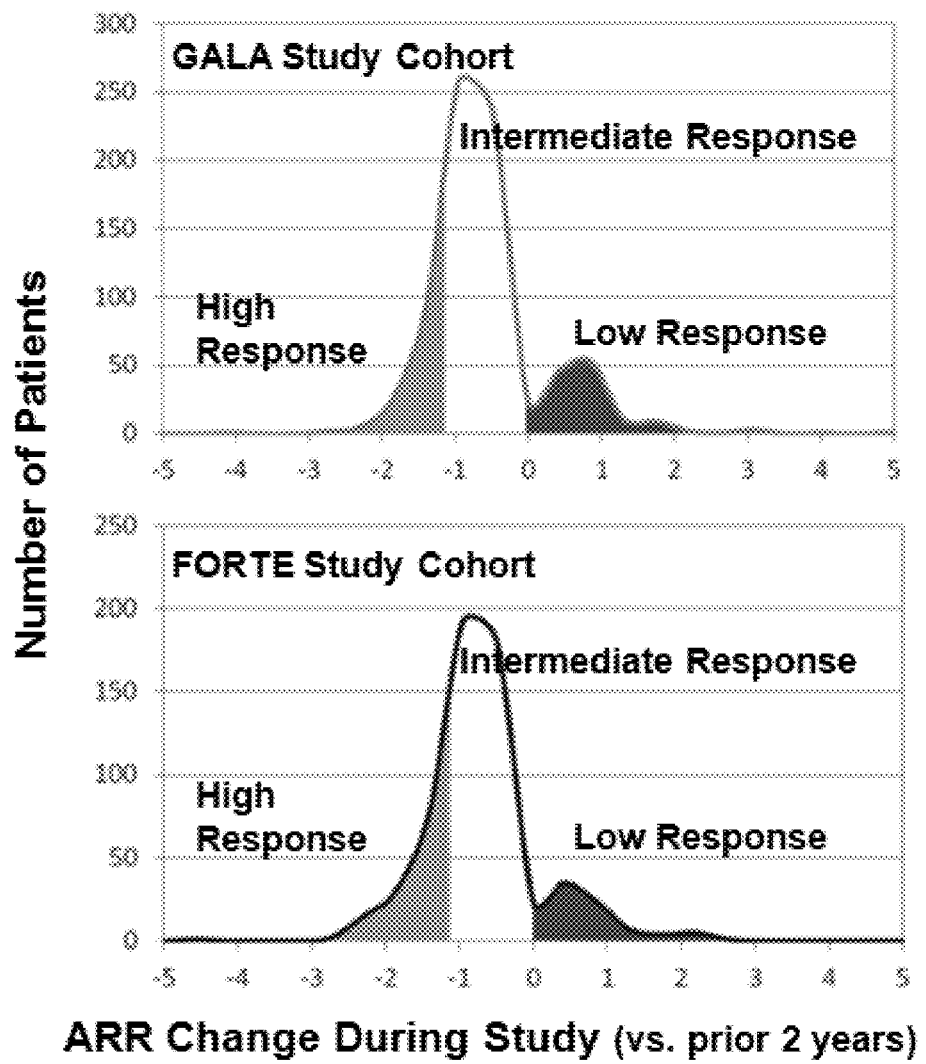
FIG. 6. shows GALA and FORTE patients were stratified by clearly defined response. High Response: improved ARR (ARR change <(−1), during study versus prior 2 years). Low Response: no change or worsening of ARR (ARR change ≥0, during study versus previous 2 years).

To identify genetic markers associated with high response to Copaxone® comprising the following characteristics: (1) high response as measured by ARR reductions, (2) predictive, not prognostic, markers: associated with response only in Copaxone®-treated patients, and not in the placebo group, (3) markers that are confirmed in an independent cohort, and (4) a subset of GALA and FORTE studies' patients with clearly defined response phenotypes (high responders versus low responders) (FIG. 6) Patient DNA samples were genotyped for 4.3 million genetic variants (Illumina HumanOmni5 array).

Association analysis, using a tiered candidate-marker and genome-wide approach, was conducted in the GALA cohort to identify GA-specific response-associated SNPs. SNPs that were not associated with placebo response and that replicated in the FORTE cohort, were selected for modeling.

Regression analysis was applied, with the threshold for distinguishing responders from non-responders was selected by analysis of receiver-operator curves. Intermediate responders were genotyped by either Illumina 5M array or focused taqman-based SNP genotyping and Sanger sequencing.

Figure 7:
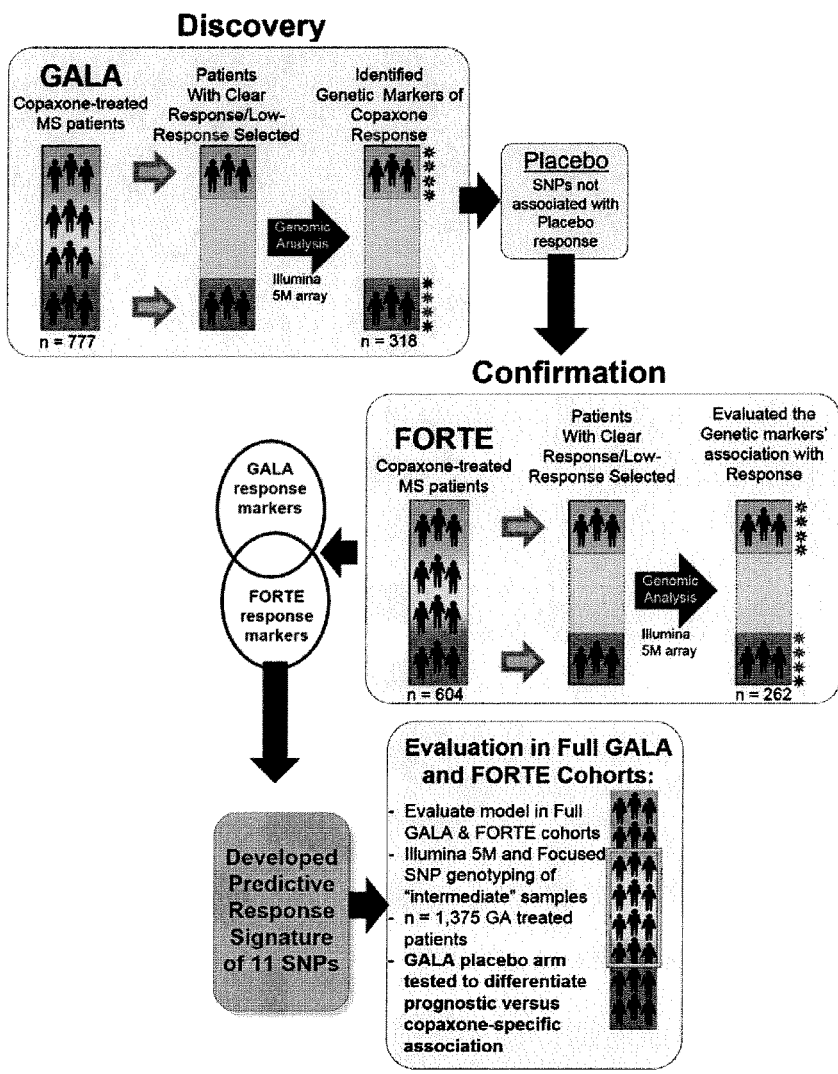
FIG. 7. shows predictive model building for GALA and FORTE cohorts.

The SNP-signature was evaluated in the full GALA/FORTE population including intermediate patients (FIG. 7). In the high reponse/low response subgroups of both GALA and FORTE, the SNP signature exhibited highly predictive characteristics (OR 6 to 8, p-value$<10^{-11}$) (Table 46). Validation of the identified model can be applied to additional independent cohorts.

The signature was associated with Copaxone®, and not placebo-response since 129 placebo-treated patients were predicted to be high Copaxone®-responders based on the signature. These patients do not show ARR reduction when treated with placebo (3% ARR reduction versus remaining placebo patients who provided DNA samples (n=252)) The SNP signature was significantly associated with high response to Copaxone in both GALA and FORTE (OR of 1.9 to 3.8, p<0.002 including sensitivity analysis) and not in placebo (OR of 0.9 to 1.2, NS).

Genetic association with response to Copaxone®, and not placebo, was identified. In Copaxone® naïve RRMS patients, the 11 SNP signature identifies high Copaxone® responders who exhibit significantly greater reductions in ARR compared to the average response observed in Copaxone® clinical trials.

TABLE 45

Baseline characteristics of PGx and ITT populations

| Study | GALA | | FORTE | |
|---|---|---|---|---|
| Population | ITT | PGx | ITT | PGx |
| N | 1404 | 1158 (82%) | 1155 | 604 (52%) |
| Age (Ave ± SD) | 37.6 ± 9.35 | 37.71 ± 9.38 | 36.27 ± 8.99 | 35.97 ± 8.82 |
| Gender (% Female) | 67.90% | 67.90% | 71.70% | 72.20% |
| Caucasian | 97.60% | 97.90% | 95.20% | 100% |
| Disease duration (years) | 3.76 ± 4.9 | 3.74 ± 4.94 | 3.16 ± 4.41 | 2.86 ± 4.05 |
| No. of Relapses in the Last 2 Years | 1.91 ± 0.91 | 1.89 ± 0.92 | 2.01 ± 1.00 | 1.97 ± 0.89 |
| Baseline EDSS | 2.79 ± 1.23 | 2.77 ± 1.21 | 2.12 ± 1.12 | 2.13 ± 1.12 |

TABLE 46

Genes of the 11 SNP Signature

| Genes of 11-SNP Signature * | GALA GA-treated OR | FORTE GA-treated OR |
|---|---|---|
| HLA-DRB1*15:01 | 0.7 | 0.6 |
| HLA gene region | 1.7 | 1.8. |
| Myelin basic protein gene | 0.7 | 0.6 |
| Receptor-tyrosine protein phosphatase gene | 0.2 | 0.3 |
| Arachidonate 5-lipoxygenase-activating protein | 1.6 | 1.6 |
| Membrane-associated guanylate kinase | 2.2 | 5.6 |
| Solute carrier family 5 (low affinity glucose co-transporter) gene | Inf. | Inf. |
| HLA gene region | 0.5 | 0.5 |
| Mitogen-activated protein kinase gene region | 0.05 | 0.1 |
| Radiation resistance-associated gene protein | 0.2 | 0.1 |
| Glutamate/neutral amino acid transporter | 3.3 | 1.9 |

*All SNPs met statistical significance

Example 19

Additional genotyping of the 11 SNPs of the predictive model (rs3135391, rs1894408, kgp7747883, kpg6599438, rs10162089, rs16886004, kgp8110667, kgp8817856, kgp24415534, kgp6214351, rs759458) was conducted on the remaining portion of the patients from the GALA and FORTE cohorts, for which DNA was available (FIG. 8).

When analysis was conducted for all genotyped patients of the Gala and FORTE cohorts, based on the predictive model (11 SNPs and 2 clinical variables), 34% of GALA, and 42% of FORTE-patients were classified as "predicted responders".

In the GALA Copaxone treated patients, the annualized relapse rate (ARR) of the "predicted responders" (0.185±0.032 standard error of the mean) was reduced (improved) by 51% compared to the "predicted non-responders" (0.374±0.038) (p-value=0.0028) and by 64% compared to the placebo (0.510±0.062) (p-value<0.0001).

In the FORTE Copaxone treated patients, the annualized relapse rate (ARR) of the "predicted responders" (0.102±0.020 standard error of the mean) was reduced (improved) by 72% compared to the "predicted non-responders" (0.368±0.039) (p-value<0.0001).

In some embodiments, the at least one single nucleotide polymorphisms (SNPs) are selected from the group consisting of kgp24415534, kgp6214351, kgp6599438, kgp7747883, kgp8110667, kgp8817856, rs10162089, rs16886004, rs1894408, rs3135391, and rs759458.

In some embodiments, the at least one single nucleotide polymorphisms (SNPs) comprise 2, 3, 4, 5, 6, 7, 8, 9 or 10 of the SNPs selected from the group consisting of kgp24415534, kgp6214351, kgp6599438, kgp7747883, kgp8110667, kgp8817856, rs10162089, rs16886004, rs1894408, rs3135391 and rs759458.

In some embodiments, the at least one single nucleotide polymorphisms (SNPs) are selected from the group consisting of kgp24415534, kgp6214351, kgp6599438, kgp7747883, kgp8110667, kgp8817856, rs10162089, rs16886004, rs1894408, and rs759458.

In some embodiments, the at least one single nucleotide polymorphisms (SNPs) comprise 2, 3, 4, 5, 6, 7, 8, 9 or 10 of the SNPs selected from the group consisting of kgp24415534, kgp6214351, kgp6599438, kgp7747883, kgp8110667, kgp8817856, rs10162089, rs16886004, rs1894408 and rs759458.

In some embodiments, the at least one SNPs is selected from the group further comprising rs3135391.

In some embodiments, if rs3135391 is the at least one SNP selected, then selecting at least one SNP other than rs3135391.

In some embodiments, the genotype of the subject at the location corresponding to the location of one or more of the SNPs is determined by indirect genotyping.

In some embodiments, the genotype of the subject at the location corresponding to the location of one or more of the SNPs is determined indirectly by determining the genotype of the subject at a location corresponding to the location of at least one SNP that is in linkage disequilibrium with the one or more SNPs.

In some embodiments, the genotype is determined at locations corresponding to the locations of 2, 3, 4, 5, 6, 7, 8, 9, 10, 11, 12, 13, 14, 15, 16, or more SNPs.

In some embodiments, one or more SNPs is selected from the group consisting of kgp24415534, kgp6214351, kgp6599438, kgp7747883, kgp8110667, kgp8817856, rs10162089, rs16886004, rs1894408, rs3135391, and rs759458.

In some embodiments, one or more SNPs comprise 2, 3, 4, 5, 6, 7, 8, or 10 of the SNPs selected from the group consisting of kgp24415534, kgp6214351, kgp6599438, kgp7747883, kgp8110667, kgp8817856, rs10162089, rs16886004, rs1894408, rs3135391, and rs759458.

In some embodiments, one or more SNPs is selected from the group consisting of kgp24415534, kgp6214351, kgp6599438, kgp7747883, kgp8110667, kgp8817856, rs10162089, rs16886004, rs1894408, and rs759458.

In some embodiments, one or more SNPs comprise 2, 3, 4, 5, 6, 7, 8, or 10 of the SNPs selected from the group consisting of kgp24415534, kgp6214351, kgp6599438, kgp7747883, kgp8110667, kgp8817856, rs10162089, rs16886004, rs1894408, and rs759458.

In some embodiments, the one or more SNPs is selected from the group further comprising rs3135391.

In some embodiments, if rs3135391 is the one SNP selected, then selecting at least one SNP other than rs3135391.

In some embodiments, the method further comprising applying the algorithm depicted in FIG. 8 or FIG. 9 to identify the subject as a predicted responder or as a predicted non-responder to glatiramer acetate.

In some embodiments the kit for identifying a human subject afflicted with multiple sclerosis or a single clinical attack consistent with multiple sclerosis as a predicted responder or as a predicted non-responder to glatiramer acetate, or for identifying a human subject afflicted with multiple sclerosis or a single clinical attack consistent with multiple sclerosis who is predicted to have a slower course of disease progression, the kit comprising
   a) at least one probe specific for a location corresponding to the location of at least one SNP;
   b) at least one pair of PCR primers designed to amplify a DNA segment which includes a location corresponding to the location of at least one SNP;
   c) at least one pair of PCR primers designed to amplify a DNA segment which includes a location corresponding to the location of at least one SNP and at least one probe specific for a location corresponding to the location of at least one SNP;
   d) a reagent for performing a method selected from the group consisting of restriction fragment length polymorphism (RFLP) analysis, sequencing, single strand conformation polymorphism analysis (SSCP), chemical cleavage of mismatch (CCM), gene chip and denaturing high performance liquid chromatography (DHPLC) for determining the identity of at least one SNP; or e) reagents for TaqMan Open Array assay designed for determining the genotype at a location corresponding to the location of at least one SNP, wherein the at least one SNP is selected from the group consisting of kgp24415534, kgp6214351, kgp6599438, kgp7747883, kgp8110667, kgp8817856, rs10162089, rs16886004, rs1894408, rs3135391, and rs759458; or wherein the at least one SNP is selected from the group consisting of kgp24415534, kgp6214351, kgp6599438, kgp7747883, kgp8110667, kgp8817856, rs10162089, rs16886004, rs1894408, and rs759458.

In some embodiments, the kit further comprising applying the algorithm depicted in FIG. 8 or FIG. 9 to identify the subject as a predicted responder or as a predicted non-responder to glatiramer acetate.

Example 20

Analysis was conducted for all genotyped patients of the Gala and FORTE cohorts, based on the 11 SNPs in the predictive model, but without including the clinical variables, and using a threshold at ~30% of the population classified as "predicted responders" (FIG. 9).

In the GALA Copaxone treated patients, the annualized relapse rate (ARR) of the "predicted responders" (0.131±0.026 standard error of the mean) was reduced (improved) by 62% compared to the "predicted non-responders" (0.382±0.037) (p-value<0.0001) and by 71% compared to the placebo (0.488±0.058) (p-value<0.0001).

In the FORTE Copaxone treated patients, the annualized relapse rate (ARR) of the "predicted responders" (0.145±0.029 standard error of the mean) was reduced (improved) by 50% compared to the "predicted non-responders" (0.290±0.03) (p-value=0.0113).

In some embodiments, the method further comprising applying the algorithm depicted in FIG. 9 to identify the subject as a predicted responder or as a predicted non-responder to glatiramer acetate.

In some embodiments, the method further comprising applying the algorithm depicted in FIG. 8 or FIG. 9 to identify the subject as a predicted responder or as a predicted non-responder to glatiramer acetate.

In some embodiments, the kit further comprising applying the algorithm depicted in FIG. 8 or FIG. 9 to identify the subject as a predicted responder or as a predicted non-responder to glatiramer acetate.

Example 21

Additional genotyping of 10 SNPs of the predictive model (rs3135391, rs1894408, kpg6599438, rs10162089, rs16886004, kgp8110667, kgp8817856, kgp24415534, kgp6214351, rs759458) was conducted on the remaining portion of the patients from the GALA and FORTE cohorts, for which DNA was available.

When analysis was conducted for all genotyped patients of the Gala and FORTE cohorts, based on the 10 SNPs and 2 clinical variables, 34% of GALA, and 42% of FORTE-patients were classified as "predicted responders".

In the GALA Copaxone treated patients, the annualized relapse rate (ARR) of the "predicted responders" (0.185±0.032 standard error of the mean) was reduced (improved) by 51% compared to the "predicted non-responders" (0.374±0.038) (p-value=0.0028) and by 64% compared to the placebo (0.510±0.062) (p-value<0.0001).

In the FORTE Copaxone treated patients, the annualized relapse rate (ARR) of the "predicted responders" (0.102±0.020 standard error of the mean) was reduced (improved) by 72% compared to the "predicted non-responders" (0.368±0.039) (p-value<0.0001).

In some embodiments, the genotype is determined at locations corresponding to the locations of 2, 3, 4, 5, 6, 7, 8, 9, 10, 11, 12, 13, 14, 15, 16, or more SNPs.

In some embodiments, one or more SNPs is selected from the group consisting of kgp24415534, kgp6214351, kgp6599438, kgp8110667, kgp8817856, rs10162089, rs16886004, rs1894408, rs3135391, and rs759458.

In some embodiments, one or more SNPs is selected from the group consisting of kgp24415534, kgp6214351, kgp6599438, kgp8110667, kgp8817856, rs10162089, rs16886004, rs1894408, and rs759458.

In some embodiments, one or more SNPs is selected from the group further comprising rs3135391.

In some embodiments, one or more SNPs comprise 2, 3, 4, 5, 6, 7, 8, 9 or 10 of the SNPs selected from the group consisting of kgp24415534, kgp6214351, kgp6599438, kgp8110667, kgp8817856, rs10162089, rs16886004, rs1894408, rs3135391, and rs759458.

In some embodiments, if rs3135391 is the one SNP selected, then selecting at least one SNP other than rs3135391.

In some embodiments, the at least one single nucleotide polymorphisms (SNPs) comprise 2, 3, 4, 5, 6, 7, 8, 9 or 10 of the SNPs selected from the group consisting of kgp24415534, kgp6214351, kgp6599438, kgp8110667, kgp8817856, rs10162089, rs16886004, rs1894408, rs3135391 and rs759458.

In some embodiments, if rs3135391 is the at least one SNP selected, then selecting at least one SNP other than rs3135391.

In some embodiments, the at least one SNP is selected from the group further comprising rs3135391.

In some embodiments, the genotype of the subject at the location corresponding to the location of one or more of the SNPs is determined by indirect genotyping.

In some embodiments, the genotype of the subject at the location corresponding to the location of one or more of the SNPs is determined indirectly by determining the genotype of the subject at a location corresponding to the location of at least one SNP that is in linkage disequilibrium with the one or more SNPs.

In some embodiments the kit for identifying a human subject afflicted with multiple sclerosis or a single clinical attack consistent with multiple sclerosis as a predicted responder or as a predicted non-responder to glatiramer acetate, or for identifying a human subject afflicted with multiple sclerosis or a single clinical attack consistent with multiple sclerosis who is predicted to have a slower course of disease progression, the kit comprising a) at least one probe specific for a location corresponding to the location of at least one SNP;

b) at least one pair of PCR primers designed to amplify a DNA segment which includes a location corresponding to the location of at least one SNP;

c) at least one pair of PCR primers designed to amplify a DNA segment which includes a location corresponding to the location of at least one SNP and at least one probe specific for a location corresponding to the location of at least one SNP;

d) a reagent for performing a method selected from the group consisting of restriction fragment length polymorphism (RFLP) analysis, sequencing, single strand conformation polymorphism analysis (SSCP), chemical cleavage of mismatch (CCM), gene chip and denaturing high performance liquid chromatography (DHPLC) for determining the identity of at least one SNP; or e) reagents for TaqMan Open Array assay designed for determining the genotype at a location corresponding to the location of at least one SNP, wherein the at least one SNP is selected from the group consisting of kgp24415534, kgp6214351, kgp6599438, kgp8110667, kgp8817856, rs10162089, rs16886004, rs1894408, rs3135391, and rs759458; or wherein the at least one SNP is selected from the group consisting of kgp24415534, kgp6214351, kgp6599438, kgp8110667, kgp8817856, rs10162089, rs16886004, rs1894408, and rs759458.

In some embodiments, the method further comprising applying the algorithm depicted in FIG. 8 or FIG. 9 to identify the subject as a predicted responder or as a predicted non-responder to glatiramer acetate.

In some embodiments, the kit further comprising applying the algorithm depicted in FIG. 8 or FIG. 9 to identify the subject as a predicted responder or as a predicted non-responder to glatiramer acetate.

Biology of High Response to Copaxone®

Identified genes are associated with Copaxone® (glatiramer acetate, or GA) mechanism of action. These genes include: (1) Myelin Basic Protein (MBP), which is associated with Copaxone® response (38), and Copaxone® designed to mimic MBP; (2) MHC region (3 SNPs), including HLA-DRB1*15:01 (37) involved in antigen processing and presentation and is associated with Copaxone® response and MS susceptibility or severity; and (3) arachidonate 5-lipoxygenase-activating protein, involved in synthesis of leukotrienes (inflammation) and associated with Copaxone® response (40).

Identified genes are also associated with MS severity and/or the brain. These genes include: (1) Membrane-associated guanylate kinase, a synaptic junction scaffold molecule exclusively expressed in brain and shown to modulate MS severity; (2) Glutamate/neutral amino acid transporter, which transports glutamate and alanine (2 of the 4 amino acid components of Copaxone®), as well as serine, cysteine, and threonine and has highest expression in brain; (3) Radiation resistance-associated gene protein, which is highly expressed in brain and has a role in axis formation and autophagy; and (4) Receptor-tyrosine protein phosphatase, associated with Copaxone® response, and tyrosine phosphorylation involved in myelin formation, differentiation of oligodendrocytes and Schwann cells, and recovery from demyelinating lesions.

REFERENCES CITED

1. Noseworthy J H, Lucchinetti C, Rodriguez M, Weinshenker B G. Multiple sclerosis. N Engl J Med 2000; 343:938-52.
2. Guideline on clinical investigation of medicinal products for the treatment of multiple sclerosis EMEA, London 16 Sep. 2006.
3. Bjartmar C, Fox R J. Pathological mechanisms and disease progression of multiple sclerosis: therapeutic implications. Drugs of Today 2002; 38:17-29.
4. Fleming J O. Diagnosis and management of multiple sclerosis. 1$^{st}$ ed. New York: Professional communications, Inc., 2002.
5. Anderson D W, Ellenberg J H, Leventhal C M et al. Revised estimate of the prevalence of multiple sclerosis in the United States. Ann Neurol 1992; 31:333-36.
6. Compston A, Lassmann H, McDonald I. The story of multiple sclerosis. In: Compston A, Confavreux C, Lassman H, Mcdonald I, Miller D, Noseworthy J H, Smith K, Wekerle H, editors. McAlpine's Multiple Sclerosis. London: Churchill Livingstone; 2006. P. 3-68.
7. Revel M., Pharmacol. Ther., 100(1):49-62 (2003).
8. Martinelli B F, Rovaris M, Johnson K P, Miller A, Wolinsky J S, Ladkani D, Shifroni G, Comi G, Filippi M. Effects of glatiramer acetate on relapse rate and accumulated disability in multiple sclerosis: meta-analysis of three double-blind, randomized, placebo-controlled clinical trials. Mult Scler. 2003 Aug. 9(4):349-55.
9. Mikol D D, Barkhof F, Chang P, Coyle P K, Jeffery D R, Schwid S R, Stubinski B, Uitdehaag B M; REGARD study group. Lancet Neurol. 2008 Oct. 7(10):903-14. Epub 2008 Sep. 11.
10. BECOME TRIAL, Presented at the 23$^{rd}$ Congress of the European Committee for Treatment and Research in Multiple Sclerosis (ECTRIMS) in Prague, Czech Republic.
11. Comi G, Filippi M and Wolinsky J S. European/Canadian multicenter, double-blind randomized, placebo controlled study of the effects of glatiramer acetate on magnetic resonance imaging-measured disease activity and burden in patients with relapsing-remitting multiple sclerosis. Ann Neurol 2001; (49):290-297.
12. Fridkis H M, Aharoni R, Teitelbaum D, Arnon R, Sela M, Strominger J L. Binding of random copolymers of three amino acids to class I I MHC molecules. Int. Immunol. 1999 May; 11(5):635-41.
13. Dhib-Jalbut S S, Zhan M, Johnson K P, Martin R. Glatiramer acetate reactive blood mononuclear cells respond to myelin antigens with a Th-2 biased phenotype. J Neuroimmunology 2003; 140:163-171.
14. Chen M, Gran B, Costello K, Johnson K P, Martin R, Dhib-Jalbut S. Glatiramer acetate induces a Th-2 biased response and cross-reactivity with myelin basic protein in patients with M S. Multiple Sclerosis 2001; 7:209-219.
15. Weber M S, Prod'homme T, Youssef S, Dunn S E, Rundle C D, Lee L, Patarroyo J C, Stuve O, Sobel R A, Steinman L, Zamvil S S. Type II monocytes modulate T cell-mediated central nervous sytem autoimmune disease. Nat Med (2007) 13:935-943.
16. Aharoni R, Kayhan B, Ellam R, Sela M, and Arnon R. Glatiramer acetate-specific T cells in the brain express T helper 2/3 cytokines and brain-derived neurotrophic factor in situ. PNAS August 2003; 100(24):14157-62.
17. Sarchielli P, Zaffaroni M, Floridi A, Greco L, Candeliere A, Mattioni A, Tenaglia 5, Di Filippo M, Calabresi P. Production of brain-derived neurotrophic factor by mononuclear cells of patients with multiple sclerosis treated with glatiramer acetate, interferon-beta 1a, and high doses of immunoglobulins. Mult Scler 2007 Apr. 13(3):313-31. Epub 2007 Jan. 29.
18. Bornstein, M B, Miller, A, Slagle, S, et al. A pilot trial of Cop 1 in exacerbating remitting multiple sclerosis. *New Eng J Med* 1987; 317: 408-14.
19. Comi, G, Fillippi, M, Wolinsky, J S, et al. European/Canadian multicenter, double-blind, randomized, placebo-controlled study of the effects of glatiramer acetate on magnetic resonance imagine-measured disease activity and burden in patients with relapsing multiple sclerosis. *Ann Neurol* 2001; 49: 290-7.
20. Johnson, K P, Brooks, B R, Cohen, J A, et al. Extended use of glatiramer acetate (Copaxone) is well tolerated and maintains its clinical effect on multiple sclerosis relapse rate and degree of disability. *Neurology* 1998; 50:701-8.
21. Bornstein, M B, Miller, A, Slagle, S, et al. A placebo-controlled, double-blind, randomized, two-center, pilot trial of Cop-1 in chronic progressive multiple sclerosis. *Neurology* 1991; 41: 533-39.
22. Wolinsky, J S, Narayana, P A, O'Conner, P, et al. Glatiramer acetate in primary progressive multiple sclerosis: Results of a multinational, multicenter, double-blind, placebo-controlled trial. *Ann Neurol* 2007; 61:14-24.
23. Comi G, Filippi M, Treatment with glatiramer acetate delays conversion to clinically definite multiple sclerosis (CDMS) in patients with clinically isolated syndromes (CIS). *Neurology* 2008; 71 (2): 153.
24. Tselis, A, Khan, O, Lisak, R P, Glatiramer acetate in the treatment of multiple sclerosis. *Neuropsychiatric Dis Treat* 2007; 3(2):259-67.
25. Wolinsky, J S, The use of glatiramer acetate in the treatment of multiple sclerosis. *Adv Neurol* 2006; 273-92.
26. Comi G, Cohen J A, Filippi M, Results from a phase III, one-year, randomized, double-blind, parallel-group, dose-comparison study with glatiramer acetate in relapsing-remitting multiple sclerosis. *Mult Scler* 2008; 14(suppl 1):S299.
27. Comi G, Filippi M. Presented at: 60 Annual Meeting of the American Academy of Neurology: April 12-19; Chicago, Ill. Abstract LBS.003.
28. Johnson D, Hafler D A, Fallis R J, Lees M B, Brady R O, Quarles R H, Weiner H L., "Cell-mediated immunity to myelin-associated glycoprotein, proteolipid protein, and myelin basic protein in multiple sclerosis.", *J Neuroimmunol.* 1986 Nov. 13 (1):99-108.
29. Brex P A et al., "A longitudinal study of abnormalities on MRI and disability from multiple sclerosis", *N Engl J Med* 2002 Jan. 17, 346(3):158-64.
30. Frohman E M et al., "The utility of MRI in suspected M S: report of the Therapeutics and Technology Assessment Subcommittee of the American Academy of Neurology", *Neurology,* 2003, Sep. 9, 61(5):602-11.
31. Poser C M. et al. New diagnostic criteria for multiple sclerosis: Guidelines for research protocols. Ann. Neurol., 13(3): 227-31, 1983
32. Neurostatus, slightly modified from J. F. Kurtzke Neurology 1983:33, 1444-52; L. Kappos, Dept. of Neurology, University Hospital, CH-4031/Basel, Switzerland.
33. Farina C, Then Bergh F, Albrecht H, Meinl E, Yassouridis A, Neuhaus O, Hohlfeld R. Treatment of multiple sclerosis with Copaxone (COP): Elispot assay detects COP-induced interleukin-4 and interferon-gamma response in blood cells. Brain. 2001 April; 124(Pt 4):705-19.
34. U.S. Pat. No. 7,855,176, issued Dec. 21, 2010 (Altman et al.).
35. U.S. Patent Application Publication No. US 2011-0046065 A1, published Feb. 24, 2011 (Klinger).
36. Byun et al. "Genome-wide-169-harmacogenomics analysis of the response to interferon beta therapy in multiple sclerosis," Arch Neurol. 2008 March; 65(3):337-94. Epub 2008 Jan. 19.
37. Fusco, C. et al. "HLA-DRB1*1501 and response to copolymer-1 therapy in relapsing-remitting multiple sclerosis," Neurology. 2001 Dec. 11; 57(11):1976-9.
38. Grossman et al. "Pharmacogenetics of glatiramer acetate therapy for multiple sclerosis reveals drug-response markers," Pharmacogenet Genomics. 2007 August; 17(8): 657-66.
39. PCT International Application Publication No. WO2006/116602, published Nov. 2, 2006 (Lancet et al).
40. PCT International Application Publication No. WO2013/0556683, published Apr. 18, 2013 (Tchelet et al).

What is claimed is:

1. A method for treating a human subject afflicted with multiple sclerosis or a single clinical attack consistent with multiple sclerosis with a pharmaceutical composition comprising glatiramer acetate and a pharmaceutically acceptable carrier, comprising the steps of:
   (i) determining a genotype of the subject at single nucleotide polymorphism (SNP) kgp8817856;
   (ii) identifying the subject as a predicted responder to glatiramer acetate if the genotype of the subject contains one or more G alleles at the location of kgp8817856; and
   (iii) administering the pharmaceutical composition comprising glatiramer acetate and a pharmaceutically acceptable carrier to the subject only if the subject is identified as a predicted responder to glatiramer acetate.

2. The method of claim 1, wherein administering the pharmaceutical composition comprising glatiramer acetate and a pharmaceutically acceptable carrier comprises administering to the human subject three subcutaneous injections of the pharmaceutical composition over a period of seven days with at least one day between every subcutaneous injection.

3. The method of claim 1, wherein the pharmaceutical composition is
   (a) a unit dose of a 1 ml aqueous solution comprising 40 mg of glatiramer acetate;
   (b) a unit dose of a 1 ml aqueous solution comprising 20 mg of glatiramer acetate; or
   (c) a unit dose of a 0.5 ml aqueous solution comprising 20 mg of glatiramer acetate.

4. The method of claim 1, wherein the pharmaceutical composition comprising glatiramer acetate and a pharmaceutically acceptable carrier is administered as a monotherapy, or in combination with at least one other multiple sclerosis drug.

5. The method of claim 1, wherein
   (a) the genotype is determined from a nucleic acid-containing sample that has been obtained from the subject;
   (b) determining the genotype comprises using a method selected from the group consisting of restriction fragment length polymorphism (RFLP) analysis, sequencing, single strand conformation polymorphism analysis (SSCP), chemical cleavage of mismatch (CCM), denaturing high performance liquid chromatography (DHPLC), Polymerase Chain Reaction (PCR) and an array, or a combination thereof; or
   (c) the genotype is determined using at least one pair of PCR primers and at least one probe.

6. The method of claim 1, wherein the array is selected from the group consisting of a gene chip, and a TaqMan Open Array, wherein if the array is a gene chip, then the gene chip is selected from the group consisting of a DNA array, a DNA microarray, a DNA chip, and a whole genome genotyping array.

7. The method of claim 1, wherein determining the genotype of the subject at the location corresponding to the location of the said one or more SNPs comprises:
 (a) obtaining DNA from a sample that has been obtained from the subject;
 (b) optionally amplifying the DNA; and
 (c) subjecting the DNA or the amplified DNA to a method selected from the group consisting of restriction fragment length polymorphism (RFLP) analysis, sequencing, single strand conformation polymorphism analysis (SSCP), chemical cleavage of mismatch (CCM), denaturing high performance liquid chromatography (DHPLC), Polymerase Chain Reaction (PCR) and an array, or a combination thereof, for determining the identity the one or more SNPs, wherein
  i) the array comprises a plurality of probes suitable for determining the identity of the one or more SNPs; or
  ii) the array is a gene chip, and the gene chip is a whole genome genotyping array.

8. The method of claim 1, wherein the human subject is a naïve patient, has been previously administered glatiramer acetate, or has been previously administered a multiple sclerosis drug other than glatiramer acetate.

9. The method of claim 1, wherein
 (a) the genotype of the subject at the location corresponding to the location of one or more of the SNPs is determined indirectly by determining the genotype of the subject at a location corresponding to the location of at least one SNP that is in linkage disequilibrium with the one or more SNPs; or
 (b) the genotype of the subject at the location corresponding to the location of the one or more SNPs is determined by indirect genotyping, and
 the indirect genotyping allows identification of the genotype of the subject at the location corresponding to the location of the one or more SNPs with a probability of at least 85%, at least 90%, or at least 99%.

10. The method of claim 1, further comprising determining the log number of relapses in the last two years for the human subject; or determining the baseline Expanded Disability Status Scale (EDSS) score for the human subject.

11. The method of claim 1, further comprising applying the algorithm depicted in FIG. 8 or in FIG. 9 to identify the subject as a predicted responder or as a predicted non-responder to glatiramer acetate.

12. The method of claim 1, wherein
 (a) step (i) further comprises determining a genotype of the subject at one or more single nucleotide polymorphism (SNP):
  kgp10090631, kgp1009249, kgp10152733, kgp10224254, kgp10305127, kgp10351364, kgp10372946, kgp10404633, kgp10412303, kgp10523170, kgp1054273, kgp10558725, kgp10564659, kgp10591989, kgp10594414, kgp10619195, kgp10620244, kgp10632945, kgp10633631, kgp10679353, kgp10788130, kgp10826273, kgp10910719, kgp10922969, kgp10948564, kgp10967046, kgp10974833, kgp1098237, kgp11002881, kgp11010680, kgp11077373, kgp11141512, kgp11206453, kgp11210903, kgp1124492, kgp11281589, kgp11285862, kgp11328629, kgp11356379, kgp11407560, kgp11453406, kgp11467007, kgp11514107, kgp11543962, kgp11580695, kgp11627530, kgp11633966, kgp11686146, kgp11702474, kgp11711524, kgp11768533, kgp11804835, kgp11843177, kgp12008955, kgp12083934, kgp12182745, kgp12230354, kgp1224440, kgp12371757, kgp124162, kgp12426624, kgp12557319, kgp1285441, kgp13161760, kgp1355977, kgp1371881, kgp15390522, kgp1683448, kgp1688752, kgp1699628, kgp1753445, kgp1779254, kgp1786079, kgp18379774, kgp18432055, kgp18525257, kgp1912531, kgp19568724, kgp20163979, kgp2023214, kgp2045074, kgp20478926, kgp2092817, kgp21171930, kgp2245775, kgp2262166, kgp22778566, kgp22793211, kgp22811918, kgp22823022, kgp2282938, kgp2299675, kgp23298674, kgp2356388, kgp23672937, kgp23737989, kgp2388352, kgp2391411, kgp24131116, kgp24415534, kgp2446153, kgp2451249, kgp2465184, kgp24729706, kgp24753470, kgp25191871, kgp25216186, kgp25543811, kgp25921291, kgp25952891, kgp26026546, kgp26271158, kgp2638591, kgp26528455, kgp26533576, kgp2688306, kgp26995430, kgp270001, kgp2709692, kgp2715873, kgp27500525, kgp27571222, kgp27640141, kgp2788291, kgp279772, kgp28532436, kgp28586329, kgp28687699, kgp28817122, kgp2923815, kgp29367521, kgp293787, kgp2958113, kgp2959751, kgp297178, kgp29794723, kgp30282494, kgp3048169, kgp304921, kgp3182607, kgp3202939, kgp3205849, kgp3218351, kgp3267884, kgp3276689, kgp337461, kgp3418770, kgp3450875, kgp345301, kgp3477351, kgp3496814, kgp355027, kgp355723, kgp3593828, kgp3598409, kgp3651767, kgp3669685, kgp3730395, kgp3812034, kgp3854180, kgp3933330, kgp3951463, kgp3984567, kgp3991733, kgp4011779, kgp4056892, kgp4096263, kgp4127859, kgp4155998, kgp4162414, kgp4223880, kgp4346717, kgp4370912, kgp4418535, kgp4420791, kgp4479467, kgp4524468, kgp4543470, kgp4559907, kgp4573213, kgp4634875, kgp4705854, kgp4734301, kgp4755147, kgp4812831, kgp4842590, kgp485316, kgp487328, kgp4898179, kgp5002011, kgp5014707, kgp5017029, kgp5053636, kgp5068397, kgp512180, kgp5144181, kgp5159037, kgp5216209, kgp5292386, kgp5334779, kgp5388938, kgp5409955, kgp5440506, kgp5441587, kgp5483926, kgp55646, kgp5564995, kgp5579170, kgp5680955, kgp5869992, kgp5908616, kgp6023196, kgp6032617, kgp6038357, kgp6076976, kgp6091119, kgp6127371, kgp61811, kgp6190988, kgp6214351, kgp6228750, kgp6236949, kgp6469620, kgp6505544, kgp6507761, kgp652534, kgp6539666, kgp6567154, kgp6599438, kgp6603796, kgp6666134, kgp6700691, kgp6737096, kgp6768546, kgp6772915, kgp6835138, kgp6959492, kgp6996560, kgp7059449, kgp7063887, kgp7077322, kgp7092772, kgp7117398, kgp7121374, kgp7178233, kgp7181058, kgp7186699, kgp7189498, kgp7242489, kgp7331172, kgp7416024, kgp7481870, kgp7506434, kgp7521990, kgp759150, kgp767200, kgp7714238, kgp7730397, kgp7747883, kgp7792268,

247 kgp7802182, kgp7804623, kgp7924485, kgp8030775, kgp8036704, kgp8046214, kgp8106690, kgp8107491, kgp8110667, kgp8169636, kgp8174785, kgp8178358, kgp8183049, kgp8192546, kgp8200264, kgp8303520, kgp8335515, kgp8372910, kgp841428, kgp8437961, kgp8440036, kgp85534, kgp8599417, kgp8602316, kgp8615910, kgp8767692, kgp8777935, kgp8793915, kgp8796185, kgp8869954, kgp8990121, kgp9018750, kgp9071686, kgp9078300, kgp9320791, kgp9354462, kgp9354820, kgp9368119, kgp9410843, kgp9421884, kgp9450430, kgp9530088, kgp9551947, kgp9601362, kgp9627338, kgp9627406, kgp9669946, kgp9699754, kgp971582, kgp97310, kgp974569, kgp9795732, kgp9806386, kgp9854133, kgp9884626, rs10049206, rs10124492, rs10125298, rs10162089, rs10201643, rs10203396, rs10251797, rs10278591, rs10489312, rs10492882, rs10498793, rs10501082, rs10510774, rs10512340, rs1079303, rs10815160, rs10816302, rs10841322, rs10841337, rs10954782, rs11002051, rs11022778, rs11029892, rs11029907, rs11029928, rs11083404, rs11085044, rs11136970, rs11147439, rs11192461, rs11192469, rs11559024, rs1157449, rs11648129, rs11691553, rs12013377, rs12494712, rs12943140, rs13002663, rs13394010, rs13415334, rs13419758, rs1380706, rs1387768, rs1410779, rs1478682, rs1508102, rs1532365, rs1544352, rs1545223, rs1579771, rs1604169, rs1621509, rs1644418, rs16886004, rs16895510, rs16901784, rs16927077, rs16930057, rs17029538, rs17224858, rs17238927, rs17329014, rs17400875, rs17449018, rs17577980, rs17638791, rs1858973, rs1886214, rs1894406, rs1894407, rs1894408, rs196295, rs196341, rs196343, rs197523, rs1979992, rs1979993, rs2043136, rs2058742, rs2071469, rs2071470, rs2071472, rs2074037, rs2136408, rs2139612, rs2175121, rs2241883, rs2309760, rs2325911, rs241435, rs241440, rs241442, rs241443, rs241444, rs241445, rs241446, rs241447, rs241449, rs241451, rs241452, rs241453, rs241454, rs241456, rs2453478, rs2598360, rs2621321, rs2621323, rs2660214, rs2816838, rs2824070, rs2839117, rs2845371, rs2857101, rs2857103, rs2857104, rs2926455, rs2934491, rs3135388, rs3218328, rs343087, rs343092, rs3767955, rs3792135, rs3799383, rs3803277, rs3815822, rs3818675, rs3829539, rs3885907, rs3899755, rs4075692, rs4143493, rs419132, rs423239, rs4254166, rs4356336, rs4360791, rs4449139, rs4584668, rs4669694, rs4709792, rs4738738, rs4769060, rs4780822, rs4782279, rs4822644, rs484482, rs4894701, rs5024722, rs502530, rs543122, rs6032205, rs6032209, rs6110157, rs623011, rs6497396, rs6535882, rs6687976, rs6718758, rs6835202, rs6840089, rs6845927, rs6895094, rs6899068, rs7020402, rs7024953, rs7028906, rs7029123, rs7062312, rs714342, rs7187976, rs7191155, rs720176, rs7217872, rs7228827, rs7348267, rs7496451, rs7524868, rs7563131, rs7579987, rs759458, rs7666442, rs7670525, rs7672014, rs7677801, rs7725112, rs7844274, rs7850, rs7860748, rs7862565, rs7864679, rs7928078, rs7948420, rs8035826, rs8050872, rs8053136, rs8055485, rs823829,

248 rs858341, rs9315047, rs931570, rs9346979, rs9376361, rs9393727, rs9501224, rs9508832, rs950928, rs9579566, rs9597498, rs9670531, rs9671124, rs9671182, rs9817308, rs9834010, rs9876830, rs9913349, rs9931167 or rs9931211, and wherein step (ii) further comprises identifying the subject as a predicted responder to glatiramer acetate if the genotype of the subject contains one or more A alleles at the location of kgp10152733, kgp10224254, kgp10305127, kgp10351364, kgp10372946, kgp10404633, kgp10564659, kgp10591989, kgp10594414, kgp10619195, kgp10620244, kgp10633631, kgp10974833, kgp11002881, kgp11285862, kgp11328629, kgp11407560, kgp11514107, kgp11627530, kgp11702474, kgp11711524, kgp11768533, kgp11804835, kgp12083934, kgp12182745, kgp12230354, kgp1224440, kgp124162, kgp12557319, kgp1371881, kgp1699628, kgp1753445, kgp1779254, kgp1786079, kgp18379774, kgp18525257, kgp20163979, kgp2023214, kgp20478926, kgp21171930, kgp2262166, kgp22778566, kgp2465184, kgp24753470, kgp25191871, kgp25216186, kgp25952891, kgp26026546, kgp26533576, kgp27500525, kgp27571222, kgp28532436, kgp28586329, kgp28817122, kgp2958113, kgp29794723, kgp30282494, kgp304921, kgp3205849, kgp3218351, kgp3276689, kgp337461, kgp345301, kgp355027, kgp355723, kgp3593828, kgp3812034, kgp3951463, kgp4162414, kgp4223880, kgp4418535, kgp4543470, kgp4573213, kgp4634875, kgp4755147, kgp4842590, kgp485316, kgp5068397, kgp5334779, kgp5483926, kgp5564995, kgp5869992, kgp5908616, kgp6032617, kgp6038357, kgp6076976, kgp6091119, kgp6127371, kgp61811, kgp6214351, kgp6228750, kgp6236949, kgp6469620, kgp6505544, kgp6507761, kgp6666134, kgp6700691, kgp6772915, kgp6959492, kgp7077322, kgp7117398, kgp7178233, kgp7186699, kgp7506434, kgp759150, kgp7730397, kgp7802182, kgp7804623, kgp7924485, kgp8030775, kgp8036704, kgp8046214, kgp8106690, kgp8110667, kgp8178358, kgp8200264, kgp8372910, kgp841428, kgp8602316, kgp8615910, kgp8793915, kgp8796185, kgp8990121, kgp9018750, kgp9354462, kgp9368119, kgp9410843, kgp9450430, kgp9530088, kgp9627338, kgp9669946, kgp97310, kgp974569, kgp9806386, kgp9884626, rs10049206, rs10124492, rs10125298, rs10162089, rs10203396, rs10251797, rs10278591, rs10489312, rs10492882, rs10498793, rs10501082, rs10510774, rs10512340, rs10815160, rs10816302, rs10841337, rs11029892, rs11029928, rs11192469, rs11559024, rs11648129, rs12013377, rs13394010, rs13415334, rs1478682, rs1544352, rs1545223, rs1604169, rs1621509, rs1644418, rs17029538, rs17400875, rs17449018, rs17577980, rs1858973, rs1894406, rs1894407, rs197523, rs2058742, rs2071469, rs2071472, rs2139612, rs2241883, rs2309760, rs241440, rs241442, rs241444, rs241445, rs241446, rs241449, rs241453, rs241456, rs2453478, rs2660214, rs2824070, rs2845371, rs2857103, rs2926455, rs343087, rs343092, rs3767955, rs3792135, rs3829539, rs3899755, rs4075692, rs4143493, rs423239, rs4254166, rs4356336, rs4584668, rs4780822, rs4782279, rs5024722, rs6032209, rs6110157, rs623011, rs6497396, rs6845927, rs6895094, rs6899068, rs7024953, rs7028906, rs7029123, rs7062312, rs7187976, rs7191155, rs720176, rs7228827, rs7496451, rs7563131, rs759458, rs7666442, rs7670525, rs7677801, rs7725112, rs7850, rs7862565, rs7948420, rs8035826, rs8053136, rs8055485, rs823829, rs9315047, rs9501224, rs9508832, rs950928, rs9597498, rs9670531, rs9671124, rs9817308, rs9834010, rs9876830 or rs9931211, one or more C alleles at the location of kgp10910719, kgp11077373, kgp11453406, kgp12426624, kgp2045074, kgp22811918, kgp23298674, kgp2709692, kgp28687699, kgp3496814, kgp3669685, kgp3730395, kgp4056892, kgp4370912, kgp5053636, kgp5216209, kgp5292386, kgp6023196, kgp652534, kgp7059449, kgp7189498, kgp7521990, kgp7792268, kgp8303520, kgp9320791, kgp9795732, rs10201643, rs11022778, rs11136970, rs11147439, rs11691553, rs1579771, rs16901784, rs2136408, rs2325911, rs241443, rs2857104, rs3803277, rs3885907, rs4738738, rs4894701, rs502530, rs6032205, rs6687976, rs6718758, rs6835202, rs714342, rs7524868, rs7844274, rs9393727 or rs9671182, one or more G alleles at the location of kgp10090631, kgp1009249, kgp10412303, kgp10523170, kgp1054273, kgp10558725, kgp10632945, kgp10679353, kgp10788130, kgp10826273, kgp10922969, kgp10948564, kgp10967046, kgp1098237, kgp11010680, kgp11141512, kgp11206453, kgp11210903, kgp1124492, kgp11281589, kgp11356379, kgp11467007, kgp11543962, kgp11580695, kgp11633966, kgp11686146, kgp11843177, kgp12008955, kgp12371757, kgp1285441, kgp13161760, kgp1355977, kgp15390522, kgp1683448, kgp1688752, kgp1912531, kgp19568724, kgp2092817, kgp2245775, kgp22793211, kgp22823022, kgp2282938, kgp2299675, kgp2356388, kgp23672937, kgp23737989, kgp2388352, kgp2391411, kgp24131116, kgp24415534, kgp2446153, kgp2451249, kgp24729706, kgp25543811, kgp25921291, kgp26271158, kgp2638591, kgp26528455, kgp2688306, kgp26995430, kgp270001, kgp2715873, kgp27640141, kgp2788291, kgp2923815, kgp29367521, kgp293787, kgp2959751, kgp297178, kgp3048169, kgp3182607, kgp3202939, kgp3267884, kgp3418770, kgp3450875, kgp3477351, kgp3598409, kgp3651767, kgp3854180, kgp3933330, kgp3984567, kgp4011779, kgp4096263, kgp4127859, kgp4155998, kgp4346717, kgp4420791, kgp4479467, kgp4524468, kgp4559907, kgp4705854, kgp4734301, kgp4812831, kgp487328, kgp4898179, kgp5002011, kgp5014707, kgp5017029, kgp512180, kgp5144181, kgp5159037, kgp5388938, kgp5409955, kgp5440506, kgp5441587, kgp55646, kgp5579170, kgp5680955, kgp6190988, kgp6539666, kgp6567154, kgp6599438, kgp6603796, kgp6737096, kgp6768546, kgp6835138, kgp6996560, kgp7063887, kgp7092772, kgp7121374, kgp7181058, kgp7331172, kgp7416024, kgp7481870, kgp767200, kgp7714238, kgp7747883, kgp8107491, kgp8169636, kgp8174785, kgp8183049, kgp8192546, kgp8335515, kgp8437961, kgp8440036, kgp85534, kgp8599417, kgp8767692, kgp8777935, kgp8869954, kgp9071686, kgp9078300, kgp9354820, kgp9421884, kgp9551947, kgp9601362, kgp9627406, kgp9699754, kgp971582, kgp9854133, rs1079303, rs10841322, rs10954782, rs11002051, rs11029907, rs11083404, rs11085044, rs11192461, rs1157449, rs12494712, rs12943140, rs13002663, rs13419758, rs1380706, rs1387768, rs1410779, rs1508102, rs1532365, rs16886004, rs16895510, rs16927077, rs16930057, rs17224858, rs17238927, rs17329014, rs17638791, rs1886214, rs1894408, rs196295, rs196341, rs196343, rs1979992, rs1979993, rs2043136, rs2071470, rs2074037, rs2175121, rs241435, rs241447, rs241451, rs241452, rs241454, rs2598360, rs2621321, rs2621323, rs2816838, rs2839117, rs2857101, rs2934491, rs3135388, rs3218328, rs3799383, rs3815822, rs3818675, rs419132, rs4360791, rs4449139, rs4669694, rs4709792, rs4769060, rs4822644, rs484482, rs543122, rs6535882, rs6840089, rs7020402, rs7217872, rs7348267, rs7579987, rs7672014, rs7860748, rs7864679, rs7928078, rs8050872, rs858341, rs931570, rs9346979, rs9376361, rs9579566, rs9913349 or rs9931167, or one or more T alleles at the location of kgp18432055, kgp279772, kgp3991733 or kgp7242489, thereby identifying a human subject afflicted with multiple sclerosis or a single clinical attack consistent with multiple sclerosis as a predicted responder or as a predicted non-responder to glatiramer acetate;

(b) step (i) further comprises determining a genotype of the subject at one or more single nucleotide polymorphism (SNP): rs10988087, rs1573706, rs17575455, rs2487896, rs3135391, rs6097801 or rs947603, and wherein step (ii) further comprises identifying the subject as a predicted responder to glatiramer acetate if the genotype of the subject contains one or more A alleles at the location of rs10988087, one or more C alleles at the location of rs17575455, or one or more G alleles at the location of rs1573706, rs2487896, rs3135391, rs6097801 or rs947603, thereby identifying a human subject afflicted with multiple sclerosis or a single clinical attack consistent with multiple sclerosis as a predicted responder or as a predicted non-responder to glatiramer acetate; or (c) step (i) further comprises determining a genotype of the subject at one or more single nucleotide polymorphism (SNP)

kgp10148554, kgp10215554, kgp10762962, kgp10836214, kgp10989246, kgp11285883, kgp11604017, kgp11755256, kgp1211163, kgp12253568, kgp12562255, kgp1432800, kgp1682126, kgp1758575, kgp2176915, kgp22839559, kgp24521552, kgp2877482, kgp2920925, kgp2993366, kgp3188, kgp3287349, kgp3420309, kgp3488270, kgp3598966, kgp3624014, kgp3697615, kgp394638, kgp4037661, kgp4137144, kgp433351, kgp4456934, kgp4575797, kgp4591145, kgp4892427, kgp4970670, kgp4985243, kgp5252824, kgp5326762, kgp541892, kgp5691690, kgp5747456, kgp5894351, kgp5924341, kgp5949515, kgp6042557, kgp6081880, kgp6194428, kgp6213972, kgp625941, kgp6301155, kgp6429231, kgp6828277, kgp6889327, kgp6990559, kgp7006201, kgp7151153, kgp7161038, kgp7653470, kgp7778345, kgp7932108, kgp8145845, kgp8644305, kgp8847137, kgp9143704, kgp9409440, kgp956070, kgp9909702, kgp9927782, rs10038844, rs1026894, rs10495115, rs11562998, rs11563025, rs11750747, rs11947777, rs12043743, rs12233980, rs12341716, rs12472695, rs12881439, rs13168893, rs13386874, rs1357718, rs1393037, rs1393040, rs1397481, rs1474226, rs1508515, rs1534647, rs16846161, rs1715441, rs17187123, rs17245674, rs17419416, rs1793174, rs1883448, rs1905248, rs209568, rs2354380, rs2618065, rs263247, rs2662, rs28993969, rs34647183, rs35615951, rs3768769, rs3847233, rs3858034, rs3858035, rs3858036, rs3858038, rs3894712, rs4740708, rs4797764, rs4978567, rs528065, rs6459418, rs6577395, rs6811337, rs7119480, rs7123506, rs7231366, rs7680970, rs7684006, rs7696391, rs7698655, rs7819949, rs7846783, rs7949751, rs7961005, rs8000689, rs8018807, rs961090, rs967616, rs9948620 or rs9953274, and wherein step (ii) further comprises identifying the subject as a predicted responder to glatiramer acetate if the genotype of the subject contains one or more A alleles at the location of kgp10762962, kgp11285883, kgp11604017, kgp1211163, kgp12253568, kgp12562255, kgp2176915, kgp24521552, kgp2877482, kgp2993366, kgp3188, kgp3624014, kgp394638, kgp4037661, kgp433351, kgp4456934, kgp4575797, kgp4591145, kgp4892427, kgp4970670, kgp4985243, kgp5252824, kgp5326762, kgp541892, kgp5747456, kgp5894351, kgp6042557, kgp6081880, kgp6194428, kgp6429231, kgp7006201, kgp7151153, kgp7161038, kgp7653470, kgp8145845, kgp8644305, kgp9143704, kgp9409440, kgp9909702, kgp9927782, rs10038844, rs10495115, rs11750747, rs12341716, rs12881439, rs13168893, rs1393040, rs1474226, rs1534647, rs1715441, rs17187123, rs17245674, rs17419416, rs1793174, rs1883448, rs1905248, rs263247, rs34647183, rs35615951, rs3847233, rs3858038, rs4740708, rs528065, rs6459418, rs6577395, rs6811337, rs7680970, rs7684006, rs7698655, rs7961005, rs8018807, rs9948620 or rs9953274, one or more C alleles at the location of kgp10836214, kgp1432800, kgp22839559, kgp6301155, kgp6828277, rs2354380, rs2662, rs3858035, rs3894712, rs4797764 or rs7696391, one or more G alleles at the location of kgp10148554, kgp10215554, kgp10989246, kgp11755256, kgp1682126, kgp1758575, kgp2920925, kgp3287349, kgp3420309, kgp3488270, kgp3598966, kgp3697615, kgp4137144, kgp5691690, kgp5924341, kgp5949515, kgp6213972, kgp625941, kgp6889327, kgp6990559, kgp7778345, kgp7932108, kgp8847137, kgp956070, rs1026894, rs11562998, rs11563025, rs11947777, rs12233980, rs12472695, rs13386874, rs1357718, rs1393037, rs1397481, rs1508515, rs16846161, rs209568, rs2618065, rs28993969, rs3768769, rs3858034, rs3858036, rs4978567, rs7119480, rs7123506, rs7231366, rs7819949, rs7846783, rs7949751, rs8000689, rs961090 or rs967616, or one or more T alleles at the location of rs12043743, thereby identifying a human subject afflicted with multiple sclerosis or a single clinical attack consistent with multiple sclerosis as a predicted responder to glatiramer acetate.

13. The method of claim 12, comprising determining the genotype at one or more single nucleotide polymorphism (SNP) kgp24415534, kgp6214351, kgp6599438, kgp7747883, kgp8110667, rs10162089, rs16886004, rs1894408 or rs759458.

14. The method of claim 12, comprising determining the genotype at one or more single nucleotide polymorphism (SNP) kgp24415534, kgp6214351, kgp6599438, kgp7747883, kgp8110667, rs10162089, rs16886004, rs1894408, rs3135391 or rs759458.

15. The method of claim 12, comprising determining the genotype at one or more single nucleotide polymorphism (SNP): kgp24415534, kgp6214351, kgp6599438, kgp8110667, rs10162089, rs16886004, rs1894408, rs3135391 or rs759458, wherein if rs3135391 is the one SNP selected, then selecting at least one SNP other than rs3135391.

16. A method of identifying a human subject afflicted with multiple sclerosis or a single clinical attack consistent with multiple sclerosis as a predicted responder or as a predicted non-responder to glatiramer acetate, the method comprising the steps of:

(i) determining using a probe or primer the genotype of the subject at single nucleotide polymorphism (SNP) kgp8817856; and (ii) identifying the human subject as a predicted responder to glatiramer acetate if the genotype of the subject contains one or more G alleles at the location of kgp8817856, or identifying the human subject as a predicted non-responder to glatiramer acetate if the genotype of the subject contains no G alleles at the location of kgp8817856, thereby identifying a human subject afflicted with multiple sclerosis or a single clinical attack consistent with multiple sclerosis as a predicted responder or as a predicted non-responder to glatiramer acetate.

17. The method of claim 16, wherein (a) step (i) further comprises determining a genotype of the subject at one or more single nucleotide polymorphism (SNP):

kgp10090631, kgp1009249, kgp10152733, kgp10224254, kgp10305127, kgp10351364, kgp10372946, kgp10404633, kgp10412303, kgp10523170, kgp1054273, kgp10558725, kgp10564659, kgp10591989, kgp10594414, kgp10619195, kgp10620244, kgp10632945, kgp10633631, kgp10679353, kgp10788130, kgp10826273, kgp10910719, kgp10922969, kgp10948564, kgp10967046, kgp10974833, kgp1098237, kgp11002881, kgp11010680, kgp11077373, kgp11141512, kgp11206453, kgp11210903, kgp1124492, kgp11281589, kgp11285862, kgp11328629, kgp11356379, kgp11407560, kgp11453406, kgp11467007, kgp11514107, kgp11543962, kgp11580695, kgp11627530, kgp11633966, kgp11686146, kgp11702474, kgp11711524, kgp11768533, kgp11804835, kgp11843177, kgp12008955, kgp12083934, kgp12182745, kgp12230354, kgp1224440, kgp12371757, kgp124162, kgp12426624, kgp12557319, kgp1285441, kgp13161760, kgp1355977, kgp1371881, kgp15390522, kgp1683448, kgp1688752, kgp1699628, kgp1753445, kgp1779254, kgp1786079, kgp18379774, kgp18432055, kgp18525257, kgp1912531, kgp19568724, kgp20163979, kgp2023214, kgp2045074, kgp20478926, kgp2092817, kgp21171930, kgp2245775, kgp2262166, kgp22778566, kgp22793211, kgp22811918, kgp22823022, kgp2282938, kgp2299675, kgp23298674, kgp2356388, kgp23672937, kgp23737989, kgp2388352, kgp2391411, kgp24131116, kgp24415534, kgp2446153, kgp2451249, kgp2465184, kgp24729706, kgp24753470, kgp25191871, kgp25216186, kgp25543811, kgp25921291, kgp25952891, kgp26026546, kgp26271158, kgp2638591, kgp26528455, kgp26533576, kgp2688306, kgp26995430, kgp270001, kgp2709692, kgp2715873, kgp27500525, kgp27571222, kgp27640141, kgp2788291, kgp279772, kgp28532436, kgp28586329, kgp28687699, kgp28817122, kgp2923815, kgp29367521, kgp293787, kgp2958113, kgp2959751, kgp297178, kgp29794723, kgp30282494, kgp3048169, kgp304921, kgp3182607, kgp3202939, kgp3205849, kgp3218351, kgp3267884, kgp3276689, kgp337461, kgp3418770, kgp3450875, kgp345301, kgp3477351, kgp3496814, kgp355027, kgp355723, kgp3593828, kgp3598409, kgp3651767, kgp3669685, kgp3730395, kgp3812034, kgp3854180, kgp3933330, kgp3951463, kgp3984567, kgp3991733, kgp4011779, kgp4056892, kgp4096263, kgp4127859, kgp4155998, kgp4162414, kgp4223880, kgp4346717, kgp4370912, kgp4418535, kgp4420791, kgp4479467, kgp4524468, kgp4543470, kgp4559907, kgp4573213, kgp4634875, kgp4705854, kgp4734301, kgp4755147, kgp4812831, kgp4842590, kgp485316, kgp487328, kgp4898179, kgp5002011, kgp5014707, kgp5017029, kgp5053636, kgp5068397, kgp512180, kgp5144181, kgp5159037, kgp5216209, kgp5292386, kgp5334779, kgp5388938, kgp5409955, kgp5440506, kgp5441587, kgp5483926, kgp55646, kgp5564995, kgp5579170, kgp5680955, kgp5869992, kgp5908616, kgp6023196, kgp6032617, kgp6038357, kgp6076976, kgp6091119, kgp6127371, kgp61811, kgp6190988, kgp6214351, kgp6228750, kgp6236949, kgp6469620, kgp6505544, kgp6507761, kgp652534, kgp6539666, kgp6567154, kgp6599438, kgp6603796, kgp6666134, kgp6700691, kgp6737096, kgp6768546, kgp6772915, kgp6835138, kgp6959492, kgp6996560, kgp7059449, kgp7063887, kgp7077322, kgp7092772, kgp7117398, kgp7121374, kgp7178233, kgp7181058, kgp7186699, kgp7189498, kgp7242489, kgp7331172, kgp7416024, kgp7481870, kgp7506434, kgp7521990, kgp759150, kgp767200, kgp7714238, kgp7730397, kgp7747883, kgp7792268, kgp7802182, kgp7804623, kgp7924485, kgp8030775, kgp8036704, kgp8046214, kgp8106690, kgp8107491, kgp8110667, kgp8169636, kgp8174785, kgp8178358, kgp8183049, kgp8192546, kgp8200264, kgp8303520, kgp8335515, kgp8372910, kgp841428, kgp8437961, kgp8440036, kgp85534, kgp8599417, kgp8602316, kgp8615910, kgp8767692, kgp8777935, kgp8793915, kgp8796185, kgp8869954, kgp8990121, kgp9018750, kgp9071686, kgp9078300, kgp9320791, kgp9354462, kgp9354820, kgp9368119, kgp9410843, kgp9421884, kgp9450430, kgp9530088, kgp9551947, kgp9601362, kgp9627338, kgp9627406, kgp9669946, kgp9699754, kgp971582, kgp97310, kgp974569, kgp9795732, kgp9806386, kgp9854133, kgp9884626, rs10049206, rs10124492, rs10125298, rs10162089, rs10201643, rs10203396, rs10251797, rs10278591, rs10489312, rs10492882, rs10498793, rs10501082, rs10510774, rs10512340, rs1079303, rs10815160, rs10816302, rs10841322, rs10841337, rs10954782, rs11002051, rs11022778, rs11029892, rs11029907, rs11029928, rs11083404, rs11085044, rs11136970, rs11147439, rs11192461, rs11192469, rs11559024, rs1157449, rs11648129, rs11691553, rs12013377, rs12494712, rs12943140, rs13002663, rs13394010, rs13415334, rs13419758, rs1380706, rs1387768, rs1410779, rs1478682, rs1508102, rs1532365, rs1544352, rs1545223, rs1579771, rs1604169, rs1621509, rs1644418, rs16886004, rs16895510, rs16901784, rs16927077, rs16930057, rs17029538, rs17224858, rs17238927, rs17329014, rs17400875, rs17449018, rs17577980, rs17638791, rs1858973, rs1886214, rs1894406, rs1894407, rs1894408, rs196295, rs196341, rs196343, rs197523, rs1979992, rs1979993, rs2043136, rs2058742, rs2071469, rs2071470, rs2071472, rs2074037, rs2136408, rs2139612, rs2175121, rs2241883, rs2309760, rs2325911, rs241435, rs241440, rs241442, rs241443, rs241444, rs241445, rs241446, rs241447, rs241449, rs241451, rs241452, rs241453, rs241454, rs241456, rs2453478, rs2598360, rs2621321, rs2621323, rs2660214, rs2816838, rs2824070, rs2839117, rs2845371, rs2857101, rs2857103, rs2857104, rs2926455, rs2934491, rs3135388, rs3218328, rs343087, rs343092, rs3767955, rs3792135, rs3799383, rs3803277, rs3815822, rs3818675, rs3829539, rs3885907, rs3899755, rs4075692, rs4143493, rs419132, rs423239, rs4254166, rs4356336, rs4360791, rs4449139, rs4584668, rs4669694, rs4709792, rs4738738, rs4769060, rs4780822, rs4782279, rs4822644, rs484482, rs4894701, rs5024722, rs502530, rs543122, rs6032205, rs6032209, rs6110157, rs623011, rs6497396, rs6535882, rs6687976, rs6718758, rs6835202, rs6840089, rs6845927, rs6895094, rs6899068, rs7020402, rs7024953, rs7028906, rs7029123, rs7062312, rs714342, rs7187976, rs7191155, rs720176, rs7217872, rs7228827, rs7348267, rs7496451, rs7524868, rs7563131, rs7579987, rs759458, rs7666442, rs7670525, rs7672014, rs7677801, rs7725112, rs7844274, rs7850, rs7860748, rs7862565, rs7864679, rs7928078, rs7948420, rs8035826, rs8050872, rs8053136, rs8055485, rs823829, rs858341, rs9315047, rs931570, rs9346979, rs9376361, rs9393727, rs9501224, rs9508832, rs950928, rs9579566, rs9597498, rs9670531, rs9671124, rs9671182, rs9817308, rs9834010, rs9876830, rs9913349, rs9931167 or rs9931211, and wherein step (ii) further comprises identifying the subject as a predicted responder to glatiramer acetate if the genotype of the subject contains one or more A alleles at the location of kgp10152733, kgp10224254, kgp10305127, kgp10351364, kgp10372946, kgp10404633, kgp10564659, kgp10591989, kgp10594414, kgp10619195, kgp10620244, kgp10633631, kgp10974833, kgp11002881, kgp11285862, kgp11328629, kgp11407560, kgp11514107, kgp11627530, kgp11702474, kgp11711524, kgp11768533, kgp11804835, kgp12083934, kgp12182745, kgp12230354, kgp1224440, kgp124162, kgp12557319, kgp1371881, kgp1699628, kgp1753445, kgp1779254, kgp1786079, kgp18379774, kgp18525257, kgp20163979, kgp2023214, kgp20478926, kgp21171930, kgp2262166, kgp22778566, kgp2465184, kgp24753470, kgp25191871, kgp25216186, kgp25952891, kgp26026546, kgp26533576, kgp27500525, kgp27571222, kgp28532436, kgp28586329, kgp28817122, kgp2958113, kgp29794723, kgp30282494, kgp304921, kgp3205849, kgp3218351, kgp3276689, kgp337461, kgp345301, kgp355027, kgp355723, kgp3593828, kgp3812034, kgp3951463, kgp4162414, kgp4223880, kgp4418535, kgp4543470, kgp4573213, kgp4634875, kgp4755147, kgp4842590, kgp485316, kgp5068397, kgp5334779, kgp5483926, kgp5564995, kgp5869992, kgp5908616, kgp6032617, kgp6038357, kgp6076976, kgp6091119, kgp6127371, kgp61811, kgp6214351, kgp6228750, kgp6236949, kgp6469620, kgp6505544, kgp6507761, kgp6666134, kgp6700691, kgp6772915, kgp6959492, kgp7077322, kgp7117398, kgp7178233, kgp7186699, kgp7506434, kgp759150, kgp7730397, kgp7802182, kgp7804623, kgp7924485, kgp8030775, kgp8036704, kgp8046214, kgp8106690, kgp8110667, kgp8178358, kgp8200264, kgp8372910, kgp841428, kgp8602316, kgp8615910, kgp8793915, kgp8796185, kgp8990121, kgp9018750, kgp9354462, kgp9368119, kgp9410843, kgp9450430, kgp9530088, kgp9627338, kgp9669946, kgp97310, kgp974569, kgp9806386, kgp9884626, rs10049206, rs10124492, rs10125298, rs10162089, rs10203396, rs10251797, rs10278591, rs10489312, rs10492882, rs10498793, rs10501082, rs10510774, rs10512340, rs10815160, rs10816302, rs10841337, rs11029892, rs11029928, rs11192469, rs11559024, rs11648129, rs12013377, rs13394010, rs13415334, rs1478682, rs1544352, rs1545223, rs1604169, rs1621509, rs1644418, rs17029538, rs17400875, rs17449018, rs17577980, rs1858973, rs1894406, rs1894407, rs197523, rs2058742, rs2071469, rs2071472, rs2139612, rs2241883, rs2309760, rs241440, rs241442, rs241444, rs241445, rs241446, rs241449, rs241453, rs241456, rs2453478, rs2660214, rs2824070, rs2845371, rs2857103, rs2926455, rs343087, rs343092, rs3767955, rs3792135, rs3829539, rs3899755, rs4075692, rs4143493, rs423239, rs4254166, rs4356336, rs4584668, rs4780822, rs4782279, rs5024722, rs6032209, rs6110157, rs623011, rs6497396, rs6845927, rs6895094, rs6899068, rs7024953, rs7028906, rs7029123, rs7062312, rs7187976, rs7191155, rs720176, rs7228827, rs7496451, rs7563131, rs759458, rs7666442, rs7670525, rs7677801, rs7725112, rs7850, rs7862565, rs7948420, rs8035826, rs8053136, rs8055485, rs823829, rs9315047, rs9501224, rs9508832, rs950928, rs9597498, rs9670531, rs9671124, rs9817308, rs9834010, rs9876830 or rs9931211, one or more C alleles at the location of kgp10910719, kgp11077373, kgp11453406, kgp12426624, kgp2045074, kgp22811918, kgp23298674, kgp2709692, kgp28687699, kgp3496814, kgp3669685, kgp3730395, kgp4056892, kgp4370912, kgp5053636, kgp5216209, kgp5292386, kgp6023196, kgp652534, kgp7059449, kgp7189498, kgp7521990, kgp7792268, kgp8303520, kgp9320791, kgp9795732, rs10201643, rs11022778, rs11136970, rs11147439, rs11691553, rs1579771, rs16901784, rs2136408, rs2325911, rs241443, rs2857104, rs3803277, rs3885907, rs4738738, rs4894701, rs502530, rs6032205, rs6687976, rs6718758, rs6835202, rs714342, rs7524868, rs7844274, rs9393727 or rs9671182, one or more G alleles at the location of kgp10090631, kgp1009249, kgp10412303, kgp10523170, kgp1054273, kgp10558725, kgp10632945, kgp10679353, kgp10788130, kgp10826273, kgp10922969, kgp10948564, kgp10967046, kgp1098237, kgp11010680, kgp11141512, kgp11206453, kgp11210903, kgp1124492, kgp11281589, kgp11356379, kgp11467007, kgp11543962, kgp11580695, kgp11633966, kgp11686146, kgp11843177, kgp12008955, kgp12371757, kgp1285441, kgp13161760, kgp1355977, kgp15390522, kgp1683448, kgp1688752, kgp1912531, kgp19568724, kgp2092817, kgp2245775, kgp22793211, kgp22823022, kgp2282938, kgp2299675, kgp2356388, kgp23672937, kgp23737989, kgp2388352, kgp2391411, kgp24131116, kgp24415534, kgp2446153, kgp2451249, kgp24729706, kgp25543811, kgp25921291, kgp26271158, kgp2638591, kgp26528455, kgp2688306, kgp26995430, kgp270001, kgp2715873, kgp27640141, kgp2788291, kgp2923815, kgp29367521, kgp293787, kgp2959751, kgp297178, kgp3048169, kgp3182607, kgp3202939, kgp3267884, kgp3418770, kgp3450875, kgp3477351, kgp3598409, kgp3651767, kgp3854180, kgp3933330, kgp3984567, kgp4011779, kgp4096263, kgp4127859, kgp4155998, kgp4346717, kgp4420791, kgp4479467, kgp4524468, kgp4559907, kgp4705854, kgp4734301, kgp4812831, kgp487328, kgp4898179, kgp5002011, kgp5014707, kgp5017029, kgp512180, kgp5144181, kgp5159037, kgp5388938, kgp5409955, kgp5440506, kgp5441587, kgp55646, kgp5579170, kgp5680955, kgp6190988, kgp6539666, kgp6567154, kgp6599438, kgp6603796, kgp6737096, kgp6768546, kgp6835138, kgp6996560, kgp7063887, kgp7092772, kgp7121374, kgp7181058, kgp7331172, kgp7416024, kgp7481870, kgp767200, kgp7714238, kgp7747883, kgp8107491, kgp8169636, kgp8174785, kgp8183049, kgp8192546, kgp8335515, kgp8437961, kgp8440036, kgp85534, kgp8599417, kgp8767692, kgp8777935, kgp8869954, kgp9071686, kgp9078300, kgp9354820, kgp9421884, kgp9551947, kgp9601362, kgp9627406, kgp9699754, kgp971582, kgp9854133, rs1079303, rs10841322, rs10954782, rs11002051, rs11029907, rs11083404, rs11085044, rs11192461, rs1157449, rs12494712, rs12943140, rs13002663, rs13419758, rs1380706, rs1387768, rs1410779, rs1508102, rs1532365, rs16886004, rs16895510, rs16927077, rs16930057, rs17224858, rs17238927, rs17329014, rs17638791, rs1886214, rs1894408, rs196295, rs196341, rs196343, rs1979992, rs1979993, rs2043136, rs2071470, rs2074037, rs2175121, rs241435, rs241447, rs241451, rs241452, rs241454, rs2598360, rs2621321, rs2621323, rs2816838, rs2839117, rs2857101, rs2934491, rs3135388, rs3218328, rs3799383, rs3815822, rs3818675, rs419132, rs4360791, rs4449139, rs4669694, rs4709792, rs4769060, rs4822644, rs484482, rs543122, rs6535882, rs6840089, rs7020402, rs7217872, rs7348267, rs7579987, rs7672014, rs7860748, rs7864679, rs7928078, rs8050872, rs858341, rs931570, rs9346979, rs9376361, rs9579566, rs9913349 or rs9931167, or one or more T alleles at the location of kgp18432055, kgp279772, kgp3991733 or kgp7242489, thereby identifying a human subject afflicted with multiple sclerosis or a single clinical attack consistent with multiple sclerosis as a predicted responder or as a predicted non-responder to glatiramer acetate;

(b) step (i) further comprises determining a genotype of the subject at one or more single nucleotide polymorphism (SNP): rs10988087, rs1573706, rs17575455, rs2487896, rs3135391, rs6097801 or rs947603, and wherein step (ii) further comprises identifying the subject as a predicted responder to glatiramer acetate if the genotype of the subject contains one or more A alleles at the location of rs10988087, one or more C alleles at the location of rs17575455, or one or more G alleles at the location of rs1573706, rs2487896, rs3135391, rs6097801 or rs947603, thereby identifying a human subject afflicted with multiple sclerosis or a single clinical attack consistent with multiple sclerosis as a predicted responder or as a predicted non-responder to glatiramer acetate; or (c) step (i) further comprises determining a genotype of the subject at one or more single nucleotide polymorphism (SNP)

kgp10148554, kgp10215554, kgp10762962, kgp10836214, kgp10989246, kgp11285883, kgp11604017, kgp11755256, kgp1211163, kgp12253568, kgp12562255, kgp1432800, kgp1682126, kgp1758575, kgp2176915, kgp22839559, kgp24521552, kgp2877482, kgp2920925, kgp2993366, kgp3188, kgp3287349, kgp3420309, kgp3488270, kgp3598966, kgp3624014, kgp3697615, kgp394638, kgp4037661, kgp4137144, kgp433351, kgp4456934, kgp4575797, kgp4591145, kgp4892427, kgp4970670, kgp4985243, kgp5252824, kgp5326762, kgp541892, kgp5691690, kgp5747456, kgp5894351, kgp5924341, kgp5949515, kgp6042557, kgp6081880, kgp6194428, kgp6213972, kgp625941, kgp6301155, kgp6429231, kgp6828277, kgp6889327, kgp6990559, kgp7006201, kgp7151153, kgp7161038, kgp7653470, kgp7778345, kgp7932108, kgp8145845, kgp8644305, kgp8847137, kgp9143704, kgp9409440, kgp956070, kgp9909702, kgp9927782, rs10038844, rs1026894, rs10495115, rs11562998, rs11563025, rs11750747, rs11947777, rs12043743, rs12233980, rs12341716, rs12472695, rs12881439, rs13168893, rs13386874, rs1357718, rs1393037, rs1393040, rs1397481, rs1474226, rs1508515, rs1534647, rs16846161, rs1715441, rs17187123, rs17245674, rs17419416, rs1793174, rs1883448, rs1905248, rs209568, rs2354380, rs2618065, rs263247, rs2662, rs28993969, rs34647183, rs35615951, rs3768769, rs3847233, rs3858034, rs3858035, rs3858036, rs3858038, rs3894712, rs4740708, rs4797764, rs4978567, rs528065, rs6459418, rs6577395, rs6811337, rs7119480, rs7123506, rs7231366, rs7680970, rs7684006, rs7696391, rs7698655, rs7819949, rs7846783, rs7949751, rs7961005, rs8000689, rs8018807, rs961090, rs967616, rs9948620 or rs9953274, and wherein step (ii) further comprises identifying the subject as a predicted responder to glatiramer acetate if the genotype of the subject contains one or more A alleles at the location of kgp10762962, kgp11285883, kgp11604017, kgp1211163, kgp12253568, kgp12562255, kgp2176915, kgp24521552, kgp2877482, kgp2993366, kgp3188, kgp3624014, kgp394638, kgp4037661, kgp433351, kgp4456934, kgp4575797, kgp4591145, kgp4892427, kgp4970670, kgp4985243, kgp5252824, kgp5326762, kgp541892, kgp5747456, kgp5894351, kgp6042557, kgp6081880, kgp6194428, kgp6429231, kgp7006201, kgp7151153, kgp7161038, kgp7653470, kgp8145845, kgp8644305, kgp9143704, kgp9409440, kgp9909702, kgp9927782, rs10038844, rs10495115, rs11750747, rs12341716, rs12881439, rs13168893, rs1393040, rs1474226, rs1534647, rs1715441, rs17187123, rs17245674, rs17419416, rs1793174, rs1883448, rs1905248, rs263247, rs34647183, rs35615951, rs3847233, rs3858038, rs4740708, rs528065, rs6459418, rs6577395, rs6811337, rs7680970, rs7684006, rs7698655, rs7961005, rs8018807, rs9948620 or rs9953274, one or more C alleles at the location of kgp10836214, kgp1432800, kgp22839559, kgp6301155, kgp6828277, rs2354380, rs2662, rs3858035, rs3894712, rs4797764 or rs7696391, one or more G alleles at the location of kgp10148554, kgp10215554, kgp10989246, kgp11755256, kgp1682126, kgp1758575, kgp2920925, kgp3287349, kgp3420309, kgp3488270, kgp3598966, kgp3697615, kgp4137144, kgp5691690, kgp5924341, kgp5949515, kgp6213972, kgp625941, kgp6889327, kgp6990559, kgp7778345, kgp7932108, kgp8847137, kgp956070, rs1026894, rs11562998, rs11563025, rs11947777, rs12233980, rs12472695, rs13386874, rs1357718, rs1393037, rs1397481, rs1508515, rs16846161, rs209568, rs2618065, rs28993969, rs3768769, rs3858034, rs3858036, rs4978567, rs7119480, rs7123506, rs7231366, rs7819949, rs7846783, rs7949751, rs8000689, rs961090 or rs967616, or
one or more T alleles at the location of rs12043743, thereby identifying a human subject afflicted with multiple sclerosis or a single clinical attack consistent with multiple sclerosis as a predicted responder to glatiramer acetate.

18. The method of claim 17, comprising determining the genotype at one or more single nucleotide polymorphism (SNP) of: kgp24415534, kgp6214351, kgp6599438, kgp7747883, kgp8110667, rs10162089, rs16886004, rs1894408 or rs759458.

19. The method of claim 17, comprising determining the genotype at one or more single nucleotide polymorphism (SNP) of: kgp24415534, kgp6214351, kgp6599438, kgp7747883, kgp8110667, rs10162089, rs16886004, rs1894408, rs3135391 or rs759458.

20. The method of claim 17, comprising determining the genotype at one or more single nucleotide polymorphism (SNP) of: kgp24415534, kgp6214351, kgp6599438, kgp8110667, rs10162089, rs16886004, rs1894408, rs3135391 or rs759458,
   wherein if rs3135391 is the one SNP selected, then selecting at least one SNP other than rs3135391.

* * * * *